(12) United States Patent
Oh et al.

(10) Patent No.: US 8,691,569 B2
(45) Date of Patent: *Apr. 8, 2014

(54) MICROCARRIERS FOR STEM CELL CULTURE

(75) Inventors: Steve Oh, Singapore (SG); Shaul Reuveny, Singapore (SG); Allen Chen, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 0 days.

This patent is subject to a terminal disclaimer.

(21) Appl. No.: 12/917,210

(22) Filed: Nov. 1, 2010

(65) Prior Publication Data

US 2011/0129919 A1 Jun. 2, 2011

Related U.S. Application Data

(63) Continuation-in-part of application No. 12/921,599, filed as application No. PCT/SG2009/000088 on Mar. 17, 2009, application No. 12/917,210, which is a continuation-in-part of application No. 12/497,591, filed on Jul. 3, 2009, which is a continuation-in-part of application No. PCT/SG2009/000088, filed on Mar. 17, 2009, now abandoned.

(60) Provisional application No. 61/069,694, filed on Mar. 17, 2008, provisional application No. 61/110,256, filed on Oct. 31, 2008, provisional application No. 61/148,064, filed on Jan. 29, 2009, provisional application No. 61/155,940, filed on Feb. 27, 2009.

(51) Int. Cl.
 *C12N 5/07* (2010.01)
 *C12N 5/02* (2006.01)

(52) U.S. Cl.
 USPC .......................... 435/363; 435/403; 435/377

(58) Field of Classification Search
 USPC .......................................... 435/363, 403, 377
 See application file for complete search history.

(56) References Cited

U.S. PATENT DOCUMENTS

| | | | |
|---|---|---|---|
| 4,975,377 A | 12/1990 | Key | |
| 5,858,747 A | 1/1999 | Schinstine et al. | |
| 6,387,369 B1 | 5/2002 | Pittenger et al. | |
| 6,637,437 B1 | 10/2003 | Hungerford et al. | |
| 6,662,805 B2 | 12/2003 | Frondoza et al. | |
| 6,886,568 B2 | 5/2005 | Frondoza et al. | |
| 7,790,456 B2 | 9/2010 | Terstegge et al. | |
| 2001/0014475 A1 | 8/2001 | Frondoza et al. | |
| 2001/0051834 A1 | 12/2001 | Frondoza et al. | |
| 2002/0090619 A1 | 7/2002 | Pfeiffer et al. | |
| 2004/0044408 A1 | 3/2004 | Hungerford et al. | |
| 2004/0117033 A1 | 6/2004 | Frondoza et al. | |
| 2005/0054101 A1 | 3/2005 | Felder et al. | |
| 2005/0129776 A1 | 6/2005 | Montero-Menei et al. | |
| 2005/0147959 A1 | 7/2005 | Frondoza et al. | |
| 2005/0260748 A1 | 11/2005 | Chang et al. | |
| 2005/0265980 A1 | 12/2005 | Chen et al. | |
| 2007/0010011 A1 | 1/2007 | Parsons et al. | |
| 2007/0020754 A1 | 1/2007 | Yuge et al. | |
| 2007/0082328 A1 | 4/2007 | Rudd | |
| 2007/0264713 A1 | 11/2007 | Terstegge et al. | |
| 2008/0138415 A1 | 6/2008 | Hussain et al. | |
| 2008/0166328 A1 | 7/2008 | Harmon et al. | |
| 2010/0093053 A1 | 4/2010 | Oh et al. | |
| 2010/0124781 A1 | 5/2010 | Nelson | |
| 2010/0137811 A1 | 6/2010 | Yuge et al. | |
| 2010/0291219 A1 | 11/2010 | Karp et al. | |
| 2011/0014693 A1 | 1/2011 | Oh et al. | |
| 2011/0111498 A1 | 5/2011 | Oh et al. | |
| 2011/0143433 A1 | 6/2011 | Oh et al. | |
| 2011/0294210 A1 | 12/2011 | Oh et al. | |
| 2012/0028352 A1 | 2/2012 | Oh et al. | |

FOREIGN PATENT DOCUMENTS

| | | |
|---|---|---|
| WO | WO 03/029418 | 4/2003 |
| WO | WO 2006/091921 A2 | 8/2006 |
| WO | WO 2007/012144 | 2/2007 |

(Continued)

OTHER PUBLICATIONS

Zhang et al. Nature Biotechnology 19:1129-1133, 2001.*
Stem Cells: Scientific Progress and Future Research Directions. Department of Health and Human Services. Jun. 2001. 2:The embryonic stem cell, pp. 5-10.*
Stem Cells: Scientific Progress and Future Research Directions. Department of Health and Human Services. Jun. 2001. 4:The adult stem cell, pp. 23-42.*
Sun et al. (2010) "Cell proliferation of human bone marrow mesenchymal stem cells on biodegradable microcarriers enhances in vitro differentiation potential", Cell Prolif., 43:445-456.

(Continued)

*Primary Examiner* — Marcia S Noble
(74) *Attorney, Agent, or Firm* — Swanson & Bratschun, LLC

(57) ABSTRACT

We disclose a particle comprising a matrix coated thereon and having a positive charge, the particle being of a size to allow aggregation of primate or human stem cells attached thereto. The particle may comprise a substantially elongate, cylindrical or rod shaped particle having a longest dimension of between 50 μm and 400 μm, such as about 200 μm. It may have a cross sectional dimension of between 20 μm and 30 μm. The particle may comprise a substantially compact or spherical shaped particle having a size of between about 20 μm and about 120 μm, for example about 65 μm. We also disclose a method of propagating primate or human stem cells, the method comprising: providing first and second primate or human stem cells attached to first and second respective particles, allowing the first primate or human stem cell to contact the second primate or human stem cell to form an aggregate of cells and culturing the aggregate to propagate the primate or human stem cells for at least one passage. A method of propagating human embryonic stem cells (hESCs) in long term suspension culture using microcarriers coated in Matrigel or hyaluronic acid is also disclosed. We also disclose a method for differentiating stem cells.

15 Claims, 305 Drawing Sheets
(209 of 305 Drawing Sheet(s) Filed in Color)

(56) References Cited

FOREIGN PATENT DOCUMENTS

| WO | WO 2007/030469 A2 | 3/2007 |
|---|---|---|
| WO | WO 2007/030870 | 3/2007 |
| WO | WO 2007/070964 | 6/2007 |
| WO | WO 2007/149926 | 12/2007 |
| WO | WO 2008/004990 | 1/2008 |
| WO | WO 2008/005520 A2 | 1/2008 |
| WO | WO 2008/015682 | 2/2008 |
| WO | WO 2009/006422 | 1/2009 |
| WO | WO 2009/139703 A1 | 11/2009 |
| WO | WO 2010/059775 | 5/2010 |

OTHER PUBLICATIONS

Sart et al. (2010) "Influence of culture parameters on ear mesenchymal stem cells expanded on microcarriers", Journal of Biotechnology 150:149-160.

Kedong et al. (2010) "Simultaneous expansion and harvest of hematopoietic stem cells and mesenchymal stem cells derived from umbilical cord blood", J Mater Sci: Mater Med 21:3183-3193.

Yang et al. (2010) "Suspension Culture of Mammalian Cells Using Thermosensitive Microcarrier That Allows Cell Detachment Without Proteolytic Enzyme Treatment", Cell Transplantation, 19:1223-1132.

Ogura (2004) J. Oral Sci. 46(4):207-213, "Differentiation of the human mesenchymal stem cells derived from bone marrow and enhancement of cell attachment by fibronectin".

Kaisermayer (2007) "Influence of Microcarrier Surface Modification on Adhesion and Product Formation of Mammalian Cell," Dissertation zur Erlangung des Doktogrades an der Universitat fur Bodenkultur, Wien, Mai, pp. 1-153.

Choo et al. (2006) Journal of Biotechnology 122:130-141, "Immortalized feeders for the scale-up of human embryonic stem cells in feeder and feeder-free conditions".

Fernandes et al. Poster entitled "Maintenance of pluripotency of human embryonic stem cells expanded in microcarrier-based stirred cultures" presentd at 21st ESACT meeting on Jun. 7-10, 2009 in Dublin, Ireland.

Fernandes et al. (2009) Brazilian Journal of Medical and Biological Research, 42:515-522, "Successful scale-up of human embryonic stem cell production in a stirred microcarrier culture system".

Fok and Zandstra (2005) Stem Cells 23:1333-1342, "Shear-Controlled Single-Step Mouse Embryonic Stem Cell Expansion and Embryoid Body-Based Differentiation".

Frauenschuh et al. (2007) Biotechnol. Prog., 23:187-193, "A Microcarrier-Based Cultivation System for Expansion of Primary Mesenchymal Stem Cells".

Graichen et al. (2007) Differentiation DOI:10.111/j.1432-0436. 2007.00236.x, "Enhanced cardiomyogenesis of human embryonic stem cells by a small molecular inhibitor of p38 MAPK".

Hay et al. (Aug. 26, 2008) PNAS 105(34):12301-12306, "Highly efficient differentiation of hESCs to functional hepatic endoderm requires ActivinA and Wnt3a signaling".

Ilic et al. (2009) Stem cells and development 18(9):1343-1350, DOI: 10.1089/scd.2008.0416, "Derivation of human embryonic stem cell lines from biopsied blastomeres on human feeders with a minimal exposure to xenomaterials".

Itskovitz-Eldor et al. (2000) Molecular Medicine 6(2):88-95, "Differentiation of Human Embryonic Stem Cells into Embryoid Bodies Comprising the Three Embryonic Germ Layers".

Jaenisch (Dec. 12, 2008) Stem Cells Express, doi: 10.1634/stemcells. 2008-1019, "Celebrating 10 Years of hESC Lines: An Interview with Rudolf Jaenisch".

Jo et al. (2008) Cell Tissue Res 334:423-433, "Fetal mesenchymal stem cells derived from human umbilical cord sustain primitive characteristics during extensive expansion".

Kehoe et al. (2009) Tissue Engineering: Part A, 1-17, "Scalable Stirred-Suspension Bioreactor Culture of Human Pluripotent Stem Cells".

Kim et al. (2007) Cloning and Stem Cells 9(4):581-594, "Ex Vivo Characteristics of Human Amniotic Membrane-Derived Stem Cells".

King and Miller (2007) Current Opinion in Chemical Biology 11:394-398, "Bioreactor development for stem cell expansion and controlled differentiation".

Krawetz et al. (2009) Tissue Engineering: Part C Methods Article, DOI: 10.1089/ten.tec.2009.0228, "Large-Scale Expansion of Pluripotent Human Embryonic Stem Cells in Stirred Suspension Bioreactors".

Kroon et al. (Apr. 2008) Nat Biotechnol. 26(4):443-452, "Pancreatic endoderm derived from human embryonic stem cells generates glucose-responsive insulin-secreting cells in vivo".

Lei et al. Cell Research (2007) 17:682-688, "Xeno-free derivation and culture of human embryonic stem cells: current status, problems and challenges".

Lian et al. (2007) Stem Cells: 25:425-436, "Derivation of Clinically Compliant MSCs from CD105+, CD24− Differentiated Human ESCs".

Lock et al. (2009) Tissue Engineering: Part A. vol. 15, DOI: 10.1089/ten.tea.2008.0455, "Expansion and Differentiation of Human Embryonic Stem Cells to Endoderm Progeny in a Microcarrier Stirred-Suspension Culture".

Lu et al. (Apr. 11, 2006) PNAS, 103(15):5688-5693, "Defined culture conditions of human embyonic stem cells".

Newman and McBurney (2004) Biomaterials 25:5763-5771, "Poly(D,L-lactic-co-glycolic acid) microspheres as biodegradable microcarriers for pluripotent stem cells".

Nie et al. (2009) Biotechnol Prog 25(1):20-31, published online (Feb. 5, 2009): DOI: 10.1002/btpr.110, "Scalable Culture and Cryopreservation of Human Embryonic Stem Cells on Microcarriers".

Niebruegge et al. (Feb. 1, 2009) Biotechnology and Bioengineering, 102(2):493-507, "Generation of Human Embryonic Stem Cell-Derived Mesoderm And Cardiac Cells Using Size-Specified Aggregates in an Oxygen-Controlled Bioreactor".

Oh and Choo (Winter 2008) Drug Discovery Today: Technologies 5(4):e125-e130, DOI: 10.1016/j.ddtec.2008.10.001 "Advances and perspectives in human and mouse embryonic stem cell bioprocessing".

Oh and Choo (Jun. 23, 2006) Cytotechnology 50:181-190, "Human embryonic stem cell technology: large scale cell amplification and differentiation".

Oh et al. (Epub ahead of print, Mar. 4, 2009) Stem Cell Research, DOI: 10.1016/j.scr.2009.02.005, "Long-term microcarrier suspension cultures of human embryonic stem cells".

Pereira et al. (2008) J. Tissue Eng Regen Med 2:394-399, "Reproducible methodology for the isolation of mesenchymal stem cells from human umbilical cord and its potential for cardiomyocyte generation".

Phillips et al. (2008) Journal of Biotechnology 134:79-87, "Efficient expansion of clinical-grade human fibroblasts on microcarriers: Cells suitable for ex vivo expansion of clincal-grade hESCs".

Phillips et al. (2008) Journal of Biotechnology 138:24-32, "Attachment and growth of human embryonic stem cells on microcarriers".

Schop et al. (2008) Journal of Tissue Engineering and Regenerative Medicine, 2:126-135, "Expansion of mesenchymal stem cells using a microcarrier-based cultivation system: growth and metabolism".

Troyer and Weiss (2008) Stem Cells; 26:591-599, "Concise Review: Wharton's Jelly-Derived Cells Are a Primitive Stromal Cell Population".

Yamanaka (Jul. 2007) Cell Stem Cell 1, DOI: 10.1016/j.stem.2007. 05.012, "Strategies and New Developments in the Generation of Patient-Specific Pluripotent Stem Cells".

Yang et al. (2007) Biomaterials, 28:3110-3120, "Ex vivo expansion of rat bone marrow mesenchymal stromal cells on microcarrier beads in spin culture".

ISR and Written Opinion issued in PCT/SG2009/000088, Oct. 13, 2009.

IPRP issued in PCT/SG2009/000088, Mar. 5, 2010.

Frondoza et al. (1996) Biomaterials 17:879-888 "Human chondrocytes proliferate and produce matrix components in microcarrier suspension culture".

(56) References Cited

OTHER PUBLICATIONS

GE Healthcare (2005) GE Microcarrier Cell Culture Technical Manual "Microcarrier Cell Culture: Principles and Methods" 175 pages.

Abranches et al. (2007) Biotechnology and Bioengineering 96(6):1211-1221 "Expansion of Mouse Embryonic Stem Cells on Microcarriers".

Fernandes et al. (2007) Journal of Biotechnology 132:227-236 "Mouse embryonic stem cell expansion in a microcarrier-based stirred culture system".

Knippenberg et al. (2005) Tissue Engineering 11(11/12):1780-1788 "Adipose Tissue-Derived Mesenchymal Stem Cells Acquire Bone Cell-Like Responsiveness to Fluid Shear Stress on Osteogenic Stimulation".

Kruyt et al. (2003) Tissue Engineering 9(2):327-336 "Viable Osteogenic Cells are Obligatory for Tissue-Engineered Ectopic Bone Formation in Goats".

Mauney et al. (2005) Tissue Engineering 11(5/6):787-802 "Role of Adult Mesenchymal Stem Cells in Bone Tissue-Engineering Applications: Current Status and Future Prospects".

Moioli et al. (2006) Tissue Engineering 12(3):537-546 "Substained Release of TGFβ3 from PLGA Microspheres and Its Effect on Early Osteogenic Differentiation of Human Mesenchymal Stem Cells".

Wu et al. (2003) Association of Pathophysiology 11(1):15-21 "Cultivation of Human Mesenchymal Stem Cells on Macroporous CultiSpher G Microcarriers" Abstract Only.

\* cited by examiner

FIGURE10B
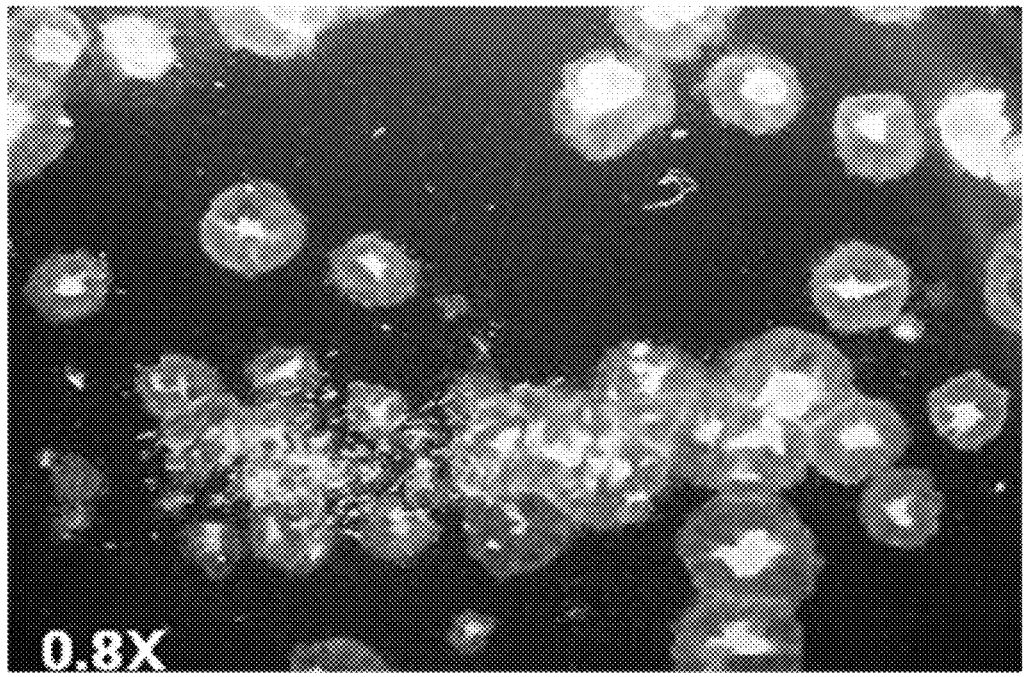
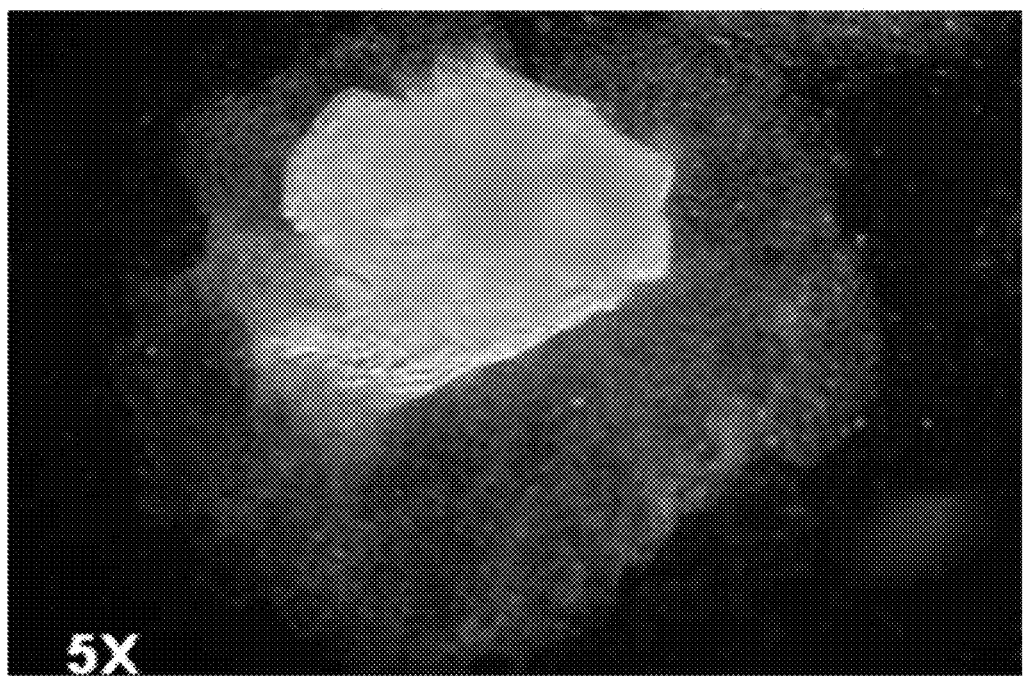

| Key | Name | Parameter |
|---|---|---|
| —— | CONTROL | |
| ......... | OCT-4 | 68% |
| ——— | SSEA-4 | 88% |
| ——— | TRA-1-60 | 78% |

| Key | Name | Parameter Gate |
|---|---|---|
| — | Data.013 | control |
|  | Data.014 | oct 4 - 62.3% |
|  | Data.015 | ssea 4 - 97.5% |
|  | Data.016 | tra 1 60 - 86.1% |

| Key | Name | Parameter Gate |
|---|---|---|
| —— | Data.001 | control |
| ~~~ | Data.002 | oct 4 - 68.6% |
| ~~~ | Data.003 | ssea 4 - 97.8% |
| ~~~ | Data.004 | tra 1 60 - 88.3% |

Day 0

FIGURE 37
 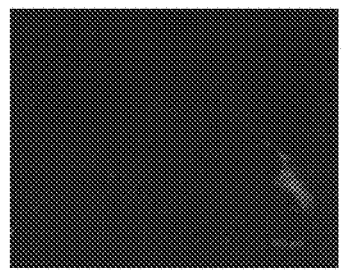 Staining with DAPI
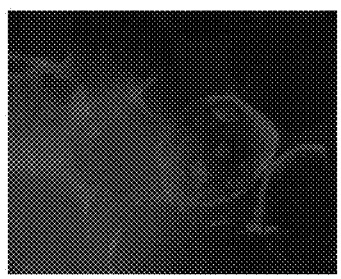 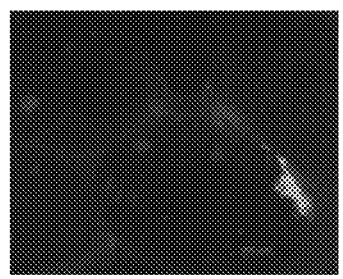 Staining with Phalloidin-Alexafluor 488
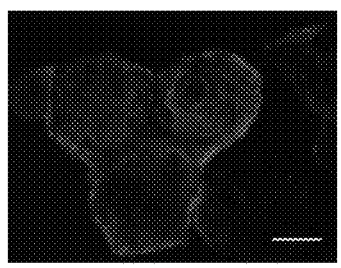 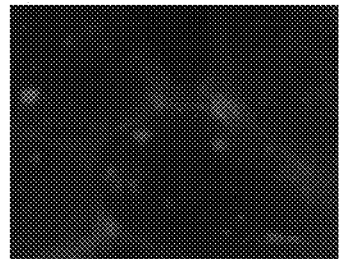 Staining with anti Tra-1-60-RPE
SH1010        SM1010

Day 0

Day 15

FIGURE 42
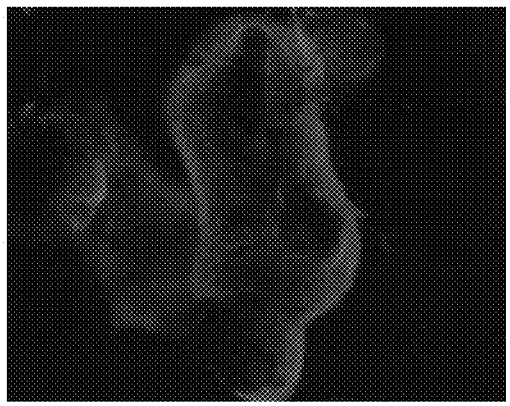
Staining with DAPI
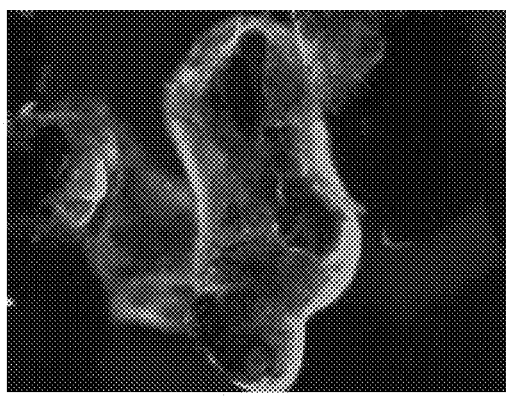
Staining with Phalloidin-Alexafluor 488
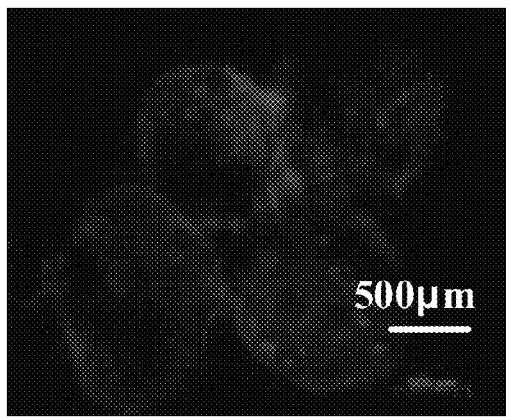
Staining with anti Tra1-60-RPE Day 0

Day 7

Comparison of hESC growth on cellulose microcarriers vs. 2D colony cultures

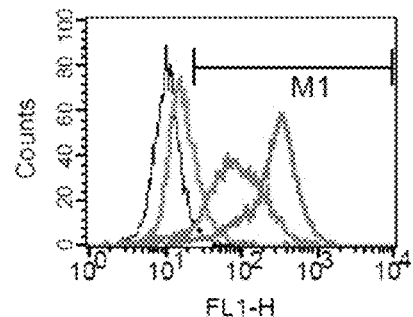
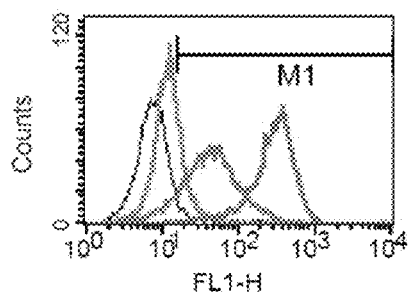
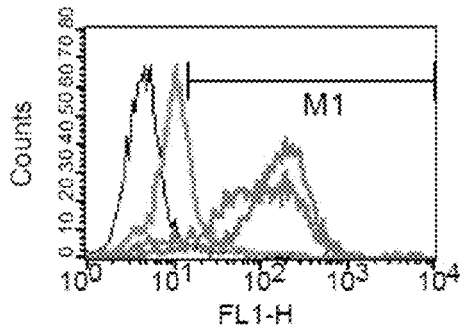
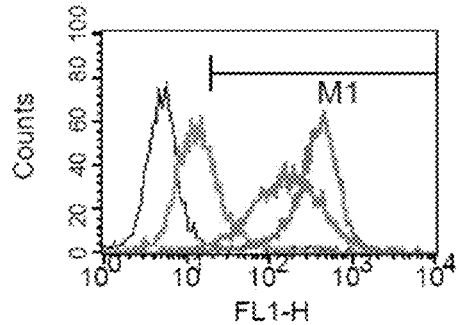
Figure 53

P25 on microcarriers

Teratomas

Observations of HES-3 in spinner flask 2 cultures
Day 4 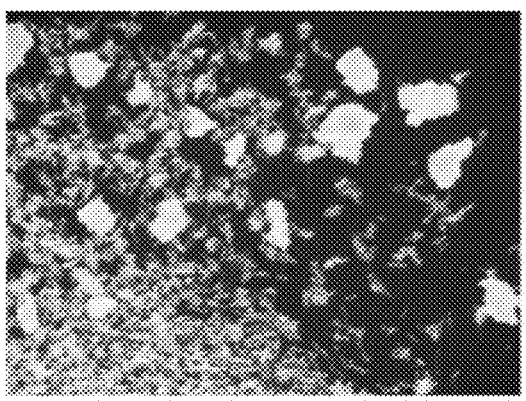 Day 5 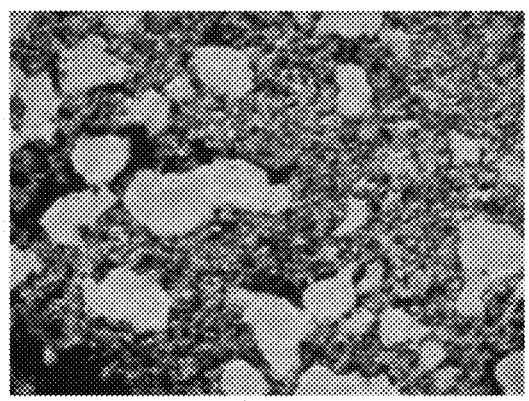
Figure 72

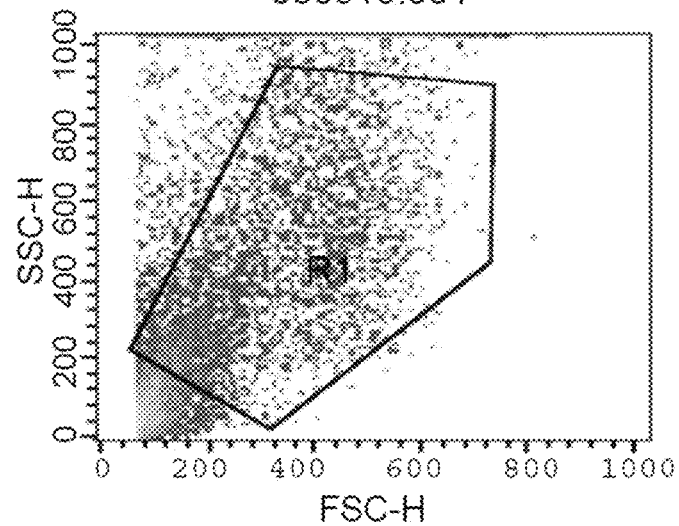
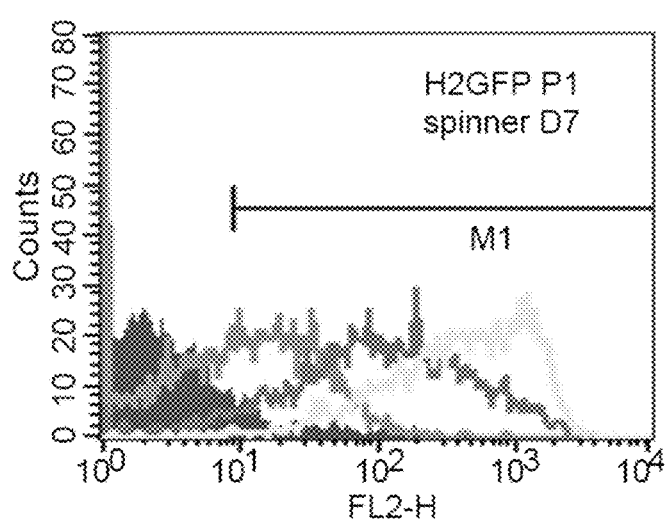
Figure 75 Cont...

Spinner Flask Pictures
Day 5 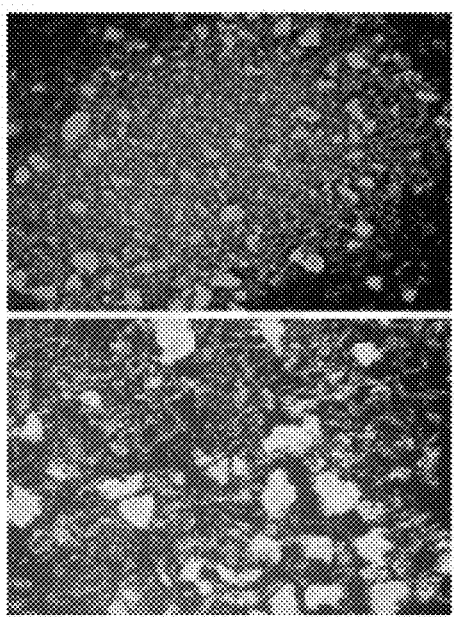 Day 7 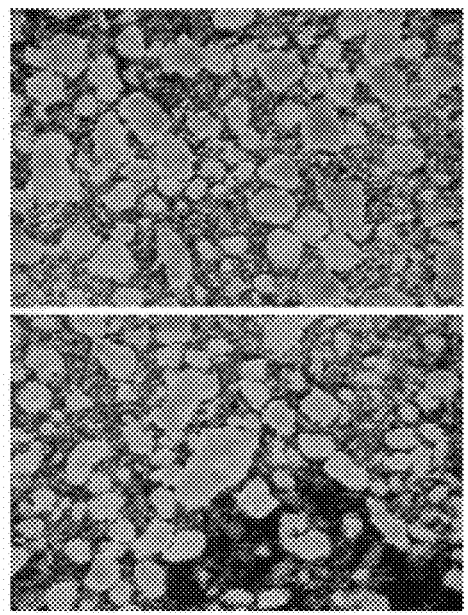
Figure 76

Spinner vs. 2D colony cultures
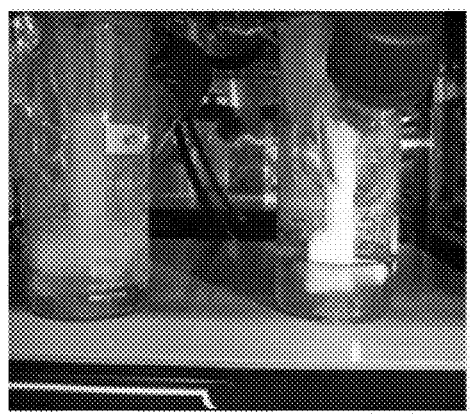 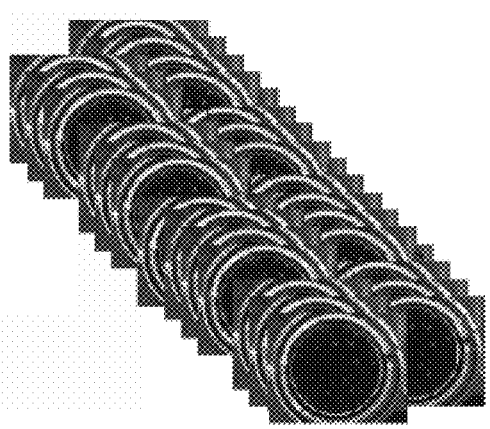
One 100ml spinner culture = 350 million hESC
Equivalent to 175 OCDs each with 2 million hESC
Scalable method for expansion of pluripotent hESC on microcarriers in suspension culture
Figure 77

Co-culture of hESC with feeders on microcarriers

| Key | Name | Parameter | Gate |
|---|---|---|---|
| —— | Data.009 | CONTROL | |
| —— | Data.010 | OCT 4 - 63.8% | |
| —— | Data.011 | SSEA 4 - 99.3% | |
| —— | Data.012 | TRA 1 60 - 96.5% | |

| PL | PLMG | PL+MG | PR | PRMG | PR+MG |
|---|---|---|---|---|---|
| Poly-lysine | Polylysine coupled with matrigel | Poly lysine coated with matrigel | Protamine | Protamine coupled with matrigel | Protamine coated with matrigel |

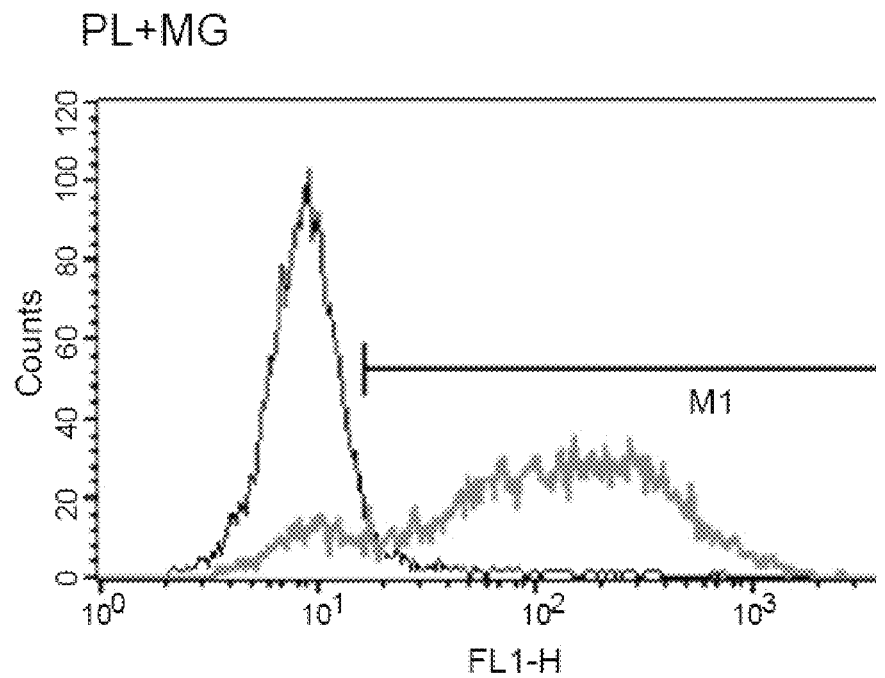
Figure 88 Cont…

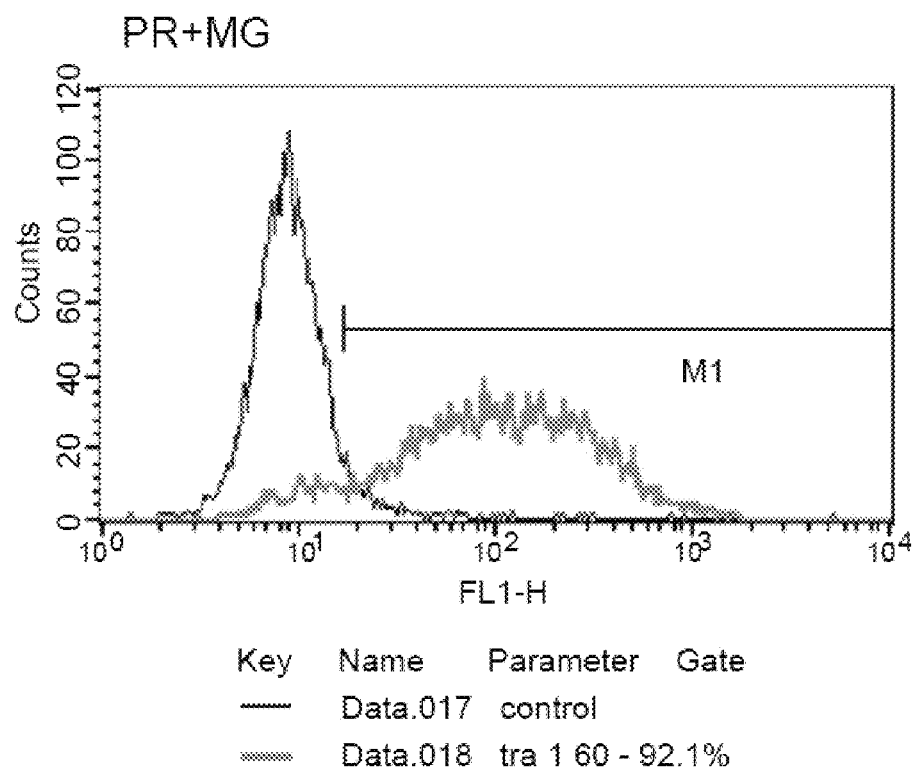
| PL | PLMG | PL+MG | PR | PRMG | PR+MG |
|---|---|---|---|---|---|
| Poly-lysine | Polylysine coupled with matrigel | Poly lysine coated with matrigel | Protamine | Protamine coupled with matrigel | Protamine coated with matrigel |
Figure 89 Cont…

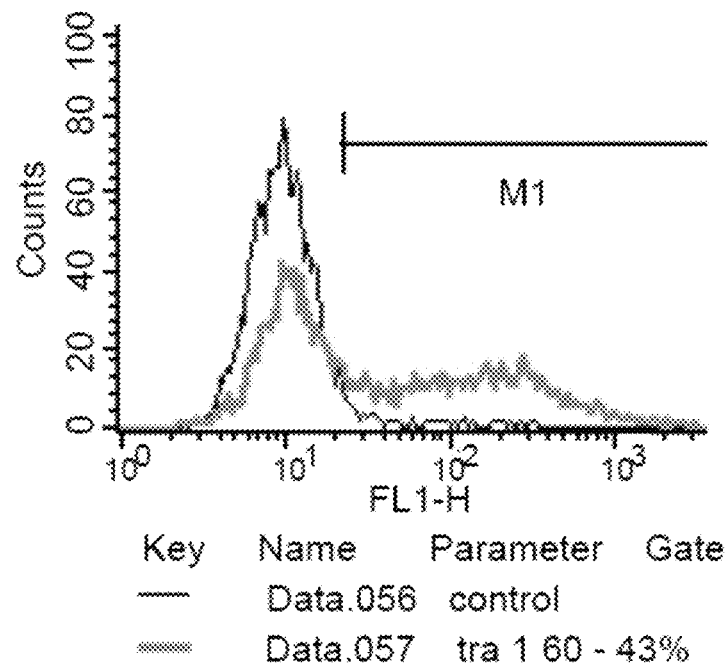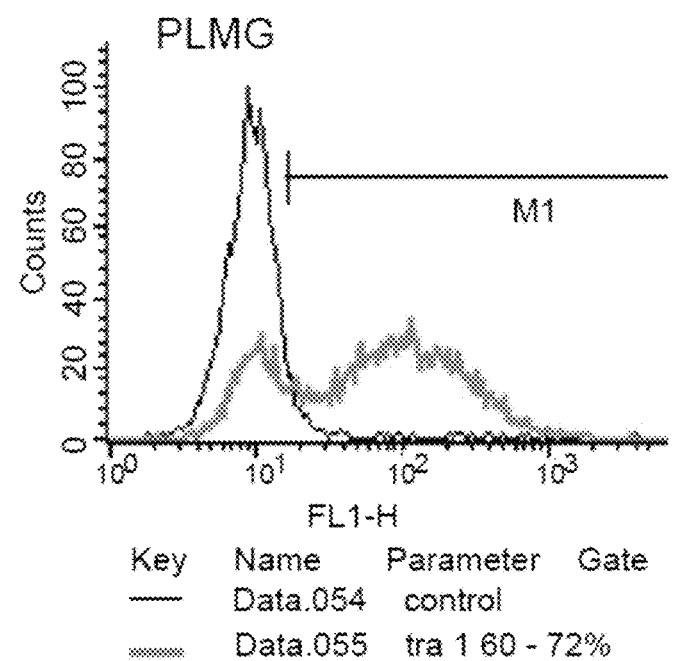
Figure 90

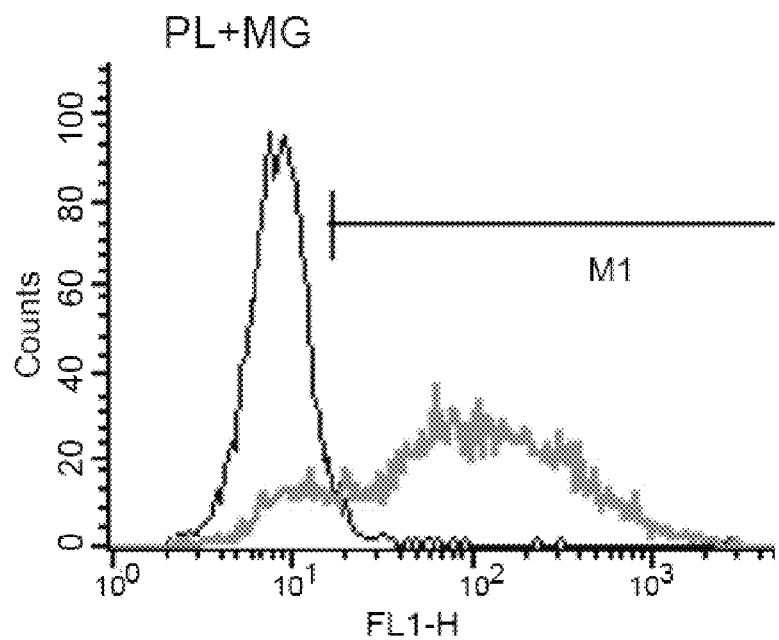
Figure 90 Cont…

Passage 4

Tosoh bead coated with Poly-L-Lysine and coated with Matrigel

Tosoh bead coated with Protamine and coated with Matrigel

Cytodex 3 without Matrigel, non-agitated

Cytodex 3 without Matrigel agitated at 100 rpm

Cytodex 3 coated with Matrigel, non-agitated

Cytodex 3 coated with Matrigel agitated at 100 rpm

HES-3 P11 on Cytodex 3 with matrigel

- Higher cell concentration has been achieved when carriers were coated with Mgel.
- Higher cell concentration has been achieved when using Cytodex 1 with Mgel ($6 \times 10^6$ cells/well or $1.2 \times 10^6$ cells/mL), similar values as DE53 (cellulose carriers).

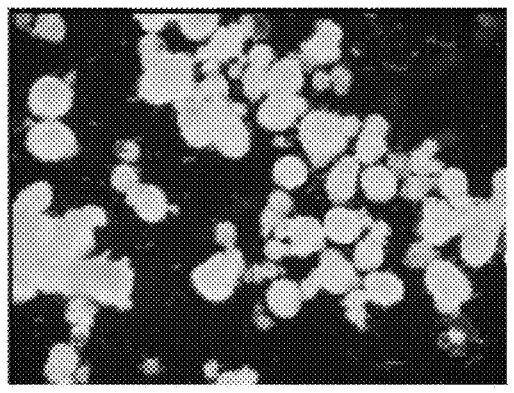
DE53-HA+Collagen I
(2x magnification)
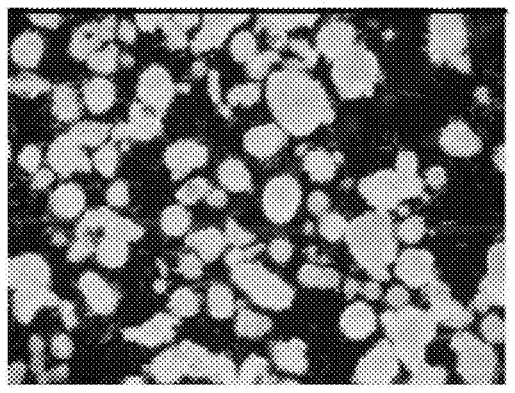
DE53-HA+Collagen I + Fibronectin
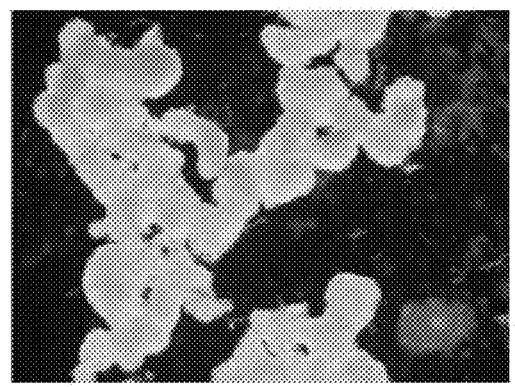
DE53-HA+Collagen IV+ Laminin
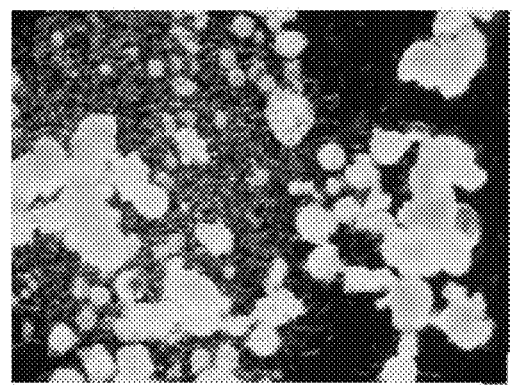
DE53-HA+Collagen IV
Figure 128

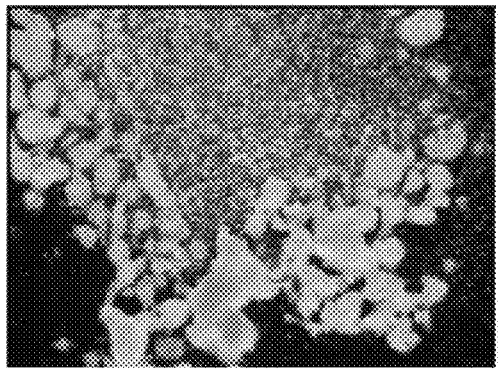
DE53-HS+Collagen I
(2x magnification)
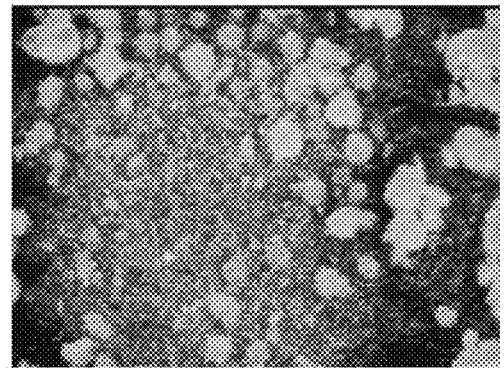
DE53-HS+Collagen I + Fibronectin
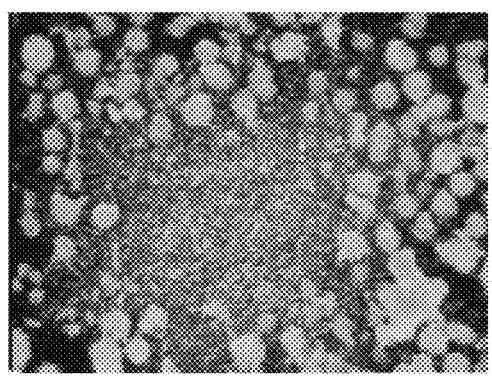
DE53-HS+Collagen IV+ Laminin
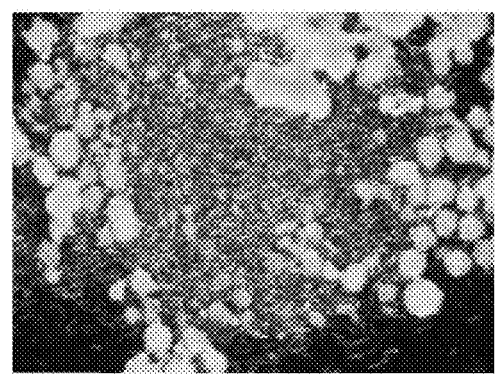
DE53-HS+Collagen IV
Figure 129

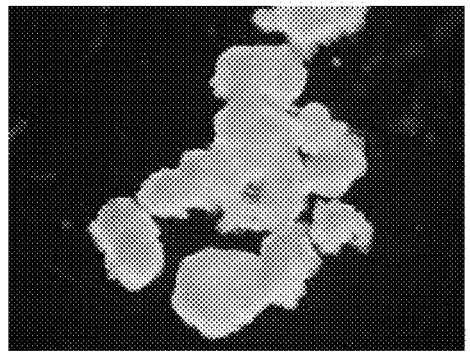
DE53-HA+Collagen I
+Collagen IV+Laminin
+Fibronectin
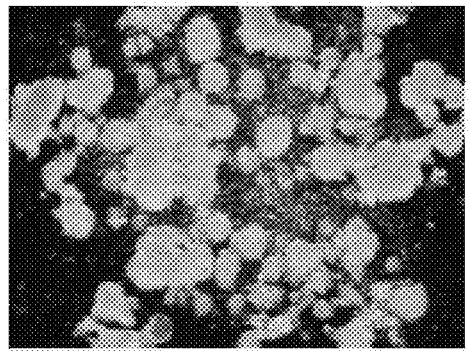
DE53-HS+Collagen I
+Collagen IV+Laminin
+Fibronectin
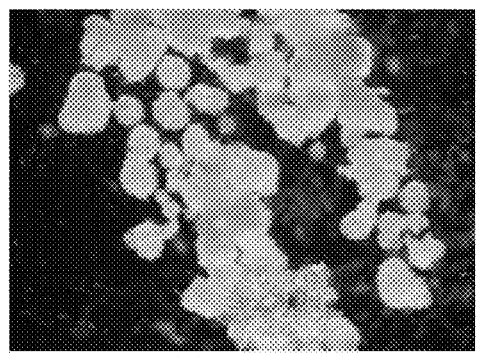
DE53-HA-HA+Collagen I
+Collagen IV+Laminin
+Fibronectin
Figure 131

FACS- P3
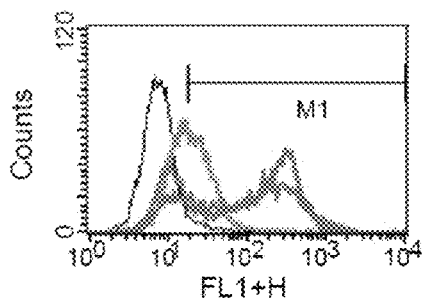
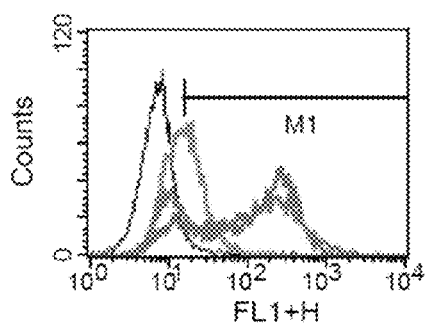
| Key | Name | Parameter | Gate |
|---|---|---|---|
| — | Data.001 | control | |
| | Data.002 | oct 4 - 65.7% | |
| | Data.003 | ssea 4- 78% | |
| | Data.004 | tran 1 60 - 62.3% | |
H3P33KKP59
P3 HA+COL1+FN
280308
| Key | Name | Parameter | Gate |
|---|---|---|---|
| — | Data.005 | control | |
| | Data.006 | oct 4 - 55.7% | |
| | Data.007 | ssea 4 - 82% | |
| | Data.008 | tra 1 60 - 69% | |
H3P33KKP59
P3 HA+COL4+FN
280308
HA= Hyaluronic Acid    Col I= Collagen I    FN= Fibronectin
HS= Heparin Sodium Salt    Col IV= Collagen IV    LM= Laminin
Figure 132

FACS- P3
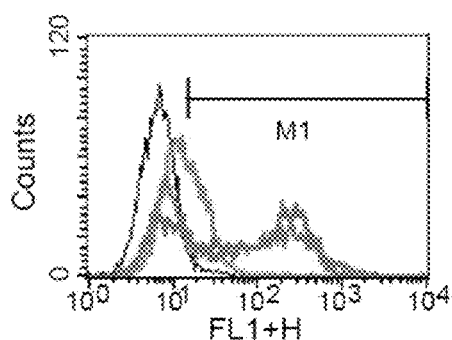 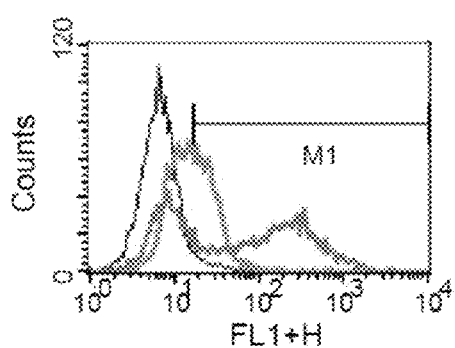
| Key | Name | Parameter | Gate |
|---|---|---|---|
| — | Data.017 | control | |
|  | Data.018 | oct 4 - 53% | |
|  | Data.019 | ssea 4- 65% | |
|  | Data.020 | tran 1 60 - 51% | |
| Key | Name | Parameter | Gate |
|---|---|---|---|
| — | Data.021 | control | |
|  | Data.022 | oct 4 - 59% | |
|  | Data.023 | tra 1 60 - 57% | |
H3P33KKP59
P3 HS+COL1+FN
280308
H3P33KKP59
P3 HS+COL4+FN
280308
HA= Hyaluronic Acid   Col I= Collagen I   FN= Fibronectin
HS= Heparin Sodium Salt  Col IV= Collagen IV  LM= Laminin
Figure 134

FACS- P3
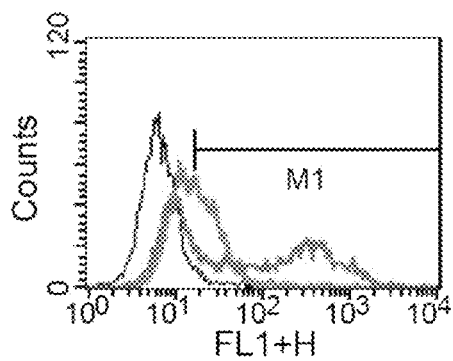
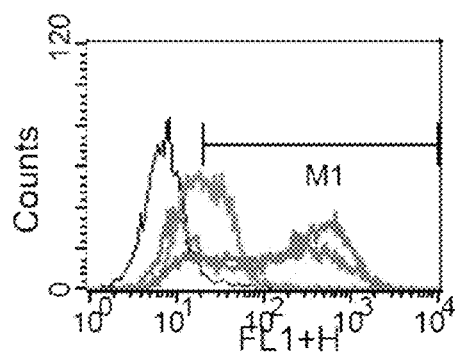
| Key | Name | Parameter | Gate | Key | Name | Parameter | Gate |
|---|---|---|---|---|---|---|---|
| — | Data.024 | control | | — | Data.027 | control | |
| ---- | Data.025 | oct 4 - 62.9% | | ---- | Data.028 | oct 4 - 69.3% | |
| ---- | Data.026 | tran 1 60 - 54% | | ---- | Data.029 | SSEA 4 - 8% | |
| | | | | ---- | Data.030 | tra 1 60 - 57% | |
H3P33KKP59
P3 HS+COL1+FN+LM
280308
H3P33KKP59
P3 HS+COL4+FN+LM
280308
HA= Hyaluronic Acid     Col I= Collagen I     FN= Fibronectin
HS= Heparin Sodium Salt    Col IV= Collagen IV    LM= Laminin
Figure 135

FACS of HA coated microcarriers
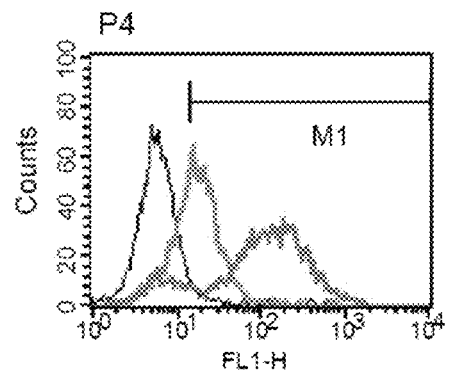
| Key | Name | Parameter Gate |
|---|---|---|
| —— | Data.037 | control |
| —— | Data.038 | OCT 4 - 71% |
| —— | Data.039 | TRA 1 60 - 85% |
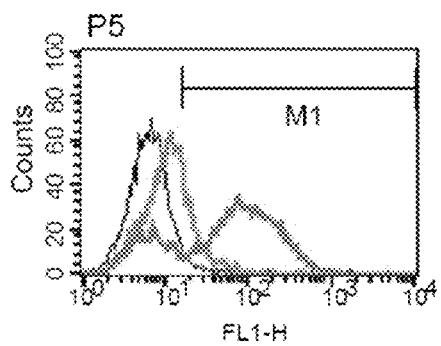
| Key | Name | Parameter Gate |
|---|---|---|
| —— | Data.040 | control |
| —— | Data.041 | oct 4 - 38% |
| —— | Data.042 | tra 1 60 - 72% |
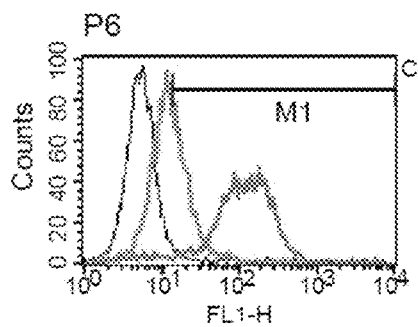
| Key | Name | Parameter Gate |
|---|---|---|
| —— | Data.055 | CONTROL |
| —— | Data.056 | OCT 4 - 66% |
| —— | Data.057 | TRA 1 60 - 94% |
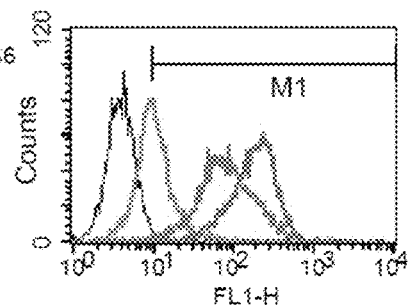
| Key | Name | Parameter Gate |
|---|---|---|
| —— | Data.001 | CONTROL |
| —— | Data.002 | OCT 4 - 73% |
| —— | Data.003 | SSEA 4 - 98% |
| —— | Darta.004 | TRA 1 60 - 97% |
Figure 137

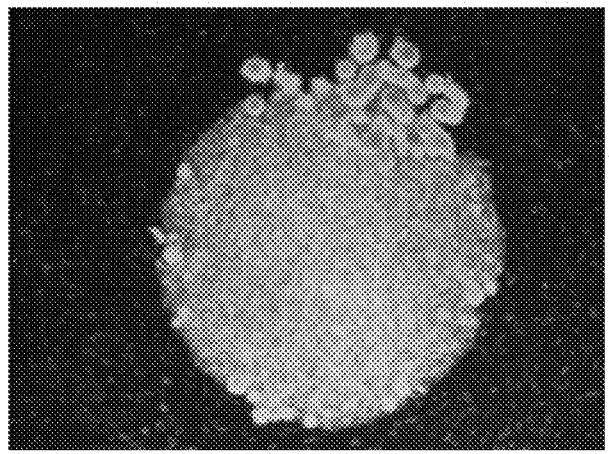
DE53 coupled with Hyaluronic acid P6- 0.071mg HA/mg DE53 or 1:10 dilution (0.8x)
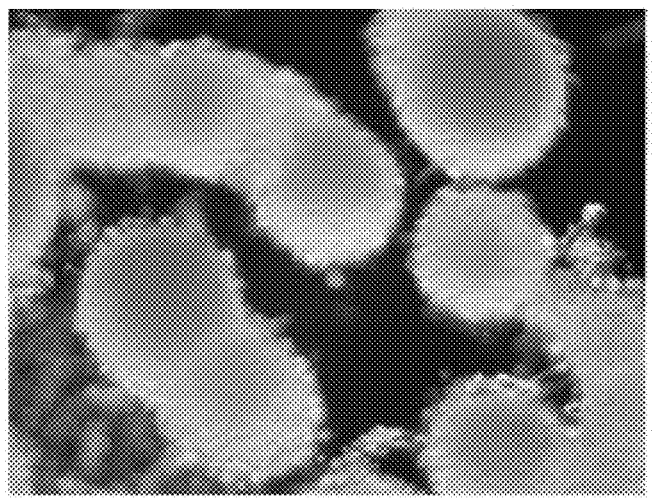
DE53 coupled with Hyaluronic acid P6 (5x)
Figure 139

General Amino Acid Analysis (HPLC) of Spent Media

Table 1

| Amino Acids | Consumed | No Significant change | Production |
|---|---|---|---|
| Alanine | | | |
| Arginine | ✓ | | |
| Asparagine | | ✓ | |
| Aspartic Acid | | ✓ | |
| Cystine | ✓ | | |
| Glutamine | ✓ | | |
| Glutamic Acid | | | ✓ |
| Glycine | | ✓ | |
| Histidine | | ✓ | |
| Isoleucine | ✓ | | |
| Leucine | ✓ | | |
| Lysine | | ✓ | |
| Methionine | ✓ | | |
| Phenylalanine | | ✓ | |
| Proline | | | ✓ |
| Serine | ✓ | | |
| Threonine | | ✓ | |
| Tyrosine | | ✓ | |
| valine | | ✓ | |

Figure 141

Amino Acid Analysis of Spent Media from StemPRO and mTeSR1

Table 2

|  | mTeSR1 | | StemPRO | |
|---|---|---|---|---|
| Amino Acids | Perecentage(%) | Amount | Percentage(%) | Amount |
| Aspartic Acid | -11.7 | 17→15 | -6.7 | 15→14 |
| Glutamic Acid | +48.3 | 60→89 | +31.6 | 39→57 |
| Asparagine | -4.3 | 23→22 | -4 | 25→24 |
| Serine | -29.6 | 27→29 | -21.9 | 32→25 |
| Histidine | 0 | Maintains about 22 | -8 | 25→23 |
| Glutamine | -22.8 | 364→281 | +23.2 | 181→223 |
| Glycine | -8 | 25→22 | 0 | Maintains about 27 |
| Arginine | -14.6 | 96→82 | -18.8 | 117→95 |
| Threonine | 0 | Maintains about 47 | -5.7 | 53→50 |
| Alanine | +18.8 | 32→38 | -6.9 | 259→241 |
| Proline | +35.5 | 31→42 | +20.0 | 30→36 |
| Cystine | -17.9 | 28→23 | 39.1 | 23→14 |
| Tyrosine | 0 | Maintains about 34 | -7.5 | 40→37 |
| Valine | -2.4 | 41→41 | -12.0 | 50→44 |
| Methionine | -20.0 | 15→12 | -23.5 | 17→13 |
| Lysine | 0 | Maintains about 60 | -10.8 | 74→66 |
| Isoleucine | 0 | Maintains about 38 | -17.0 | 47→39 |
| Leucine | -17.8 | 45→37 | -89.4 | 47→5 |
| Phenylalanine | 0 | Maintains about 30 | -11.1 | 36→32 |

− Consumption    + Production

Figure 142

Co-culture of hESC with feeders on microcarriers

Table 3

|  | Seeding density at 8E5 cells/well | Seeding density at 0.75 to 8E5 cells/well |
|---|---|---|
| Passage number | P0 | P1 |
| Feeders on Cytodex 3 hESC on DE53 | 3.7 E6 cells/well | 4.3 E6 cells/well |
| Feeders on Tosoh polylysine hESC on DE53 | 4.2 E6 cells/we-ll | 4.9 E6 cells/well |
| Feeders on matrigel DE53 hESC on DE 53 | 3.7 E6 cells/well | 5.9 E6 cells/well |
| hESC on matrigel coated DE53 (seed at 1E6) | 4.3 E6 cells/well |  |

Figure 143

Co-culture of hESC with feeders on microcarriers

Table 4

| | Seeding density at 8E5 cells/well | Seeding density at 0.75 to 8E5 cells/well | Seeding density at 0.8 E5 to 1E6 cells/well |
|---|---|---|---|
| Passage number | P0 | P1 | P2 |
| Feeders on Cytodex 3 hESC on DE53 | 3.7 E6 cells/well | 4.3 E6 cells/well | 4.05 E6 cells/well |
| Feeders on tosoh polylysine hESC on DE53 | 4.2 E6 cells/we-ll | 4.9 E6 cells/well | 3.4 E6 cells/well |
| Feeders on matrigel DE53 hESC on DE 53 | 3.7 E6 cells/well | 5.9 E6 cells/well | 4.7 E6 cells/well |
| hESC on matrigel coated DE53 (seed at 1E6) | 4.3 E6 cells/well | 2 E6 cells/well | 2 E6 cells/well |

Figure 144 hESC culture on Tosoh carriers

Table 5

| Type of Bead | Particle size | Coating | Passage 0 | Passage 1 |
|---|---|---|---|---|
| Toyopearl TSKgel Tresyl 5Pw | 10μm | 4mg protamine (96 mg protamine/g dry beads) | 2 E6 cells/well | 4.4e5 cells/well |
| Toyopearl TSKgel Tresyl 5Pw | 10μm | 0.2mg protamine (4.8mg protamine/g dry beads)+mgel | 1.99 E6 cells/well | 5.98 cells/well |
| Toyopearl TSKgel Tresyl 5Pw | 10μm | 4mg protamine+mgel | 1.84 E6 cells/well | 4.56 cells/well |
| Toyopearl AF-Tresyl-650M | 65μm | 4mg protamine+mgel | 1.71 E6 cells/well | 6.18 cells/well |

Total nuclei count on day 7.
Note: Seeding density at 1E6 cells/well (5ml media per well) for passage 0 and split ratio of 1:4 for passage 1

Figure 145

Cells were seeded at 4 to 8 E5 cells/well and counts taken at day 7

Table 6

| Large 65 micron Tosoh microcarriers (Sample ID) | Passage 0, E6 Cells/ml | Passage 1, E6 Cells/well | Passage 2, E6 Cells/well | Passage 3, E6 Cells/well | Passage 4, E6 Cells/well |
|---|---|---|---|---|---|
| Poly-lysine (PL) | 4.74 | 3.37 | 1.3 | 1.73 | NA |
| Polylysine coupled with matrigel (PLMG) | 3.18 | 3.29 | 2.7 | 2.46 | NA |
| Poly lysine coated with matrigel (PL+MG) | 3.72 | 3.40 | 6.2 | 3.2 | 4.36 |
| Protamine (PR) | 3.9 | 4.30 | 1.2 | 1.99 | NA |
| Protamine coupled with matrigel (PRMG) | 4.32 | 3.80 | 1.5 | 5.55 | NA |
| Protamine coated with matrigel (PR+MG) | 4.5 | 3.46 | 3.2 | 5.15 | 5 |

Figure 146 hESC on Cytodex 3 microcarriers

Nuclei count results

| Sample ID | P0, E6 cells | P1, E6 cells | P3, E6 Cells |
|---|---|---|---|
| Static-cytodex 3 w/o matrigel | 0.5 | 2 | 5.2 |
| Static- cytodex 3 with matrigel | 1.7 | 9.9 | 8.1 |
| Agitation- cytodex 3 w/o matrigel | 1.2 | 1.2 | 4.6 |
| Agitation- cytodex 3 with matrigel | 1.67 | 3.9 | 6.9 |

Note: Seeding density at 8E5 cells/well and counts taken at day 7

Figure 147

P0 of new extracellular matrix coatings on DE53 cellulose carriers

Cells were seded at 4 E5 cells/well and counts taken at day 7
Control: KO = 43.5 E5 cells/well; CM = 4.4 E5 cells/well Table 8

| Dilution ratio | Chondroitin Sulfate (Stock conc. 0.41 g/ml) | Heparin (Stock conc. 0.2 g/ml) | Hyaluronic Acid (Stock conc. 7.09 mg/ml) |
|---|---|---|---|
| 1:10 | NA | 9.6 E5 cells/well | 1.17 E6 cells/well |
| 1:20 | 8.3 E5 cells/well | 1.03 E6 cells/well | 7.7 E5 cells/well |
| 1:40 | 6.5 E5 cells/well | 1.18 E6 cells/well | 8.3 E5 cells/well |
| 1:80 | 5.5 E5 cells/well | 1.12 E6 cells/well | 5.4 E6 cells/well |

Figure 148

P1 of new extracellular matrix coatings on DE53 cellulose carriers

Cells were seded at 4 E5 cells/well and counts taken at day 7
Control: KO = 1.42 E6 cells/well Table 9

| Dilution ratio | Chondroitin Sulfate (Stock conc. 0.41 g/ml) | Heparin (Stock conc. 0.2 g/ml) | Hyaluronic Acid (Stock conc. 7.09 mg/ml) |
|---|---|---|---|
| 1:10 | 1.53 E6 cells/well | 1.58 E6 cells/well | 1.67 E6 cells/well |
| 1:20 | 1.84 E6 cells/well | 1.26 E6 cells/well | 1.33 E6 cells/well |
| 1:40 | 2.09 E6 cells/well | 1.47 E6 cells/well | 1.44 E6 cells/well |
| 1:80 | 1.72 E6 cells/well | 1.58 E6 cells/well | 1.17 E6 cells/well |

Figure 149

P1 of new extracellular matrix coatings on DE53 cellulose carriers

Table 10

| Sample ID | Passage 0, E6 Cells/well | Pasage 1, E6 Cells/well |
|---|---|---|
| Fibronectin (FN) | 8.2 | 2.98 |
| Hyaluronic Acid (HA), Heparin Sodium Salt (HS), FN | 3.9 | 0.972 |
| HA, HS | 3.0 | 1.42 |
| HA, FN | 9.0 | 5.18 |
| HA | 10.2 | 1.11 |

Cells were seeded at 4 E5 cells/well and counts taken at day 7

Figure 150

P1 and P2 of protein coatings (with Collagen I, IV and Laminin)

Cells were seeded at 4 E5 cells/well and counts taken at day 7

Nuclei count results     Table 11

| Sample ID | P1, E6 cells | P2, E6 cells | P3, E6 cells |
|---|---|---|---|
| HA+col I+FN | 8.07 | 5.59 | 4.82 |
| HA+col IV+FN | 8.46 | 3.87 | 2.00 |
| HA+col I+FN+LM | 9.56 | 6.78 | 1.37 |
| HA+col IV+FN+LM | 9.12 | 4.02 | 2.61 |
| HS+col I+FN | 5.49 | 3.78 | 4.35 |
| HS+col IV+FN | 5.82 | 3.9 | 6.26 |
| HS+col I+FN=LM | 6.36 | 7.53 | 4.16 |
| HS+col IV+FN+LM | 6.39 | 4.2 | 2.14 |

HA= Hyaluronic Acid        Col I= Collagen I        FN= Fibronectin
HS= Heparin Sodium Salt    Col IV= Collagen IV      LM= Laminin

Figure 151

Specific glutamine and glucose consumption rates and lactate and ammonia production rates More efficient metabolism on microcarriers vs. 2D colony cultures hESC on Tosoh Beads based micro carriers Protamine coupled Tosoh beads coated with matrigel
-Seeded from H3P33KKP31

Human iPS on cellulose microcarriers
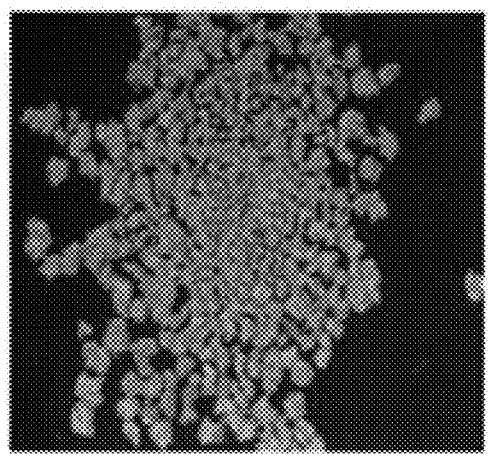
0.8x
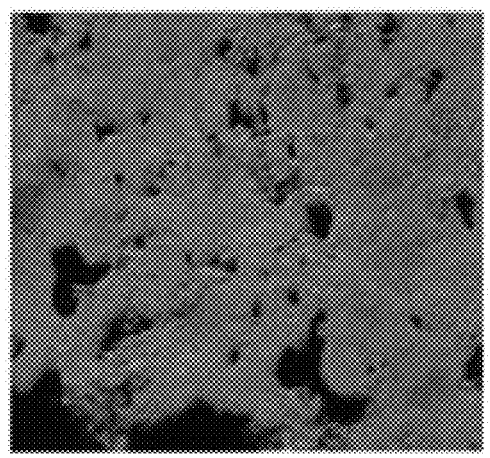
5x
Figure 162

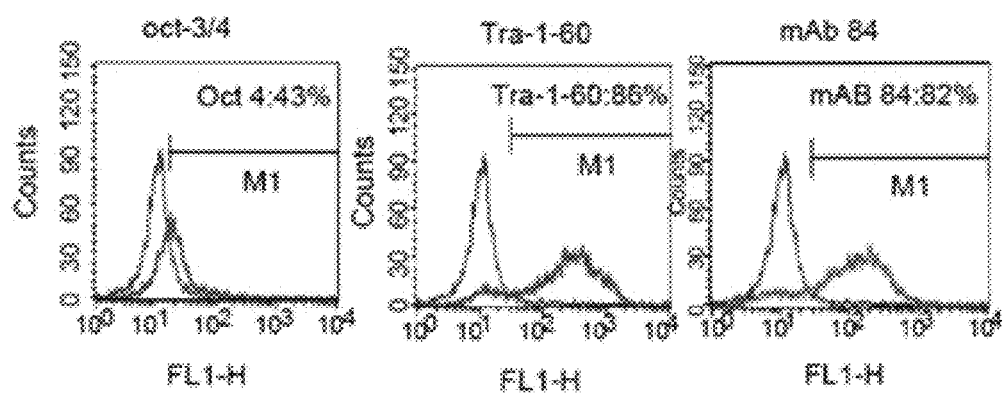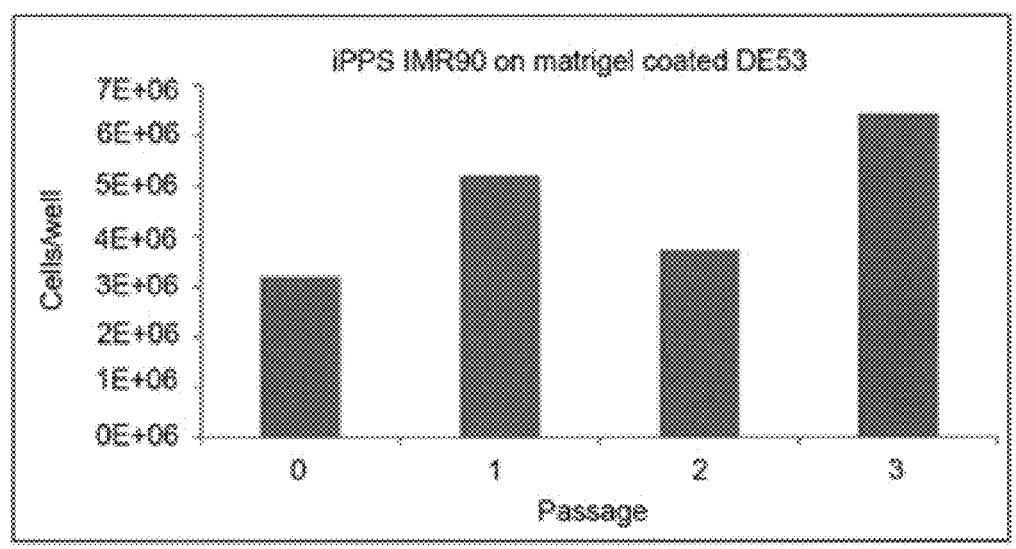
Figure 163

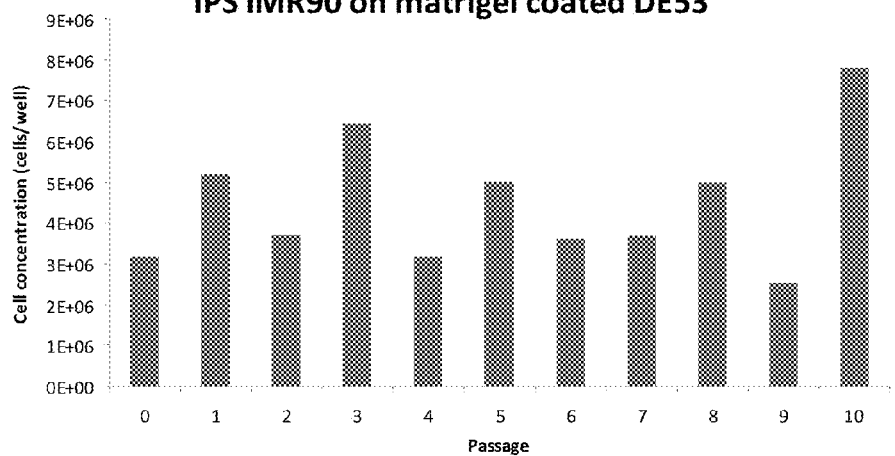
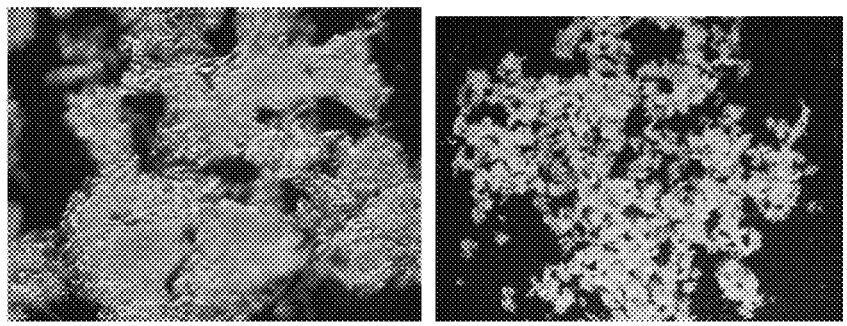
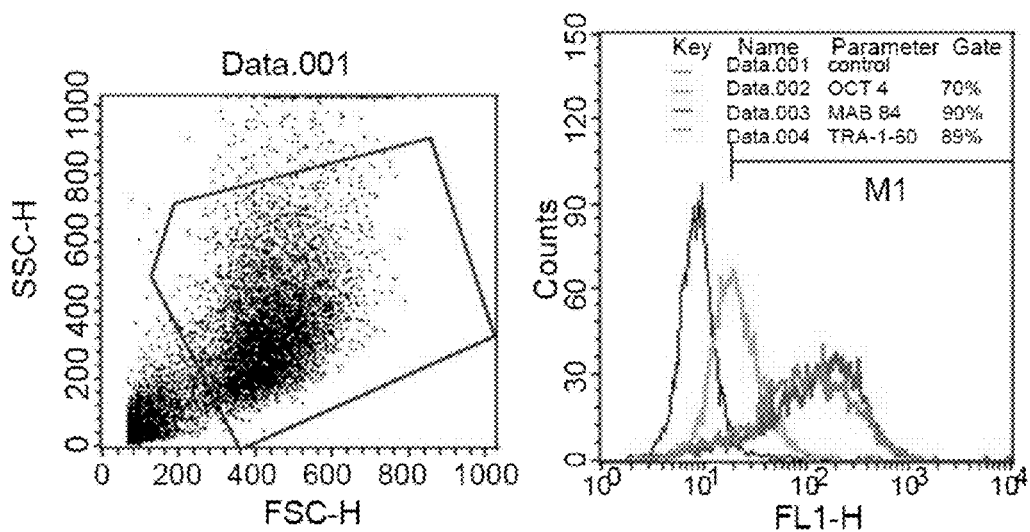
Figure 164

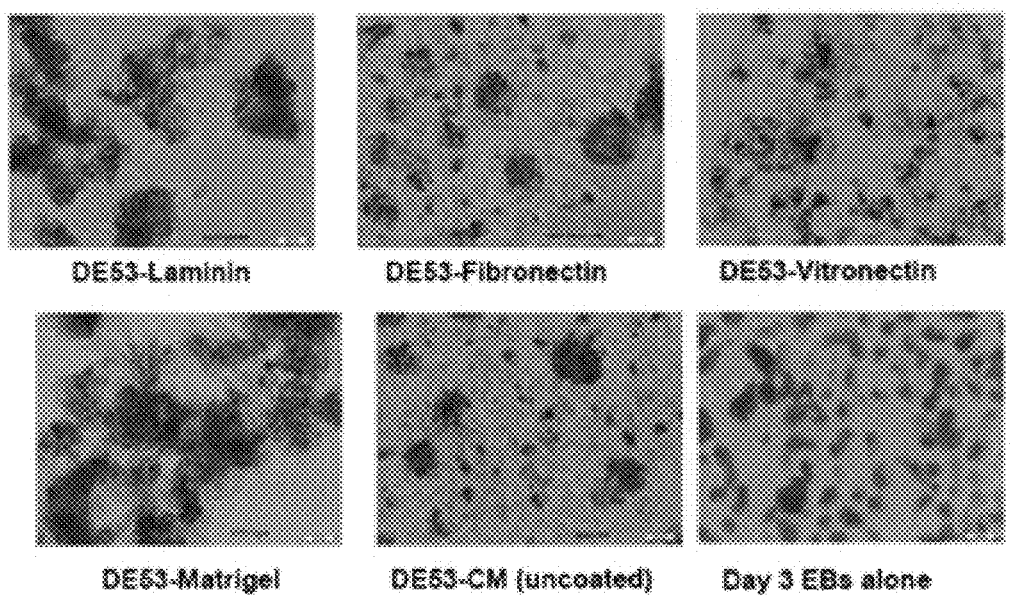

| Microcarriers | Coatings |
|---|---|
| DE53 cellulose (3 mg/ml) | Conditioned media (uncoated) |
| DE53 cellulose (4 mg/ml) | Laminin (4 ug/ml) |
| DE53 cellulose (4 mg/ml) | Fibronectin (20 ug/ml) |
| DE53 cellulose (4 mg/ml) | Vitronectin (4 ug/ml) |
| Tosoh 65 protamine (9,600 beads/ml) | Conditioned media (uncoated) |
| Tosoh 65 protamine (9,600 beads/ml) | Laminin (4 ug/ml) |

Figure 165

Differentiation on cellulose microcarriers with different coatings

DE53-Laminin   DE53-Fibronectin   DE53-Vitronectin
DE53-Matrigel   DE53-CM (uncoated)   Day 3 EBs alone

Figure 166

| Label | [Xv] Seeding (e6/well) | [DE53] (mg/well) | Medium |
|---|---|---|---|
| 1 | 3 | 15 | bSFS (control) |
| 2 | 3 | 15 | bSFS + Hy-soy (0.1%) |
| 3 | 3 | 15 | bSFS + Lip Mixture (1x) |
| 4 | 3 | 15 | bSFS + BSA (1%) |
| 5 | 3 | 15 | bSFS + Lip Mixture (1x) + Hy-Soy |
| 6 | 3 | 15 | bSFS + Lip Mixture (1x) + Hy-Soy+ BSA |

**Differentiation with different media supplements
with hESC seeded from microcarriers to microcarriers**

Different additives added to serun free media bSFS or DMEM/F12
+ SB203580 (5µM) for differentiation on micarocarriers

A) BSFS

B) BSFS + Lipid mixture.

C) DMEM/F12 (with Glutamax, glucose, without insulin, transferrin, selenite).

D) DMEM/F12 (with Glutamax, glucose, without insulin, transferrin, selenite) + Lipid Mixture.

E) BSFS + BSA (0.1%)

F) BSFS + Hy-Soy (0.1%)

Figure 172

| | Spinner 1 | Spinner 2 | Spinner 3 |
|---|---|---|---|
| [mg] Carriers/ml | 1.5 | 3 | 5 |
| no of cells/carrier | 12 | 12 | 12 |
| Cells/ml | 6.0E+04 | 1.0E+05 | 1.8E+05 |
| Cells/cm$^2$ | 1.3E+04 | 1.3E+04 | 1.3E+04 |
| Doubling Time [h] | 103 | 126 | 385 |

|  | Spinner 1 | Spinner 2 | Spinner 3 |
|---|---|---|---|
| [mg] Carriers/ml | 3.0 | 3.0 | 3.0 |
| no of cells/carrier | 5 | 8 | 14 |
| Cells/ml | 4.5E.04 | 7.2E.04 | 1.3E.05 |
| Cells/cm$^2$ | 5.6E.03 | 8.9E.03 | 1.6E.04 |
| Doubling Time [h] | 116 | 133 | 204 |

|  | Monolayer | Spinner |
|---|---|---|
| [mg] Microcarriers/ml | NA | 3,0 |
| No. of cells/Carrier | NA | 7,5 |
| cells/ml | 5.57E4 | 6.75E4 |
| cells/cm$^2$ | 7.00E3 | 8.30E3 |
| Doubling Time [h] | 47 | 37 |

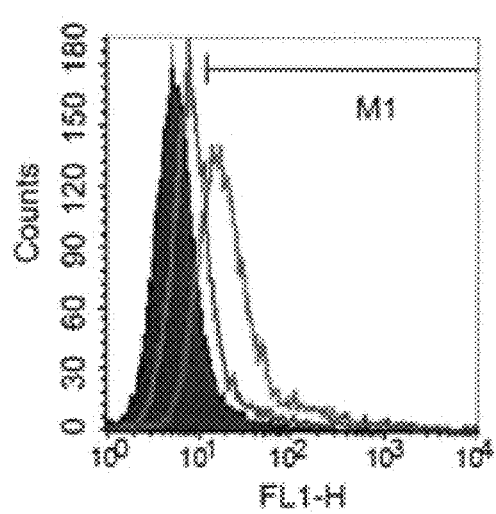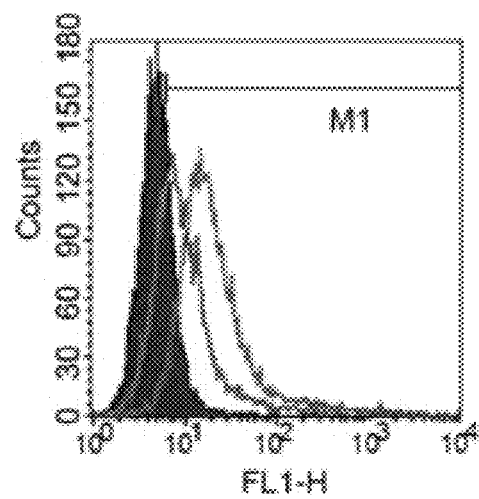
Figure 202

|  | Primers | Fold Change | Regulation | Agarose Gel | |
|---|---|---|---|---|---|
|  |  |  |  | hESC | Cardio |
| Pluripotent | NANOG | 2.06E-03 | ♦ ♦ | | |
|  | OCT 4 | 4.75E-04 | ♦ ♦ | | |
| Ectoderm | SOX 1 | 0.41 | ♦ | | |
| Endoderm | SOX 17 | 1.89 | ■ | | |
| Mesoderm | Tbra | 0.06 | ♦ | | |
| Early Cardio | MESP-1 | 0.76 | ■ | | |
|  | NKX 2.5 | 8.46 | ♦ | | |
| Late Cardio | MHC | 52297.95 | ♦ ♦ ♦ | | |
|  | MLC | 17.02 | ♦ | | |
|  | ANF | 62.74 | ♦ ♦ | | |

Figure 203A hESC morphology on seven types of microcarriers

- *Cells on smaller microcarriers (Tosoh65, Tosoh10) formed cell-microcarrier aggregates with the microcarriers embedded inside.*

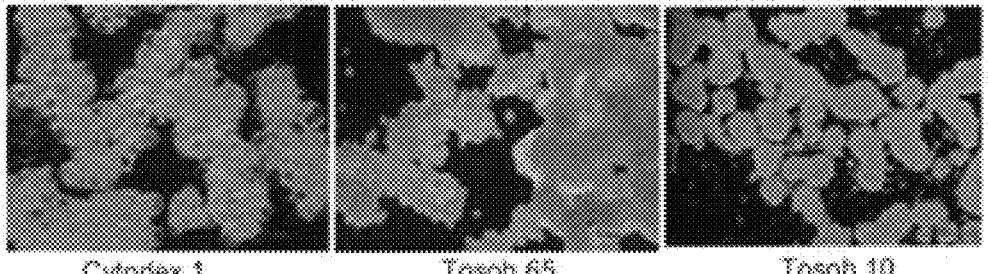

Cytodex 1　　　Tosoh 65　　　Tosoh 10

- *Similar cell growth on both microporous and smooth microcarriers*

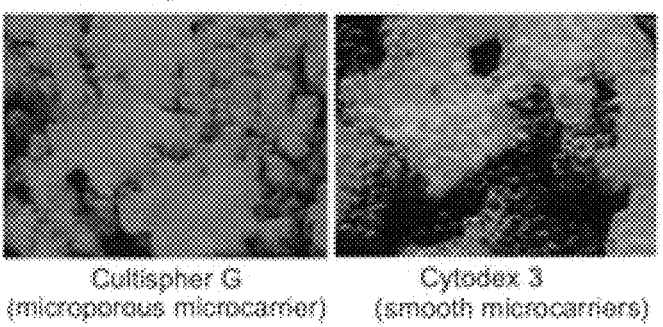

Cultispher G　　　Cytodex 3
(microporous microcarrier)　(smooth microcarriers)

- *Poor cell growth on negative charged microcarriers*

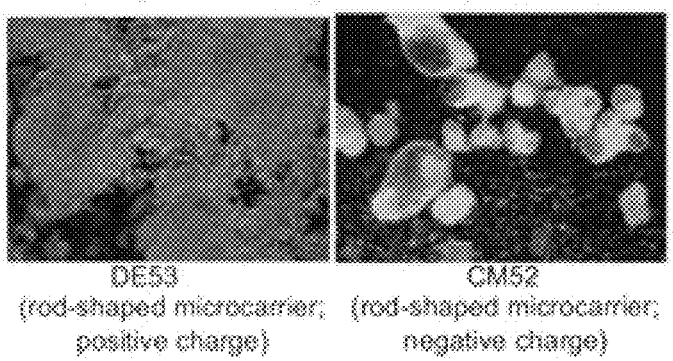

DE53　　　　　CM52
(rod-shaped microcarrier;　(rod-shaped microcarrier;
positive charge)　　　negative charge)

Figure 208A

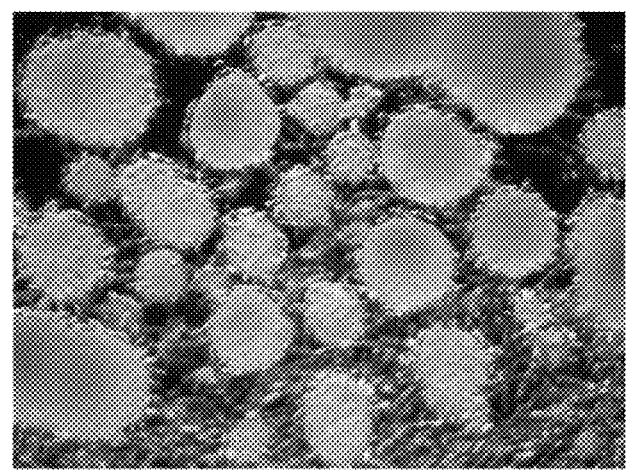
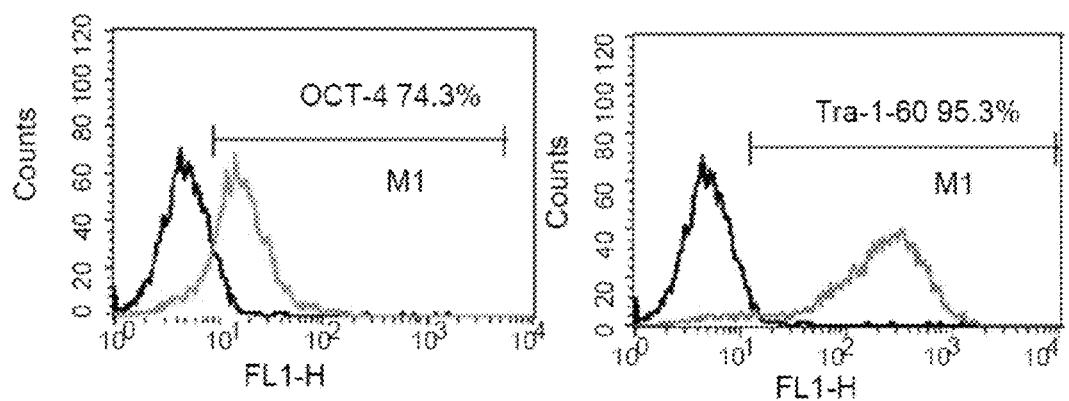
Figure 209B

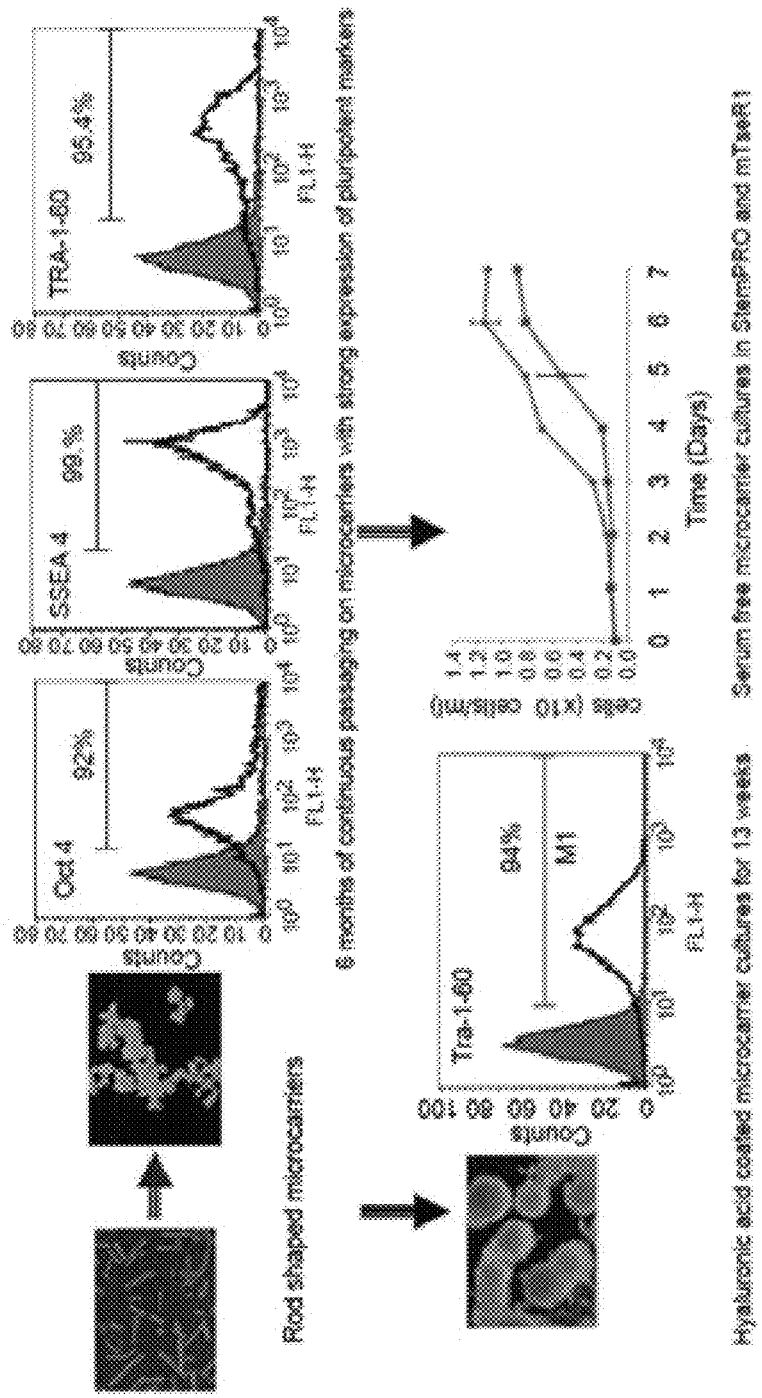

b) Spinner cultures of hESC on microcarriers

HES-2 cells are more robust in agitated cultures, have high expression of pluripotent markers and can be serially passaged.

HES-3 cells partially down regulated
Mab 84 and Tra-1-60 expression

3) Differentiation of hESC on microcarriers to cardiomyocytes

Uncoated microcarriers      Laminin coated microcarriers

Percentage of beating cardiomyocytes with laminin coating vs. uncoated

4) Long term culture of human iPS cells on microcarriers

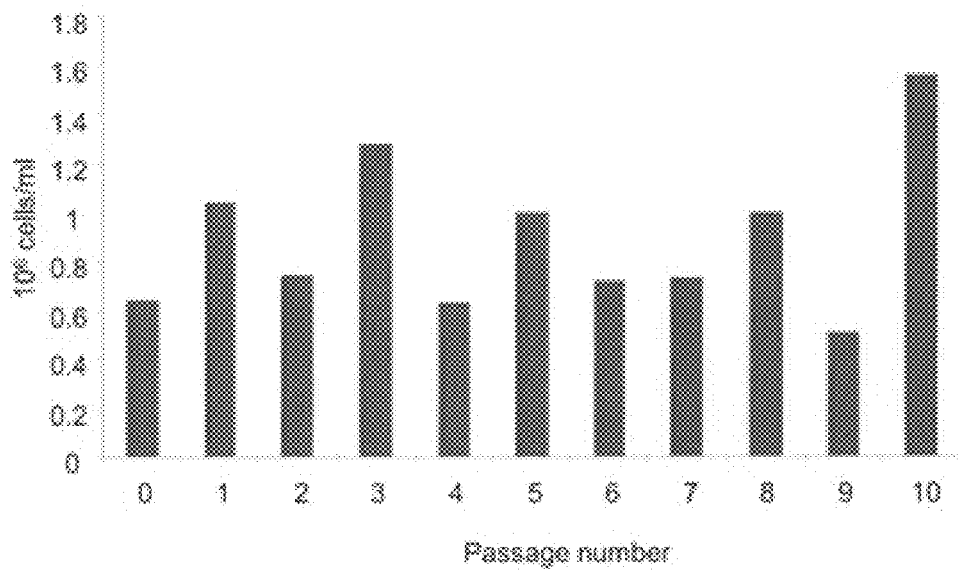
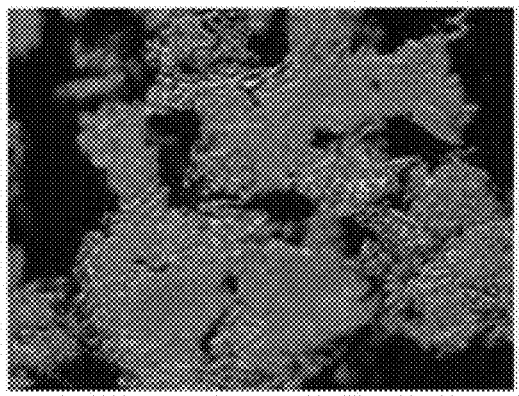
Continuous microcarrier cultures of human iPS (IMR) cells in Conditioned media with 100ng/ml/bFGF
Figure 214A

MICROCARRIERS FOR STEM CELL CULTURE

This application is a continuation in part of U.S. application Ser. No. 12/921,599, filed Sep. 9, 2010, and a continuation in part of U.S. application Ser. No. 12/497,591, filed Jul. 3, 2009, each of which is a 35 U.S.C. §371 national phase application of PCT/SG2009/000088, filed Mar. 17, 2009 (WO 2009/116951), each of which is entitled "Microcarriers for Stem Cell Culture". PCT/SG2009/000088 is a non-provisional application of U.S. provisional application Ser. No. 61/069,694, filed Mar. 17, 2008; U.S. provisional application Ser. No. 61/110,256, filed Oct. 31, 2008, U.S. provisional application Ser. No. 61/148,064, filed Jan. 29, 2009 and U.S. provisional application Ser. No. 61/155,940, filed Feb. 27, 2009. Each of these references is incorporated herein by reference in its entirety.

FIELD

The present invention relates to the fields of cell biology, molecular biology and biotechnology. More particularly, the invention relates to a method of culturing stem cells on particulate carriers.

BACKGROUND

Stem cells, unlike differentiated cells have the capacity to divide and either self-renew or differentiate into phenotypically and functionally different daughter cells (Keller, Genes Dev. 2005; 19:1129-1155; Wobus and Boheler, Physiol Rev. 2005; 85:635-678; Wiles, Methods in Enzymology. 1993; 225:900-918; Choi et al, Methods Mol. Med. 2005; 105:359-368).

Human embryonic stem cells (hESC) are pluripotent cells with the capability of differentiating into a variety of stem cell types. The pluripotency of stem cells such as embryonic stem cells (ESCs) and their ability to differentiate into cells from all three germ layers makes these an ideal source of cells for regenerative therapy for many diseases and tissue injuries (Keller, Genes Dev. 2005; 19:1129-1155; Wobus and Boheler, Physiol Rev. 2005; 85:635-678).

Expansion of stem cells to large quantities, requiring one or more passages, is a pre-requisite for cell therapy.

Currently, stem cells (including human embryonic stem cells, hESC) which grow as colonies are routinely maintained on plastic culture surfaces in 2 dimensional (2D) growth. Expansion to larger quantities on 2D culture would necessitate the use of large surface areas. The manual nature of passaging the cells by repeated pipetting or enzymatic treatment to break up these 2D colonies to smaller sizes would become impractical. Preparing numerous plates for seeding large surface areas can become subject to handling errors. Furthermore, very large surface areas such as Nunc trays for example, would be needed.

Accordingly, the current methods of growing stem cells as 2D colony cultures on coated plastic surfaces are not amenable to scale up and the experimental conditions under which culture is carried out is generally not amenable to good control. The prior art includes a number of attempts to culture stem cells in a 3 dimensional ("3D") environment, such as on microcarriers in suspension culture. Except for a few studies of mouse embryonic stem cells on microcarriers (Fernandes et al., 2007; Abranches et al., 2007; King and Miller, 2007) and differentiating hESC in suspension culture as embryoid bodies (Dang et al., 2004; Fok and Zandstra, 2005; Cameron et al., 2006), there is no robust method of long term, serial culturing of hESC in suspension culture.

It is known in the art for embryonic stem cells to be differentiated as "embryoid bodies" in suspension culture. Such embryoid bodies comprise a mass of already differentiated cells. For example, Gerecht Nir et al (2004) described the use of a rotating-wall bioreactor to culture embryoid bodies. Embryoid body culture was also shown using agitation systems by Zandstra et al (2003), Dang et al (2004) and Wartenberg et al (1998). Embryoid body suspension culture has also been reported by Dang and Zandstra (2005) and King and Miller (2007). Such techniques are suitable for culturing these tissue-like embryoid body aggregates comprising differentiated stem cells, but not for undifferentiated stem cells.

Fok and Zandstra (2005) described stirred-suspension culture systems for the propagation of undifferentiated mouse embryonic stem cells (mESCs). The stirred-suspension culture systems comprised microcarrier and aggregate cultures. Mouse embryonic stem cells cultured on glass microcarriers had population doubling times comparable to tissue-culture flask controls. Upon removal of leukemia inhibitory factor, the mESC aggregates developed into embryoid bodies (EBs) capable of multilineage differentiation. Suspension cultures of mouse ESCs are also described in King and Miller (2005). However, King and Miller (2005) state that "expansion of undifferentiated human ESCs (hESCs) is more difficult than for mESCs and has not yet been reported in stirred cultures".

US2007/0264713 (Terstegge) discloses an attempt at culturing human embryonic stem cells on microcarriers. Human embryonic stem cells are introduced together with Cytodex3 (Amersham) microcarriers into a spinner or a bioreactor together with conditioned medium in various volumes. The culture is agitated at 20-30 rpm 30 minutes in an hour. The culture is maintained for various times between 10 days and 6 weeks. However, at no time were any of the cultures passaged or sub-cultured, which is an essential requirement for large scale continuous production of stem cells. Demonstration of continuous passaging and the ability to sub-culture along with 'good' (exponential) growth rate on microcarriers are essential requirements for large-scale production of stem cells. This was not demonstrated by the work of Terstegge et al.

WO2008/004990 describes attempts to culture stem cells in the absence of feeder cells and contemplates the use of microcarriers. It is concerned with cultures in which Matrigel is not used. WO2008/004990 describes the effect of positively charged surfaces in the inhibition of stem cell differentiation.

In Phillips et al., 2008 (Journal of Biotechnology 138 (2008) 24-32) an attempt to culture hESC on microcarriers by seeding aggregates as well as single cells is reported. Initially, 3-fold expansion was achieved over 5 days, however with each successive passage cell expansion was reduced until cells could not be passaged beyond week 6.

Previous attempts to use commercially available microcarriers such as Cytodex 1 and 3 for scale up culture of human embryonic stem cells (hESCs) were unsuccessful. The hESC cultures died or differentiated on the carriers and could not be propagated (Oh & Choo, 2006).

Stable and continuous growth in suspension of undifferentiated, pluripotent cells from primates, including human stem cells, has not been achieved so far. No one has previously demonstrated successive passage of primate or human stem cells, particularly embryonic stem cells, in suspension culture.

The large scale differentiation of stem cells into other useful cell types is also of major importance. For example, large number of cardiomyocytes are required to conduct clinical trials, drug discovery and also to develop potential future cell therapies. Since human embryonic stem cells (hESC) are pluripotent and can differentiate to all germ layers, hESC can provide a source of cardiomyocytes and other cell types for these uses. So far, few hESC derived cardiomyocyte differentiation protocols have been described by the scientific community, but the scalability of the proposed bioprocesses is not clear.

The invention seeks to solve these and other problems in the art.

SUMMARY

The present invention provides a method of differentiating stem cells in vitro towards cells of the neural lineage. Culture and/or differentiation of the cells is preferably performed on microcarriers, preferably in suspension culture.

In one aspect of the present invention, a method of culturing and differentiating stem cells in vitro is provided, the method comprising:
  (i) attaching stem cells to a plurality of first microcarriers to form microcarrier-stem cell complexes, wherein the surface of the first microcarriers is coated in a first matrix;
  (ii) culturing the microcarrier-stem cell complexes in suspension culture;
  (iii) passaging the cultured cells from (ii); and
  (iv) repeating steps (i)-(iii) through at least 2 passages,
wherein stem cells in the culture after step (iv) are pluripotent or multipotent, the method further comprising:
  (v) attaching pluripotent or multipotent stem cells obtained after step (iv) to a plurality of second microcarriers to form microcarrier-stem cell complexes, wherein the surface of the second microcarriers is coated in a second matrix or is uncoated; and
  (vi) culturing the microcarrier-stem cell complexes from (v) in suspension culture under conditions that induce the differentiation of the stem cells to the neural cell lineage.

The stem cells may be embryonic stem cells, or induced pluripotent stem cells, and may be human or primate. The microcarriers may have any shape, physical or chemical property or characteristic as described herein. In some embodiments they are rod-shaped, in other embodiments they are spherical.

In some embodiments the first and second matrix are the same matrix material, in other embodiments they may be different matrix materials.

The stem cells may be differentiated into neural precursors, neurons, or astrocytes.

The method may further comprise:
  (vii) attaching differentiated stem cells obtained from step (vi) to a plurality of third microcarriers to form microcarrier-stem cell complexes, wherein the surface of the third microcarriers is coated in a third matrix or is uncoated; and
  (viii) culturing the microcarrier-stem cell complexes from (vii) in suspension culture under conditions that induce the further differentiation of the differentiated stem cells.

In some embodiments the third matrix material is the same as one of the first and second matrix materials, in other embodiments it is different.

The present invention also provides a differentiated cell of the neural lineage obtained by the method described above. The present invention also provides a neural precursor cell, neuron, or astrocyte obtained by the method.

In another aspect of the present invention a method of differentiating stem cells in vitro, comprising attaching pluripotent or multipotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation The stem cells may be embryonic stem cells, or induced pluripotent stem cells, and may be human or primate. The microcarriers may have any shape, physical or chemical property or characteristic as described herein. In some embodiments they are rod-shaped, in other embodiments they are spherical.

The stem cells may be differentiated into neural precursors, neurons, or astrocytes.

The present invention also provides a differentiated cell of the neural lineage obtained by the method described above. The present invention also provides a neural precursor cell, neuron, or astrocyte obtained by the method.

The present invention provides a method for the stable and long term culturing of human or primate embryonic stem cells in in vitro culture. Using this method human embryonic stem cells can be continually expanded between each passage and the pluripotency of the expanded human embryonic stem cell population is maintained beyond at least passage 5 and regularly beyond passage 10.

Importantly, the inventors have found that culture and differentiation of stem cells on microcarriers can be improved where the microcarriers are coated in a matrix that preferably comprises extra cellular matrix components. The matrix may comprise one or more of Matrigel™ (BD Biosciences), hyaluronic acid, laminin, fibronectin, vitronectin, collagen, elastin, heparan sulphate, dextran, dextran sulphate, chondroitin sulphate or a mixture of laminin, collagen I, heparan sulfate proteoglycans, and entactin 1.

For growth and proliferation of stem cells a preferred matrix comprises or consists of one or more of Matrigel™, hyaluronic acid, laminin or a mixture of laminin, collagen I, heparan sulfate proteoglycans, and entactin 1.

For differentiation of stem cells a preferred matrix comprises or consists of one or more of laminin, fibronectin, vitronectin, Matrigel™ or a mixture of laminin, collagen I, heparan sulfate proteoglycans, and entactin 1.

In one aspect the present invention relates to the growth and proliferation of stem cells on microcarriers in suspension culture through a plurality of passages whilst retaining the pluripotent status of stem cells in the culture. The microcarriers are coated in a matrix, preferably having an extracellular component, and are seeded with the stem cells. Preferably, the microcarriers are positively charged. The stem cells are cultured in suspension culture, preferably to expand the number of stem cells in the culture. Cultured stem cells are then passaged and passaged stem cells are seeded on microcarriers having the same or different matrix coating. In this way stem cells can be taken through a plurality of passages, e.g. at least 3 passages, with the cultured and passaged stem cells retaining pluripotent status. Using this method proliferation of stem cells is seen during each cycle of culture between passages and can be maintained over many (at least 10) passages.

This culture method permits the continuous growth and passaging of stem cells in in vitro culture thereby providing a method for expanding stem cells having pluripotent potential to therapeutically useful numbers.

Although continuous passage of stem cells on microcarriers will often be preferred, as part of the method of the present invention the stem cells may be transferred from culture on microcarriers to other culture systems, e.g. 2D colony culture, followed by return to suspension microcarrier culture.

The method preferably involves the steps of attachment of stem cells to matrix coated microcarriers during each cycle of culture prior to passage. However, it is permissible for some cycles of culture to be undertaken on non-coated microcarriers, although an overall total of at least 3 culture cycles followed by passage will preferably be conducted on matrix coated microcarriers. More preferably this will be one of at least 4, 5, 6, 7, 8, 9, 10, 11, 12, 13, 14, 15, 16, 17, 18, 19, 20, 21, 22, 23, 24, 25 or more culture cycles.

The methods of the present invention therefore provide for the long term passaging of pluripotent stem cells in in vitro culture, wherein the stem cells are stably cultured and passaged to preserve their pluripotent status.

A further aspect of the present invention relates to the differentiation of pluripotent stem cells attached to microcarriers.

In some embodiments pluripotent stem cells may be grown to a required cell density for differentiation by employing the microcarrier culture method described in the aspect above. Once the required cell density is obtained the culture conditions may be changed to induce the differentiation of stem cells attached to the microcarriers. For differentiation the same or different microcarriers may be used compared with those used for growth of the stem cells. Similarly, the same or different matrix coating may be used. For example, a first microcarrier having a first coating may be used for the growth and proliferation of pluripotent stem cells and a second microcarrier having a second coating may be used for the differentiation of those stem cells. For differentiation the microcarrier may be uncoated.

The use of microcarrier culture for both proliferation of stem cells and for their differentiation has the advantages of avoiding the need to re-seed the differentiation culture, of the proliferation culture providing a high number of pluripotent cells for differentiation and the convenience of changing from proliferation to differentiation by changing the culture conditions.

In other embodiments pluripotent stem cells for differentiation may be grown to a required cell density by other culture methods, for example by 2D colony culture. Those cells are then attached to microcarriers having a matrix coating and cultured in suspension culture under conditions that induce the differentiation of the stem cells.

In some embodiments cells that have already undergone differentiation (but preferably not terminal differentiation) may be attached to microcarriers having a matrix coating or uncoated microcarriers and cultured in suspension culture under conditions that induce the differentiation of the stem cells.

According to one aspect of the present invention there is provided a method of culturing stem cells in suspension culture in vitro, the method comprising:
 (i) attaching stem cells to a plurality of microcarriers to form microcarrier-stem cell complexes, wherein the surface of the microcarriers is coated in a matrix;
 (ii) culturing the microcarrier-stem cell complexes in suspension culture;
 (iii) passaging the cultured cells from (ii); and
 (iv) repeating steps (i)-(iii) through at least 3 passages,
wherein stem cells in the culture after step (iv) are pluripotent.

The stem cells are preferably embryonic stem cells, or induced pluripotent stem cells, and are preferably primate or human.

The matrix preferably comprises an extracellular matrix component. More preferably the matrix comprises one or more of Matrigel™ (BD Biosciences), hyaluronic acid, laminin, fibronectin, vitronectin, collagen, elastin, heparan sulphate, dextran, dextran sulphate, chondroitin sulphate. The matrix may comprise a mixture of laminin, collagen I, heparan sulfate proteoglycans, and entactin 1.

The microcarrier may comprise or consist of one or more of cellulose, dextran, hydroxylated methacrylate, collagen, gelatin, polystyrene, plastic, glass, ceramic, silicone. Alternatively, the microcarrier may be a macroporous or microporous carboseed microcarrier. The microcarrier may be coupled with protamine or polylysine.

The microcarrier is preferably positively charged and preferably has a positive surface charge. It may be hydrophilic. The microcarrier is preferably rod-shaped, e.g. cylindrical, or substantially spherical in shape.

Preferably, in step (ii) the stem cells are cultured for a period of time sufficient to expand the number of stem cells in the culture. In some embodiments, in each repeat cycle the stem cells of step (i) are obtained from the passaged cells of step (iii) of the preceding repeat cycle.

In embodiments of the present invention steps (i)-(iii) are repeated through one of: at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, at least 100 passages.

In preferred embodiments in at least 60% of the cycles of steps (i)-(iii) the microcarriers are coated in a matrix. Alternatively this may be one of at least 70%, 80%, 90%, or 95%. During successive cycles of steps (i)-(iii) the microcarriers may be coated in the same matrix, or the matrix may be different or absent in first and second consecutive cycles of steps (i)-(iii).

In preferred embodiments, after step (iv) at least 60% of the stem cells in the culture are pluripotent. Alternatively this may be one of at least 70%, 80%, 90%, or 95%.

In preferred embodiments, after step (iv) at least 60% of the stem cells in the culture express one, two, three or all of Oct4, SSEA4, TRA-1-60 and Mab84. Alternatively this may be one of at least 70%, 80%, 90%, or 95%.

In some embodiments the method may comprise culturing the stem cells in serum free media, or stem cell conditioned media, or feeder cell free conditions.

In other embodiments feeder cells may be attached to the microcarriers. The feeder cells may be attached to microcarriers which are different to the microcarriers to which the stem cells are attached.

The present invention includes a pluripotent stem cell obtained by the method of the present invention.

In further embodiments the method may further comprise the step of inducing differentiation of the stem cells obtained after step (iv). This may be achieved by placing the microcarrier-stem cell complexes under conditions which induce the differentiation of the stem cells. Alternatively, after step (iv) the method may comprise the step of separating stem cells from the microcarriers and culturing the separated stem cells in non-microcarrier culture under conditions which induce differentiation of the stem cells.

Thus, in some embodiments the method may further comprise the differentiation of pluripotent stem cells, comprising:

(v) attaching pluripotent stem cells obtained after step (iv) to a plurality of second microcarriers to form microcarrier-stem cell complexes, wherein the surface of the second microcarriers is coated in a second matrix or is uncoated; and (vi) culturing the microcarrier-stem cell complexes from (v) in suspension culture under conditions that induce the differentiation of the stem cells.

The first and second matrix may be the same or different. The first and second microcarriers may be the same or different.

In some embodiments a further differentiation may be induced, wherein the method further comprises:

(vii) attaching differentiated stem cells obtained from step (vi) to a plurality of third microcarriers to form microcarrier-stem cell complexes, wherein the surface of the third microcarriers is coated in a third matrix or is uncoated; and (viii) culturing the microcarrier-stem cell complexes from (vii) in suspension culture under conditions that induce the further differentiation of the differentiated stem cells.

The third matrix may be different to the first and second matrix or may be the same as one of the first and second matrix. The third microcarriers may be different to the first and second microcarriers or may be the same as one of the first and second microcarriers.

The present invention includes a differentiated cell obtained by the method of the present invention.

Differentiated cells obtained by a method of the invention may be cultured to form an embryoid body. The embryoid body may be attached to a microcarrier. An embryoid body so obtained forms part of the present invention.

In a further aspect of the present invention there is provided a method of culturing stem cells in suspension culture in vitro, the method comprising:

(i) attaching stem cells to a plurality of microcarriers to form microcarrier-stem cell complexes, wherein the surface of the microcarriers is coated in Matrigel™;

(ii) culturing the microcarrier-stem cell complexes in suspension culture;

(iii) passaging the cultured cells from (ii); and (iv) repeating steps (i)-(iii) through at least 7 passages, wherein stem cells in the culture after step (iv) are pluripotent, wherein the culture is free of feeder cells, wherein the number of stem cells is expanded between each passage and wherein the stem cells are human or primate embryonic stem cells or human or primate induced pluripotent stem cells.

In a further aspect of the present invention there is provided a method of culturing and differentiating stem cells in vitro, the method comprising:

(i) attaching stem cells to a plurality of first microcarriers to form microcarrier-stem cell complexes, wherein the surface of the first microcarriers is coated in a first matrix;

(ii) culturing the microcarrier-stem cell complexes in suspension culture;

(iii) passaging the cultured cells from (ii); and (iv) repeating steps (i)-(iii) through at least 3 passages, wherein stem cells in the culture after step (iv) are pluripotent, the method further comprising:

(v) attaching pluripotent stem cells obtained after step (iv) to a plurality of second microcarriers to form microcarrier-stem cell complexes, wherein the surface of the second microcarriers is coated in a second matrix or is uncoated; and (vi) culturing the microcarrier-stem cell complexes from (v) in suspension culture under conditions that induce the differentiation of the stem cells.

The first and second matrix may be the same or different. The first and second microcarriers may be the same or different.

The method may further comprise:

(vii) attaching differentiated stem cells obtained from step (vi) to a plurality of third microcarriers to form microcarrier-stem cell complexes, wherein the surface of the third microcarriers is coated in a third matrix or is uncoated; and (viii) culturing the microcarrier-stem cell complexes from (vii) in suspension culture under conditions that induce the further differentiation of the differentiated stem cells.

The third matrix may be different to the first and second matrix or the same as one of the first and second matrix. The third microcarriers may be different to the first and second microcarriers, or the same as one of the first and second microcarriers.

In a further aspect of the present invention there is provided a method of differentiating stem cells in vitro, comprising attaching pluripotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells.

The stem cells are preferably embryonic stem cells, or induced pluripotent stem cells, and are preferably primate or human.

The matrix preferably comprises an extracellular matrix component. More preferably the matrix comprises one or more of laminin, fibronectin, vitronectin, Matrigel™ (BD Biosciences), hyaluronic acid, collagen, elastin, heparan sulphate, dextran, dextran sulphate, chondroitin sulphate. The matrix may comprise a mixture of laminin, collagen I, heparan sulfate proteoglycans, and entactin 1.

The microcarrier may comprise or consist of one or more of cellulose, dextran, hydroxylated methacrylate, collagen, gelatin, polystyrene, plastic, glass, ceramic, silicone. Alternatively, the microcarrier may be a macroporous or microporous carboseed microcarrier. The microcarrier may be coupled with protamine or polylysine.

The microcarrier is preferably positively charged and preferably has a positive surface charge. It may be hydrophilic. The microcarrier is preferably rod-shaped, e.g. cylindrical, or substantially spherical in shape.

In a further aspect of the present invention the use of a microcarrier coated in a matrix for the propagation of primate or human stem cells is provided, the microcarrier being chosen from: DE-52 (Whatman), DE-53 (Whatman), QA-52 (Whatman), TSKgel Tresyl-5Pw (Tosoh) or Toyopearl AF-Tresyl-650 (Tosoh), SM1010 (Blue Membranes) and SH1010 (Blue Membranes).

The matrix preferably comprises an extracellular matrix component. More preferably the matrix comprises one or more of Matrigel™ (BD Biosciences), hyaluronic acid, laminin, fibronectin, vitronectin, collagen, elastin, heparan sulphate, dextran, dextran sulphate, chondroitin sulphate. The matrix may comprise a mixture of laminin, collagen I, heparan sulfate proteoglycans, and entactin 1.

As part of the present invention, the methods described herein may also be used to achieve the stable and long term culturing of non-pluripotent stem cells, particularly multipotent stem cells, such as adult stem cells or multipotent stem cells derived from pluripotent stem cells (for example multipotent stem cells derived from embryonic stem cells). The multipotent stem cells may be derived from human or primate pluripotent stem cells, e.g. hESCs.

By using the methods described here, multipotent stem cells (e.g. adult stem cells) can be continually expanded between each passage and the multipotency of the expanded adult stem cell population may be maintained, preferably beyond at least passage 2, more preferably beyond one of passages 3, 4, 5, 6, 7, 8, 9, 10, 11, 12, 13, 14, 15, 16, 17, 18, 19, 20, 21, 22, 23, 24, or 25.

Accordingly, the culture, growth, propagation and differentiation of multipotent stem cells may be conducted in accordance with any of the methods, aspects, embodiments and preferred features described herein for the culture, growth, differentiation and propagation of pluripotent stem cells such as human or primate embryonic stem cells. Microcarriers used for culture, growth, proliferation and/or differentiation of multipotent stem cells may be uncoated or have a matrix coating.

In accordance with this, in another aspect of the present invention a method of culturing multipotent stem cells in suspension culture in vitro is provided, the method comprising:
  (i) attaching multipotent stem cells to a plurality of microcarriers to form microcarrier-stem cell complexes;
  (ii) culturing the microcarrier-stem cell complexes in suspension culture;
wherein stem cells in the culture after step (ii) are multipotent.

In another aspect of the present invention a method of culturing multipotent stem cells in suspension culture in vitro is provided, the method comprising:
  (i) attaching multipotent stem cells to a plurality of microcarriers to form microcarrier-stem cell complexes;
  (ii) culturing the microcarrier-stem cell complexes in suspension culture;
  (iii) passaging the cultured cells from (ii); and
  (iv) repeating steps (i)-(iii) through at least 2 passages,
wherein stem cells in the culture after step (iv) are multipotent.

In some embodiments of the two aspects described immediately above the surface of the microcarriers in (i) is coated in a matrix.

Multipotent stem cells obtained by these methods are also provided.

In a further aspect of the present invention a method of culturing and differentiating multipotent stem cells in vitro is provided, the method comprising:
  (i) attaching stem cells to a plurality of first microcarriers to form microcarrier-stem cell complexes;
  (ii) culturing the microcarrier-stem cell complexes in suspension culture;
  (iii) passaging the cultured cells from (ii); and
  (iv) repeating steps (i)-(iii) through at least 2 passages,
wherein stem cells in the culture after step (iv) are multipotent, the method further comprising:
  (v) attaching multipotent stem cells obtained after step (iv) to a plurality of second microcarriers to form microcarrier-stem cell complexes, wherein the surface of the second microcarriers is coated in a second matrix or is uncoated; and
  (vi) culturing the microcarrier-stem cell complexes from (v) in suspension culture under conditions that induce the differentiation of the stem cells.

In some embodiments the surface of the microcarriers in (i) is coated in a first matrix.

In another aspect of the present invention a method of differentiating stem cells in vitro is provided, the method comprising attaching multipotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells.

Differentiated cells obtained by these methods are also provided.

According to one aspect of the present invention, we provide a particle comprising a matrix coated thereon and having a positive charge, the particle being of a size to allow aggregation of primate or human stem cells attached thereto.

The particle may comprise a substantially elongate, cylindrical or rod shaped particle or a substantially compact or spherical shaped particle.

The particle may comprise a substantially elongate, cylindrical or rod shaped particle having a longest dimension of between 50 µm and 400 µm. The particle may comprise a longest dimension of about 200 µm. The particle may comprise a shortest dimension of between 20 µm and 30 µm. The particle may comprise a cellulose cylindrical microcarrier.

The particle may comprise DE-52 (Whatman), DE-53 (Whatman) or QA-52 (Whatman).

The particle may comprise a substantially compact or spherical shaped particle having a size of between about 20 µm and about 120 µm. The particle may have a size of about 65 µm. The particle may comprise a hydrophilic microcarrier, a hydroxylated methacrylic matrix microcarrier or derivatised hydrophilic beaded microcarrier.

The particle may comprise TSKgel Tresyl-5Pw (Tosoh) or Toyopearl AF-Tresyl-650 (Tosoh).

The particle may comprise a macroporous or microporous carboseed microcarrier. The particle may comprise SM1010 (Blue Membranes) or SH1010 (Blue Membranes).

The particle may be derivatised to carry a positive charge. The particle may be coupled with tertiary amine or quaternary amine at small ion exchange capacity of 1-2 milli-equivalents per gram dry weight material of particle. The particle may be coupled with protamine sulphate or poly-L-lysine hydrobromide at a concentration of up to 20 mg/ml particles. The positive charge of the particle may be between 0.5 to 4 milli equivalent units/ml (mEq).

The matrix may comprise a physiologically relevant matrix that allows growth of the stem cells. The matrix may comprise an extracellular matrix component. The matrix may be selected from the group consisting of: Matrigel, hyaluronic acid, hyaluronic acid from bovine vitreous humor, hyaluronic acid sodium from *streptococcus*, heparan sulphate, heparan sulphate from bovine kidney, dextran sulphate, dextran sulphate sodium, heparin sulphate and chondroitin sulphate. The matrix may comprise Matrigel (BD Biosciences).

There is provided, according to another aspect of the present invention, a particle according to the aspect of the invention described above, which comprises a primate or human stem cell attached thereto.

In accordance with the aspects, embodiments and features of the present invention described herein, there is provided a particle or microcarrier that is suitable for use in the in vitro suspension culture of pluripotent or multipotent cells so as to generate new cells having pluripotent or multipotent status or cells that are the product of differentiation of the pluripotent or multipotent cells, the particle or microcarrier having a compact or elongate shape and having a longest dimension of less than about 2000 µm and a shortest dimension of more than about 10 µm, wherein the surface of the microcarrier is coated in a matrix and has a plurality of pluripotent or multipotent cells attached to said matrix. In some embodiments the matrix coating is in the form of a layer of matrix, preferably a thin layer.

In one embodiment a microcarrier is provided, wherein the microcarrier is suitable for use in the growth and/or differentiation of pluripotent or multipotent cells in in vitro suspension culture, wherein the microcarrier comprises one or more of cellulose, dextran, hydroxylated methacrylate, or collagen, and wherein the microcarrier has an elongate shape and has a longest dimension of less than about 2000 µm and a shortest dimension of more than about 10 µm, and wherein the surface of the microcarrier is coated in a matrix, and wherein one or a plurality of pluripotent or multipotent cells are attached to the matrix coating.

In some embodiments the microcarrier is rod-shaped. In some embodiments the matrix coating comprises one or more of Matrigel™ (BD Biosciences), hyaluronic acid, laminin, or fibronectin. In some embodiments the microcarrier is positively charged or has a positive surface charge. In some embodiments the longest dimension of the microcarrier is between 50 µm and 400 µm.

An aggregate comprising two or more such microcarriers is also provided.

The use of the microcarriers in the culture of pluripotent or multipotent cells in vitro to generate new cells having pluripotent or multipotent status is also provided. The use of the microcarriers in the in vitro differentiation of pluripotent or multipotent cells is also provided. Accordingly, a method of culturing pluripotent or multipotent cells in vitro to generate new cells having pluripotent or multipotent status, the method comprising culturing the microcarriers under conditions suitable for the generation of new cells having pluripotent or multipotent status, is also provided. A method of differentiating pluripotent or multipotent cells in vitro, the method comprising culturing the microcarriers under conditions that induce the differentiation of the pluripotent or multipotent cells, is also provided.

We provide, according to another aspect of the present invention, a method of propagating primate or human stem cells, the method comprising: (a) providing a first primate or human stem cell attached to a first particle; (b) providing a second primate or human stem cell attached to a second particle; (c) allowing the first primate or human stem cell to contact the second primate or human stem cell to form an aggregate of cells; and (d) culturing the aggregate to propagate the primate or human stem cells for at least one passage; in which the first and second particles each comprise a matrix coated thereon and having a positive charge, the particles being of a size to allow aggregation of primate or human stem cells attached thereto.

The particle or each particle may comprise a feature as set out in the aspects of the invention described above.

The method may enable primate or human stem cells to be continuously propagated for a plurality of passages. The method may enable primate or human stem cells to be continuously propagated for at least 5, at least 10, at least 12, at least 13 or at least 14 passages. The method may comprise passaging into or from a 2D colony culture.

The method may comprise freezing and thawing the primate or human stem cells. The method may comprise agitation at 30 rpm or more or at 100 rpm or more. The method may comprise propagating primate or human stem cells at a volume of 25 ml or more or 50 ml or more. The method may comprise propagating primate or human stem cells in a spinner suspension culture.

The propagated primate or human stem cells may retain at least one biological activity of a primate or human stem cell after the stated number of passages. The biological activity of a primate or human stem cell may be selected from the group consisting of: (i) expression of a pluripotency marker, (ii) cell viability; (iii) normal karyotype, (iv) ability to differentiate into endoderm, ectoderm and mesoderm. The biological activity of a primate or human stem cell may comprise expression of a pluripotency marker selected from the group consisting of: OCT-4, SSEA-4, TRA-1-60 and Mab84.

The method may enable primate or human stem cells to be passaged at a split ratio of 1:6 or more, 1:10 or more, 1:15 or more, 1:20 or more or 1:26 or more. The method may enable propagation of primate or human stem cells to a volumetric productivity of 2 million cells/ml or more.

The method may comprise propagating the primate or human stem cells in serum free media or stem cell conditioned media.

The method may further comprise the step of separating the primate or human stem cells from the particles.

As a another aspect of the present invention, there is provided a method for producing a differentiated cell, the method comprising propagating a primate or human stem cell according to the above aspect of the invention, and causing the primate or human stem cell to differentiate.

We provide, according to another aspect of the present invention, a method for producing an embryoid body, the method comprising propagating a primate or human stem cell according to the above described aspects of the invention and culturing the primate or human stem cell to form an embryoid body.

The present invention, in another aspect, provides a method of treating a disease in an individual in need of treatment, the method comprising propagating a primate or human stem cell according to the above described aspect of the invention, producing a differentiated cell according the above described aspect of the invention or producing an embryoid body according to the above described aspect of the invention and administering the primate or human stem cell, differentiated cell or embryoid body into the individual.

The primate or human stem cell may comprise a primate or human embryonic stem cell, a primate or human adult stem cell or a primate or human induced pluripotent stem cell.

In another aspect of the present invention, there is provided an aggregate comprising a two or more particles comprising stem cells attached thereto, each according to any of the aspects of the invention.

According to another aspect of the present invention, we provide a cell culture comprising a particle according to an aspect of the invention, or an aggregate according to the above aspect of the invention.

We provide, according to another aspect of the invention, a container comprising a particle according to an aspect of the invention, or an aggregate according to the above aspect of the invention, together with cell culture media.

There is provided, in accordance with another aspect of the present invention, a device for propagating primate or human stem cells, the device comprising a particle according to an aspect of the invention or an aggregate according to the above aspect of the invention.

The container or device may comprise a bioreactor.

As another aspect of the invention, we provide a primate or human stem cell propagated by a method according to the above described aspect of the invention, a differentiated cell produced by a method according to the above described aspect of the invention or an embryoid body produced by a method according to the above described aspect of the invention.

According to another aspect of the invention, there is provided use of a particle for the propagation and/or differentiation of primate or human stem cells, the particle being selected from the group consisting of: DE-52 (Whatman), DE-53 (Whatman), QA-52 (Whatman), TSKgel Tresyl-5Pw (Tosoh) or Toyopearl AF-Tresyl-650 (Tosoh), SM1010 (Blue Membranes) and SH1010 (Blue Membranes).

According to one aspect of the present invention a method of propagating human embryonic stem cells (hESCs) in in vitro suspension culture is provided, the method comprising:
(i) attaching hESCs to a plurality of microcarriers;
(ii) culturing the microcarriers from (i) in suspension culture for a period of time sufficient to expand the number of hESCs;
(iii) passaging the expanded population of hESCs from (ii);
(iv) repeating steps (i)-(iii) through at least 5 passages, wherein in each repeat cycle the hESCs of step (i) are obtained from the passaged cells of step (iii) of the preceding repeat cycle,
wherein hESCs in the culture after step (iv) are pluripotent, and wherein the microcarriers have:
(a) a compact shape in which the longest dimension is between 250 μm and 10 μm; or
(b) an elongate shape,
and wherein the microcarriers are coated in a matrix coating comprising one or both of Matrigel and hyaluronic acid.

The matrix coating applied to the microcarriers may optionally consist of Matrigel and/or hyaluronic acid.

In some preferred embodiments the microcarrier is substantially spherical in shape and has a diameter between 90 μm and 10 μm, more preferably between 80 μm and 40 μm or between 70 μm and 50 μm. In some embodiments the microcarrier is substantially spherical in shape and has a diameter of about 65 μm.

In other preferred embodiments the microcarrier is rod shaped. Preferably, the rod shaped microcarrier has a longest dimension of between 2000 μm to 20 μm. In preferred embodiments the microcarrier is composed of one or more of: plastic, glass, ceramic, silicone, gelatin, dextran, cellulose, hydroxylated methacrylate, polystyrene, or collagen. In particularly preferred embodiments the microcarrier is a cellulose, dextran or polystyrene microcarrier. Preferred microcarriers are chosen from: TSKgel Tresyl-5Pw (Tosoh); Toyopearl AF-Tresyl-650 (Tosoh), DE-52, DE-53, QA-52, Cytodex 1, Cytodex 3, Hillex, Hillex II. In some embodiments the microcarrier is a macroporous or microporous carboseed microcarrier. Microcarriers may be derivatised, e.g. with protamine or polylysine, to generate positive charge.

In some embodiments in step (ii) the hESC are expanded to confluency or near confluency, before passaging. The hESC may be expanded in each step (ii), or in the method as a whole, such that the population of hESC is one of at least 0.2, at least 0.4, at least half, at least 0.6, at least 0.8, or at least one order of magnitude greater than the number of hESCs attached to the microcarriers in step (i), before passaging. The hESC may be expanded in each step (ii), or in the method as a whole, such that the population of hESC is one of two, three, four, five, ten or twenty times the number of hESCs attached to the microcarriers in step (i), before passaging.

In step (iv), steps (i)-(iii) are preferably repeated through one of: at least 6 passages, at least 7 passages, at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, at least 100 passages.

In the methods described above, a significant proportion of the expanded human embryonic stem cells will be pluripotent. In preferred embodiments after step (iv) at least 60%, 70%, 80%, 90%, 95%, 96%, 97%, 98%, 99% or substantially 100% of the hESCs in the culture are pluripotent.

Pluripotency may be measured by detecting expression of one, two, three or all of Oct4, SSEA4, TRA-1-60 and Mab84. In preferred embodiments, after step (iv) at least 60%, 70%, 80%, 90%, 95%, 96%, 97%, 98%, 99% or substantially 100% of the hESCs in the culture express one, two, three or all of Oct4, SSEA4, TRA-1-60 and Mab84.

In some embodiments the method may be continued through sufficient passages to achieve a $\log^{10}$ difference in the total number of cells obtained from the culture as compared with the number of cells on initiation of the culture.

In some embodiments the human embryonic stem cells may be co-cultured with feeder cells. The feeder cells may be attached to microcarriers added to the culture. These microcarriers may optionally be coated in a matrix coating, as described herein. Alternatively feeder cells may be attached to uncoated microcarriers. In some embodiments feeder cells and stem cells may be seeded to the same microcarrier(s).

Preferably, an expansion in the number of human embryonic stem cells occurs between substantially every passage, for example the number of human embryonic stem cells increases between at least 70% of passages, more preferably between at least 80%, 90%, 95%, 96%, 97%, 98%, 99% or substantially 100% of passages.

Methods according to the present invention may comprise passaging into or from an alternative culture system, e.g. a 2D culture. Cells may be stored, e.g. frozen and thawed, in order to facilitate transfer between the culture systems.

In some embodiments the human embryonic stem cells may be cultured on other particles/surfaces for a limited period of time. For example, human embryonic stem cells from step (ii) or (iii) may be cultured on 2D culture for a limited number of passages (e.g. less than 5, more preferably less than 3, more preferably 1) before being returned to culture on matrix coated microcarriers. In similar examples, human embryonic stem cells from step (ii) or (iii) may be cultured on non-matrix coated microcarriers for a limited number of passages (e.g. less than 5, more preferably less than 3, more preferably 1) before being returned to culture on matrix coated microcarriers.

In some embodiments human embryonic stem cells may be removed from the culture method and maintained in an alternative culture system for a limited number of passages (e.g. less than 5, more preferably less than 3, more preferably 1) before being returned to suspension culture in accordance with the present invention.

In other embodiments human embryonic stem cells may be removed from the culture method and stored (e.g. as frozen cells) before being returned to suspension culture in accordance with the present invention.

In such embodiments return to suspension culture in accordance with the present invention does not require a return to the same culture. The suspension culture according to the present invention may even be continued in a different geographical location, e.g. following freezing and transport of cells.

Accordingly, in a further aspect of the present invention a method of propagating human embryonic stem cells (hESCs) in in vitro suspension culture is provided, the method comprising:

(i) attaching hESCs to a plurality of microcarriers;
(ii) culturing the microcarriers from (i) in suspension culture for a period of time sufficient to expand the number of hESCs;
(iii) passaging the expanded population of hESCs from (ii);
(iv) repeating steps (i)-(iii) through at least 5 passages, wherein in each repeat cycle the hESCs of step (i) are obtained from the passaged cells of step (iii) of the preceding repeat cycle, wherein hESCs in the culture after step (iv) are pluripotent, and wherein the microcarriers have:

(a) a compact shape in which the longest dimension is between 250 µm and 10 µm; or
(b) an elongate shape, and wherein for at least 60% of the cycles of steps (i)-(iii) the microcarriers are coated in a matrix coating comprising one or both of Matrigel and hyaluronic acid.

Preferably, for at least 70%, 80%, 90%, 95%, 97%, 98%, 99% or substantially 100% of the cycles of steps (i)-(iii) the microcarriers are coated in a matrix coating comprising one or both of Matrigel and hyaluronic acid.

Methods according to the present invention may comprise continuous or intermittent agitation of the cell culture, e.g. from about 5 to about 200 rpm, about 5 to about 150 rpm, about 5 to about 100 rpm, about 30 rpm or more or about 50 rpm or more, or about 100 rpm or more. Alternatively the methods may comprise static culture.

In some embodiments an increase in the rate or amount of agitation may be used to induce differentiation of cells, whereas a lower rate or amount of agitation may be used to expand pluripotent or multipotent cell populations without inducing significant differentiation.

To culture pluripotent or multipotent cell populations without inducing significant differentiation cultures may be agitated at from about 5 rpm to about 100 rpm, from about 5 rpm to about 50 rpm, from about 5 rpm to about 40 rpm, from about 5 rpm to about 30 rpm, from about 5 rpm to about 25 rpm, from about 5 rpm to about 20 rpm, from about 5 rpm to about 15 rpm, from about 5 rpm to about 10 rpm.

For the induction of significant differentiation cultures may be agitated at from about 25 rpm to about 200 rpm or more, e.g. from about 30 rpm to about 200 rpm or more, from about 35 rpm to about 200 rpm or more, from about 40 rpm to about 200 rpm or more, from about 45 rpm to about 200 rpm or more, from about 50 rpm to about 200 rpm or more, from about 75 rpm to about 200 rpm or more, from about 100 rpm to about 200 rpm or more.

Significant differentiation of cells may include the situation where at least about 10% of cells in the culture differentiate. Alternatively, this may be where at least one of about 15%, 20%, 25%, 30%, 35%, 40%, 45% or 50% of cells in the culture differentiate.

Accordingly, methods of the invention may comprise conducting a first part of the method at a first rate or amount of agitation in order to culture cells whilst maintaining their pluripotent or multipotent status followed by a second part in which cells are cultured at a second rate or amount of agitation in order to allow cells in the culture to differentiate. The first rate or amount is preferably less than the second rate or amount. The first part of the method may therefore expand the population of pluripotent or multipotent cells and the second part of the method may begin the process of differentiation of some or all of those cells towards the endoderm, ectoderm or mesoderm lineage.

The propagated human embryonic stem cells preferably retain at least one biological activity of a human embryonic stem cell after the stated number of passages. The biological activity may be chosen from the group consisting of: (i) expression of a pluripotency marker, (ii) cell viability; (iii) normal karyotype, (iv) ability to differentiate into endoderm, ectoderm and mesoderm. The biological activity may comprise expression of a pluripotency marker chosen from the group consisting of: OCT-4, SSEA-4, TRA-1-60 and Mab84.

Methods according to the present invention preferably enable human embryonic stem cells to be passaged at a split ratio of 1:6 or more, 1:10 or more, 1:15 or more, 1:20 or more or 1:26 or more.

Methods according to the present invention preferably enable propagation of human embryonic stem cells to a volumetric productivity of 2 million cells/ml or more.

Methods according to the present invention may further comprise the step of separating the human embryonic stem cells from the particles.

A method for producing a differentiated cell is also provided, the method comprising propagating a human embryonic stem cell according to a method of the present invention followed by causing the human embryonic stem cell to differentiate.

A method for producing an embryoid body is also provided, the method comprising propagating a human embryonic stem cell according to a method of the present invention and culturing the human embryonic stem cell to form an embryoid body.

A method of treating a disease in an individual in need of treatment is also provided, the method comprising propagating a human embryonic stem cell according to a method of the present invention, producing a differentiated cell or an embryoid body and administering the human embryonic stem cell, differentiated cell or embryoid body into the individual.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual, Second Edition, Books* 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855; and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

The patent or application file contains at least one drawing executed in color. Copies of this patent or patent application publication with color drawing(s) will be provided by the Office upon request and payment of the necessary fee.

Embodiments and experiments illustrating the principles of the invention will now be discussed with reference to the accompanying figures in which:

FIG. 1 shows microcarriers which are capable of attaching and growing hESC. Three types of microcarriers were used: rod shaped, cellulose microcarriers; small, spherical Tosoh hydrophilic microcarriers and large, spherical, microporous and macroporous carboseed microcarriers.

FIG. 6. Seeding of hESC cultures (HES-3), passaging and quality control.

FIG. 7. Seeding of hESC cultures (HES-3), passaging and quality control. 7 day cultures of hESC after trypLE treatment in 2D colony vs. microcarriers cultures. hESC on matrigel coated static cellulose microcarriers.

FIG. 8. Seeding of hESC cultures (HES-3), passaging and quality control. hESC on matrigel coated static cellulose microcarriers. FIG. 8C. FACS of pluripotent markers Oct-4, SSEA-4 and TRA-1-60 after passage 4. FIG. 8D. FACS of pluripotent markers Oct-4, SSEA-4 and TRA-1-60 after passage 6.

FIG. 10. Seeding of hESC cultures (HES-3), passaging and quality control. Replating hESC from microcarriers to matrigel coated 6 cm tissue culture petridish; P5 to P6. Nuclei Count=20 million cells/plate. FIG. 10B. Photos of replated hESC at 0.8× and 5× magnifications.

FIG. 11. Freezing of hESC cultures.

FIG. 14. Growth kinetics and metabolism in Knock Out conditioned media. Comparison of metabolism of hESC on microcarriers vs. 2D colony cultures. Specific consumption rates of glutamine and glucose profiles and lactate and ammonia production rates of hESC on microcarriers vs. 2D colony cultures

FIG. 21. Agitation at 100, 150 rpm. FACS results for agitated matrigel coated carriers at 100 and 150 rpm. Note: Both experiments were passaged from hESC on Microcarriers.

FIG. 23. FACS results for agitated matrigel coated carriers at 150 rpm for 2 consecutive weeks FACS of pluripotent markers Oct-4, SSEA-4 and TRA-1-60 of hESC on microcarriers agitated at 150 rpm at passage 1 and 2.

FIG. 26. HES2 in 2D colony cultures vs. microcarriers cultures in static and 100 rpm.

FIG. 27. Charges of carriers—DE52, DE53, Q53.

FIG. 34. Sizes and shapes of carriers—spherical carbon beads. Oct-4 GFP HES2 on Fn coated carbon microcarriers vs. control.

FIG. 37. Sizes and shapes of carriers—spherical carbon beads. Histological analysis of hESC cultures on macroporous and microporous carbon microcarriers stained with DAPI, Phalloidin and TRA-1-60.

FIG. 42. Sizes and shapes of carriers—spherical carbon beads. Histological analysis of hESC cultures on macroporous carbon microcarriers stained with DAPI, Phalloidin and TRA-1-60.

FIG. 43. Sizes and shapes of carriers—spherical carbon beads. HES2 GFP cell line grown on macroporous microcarriers vs. 2D colony control.

FIG. 46. Sizes and shapes of carriers—spherical carbon beads. 1 mm Macroporous Beads vs. 2D Controls. Extending culture to 12 days increased cell density to 1.2×10e6 cells.

FIG. 47. Co-culture and feeders on microcarriers.

FIG. 48. Co-culture and feeders on microcarriers.

FIG. 53. Oct4, SSEA4 and TRA-1-60 expression at passages 21-23 of hESC culture on Matrigel coated DE53 carriers, and following replating of passage 23 onto 2D colony culture.

FIG. 72. Morphology of the hESC in microcarrier spinner flask culture remain as tight aggregates on the microcarriers on days 4 and 5.

FIG. 76. hESC in microcarrier spinner flask culture form large aggregates of cells around the microcarriers on days 5 and 7.

FIG. 77. Density of 3.5 million cells/mil in a 100 ml spinner flask is equivalent to producing hESC in 175 organ culture dishes (OCD) each with 2 million cells/ml.

FIG. 90. Expression of pluripotent marker TRA-1-60 of hESC on matrigel coated polylysine Tosoh microcarriers at passage 3.

Figure 119:
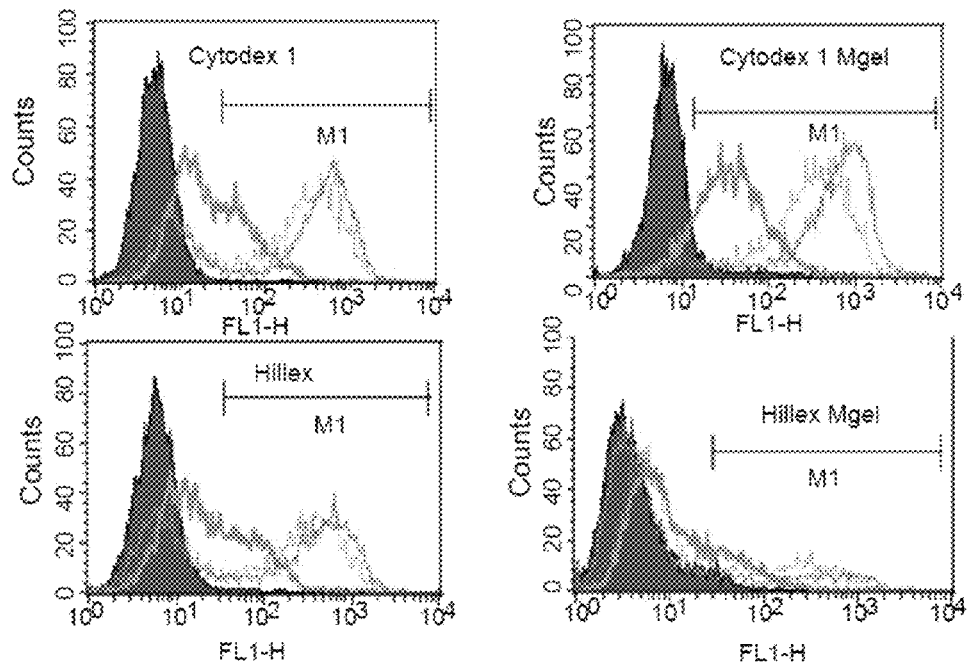
Figure 120A:
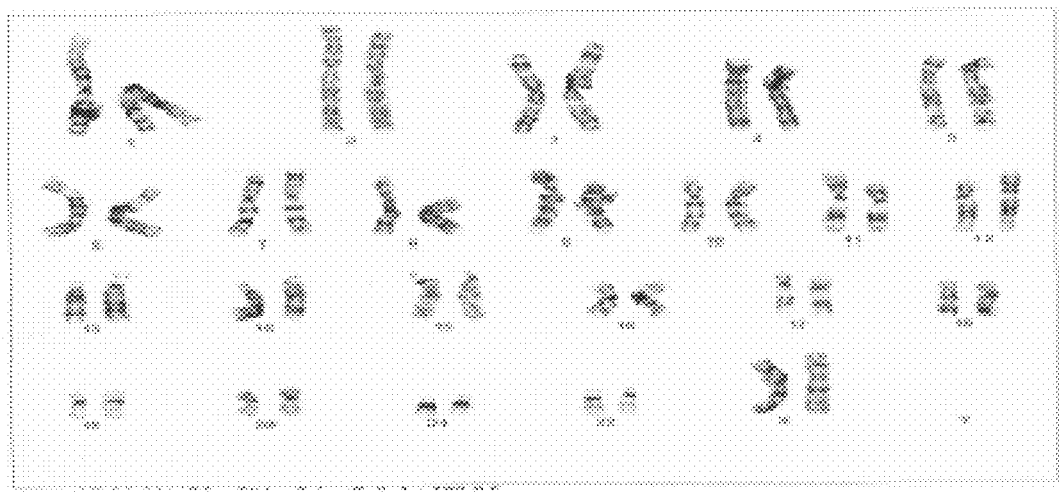
Figure 120B:
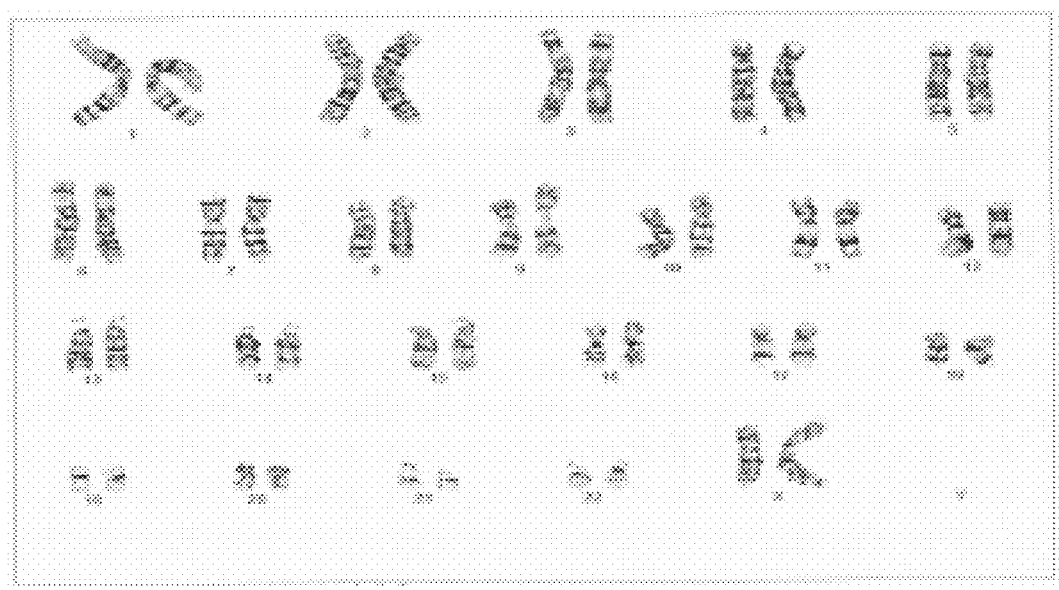
Figure 120C:
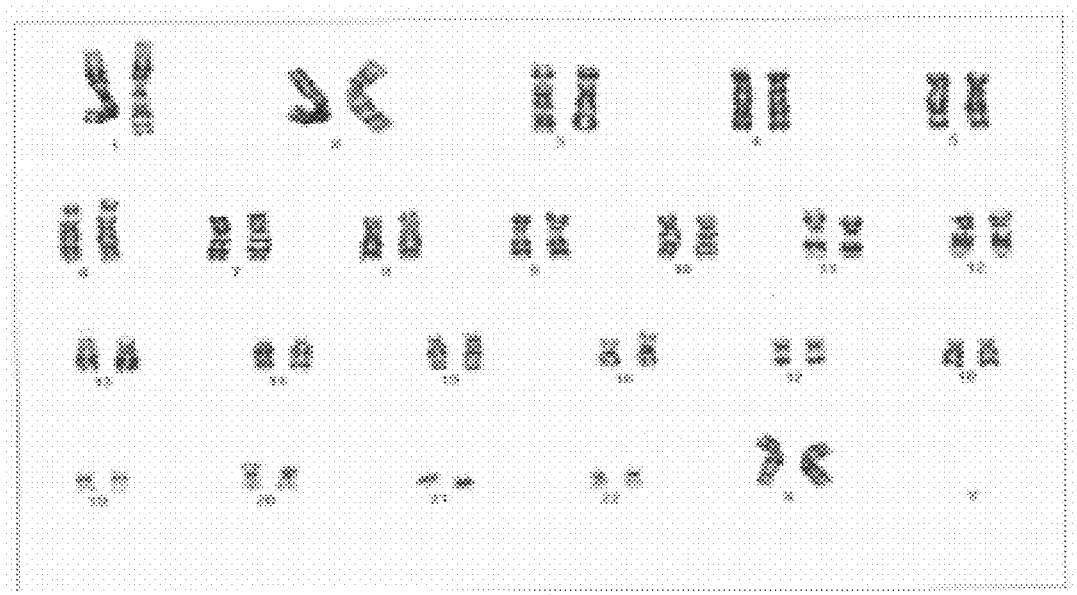
Figure 120D:
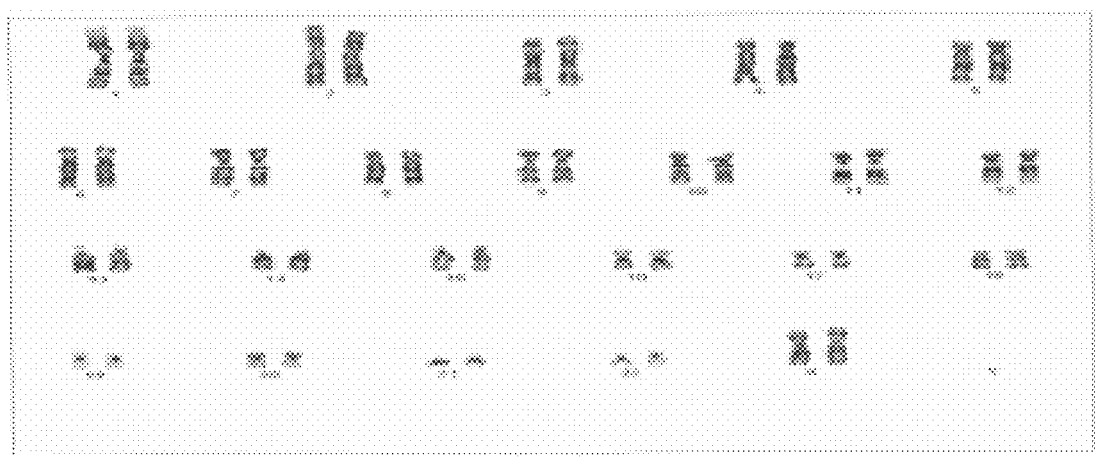

FIG. 119. At passage 13 hESC cultured on Cytodex 1 with matrigel express the 3 pluripotent markers.

FIG. 120. Karyotypes of Cytodex 1 and Hillex microcarrier cultures at passage 7. Normal hESC karyotypes for Cytodex 1 and Hillex with and without Matrigel at passage 7. (FIG. 120A) Cytodex 1 with matrigel, (FIG. 120B) Cytodex 1 without matrigel, (FIG. 120C) Hillex with Matrigel, (FIG. 120D) Hillex without Matrigel.

Figure 121:
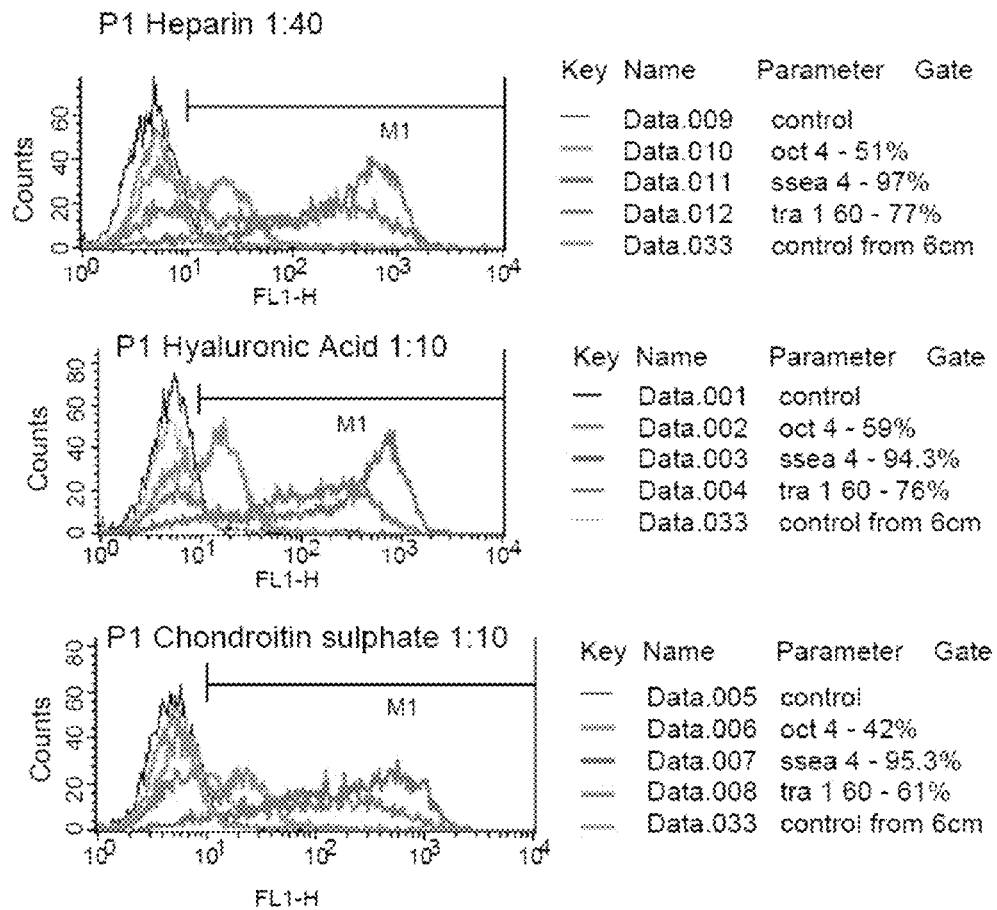

FIG. 121. Expression of pluripotent markers Oct4, SSEA4 and TRA-1-60 at passage P1 for hESC DE53 cellulose microcarrier cultures with coatings of chondroitin sulphate, heparin and hyaluronic acid.

Figure 122:
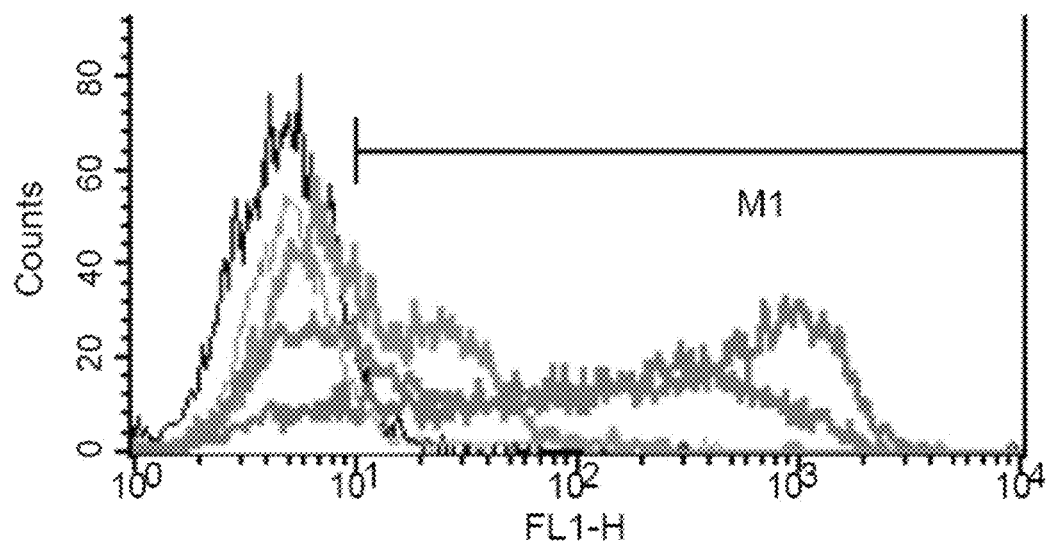

FIG. 122. Expression of pluripotent markers Oct4, SSEA4 and TRA-1-60 at passage P1 for hESC DE53 cellulose microcarrier cultures with coating of KO media.

Figure 123:
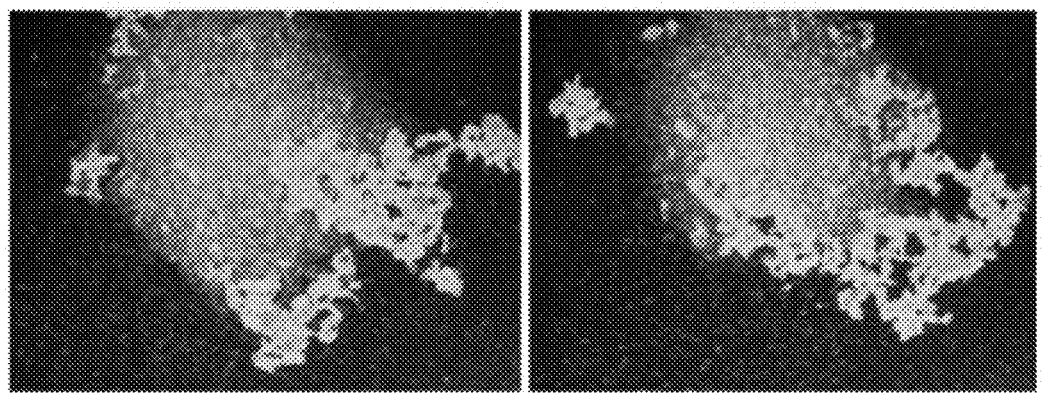

FIG. 123. DE-53 cellulose microcarriers coated with hyaluronic acid (HA)+heparin salt (HS), and with fibronectin+HS+HA.

Figure 124:
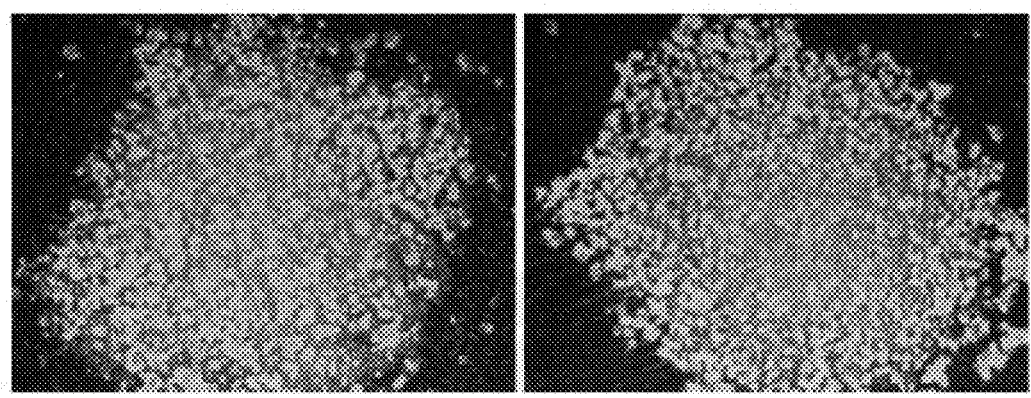

FIG. 124. DE-53 cellulose microcarriers coated with hyaluronic acid (HA), and with fibronectin+HA.

Figure 125:
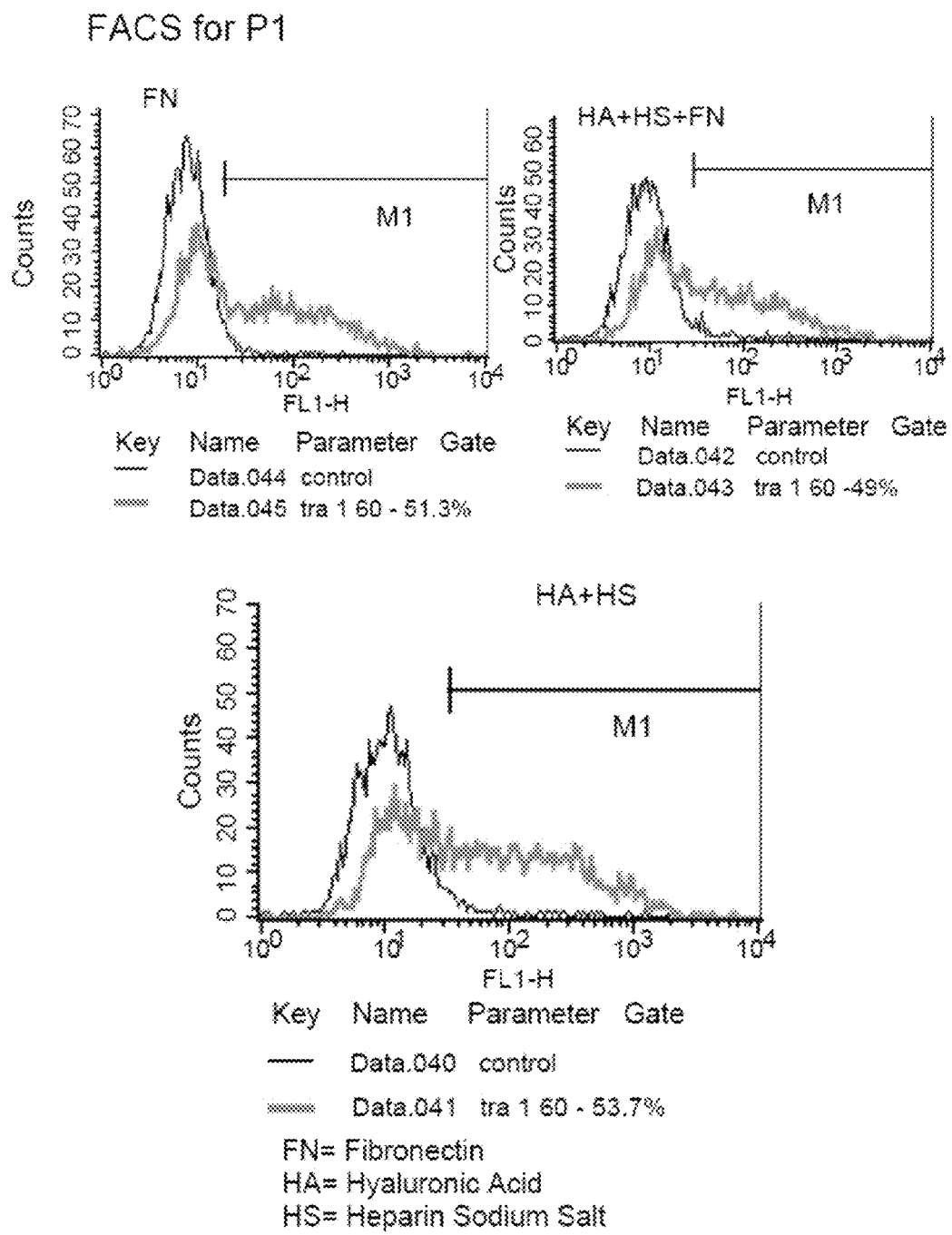

FIG. 125. Down regulation of TRA-1-60 by passage 1 with DE53 coated with fibronectin (FN); fibronectin+HS+HA; and HA+HS.

Figure 126:
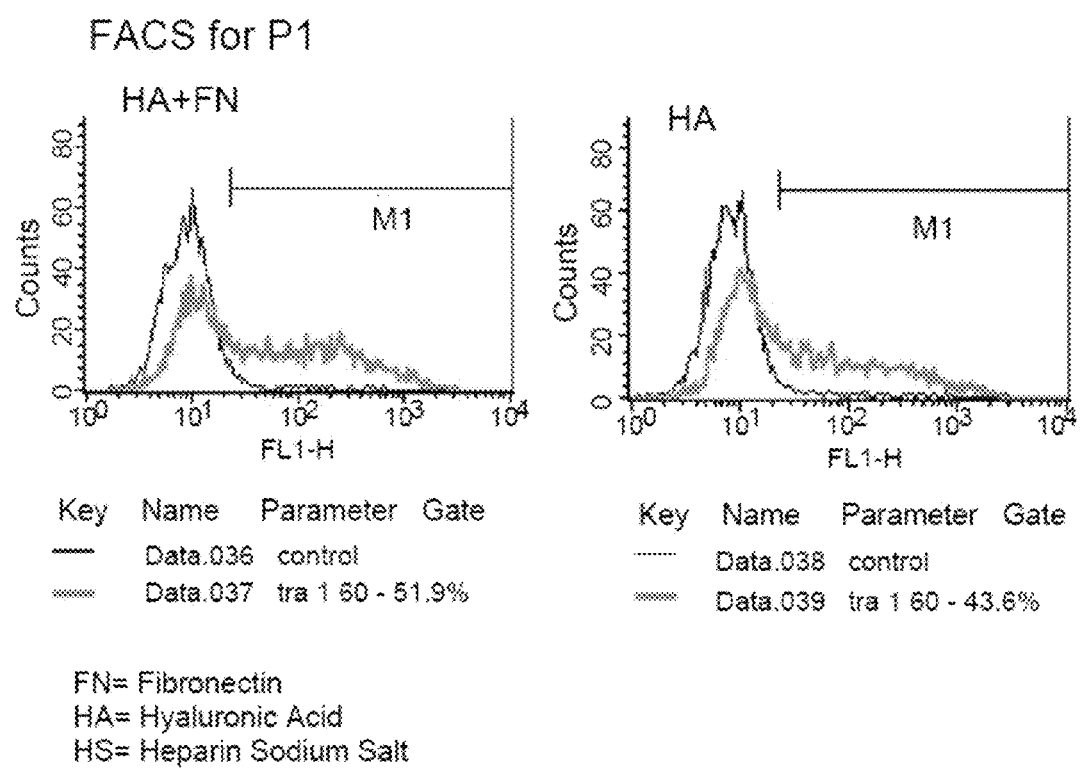

FIG. 126. Down regulation of TRA-1-60 by passage 1 with DE53 coated with HA+FN; and with HA.

Figure 127:
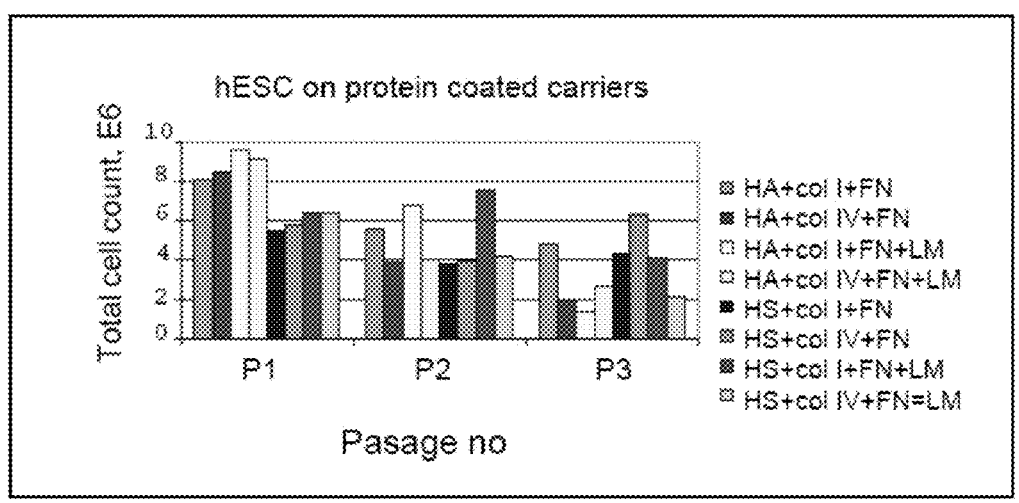

FIG. 127. Cell count at passages 1-3 with DE53 coated in combinations of HS, FN, HS, Collagen I, Collagen IV and Laminin.

FIG. 128. Morphology of hESC on different combinations of ECMs with HA coated on cellulose DE-53 microcarriers.

FIG. 129. Morphology of hESC on different combinations of ECMs with HS coated on cellulose DE-53 microcarriers.

Figure 130:
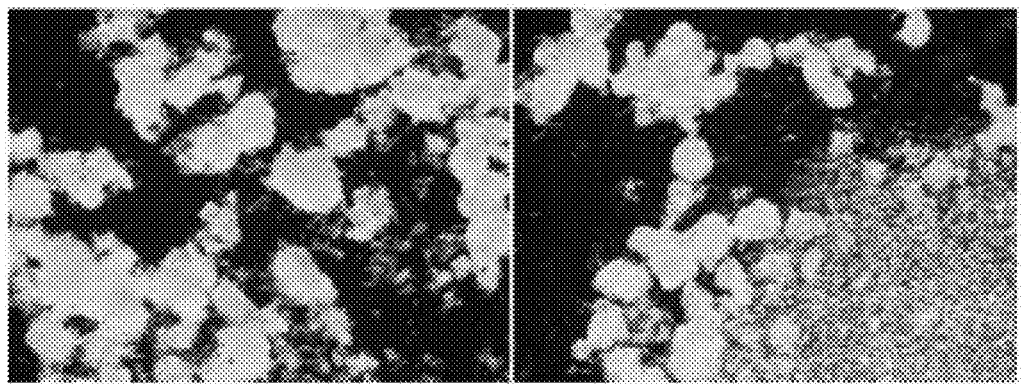

FIG. 130. Morphology of hESC on HA coated DE-53 and HS coated DE-53.

FIG. 131. Morphology of hESC on microcarriers with HA in combination with collagen I, IV, laminin and fibronectin form dense cell aggregates compared to other ECM combinations.

FIG. 132. Pluripotent markers Oct4, SSEA4 and TRA-1-60 after 3 passages continue to be expressed with HA+COL1+FN and HA+COL4+FN DE-53 matrix coatings.

Figure 133:
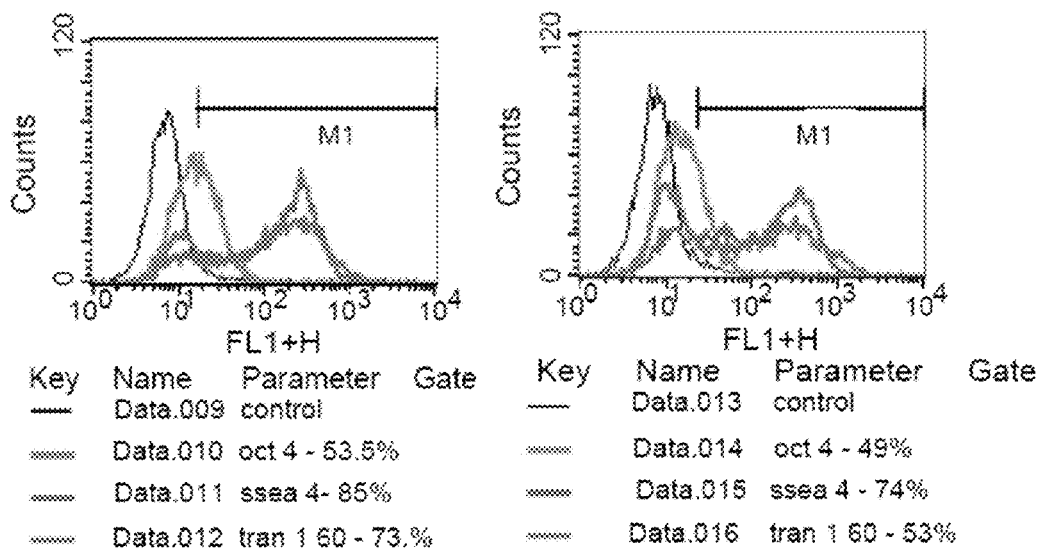

FIG. 133. Pluripotent markers Oct4, SSEA4 and TRA-1-60 after 3 passages continue to be expressed with HA+COL1+FN+LM and HA+COL4+FN+LM DE-53 matrix coatings.

FIG. 134. Pluripotent markers Oct4, SSEA4 and TRA-1-60 after 3 passages continue to be expressed with HS+COL1+FN and HS+COL4+FN DE-53 matrix coatings.

FIG. 135. Pluripotent markers Oct4, SSEA4 and TRA-1-60 after 3 passages continue to be expressed with HS+COL1+FN+LM and HS+COL4+FN+LM DE-53 matrix coatings.

Figure 136:
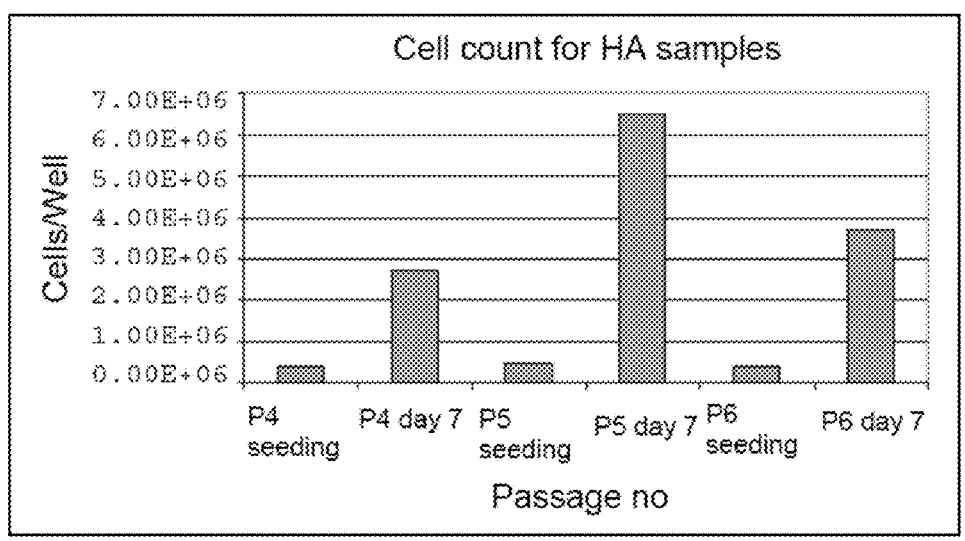

FIG. 136. Continued robust growth of hESC on HA coated DE53 cellulose microcarriers.

FIG. 137. Continued robust expression of the pluripotent markers Oct4, and TRA-1-60 on HA coated DE53 cellulose microcarriers.

Figure 138:
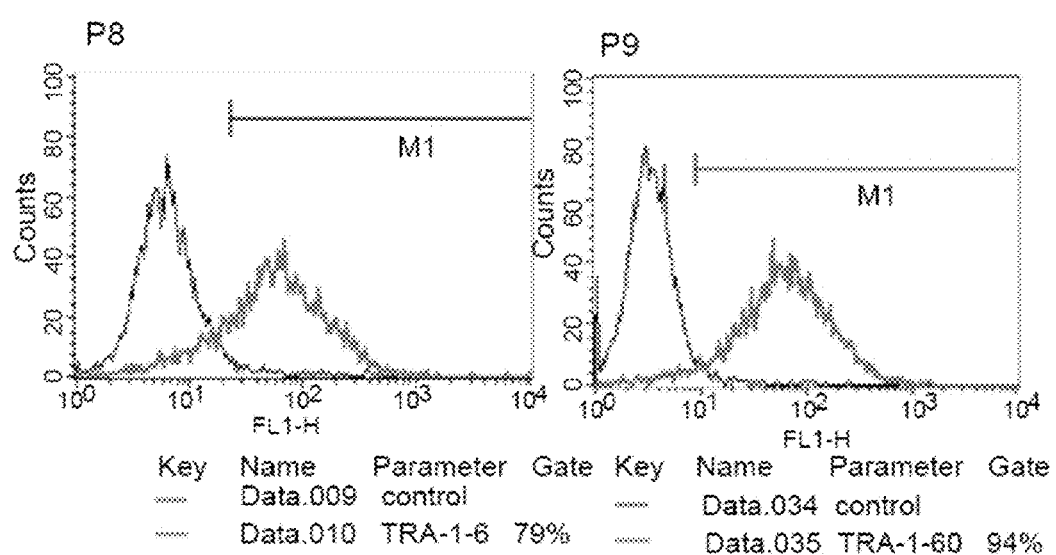

FIG. 138. Continued high expression of TRA-1-60 at passages 8 and 9 on HA coated DE53 cellulose microcarriers.

FIG. 139. Morphology of dense hESC aggregates grown on HA coated DE-53 cellulose microcarriers at passage 6 at 2 different magnifications.

Figure 140:
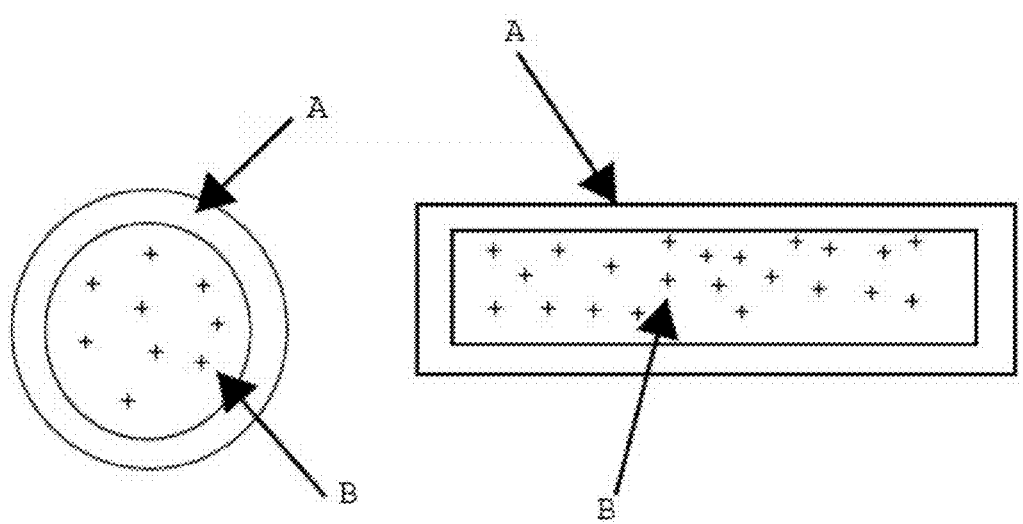

FIG. 140. Schematic illustration of microcarriers suitable for hESC suspension culture. (FIG. 140A) Extracellular matrices coatings e.g. matrigel, hyaluronic acid, heparin, fibronectin, etc. with or without adsorbed growth factors, microcarrier composition e.g. cellulose dextran hydroxylated methacrylate, polystyrene, glass, collagen, gelatin etc. (FIG. 140B) Positive change and/or gelatin/collagen microcarriers. Spherical or oval-like microcarriers (left), diameter 50 to 2000 microns. Rod or cylindrical or spiral-like microcarriers (right), length 20 to 2000 microns, diameter 5 to 50 microns.

FIG. 141. Table 1—amino acids consumed and produced by hESC in mTeSR1 and StemPRO media.

FIG. 142. Table 2—Detailed information on the individual levels of amino acids consumed and produced by hESC in mTeSR1 and StemPRO serum free media.

FIG. 143. Table 3—Cell densities of hESC in co-cultures with feeder cells on Cytodex 3 and Tosoh spherical microcarriers as well as co-culture on rod-shaped cellulose DE53 microcarriers at passage 0 and passage 1.

FIG. 144. Table 4—Cell numbers of hESC in 3 co-cultures were about 2 times higher compared to the control on matrigel coated microcarriers.

FIG. 145. Table 5—Both small (10 micron) and large (65 micron) Tosoh microcarriers with and without matrigel coatings supported hESC growth at passage 0 and passage 1.

FIG. 146. Table 6—Cell numbers of both polylysine and protamine coated Tosoh beads (65 micron) with and without matrigel for 4 passages.

FIG. 147. Table 7—Cell numbers of hESC grown are relatively stable on Cytodex 3 microcarriers coated with matrigel and without matrigel cultured in non-agitated and agitated conditions for 3 passages.

FIG. 148. Table 8—Cell numbers of hESC grown on cellulose microcarriers after 7 days with different coatings of chondroitin sulphate (CS), heparin (HS) and hyaluronic acid (HA) diluted from 1:10 to 1:80 from their initial stock concentrations, compared to controls grown with coatings of KO media and conditioned media (CM) at passage P0.

FIG. 149. Table 9—At passage P1, cell numbers of hESC are greater than 1 million/well for CS, HS and HA coated cellulose microcarriers and are similar to the control with coating of KO media.

FIG. 150. Table 10—Cell numbers at passage 0 and passage 1 for DE-53 cellulose microcarriers coated in Fibronectin (FN); Hyaluronic acid (HA)+Heparin Sodium Salt (HS)+FN; HA+HS; HS+FN; and HA.

FIG. 151. Table 11—Cell numbers at passages 1, 2 and 3 for DE-53 cellulose microcarriers coated in HA+ColI+FN; HA+ColIV+FN; HA+ColI+FN+LM; HA+ColIV+FN+LM; HS+ColI+FN; HS-FColIV+FN; HS+ColI+FN+LM; HS+ColIV+FN+LM.

Figure 152:
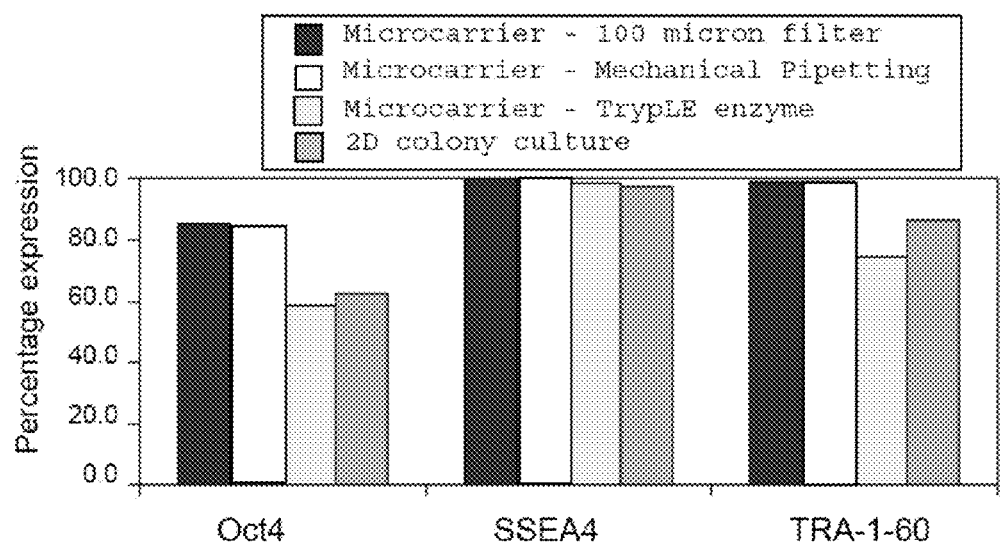

FIG. 152. Chart showing expression of Oct4, SSEA4 and TRA-1-60 following passaging using (left to right) a 100 micron filter, mechanical pipetting, TrypLE enzymic digestion and 2D colony control.

Figure 153:
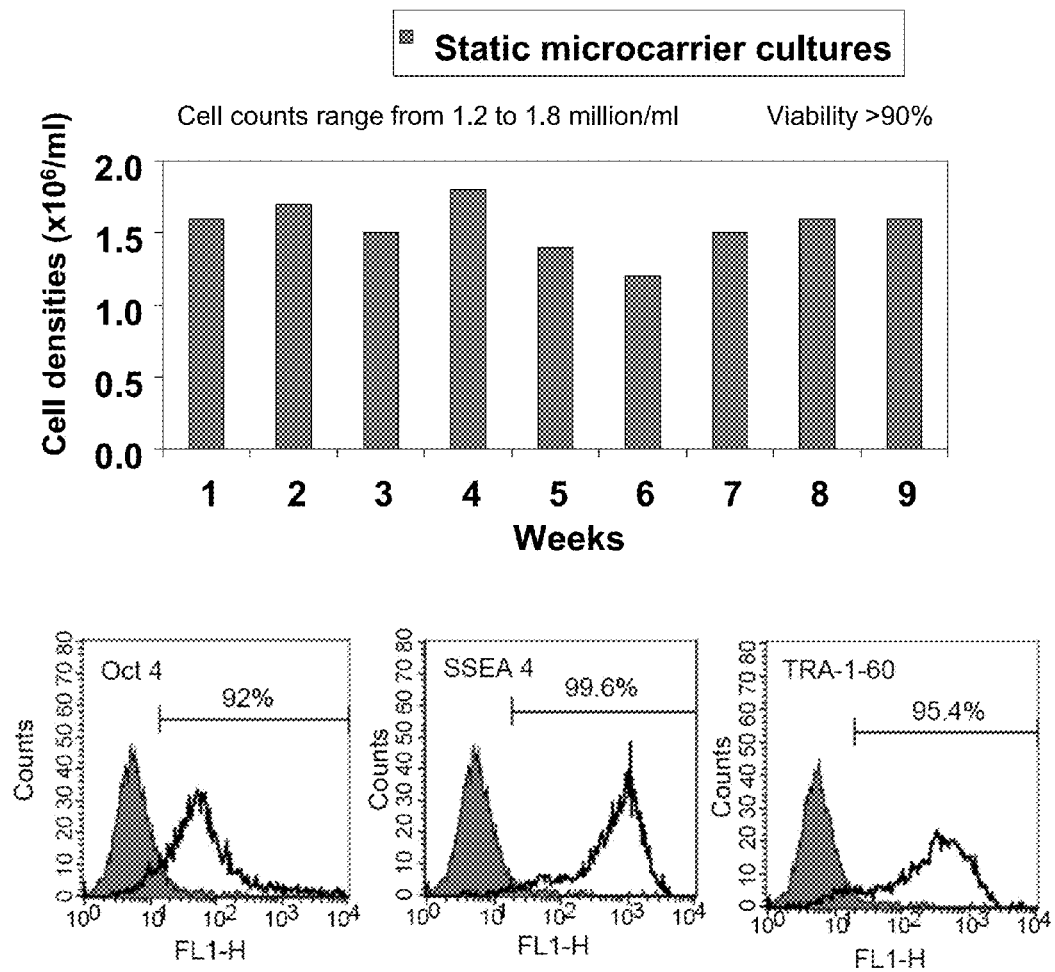

FIG. 153. Continuous passaging of hESC on microcarriers. Graph showing cell density of hESC in static microcarrier cultures over 9 weeks and charts showing expression of Oct4, SSEA4 and TRA-1-60 at passage 9.

Figure 154:
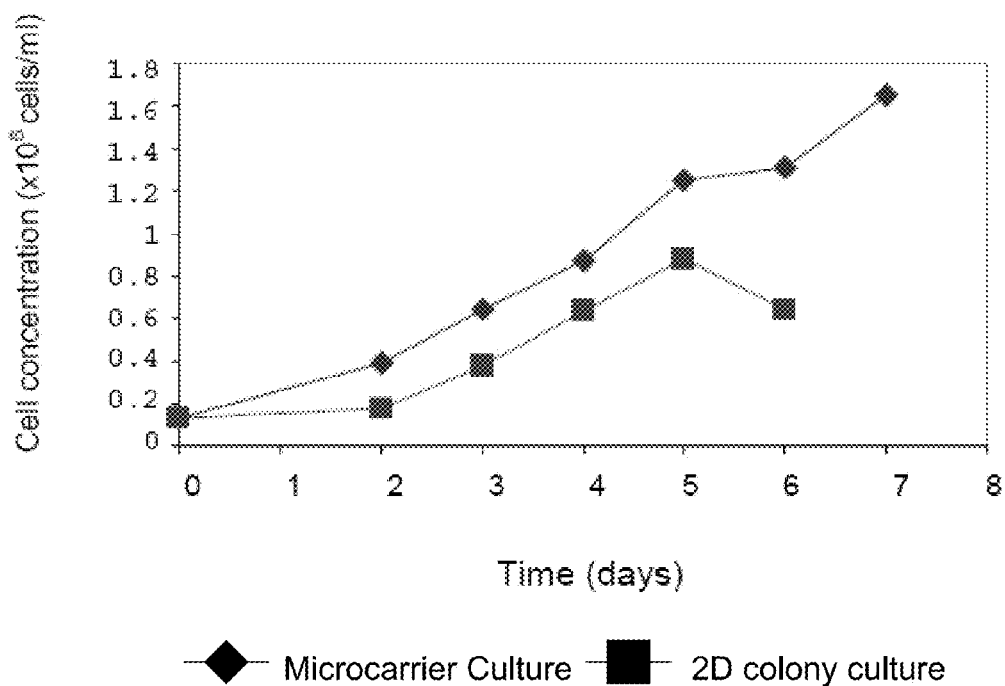
Figure 155A:
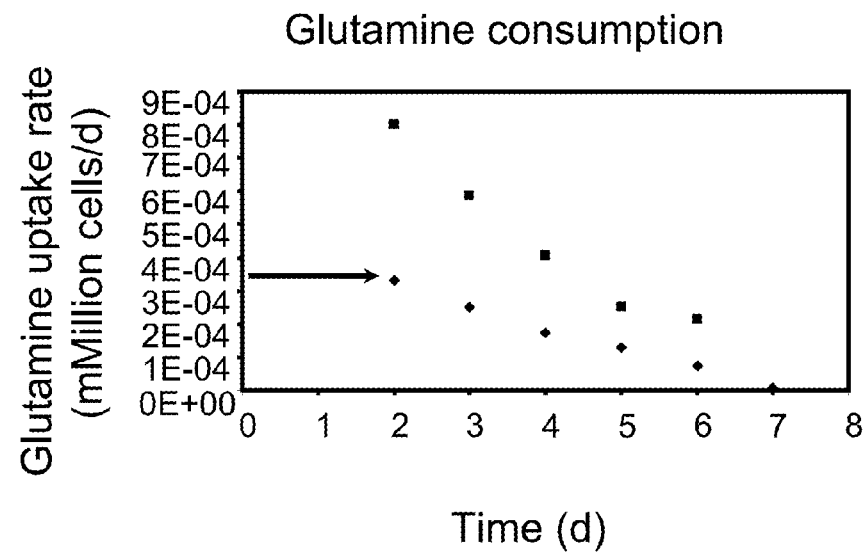
Figure 155B:
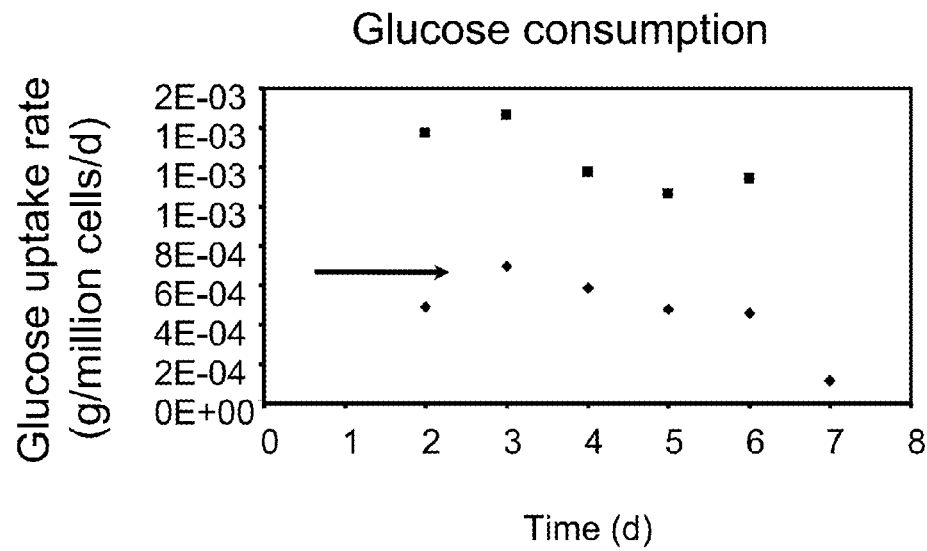
Figure 155C:
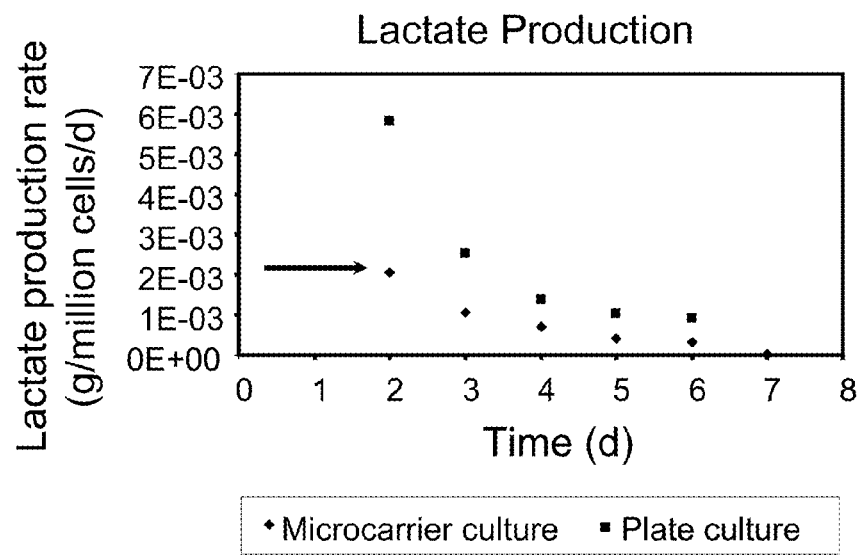
Figure 155D:
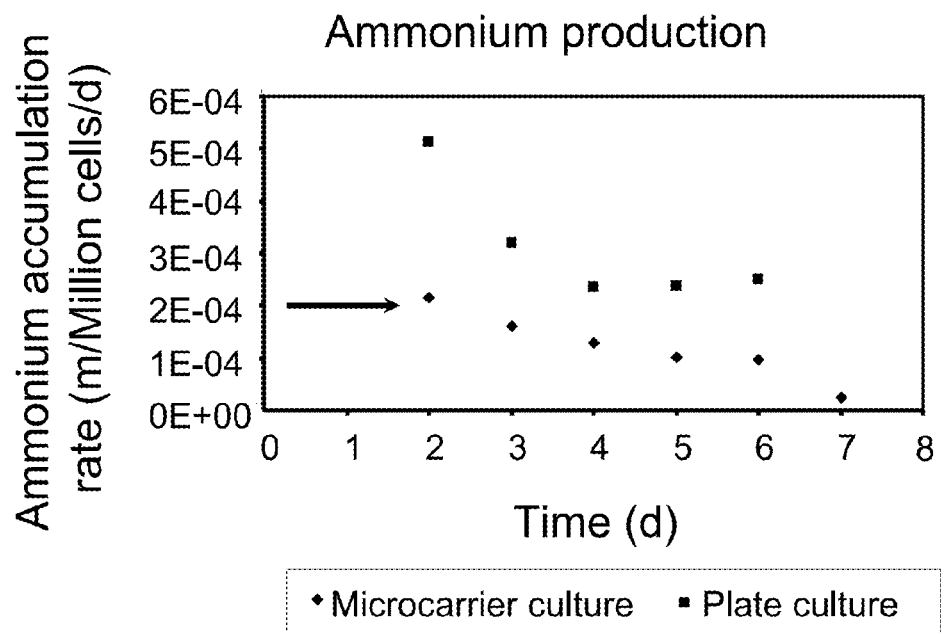

FIG. 154. Graph showing cell concentration of hESC in Microcarrier and 2D colony culture.

FIG. 155. Charts showing specific glutamine and glucose consumption rates and lactate and ammonia production rates for microcarrier and 2D colony culture. FIG. 155A shows glutamine consumption over time FIG. 155B shows glucose consumption over time; FIG. 155C shows lactate production over time; and FIG. 155D shows ammonium production over time.

Figure 156:
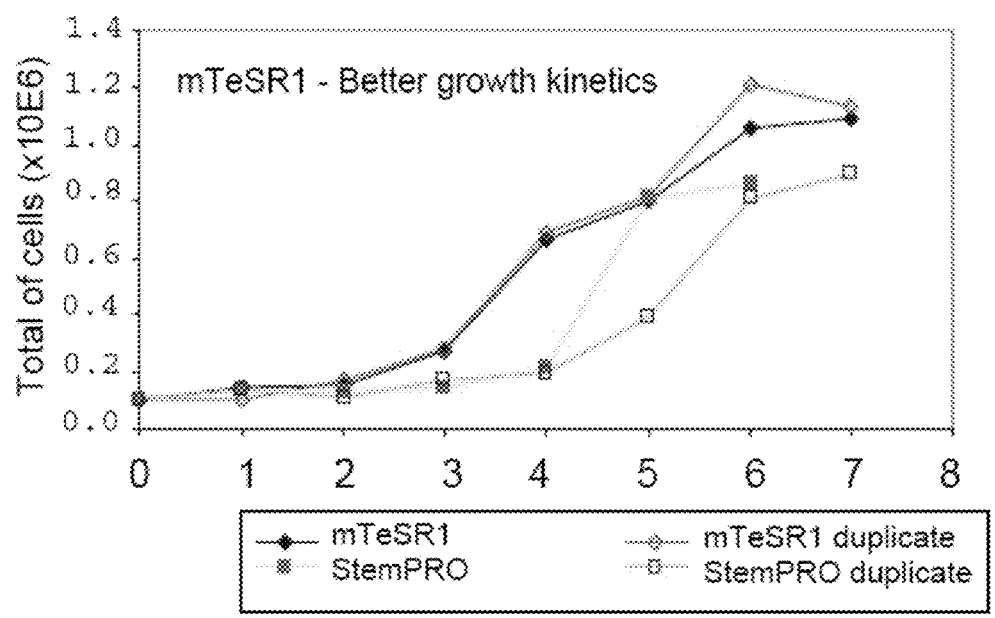

FIG. 156. Chart showing total number of hESC during microcarrier culture in two defined media (mTeSR1 and StemPRO).

Figure 157:
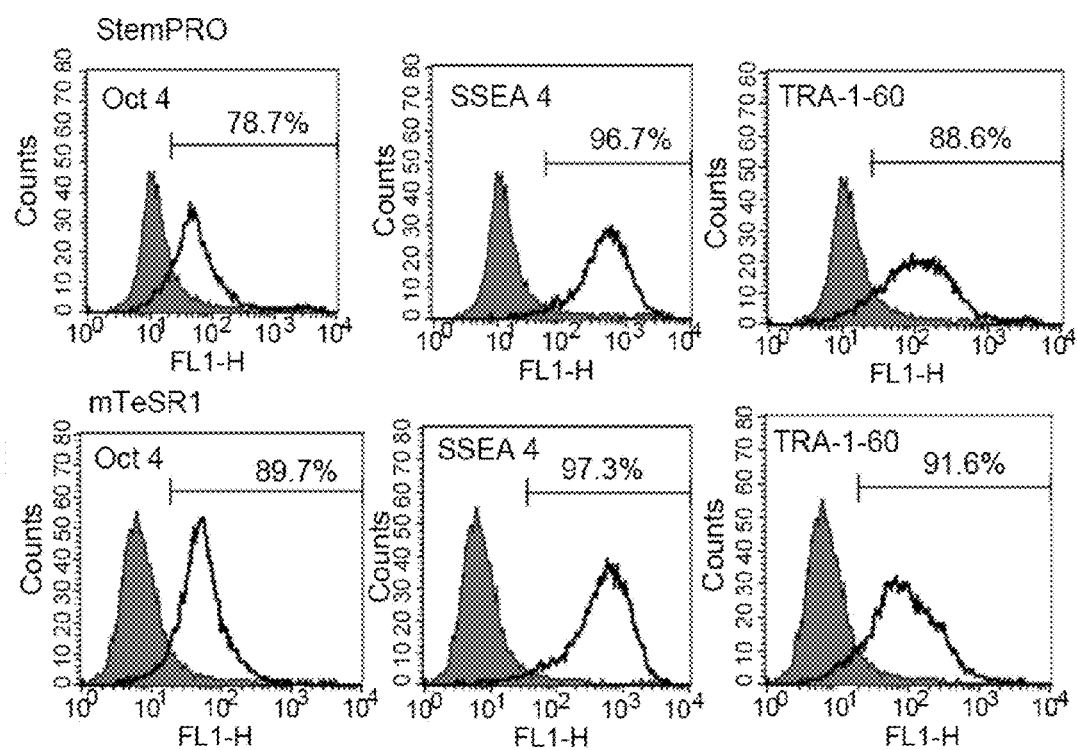
Figure 158A:
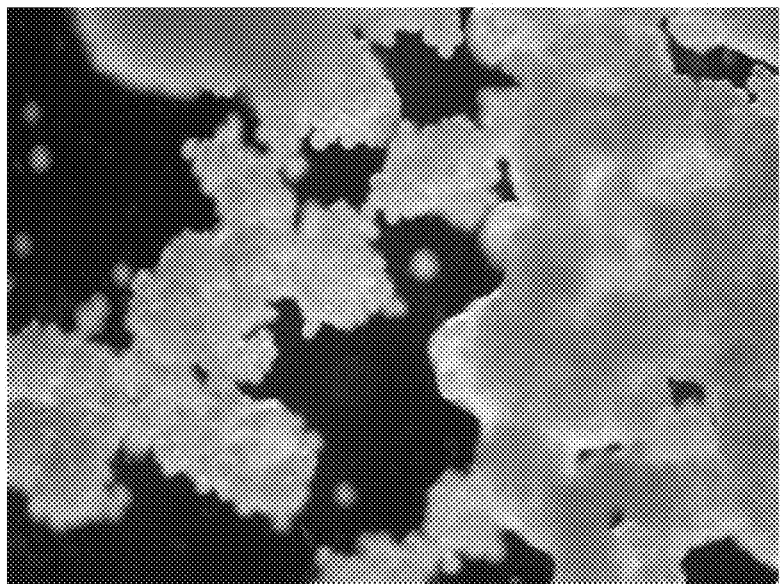
Figure 158B:
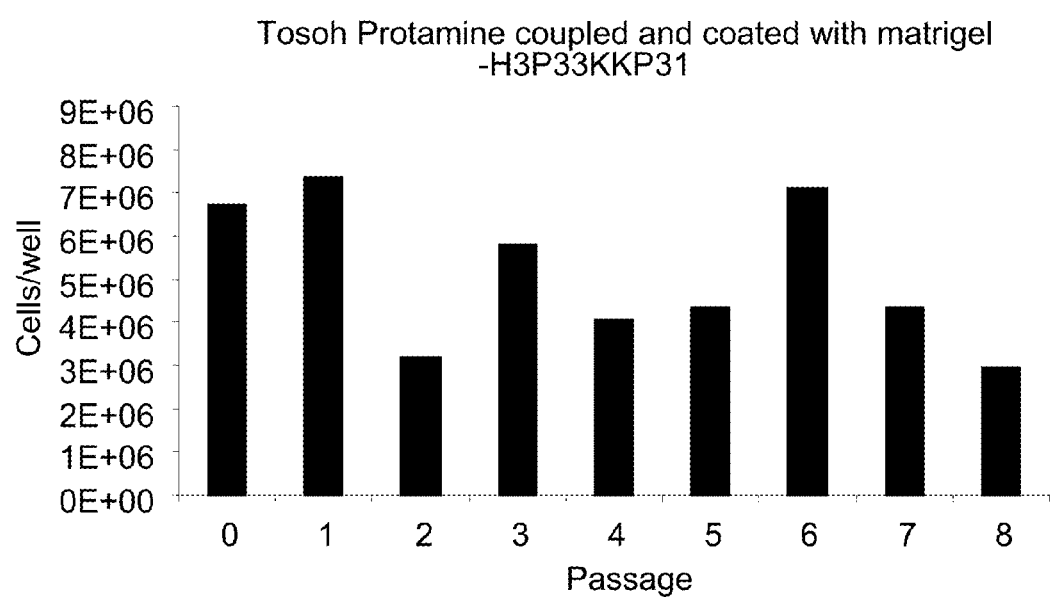
Figure 158C:
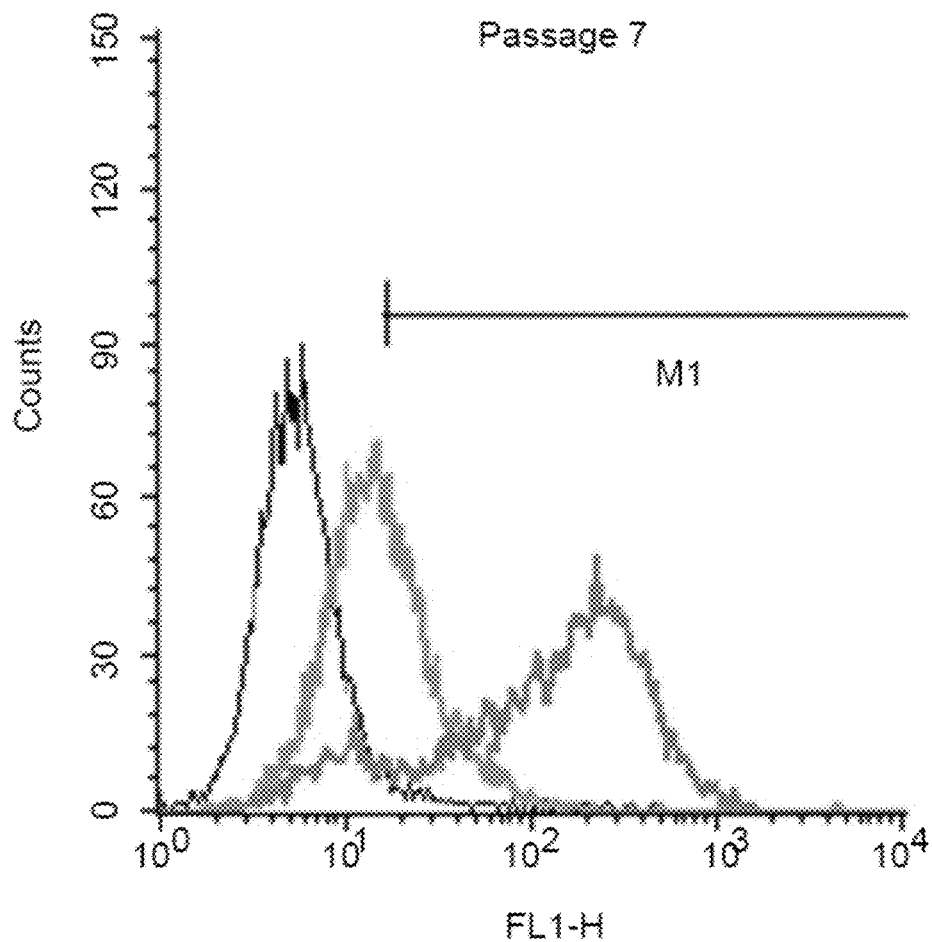
Figure 158D:
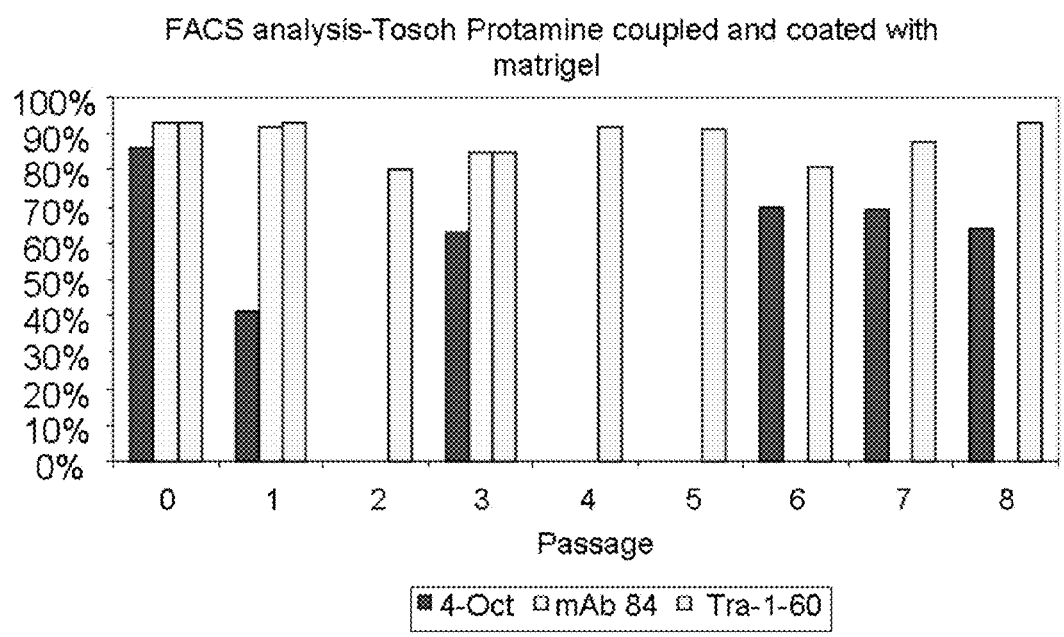

FIG. 157. Charts showing Oct4, SSEA4 and TRA-1-60 expression from hESC cultured on microcarriers in defined media (mTeSR1 and StemPRO).

FIG. 158. Micrograph (FIG. 158A) and charts (FIG. 158B) showing growth and passaging of hESC, and expression of Oct4, SSEA4 and TRA-1-60 from hESC, when cultured on Tosoh microcarriers, are shown as FACS results in FIG. 158C and in bar graph form in FIG. 158D.

Figure 159:
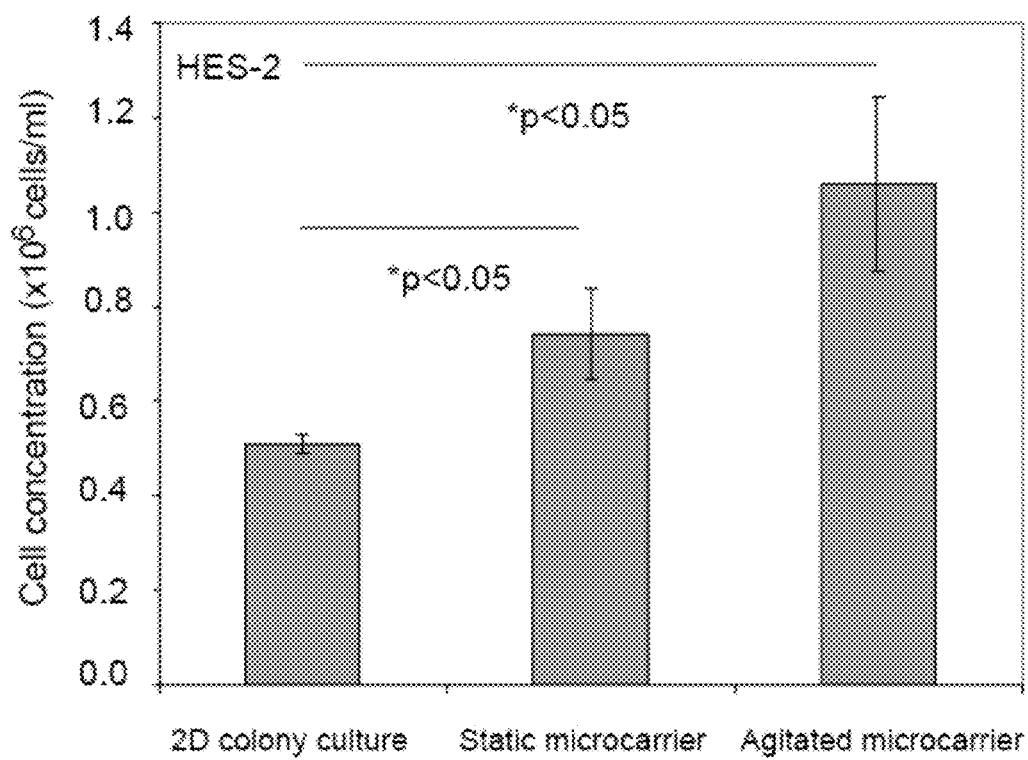

FIG. 159. Chart showing cell concentration of hESC in 2D colony culture, static microcarrier culture and agitated microcarrier culture.

Figure 160:
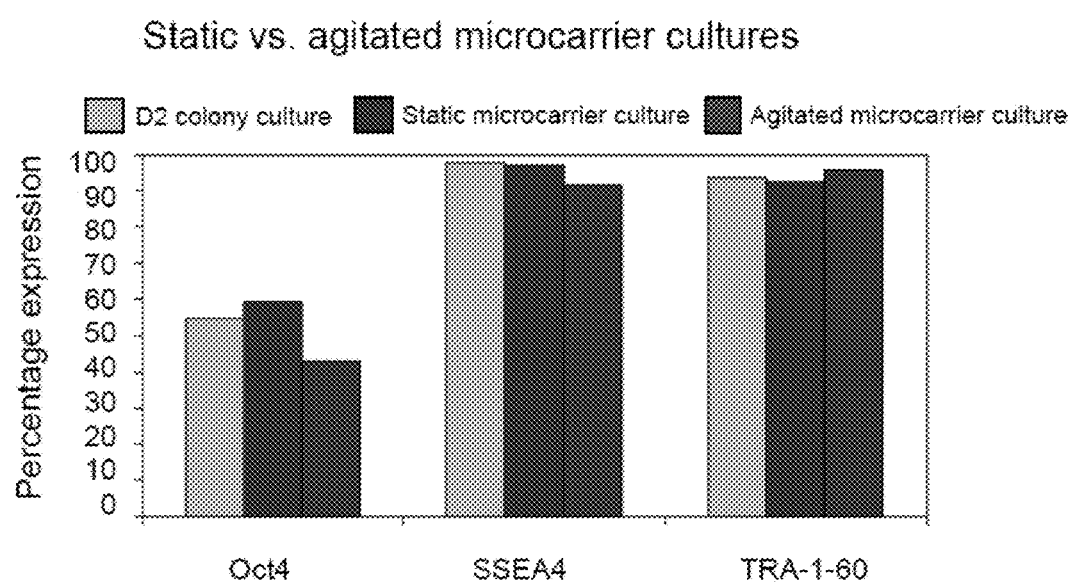

FIG. 160. Chart showing percentage expression of Oct4, SSEA4 and TRA-1-60 in (left to right) 2D colony culture, static microcarrier culture and agitated microcarrier culture.

Figure 161:
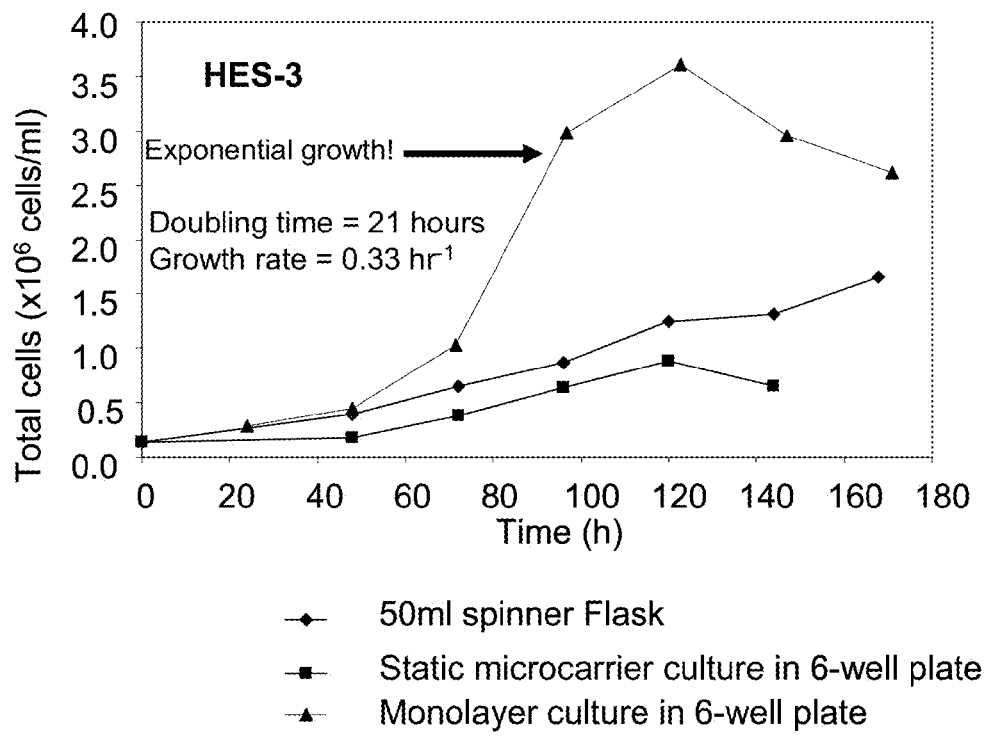

FIG. 161. Chart showing total number of cells for hESC cultured in agitated microcarrier culture (spinner flasks), static microcarrier culture and 2D monolayer culture.

FIG. 162. Micrographs showing culture of human iPS cells on cellulose microcarriers.

FIG. 163. Charts showing expression of Oct4, SSEA4 and TRA-1-60 from human iPS cells in microcarrier culture and growth of human iPS cells in microcarrier culture over 3 passages.

FIG. 164. Chart showing successful growth of human iPS cells on Matrigel coated DE53 microcarriers over 10 passages, expression of Oct4, SSEA4 and TRA-1-60 from microcarrier culture iPS cells at passage 10 and micrographs of iPS cells after 10 passages on Matrigel coated DE53 microcarriers. Matrigel coated DE53 microcarrier were used at 20 mg/well (4 mg/ml) in MEF conditioned KO-medium with 100 ng/ml bFGF (5 ml/well). Microcarriers were seeded from iPS IMR90P8MGP5 (8 passages of cultivation on feeders followed by adaptation on matrigel for 5 passages).

FIG. 165. Table showing microcarriers and different coatings used for differentiation experiments.

FIG. 166. Micrographs showing cell attachment on Laminin, Fibronectin and Vitronectin coated DE53 microcarriers compared with matrigel and uncoated DE53 microcarriers and conventional EB cultures.

Figure 167:
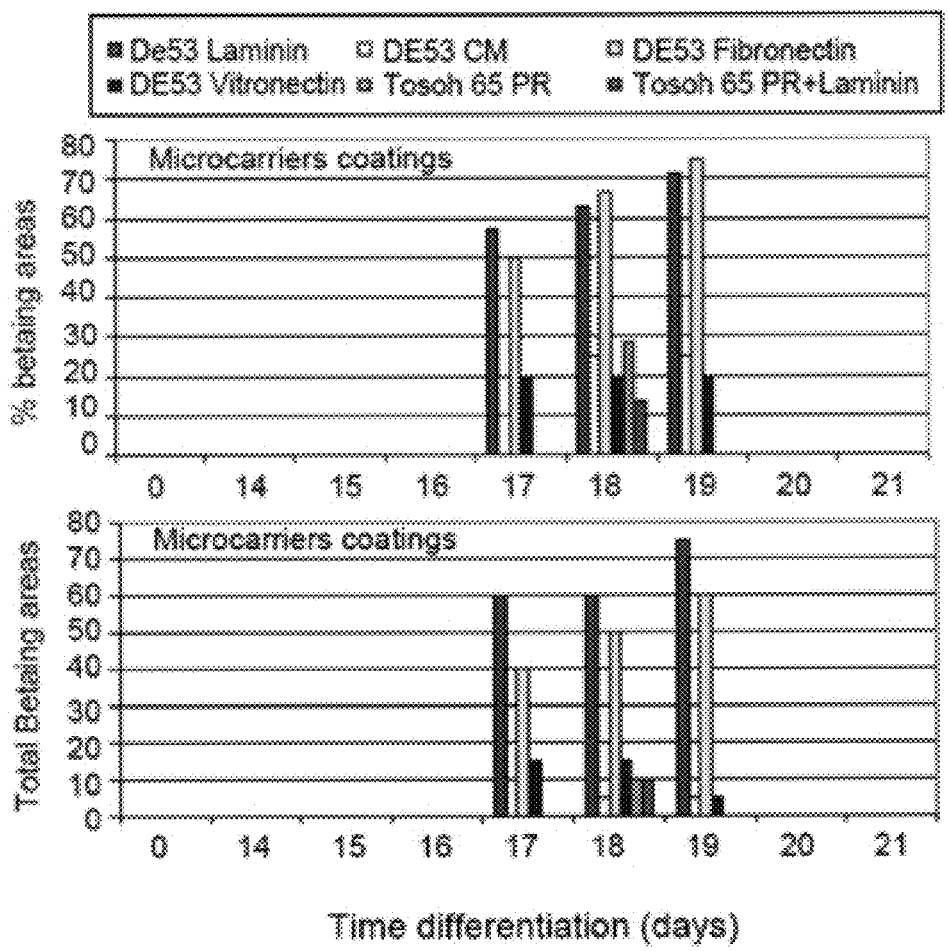

FIG. 167. Charts showing percentage of and total beating areas in cardiomyocyte differentiation experiments using DE53 microcarriers coated in Laminin, Fibronectin and Vitronectin and Tosoh 65 microcarriers coated with protamine and protamine+Laminin.

Figure 168:
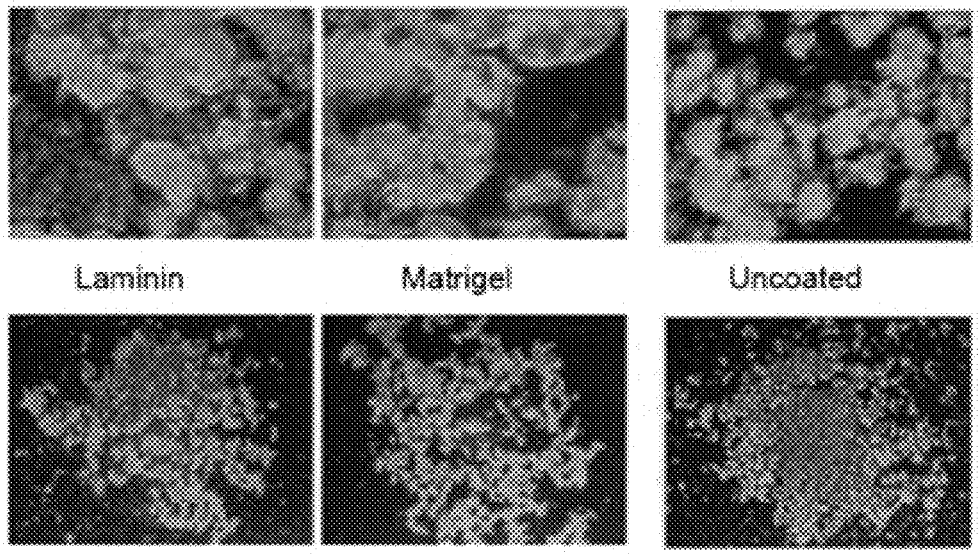

FIG. 168. Micrographs showing formation of beating aggregates in cardiomyocyte differentiation experiments on laminin, matrigel and uncoated microcarriers.

Figures 169, 170:
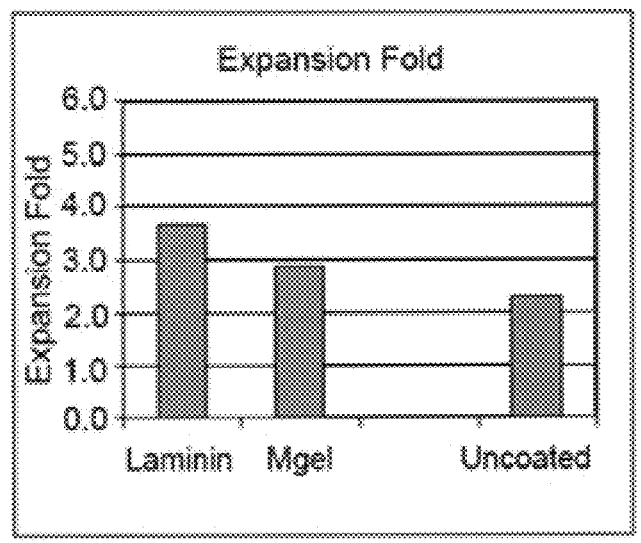

FIG. 169. Chart showing expansion of cells during cardiomyocyte differentiation experiments on laminin, matrigel and uncoated microcarriers.

FIG. 170. Table showing additives added to serum free media bSFS for differentiation on microcarriers.

Figure 171:
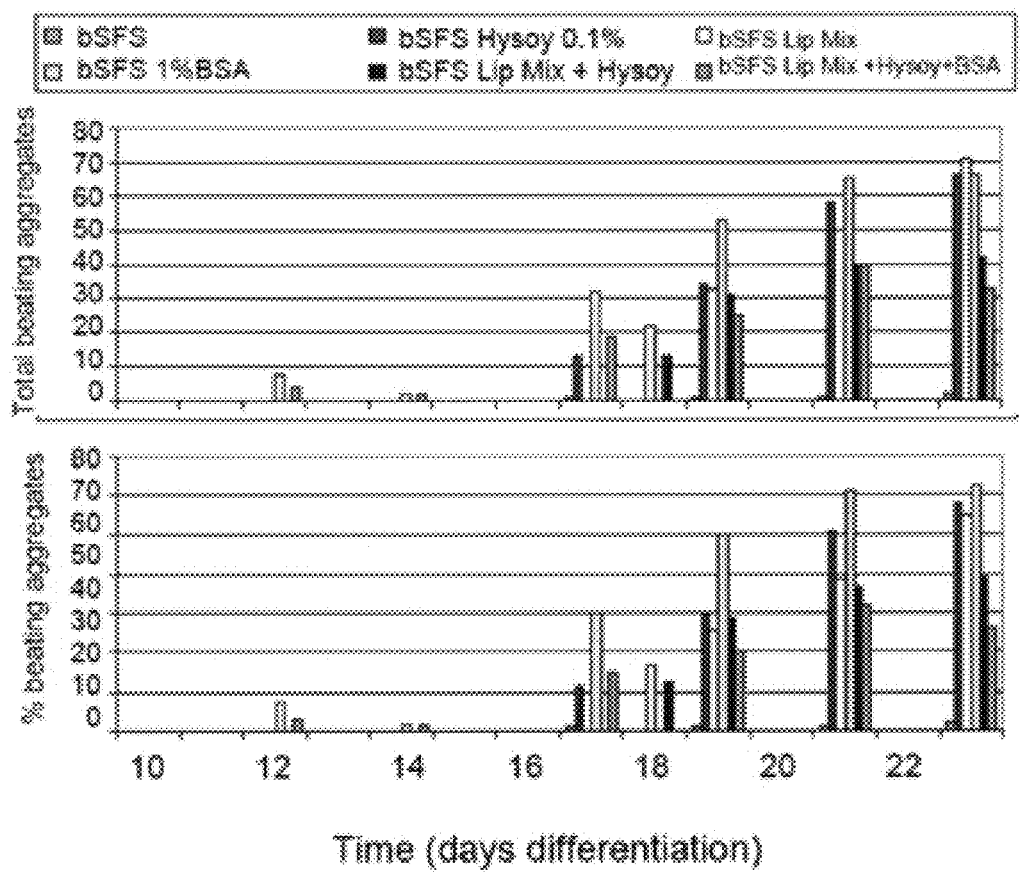

FIG. 171. Charts showing enhancement of cardiomyocyte formation by use of additives in bSFS media on uncoated microcarriers.

FIG. 172. Table showing additives added to serum free media bSFS or DMEM/F12+SB203580 for differentiation on microcarriers using hESC seeded from microcarriers to microcarriers.

Figure 173:
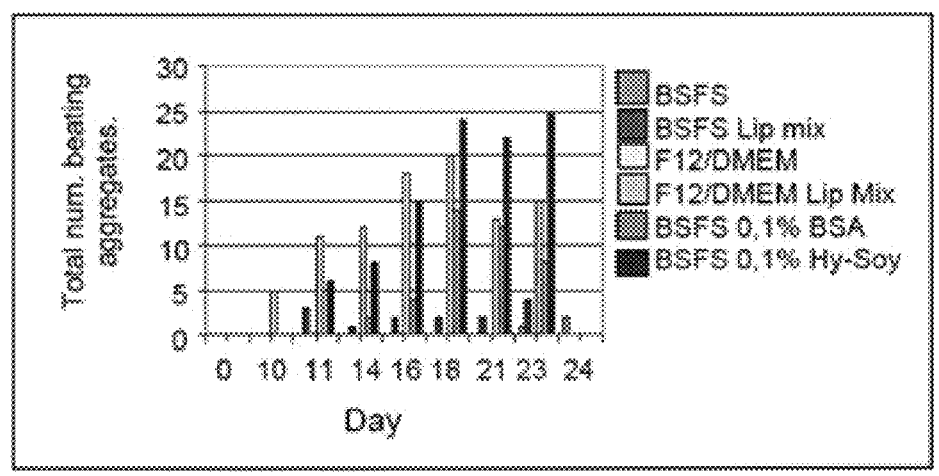

FIG. 173. Chart showing enhancement of cardiomyocyte formation from hESC seeded from microcarriers to microcarriers in the presence of additives as described in FIG. 172.

Figures 174, 175:
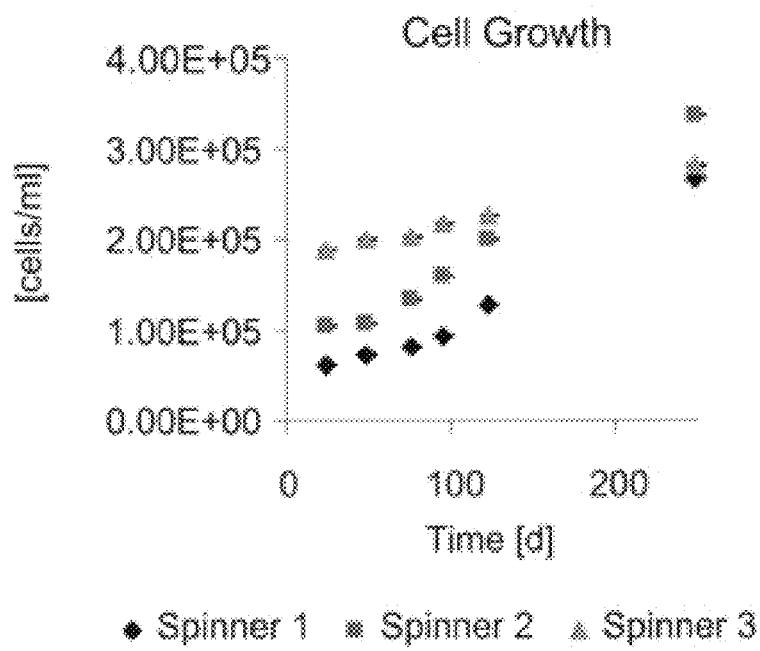

FIG. 174. Chart showing growth of hESC derived MSCs on Cytodex 3 microcarriers at microcarrier concentrations described in FIG. 175.

FIG. 175. Table showing concentration of microcarriers and cells used in Example 42.1 as well as doubling times achieved.

Figures 176, 177:
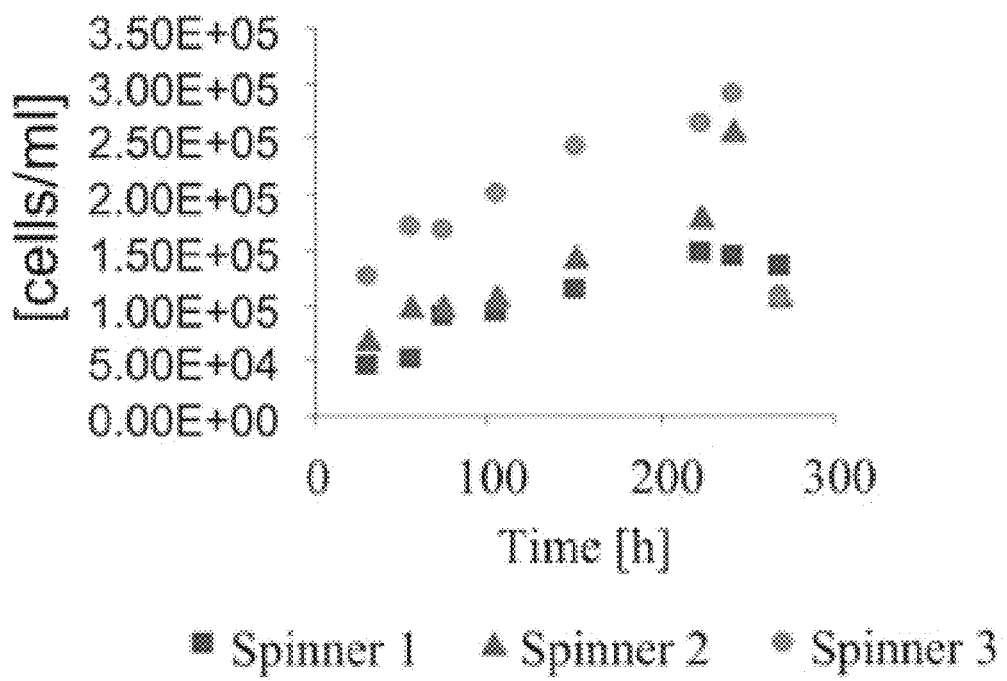

FIG. 176. Chart showing growth of hESC derived MSCs on Cytodex 3 microcarriers at cell seeding concentrations described in FIG. 177.

FIG. 177. Table showing concentration of microcarriers and cells used in Example 42.2 as well as doubling times achieved.

Figures 178, 179:
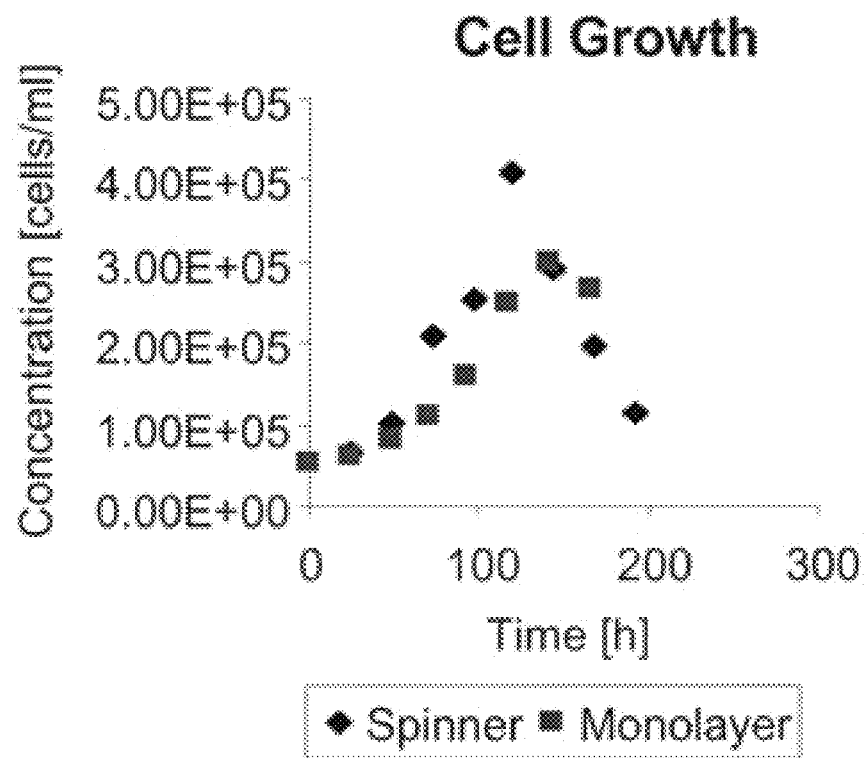

FIG. 178. Chart showing comparison of growth of hESC derived MSCs on Cytodex 3 microcarriers and in monolayer control culture.

FIG. 179. Table showing concentration of microcarriers and cells used in Example 42.3 as well as cell density and doubling times achieved.

Figures 180, 181:
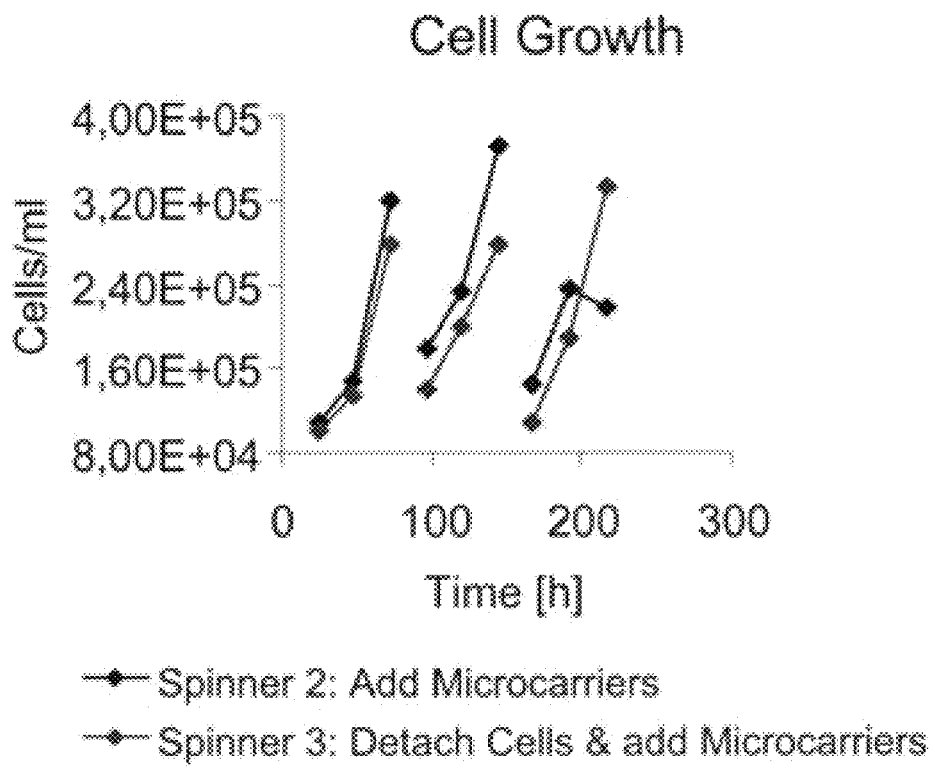

FIG. 180. Chart showing growth of hESC derived MSCs on Cytodex 3 microcarriers over 3 passages and for two methods of passage (see Example 42.4).

FIG. 181. Table showing doubling times achieved for hESC derived MSCs grown on Cytodex 3 microcarriers over 3 passages and for two methods of passage (see Example 42.4).

Figure 182:
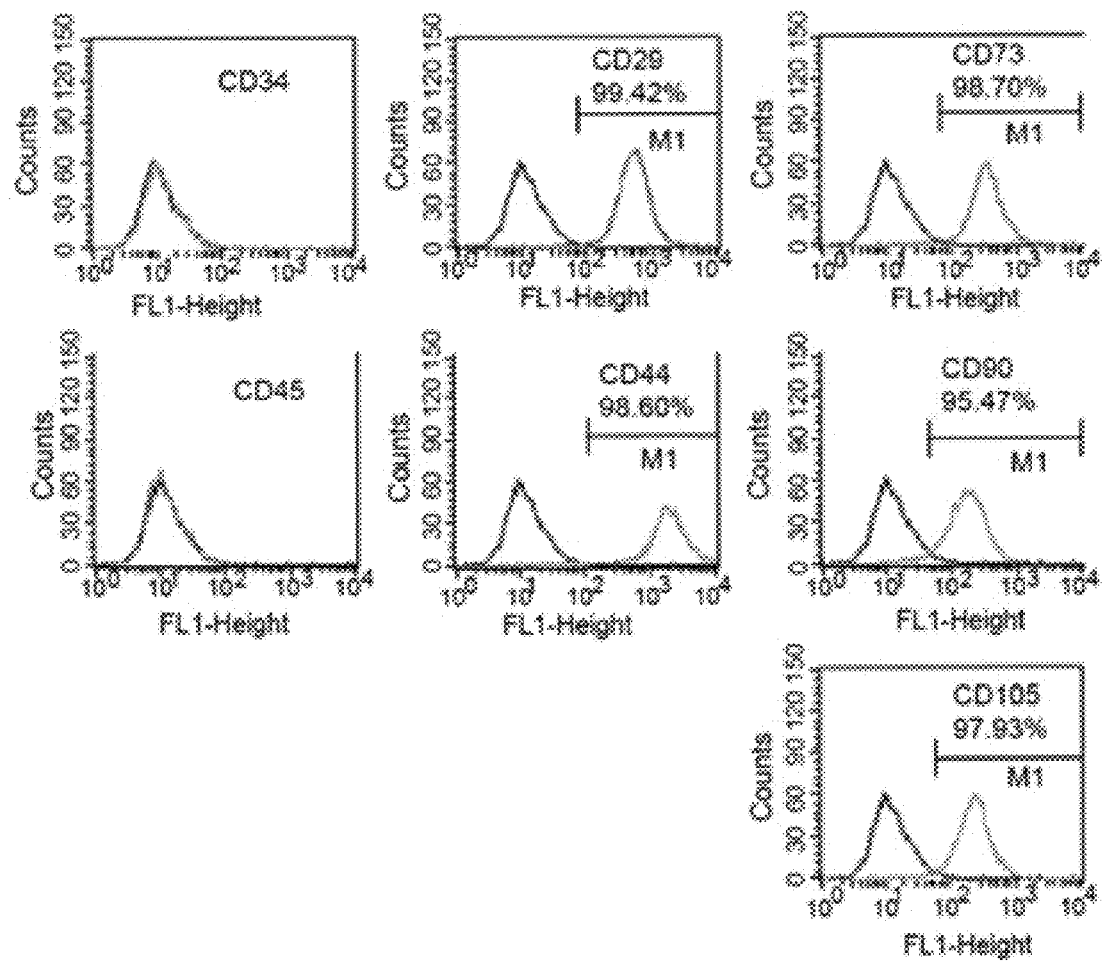

FIG. 182. FACS analysis at day 10 for MSC markers CD34, CD29, CD73, CD45, CD44, CD90 and CD105 for hESC derived MSCs grown on Cytodex 3 microcarriers over 3 passages when passaged by addition of microcarriers.

Figure 183:
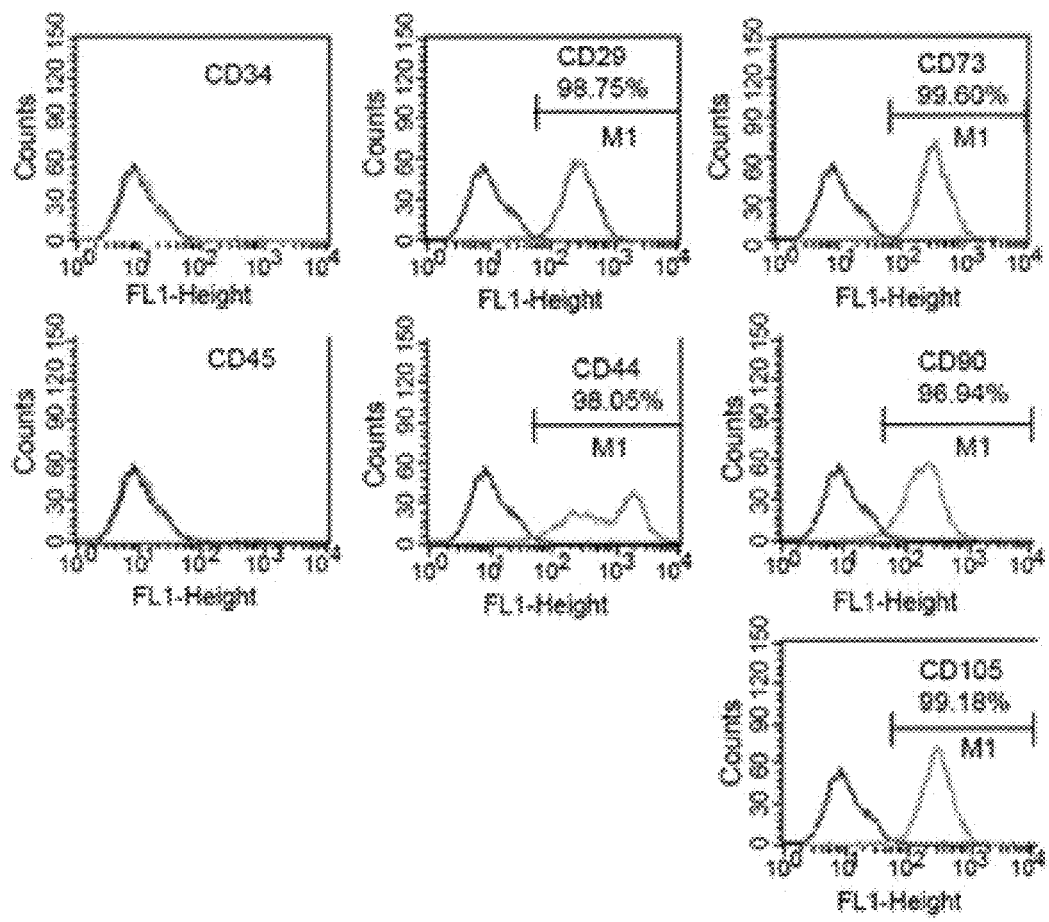

FIG. 183. FACS analysis at day 10 for MSC markers CD34, CD29, CD73, CD45, CD44, CD90 and CD105 for hESC derived MSCs grown on Cytodex 3 microcarriers over 3 passages when passaged by detachment with tryplE enzyme followed by addition of microcarriers.

Figure 184:
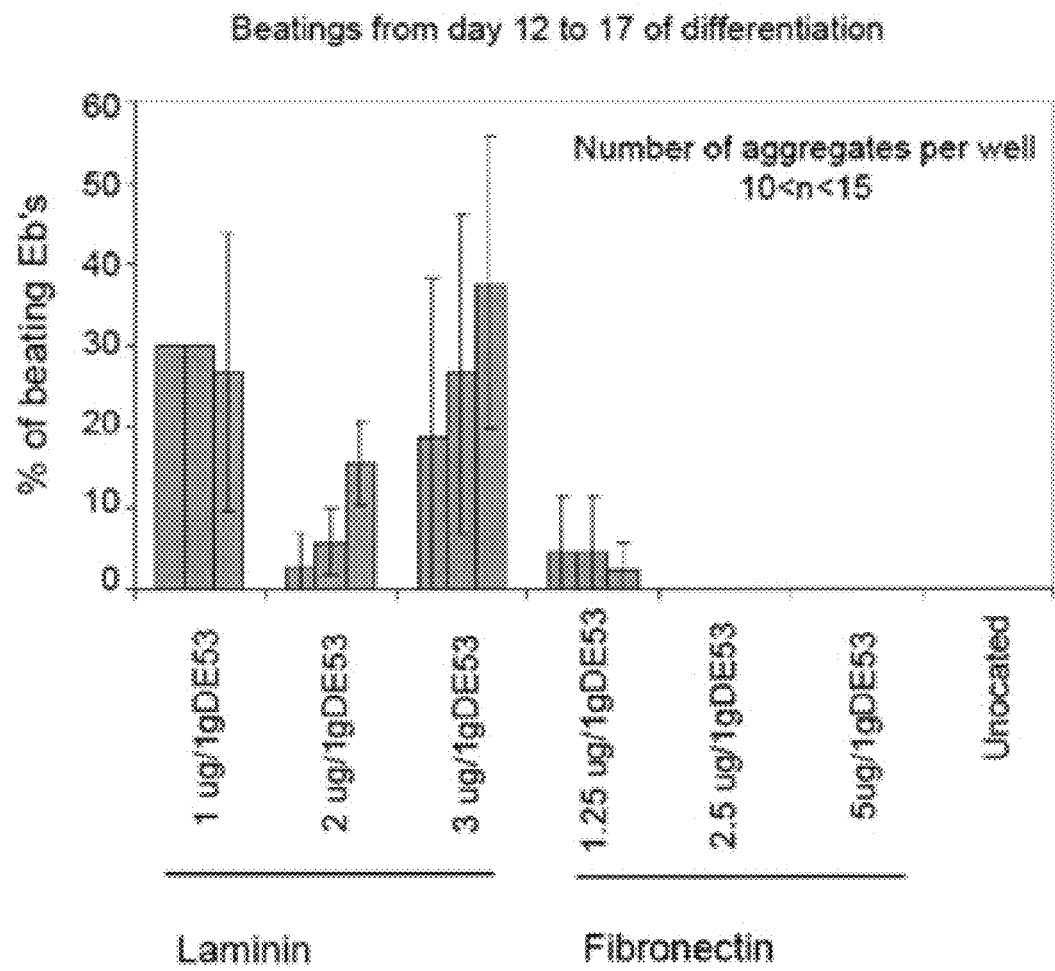

FIG. 184. Laminin coating (1 or 3 micrograms/gram of cellulose microcarriers) provides better cell attachment and hence improved numbers of beating aggregates compared to fibronectin or uncoated microcarriers.

Figure 185:
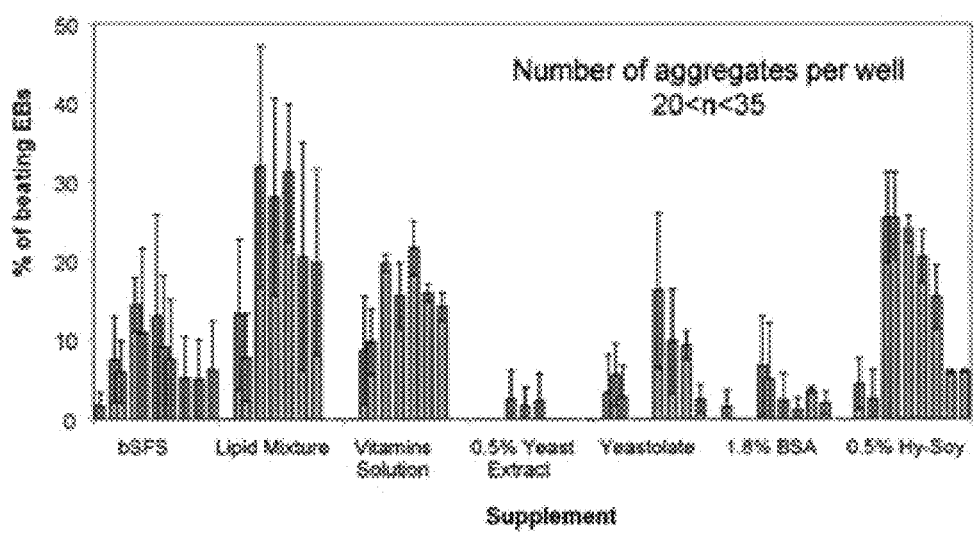
Figure 186A:
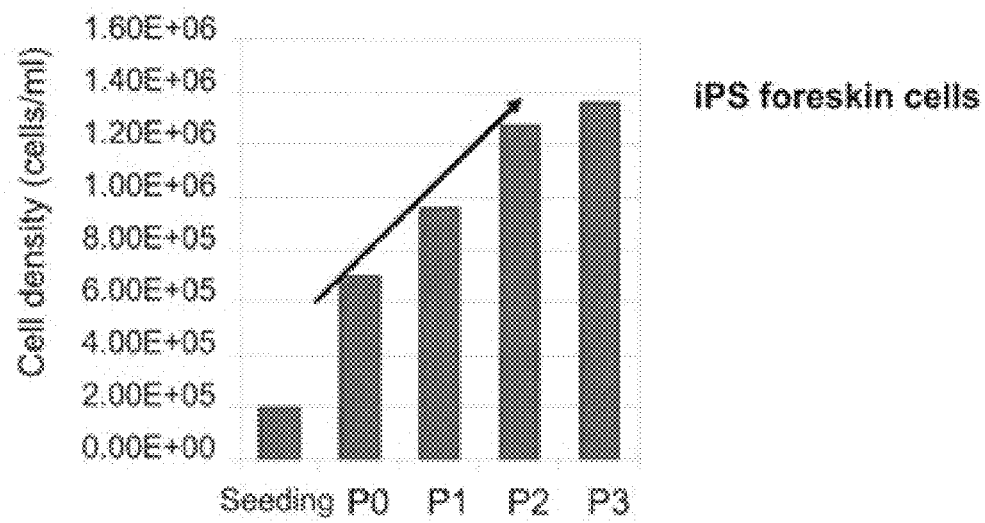
Figure 186B:
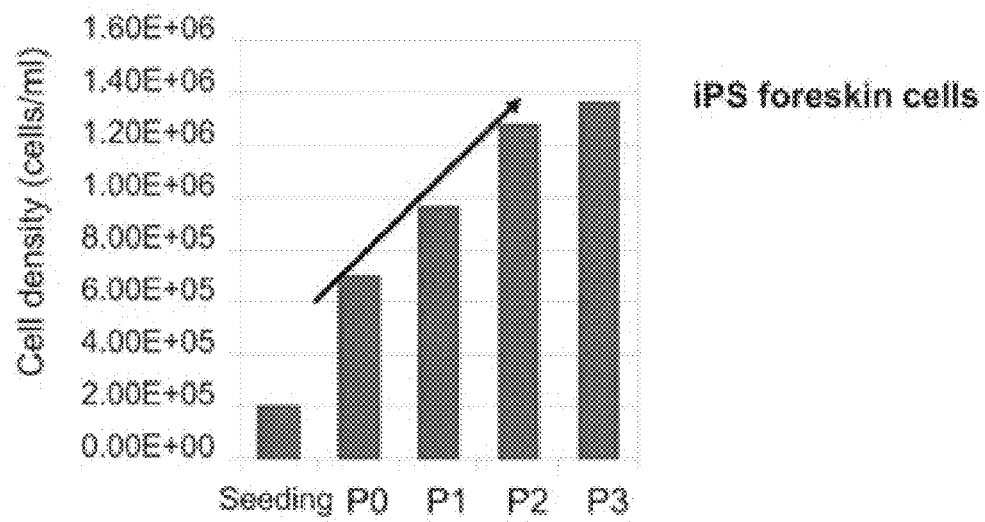
Figure 186C:
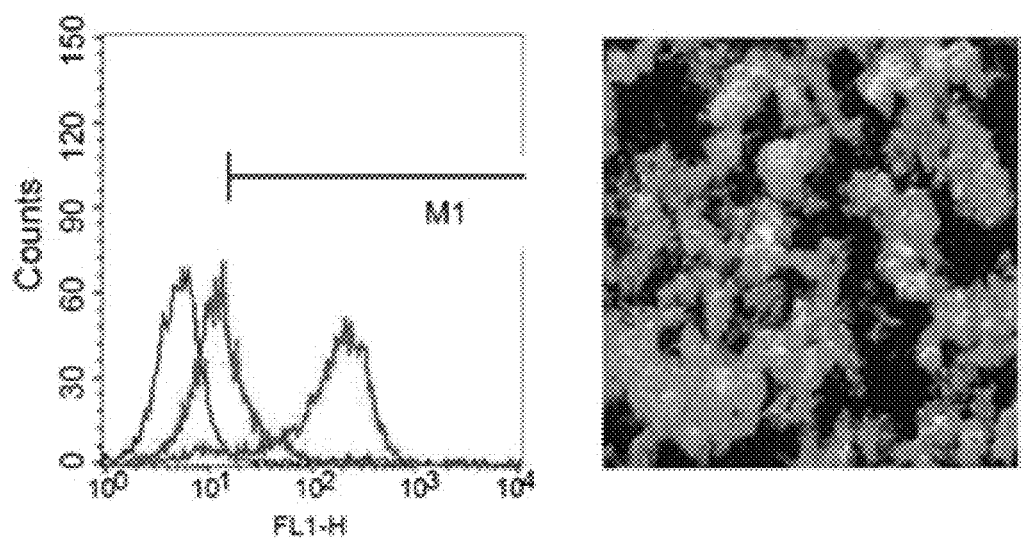
Figure 186D:
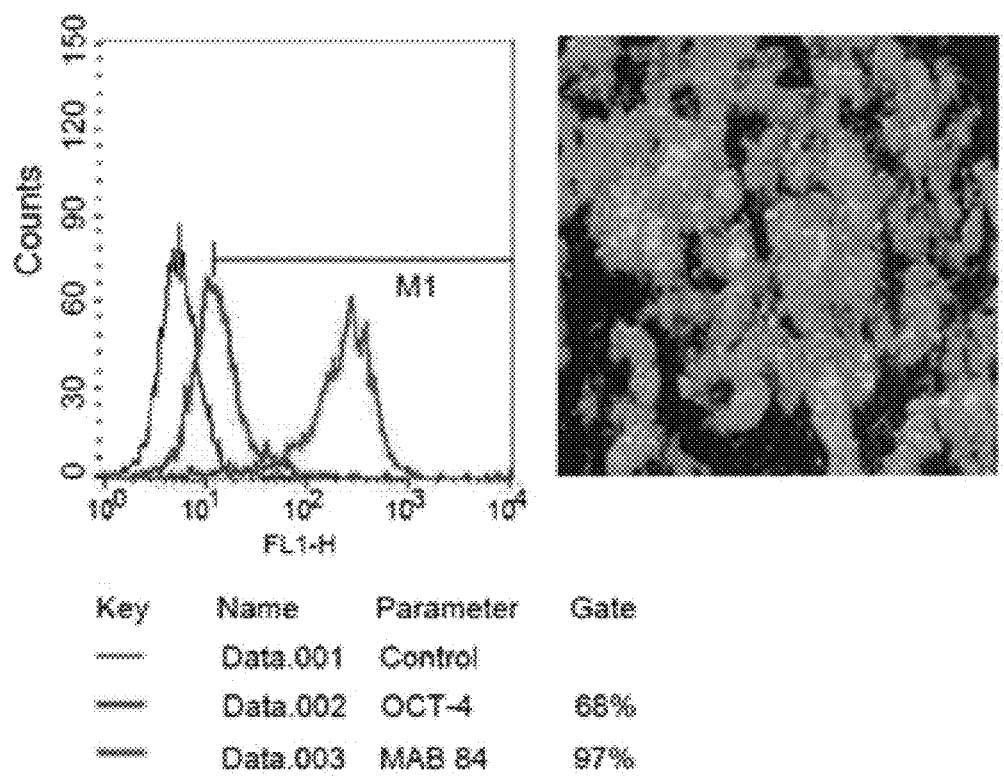

FIG. 185. Evaluation of different media supplements in laminin coated DE53 microcarrier cultures shows that chemically defined lipid mixture, Vitamin solution, and Hy-Soy (Soy hydrolysate) leads to significantly improved number of beating embryoid bodies or cardiomyocytes.

FIG. 186. Continuous passaging of 2 human iPS cell lines over 2 or 3 weeks on cellulose microcarriers in serum free media, mTeSR1, shows increasing cell numbers and stable expression of pluripotent markers, Oct-4 and mAb 84 (FIG. 186A) Density of iPS foreskin cells from seeding through passage 3; (FIG. 186B) Density of iPS IMR cells from seeding through passage 3; (FIG. 186C) FACS analysis and micrograph of IPS foreskin cells; (FIG. 186D) FACS analysis and micrograph of iPS IMR cells.

Figure 187:
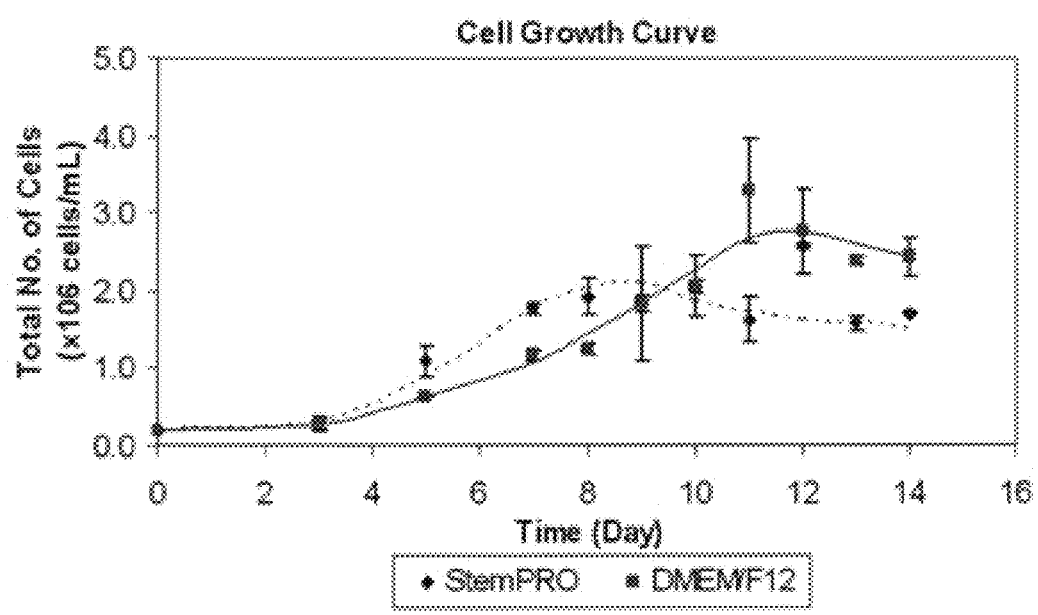

FIG. 187. Graph showing cell density of hESC obtained in controlled low glucose feeding experiments.

Figure 188:
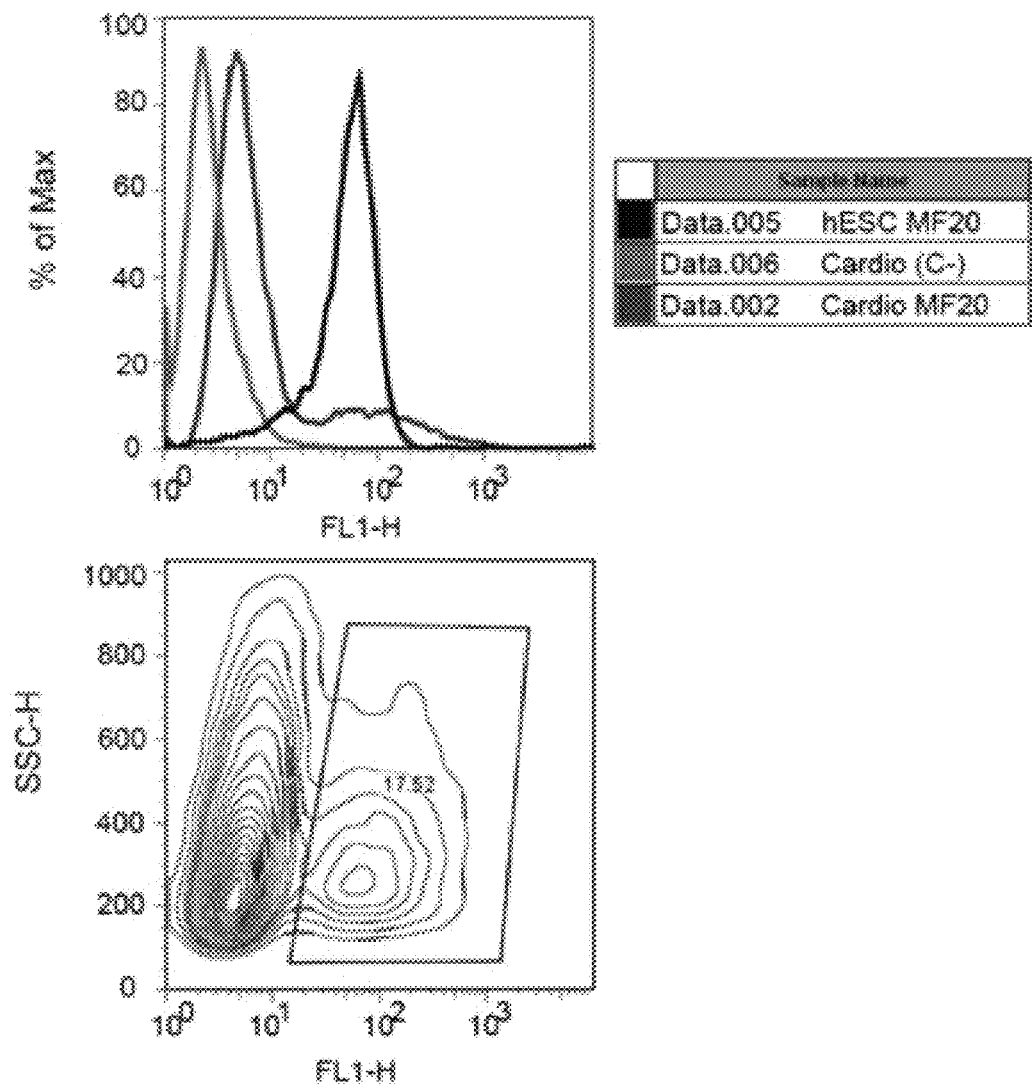

FIG. 188. Charts showing FACS characterisation of cardiomyocytes produced from H3 cell line grown on DE53 microcarriers stained with anti-myosin heavy chain (17.5%) vs. control hESC.

Figure 189:
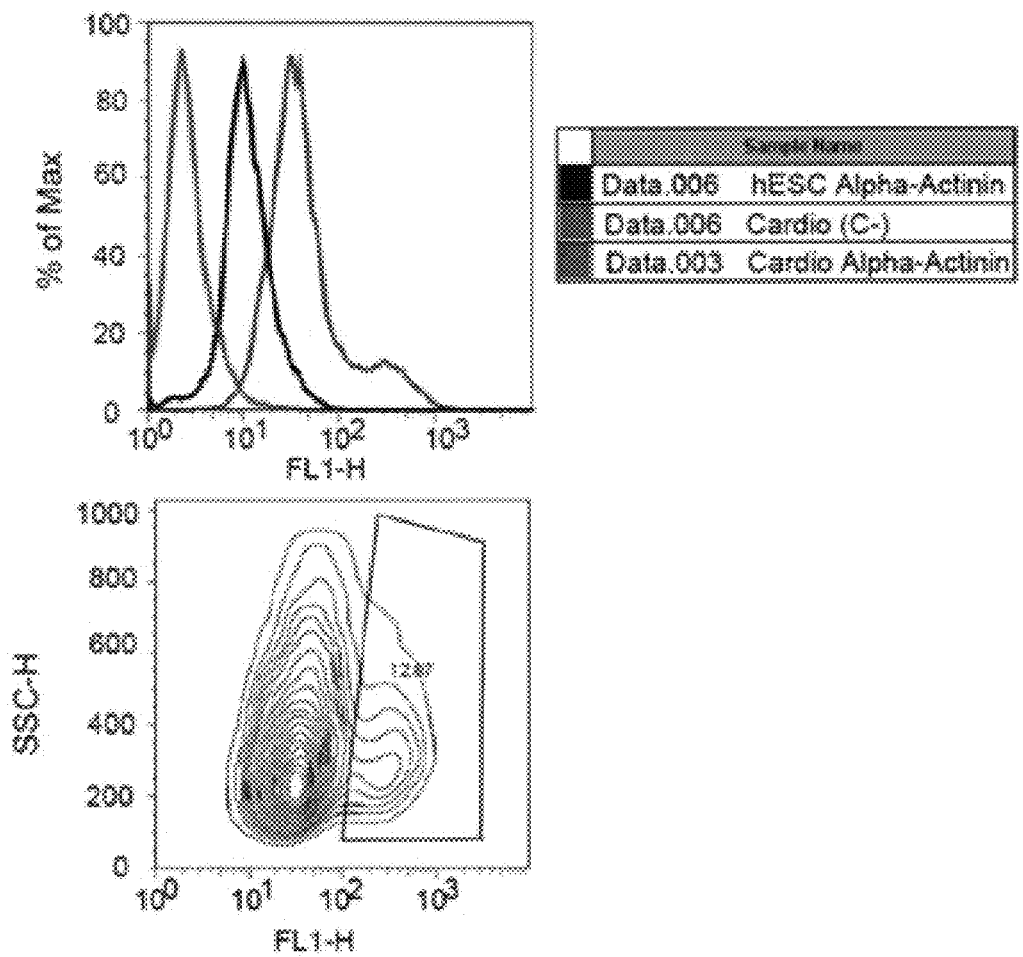

FIG. 189. Charts showing FACS characterisation of cardiomyocytes produced from H3 cell line grown on DE53 microcarriers stained with sarcomeric alpha actinin (12.9%) vs. control hESC.

Figure 190:
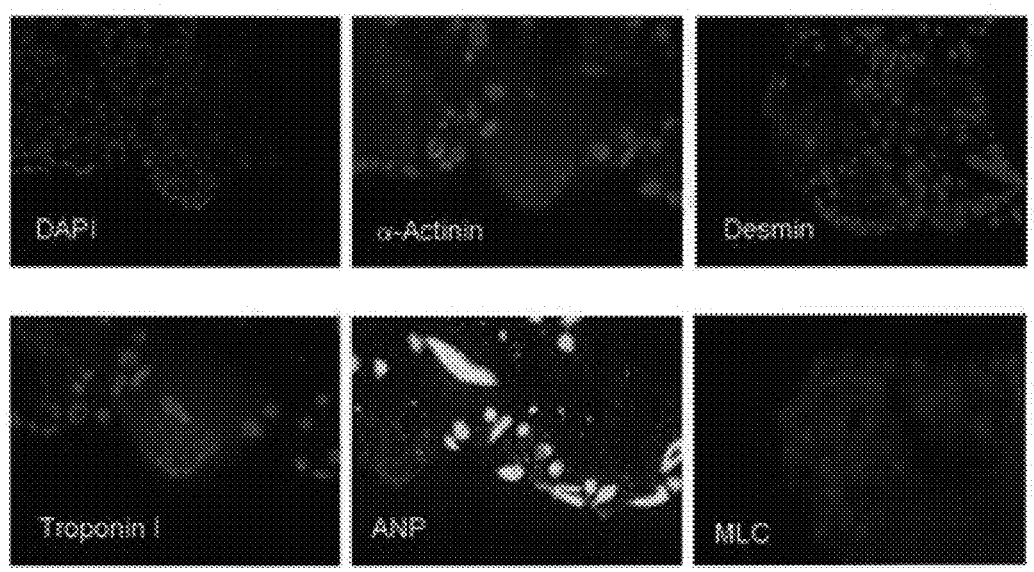

FIG. 190. Micrographs showing cardiomyocytes grown on laminin coated DE53 microcarriers stained with cardiomyocyte markers: sarcomeric alpha actinin, desmin, troponin 1, atrial natriuretic peptide (ANP), myosin light chain, and nuclear stain DAPI.

Figure 191:
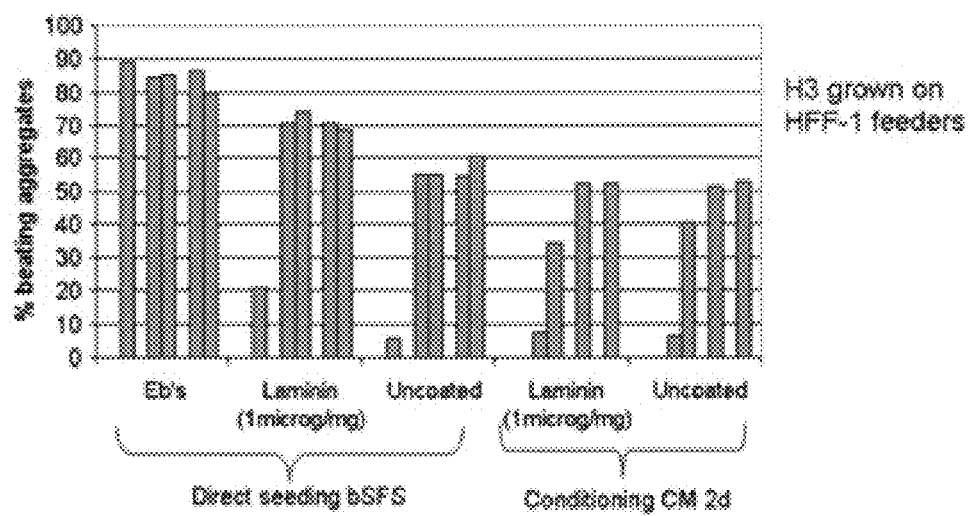

FIG. 191. Direct seeding to differentiation media vs. 2 days in conditioned media prior to differentiation. Chart showing percentage of beating aggregates formed on laminin coated and uncoated microcarriers vs. embryoid bodies (Eb's) when H3 cell line grown on human feeders is directly seeded to bSFS differentiation media or after incubation with conditioned media for 2 days.

Figure 192:
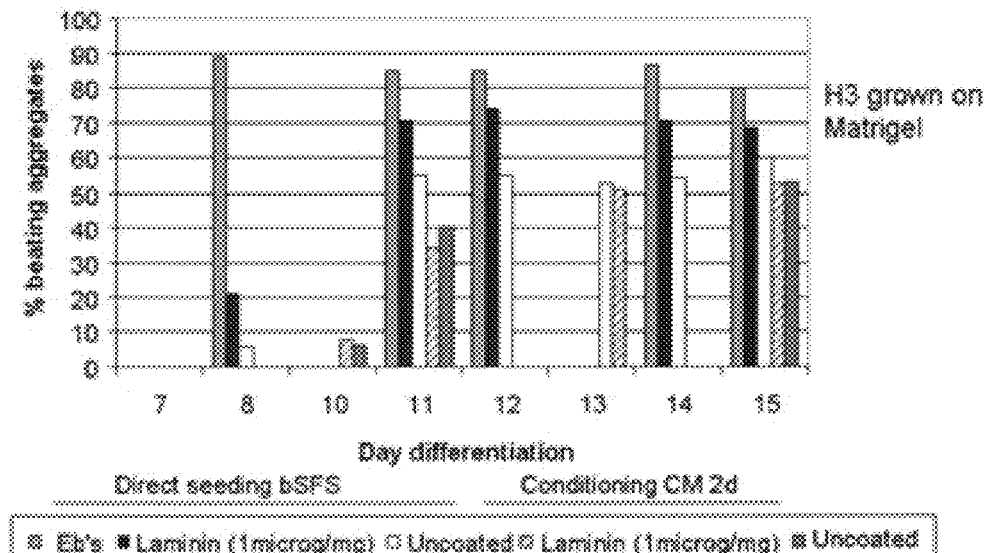

FIG. 192. Direct seeding to differentiation media vs. 2 days in conditioned media prior to differentiation. Chart showing percentage of beating aggregates formed on laminin coated and uncoated microcarriers vs. embryoid bodies (Eb's) when H3 cell line grown on Matrigel is directly seeded to bSFS differentiation media or after incubation with conditioned media for 2 days.

Figure 193:
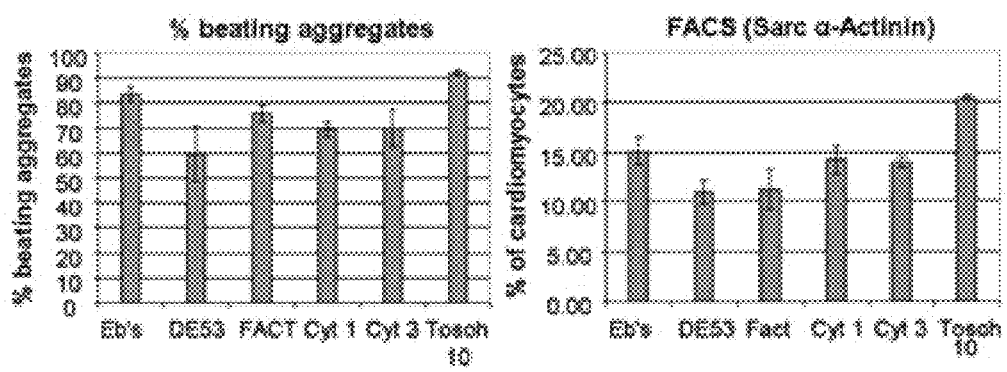

FIG. 193. Differentiation to cardiomyocytes on different microcarriers. Charts showing percentage of beating aggregates formed on different microcarriers and percentage of sarcomeric alpha actinin staining on different aggregates. Tosoh 10 appears to give the highest yield of all the microcarriers and compared to embryoid bodies.

Figure 194:
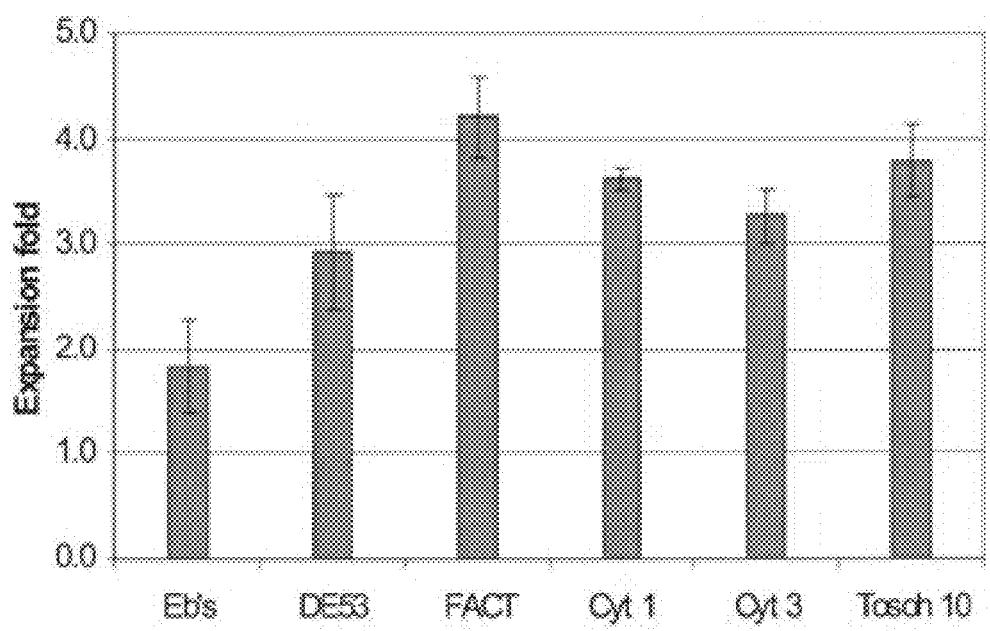

FIG. 194. Chart showing expansion fold of cardiomyocytes on different microcarriers compared to embryoid bodies. Microcarriers enables approximately 4-fold expansion compared to 2-fold in embryoid bodies.

Figure 195:
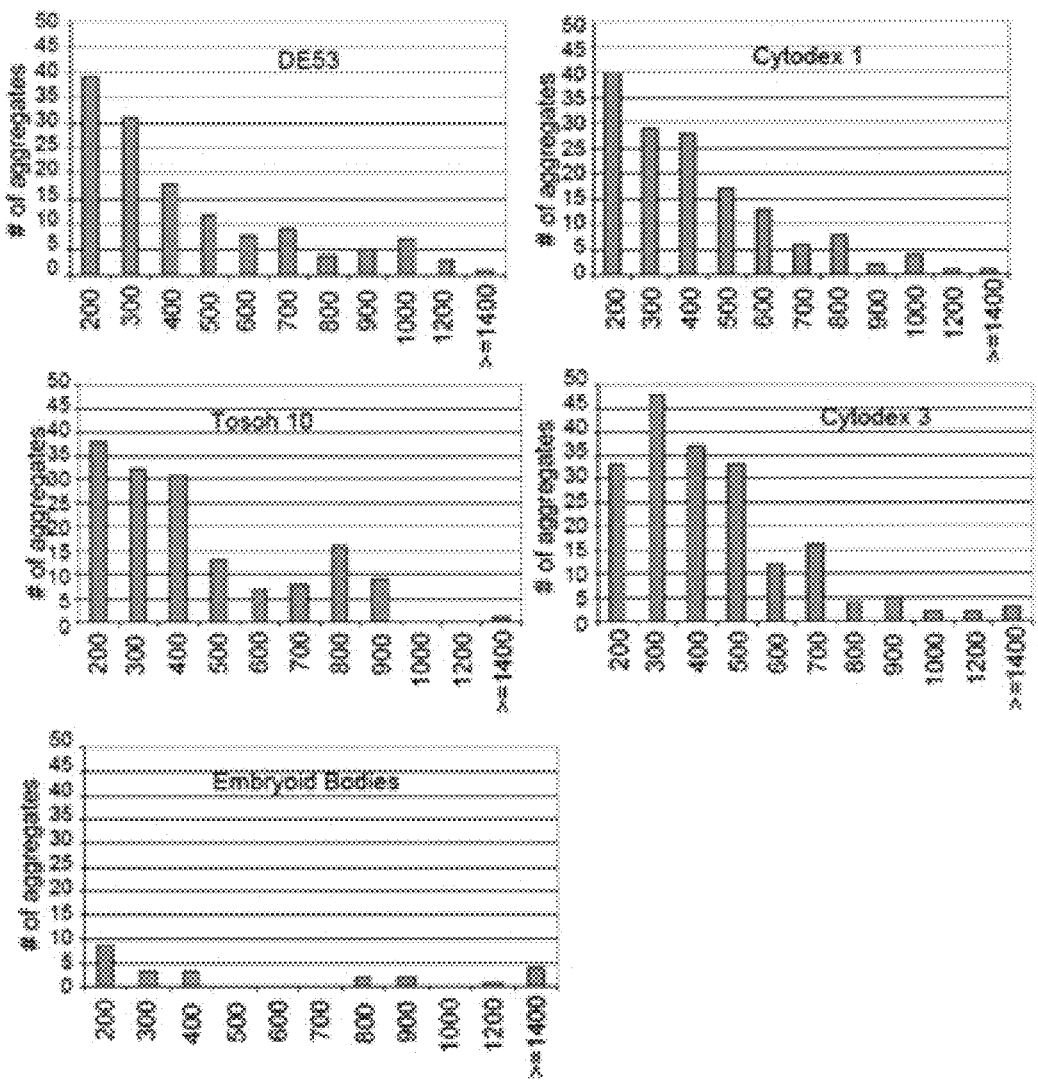

FIG. 195. Aggregates of cardiomyocytes. Charts showing size distributions of aggregates on different microcarriers. Tosoh 10 appear to have a more uniform size distribution. Embyroid bodies' sizes are very widely distributed.

Figure 196:
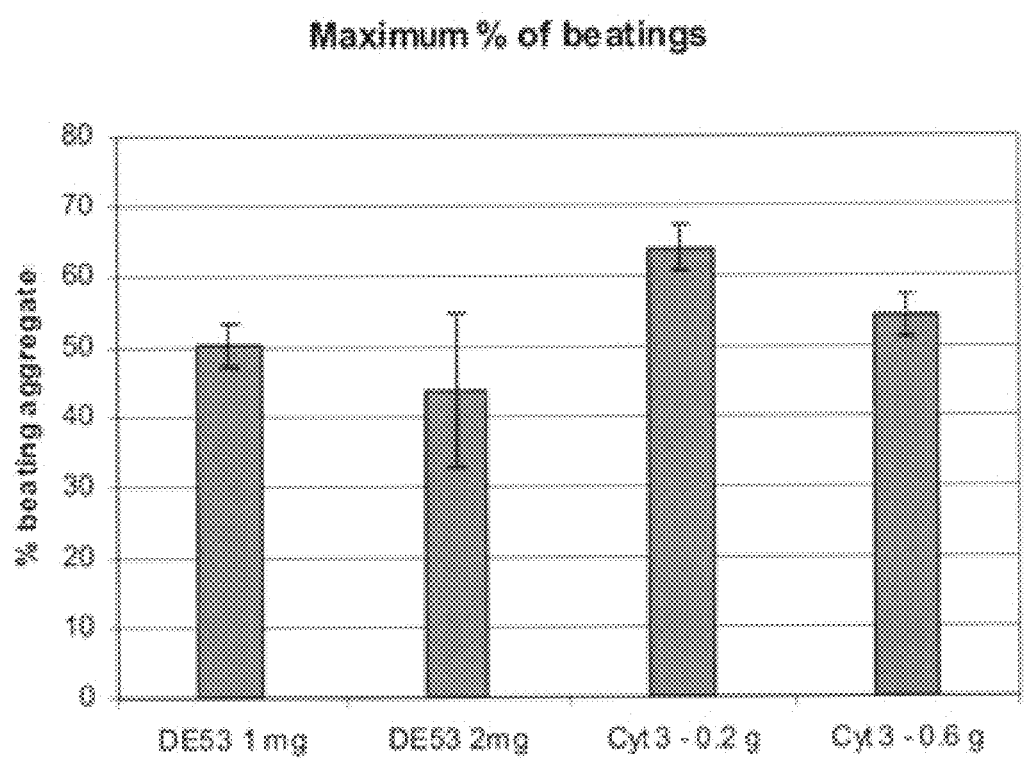

FIG. 196. Effect of microcarrier concentration on percentage of beating aggregates. Chart showing percentage of beating aggregates formed on DE53 and Cytodex 3 at different microcarrier concentrations.

Figure 197:
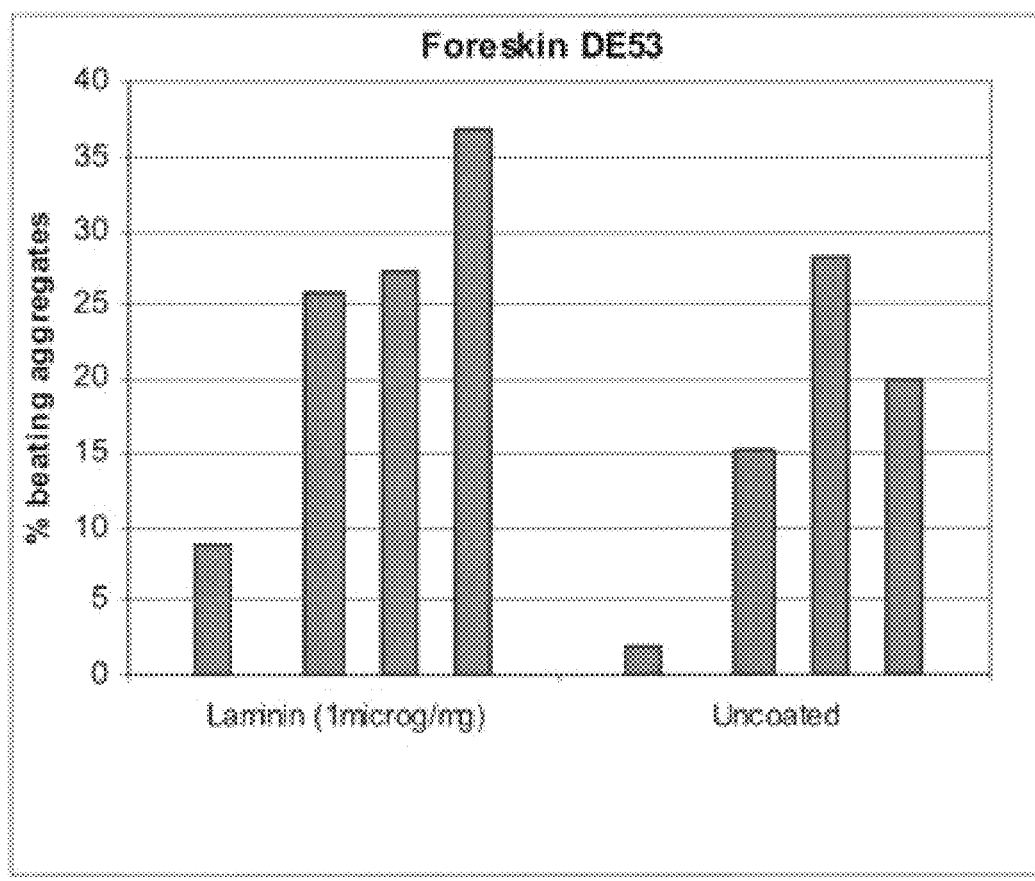

FIG. 197. Human iPS cell differentiation to cardiomyocytes. Chart showing foreskin human iPS cells from beating aggregates on laminin and uncoated DE53 microcarriers.

Figure 198:
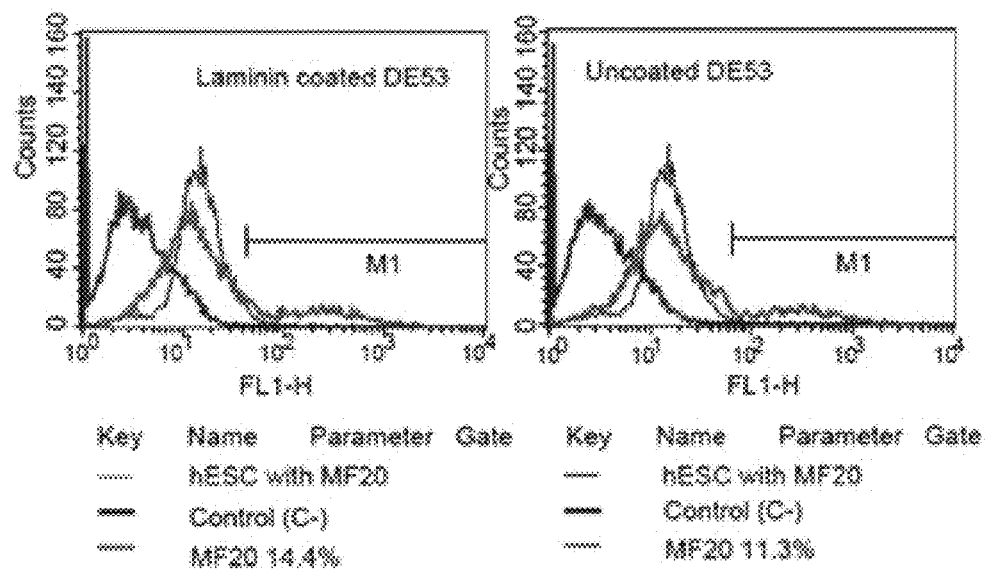

FIG. 198. Human iPS cells differentiation to cardiomyocytes. Charts showing percentage of anti-myosin chain staining by FACS of cardiomyocytes formed from human iPS cells on laminin coated and uncoated DE53 microcarriers.

Figure 199:
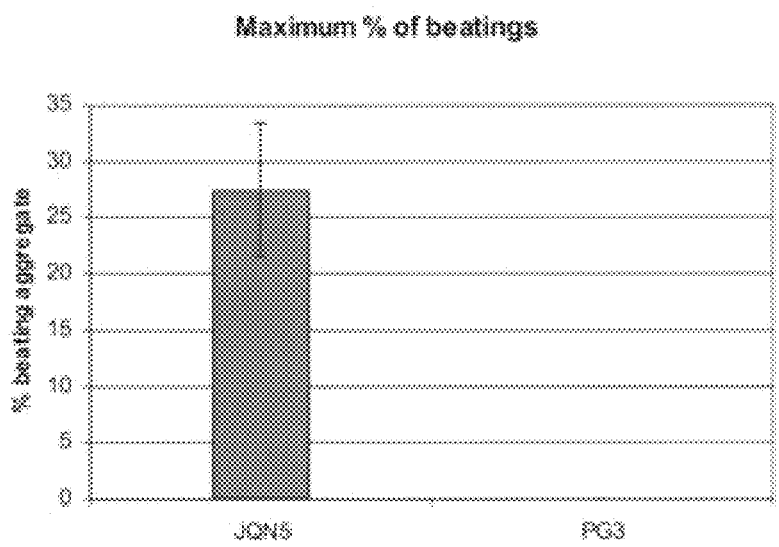

FIG. 199. Human iPS cell differentiation to cardiomyocytes. Chart showing percentage of beating aggregates formed by human iPS cells JQN5 on DE53 laminin coated microcarriers. PG3 cells didn't attach to the carriers. Human iPS cells were grown on feeders.

Figure 200:
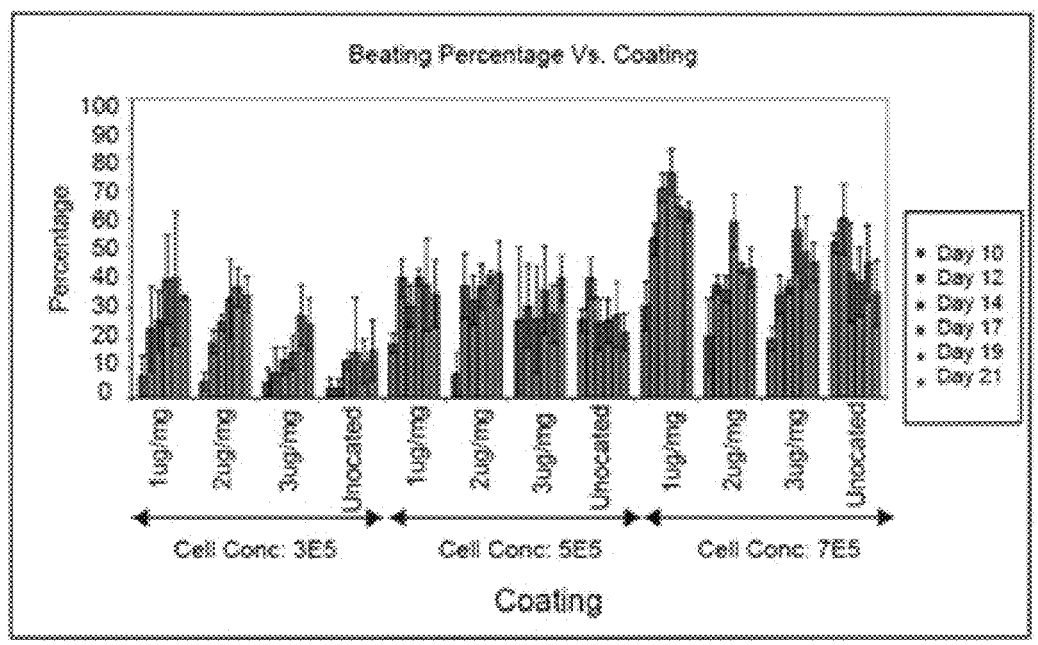

FIG. 200. Evaluation of different laminin and cell seeding concentrations on percentage of beating aggregates. Chart showing that increasing the cell seeding concentration to the microcarriers improves the number of beating aggregates. The ideal laminin concentration appears to be 1 microgram of laminin/mg of microcarriers.

Figure 201:
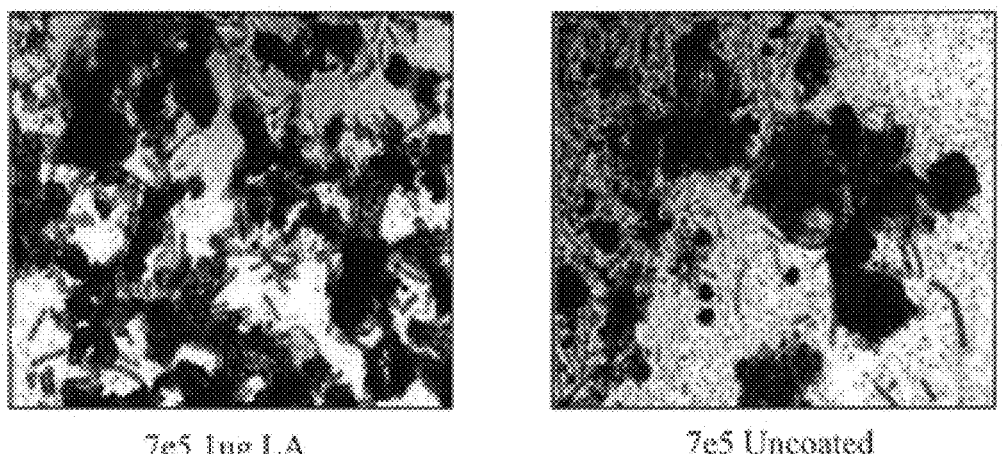

FIG. 201. Micrographs showing morphology of aggregates in laminin coated vs. uncoated microcarriers at $7 \times 10^5$ seeded cells.

FIG. 202. FACS of cardiomyocyte markers. Charts showing staining by FACS of myosin heavy chain and sarcomeric alpha actinin in laminin coated vs. uncoated microcarriers at $7 \times 10^5$ seeded cells.

Figure 203B:
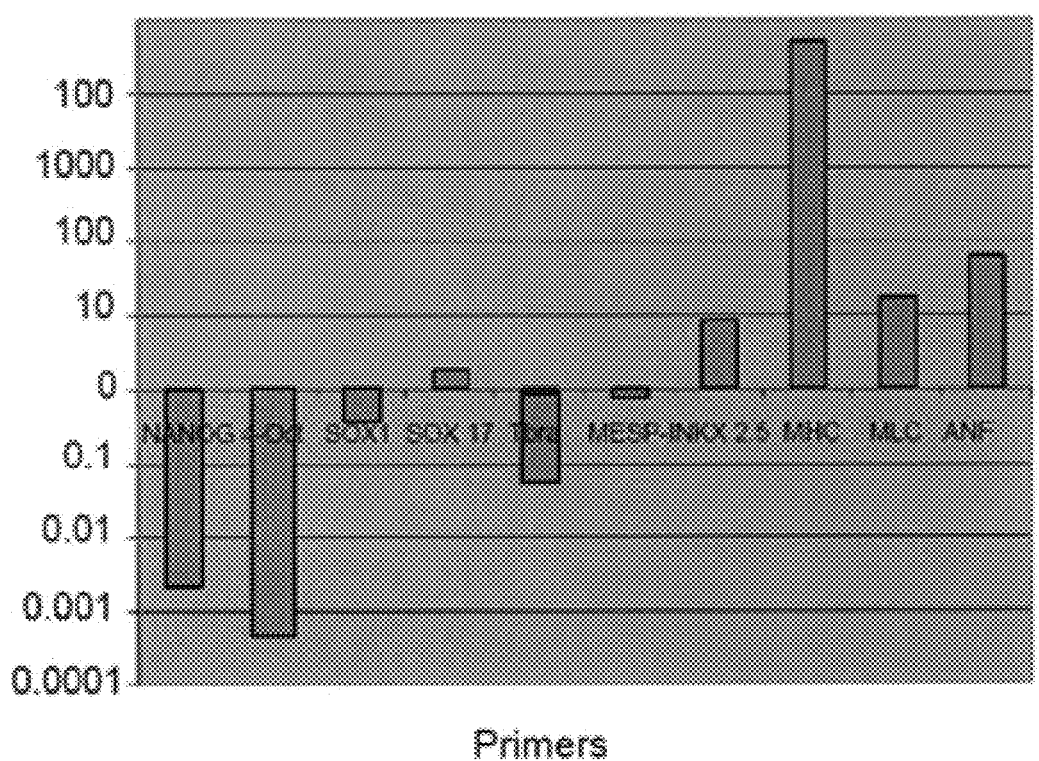

FIG. 203. Quantitative RT PCR of cardiomyocytes vs. hESC. Charts showing quantitative RT-PCR markers of pluripotency genes (decrease) and cardiomyocyte related genes (increase) in cardiomyocyte aggregates vs. hESC. FIG. 203B shows the results in a table and FIG. 203B shows the results in bar graph form for the same set of primers.

Figure 204A:
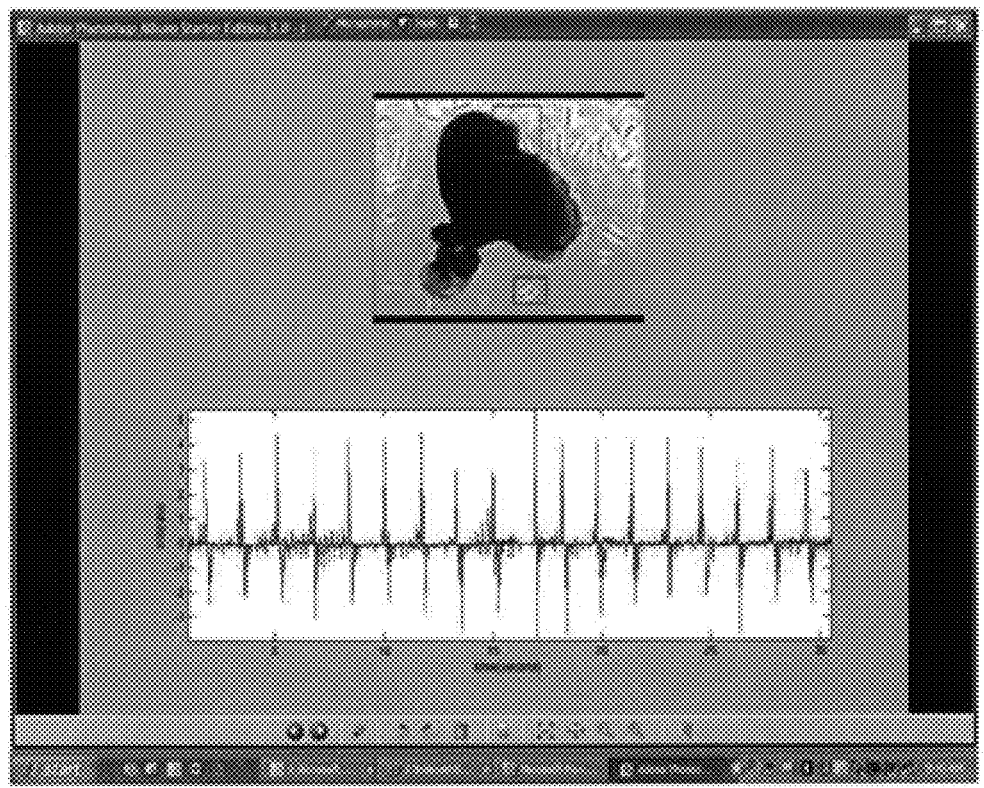
Figure 204B:
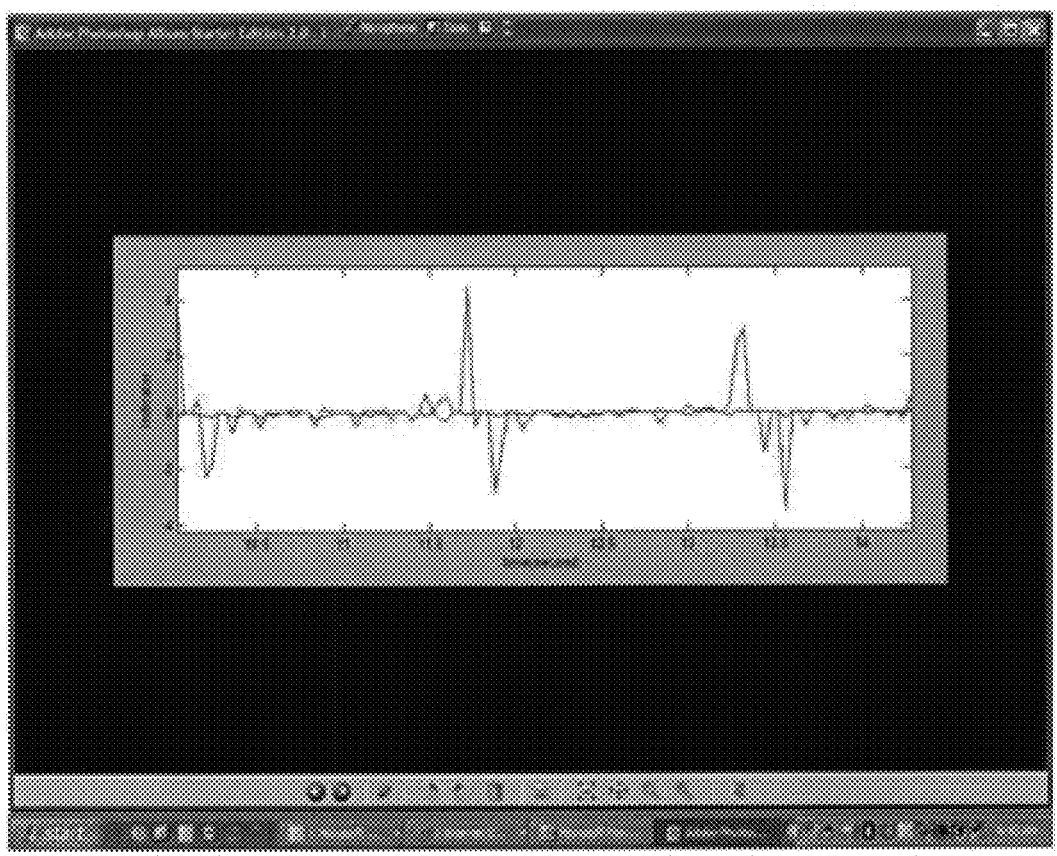

FIG. 204. (FIG. 204A) Image of beating aggregate as monitored by video imaging. Red line shows beating aggregate and blue line shows background non-beating aggregate. (FIG. 204B) Chart showing time interval between each beat of the aggregate.

Figure 205A:
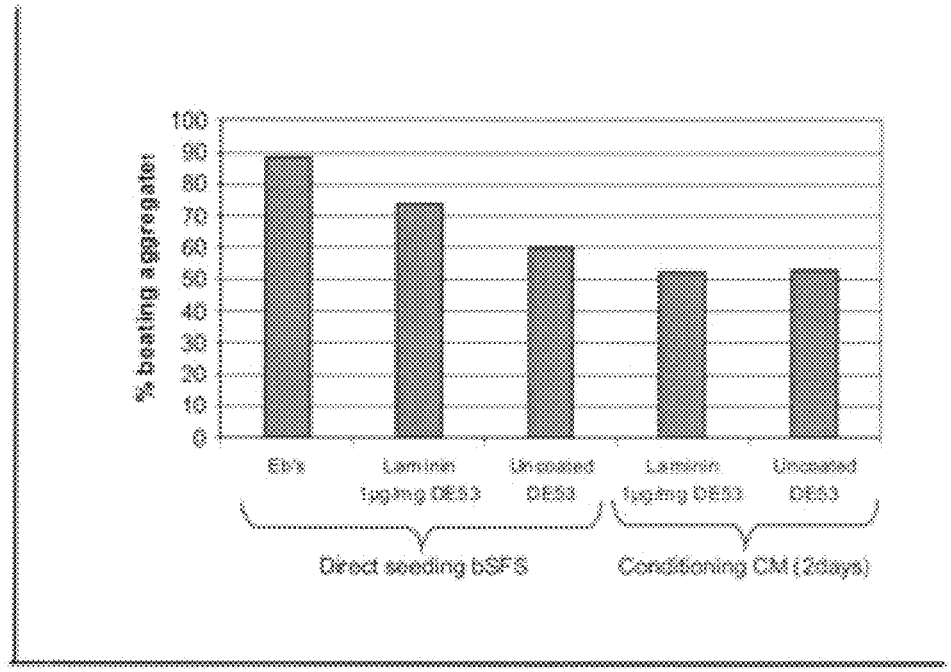
Figure 205B:
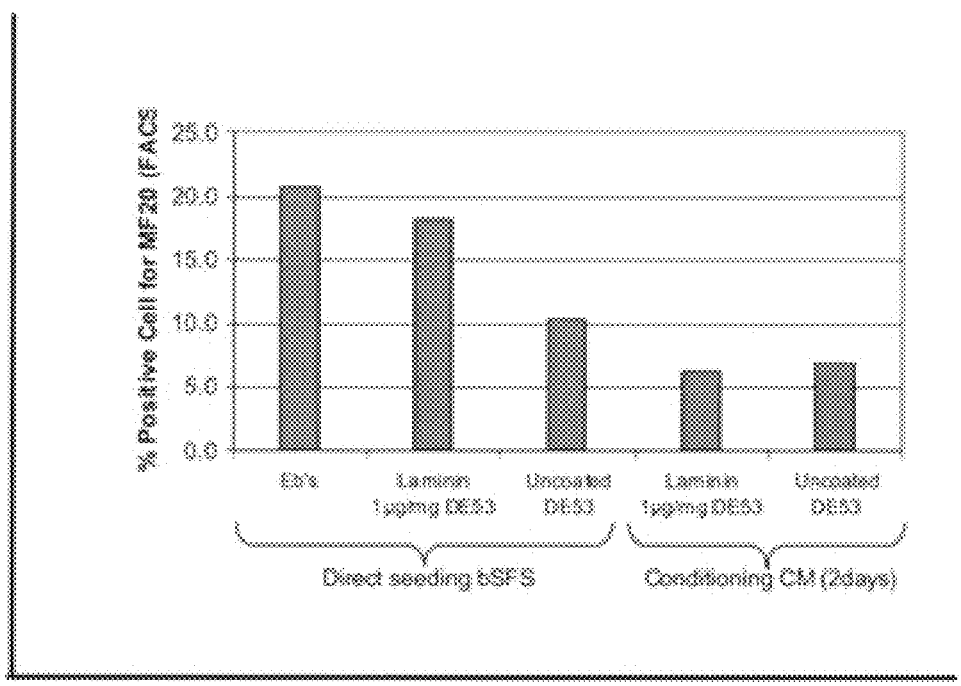

FIG. 205. (FIG. 205A) Maximum % of beating aggregates scored under the microscope between day 10 and 16 of differentiation for different seeding conditions. (FIG. 205B) Percentage of positive cells stained for MF20 (Myosin Heavy Chain) analyzed by flow cytometric analysis of cultures harvested on day 16 after differentiation.

Figure 206:
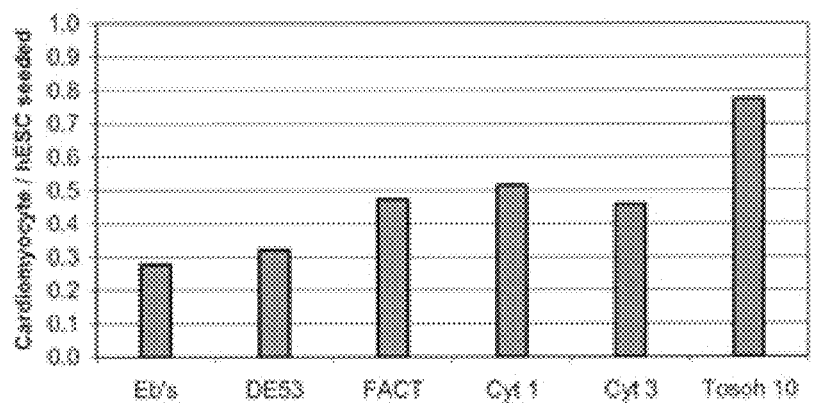

FIG. 206. Chart showing ratio of cardiomyocytes produced at the end of the culture over hESC seeded.

Figure 207A:
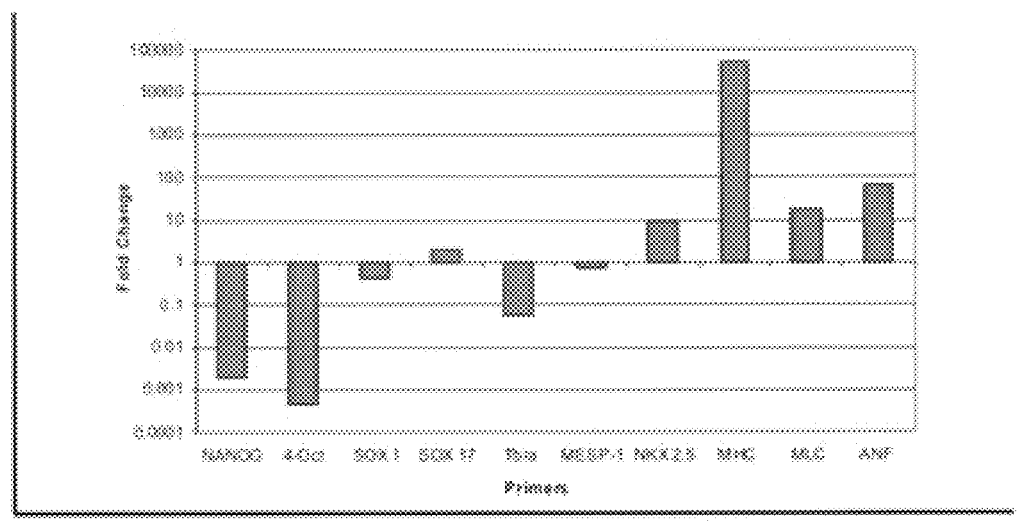
Figure 207B:
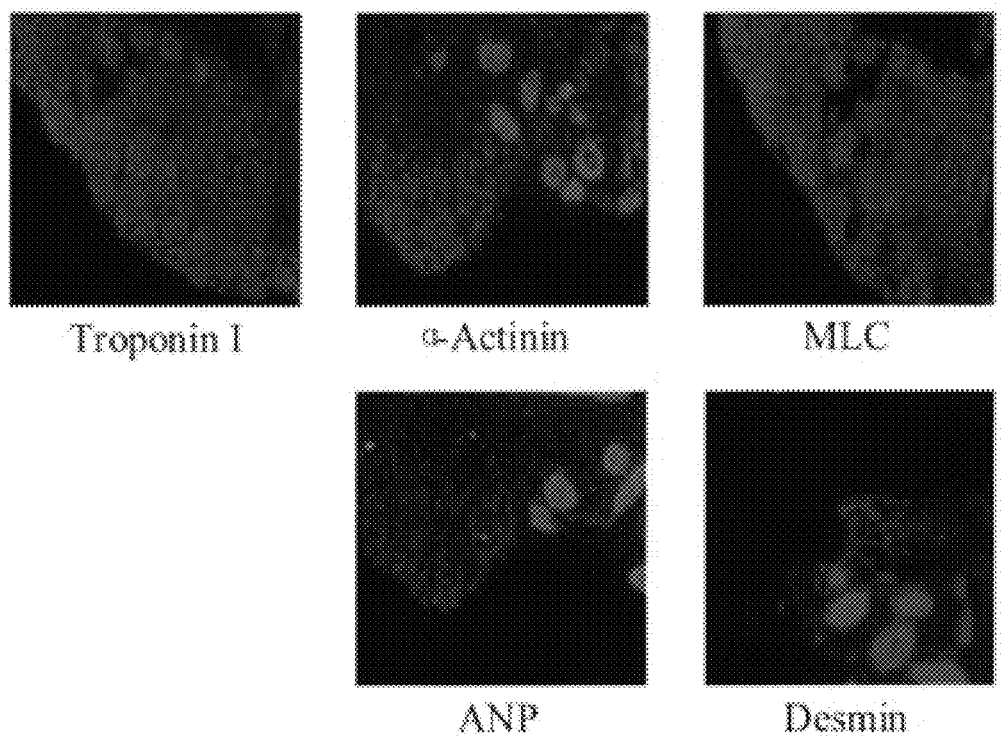

FIG. 207. (FIG. 207A) Gene expression fold change of beating aggregates in comparison with undifferentiated hESC. (FIG. 207B) Immunohistological analysis of beating aggregates with cardio specific markers: Troponin I,α-Actinin, Myosin Light Chain—MLC, Desmin (all in red) Atrial Natriuretic Peptide (ANP) in green, and DAPI nucleus staining in blue.

Figure 208B:
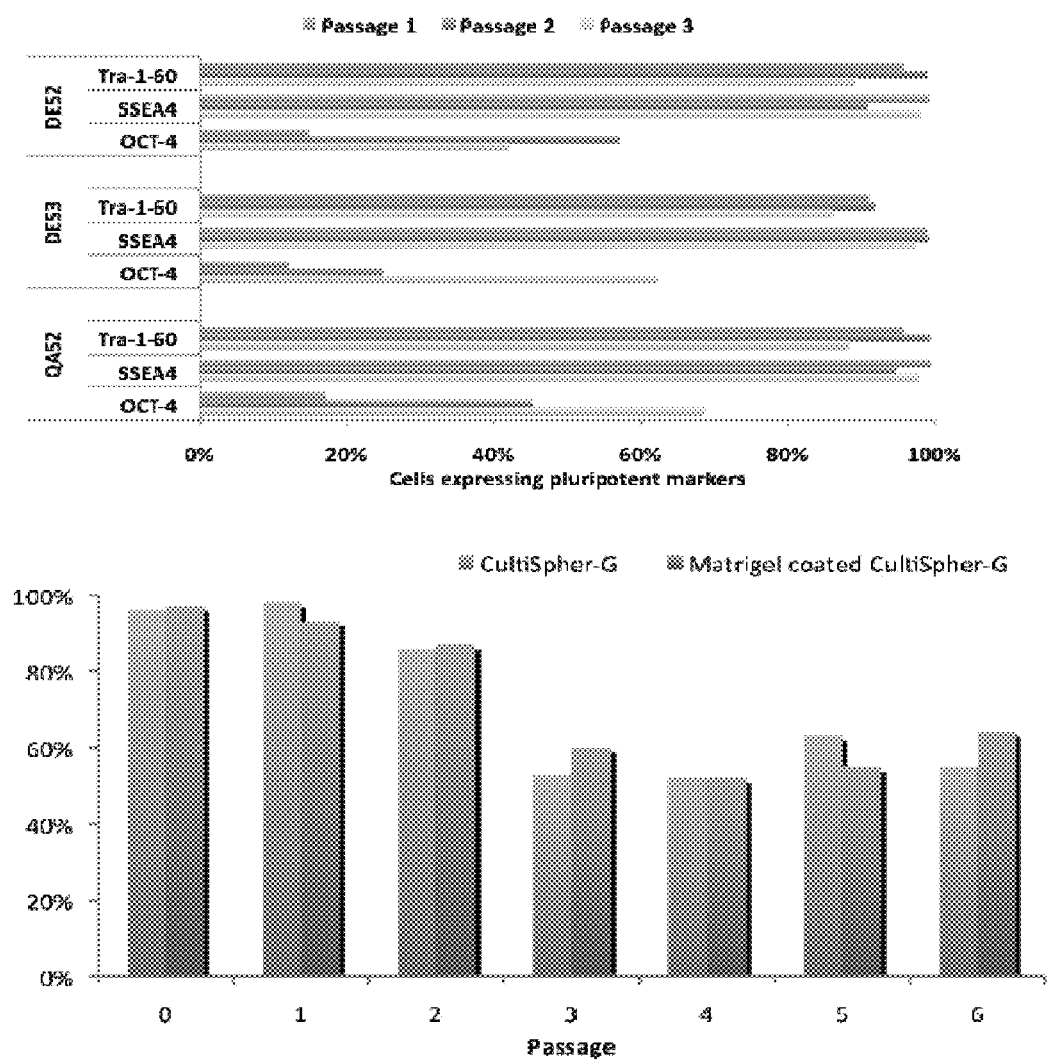
Figure 208C:
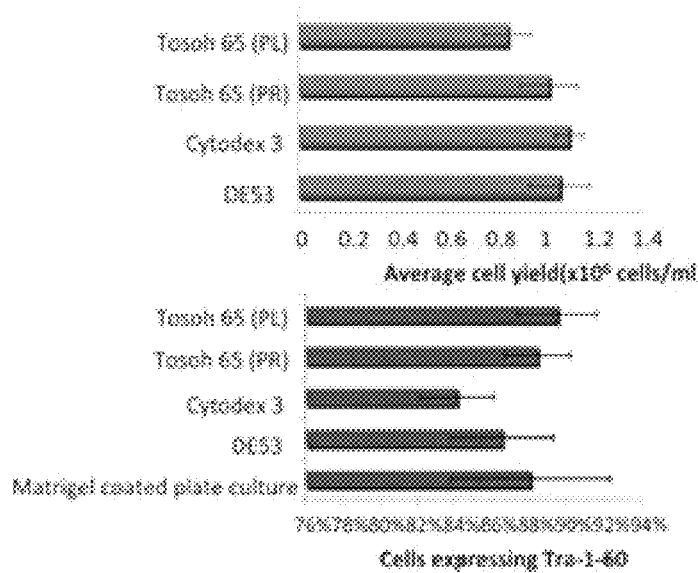
Figure 208D:
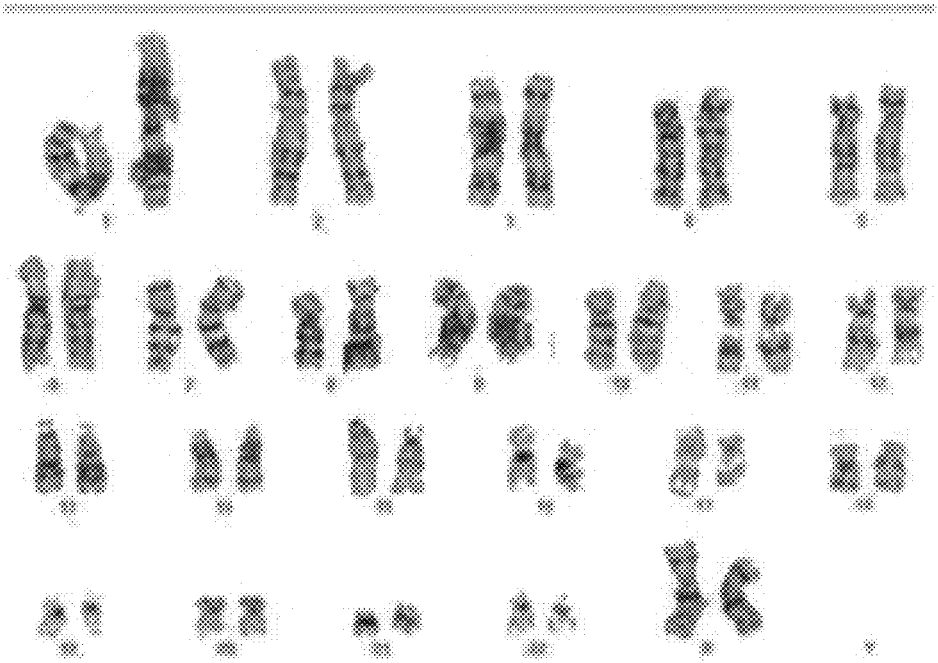

FIG. 208. (FIG. 208A) Micrographs showing hESC morphology on seven types of microcarriers (Cytodex 1, Tosoh 65, Tosoh 10, Cultispher G, Cytodex 3, DE53, CM52). Cells on smaller microcarriers (Tosoh 65, Tosoh 10) formed cell-microcarrier aggregates with the microcarriers embedded inside. Similar cell growth on both microporous and smooth microcarriers was observed. Poor cell growth on negative charged microcarriers was observed. (FIG. 208B). Charts showing effects of positive charge strength on hESC growth and pluripotency using DE52 (lower positive charge—DEAE tertiary amine), DE53 (partially quarternized DEAE) and QA52 (higher positive charge—quaternary ammonium). No significant differences in cell growth and pluripotency were observed for hESC grown on rodshaped microcarriers of different charge strength. The lower chart showing hESC growth and pluripotency on microporous microcarriers. hESC on microporous microcarrier showed differentiation after two passages while maintaining similar cell growth and without Matrigel coating. (FIG. 208C) Charts showing long term cultivation of hESC on different microcarriers. Microcarriers were able to support long term cultivation of hESC in an undifferentiated state but only when coated with Matrigel. (FIG. 208D) Normal karyotype has been observed in hESC cultured on DE53 Matrigel-coated microcarriers for 25 passages.

Figure 209A:
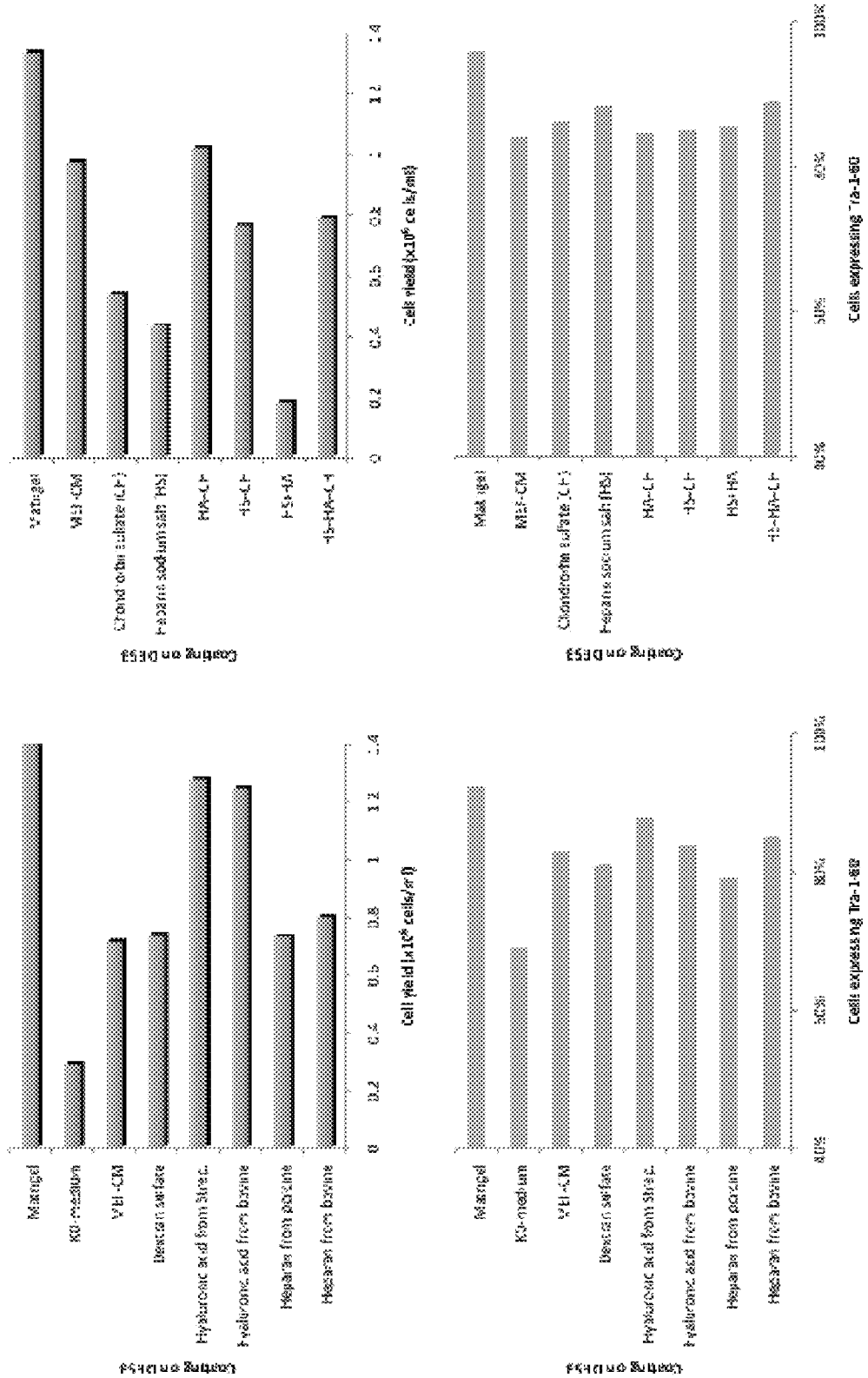

FIG. 209. FIG. 209A shows bar graphs depicting results of screening of proteoglycan and non-proteoglycan matrix components as cell attachment substrate on microcarriers. Hyaluronic Acid (HA) is a potential attachment substrate for culturing undifferentiated hESC on microcarrier. FIG. 209B shows micrograph showing that after 2 passages, only cells on DE53 coated with HA were able to maintain cell growth. FACS analysis showing expression of OCT-4 and Tra-1-60 of hESC at passage 17 on DE53 coated with hyaluronic acid.

Figure 210A:
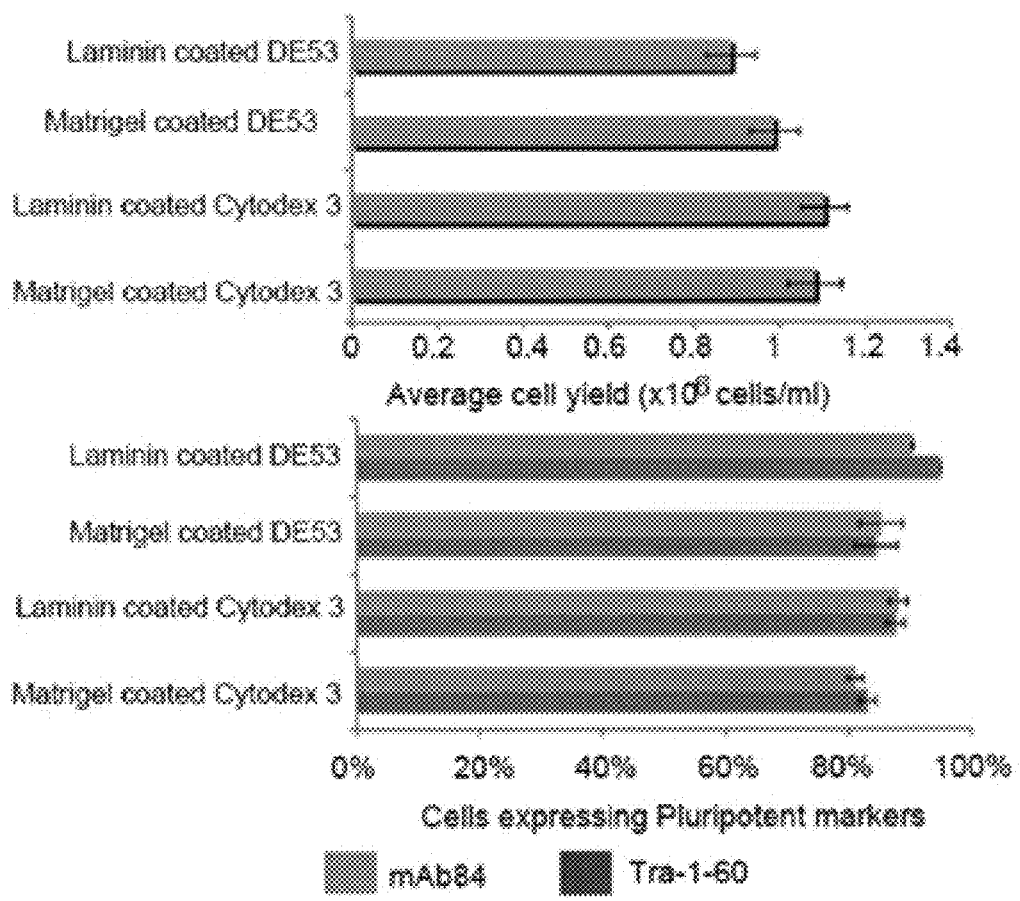
Figure 210B:
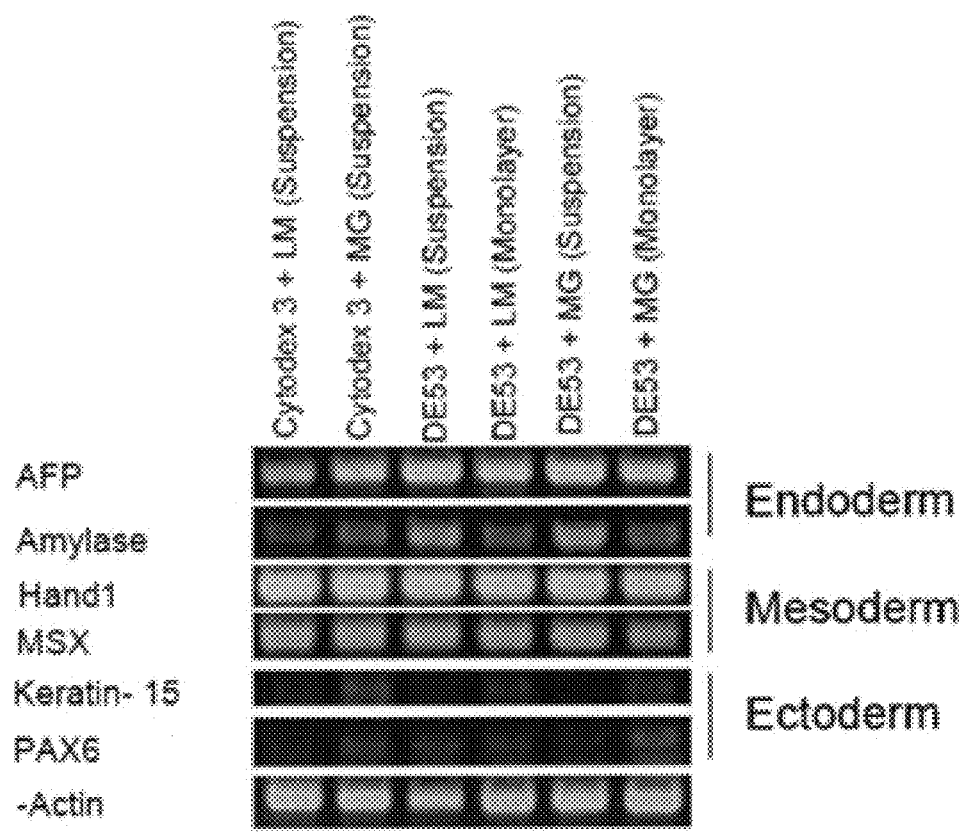
Figure 211A:
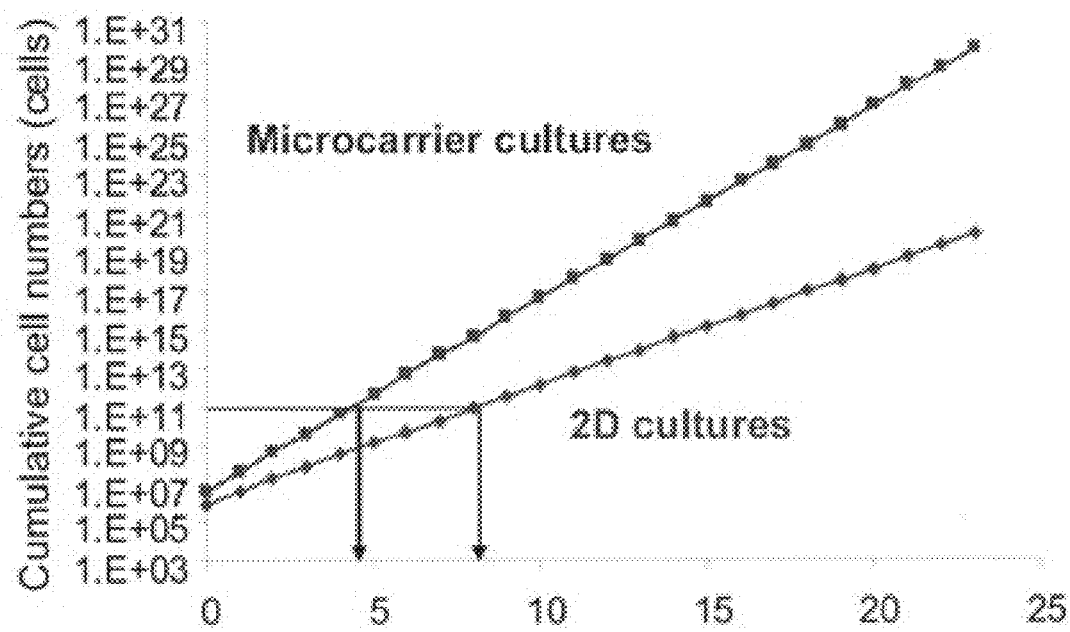
Figure 211B:
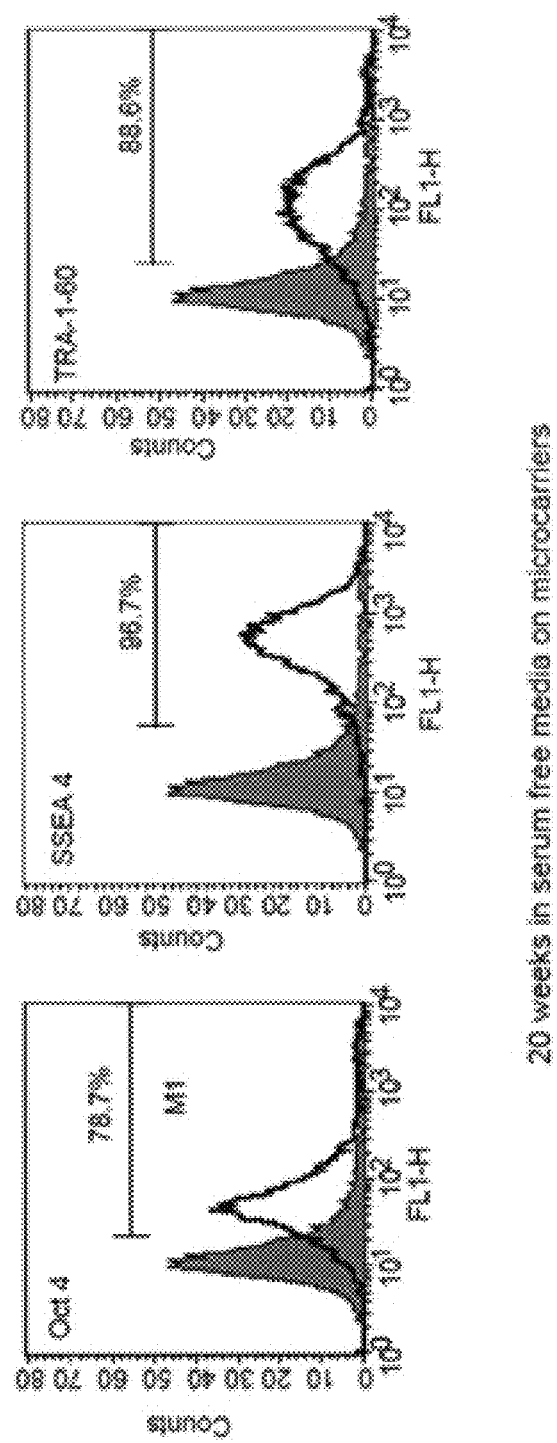
Figure 211C:
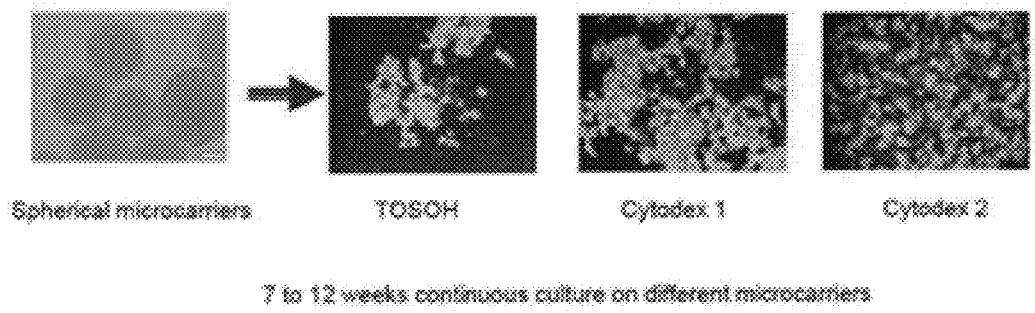
Figure 211D:
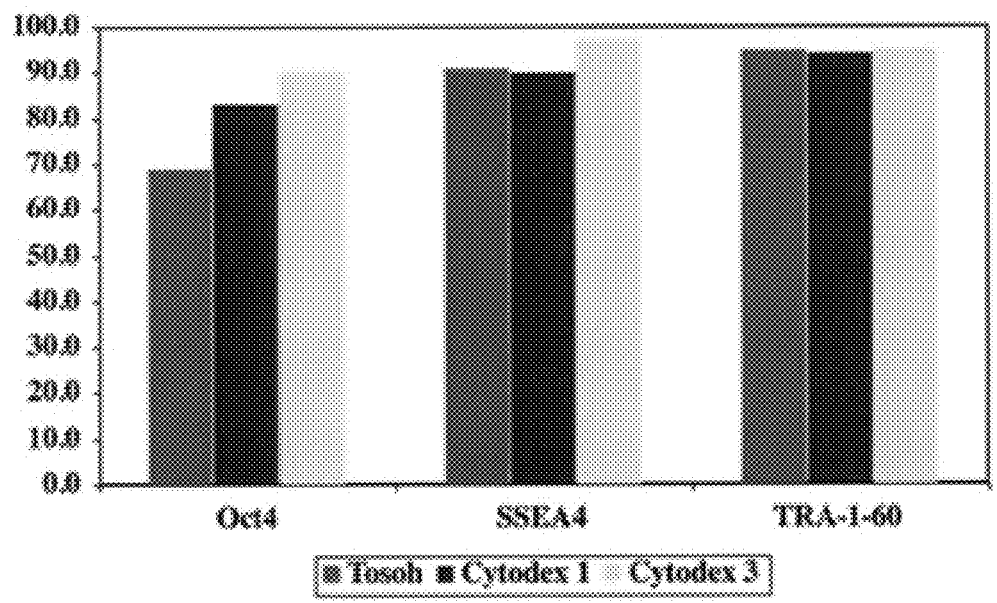
Figure 212A:
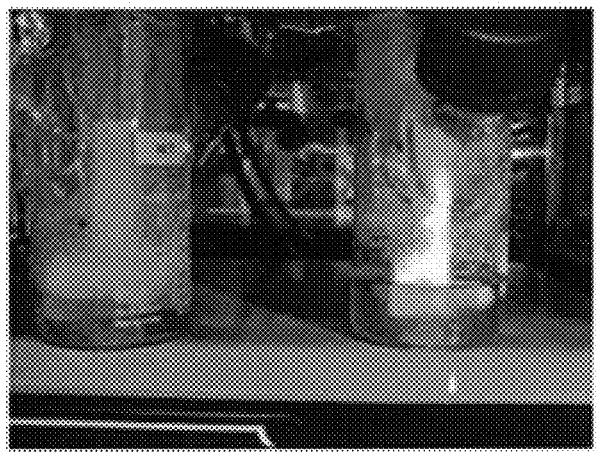
Figure 212B:
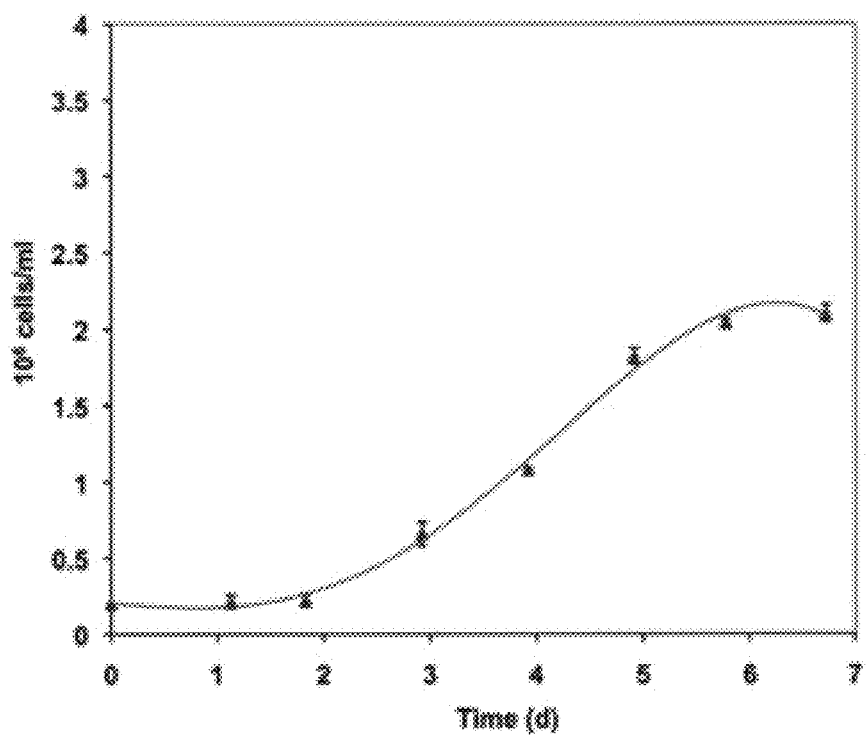
Figure 212C:
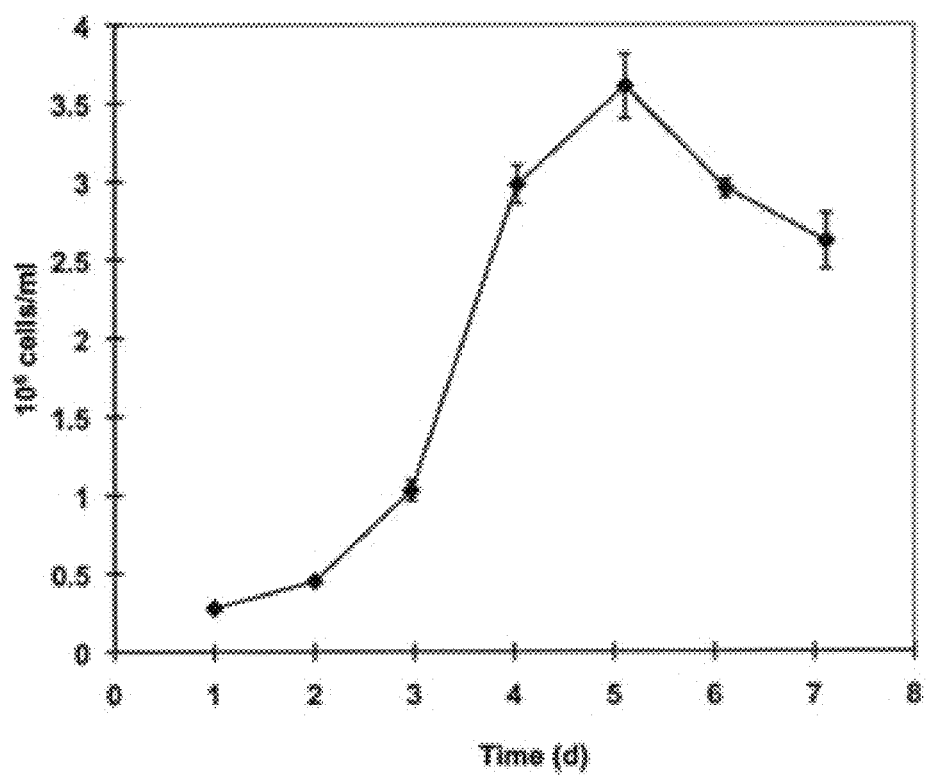
Figure 212D:
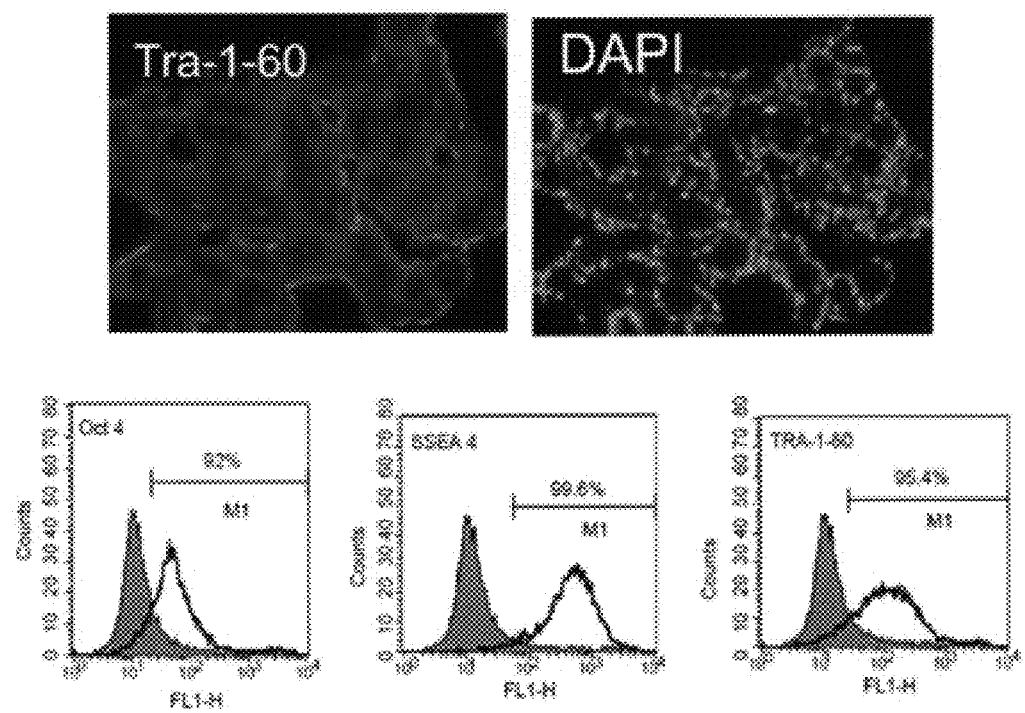
Figure 212E:
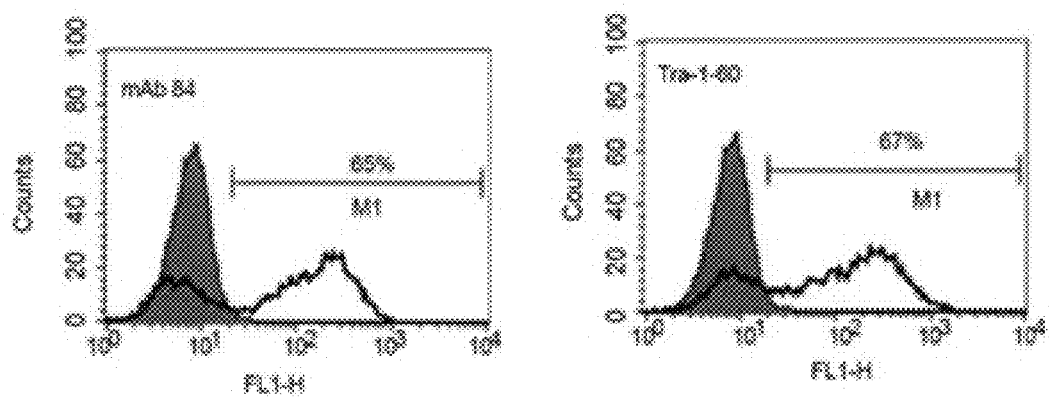

FIG. 210. Laminin as defined coating for culturing hESC on different microcarriers. Charts and gel showing that laminin-coated microcarriers were able to sustain long term cultivation of hESC and differentiation showing expression of genes from three lineages. FIG. 210A shows the results in bar graph form; FIG. 210B shows a gel blot showing the expression results.

FIG. 211. Diagrammatic illustration of results for long term culture of hESC on rod and spherical microcarriers. FIG. 211A is a graph showing cell expansion; FIG. 211B shows FACS results for Oct-4, SSEA-4, and Tra-1-60 expression. FIG. 211C shows various micrographs as labeled; and FIG. 211D shows expression in bar graph form for microcarriers.

FIG. 212. FIG. 212A is a picture showing spinner cultures of hESC on microcarriers. FIG. 212B is a graph depicting cell expansion over time. FIG. 212C is a graph depicting cell expansion over time. FIG. 212D shows micrographs (above) and FACS results (below) for marker expression. FIG. 212E shows the FACS results for mAb 84 and Tra-1-60 expression.

Figure 213A:
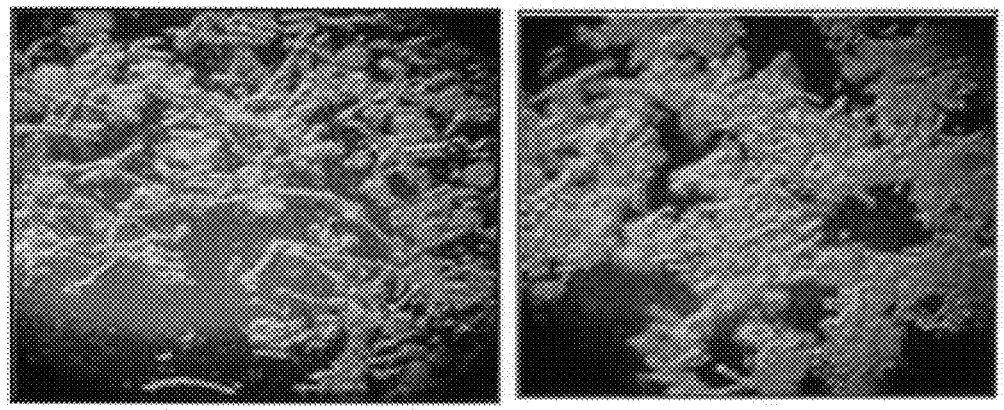
Figure 213B:
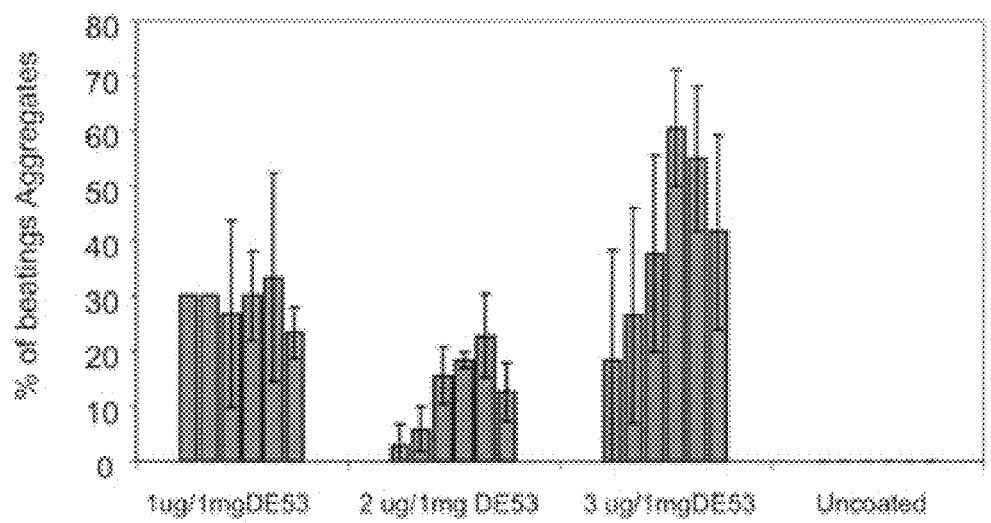
Figure 213C:
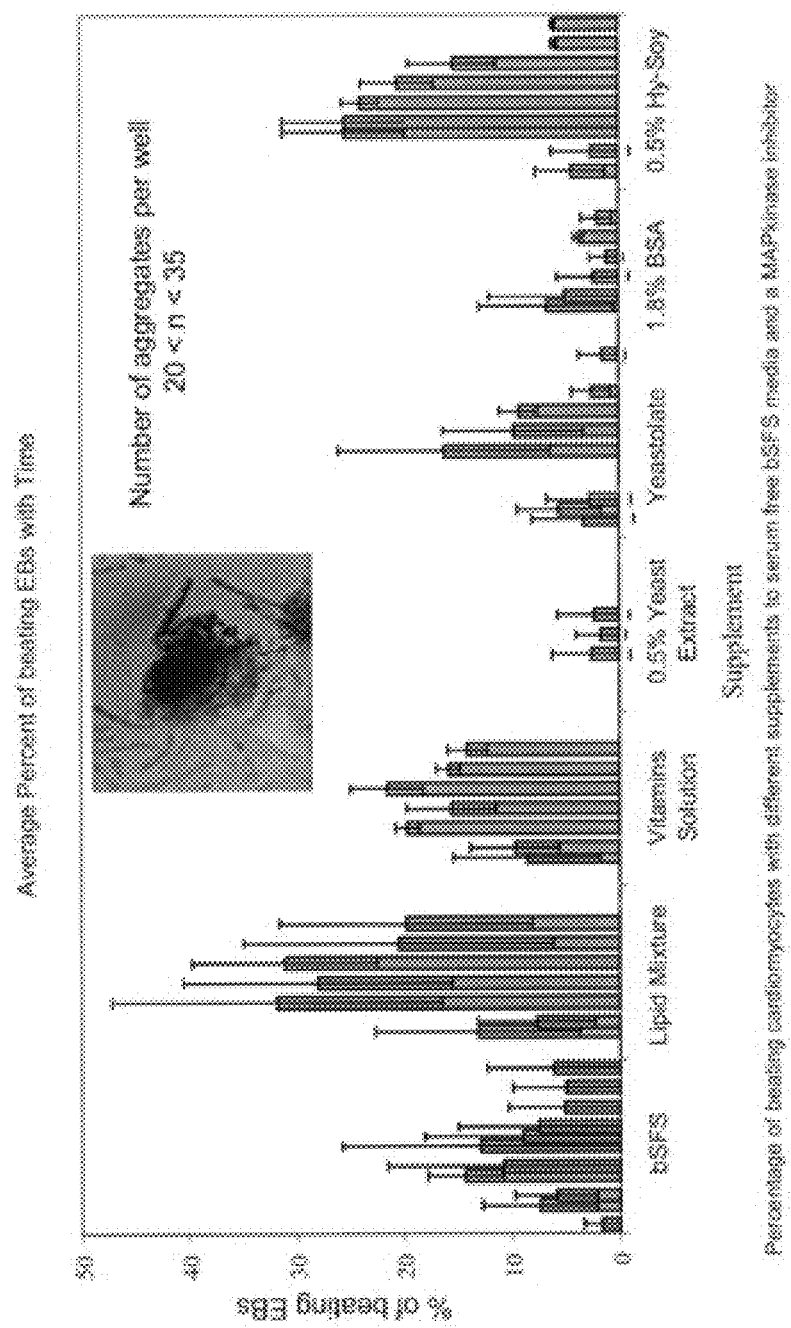

FIG. 213. FIG. 213A shows micrographs depicting cells on coated vs. uncoated microcarriers. FIG. 213B shows a bar graph depicting the percentage of beating cardiomyocytes for laminin-coated vs. uncoated microcarriers FIG. 213C shows a bar graph depicting the percentage of beating cardiomyocytes with various supplements.

Figure 214B:
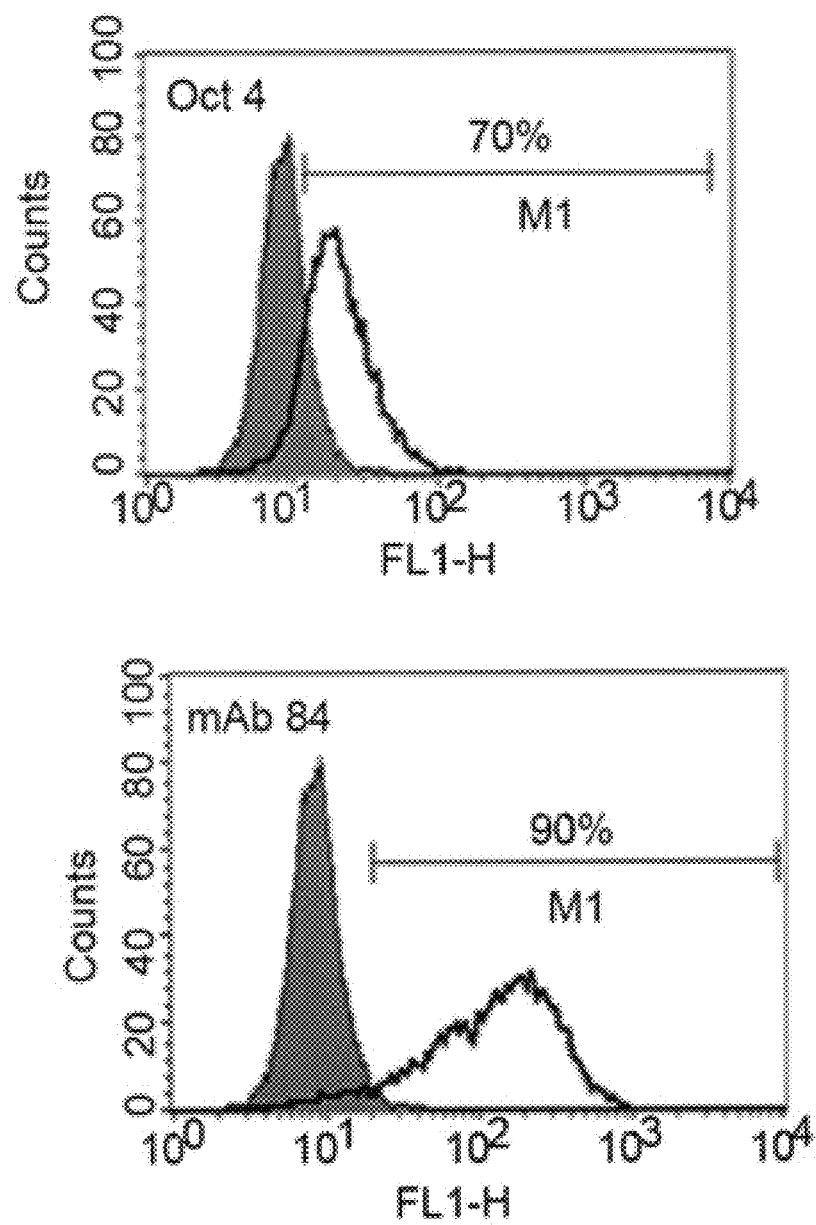

FIG. 214. FIG. 214A shows a bar graph and micrograph depicting continuous microcarriers cultures of human iPS cells (over a number of passages). FIG. 214B shows FACS results for Oct-4 and mAb 84 expression.

Figure 215:
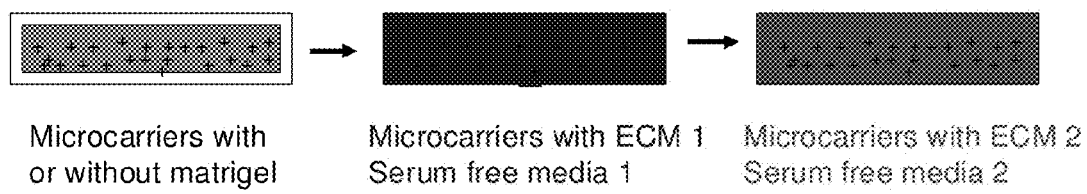

FIG. 215. Diagrammatic illustration of conclusions in respect of use of microcarrier culture for expansion and combinatorial differentiation of human ESC and iPS cells, including culture in conditioned media and serum free media, with and without Matrigel and in static and agitated conditions. In conclusion, we have developed a versatile microcarrier platform for expansion and combinatorial differentiation of human ESC and iPS cells, in conditioned media and commercial serum free media, with and without Matrigel and in static and agitated conditions.

Figure 216:
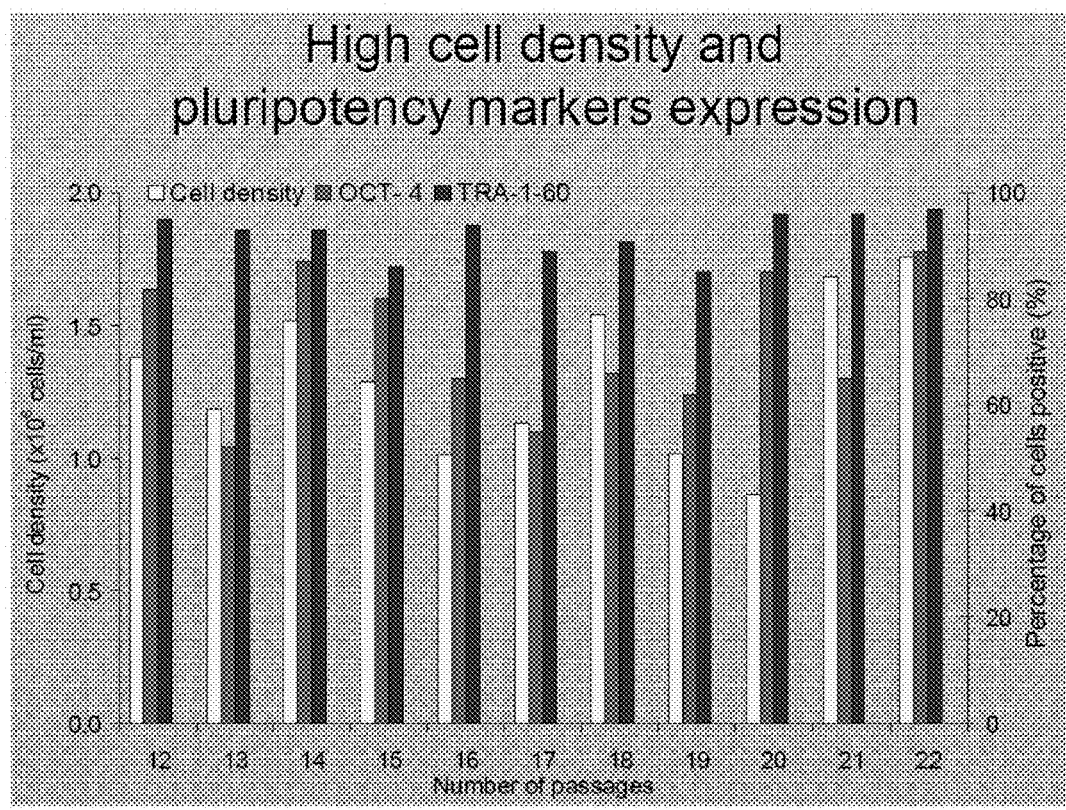

FIG. 216. Graph showing that high cell density and expression of pluripotency markers is retained in human iPS cells cultured on DE53 microcarriers over 22 passages (Example 46).

Figure 217:
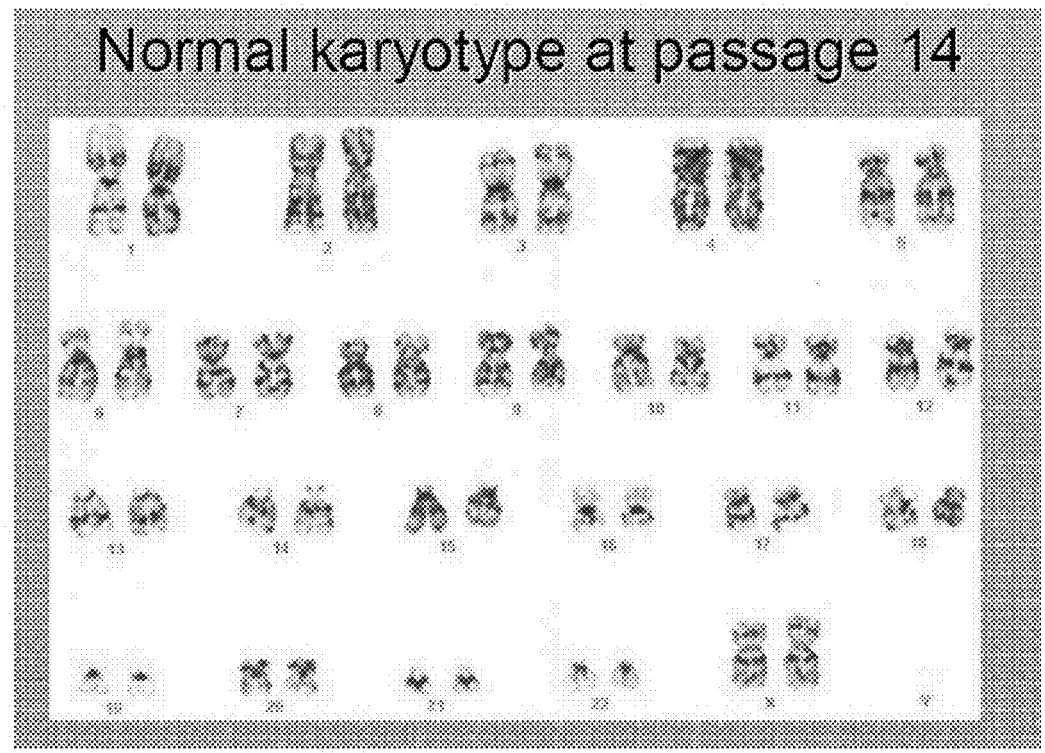

FIG. 217. Normal karyotype at passage 14 (Example 46).

Figure 218:
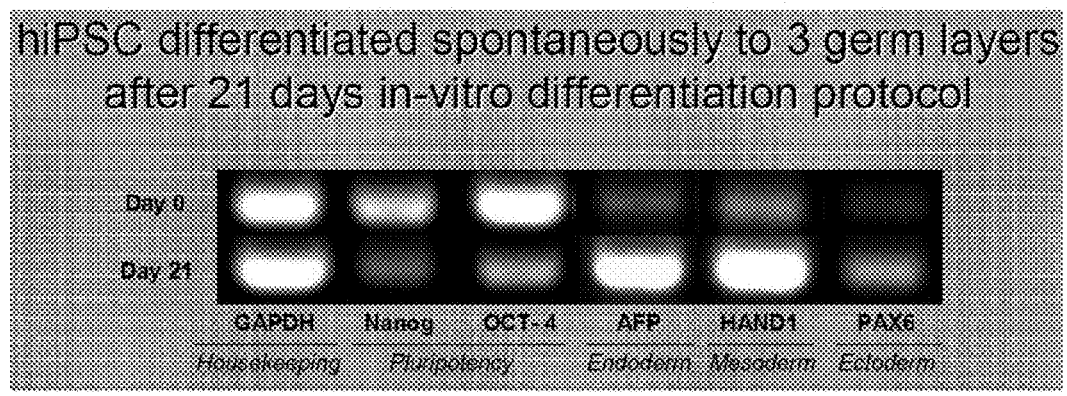

FIG. 218. Human iPS cells spontaneously differentiated into the three germ layers after 21 days in-vitro differentiation protocol (Example 46).

Figure 219:
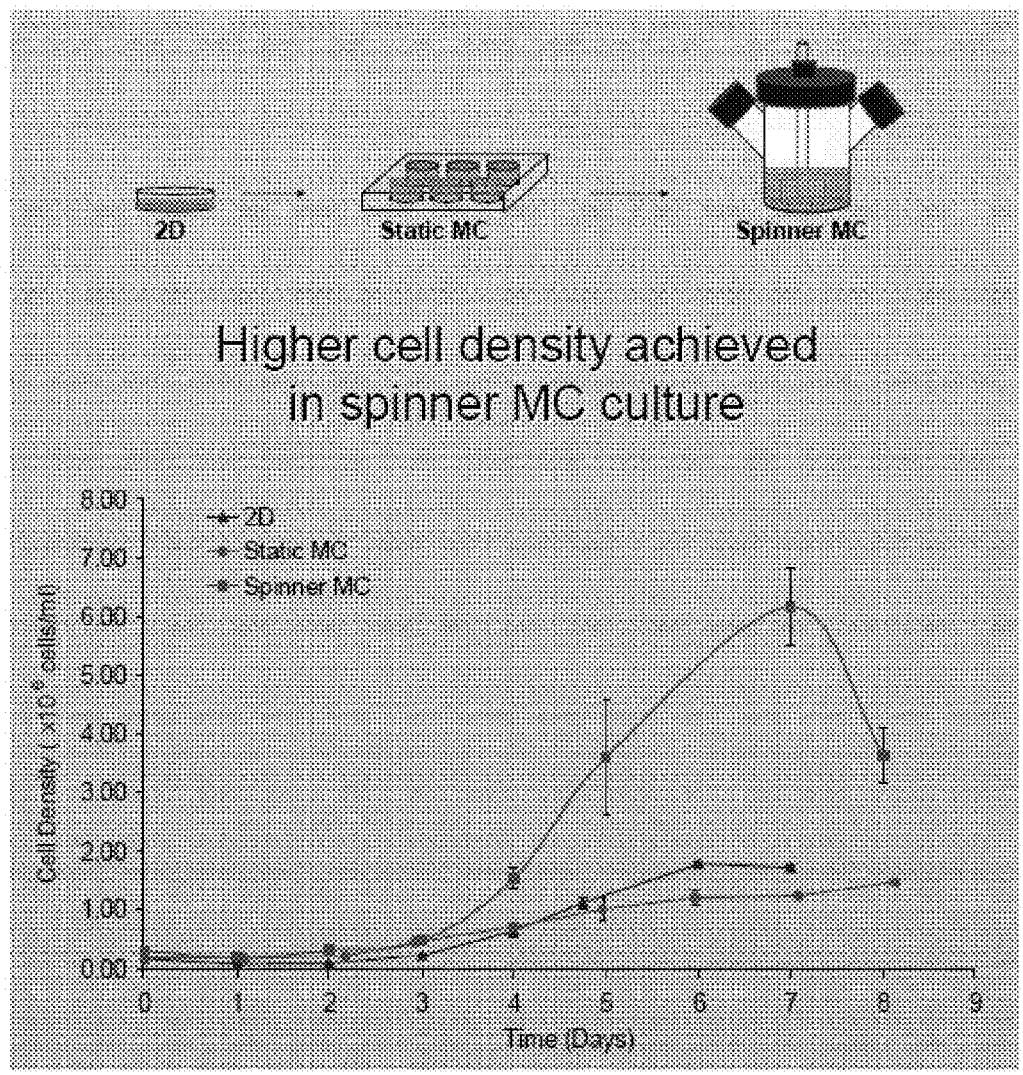

FIG. 219. Expansion of human iPS cells on microcarriers in spinner culture. Graph shows higher cell density achieved in spinner microcarrier culture (Example 46).

Figure 220:
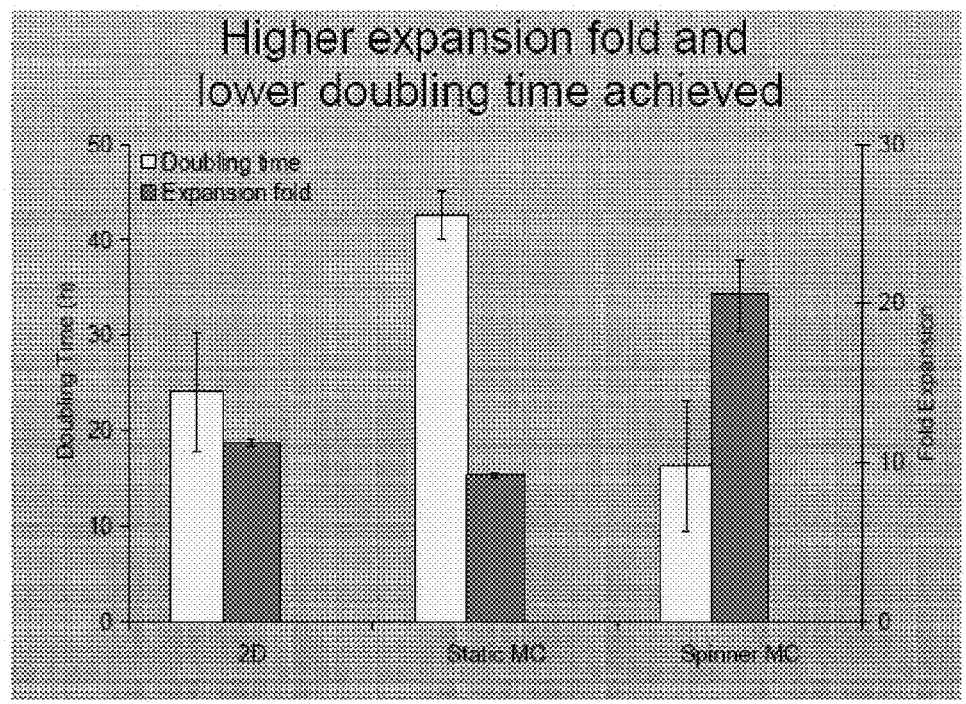

FIG. 220. Graph showing higher expansion fold and lower doubling time of human iPS cells in spinner microcarrier culture (Example 46).

Figure 221:
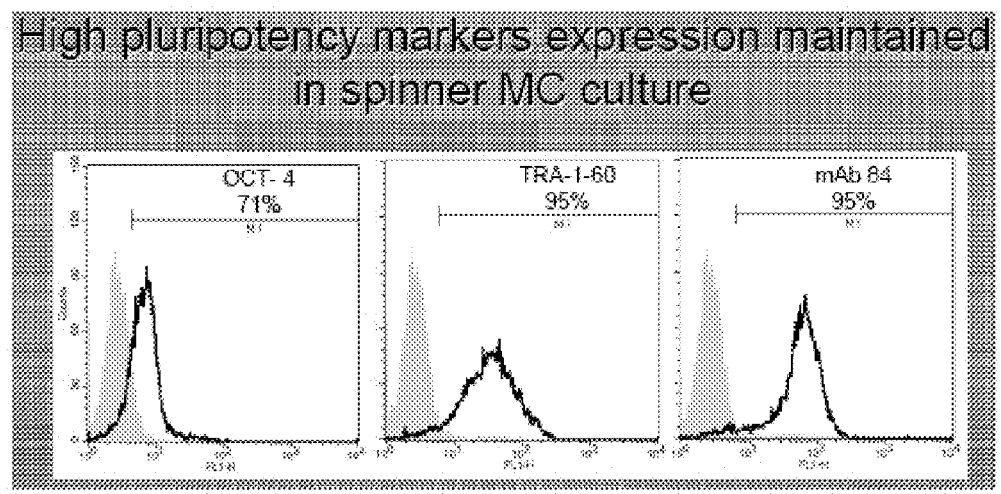

FIG. 221. Flow cytometry analysis. High pluripotency marker expression is maintained during culture of human iPS cells in spinner microcarrier culture (Example 46).

Figure 222:
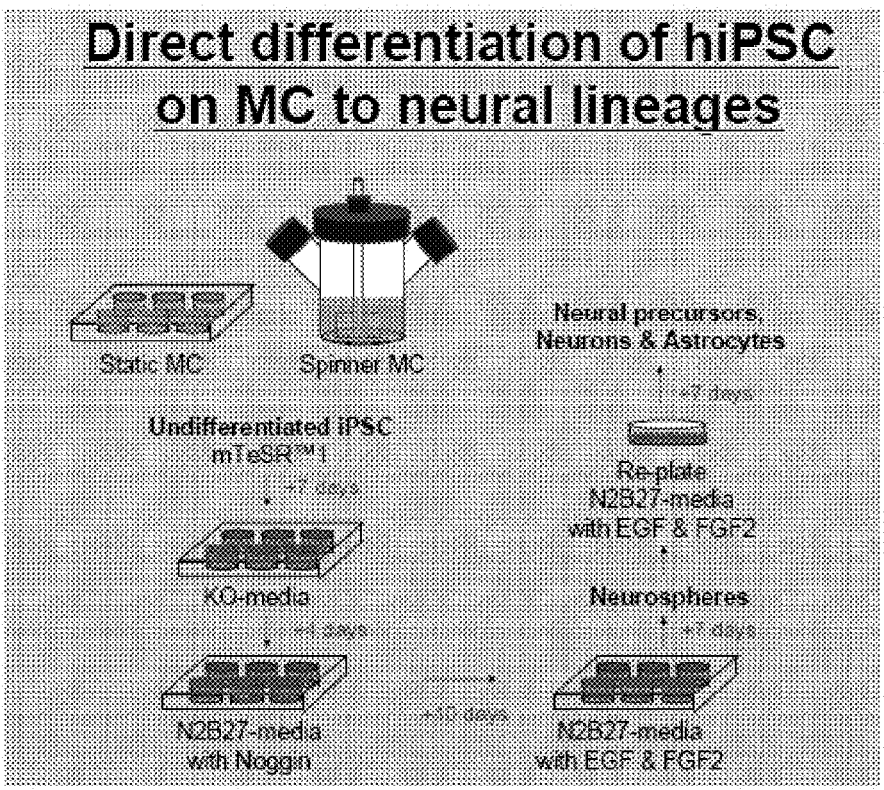

FIG. 222. Schematic showing process of direct differentiation of human iPS cells on microcarriers to neural lineages (Example 46).

Figure 223:
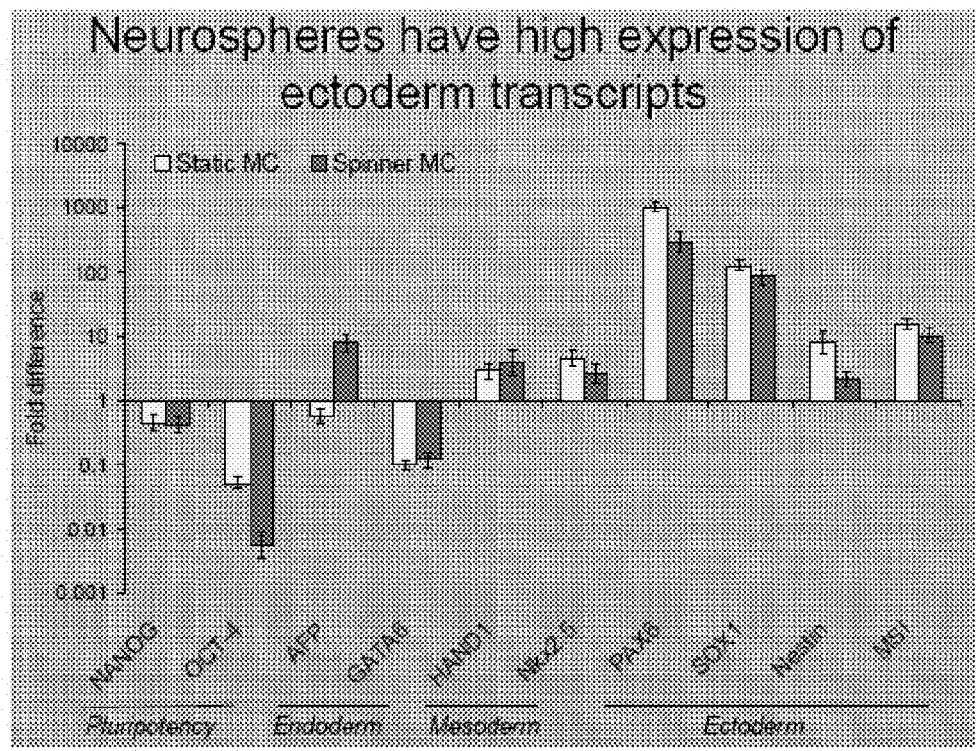

FIG. 223. Graph showing high expression of ectoderm transcripts in neurospheres (Example 46).

Figure 224:
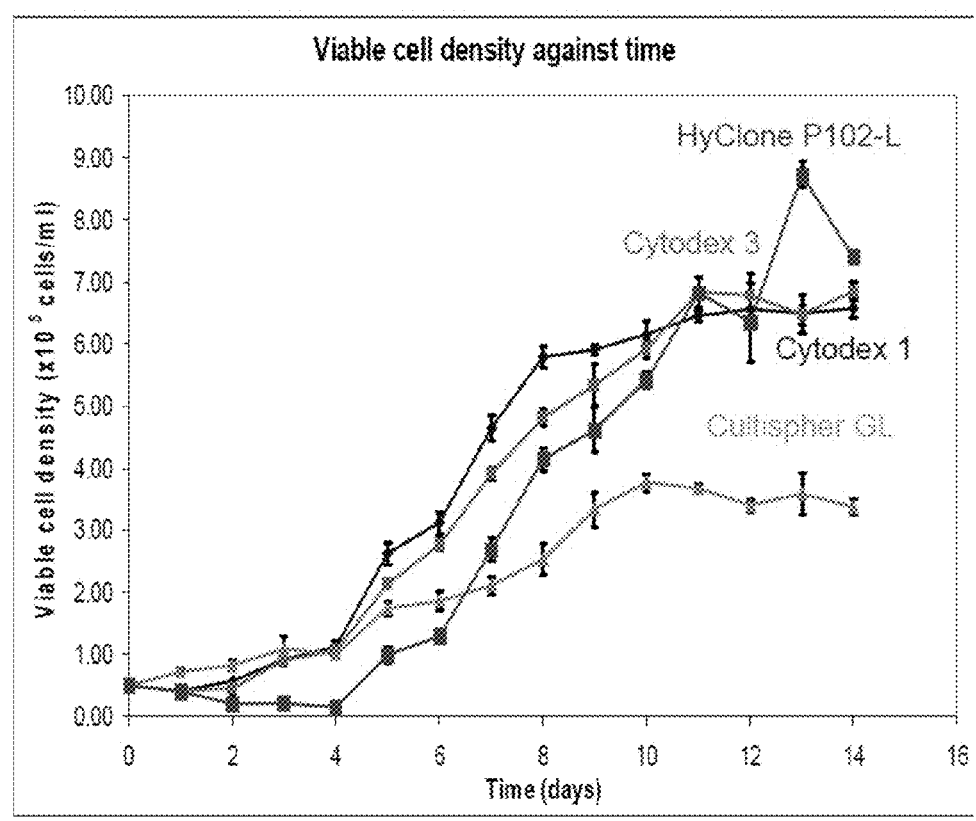

FIG. 224. Graph showing growth kinetics of hfMSC on various microcarriers (Example 47).

Figure 225:
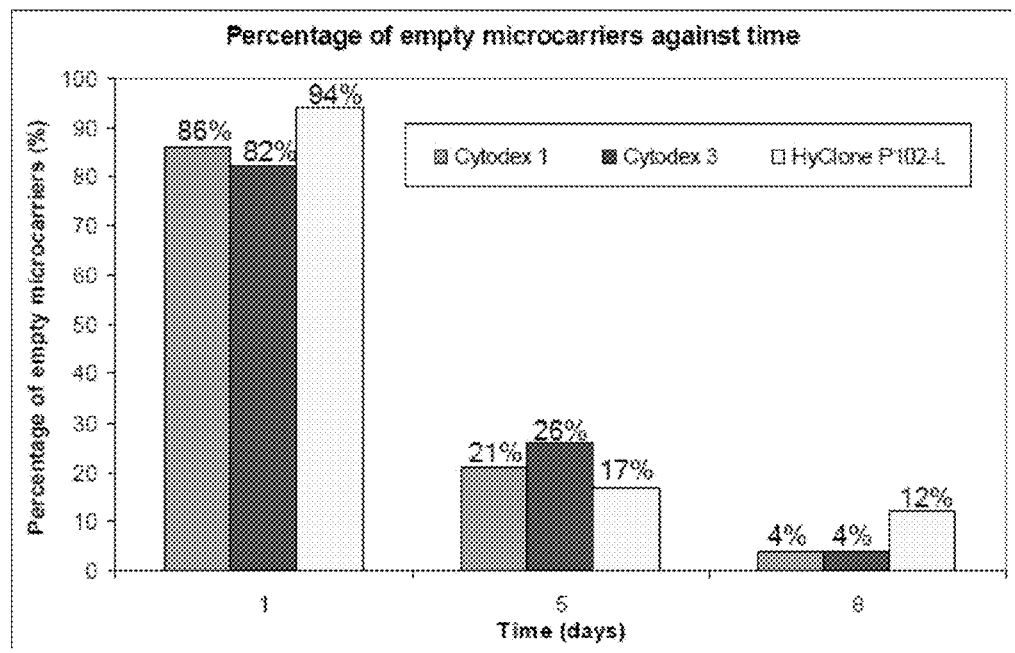

FIG. 225. Graph showing percentage of empty microcarriers against time (Example 47).

Figure 226:
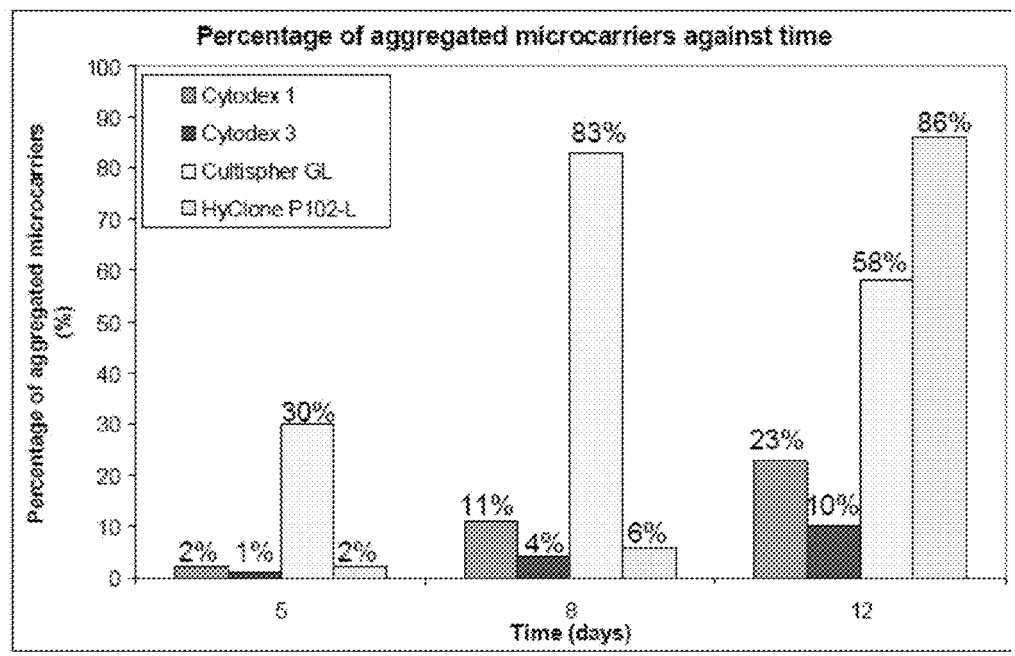

FIG. 226. Graph showing percentage of aggregated microcarriers against time (Example 47).

Figure 227A:
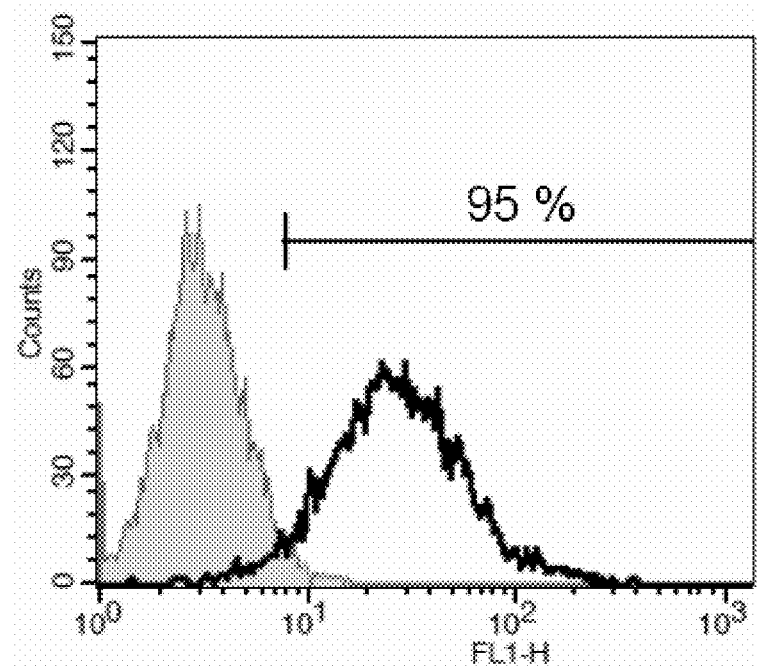
Figure 227B:
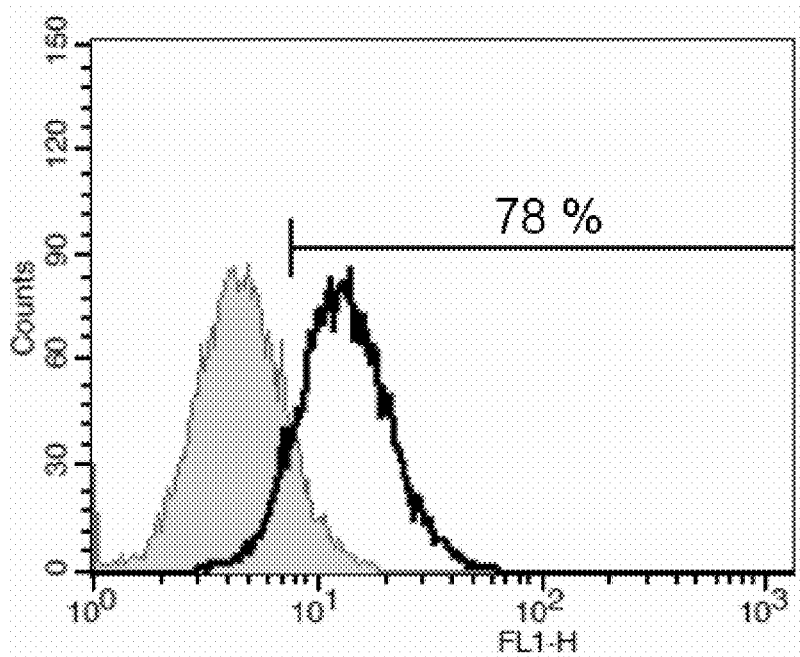

FIG. 227. Flow cytometry analysis. Expression of CD105 before osteogenic differentiation (Example 47). FACS results are depicted in FIG. 227A and FIG. 227B, with expansion and harvest of cells seeing a drop in expression (95% in FIG. 227A and 78% in FIG. 227B).

Figure 228A:
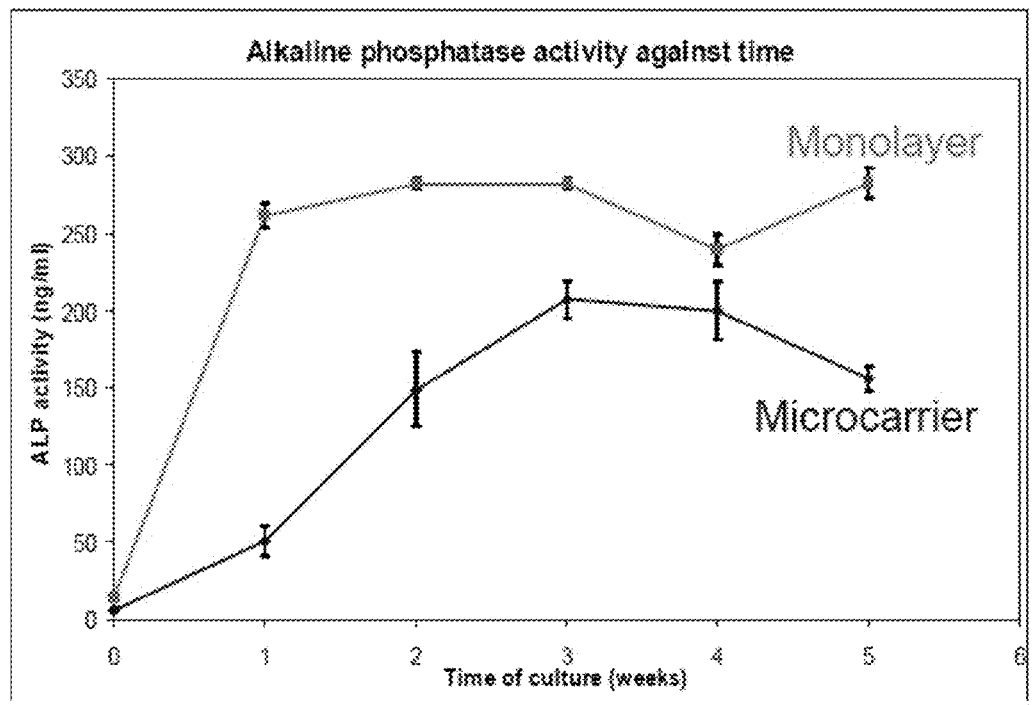
Figure 228B:
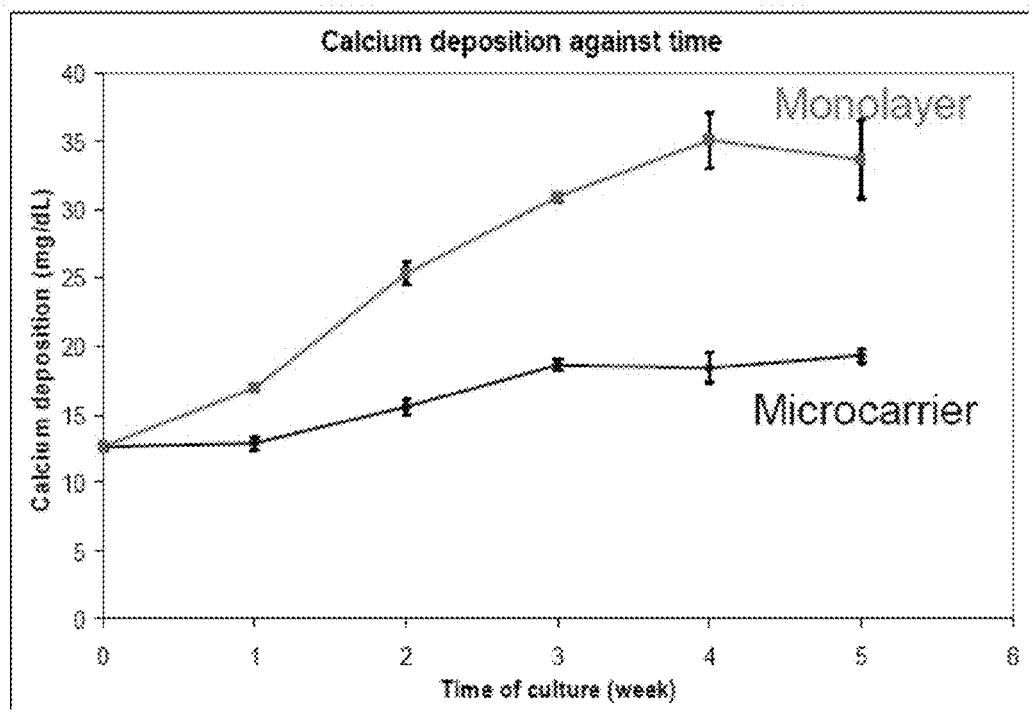

FIGS. 228A and 228B. Graphs showing (A) alkaline phosphatase activity against time for hfMSC cultured in monolayer or on microcarriers and (B) calcium deposition against time for hfMSC cultured in monolayer or on microcarriers (Example 47).

DETAILED DESCRIPTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.
Long Term Stable Propagation of hESC in Suspension Culture We have now demonstrated the long term stable propagation of human embryonic stem cells (hESCs) in suspension culture. In particular, we demonstrate that Matrigel, hyaluronic acid and laminin coating of microcarriers enables hESCs to be propagated beyond at least passage 5, and commonly beyond passages 8, 9 or 10, whilst retaining pluripotency. In this way, we have now successfully demonstrated microcarrier suspension culture in excess of 25 successive passages and have characterised the cultured cells by analysis of cell density, viability, FACS analysis of markers of pluripotency, histological analysis, and karyotype.

We have demonstrated the stability of the microcarrier culture for the long term propagation of human embryonic stem cells as measured by maintenance of growth rates, expression of the pluripotent markers Oct4, SSEA4, TRA-1-60 and Mab84, normal karyotypes after up to 23 passages, and the ability to differentiate to the 3 germ layers.

hESC on microcarriers have also been adapted to grow in serum free media and their amino acid metabolic rates have been measured. Furthermore, microcarrier cultures have been scaled up to spinner flasks with an hESC line. Co-cultures of hESC on cellulose microcarriers with feeder cells grown on spherical Cytodex 3, Tosoh and cellulose microcarriers have also been demonstrated.

We have demonstrated that 5 types of microcarriers: DE53 cellulose, Tosoh (10 and 65 micron), Cytodex 3, Cytodex 1 and Hillex, all coated with matrigel are able to support hESC in long term culture. These microcarriers without matrix coating however, are not able to support hESC beyond 5 or at best 10 passages without down regulation of pluripotent markers and a drop in cell densities.

A schematic summarising the properties of microcarriers required for culture of embryonic stem cells is shown in FIG. 140. Microcarriers can be rod or cylindrical or spiral-like with length 20 to 2000 microns, diameter 5 to 50 microns. They may also be spherical or oval-like with diameter ranging from 50 to 2000 microns. The composition of the microcarrier may be cellulose, dextran, hydroxylated methacrylate, polystyrene, glass, collagen, gelatin, macroporous or microporous carboseed or other materials. The microcarrier is preferably positively charged or of collagen/gelatin material. The microcarrier may be coated with extracellular matrices (ECMs) such as matrigel, hyaluronic acid, heparin, fibronectin, laminin, vitronectin or other ECMs. These ECMs may or may not have growth factors adsorbed to it.

In particular, we have now successfully demonstrated the following:

1. Continuous passaging of hESC on DE53 cellulose microcarriers to passage 23.
2. Characterisation of hESC cultured on cellulose microcarriers (Karyotyping, RT-PCR of embryoid bodies and teratoma formation).
3. Serum free media culture of hESC-cellulose microcarriers with amino acid metabolism data analysis.
4. Cellulose microcarrier culture of 2 hESC cell lines in spinner flasks.
5. Co-cultures of feeder cells on spherical or rod shaped microcarriers with hESC grown on rod shaped cellulose microcarriers.
6. hESC culture on small and large spherical microcarriers with Matrigel.
7. hESC culture on large microcarriers with Matrigel.
8. Hyaluronic acid coating on cellulose microcarriers for hESC culture.

Suspension Culture and Passage of Stem Cells

We have now demonstrated that it is possible to culture, propagate and passage primate and human stem cells and iPS cells on particles. In particular, we show that stem cells may be grown continuously in suspension culture and passaged. We demonstrate continuous, passageable and 3 dimensional culture of human embryonic stem cells (hESCs) on microcarriers.

We describe a method of propagating stem cells in suspension. The method of propagating may comprise growing, propagating, proliferating, culturing, expanding or increasing stem cells. The propagating stem cells are able to be passaged for one or more passages, as described below. Such propagation may be achieved through the use of microcarriers or particles with certain properties. The microcarriers or particles may comprise a charge. The microcarriers or particles may comprise a coating. A further property may comprise size.

The method of propagating stem cells may comprise the steps of providing particles. The particles may comprise a matrix coated thereon and have a positive charge. The particles may have a size to allow aggregation of primate or human stem cells attached thereto. Stem cells are allowed to attach to the particle. The cells growing on different particles are allowed to contact each other and to form aggregates. The culture is passaged for at least one passage. The stem cells may be used attached to the carriers or detached or separated from them. They may be used in an undifferentiated or pluripotent state or both, or may be differentiated into a desired cell type. They may be used to form embryoid bodies.

In order for the particles to support continuous growth, they should have a size which is compatible with the dimensions of a primate or human stem cell, such as 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm or so. Culture of primate or human stem cells on such a particle with this order of size will enable cells growing thereon to aggregate with each other and support continuous growth. Suitable compositions, shapes and sizes of particles are described in further detail below.

The Examples show that stem cell cultures such as human embryonic stem cell 2D colony cultures may be inoculated onto microcarrier particles and grown continuously for several generations with one or more passages. The stem cells may be passaged by dislodging from the surface by any means such as mechanical or enzymatic dissociation, or combination of both methods.

The microcarrier particle cultures may be grown from generation to generation on particles. Alternatively, or in addition, the cultures may be grown on conventional 2D cultures for one or more generations in between. Human stem cells growing on microcarriers may be transferred back to 2D colony cultures and vice versa.

The methods described here make available methods for efficient propagation of stem cells in undifferentiated form for the first time. They enable microcarrier cultures to be passaged onto microcarriers by mechanical or enzymatic dissociation with a splitting ratio of between 1 to 2 and 1 to 10, which is higher than possible for conventional 2D cultures. This enables more efficient utilisation of biomaterial with more rapid scale up of culture.

Volumetric yields of cells in microcarrier cultures are routinely 2 to 4 times more than 2D colony controls. The volumetric yield of human stem cells propagated by the methods described here may be up to 2 million cells/ml or more.

The methods described here enable the passaging of human stem cells from particles to particles for 10 passages or more, as described in further detail below.

The methods described here enable the propagation of stem cells that retain their pluripotent character. The Examples show that human embryonic stem cells propagated according to the methods and compositions described here are able to maintain one or more biological characteristics of stem cells. Thus, the propagated stem cells show expression of pluripotent markers, Oct-4, Tra-1-60 and SSEA-4 for 5 passages equivalent to stem cells grown as 2D colony cultures, retain a normal karyotype, and are able to differentiate into the 3 germ layers in vitro (embryoid bodies) and in vivo (teratomas).

Significantly, when anchored on the cellulose microcarriers, stem cells can be serially passaged in larger scale spinner flasks.

Any stem cells may be propagated using the methods described here. These may comprise primate stem cells, such as monkey, ape or human stem cells. The stem cells may comprise embryonic stem cells or adult stem cells. The stem cells may comprise induced pluripotent stem cells. For example, the stem cells may comprise human embryonic stem cells (hESCs). These and other stem cells suitable for use in the methods and compositions described here are described in further detail below.

The methods and compositions described here have various advantages over known "2D" culture methods. The particles are more efficient in attaching stem cells than 2D colony culture substrates. For this and other reasons, the suspension cultured cells are able to be passaged more effectively. The methods described here enable the stem cells to be frozen and thawed through several cycles. They may be frozen directly on the microcarriers and thawed onto growing medium (whether traditional plate culture, or on particulate microcarriers). The stem cells propagated on microcarriers may be grown in serum free media, which is GMP compliant.

The methods described here essentially enable the culture and maintenance of stem cells such as embryonic stem cells in an undifferentiated state. The propagated stem cells may be differentiated partially or totally, in culture (e.g., on microcarriers) or detached therefrom.

The propagated stem cells may be used to form embryoid bodies for further use. Stem cells growing on microcarriers may simply be transferred to differentiation medium to form embryoid bodies directly, in contrast with prior methods, which require an additional step of removing cells from a 2D growing surface prior to embryoid body formation. Accordingly, the methods and compositions described here enable directed differentiation of stem cells on the growing surface or substrate without removal therefrom.

The methods and compositions described here enable expansion and scale up of cultured stem cells to larger volumes. The scale up to bioreactor or industrial scale enables more productive culture of stem cells. The ability to grow stem cells on microcarriers in agitated culture means that the cultures can be scaled up into suspension conditions. Controlled bioreactors such as the Wave Bioreactor or stirred cultures may be used. This enables cells to be expanded in larger volumes compared to the current limitations of anchorage dependent 2 dimensional colony cultures. Large scale suspension culture in bioreactors up to 100's of liters is possible.

Positive Charge

The particle or microcarrier may comprise a positive charge at for example neutral pH or physiologically relevant pH such as pH 7.4 or pH 7.2. The particle may comprise a chromatography resin such as an anion exchange resin.

The quantity of positive charge is important but is not crucial and may vary, so long as it is high enough to enable cells to attach to the particle. For example, where the particles are charged by coupling with amines, such as quaternary or tertiary amines, the charge on the particle may correspond to a small ion exchange capacity of about 0.5 to 4 milli-equivalents per gram dry material (of the particle), for example between about 1 to 3.5 milli-equivalents per gram dry material (of the particle) or between about 1 to 2 milli-equivalents per gram dry material (of the particle).

The positive charge may be such that that the pKa of the particle is greater than 7 (e.g., greater than 7.4, e.g., 7.5, 8, 8.5, 9, 9.5, 10, 10.5, 11, 11.5 or more).

The particle may be derivatised by coupling for example to protamine sulphate or poly-L-lysine hydrobromide at a concentration of up to 20 mg/ml particles.

Without wishing to be bound by theory, we believe that the presence of a positive charge on the particles enables cells to attach thereto.

The particle may carry a positive charge through any means known in the art. The particle may comprise positively charged groups, or it may be derivatised to carry these.

The particle may comprise diethylaminoethyl-cellulose (DEAE-cellulose) or a derivative thereof. DEAE-cellulose comprises a microgranular cellulose which has been chemically modified such that the —CH2OH groups of the carbohydrate have been converted to an ionizable tertiary amine group. It is positively charged at neutral pH. The particle may comprise a Sephadex bead, such as DEAE-Sephadex. The particle may comprise agarose bead which may be covalently cross-linked, such as Sepharose (i.e., DEAE-Sepharose). The particle may comprise DEAE-Sephacel. DEAE-Sepharose, DEAE-Sephacel and DEAE-Sephadex are available from Sigma-Aldrich. The particle may comprise Q-Sepharose Fast Flow or S-Sepharose Fast Flow. The charged group of Q-Sepharose is a quarternary amine which carries a non-titratable positive charge.

The particle may be derivatised to carry positive charges. For example, the particle may comprise amine groups attached thereto. The amine groups may be primary amine groups, secondary amine groups, tertiary amine groups or quaternary amine groups. The amine groups may be attached to the particle by coupling the particle with amine containing compounds. Methods of coupling are well known in the art. For example, the amine may be coupled to the particle by the use of cyanogen bromide.

Crosslinkers may also be used. These are divided into homobifunctional crosslinkers, containing two identical reactive groups, or heterobifunctional crosslinkers, with two different reactive groups. Heterobifunctional crosslinkers allow sequential conjugations, minimizing polymerization. Coupling and crosslinking reagents may be obtained from a number of manufacturers, for example, from Calbiochem or Pierce Chemical Company.

The particle may be activated prior to coupling, to increase its reactivity. The compact particle may be activated using chloroacetic acid followed by coupling using EDAC/NHS—OH. Particles may also be activated using hexane di isocyanate to give primary amino group. Such activated particles may be used in combination with any heterobifunctional cross linker. The compact particle in certain embodiments is activated using divinyl sulfon. Such activated compact particles comprise moieties which can react with amino or thiol groups, on a peptide, for example.

The particle may also be activated using tresyl chloride, giving moieties which are capable of reacting with amino or thiol groups. The particle may also be activated using cyanogen chloride, giving moieties which can react with amino or thiol groups.

Cytodex 1 is based on a cross-linked dextran matrix which is substituted with positively charged N,N-diethylaminoethyl groups. The charged groups are distributed throughout the microcarrier matrix.

Uncharged Particles

The particle or microcarrier may be uncharged, or charge neutral at for example neutral pH or physiologically relevant pH such as pH 7.4 or pH 7.2.

Examples of uncharged particles include gelatine or collagen particles. For example, Cytodex 3 consists of a thin layer of denatured collagen chemically coupled to a matrix of cross-linked dextran.

Matrix Coating

The particle may be coated with a matrix, which in the context of this document refers to a layer (e.g. a thin layer or film) of substance attached to the particle such as on its surface. The matrix may comprise a biologically or compatible or physiologically relevant matrix capable of supporting growth of cells. It may comprise a substrate for cell growth.

The matrix may comprise a component of the extracellular matrix (ECM). Any of the known components of the ECM such as those capable of supporting growth of stem cells may be used. Components of the extracellular matrix are known in the art and are described in for example Alberts et al (2002), Molecular Biology of the Cell, Chapter IV and references cited therein.

The ECM component may be attached or coupled to or coated on the particle through conventional means. For example, any of the coupling reagents and crosslinkers described above may be used to couple the ECM component to the particle.

The ECM component may comprise a macromolecule such as a polysaccharide, protein, proteoglycan, glycoprotein, glycosaminoglycan (GAG), usually found covalently linked to protein in the form of proteoglycans, a fibrous protein, including elastin, fibronectin, and laminin, collagen (e.g. collagen I, collagen III, collagen IV, collagen VI) etc.

The matrix coating may comprise a glycosaminoglycan (GAG). Glycosaminoglycans comprise unbranched polysaccharide chains composed of repeating disaccharide units. One of the two sugars in the repeating disaccharide is always an amino sugar (N-acetylglucosamine or N-acetylgalactosamine), which in most cases is sulfated. The second sugar is usually a uronic acid (glucuronic or iduronic).

The matrix coating may comprise hyaluronan (also called hyaluronic acid or hyaluronate) or a derivative thereof. The hyaluronic acid may be derived from any number of sources, such as from bovine vitreous humor. A salt or base of hyaluronic acid may be employed, such as hyaluronic acid sodium. This may be from *streptococcus*.

The matrix coating may comprise laminin.

The matrix coating may comprise fibronectin.

The matrix coating may comprise vitronectin.

The matrix coating may comprise for example a GAG such as chondroitin sulfate, dermatan sulfate, heparan sulfate and keratan sulfate, for example as linked to a protein as a proteoglycan. The ECM component may comprise aggrecan, decorin, etc.

The matrix coating may comprise heparan or its derivatives such as bases or salts. The matrix coating may comprise heparan sulphate proteoglycan. The heparan sulphate proteoglycan may be derived from any number of sources, such as from bovine kidney.

The matrix coating may comprise a dextran such as dextran sulphate or dextran sulphate sodium. The matrix coating may comprise fibronectin, laminin, nidogen or Type IV collagen. The matrix coating may comprise chondroitin sulphate.

The matrix may comprise gelatin, polyomithine, or binding motifs of the RGD binding domain of fibronectin.

The matrix coating may comprise a mixture of any two or more of these components in various proportions. The matrix coating may comprise a purified or substantially purified component of the ECM. The matrix component may comprise a partially purified component of the ECM. It may comprise an ECM extract such as Matrigel.

A cell culture may comprise particles having different matrix coatings. For example, a first particle population having a first matrix coating selected from those described above and a second particle population having a second coating selected from those described above.

Matrigel

The particle may be coated with a matrix coating comprising Matrigel

Matrigel is the trade name for a gelatinous protein mixture secreted by mouse tumor cells and marketed by BD Biosciences (Bedford, Mass., USA). This mixture resembles the complex extracellular environment found in many tissues and is used by cell biologists as a substrate for cell culture.

BD Matrigel™ Matrix is a solubilised basement membrane preparation extracted from EHS mouse sarcoma, a tumor rich in ECM proteins. Its major component is laminin (about 56%), followed by collagen IV (about 31%), heparan sulfate proteoglycans, and entactin 1 (about 8%). At room temperature, BD Matrigel™ Matrix polymerizes to produce biologically active matrix material resembling the mammalian cellular basement membrane.

A common laboratory procedure is to dispense small volumes of chilled (4° C.) Matrigel onto a surface such as plastic tissue culture labware. When incubated at 37° C. (body temperature) the Matrigel proteins self-assemble producing a thin film that covers the surface.

Matrigel provides a physiologically relevant environment with respect to cell morphology, biochemical function, migration or invasion, and gene expression.

The ability of Matrigel to stimulate complex cell behaviour is a consequence of its heterogeneous composition. The chief components of Matrigel are structural proteins such as laminin and collagen which present cultured cells with the adhesive peptide sequences that they would encounter in their natural environment. Also present are growth factors that promote differentiation and proliferation of many cell types. Matrigel comprises the following growth factors (range of concentrations, average concentration): EGF (0.5-1.3 ng/ml, 0.7 ng/ml), bFGF (<0.1-0.2 pg/ml, unknown), NGF (<0.2 ng/ml, unknown), PDGF (5-48 pg/ml, 12 pg/ml), IGF-1 (11-24 ng/ml, 16 ng/ml), TGF-β (1.7-4.7 ng/ml, 2.3 ng/ml). Matrigel contains numerous other proteins in small amounts.

Alternating Matrix Coatings

In some embodiments cells may be cultured on a particle having a first matrix coating for one or more passages (e.g. 1, 2, 3, 4, 5, 6, 7, 8, 9, or 10 passages or more), before being transferred to particles having a different (second) matrix coating for one or more passages (e.g. 1, 2, 3, 4, 5, 6, 7, 8, 9, or 10 passages or more). Optionally the cells may then be transferred to particles having a matrix coating different to the second coating, e.g. back to the first matrix coating or to another matrix coating or to uncoated particles.

Particle Composition

In the methods and compositions described here, stem cells are propagated on particles or microcarriers. As the term is used in this document, a "particle" comprises any support on which a stem cell can attach or grow. The particle may be of any shape or configuration, as described below.

The particle may comprise a microcarrier, as described in the IUPAC Compendium of Chemical Terminology (2nd Edition, 1992, Vol. 64, p. 160).

The particle may comprise any material, so long as it has the physical properties which allow it to serve its purposes as described above, for example as a point of attachment or support for the stem cells. The particle may therefore comprise material which is stiff, rigid, malleable, solid, porous or otherwise, for this purpose. It may comprise a solid material, or a semi-solid, gel, etc material.

The material is at least reactive to allow attachment of positive charges and/or a matrix coating, or capable of being made reactive by an activator, but may otherwise comprise a generally inert substance. The particle may comprise a composite, such that more than one material may make up the particle. For example, the core of the particle may comprise a different material from surface portions. Thus, the core of the particle may comprise a generally inert material, while the surface portions may comprise material reactive for attachment or chemical coupling of the matrix or positive charges.

The particle may be natural in origin, or synthetic. Natural and synthetic materials and sources for obtaining them are well known in the art. The particle may have at least some mechanical resistance, at least some resistance to chemical attack, or to heat treatment, or any combination of these.

In an alternative embodiment, the particle may comprise a "non-biological" object, by which term we mean a particle which is free or substantially free of cellular material. Such a non-biological or non-cellular particle may therefore comprise a synthetic material, or a non-naturally occurring material. Various particles of various shapes are known in the art, and include for example, beads of various kinds. Embodiments of particles include microbeads, such as agarose beads, polyacrylamide beads, silica gel beads, etc.

For example, the material from which the particle is made may comprise plastic, glass, ceramic, silicone, gelatin, dextran, cellulose, hydroxylated methacrylate, polystyrene, collagen or others. For example, the particle may be made of cellulose or a derivative, such as DEAE-cellulose (as described below). The particles may comprise cellulose, modified hydrophilic beads and carbon based microcarriers.

The particle may comprise a commercially available matrix or carrier, such as a bead or microbead. The particle may comprise a resin sold for use as a chromatography matrix, such as an anion exchange resin.

The particle may comprise a cellulose microcarrier. The particle may comprise DE-52 (Whatman), DE-53 (Whatman) or QA-52 (Whatman). The particle may comprise a hydrophilic microcarrier, a hydroxylated methacrylic matrix microcarrier or derivatised hydrophilic beaded microcarrier. The particle may comprise TSKgel Tresyl-5Pw (Tosoh) or Toyopearl AF-Tresyl-650 (Tosoh). The particle may comprise a macroporous or microporous carboseed microcarrier, for example, SM1010 (Blue Membranes) or SH1010 (Blue Membranes).

The particle may be a dextran based microcarrier. The particle may comprise Cytodex 1 (GE Healthcare) or Cytodex 3 (GE Healthcare). Cytodex 1 is based on a cross-linked dextran matrix which is substituted with positively charged N,N-diethylaminoethyl groups. The charged groups are distributed throughout the microcarrier matrix. Cytodex 3 consists of a thin layer of denatured collagen chemically coupled to a matrix of cross-linked dextran.

The particle may be a polystyrene based microcarrier. The particle may comprise Hillex or Hillex II (SoloHill Engineering, Inc.). Hillex and Hillex II are modified polystyrene microcarriers having a cationic trimethyl ammonium coating.

The particle may be treated prior to allowing cells to grow thereon. Such treatment may seek to achieve greater adherence, availability of charges, biocompatibility, etc, as described elsewhere in this document.

Cellulose microcarriers such as DE-53, DE-52 and QA-52 may be rod-shaped.

A cell culture may comprise a mixture of more than one type of particle. For example, a first particle population (e.g. of compact shape particles) and a second particle population (e.g. of elongate shape particles). In some embodiments a first cell type, e.g. feeder cells, may be attached to the first particles and a second cell type, e.g. hESCs, may be attached to the second particles. Each particle type may have the same or a different matrix coating. Optionally one or both particle types may not have a matrix coating.

Beads

Beads or microbeads suitable for use include those which are used for gel chromatography, for example, gel filtration media such as Sephadex. Suitable microbeads of this sort include Sephadex G-10 having a bead size of 40-120 (Sigma Aldrich catalogue number 27, 103-9), Sephadex G-15 having a bead size of 40-120 µm (Sigma Aldrich catalogue number 27, 104-7), Sephadex G-25 having a bead size of 20-50 µm (Sigma Aldrich catalogue number 27, 106-3), Sephadex G-25 having a bead size of 20-80 µm (Sigma Aldrich catalogue number 27, 107-1), Sephadex G-25 having a bead size of 50-150 µm (Sigma Aldrich catalogue number 27, 109-8), Sephadex G-25 having a bead size of 100-300 µm (Sigma Aldrich catalogue number 27, 110-1), Sephadex G-50 having a bead size of 20-50 µm (Sigma Aldrich catalogue number 27, 112-8), Sephadex G-50 having a bead size of 20-80 µm (Sigma Aldrich catalogue number 27, 113-6), Sephadex G-50 having a bead size of 50-150 µm (Sigma Aldrich catalogue number 27, 114-4), Sephadex G-50 having a bead size of 100-300 µm (Sigma Aldrich catalogue number 27, 115-2), Sephadex G-75 having a bead size of 20-50 µm (Sigma Aldrich catalogue number 27, 116-0), Sephadex G-75 having a bead size of 40-120 µm (Sigma Aldrich catalogue number 27, 117-9), Sephadex G-100 having a bead size of 20-50 µm (Sigma Aldrich catalogue number 27, 118-7), Sephadex G-100 having a bead size of 40-120 µm (Sigma Aldrich catalogue number 27, 119-5), Sephadex G-150 having a bead size of 40-120 µm (Sigma Aldrich catalogue number 27, 121-7), and Sephadex G-200 having a bead size of 40-120 µm (Sigma Aldrich catalogue number 27, 123-3), so long as they are compatible in terms of size, as explained elsewhere in this document.

Sepharose beads, for example, as used in liquid chromatography, may also be used. Examples are Q-Sepharose, S-Sepharose and SP-Sepharose beads, available for example from Amersham Biosciences Europe GmbH (Freiburg, Germany) as Q Sepharose XL (catalogue number 17-5072-01), Q Sepharose XL (catalogue number 17-5072-04), Q Sepharose XL (catalogue number 17-5072-60), SP Sepharose XL (catalogue number 17-5073-01), SP Sepharose XL (catalogue number 17-5073-04) and SP Sepharose XL (catalogue number 117-5073-60) etc.

Particle Shape

The particle may comprise any suitable shape for cell growth, e.g., a compact shape or an elongate shape.

Compact Shape

Examples of compact shapes are generally spherical shaped particles, ellipsoid shaped particles, or granular shaped particles.

By "compact", we mean a shape which is not generally elongate. In other words, "compact" shapes are those which are generally non-elongate or unextended, or which are not extended in any one dimension. The compact shape may be one which is not generally spread out, or not long or spindly. Therefore, such "compact shapes" generally possess linear dimensions which may be generally similar, or which do not differ by a large amount.

Thus, the ratio of any two dimensions of the compact shape may be 5:1 or less, such as 4:1 or less, such as 3:1, 2.5:1, 2.4:1, 2.3:1, 2.2:1, 2.1:1, 2:1, 1.9:1, 1.8:1, 1.7:1, 1.6:1, 1.5:1, 1.4:1, 1.3:1, 1.2:1, 1.1:1, or less. For example, no two pairs of dimensions may have a ratio of 5:1 or more.

In some embodiments, the longest dimension of the compact shape is less than five times the shortest dimension of the compact shape. In other embodiments, the longest dimension of the compact shape is not significantly greater than the shortest dimension, i.e., the shape is relatively uniform.

The "longest dimension" as the term is used in this document should be taken to mean the length of the major axis, i.e., the axis containing the longest line that can be drawn through the particle. Similarly, the "shortest dimension" is the length of the minor axis, which is the axis containing the shortest line that can be drawn through the particle.

Regular shapes in which the linear dimensions are approximately the same, or are comparable, or in which the ratio of the longest dimension to the shortest dimension is less than 5:1 are included in the compact particles described here. The above ratios may therefore relate to the ratio of the longest dimension to the shortest dimension. In some embodiments, the ratio of two dimensions (such as the longest dimension to the shortest dimension) is less than 1.1:1, such as 1:1 (i.e., a regular or uniform shape).

Therefore, where applicable, the length of the particle may be less than 5× its width or diameter, such as less than 4× its width or diameter, such as less than 3×, such as less than 2× or less.

The compact shape may comprise a regular solid, a sphere, a spheroid, an oblate spheroid, a flattened spheroid, an ellipsoid, a cube, a cone, a cylinder, or a polyhedron. Polyhedra include simple polyhedra or regular polyhedra. Polyhedra include, for example, a hexahedron, holyhedron, cuboid, deltahedron, pentahedron, tetradecahedron, polyhedron, tetraflexagon, trapezohedron, truncated polyhedron, geodesic dome, heptahedron and hexecontahedron. Any of the above shapes may be used such that they are "compact", according to the definition provided above. For example, where the shape comprises an oblate spheroid, this has the appropriate oblateness such that the spheroid is compact, and not elongate.

In some embodiments, the compact shape may comprise a balloon shape, a cigar shape, a sausage shape, a disc shape, a teardrop shape, a ball shape or an elliptical shape, so long as the dimensions are as given above. The compact shape may also comprise a sphere shape, a cube shape, a cuboid shape, a tile shape, an ovoid shape, an ellipsoid shape, a disc shape, a cell shape, a pill shape, a capsule shape, a flat cylinder shape, a bean shape, a drop shape, a globular shape, a pea shape, a pellet shape, etc.

Elongate Shape

The particle may have a generally elongate shape. Examples of elongate shapes are generally rod shaped particles, cylindrical shaped particles, or stick shaped particles. The elongate particles may comprise hollow fibres.

By "elongate", we mean a shape which is not generally compact. In other words, "elongate" shapes are those which are generally extended in one dimension relative to another. The elongate shape may be one which is spread out, long or spindly. Therefore, such "elongate shapes" generally possess linear dimensions which generally differ from one another to a greater or lesser extent.

Thus, the ratio of any two dimensions of the elongate shape may be 5:1 or more, 4:1 or less, such as 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.1:1 or more, 2.2:1 or more, 2.3:1 or more, 2.4:1 or more, 2.5:1 or more, 3:1 or more, 4:1 or more, or 5:1 or more.

For example, any two pairs of dimensions may have a ratio of 5:1 or more. Thus, in some embodiments, the longest dimension of the elongate shape is more than five times the shortest dimension of the elongate shape.

Therefore, where applicable, the length of the particle may be more than 2× its width or diameter, such as more than 3× its width or diameter, such as more than 4×, such as more than 5× or more than 10×.

Elongate or rod-shaped microcarriers are especially preferred for use in the methods of the present invention. They are observed to provide a better attachment matrix for the generation of cell-microcarrier aggregates. Whilst not being limited or bound by theory, it is considered that the long axis of a rod-shaped microcarrier provides a superior attachment compared to bead (spherical) microcarriers due to the large surface area that is available for attachment enabling cell-carrier aggregation within a few hours that is stable during agitation.

Particle Size

In order for the particles to support continuous growth, they may have a size which enables cells to grow on the particles. The size of the particles also enables cells to aggregate with other cells growing on other particles. For example, it may be necessary for the size of the particle to be such that at least one dimension is compatible with the dimensions of a primate or human stem cell.

The size of the particles may be chosen empirically by selecting a particle, allowing stem cells to attach on and grow (as set out in this document and in detail in the Examples) and assaying any of a number of parameters such as growth, viability, retention of biological characters of stem cells, karyotype, etc.

As an example, the particle may comprise a compact microcarrier having a generally spherical or granular shape. Where this is the case, the compact microcarrier may have a dimension ranging between about 20 µm and about 250 µm.

The upper limit of the range of dimensions for the compact microcarrier may be about 250 µm, about 240 µm, about 230 µm, about 220 µm, about 210 µm, about 200 µm, about 190 µm, about 180 µm, about 170 µm, about 160 µm, about 150 µm, about 140 µm, about 130 µm, about 120 µm, about 110 µm, about 100 µm, about 90 µm, about 80 µm, about 70 µm, about 60 µm, about 50 µm, about 40 µm or about 30 µm.

The lower limit of the range of dimensions of the compact microcarrier may be about 20 µm, about 30 µm, 40 µm, about 50 µm, about 60 µm, about 70 µm, about 80 µm, about 90 µm, about 100 µm or about 110 µm.

The compact microcarriers may have a dimension between 120 µm to 20 µm, 110 µm to 30 µm, 100 µm to 40 µm, 90 µm to 50 µm, 80 µm to 40 µm, 70 µm to 50 µm or between 90 to 30 µm, 80 to 40 µm, 70 to 40 µm, 70 to 30 µm, 60 to 40 µm, 60 to 30 µm, 60 to 50 µm, 50 to 40 µm, 50 to 30 µm, 50 to 5 µm, 50 to 10 µm, 60 to 10 µm, 70 to 10 µm, 60 to 20 µm, 70 to 20 µm.

The compact microcarrier may have a dimension of about 20 µm, about 30 µm, 40 µm, about 50 µm, about 60 µm, about 65 µm, about 70 µm, about 80 µm, about 90 µm, about 100 µm, about 110 µm or about 120 µm.

The dimensions of the compact microcarrier may for example be about 65 µm.

The dimension may be the diameter of the microcarrier.

The compact particle may for example comprise a hydrophilic microcarrier, a hydroxylated methacrylic matrix microcarrier or derivatised hydrophilic beaded microcarrier, such as TSKgel Tresyl-5Pw (Tosoh) or Toyopearl AF-Tresyl-650 (Tosoh).

Information on TSKgel Tresyl-5Pw may be found at http://www.separations.us.tosohbioscience.com/Products/HPLCColumns/ByMode/Affinity/TSKgel+Tresyl-5PW.htm Information on Toyopearl AF-Tresyl-650 may be found at http://www.separations.us.tosohbioscience.com/Products/ProcessMedia/ByMode/AFC/ToyopearlAF-Tresyl-650.htm As another example, the particle may comprise a elongate microcarrier having a generally rod- or cylindrical shape. Where this is the case, the elongate microcarrier may have a longest dimension ranging between about 400 µm and about 50 µm.

The upper limit of the range of longest dimensions for the elongate microcarrier may be about 2000 µm, about 1900 µm, about 1800 µm, about 1700 µm, about 1600 µm, about 1500 µm, about 1400 µm, about 1300 µm, about 1200 µm, about 1100 µm, about 1000 µm, about 900 µm, about 800 µm, about 700 µm, about 600 µm, about 500 µm, about 400 µm, about 390 µm, about 380 µm, about 370 µm, about 360 µm, about 350 µm, about 340 µm, about 330 µm, about 320 µm, about 310 µm, about 300 µm, about 290 µm, about 280 µm, about 270 µm, about 260 µm, about 250 µm, about 240 µm, about 230 µm, about 220 µm, about 210 µm, about 200 µm, about 190 µm, about 180 µm, about 170 µm, about 160 µm, about 150 µm, about 140 µm, about 130 µm, about 120 µm, about 110 µm, about 100 µm, about 90 µm, about 80 µm, about 70 µm, about 60 µm or about 50 µm.

The lower limit of the range of longest dimensions of the elongate microcarrier may be about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm or about 390 µm.

The elongate microcarriers may have a longest dimension between 2000 µm to 20 µm, for example between 400 µm to 50 µm, 390 µm to 60 µm, 380 µm to 70 µm, 370 µm to 80 µm, 360 µm to 90 µm, 350 µm to 100 µm, 340 µm to 110 µm, 330 µm to 120 µm, 320 µm to 130 µm, 310 µm to 140 µm, 300 µm to 150 µm, 290 µm to 160 µm, 280 µm to 170 µm, 270 µm to 180 µm, 260 µm to 190 µm, 250 µm to 200 µm, 240 µm to 210 µm or 230 µm to 220 µm.

The longest dimension of the elongate microcarrier may for example be about 190 µm, 200 µm, 210 µm, 220 µm, etc.

The elongate microcarrier may have a shortest dimension ranging between 10 µm and 50 µm. The elongate microcarrier may have a shortest dimension of about 10 µm, about 15 µm, about 20 µm, about 25 µm, about 30 µm, about 35 µm, about 40 µm or about 45 µm.

An elongate microcarrier may be cylindrical or rod-shaped, having an approximately circular or ellipsoid cross-section, the shortest diameter of which may be in the range of about 5 µm to about 50 µm, for example one of about 10 µm, about 15 µm, about 20 µm, about 25 µm, about 30 µm, about 35 µm, about 40 µm, or about 45 µm. The diameter may be between one of: about 5 µm and 20 µm, about 10 µm and 25 µm, about 15 µm and 30 µm, about 20 µm and 35 µm, about 25 µm and 40 µm, about 30 µm and 45 µm, about 35 µm and 50 µm.

The elongate particle may for example comprise a cellulose cylindrical microcarrier, such as DE-52 (Whatman), DE-53 (Whatman) or QA-52 (Whatman).

The size and dimensions of any given microcarrier may vary, within or between batches. For example, for DE-53 rod-shaped cellulose microcarriers we measured the length and diameter of the carriers within a batch and found that the length of carrier can be between 50 and 250 µm (average length of 130±50 µm) and the diameter of the carrier can be between 17 µm and at least 50 µm (average diameter of 35±7 µm).

The particle may be porous. Porous particles enable medium to circulate within and through the growing area and this may assist cell growth. For example, the particle may comprise a macroporous or microporous carboseed microcarrier. The particle may comprise SM1010 (Blue Membranes) or SH1010 (Blue Membranes).

Culture of Stem Cells

Any suitable method of culturing stem cells, for example as set out in the Examples, may be used in the methods and compositions described here.

Any suitable container may be used to propagate stem cells according to the methods and compositions described here. Suitable containers include those described in US Patent Publication US2007/0264713 (Terstegge).

Containers may include bioreactors and spinners, for example. A "bioreactor", as the term is used in this document, is a container suitable for the cultivation of eukaryotic cells, for example animal cells or mammalian cells, such as in a large scale. A typical cultivation volume of a regulated bioreactor is between 20 ml and 500 ml.

The bioreactor may comprise a regulated bioreactor, in which one or more conditions may be controlled or monitored, for example oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 $cm^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture aggregates of cells/microcarriers may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage

The methods and compositions described here may comprise passaging, or splitting during culture. The methods may involve continuous or continual passage.

By "continual" or "continuous", we mean that our methods enable growth of stem cells on microcarriers in a fashion that enables them to be passaged, e.g., taken off the microcarriers on which they are growing and transferred to other microcarriers or particles, and that this process may be repeated at least once, for example twice, three times, four times, five times, etc (as set out below). In some cases, this may be repeated any number of times, for example indefinitely or infinitely. Most preferably the process is repeated 5 or more times, e.g. 6 or more time, 7 or more times, 8 or more times, 9 or more times, 10 or more times, 11 or more times, 12 or more times, 13 or more times, 14 or more times, 15 or more times, 16 or more times, 17 or more times, 18 or more times, 19 or more times, 20 or more times, 21 or more times, 22 or more times, 23 or more times, 24 or more times, 25 or more times. The terms "continual" or "continuous" may also be used to mean a substantially uninterrupted extension of an event, such as cell growth. For example, our methods enable the expansion of stem cells to any number of desired generations, without needing to terminate the growth or culture.

Cells in culture may be dissociated from the substrate or flask, and "split", subcultured or passaged, by dilution into tissue culture medium and replating.

Cells growing on particles may be passaged back onto particle culture. Alternatively, they may be passaged back onto conventional (2D) cultures. Tissue culture cells growing on plates may be passaged onto particle culture. Each of these methods are described in more detail below and in the Examples.

The term "passage" may generally refer to the process of taking an aliquot of a cell culture, dissociating the cells completely or partially, diluting and inoculating into medium. The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used (http://hedricklab.ucsd.edu/Protocol/COSCell.html).

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial.

The dilution may be of any suitable dilution. The cells in the cell culture may be split at any suitable ratio. For example, the cells may be split at a ratio of 1:2 or more, 1:3 or more, 1:4 or more or 1:5 or more. The cells may be split at a ratio of 1:6 or more, 1:7 or more, 1:8 or more, 1:9 or more or 1:10 or more. The split ratio may be 1:10 or more. It may be 1:11, 1:12, 1:13, 1:14, 1:15, 1:16, 1:17, 1:18, 1:19 or 1:20 or more. The split ratio may be 1:21, 1:22, 1:23, 1:24, 1:25 or 1:26 or more.

Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, passages or more. The stem cells may be passaged for 25, 30, 35, 40, 45, 50, 55, 60, 65, 70, 75, 80, 85, 90, 95 or more passages. The stem cells may be propagated indefinitely in culture.

Passages may be expressed as generations of cell growth. Our methods and compositions allow stem cells to propagate for 1, 2, 3, 4, 5, 6, 7, 8, 9, 10, 11, 12, 13, 14, 15, 16, 17, 18, 19, 20, 21, 22, 23, 24, 25 generations or more. The stem cells may be grown for 25, 30, 35, 40, 45, 50, 55, 60, 65, 70, 75, 80, 85, 90, 95 or more generations.

Passages may also be expressed as the number of cell doublings. Our methods and compositions allow stem cells to propagate for 1, 2, 3, 4, 5, 6, 7, 8, 9, 10, 11, 12, 13, 14, 15, 16, 17, 18, 19, 20, 21, 22, 23, 24, 25 cell doublings or more. The stem cells may be grown for 25, 30, 35, 40, 45, 50, 55, 60, 65, 70, 75, 80, 85, 90, 95 or more cell doublings.

The stem cells may be cultured for more than 5, more than 10, more than 15, more than 20, more than 25, more than 30, more than 40, more than 45, more than 50, more than 100, more than 200, more than 500 or more than 800 passages, generations or cell doublings. The stem cells may be maintained for 100, 200, 500 or more passages, generations or cell doublings.

Growth and Productivity

The methods and compositions described here enable the production of stem cells in quantity.

The methods may enable exponential growth of stem cells in culture. The exponential growth may or may not be accompanied by a lag phase. The exponential growth may form part or a substantial period of the growth of the cells in culture. Methods of assessing exponential growth are known in the art.

For example the specific growth rate of the cells may conform to:

$$\mu = \frac{(\ln x1 - \ln x2)}{t1 - t2}$$

Where x=cell concentration and t=time. The methods and compositions described here may enable greater productivity of cell growth compared to traditional, 2D culture methods (e.g., culture on plates). For example, the volumetric productivity of our methods may be $1 \times 10^6$ cells/well or more, such as $2.5 \times 10^6$ cells/well or more, for example 3, 4, 5, 6 or $7 \times 10^6$ cells/well or more. A well may have a diameter of about 3.5 cm or an area of about 9.5 $cm^2$. The volumetric productivity of our methods may be 1 million cells/ml or more, such as 2 million cells/ml or more, 2.5 million cells/ml or more, 3 million cells/ml or more, 3.5 million cells/ml, 1 million cells/ml or more, such as 4 million cells/ml or more, 4.5 million cells/ml or more, 5 million cells/ml or more.

Maintenance of Stem Cell Characteristics

The propagated stem cells may retain at least one characteristic of a primate or human stem cell. The stem cells may retain the characteristic after one or more passages. They may do so after a plurality of passages. They may do so after the stated number of passages as described above.

The characteristic may comprise a morphological characteristic, immunohistochemical characteristic, a molecular biological characteristic, etc. The characteristic may comprise a biological activity.

Stem Cell Characteristics

The stem cells propagated by our methods may display any of the following stem cell characteristics.

Stem cells may display increased expression of Oct4 and/or SSEA-1 and/or TRA-1-60 and/or Mab84. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of one or more pluripotency markers.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Germ Cell Tumors, in E. J. Robertson, 1987, supra). Human embryonic stem cells are typically SSEA-1 negative and SSEA-4 positive. hEG cells are typically SSEA-1 positive. Differentiation of primate pluripotent stem cells (pPS) cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, OCT-4, SSEA-4, TRA-1-60 and Mab84, etc, may be retained by the propagated stem cells.

Detection of markers may be achieved through any means known in the art, for example immunologically. Histochemical staining, flow cytometry (FACS), Western Blot, enzyme-linked immunoassay (ELISA), etc may be used.

Flow immunocytochemistry may be used to detect cell-surface markers. immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank. See U.S. Pat. No. 5,843,780 for further details.

Substantially all of the propagated cells, or a substantial portion of them, may express the marker(s). For example, the percentage of cells that express the marker or markers may be 50% or more, 60% or more, 70% or more, 80% or more, 90% or more, 93% or more, 95% or more, 97% or more, 98% or more, 99% or more, or substantially 100%.

Cell Viability

The biological activity may comprise cell viability after the stated number of passages. Cell viability may be assayed in various ways, for example by Trypan Blue exclusion.

A protocol for vital staining follows. Place a suitable volume of a cell suspension (20-200 µL) in appropriate tube add an equal volume of 0.4% Trypan blue and gently mix, let stand for 5 minutes at room temperature. Place 10 µl of stained cells in a hemocytometer and count the number of viable (unstained) and dead (stained) cells. Calculate the average number of unstained cells in each quadrant, and multiply by $2 \times 10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 98% or more, 99% or more, or substantially 100%.

Karyotype

The propagated stem cells may retain a normal karyotype during or after propagation. A "normal" karyotype is a karyotype that is identical, similar or substantially similar to a karyotype of a parent stem cell from which the stem cell is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provide routine karyotyping services, such as the Cytogenetics Lab at Oakland Calif.) and compared to published stem cell karyotypes.

All or a substantial portion of propagated cells may retain a normal karyotype. This proportion may be 50% or more, 60% or more, 70% or more, 80% or more, 90% or more, 93% or more, 95% or more, 97% or more, 98% or more, 99% or more, or substantially 100%.

Pluripotency

The propagated stem cells may retain the capacity to differentiate into all three cellular lineages, i.e., endoderm, ectoderm and mesoderm. Methods of induction of stem cells to differentiate each of these lineages are known in the art and may be used to assay the capability of the propagated stem cells. All or a substantial portion of propagated cells may retain this ability. This may be 50% or more, 60% or more, 70% or more, 80% or more, 90% or more, 93% or more, 95% or more, 97% or more, 98% or more, 99% or more, or substantially 100% of the propagated stem cells.

Co-Culture and Feeders

Our methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles.

Feeder cells, as the term is used in this document, may mean cells which are used for or required for cultivation of cells of a different type. In the context of stem cell culture, feeder cells have the function of securing the survival, proliferation, and maintenance of ES-cell pluripotency. ES-cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells growing on particles may therefore be grown in such coated containers.

The feeder cells may themselves be grown on particles. They may be seeded on particles in a similar way as described for stem cells. The stem cells to be propagated may be grown together with or separate from such feeder particles. The stem cells may therefore be grown on a layer on such feeder cell coated particles. On the other hand, the stem cells may be grown on separate particles. Any combinations of any of these arrangements are also possible, for example, a culture which comprises feeder cells grown on particles, particles with feeder cells and stem cells, and particles with stem cells growing. These combinations may be grown in containers with a feeder layer or without.

The particles on which the feeder cells are grown may be either coated or not coated in a matrix coating.

Arrangements in which feeder cells are absent or not required are also possible. For example, the cells may be grown in medium conditioned by feeder cells or stem cells.

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco#11965-092; Knockout Dulbecco's modified Eagles medium (KO DMEM), Gibco#10829-018; 200 mM L-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco#11965-092), 10% FBS (Hyclone#30071-03), and 2 mM glutamine. mEFs are propagated in T150 flasks (Corning#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (about 4000 rads gamma irradiation). Six-well culture plates (such as Falcon#304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Serum Free Media

The methods and compositions described here may include culture of stem cells in a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, SIP, PDGF, BAFF, April, SCF, Flt-3 ligand, Wnt3A and others. The growth factor(s) may be used at any suitable concentration such as between 1 pg/ml to 500 ng/ml.

Media Supplements

Culture media may be supplemented with one or more additives. For example, these may be selected from one or more of: a lipid mixture, Bovine Serum Albumin (e.g. 0.1% BSA), hydrolysate of soybean protein.

Stem Cells

As used in this document, the term "stem cell" refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells.

In general, reference herein to stem cells (plural) may include the singular (stem cell). In particular, methods of culturing and differentiating stem cells may includes single cell and aggregate culturing techniques.

In the present invention stem cell cultures may be of aggregates or single cells.

Totipotent Stem Cells

The term "totipotent" cell refers to a cell which has the potential to become any cell type in the adult body, or any cell of the extraembryonic membranes (e.g., placenta). Thus, the only totipotent cells are the fertilized egg and the first 4 or so cells produced by its cleavage.

Pluripotent Stem Cells

"Pluripotent stem cells" are true stem cells, with the potential to make any differentiated cell in the body. However, they cannot contribute to making the extraembryonic membranes which are derived from the trophoblast. Several types of pluripotent stem cells have been found.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen. For example, adult stem cells may be mesenchymal stem cells, haematopoietic stem cells, mammary stem cells, endothelial stem cells, or neural stem cells. Adult stem cells may be multipotent.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Markers for stem cells and methods of their detection are described elsewhere in this document (under "Maintenance of Stem Cell Characteristics").

Sources of Stem Cells

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells.

U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors.

U.S. Pat. No. 5,968,829 reports neural stem cells obtained from embryonic forebrain and cultured with a medium comprising glucose, transferrin, insulin, selenium, progesterone, and several other growth factors.

Primary liver cell cultures can be obtained from human biopsy or surgically excised tissue by perfusion with an appropriate combination of collagenase and hyaluronidase. Alternatively, EP 0 953 633 A1 reports isolating liver cells by preparing minced human liver tissue, resuspending concentrated tissue cells in a growth medium and expanding the cells in culture. The growth medium comprises glucose, insulin, transferrin, $T_3$, FCS, and various tissue extracts that allow the hepatocytes to grow without malignant transformation.

The cells in the liver are thought to contain specialized cells including liver parenchymal cells, Kupffer cells, sinusoidal endothelium, and bile duct epithelium, and also precursor cells (referred to as "hepatoblasts" or "oval cells") that have the capacity to differentiate into both mature hepatocytes or biliary epithelial cells (L. E. Rogler, Am. J. Pathol. 150:591, 1997; M. Alison, Current Opin. Cell Biol. 10:710, 1998; Lazaro et al., Cancer Res. 58:514, 1998).

U.S. Pat. No. 5,192,553 reports methods for isolating human neonatal or fetal hematopoietic stem or progenitor cells. U.S. Pat. No. 5,716,827 reports human hematopoietic cells that are Thy-1 positive progenitors, and appropriate growth media to regenerate them in vitro. U.S. Pat. No. 5,635,387 reports a method and device for culturing human hematopoietic cells and their precursors. U.S. Pat. No. 6,015,554 describes a method of reconstituting human lymphoid and dendritic cells.

U.S. Pat. No. 5,486,359 reports homogeneous populations of human mesenchymal stem cells that can differentiate into cells of more than one connective tissue type, such as bone, cartilage, tendon, ligament, and dermis. They are obtained from bone marrow or periosteum. Also reported are culture conditions used to expand mesenchymal stem cells. WO 99/01145 reports human mesenchymal stem cells isolated from peripheral blood of individuals treated with growth factors such as G-CSF or GM-CSF. WO 00/53795 reports adipose-derived stem cells and lattices, substantially free of adipocytes and red cells. These cells reportedly can be expanded and cultured to produce hormones and conditioned culture media.

Stem cells of any vertebrate species can be used. Included are stem cells from humans; as well as non-human primates, domestic animals, livestock, and other non-human mammals such as rodents, mice, rats, etc.

Amongst the stem cells suitable for use in the methods and compositions described here are primate (pPS) or human pluripotent stem cells derived from tissue formed after gestation, such as a blastocyst, or fetal or embryonic tissue taken any time during gestation. Non-limiting examples are primary cultures or established lines of embryonic stem cells.

Embryonic Stem Cells

Embryonic stem cells may be isolated from blastocysts of members of primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts may be obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated. embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (.about.200 U/mL; Gibco) or by selection of individual colonies by micropipette. Clump sizes of about 50 to 100 cells are optimal.

Embryonic Germ Cells

Human Embryonic Germ (hEG) cells may be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm$^3$ chunks. The tissue is then pipetted through a 100 μL tip to further disaggregate the cells. It is incubated at 37 degrees C. for about 5 min, then about 3.5 mL EG growth medium is added. EG growth medium is DMEM, 4500 mg/L D-glucose, 2200 mg/L mM sodium bicarbonate; 15% embryonic stem (ES) qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37 degrees C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad γ-irradiation. Suitable feeders are STO cells (ATCC Accession No. CRL 1503). 0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Induced Pluripotent Stem Cells

The methods and compositions described here may be used for the propagation of induced pluripotent stem cells.

Induced pluripotent stem cells, commonly abbreviated as iPS cells or iPSCs, are a type of pluripotent stem cell artificially derived from a non-pluripotent cell, typically an adult somatic cell, for example fibroblasts, lung or B cells, by inserting certain genes. iPS cells are reviewed and discussed in Takahashi, K. & Yamanaka (2006), Yamanaka S, et. al. (2007), Wernig M, et. al. (2007), Maherali N, et. al. (2007) and Thomson J A, Yu J, et al. (2007) and Takahashi et al., (2007).

iPS cells are typically derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

Sources of Pluripotent Cells

Some aspects and embodiments of the present invention are concerned with the use of pluripotent cells. Embryonic stem cells and induced pluripotent stem cells are described as examples of such cells.

Embryonic stem cells have traditionally been derived from the inner cell mass (ICM) of blastocyst stage embryos (Evans, M. J., and Kaufman, M. H. (1981). Establishment in culture of pluripotential cells from mouse embryos. Nature 292, 154-156. Martin, G. R. (1981). Isolation of a pluripotent cell line from early mouse embryos cultured in medium conditioned by teratocarcinoma stem cells. Proc. Natl. Acad. Sci. USA 78, 7634-7638. Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147). In isolating embryonic stem cells these methods may cause the destruction of the embryo.

Several methods have now been provided for the isolation of pluripotent stem cells that do not lead to the destruction of an embryo, e.g. by transforming adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported Ming et al., Pluripotency of mesenchymal stem cells derived from adult marrow.

Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 ⁿ2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4):581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

The present invention includes the use of pluripotent or multipotent stem cells obtained from any of these sources or created by any of these methods. In some embodiments, the pluripotent or multipotent cells used in the methods of the present invention have been obtained by a method that does not cause the destruction of an embryo. More preferably in some embodiments, the pluripotent or multipotent cells used in the methods of the present invention have been obtained by a method that does not cause the destruction of a human or mammalian embryo. As such, methods of the invention may be performed using cells that have not been prepared exclusively by a method which necessarily involves the destruction of human embryos from which those cells may be derived. This optional limitation is specifically intended to take account of Decision G0002/06 of 25 Nov. 2008 of the Enlarged Board of Appeal of the European Patent Office.

Mesenchymal Stem Cells

Mesenchymal stem cells are multipotent progenitor cells having the ability to generate cartilage, bone, muscle, tendon, ligament, fat and other connective tissues. They are capable of differentiation into a wide variety of cell types, including bone cells (osteoblasts), cartilage cells (chondrocytes), muscle cells (myocytes) and fat cells (adipocytes) (e.g. see Rastegar et al. World Journal of Stem cells 2010 Aug. 26; 2(4): 67-80).

These primitive progenitors exist postnatally and exhibit stem cell characteristics, namely low incidence and extensive renewal potential. These properties in combination with their developmental plasticity have generated tremendous interest in the potential use of mesenchymal stem cells to replace damaged tissues.

Mesenchymal stem cells can be isolated from a range of tissue types, including bone marrow, muscle, fat, dental pulp, adult tissue, fetal tissue, neonatal tissue, and umbilical cord. Mesenchymal stem cells may be obtained from non-human mammals, or from humans.

Human bone marrow mesenchymal stem cells can be isolated and detected using selective markers, such as STRO-I, from a CD34+ fraction indicating their potential for marrow repopulation. These cell surface markers are only found on the cell surface of mesenchymal stem cells and are an indication of the cells pluripotency.

Differentiation/Embryoid Bodies

The cultured stem cells may be differentiated into any suitable cell type by using differentiation techniques known to those of skill in the art.

We describe a process for producing differentiated cells, the method comprising propagating a stem cell by a method as described herein, and then differentiating the stem cell in accordance with known techniques. For example, we provide for methods of differentiating to ectoderm, mesoderm and endoderm, as well as to cardiomyocytes, adipocytes, chondrocytes and osteocytes, etc. We further provide embryoid bodies and differentiated cells obtainable by such methods. Cell lines made from such stem cells and differentiated cells are also provided.

Methods of differentiating stem cells are known in the art and are described in for example Itskovitz-Eldor (2000) and Graichen et al (2007), Kroon et al (2008) and Hay et al (2008), WO 2007/030870, WO 2007/070964, Niebrugge et al (2009), R Passier et al. 2005, P W Burridge et al. 2006, M A Laflamme et al. 2007, L Yang et al. 2008, and X Q Xu et al. 2008. The cultured stem cells may also be used for the formation of embryoid bodies. Embryoid bodies, and methods for making them, are known in the art. The term "embryoid body" refers to spheroid colonies seen in culture produced by the growth of embryonic stem cells in suspension. Embryoid bodies are of mixed cell types, and the distribution and timing of the appearance of specific cell types corresponds to that observed within the embryo. Embryoid bodies may be generated by plating out embryonic stem cells onto media such as semisolid media. Methylcellulose media may be used as described in Lim et al, Blood. 1997; 90:1291-1299.

Embryonic stem cells may be induced to form embryoid bodies, for example using the methods described in Itskovitz-Eldor (2000). The embryoid bodies contain cells of all three embryonic germ layers.

The embryoid bodies may be further induced to differentiate into different lineages for example by exposure to the appropriate induction factor or an environmental change. Graichen et al (2007) describes the formation of cardiomyocytes from human embryonic stem cells by manipulation of the p38MAP kinase pathway. Graichen demonstrates induction of cardiomyocyte formation from stem cells by exposure to a specific inhibitor of p38 MAP kinase such as SB203580 at less than 10 micromolar.

Differentiated cells may be employed for any suitable purpose, such as regenerative therapy, as known in the art.

Stem cells obtained through culture methods and techniques according to this invention may be used to differentiate into another cell type for use in a method of medical treatment. Thus, the differentiated cell type may be derived from a stem cell obtained by the culture methods and techniques described herein which has subsequently been permitted to differentiate. The differentiated cell type may be considered as a product of a stem cell obtained by the culture methods and techniques described herein which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Differentiation on Microcarriers

In accordance with the present invention stem cells, particularly embryonic stem cells and iPS, may be induced to differentiate during suspension culture on microcarriers.

Embryonic stem cells may be induced to differentiate into the three primary germ layers: ectoderm, endoderm and mesoderm and their derivatives. Embryonic stem cells may be induced to form embryoid bodies. A range of cell types or tissues may therefore be obtained, for example cardiomyocytes, cardiac mesoderm, hepatocytes, hepatic endoderm, pancreatic islet cells, pancreatic endoderm, insulin producing cells, neural tissue, neuroectoderm, epidermal tissue, surface ectoderm, bone, cartilage, muscle, ligament, tendon or other connective tissue.

Methods for the differentiation of stem cells and the formation of embryoid bodies are described above, and are applicable to the differentiation of stem cells in microcarrier culture.

Methods of differentiation of stem cells during microcarrier culture may require the microcarrier to be coated in a matrix coating as described above. For example, suitable coatings may include one or more of: Matrigel, Laminin, Fibronectin, Vitronectin, Hyaluronic Acid.

Methods of differentiation of stem cells during microcarrier culture may include the addition of supplements to the culture media. For example, supplements may include Bovine Serum Albumin, Lipids or Hy-Soy (Sigma-Aldrich—this is an enzymatic hydrolysate of soybean protein).

Methods of differentiation of stem cells during microcarrier culture may involve an initial culture and propagation of the stem cells in either 2D culture or in 3D suspension microcarrier culture followed by induction of differentiation during microcarrier culture.

Methods of differentiation may involve differentiation of cells without forming embryoid bodies.

Neural Differentiation

Stem cells can be induced to differentiate to the neural lineage by culture in media containing appropriate differentiation factors. Such factors may include one or more of activin A, retinoic acid, basic fibroblast growth factor (bFGF), and antagonists of bone morphogenetic protein (BMP), such as noggin (Niknejad et al. European Cells and Materials Vol. 19 2010 pages 22-29).

Cells differentiating towards the neural lineage may be identified by expression of neural markers, such as Pax6, Nestin, Map2, β-tubulin III and GFAP. Cells of the neural lineage may cluster to form neurospheres (which may be nestin-positive cell aggregates), and these may be expanded by application of selected growth factors such as EGF and/or FGF1 and/or FGF2.

Uses

The methods and compositions described here may be employed for various means.

For example, the particles described here may be provided as research tools or lab reagents for simpler culture of stem cells. They may be used for expansion of undifferentiated stem cells on microcarriers for generating differentiated cells. This could be developed into a contract manufacturing capability. Stem cells may be expanded and optionally differentiated for use in drug testing. The particles or microcarriers may be labelled for combinatorial differentiation of stem cells in different media conditions.

Stem cells propagated by the methods described here may be used for a variety of commercially important research, diagnostic, and therapeutic purposes. The stem cells may be used directly for these purposes, or may be differentiated into any chosen cell type using methods known in the art. Progenitor cells may also be derived from the stem cells. The differentiated cells or progenitor cells, or both, may be used in place of, or in combination with, the stem cells for the same purposes. Thus, any use described in this document for stem cells applies equally to progenitor cells and differentiated cells derived from the stem cells. Similarly, any uses of differentiated cells will equally apply to those stem cells for which they are progenitors, or progenitor cells.

The uses for stem cells, etc are generally well known in the art, but will be described briefly here.

Therapeutic Uses

The methods and compositions described here may be used to propagate stem cells for regenerative therapy. Stem cells may be expanded and directly administered into a patient. They may be used for the repopulation of damaged tissue following trauma.

Embryonic stem cells may be used directly, or used to generate ectodermal, mesodermal or endodermal progenitor cell populations, for regenerative therapy. Progenitor cells may be made by ex vivo expansion or directly administered into a patient. They may also be used for the re-population of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Embryonic stem cells may be used as sources of ectodermal, mesodermal or endodermal progenitor cells for the treatment of degenerative diseases such as diabetes, Alzheimer's disease, Parkinson's disease, etc. Embryonic stem cells may be used as sources of mesodermal or endodermal progenitors for NK or dendritic cells for immunotherapy for cancer.

The methods and compositions described here enable the production of ectodermal, mesodermal or endodermal progenitor cells, which may of course be made to further differentiate using methods known in the art to terminally differentiated cell types.

Thus, any uses of terminally differentiated cells will equally attach to those ectodermal, mesodermal or endodermal progenitor cells (or stem cells) for which they are sources.

Stem cells, ectodermal, mesodermal or endodermal progenitor cells and differentiated cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Libraries

For example, populations of undifferentiated and differentiated cells may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

Drug Screening

Stem cells and differentiated cells may also be used to screen for factors (such as solvents, small molecule drugs, peptides, polynucleotides, and the like) or environmental conditions (such as culture conditions or manipulation) that affect the characteristics of stem cells or differentiated cells.

Stem cells may be used to screen for factors that promote pluripotency, or differentiation. In some applications, differentiated cells are used to screen factors that promote maturation, or promote proliferation and maintenance of such cells in long-term culture. For example, candidate maturation factors or growth factors are tested by adding them to cells in different wells, and then determining any phenotypic change that results, according to desirable criteria for further culture and use of the cells.

Particular screening applications relate to the testing of pharmaceutical compounds in drug research. The reader is referred generally to the standard textbook "In vitro Methods in Pharmaceutical Research", Academic Press, 1997, and U.S. Pat. No. 5,030,015), as well as the general description of drug screens elsewhere in this document. Assessment of the activity of candidate pharmaceutical compounds generally involves combining the stem cells or differentiated cells with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Tissue Regeneration

Stem cells propagated according to the methods and compositions described here (and differentiated cells derived therefrom) may be used for therapy, for example tissue reconstitution or regeneration in an individual patient in need thereof. The cells may be administered in a manner that permits them to graft to the intended tissue site and reconstitute or regenerate the functionally deficient area.

Propagated stem cells or differentiated cells derived therefrom may be used for tissue engineering, such as for the growing of skin grafts. They may be used for the bioengineering of artificial organs or tissues, or for prosthetics, such as stents.

Differentiated cells may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells. Differentiated cells may be used for tissue engineering, such as for the growing of skin grafts. Modulation of stem cell differentiation may be used for the bioengineering of artificial organs or tissues, or for prosthetics, such as stents.

In another example, neural stem cells are transplanted directly into parenchymal or intrathecal sites of the central nervous system, according to the disease being treated. Grafts are done using single cell suspension or small aggregates at a density of 25,000-500,000 cells per .mu.L (U.S. Pat. No. 5,968,829). The efficacy of neural cell transplants can be assessed in a rat model for acutely injured spinal cord as described by McDonald et al. (Nat. Med. 5:1410, 1999. A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

Certain neural progenitor cells are designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells as made according to the methods described here may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Hepatocytes and hepatocyte precursors prepared using our methods can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cardiomyocytes may be prepared by inducing differentiation of stem cells by modulation of the MAP kinase pathway for example with SB203580, a specific p38 MAP kinase inhibitor, as described in Graichen et al (2007). The efficacy of such cardiomyocytes may be assessed in animal models for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modelled using an embolization coil in the distal portion of the left anterior descending artery (Watanabe et al., Cell Transplant. 7:239, 1998), and efficacy of treatment can be evaluated by histology and cardiac function. Cardiomyocyte preparations can be used in therapy to regenerate cardiac muscle and treat insufficient cardiac function (U.S. Pat. No. 5,919,449 and WO 99/03973).

Cancer

Stem cells propagated according to the methods and compositions described here and differentiated cells derived therefrom may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

Stem cells propagated and optionally differentiated according to the methods and compositions described here may also be used in combination with anticancer agents such as endostatin and angiostatin or cytotoxic agents or chemotherapeutic agent. For example, drugs such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Caminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Further Aspects

We describe a method of propagating human stem cells, the method comprising the steps of: (a) providing a first microparticle with a human stem cell attached thereto; (b) allowing the first microparticle to contact a second microparticle comprising a second human stem cell attached thereto to form an aggregate; and (c) culturing the aggregate; in which each of the first and the second microparticles comprises a matrix coated thereon and having a positive charge.

We describe a method of propagating human stem cells on a carrier, in which the carrier bears a positive charge, is coated with an extracellular matrix component, and is of a size which allows the stem cells to form an aggregate of carriers.

We describe a method of propagating human stem cells, the method comprising the steps of: (a) providing a plurality of microparticles with human stem cells attached thereto, each microparticle comprising a positive charge and a matrix coated thereon; (b) aggregating the plurality of microparticles to form an aggregate; and (c) culturing the aggregate.

We describe a method of propagating human stem cells, the method comprising the steps of: (a) providing a microparticle comprising a positive charge and a matrix coated thereon; (b) allowing a human stem cell to attach to the particle; and (c) aggregating microparticles with stem cells attached thereon to thereby propagate the human stem cells.

The following numbered paragraphs (paras.) contain statements of broad combinations of the inventive technical features herein disclosed:—

1. A particle comprising a matrix coated thereon and having a positive charge, the particle being of a size to allow aggregation of primate or human stem cells attached thereto.

2. A particle according to Paragraph 1, which comprises a substantially elongate, cylindrical or rod shaped particle or a substantially compact or spherical shaped particle.

3. A particle according to Paragraph 1 or 2, which comprises a substantially elongate, cylindrical or rod shaped particle having a longest dimension of between 50 µm and 400 µm.

4. A particle according to Paragraph 3, which comprises a longest dimension of about 200 µm.

5. A particle according to Paragraph 3 or 4, which comprises a shortest dimension of between 20 µm and 30 µm.

6. A particle according to any preceding paragraph, which comprises a cellulose cylindrical microcarrier.

7. A particle according to any preceding paragraph, which comprises DE-52 (Whatman), DE-53 (Whatman) or QA-52 (Whatman).

8. A particle according to Paragraph 1 or 2, which comprises a substantially compact or spherical shaped particle having a size of between about 20 µm and about 120 µm.

9. A particle according to Paragraph 8 which has a size of about 64 µm.

10. A particle according to any of Paragraphs 1, 2, 8 and 9, which comprises a hydrophilic microcarrier, a hydroxylated methacrylic matrix microcarrier or derivatised hydrophilic beaded microcarrier.

11. A particle according to any of Paragraphs 1, 2, 8, 9 and 10, which comprises TSKgel Tresyl-5Pw (Tosoh) or Toyopearl AF-Tresyl-650 (Tosoh).

12. A particle according to Paragraph 1 or 2, in which the particle comprises a macroporous or microporous carboseed microcarrier.

13. A particle according to Paragraph 12, in which the particle comprises SM1010 (Blue Membranes) or SH1010 (Blue Membranes).

14. A particle according to any preceding paragraph which is derivatised to carry a positive charge.

15. A particle according to any preceding paragraph which is coupled with tertiary amine or quaternary amine at small ion exchange capacity of 1-2 milli-equivalents per gram dry weight material of particle.

16. A particle according to any preceding paragraph which is coupled with protamine sulphate or poly-L-lysine hydrobromide at a concentration of up to 20 mg/ml particles.

17. A particle according to any preceding paragraph, in which the positive charge is between 0.5 to 4 milli equivalent units/ml (mEq).

18. A particle according to any preceding paragraph, in which the matrix is a physiologically relevant matrix that allows growth of the stem cells.

19. A particle according to any preceding paragraph, in which the matrix comprises an extracellular matrix component.

20. A particle according to any preceding paragraph, in which the matrix is selected from the group consisting of: Matrigel, laminin, fibronectin, vitronectin, hyaluronic acid, hyaluronic acid from bovine vitreous humor, hyaluronic acid sodium from *streptococcus*, heparan sulphate, heparan sulphate from bovine kidney, dextran sulphate, dextran sulphate sodium, heparin sulphate and chondroitin sulphate.

21. A particle according to any preceding paragraph, in which the matrix comprises Matrigel (BD Biosciences).

22. A particle according to any preceding paragraph, which comprises a primate or human stem cell attached thereto.

23. A method of propagating primate or human stem cells, the method comprising:
  (a) providing a first primate or human stem cell attached to a first particle;
  (b) providing a second primate or human stem cell attached to a second particle;
  (c) allowing the first primate or human stem cell to contact the second primate or human stem cell to form an aggregate of cells; and
  (d) culturing the aggregate to propagate the primate or human stem cells for at least one passage;
  in which the first and second particles each comprise a matrix coated thereon and having a positive charge, the particles being of a size to allow aggregation of primate or human stem cells attached thereto.

24. A method according to Paragraph 23, in which the particle or each particle comprises a feature as set out in any of Paragraphs 2 to 22.

25. A method according to Paragraph 23 or 24, in which the method enables primate or human stem cells to be continuously propagated for a plurality of passages.

26. A method according to Paragraph 23, 24 or 25, in which the method enables primate or human stem cells to be continuously propagated for at least 5, at least 10, at least 12, at least 13 or at least 14 passages.

27. A method according to any of Paragraphs 23 to 26, in which the method comprises passaging into or from a 2D colony culture.

28. A method according to any of Paragraphs 23 to 27, in which the method comprises freezing and thawing the primate or human stem cells.

29. A method according to any of Paragraphs 23 to 28, in which the method comprises agitation at 30 rpm or more or at 100 rpm or more.

30. A method according to any of Paragraphs 23 to 29, in which the method comprises propagating primate or human stem cells at a volume of 25 ml or more or 50 ml or more.

31. A method according to any of Paragraphs 23 to 30, in which the method comprises propagating primate or human stem cells in a spinner suspension culture.

32. A method according to any of Paragraphs 23 to 31, in which the propagated primate or human stem cells retain at least one biological activity of a primate or human stem cell after the stated number of passages.

33. A method according to Paragraph 32, in which the biological activity of a primate or human stem cell is selected from the group consisting of: (i) expression of a pluripotency marker, (ii) cell viability; and (iii) normal karyotype, (iv) ability to differentiate into endoderm, ectoderm and mesoderm.

34. A method according to Paragraph 32 or 33, in which the biological activity of a primate or human stem cell comprises expression of a pluripotency marker selected from the group consisting of: OCT-4, SSEA-4, TRA-1-60 and Mab 84.

35. A method according to any of Paragraphs 23 to 34, in which the method enables primate or human stem cells to be passaged at a split ratio of 1:6 or more, 1:10 or more, 1:15 or more, 1:20 or more or 1:26 or more.

36. A method according to any of Paragraphs 23 to 35, in which the method enables propagation of primate or human stem cells to a volumetric productivity of 2 million cells/ml or more.

37. A method according to any of Paragraphs 23 to 36, in which the method comprises propagating the primate or human stem cells in serum free media or stem cell conditioned media.

38. A method according to any of Paragraphs 23 to 37, further comprising the step of separating the primate or human stem cells from the particles.

39. A method for producing a differentiated cell, the method comprising propagating a primate or human stem cell according to any of Paragraphs 23 to 38, followed by causing the primate or human stem cell to differentiate.

40. A method for producing an embryoid body, the method comprising propagating a primate or human stem cell according to any of Paragraphs 23 to 37 and culturing the primate or human stem cell to form an embryoid body.

41. A method of treating a disease in an individual in need of treatment, the method comprising propagating a primate or human stem cell according to any of Paragraphs 23 to 38, producing a differentiated cell according to Paragraph 39 or producing an embryoid body according to Paragraph 40 and administering the primate or human stem cell, differentiated cell or embryoid body into the individual.

42. A particle or method according to any preceding paragraph, in which the primate or human stem cell comprises a primate or human embryonic stem cell, a primate or human adult stem cell or a primate or human induced pluripotent stem cell.

43. An aggregate comprising a two or more particles comprising stem cells attached thereto, each according to any of Paragraphs 1 to 22 or 42.

44. A cell culture comprising a particle according to any of Paragraphs 1 to 22 or 42, or an aggregate according to Paragraph 43.

45. A container comprising a particle according to any of Paragraphs 1 to 22 or 42, or an aggregate according to Paragraph 43, together with cell culture media.

46. A device for propagating primate or human stem cells, the device comprising a particle according to any of Paragraphs 1 to 22 or 42 or an aggregate according to Paragraph 43.

47. A container according to Paragraph 45 or device according to Paragraph 46 which is a bioreactor.

48. A primate or human stem cell propagated by a method according to any of Paragraphs 23 to 38, a differentiated cell produced by a method according to Paragraph 39 or an embryoid body produced by a method according to Paragraph 40.

49. Use of a particle for the propagation of primate or human stem cells, the particle being selected from the group consisting of: DE-52 (Whatman), DE-53 (Whatman), QA-52 (Whatman), TSKgel Tresyl-5Pw (Tosoh) or Toyopearl AF-Tresyl-650 (Tosoh), SM1010 (Blue Membranes) and SH1010 (Blue Membranes).

50. A particle, method, aggregate, cell culture, container, device, primate or human stem cell, differentiated cell substantially as hereinbefore described with reference to and as shown in FIGS. 1 to 50 of the accompanying drawings.

51. A method of propagating human embryonic stem cells (hESCs) in in vitro suspension culture, the method comprising:
(i) attaching hESCs to a plurality of microcarriers;
(ii) culturing the microcarriers from (i) in suspension culture for a period of time sufficient to expand the number of hESCs;
(iii) passaging the expanded population of hESCs from (ii);
(iv) repeating steps (i)-(iii) through at least 5 passages, wherein in each repeat cycle the hESCs of step (i) are obtained from the passaged cells of step (iii) of the preceding repeat cycle,
wherein hESCs in the culture after step (iv) are pluripotent, and wherein the microcarriers have:
(a) a compact shape in which the longest dimension is between 90 μm and 10 μm; or
(b) an elongate shape,
and wherein the microcarriers are coated in a matrix coating comprising one or more of Matrigel, laminin, fibronectin, vitronectin, and hyaluronic acid.

52. The method of paragraph 51 wherein the microcarrier is substantially spherical in shape and has a diameter between 90 μm and 10 μm.

53. The method of paragraph 51 wherein the microcarrier is rod shaped.

54. The method of paragraph 51 wherein the microcarrier is rod shaped and has a longest dimension of between 2000 μm to 20 μm.

55. The method of any one of paragraphs 51 to 54 wherein the microcarrier is composed of one or more of: plastic, glass, ceramic, silicone, gelatin, dextran, cellulose, hydroxylated methacrylate, polystyrene and/or collagen.

56. The method of any one of paragraphs 51 to 54 wherein the microcarrier is a cellulose, dextran or polystyrene microcarrier.

57. The method of any one of paragraphs 51 to 56 wherein in step (ii) the hESC are expanded to confluency or near confluency.

58. The method of any one of paragraphs 51 to 57 wherein in step (iv), steps (i)-(iii) are repeated through one of: at least 6 passages, at least 7 passages, at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, at least 100 passages.

59. The method of any one of paragraphs 51 to 58 wherein after step (iv) at least 60% of the hESCs in the culture are pluripotent.

60. The method of any one of paragraphs 51 to 58 wherein after step (iv) at least 90% of the hESCs in the culture are pluripotent.

61. The method of any one of paragraphs 51 to 60 wherein after step (iv) at least 60% of the hESCs in the culture express one, two or all of Oct4, SSEA4, TRA-1-60 and Mab 84.

62. The method of any one of paragraphs 51 to 60 wherein after step (iv) at least 90% of the hESCs in the culture express one, two or all of Oct4, SSEA4, TRA-1-60 and Mab 84.

63. A method of propagating human embryonic stem cells (hESCs) in in vitro suspension culture, the method comprising:
  (i) attaching hESCs to a plurality of microcarriers;
  (ii) culturing the microcarriers from (i) in suspension culture for a period of time sufficient to expand the number of hESCs;
  (iii) passaging the expanded population of hESCs from (ii);
  (iv) repeating steps (i)-(iii) through at least 5 passages, wherein in each repeat cycle the hESCs of step (i) are obtained from the passaged cells of step (iii) of the preceding repeat cycle,
  wherein hESCs in the culture after step (iv) are pluripotent, and wherein the microcarriers have:
  (a) a compact shape in which the longest dimension is between 90 μm and 10 μm; or
  (b) an elongate shape,
  and wherein for at least 60% of the cycles of steps (i)-(iii) the microcarriers are coated in a matrix coating comprising one or more of Matrigel, laminin, fibronectin, vitronectin, and hyaluronic acid.

64. The method of paragraph 63 wherein for at least 70% of the cycles of steps (i)-(iii) the microcarriers are coated in a matrix coating comprising one or both of Matrigel and hyaluronic acid.

65. The method of paragraph 63 wherein for at least 90% of the cycles of steps (i)-(iii) the microcarriers are coated in a matrix coating comprising one or more of Matrigel, laminin, fibronectin, vitronectin, and hyaluronic acid.

The following numbered paragraphs (paras.) contain further statements of broad combinations of the inventive technical features herein disclosed:—

1. A method of culturing stem cells in suspension culture in vitro, the method comprising:
  (i) attaching stem cells to a plurality of microcarriers to form microcarrier-stem cell complexes, wherein the surface of the microcarriers is coated in a matrix;
  (ii) culturing the microcarrier-stem cell complexes in suspension culture;
  (iii) passaging the cultured cells from (ii); and
  (iv) repeating steps (i)-(iii) through at least 3 passages,
  wherein stem cells in the culture after step (iv) are pluripotent.

2. The method of paragraph 1 wherein the stem cells are embryonic stem cells, or induced pluripotent stem cells.

3. The method of paragraph 1 or 2 wherein the stem cells are primate or human.

4. The method of any one of paragraphs 1 to 3 wherein steps (i)-(iii) are repeated through at least 5 passages, or at least 7 passages, or at least 10 passages.

5. The method of any one of paragraphs 1 to 4 wherein the microcarriers are rod-shaped.

6. The method of any one of paragraphs 1 to 5 wherein the matrix comprises an extracellular matrix component.

7. The method of any one of paragraphs 1 to 5 wherein the matrix comprises one or more of Matrigel™ (BD Biosciences), hyaluronic acid, laminin, fibronectin, vitronectin, collagen, elastin, heparan sulphate, dextran, dextran sulphate, chondroitin sulphate.

8. The method of any one of paragraphs 1 to 5 wherein the matrix comprises a mixture of laminin, collagen I, heparan sulfate proteoglycans, and entactin 1.

9. The method of any one of paragraphs 1 to 8 wherein the microcarrier comprises or consists of one or more of cellulose, dextran, hydroxylated methacrylate, collagen, gelatin, polystyrene, plastic, glass, ceramic, silicone.

10. The method of any one of paragraphs 1 to 8 wherein the microcarrier is a macroporous or microporous carboseed microcarrier.

11. The method of any one of paragraphs 1 to 10 wherein the microcarrier is coupled with protamine or polylysine.

12. The method of any one of paragraphs 1 to 11 wherein the microcarrier is positively charged.

13. The method of any one of paragraphs 1 to 12 wherein the microcarrier has a positive surface charge.

14. The method of any one of paragraphs 1 to 13 wherein the microcarrier is hydrophilic.

15. The method of any one of paragraphs 1 to 4 or 6 to 14 wherein the microcarriers have a substantially spherical shape.

16. The method of any one of paragraphs 1 to 15 wherein in step (ii) the stem cells are cultured for a period of time sufficient to expand the number of stem cells in the culture.

17. The method of any one of paragraphs 1 to 16 wherein in each repeat cycle the stem cells of step (i) are obtained from the passaged cells of step (iii) of the preceding repeat cycle.

18. The method of any one of paragraphs 1 to 17 wherein in step (iv), steps (i)-(iii) are repeated through one of: at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, at least 100 passages.

19. The method of any one of paragraphs 1 to 18 wherein for at least 60% of the cycles of steps (i)-(iii) the microcarriers are coated in a matrix.

20. The method of any one of paragraphs 1 to 19 wherein in cycles of steps (i)-(iii) the microcarriers are coated in the same matrix.

21. The method of any one of paragraphs 1 to 20 wherein the matrix is different or absent in first and second consecutive cycles of steps (i)-(iii).

22. The method of any one of paragraphs 1 to 21 wherein after step (iv) at least 60% of the stem cells in the culture are pluripotent.

23. The method of any one of paragraphs 1 to 22 wherein after step (iv) at least 60% of the stem cells in the culture express one, two, three or all of Oct4, SSEA4, TRA-1-60 and Mab84.

24. The method of any one of paragraphs 1 to 23 wherein the method comprises culturing the stem cells in serum free media, or stem cell conditioned media, or feeder cell free conditions.

25. The method of any one of paragraphs 1 to 24 wherein feeder cells are also attached to the microcarriers.

26. The method of any one of paragraphs 1 to 24 wherein the culture further comprises feeder cells attached to microcarriers which are different to the microcarriers to which the stem cells are attached.

27. Pluripotent stem cells obtained by the method of any one of paragraphs 1 to 26.

28. The method of any one of paragraphs 1 to 26 further comprising the step of inducing differentiation of the stem cells obtained after step (iv).

29. The method of paragraph 28 wherein the method comprises placing the microcarrier-stem cell complexes under conditions which induce the differentiation of the stem cells.

30. The method of any one of paragraphs 1 to 26 wherein after step (iv) the method comprises the step of separating stem cells from the microcarriers and culturing the separated stem cells in non-microcarrier culture under conditions which induce differentiation of the stem cells.

31. The method of any one of paragraphs 1 to 26 further comprising the differentiation of pluripotent stem cells, comprising:
  (v) attaching pluripotent stem cells obtained after step (iv) to a plurality of second microcarriers to form microcarrier-stem cell complexes, wherein the surface of the second microcarriers is coated in a second matrix or is uncoated; and
  (vi) culturing the microcarrier-stem cell complexes from (v) in suspension culture under conditions that induce the differentiation of the stem cells.

32. The method of paragraph 31 wherein the first and second matrix are the same.

33. The method of paragraph 31 wherein the first and second matrix are different.

34. The method of any one of paragraphs 31 to 33 wherein the first and second microcarriers are the same.

35. The method of any one of paragraphs 31 to 33 wherein the first and second microcarriers are different.

36. The method of any one of paragraphs 31 to 35 wherein the method further comprises:
  (vii) attaching differentiated stem cells obtained from step (vi) to a plurality of third microcarriers to form microcarrier-stem cell complexes, wherein the surface of the third microcarriers is coated in a third matrix or is uncoated; and
  (viii) culturing the microcarrier-stem cell complexes from (vii) in suspension culture under conditions that induce the further differentiation of the differentiated stem cells.

37. The method of paragraph 36 wherein the third matrix is different to the first and second matrix.

38. The method of paragraph 36 wherein the third matrix is the same as one of the first and second matrix.

39. The method of any one of paragraphs 36 to 38 wherein the third microcarriers are different to the first and second microcarriers.

40. The method of any one of paragraphs 36 to 38 wherein the third microcarriers are the same as one of the first and second microcarriers.

41. A differentiated cell obtained by the method of any one of paragraphs 28 to 40.

42. The method of any one of paragraphs 28 to 40 wherein the differentiated cells are cultured to form an embryoid body.

43. An embryoid body obtained by the method of paragraph 42.

44. A method of culturing stem cells in suspension culture in vitro, the method comprising:
  (i) attaching stem cells to a plurality of microcarriers to form microcarrier-stem cell complexes, wherein the surface of the microcarriers is coated in Matrigel™;
  (ii) culturing the microcarrier-stem cell complexes in suspension culture;
  (iii) passaging the cultured cells from (ii); and
  (iv) repeating steps (i)-(iii) through at least 7 passages,
wherein stem cells in the culture after step (iv) are pluripotent, wherein the culture is free of feeder cells, wherein the number of stem cells is expanded between each passage and wherein the stem cells are human or primate embryonic stem cells or human or primate induced pluripotent stem cells.

45. A method of culturing and differentiating stem cells in vitro, the method comprising:
  (i) attaching stem cells to a plurality of first microcarriers to form microcarrier-stem cell complexes, wherein the surface of the first microcarriers is coated in a first matrix;
  (ii) culturing the microcarrier-stem cell complexes in suspension culture;
  (iii) passaging the cultured cells from (ii); and
  (iv) repeating steps (i)-(iii) through at least 3 passages,
wherein stem cells in the culture after step (iv) are pluripotent, the method further comprising:
  (v) attaching pluripotent stem cells obtained after step (iv) to a plurality of second microcarriers to form microcarrier-stem cell complexes, wherein the surface of the second microcarriers is coated in a second matrix or is uncoated; and
  (vi) culturing the microcarrier-stem cell complexes from (v) in suspension culture under conditions that induce the differentiation of the stem cells.

46. The method of paragraph 45 wherein the stem cells are embryonic stem cells, or induced pluripotent stem cells.

47. The method of paragraph 45 or 46 wherein the stem cells are primate or human.

48. The method of any one of paragraphs 45 to 47 wherein the microcarriers are rod-shaped.

49. The method of any one of paragraphs 45 to 48 wherein the first and second matrix are the same.

50. The method of any one of paragraphs 45 to 48 wherein the first and second matrix are different.

51. The method of any one of paragraphs 45 to 50 wherein the first and second microcarriers are the same.

52. The method of any one of paragraphs 45 to 50 wherein the first and second microcarriers are different.

53. The method of any one of paragraphs 45 to 52 wherein the method further comprises:
  (vii) attaching differentiated stem cells obtained from step (vi) to a plurality of third microcarriers to form microcarrier-stem cell complexes, wherein the surface of the third microcarriers is coated in a third matrix or is uncoated; and
  (viii) culturing the microcarrier-stem cell complexes from (vii) in suspension culture under conditions that induce the further differentiation of the differentiated stem cells.

54. The method of paragraph 53 wherein the third matrix is different to the first and second matrix.

55. The method of paragraph 53 wherein the third matrix is the same as one of the first and second matrix.

56. The method of any one of paragraphs 53 to 55 wherein the third microcarriers are different to the first and second microcarriers.

57. The method of any one of paragraphs 53 to 55 wherein the third microcarriers are the same as one of the first and second microcarriers.

58. A method of differentiating stem cells in vitro, comprising attaching pluripotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells.

59. The method of paragraph 58 wherein the stem cells are embryonic stem cells, or induced pluripotent stem cells.

60. The method of paragraph 58 or 59 wherein the stem cells are primate or human.

61. The method of any one of paragraphs 58 to 60 wherein the microcarriers are rod-shaped.

62. The method of any one of paragraphs 58 to 61 wherein the matrix comprises an extracellular matrix component.

63. The method of any one of paragraphs 58 to 61 wherein the matrix comprises one or more of laminin, fibronectin, vitronectin, Matrigel™ (BD Biosciences), hyaluronic acid, collagen, elastin, heparan sulphate, dextran, dextran sulphate, chondroitin sulphate.

64. The method of any one of paragraphs 58 to 61 wherein the matrix comprises a mixture of laminin, collagen I, heparan sulfate proteoglycans, and entactin 1.

65. The method of any one of paragraphs 58 to 64 wherein the microcarrier comprises or consists of one or more of cellulose, dextran, hydroxylated methacrylate, collagen, gelatin, polystyrene, plastic, glass, ceramic, silicone.

66. The method of any one of paragraphs 58 to 64 wherein the microcarrier is a macroporous or microporous carboseed microcarrier.

67. The method of any one of paragraphs 58 to 66 wherein the microcarrier is coupled with protamine or polylysine.

68. The method of any one of paragraphs 58 to 67 wherein the microcarrier is positively charged.

69. The method of any one of paragraphs 58 to 68 wherein the microcarrier has a positive surface charge.

70. The method of any one of paragraphs 58 to 69 wherein the microcarrier is hydrophilic.

71. The method of any one of paragraphs 58 to 60 or 62 to 70 wherein the microcarriers have a substantially spherical shape.

72. A method of culturing multipotent stem cells in suspension culture in vitro, the method comprising:
 (i) attaching multipotent stem cells to a plurality of microcarriers to form microcarrier-stem cell complexes;
 (ii) culturing the microcarrier-stem cell complexes in suspension culture;
 wherein stem cells in the culture after step (ii) are multipotent.

73. The method of paragraph 72 wherein in (i) the surface of the microcarriers is coated in a matrix.

74. The method of paragraph 72 or 73 further comprising the step of inducing differentiation of the stem cells obtained after step (ii).

75. The method of paragraph 74 wherein the method comprises placing the microcarrier-stem cell complexes under conditions which induce the differentiation of the stem cells.

76. The method of any one of paragraphs 72 to 75 wherein after step (ii) the method comprises the step of separating stem cells from the microcarriers and culturing the separated stem cells in non-microcarrier culture under conditions which induce differentiation of the stem cells.

77. A method of culturing multipotent stem cells in suspension culture in vitro, the method comprising:
 (i) attaching multipotent stem cells to a plurality of microcarriers to form microcarrier-stem cell complexes;
 (ii) culturing the microcarrier-stem cell complexes in suspension culture;
 (iii) passaging the cultured cells from (ii); and
 (iv) repeating steps (i)-(iii) through at least 2 passages,
 wherein stem cells in the culture after step (iv) are multipotent.

78. The method of paragraph 77 wherein in (i) the surface of the microcarriers is coated in a matrix.

79. Multipotent stem cells obtained by the method of any one of paragraphs 72, 73, 77 or 78.

80. The method of paragraph 77 or 78 further comprising the step of inducing differentiation of the stem cells obtained after step (iv).

81. The method of paragraph 80 wherein the method comprises placing the microcarrier-stem cell complexes under conditions which induce the differentiation of the stem cells.

82. The method of any one of paragraphs 77 to 81 wherein after step (iv) the method comprises the step of separating stem cells from the microcarriers and culturing the separated stem cells in non-microcarrier culture under conditions which induce differentiation of the stem cells.

83. The method of paragraph 77 further comprising the differentiation of multipotent stem cells, comprising:
 (v) attaching multipotent stem cells obtained after step (iv) to a plurality of second microcarriers to form microcarrier-stem cell complexes, wherein the surface of the second microcarriers is coated in a second matrix or is uncoated; and
 (vi) culturing the microcarrier-stem cell complexes from (v) in suspension culture under conditions that induce the differentiation of the stem cells.

84. A differentiated cell obtained by the method of any one of paragraphs 74 to 83.

85. A method of culturing and differentiating multipotent stem cells in vitro, the method comprising:
 (i) attaching stem cells to a plurality of first microcarriers to form microcarrier-stem cell complexes;
 (ii) culturing the microcarrier-stem cell complexes in suspension culture;
 (iii) passaging the cultured cells from (ii); and
 (iv) repeating steps (i)-(iii) through at least 2 passages,
 wherein stem cells in the culture after step (iv) are multipotent, the method further comprising:
 (v) attaching multipotent stem cells obtained after step (iv) to a plurality of second microcarriers to form microcarrier-stem cell complexes, wherein the surface of the second microcarriers is coated in a second matrix or is uncoated; and
 (vi) culturing the microcarrier-stem cell complexes from (v) in suspension culture under conditions that induce the differentiation of the stem cells.

86. The method of paragraph 85 wherein in (i) the surface of the microcarriers is coated in a first matrix.

87. A method of differentiating stem cells in vitro, comprising attaching multipotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells.

88. The method of any one of paragraphs 72 to 87 wherein the stem cells are adult stem cells, or multipotent stem cells derived from pluripotent stem cells.

89. The method of any one of paragraphs 72 to 88 wherein the microcarriers are rod-shaped.

90. The method of any one of paragraphs 72 to 89 wherein the matrix comprises an extracellular matrix component.

91. The method of any one of paragraphs 72 to 89 wherein the matrix comprises one or more of Matrigel™ (BD Biosciences), hyaluronic acid, laminin, fibronectin, vitronectin, collagen, elastin, heparan sulphate, dextran, dextran sulphate, chondroitin sulphate.

92. The method of any one of paragraphs 72 to 89 wherein the matrix comprises a mixture of laminin, collagen I, heparan sulfate proteoglycans, and entactin 1.

93. The method of any one of paragraphs 72 to 92 wherein the microcarrier comprises or consists of one or more of cellulose, dextran, hydroxylated methacrylate, collagen, gelatin, polystyrene, plastic, glass, ceramic, silicone.

94. The method of any one of paragraphs 72 to 92 wherein the microcarrier is a macroporous or microporous carboseed microcarrier.

95. The method of any one of paragraphs 72 to 94 wherein the microcarrier is positively charged.

96. The method of any one of paragraphs 72 to 95 wherein the microcarrier has a positive surface charge.

97. The method of any one of paragraphs 72 to 96 wherein in step (ii) the stem cells are cultured for a period of time sufficient to expand the number of stem cells in the culture.

98. The method of any one of paragraphs 77 to 97 wherein in each repeat cycle the stem cells of step (i) are obtained from the passaged cells of step (iii) of the preceding repeat cycle.

99. The method of any one of paragraphs 77 to 98 wherein in step (iv), steps (i)-(iii) are repeated through one of: at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, at least 100 passages.

100. Use of a microcarrier coated in a matrix for the propagation and/or differentiation of primate or human stem cells, the microcarrier being chosen from: DE-52 (Whatman), DE-53 (Whatman), QA-52 (Whatman), TSKgel Tresyl-5Pw (Tosoh) or Toyopearl AF-Tresyl-650 (Tosoh), SM1010 (Blue Membranes) and SH1010 (Blue Membranes).

101. The use of paragraph 100 wherein the matrix comprises one or more of Matrigel™ (BD Biosciences), hyaluronic acid, laminin, fibronectin, vitronectin, collagen, elastin, heparan sulphate, dextran, dextran sulphate, chondroitin sulphate.

102. The use of paragraph 100 wherein the matrix comprises a mixture of laminin, collagen I, heparan sulfate proteoglycans, and entactin 1.

103. A microcarrier suitable for use in the growth and/or differentiation of pluripotent or multipotent cells in in vitro suspension culture, wherein the microcarrier comprises one or more of cellulose, dextran, hydroxylated methacrylate, or collagen, and wherein the microcarrier has an elongate shape and has a longest dimension of less than about 2000 µm and a shortest dimension of more than about 10 µm, and wherein the surface of the microcarrier is coated in a matrix, and wherein one or a plurality of pluripotent or multipotent cells are attached to the matrix coating.

104. The microcarrier of paragraph 103 wherein the microcarrier is rod-shaped.

105. The microcarrier of paragraph 103 or 104 wherein the matrix coating comprises one or more of Matrigel™ (BD Biosciences), hyaluronic acid, laminin, or fibronectin.

106. The microcarrier of any one of paragraphs 103 to 105 wherein the cells are pluripotent cells.

107. The microcarrier of any one of paragraphs 103 to 106 wherein the pluripotent cells are primate or human embryonic stem cells, or induced pluripotent stem cells.

108. The microcarrier of any one of paragraphs 103 to 107 wherein the microcarrier is positively charged.

109. The microcarrier of any one of paragraphs 103 to 108 wherein the microcarrier has a positive surface charge.

110. The microcarrier of any one of paragraphs 103 to 109 having a longest dimension of between 50 µm and 400 µm.

111. An aggregate comprising two or more microcarriers having pluripotent or multipotent cells attached thereto, each according to any one of paragraphs 103 to 110.

112. Use of a microcarrier according to any one or paragraphs 103 to 110 in the culture of pluripotent or multipotent cells in vitro to generate new cells having pluripotent or multipotent status.

113. Use of a microcarrier according to any one or paragraphs 103 to 110 in the in vitro differentiation of pluripotent or multipotent cells.

114. A method of culturing pluripotent or multipotent cells in vitro to generate new cells having pluripotent or multipotent status, the method comprising culturing a microcarrier according to any one or paragraphs 103 to 110 under conditions suitable for the generation of new cells having pluripotent or multipotent status.

115. A method of differentiating pluripotent or multipotent cells in vitro, the method comprising culturing a microcarrier according to any one or paragraphs 103 to 110 under conditions that induce the differentiation of the pluripotent or multipotent cells.

The following numbered paragraphs (paras.) contain further statements of broad combinations of the inventive technical features herein disclosed:—

1. A method of culturing and differentiating stem cells in vitro, the method comprising:
   (i) attaching stem cells to a plurality of first microcarriers to form microcarrier-stem cell complexes, wherein the surface of the first microcarriers is coated in a first matrix;
   (ii) culturing the microcarrier-stem cell complexes in suspension culture;
   (iii) passaging the cultured cells from (ii); and
   (iv) repeating steps (i)-(iii) through at least 3 passages,
   wherein stem cells in the culture after step (iv) are pluripotent or multipotent, the method further comprising:
   (v) attaching pluripotent or multipotent stem cells obtained after step (iv) to a plurality of second microcarriers to form microcarrier-stem cell complexes, wherein the surface of the second microcarriers is coated in a second matrix or is uncoated; and
   (vi) culturing the microcarrier-stem cell complexes from (v) in suspension culture under conditions that induce the differentiation of the stem cells.

2. The method of paragraph 1 wherein the stem cells are embryonic stem cells, or induced pluripotent stem cells.

3. The method of paragraph 1 wherein the stem cells are primate or human.

4. The method of paragraph 1 wherein the microcarriers are rod-shaped.

5. The method of paragraph 1 wherein the first and second matrix are the same.

6. The method of paragraph 1 wherein the first and second matrix are different.

7. The method of paragraph 1 wherein the stem cells are differentiated into cardiomyocytes.

8. The method of paragraph 1 wherein the method further comprises:
   (vii) attaching differentiated stem cells obtained from step (vi) to a plurality of third microcarriers to form microcarrier-stem cell complexes, wherein the surface of the third microcarriers is coated in a third matrix or is uncoated; and
   (viii) culturing the microcarrier-stem cell complexes from (vii) in suspension culture under conditions that induce the further differentiation of the differentiated stem cells.

9. A differentiated cell obtained by the method of paragraph 1.

10. A cardiomyocyte obtained by the method of paragraph 1.

11. A method of differentiating stem cells in vitro, comprising attaching pluripotent or multipotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells.

12. The method of paragraph 11 wherein the stem cells are embryonic stem cells, or induced pluripotent stem cells.

13. The method of paragraph 11 wherein the stem cells are primate or human.

14. The method of paragraph 11 wherein the microcarriers are rod-shaped.

15. The method paragraph 11 wherein the matrix comprises one or more of laminin, fibronectin, vitronectin, Matrigel™ (BD Biosciences), hyaluronic acid, collagen, elastin, heparan sulphate, dextran, dextran sulphate, chondroitin sulphate.

16. The method of paragraph 11 wherein the matrix comprises a mixture of laminin, collagen I, heparan sulfate proteoglycans, and entactin 1.

17. The method of paragraph 11 wherein the microcarrier comprises or consists of one or more of cellulose, dextran, hydroxylated methacrylate, collagen, gelatin, polystyrene, plastic, glass, ceramic, silicone.

18. The method of paragraph 11 wherein the stem cells are differentiated into cardiomyocytes.

19. A differentiated cell obtained by the method of paragraph 11.

20. A cardiomyocyte obtained by the method of paragraph 11.

The following numbered paragraphs (paras.) contain further statements of broad combinations of the inventive technical features herein disclosed:—

1. A method of culturing and differentiating stem cells in vitro, the method comprising:
   (i) attaching stem cells to a plurality of first microcarriers to form microcarrier-stem cell complexes, wherein the surface of the first microcarriers is coated in a first matrix;
   (ii) culturing the microcarrier-stem cell complexes in suspension culture;
   (iii) passaging the cultured cells from (ii); and
   (iv) repeating steps (i)-(iii) through at least 2 passages, wherein stem cells in the culture after step (iv) are pluripotent or multipotent, the method further comprising:
   (v) attaching pluripotent or multipotent stem cells obtained after step (iv) to a plurality of second microcarriers to form microcarrier-stem cell complexes, wherein the surface of the second microcarriers is coated in a second matrix or is uncoated; and
   (vi) culturing the microcarrier-stem cell complexes from (v) in suspension culture under conditions that induce the differentiation of the stem cells to the neural cell lineage.

2. The method of paragraph 1 wherein the stem cells are embryonic stem cells, or induced pluripotent stem cells.

3. The method of paragraph 1 wherein the stem cells are human or primate.

4. The method of paragraph 1 wherein the microcarriers are rod-shaped.

5. The method of paragraph 1 wherein the first and second matrix are the same.

6. The method of paragraph 1 wherein the first and second matrix are different.

7. The method of paragraph 1 wherein the stem cells are differentiated into neural precursors, neurons, or astrocytes.

8. The method of paragraph 1 wherein the method further comprises:
   (vii) attaching differentiated stem cells obtained from step (vi) to a plurality of third microcarriers to form microcarrier-stem cell complexes, wherein the surface of the third microcarriers is coated in a third matrix or is uncoated; and
   (viii) culturing the microcarrier-stem cell complexes from (vii) in suspension culture under conditions that induce the further differentiation of the differentiated stem cells.

9. A differentiated cell of the neural lineage obtained by the method of paragraph 1.

10. A neural precursor cell, neuron, or astrocyte obtained by the method of paragraph 1.

11. A method of differentiating stem cells in vitro, comprising attaching pluripotent or multipotent stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells to cells of the neural cell lineage.

12. The method of paragraph 11 wherein the stem cells are embryonic stem cells, or induced pluripotent stem cells.

13. The method of paragraph 11 wherein the stem cells are human or primate.

14. The method of paragraph 11 wherein the microcarriers are rod-shaped.

15. The method paragraph 11 wherein the matrix comprises one or more of laminin, fibronectin, vitronectin, Matrigel™ (BD Biosciences), hyaluronic acid, collagen, elastin, heparan sulphate, dextran, dextran sulphate, chondroitin sulphate.

16. The method of paragraph 11 wherein the matrix comprises a mixture of laminin, collagen I, heparan sulfate proteoglycans, and entactin 1.

17. The method of paragraph 11 wherein the microcarrier comprises or consists of one or more of cellulose, dextran, hydroxylated methacrylate, collagen, gelatin, polystyrene, plastic, glass, ceramic, silicone.

18. The method of paragraph 11 wherein the stem cells are differentiated into neural precursors, neurons, or astrocytes.

19. A differentiated cell of the neural lineage obtained by the method of paragraph 11.

20. A neural precursor cell, neuron, or astrocyte obtained by the method of paragraph 11.

The following numbered paragraphs (paras.) contain further statements of broad combinations of the inventive technical features herein disclosed:—

1. A method of culturing mesenchymal stem cells (MSCs) in suspension culture in vitro, the method comprising:
    (i) attaching mesenchymal stem cells to a plurality of microcarriers to form microcarrier-stem cell complexes;
    (ii) culturing the microcarrier-mesenchymal stem cell complexes in suspension culture.
2. The method of paragraph 1, wherein stem cells in the culture after step (ii) are multipotent.
3. The method of paragraph 1 wherein in (i) the surface of the microcarriers is coated in a matrix.
4. The method of paragraph 1 further comprising the step of inducing differentiation of the stem cells obtained after step (ii).
5. The method of paragraph 1 further comprising the step of inducing differentiation of the stem cells obtained after step (ii) towards the osteogenic lineage, or into bone cells or bone precursor cells.
5. The method of paragraph 1 wherein the method comprises placing the microcarrier-stem cell complexes under conditions which induce the differentiation of the stem cells.
6. The method of paragraph 1 wherein the method comprises placing the microcarrier-stem cell complexes under conditions which induce the differentiation of the stem cells towards the osteogenic lineage, or into bone cells or bone precursor cells.
7. The method of paragraph 1 wherein after step (ii) the method comprises the step of separating stem cells from the microcarriers and culturing the separated stem cells in non-microcarrier culture under conditions which induce differentiation of the stem cells.
8. The method of paragraph 1 wherein after step (ii) the method comprises the step of separating stem cells from the microcarriers and culturing the separated stem cells in non-microcarrier culture under conditions which induce differentiation of the stem cells towards the osteogenic lineage, or into bone cells or bone precursor cells.
9. The method of paragraph 1 wherein the mesenchymal stem cells are fetal mesenchymal stem cells.
10. The method of paragraph 1 wherein the mesenchymal stem cells are human mesenchymal stem cells.
11. Mesenchymal stem cells obtained by the method of paragraph 1.
12. A method of culturing mesenchymal stem cells (MSCs) in suspension culture in vitro, the method comprising:
    (i) attaching mesenchymal stem cells to a plurality of microcarriers to form microcarrier-stem cell complexes;
    (ii) culturing the microcarrier-stem cell complexes in suspension culture;
    (iii) passaging the cultured cells from (ii); and
    (iv) repeating steps (i)-(iii) through at least 2 passages,
    wherein stem cells in the culture after step (iv) are multipotent.
13. The method of paragraph 12 wherein in (i) the surface of the microcarriers is coated in a matrix.
14. The method of paragraph 12 further comprising the step of inducing differentiation of the stem cells obtained after step (iv).
15. The method of paragraph 12 wherein the method comprises placing the microcarrier-stem cell complexes under conditions which induce the differentiation of the stem cells.
16. The method of paragraph 12 wherein after step (iv) the method comprises the step of separating stem cells from the microcarriers and culturing the separated stem cells in non-microcarrier culture under conditions which induce differentiation of the stem cells.
17. The method of paragraph 12 further comprising the differentiation of the multipotent stem cells, comprising:
    (v) attaching multipotent stem cells obtained after step (iv) to a plurality of second microcarriers to form microcarrier-stem cell complexes, wherein the surface of the second microcarriers is coated in a second matrix or is uncoated; and
    (vi) culturing the microcarrier-stem cell complexes from (v) in suspension culture under conditions that induce the differentiation of the stem cells.
18. A method of culturing and differentiating mesenchymal stem cells in vitro, the method comprising:
    (i) attaching mesenchymal stem cells to a plurality of first microcarriers to form microcarrier-stem cell complexes;
    (ii) culturing the microcarrier-stem cell complexes in suspension culture;
    (iii) passaging the cultured cells from (ii); and
    (iv) repeating steps (i)-(iii) through at least 2 passages,
    wherein stem cells in the culture after step (iv) are multipotent, the method further comprising:
    (v) attaching multipotent stem cells obtained after step (iv) to a plurality of second microcarriers to form microcarrier-stem cell complexes, wherein the surface of the second microcarriers is coated in a second matrix or is uncoated; and
    (vi) culturing the microcarrier-stem cell complexes from (v) in suspension culture under conditions that induce the differentiation of the stem cells.
19. The method of paragraph 18 wherein in (i) the surface of the microcarriers is coated in a first matrix.
20. A method of differentiating mesenchymal stem cells in vitro, comprising attaching mesenchymal stem cells to a plurality of microcarriers to form microcarrier-stem cell complexes, wherein the surface of the microcarriers is coated in a matrix or is uncoated, and culturing the microcarrier-stem cell complexes in suspension culture under conditions that induce the differentiation of the stem cells.

EXAMPLES

Introduction to Examples and Experimental Results

We have developed a facile and robust platform technology using a variety of rod shaped and spherical microcarriers with different extracellular matrix coatings (e.g. matrigel, laminin and hyaluronic acid), which are able to support the continuous propagation of undifferentiated hESC in 3-dimensional suspension cultures. Microcarrier cultures typically achieved 2 to 4-fold higher cell densities than in feeder-free 2D colony cultures. Stable, continuous propagation of two hESC lines on microcarriers has been demonstrated in conditioned media for 6 months. Microcarrier cultures were also demonstrated in two serum free defined media (StemPro and mTeSR1). Microcarrier cultures achieved even higher cell concentrations in suspension spinner flasks, thus opening the prospect of propagation in controlled bioreactors.

We demonstrate robust, serial culture and passaging of hESC on microcarriers while retaining their pluripotent markers. Growth kinetics and metabolism of microcarrier cultures (MC) were compared with 2D colony cultures and suspension MC of hESC was demonstrated with 2 cell lines. We also demonstrate the differentiation of hESC into cardiomyocytes whilst in microcarrier suspension culture.

We have demonstrated that matrigel coated cellulose microcarriers, like 2D colony cultures, allow simple and routine passaging of hESC without differentiation. This passaging can be performed easily by both mechanical dissociation (by passing through a 100 micron mesh or by manual pipetting) and enzymatic dissociation (TrypLE enzyme or collagenase) methods. Microcarriers can be seeded directly from 2D colony cultures or reseeded from MC to 2D colony cultures. The expressions of the 3 canonical markers of pluripotency, Oct4, SSEA4 and TRA-1-60, after passaging of HES-3 cells by these methods are equivalent to the control 2D colony culture (FIG. 152), the cell densities achieved in microcarrier passaged by mechanical or enzymatic methods were similar.

After mechanical passage of hESC the cells rapidly colonised the naked microcarriers on day 1 and become fully confluent cell-microcarrier aggregates on day 6. Histological analysis of microcarriers show that hESC form multi-layers of cells on the microcarriers and all of the cells stained positive for TRA-1-60. When hESC microcarriers were replated onto 2D colony culture, they spread onto the matrigel coated surface and increase in cell density by 4-fold over 7 days, with greater than 90% viability and continue to express the 3 stem cell markers, Oct4, SSEA4 and TRA-1-60. After 9 weeks of continuous passaging, hESC still retained high expression levels of these pluripotent markers and typically achieved 1.2 to 1.8 million cells/ml in a 6-well plate with viability above 90%. Normal karyotype of MC propagated in conditioned media up to 25 passages (6 months) was demonstrated for 2 cell lines (HES-2 and HES3).

The karyotype for HES-2 and HES-3 at passage 14 and 25 respectively, remains normal. Microcarriers retained their ability to differentiate into embryoid bodies with cells expressing genes from the ectoderm, mesoderm and endoderm and also formed teratomas in SCID mice with tissues representing the 3 germ layers.

Growth kinetics and metabolism of MC in conditioned media were compared with conventional 2D colony cultures. The 2D colony cultures typically attained maximal confluent cell density of 0.8 million cells/ml (or 4 million cells/well in a 6-well plate) by day 5. Whereas MC continued growing, reaching twice the cell densities of 1.6 million cells/ml by day 7, due to the increased surface area available for 3D growth as cell microcarrier aggregates. Daily glucose and glutamine consumption and lactate and ammonium production levels were similar for both cultures. However, the specific metabolite consumption rates and waste production rates were about 50% lower for microcarriers due to the high cell numbers achieved compared to 2D colony cultures indicating a more efficient metabolism in the former. We have routinely propagated microcarriers beyond 23 passages which were typically passaged weekly at a split ratio of 1:10, maintaining over 90% viability, compared to 1:4 for 2D colony cultures.

Furthermore, HES-3 cells were adapted to grow in mTeSR1 and StemPRO serum free media on microcarriers beyond 20 passages (5 months). Normal karyotypes were observed at passage 19 and 20 respectively and pluripotent markers were maintained.

Growth kinetics of hESC in a 50 ml spinner flask MC, further demonstrated that HES-3 cells achieved a superior density of 3.5 million cells/ml compared to the static microcarrier (1.5 million cells/ml) and the 2D colony (0.8 million cells/ml) cultures. The doubling time of 21 hours (specific growth rate of 0.033 hr−1) was also faster in the spinner flask culture compared to the typical doubling times of 30 hours for the static microcarriers and 33 hours for the 2D colony culture. The faster cell growth in spinner cultures may be attributed to better oxygen transfer in the agitated environment.

To assess long term suspension culture, a second hESC line, HES-2 was also passaged continuously for 7 weeks in 6-well plates as static and agitated MC and compared to the 2D colony control. Both static and agitated microcarriers achieved significantly higher maximum cell densities than the 2D colony culture. Pluripotent markers of Oct4, TRA-1-60 and SSEA4 continue to be robustly expressed in the static and agitated microcarriers compared to the control.

Despite the progress in automation technologies, the limitation of growing ESC on surfaces is that the increase in cell density is restricted to the available area. Therefore for therapeutic applications, where very large volumes of cell cultures may eventually be required, in liters per batch production run, it is necessary to develop bioprocesses which do not scale on 2D culture surfaces but rather in 3D environments such as in suspension bioreactors.

Until now, expansion of undifferentiated human ESCs on microcarriers has proved to be more difficult than for mouse ESCs. We report for the first time, a facile and robust method for maintaining undifferentiated human embryonic stem cells (hESC) in 3-dimensional (3D) suspension cultures on matrigel coated microcarriers which achieved 2 to 4-fold higher cell densities than in 2-dimensional (2D) colony cultures. Stable, continuous propagation of hESC on microcarriers has been demonstrated in conditioned media and two serum free defined media (StemPro and mTeSR1).

Based on the spinner flask data, microcarriers achieved even higher cell concentrations and has the potential to enable facile expansion of hESC in larger volumes instead of expansion on surfaces. For example, a 100 ml suspension culture can produce the equivalent of 175 organ culture dishes of hESC. In future, it would also be possible to further optimize these cultures by controlling parameters such as pH, dissolved $O_2$ and feeding strategies in bioreactors.

We have also broadened the use of these microcarriers for other cell lines such as human iPS cells and differentiation of hESC. The development of a scalable bioprocess for cardiomyocyte production on a microcarrier suspension culture platform was also investigated. Medium reformulation and cell aggregate formation were identified as important parameters in our preliminary studies. The bSFS medium (serum and insulin free medium supplemented with 5 µM of a p38 inhibitor defined previously by Zweigert et al.) was supplemented with BSA, Hy-Soy, lipid mixture or yeastolate. The enriched medium enhances cell growth and activity, significantly increases the fold of cell expansion, and improves the differentiation efficiency of this platform, achieving up to 60% of beating aggregates. To improve cell attachment on the carrier surface, several extracellular matrixes have been evaluated (uncoated, vitronectin, laminin, fibronectin, and matrigel). The most efficient differentiation results were obtained when carriers were coated with laminin or fibronectin (up to 70% of beating aggregates in both cases). These results support the use of 3-dimensional microcarrier suspension culture as a scalable cardiomyocyte production platform.

In summary, we have demonstrated that 3D microcarriers can be a simple, stable and robust alternative method of culturing hESC instead of 2D colony cultures. Microcarriers will be amenable to scale up as controlled bioprocesses in bioreactors, and also facilitate directed differentiation of hESC.

Example 1

Suspension Culture of Human Embryonic Stem Cells

We demonstrate the use of several types of microcarriers that support the growth of hESC in an undifferentiated state. The main findings are highlighted in FIGS. 1 to 5.

The following 3 classes of microcarriers (see FIG. 1) have been tested which are capable of growing hESC in 3D, namely: rod shaped, cellulose microcarriers (DE52, DE53 and Q53); small, spherical Tosoh hydrophilic microcarriers (10 and 65 microns in diameter); large, spherical, microporous and macroporous carboseed microcarriers.

Figure 1A:
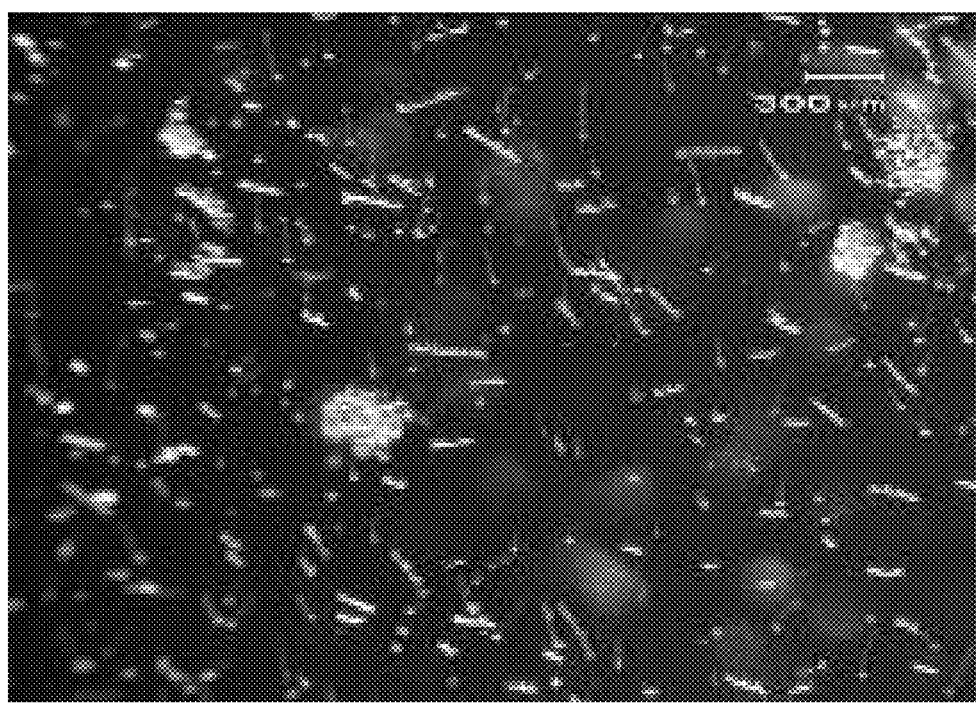
FIG. 1A shows cellulose microcarriers.
Figure 1B:
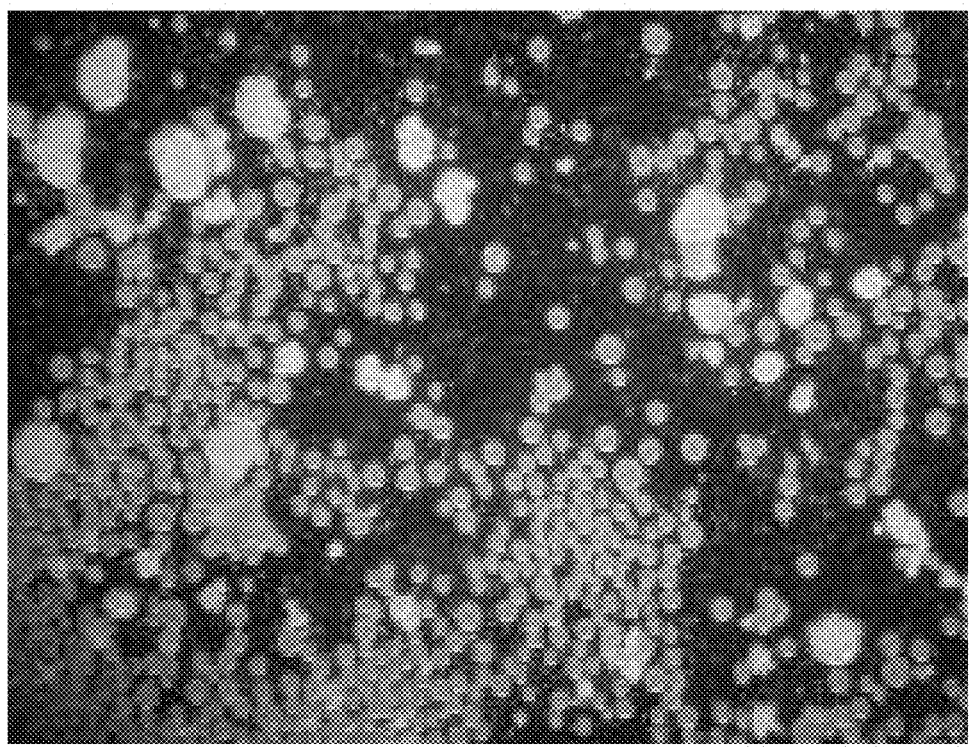
FIG. 1B shows Tosoh (hydrophilic) microcarriers.
Figure 1C:
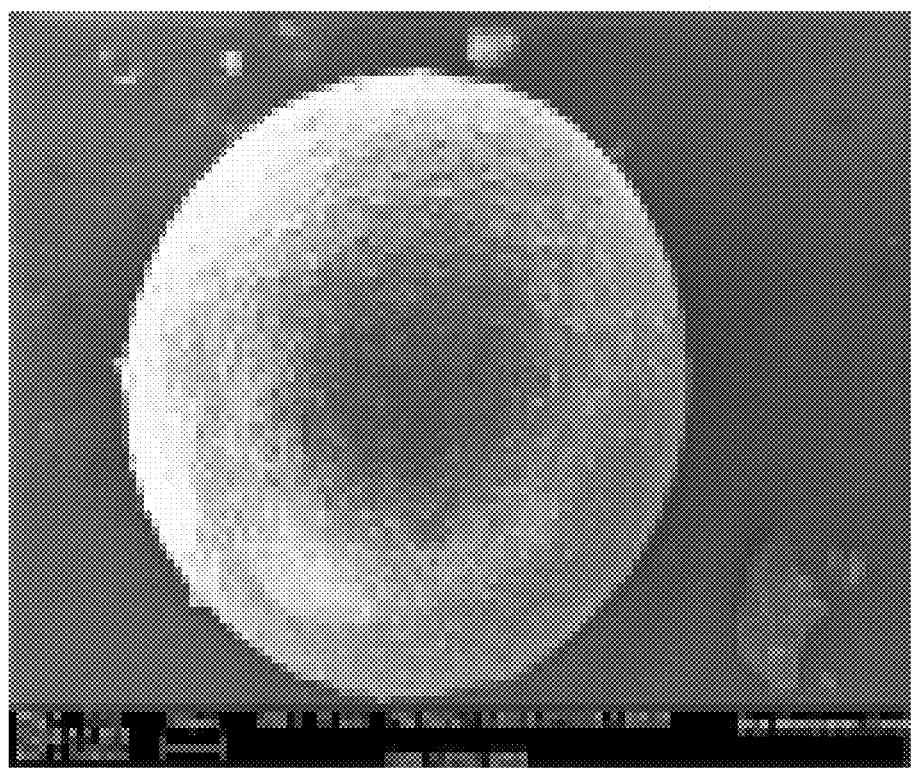
FIG. 1C shows microporous carboseeds.
Figure 1D:
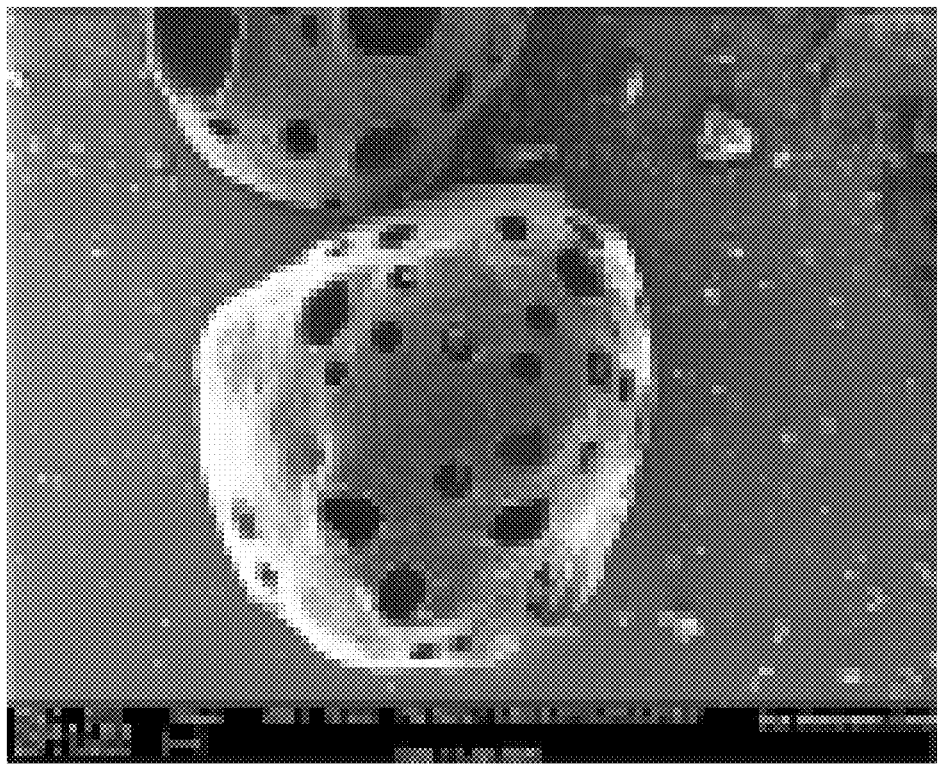
FIG. 1D shows macroporous carboseeds.
Figure 2:
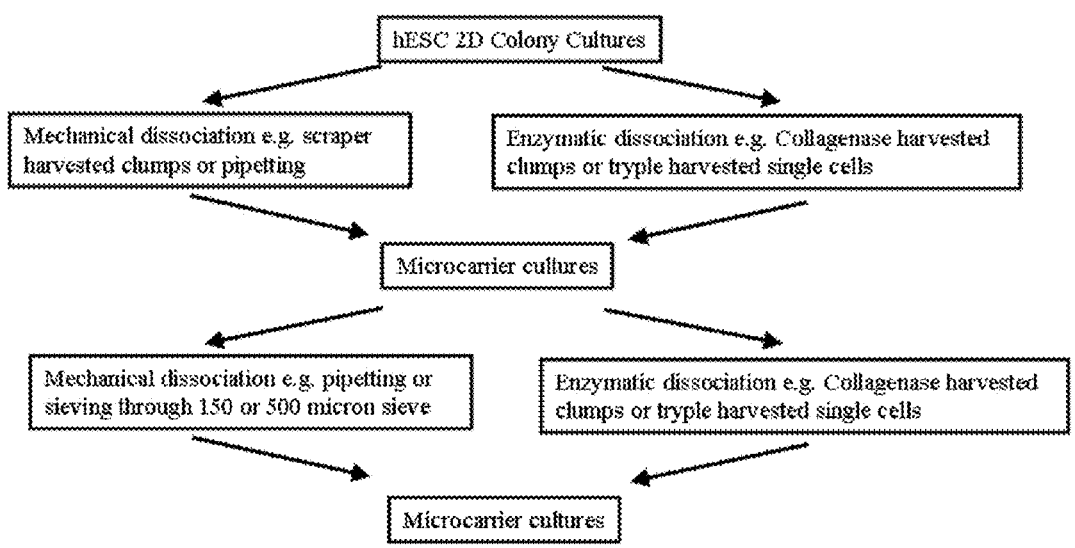
FIG. 2. Seeding of hESC cultures (HES-2 & HES-3), passaging and quality control. Workflow of transferring colony 2D cultures to microcarriers by mechanical or enzymatic dissociation, and passaging microcarrier cultures to by microcarriers by both methods.

FIG. 2 shows the work flow of microcarrier cultures. Conventional 2D colony cultures can be passaged onto microcarriers by 2 sets of methods, mechanical dissociation, e.g. using a cell scraper or pipette, or by enzymatic dissociation, e.g. collagenase harvested clumps or trypLE harvested single cells. These microcarrier cultures can further be passaged onto other microcarriers by mechanical dissociation, e.g. using a pipette, sieving through either 100 micron or 500 micron sieves, or by enzymatic dissociation, e.g. collagenase or trypLE harvested clumps.

Figure 3:
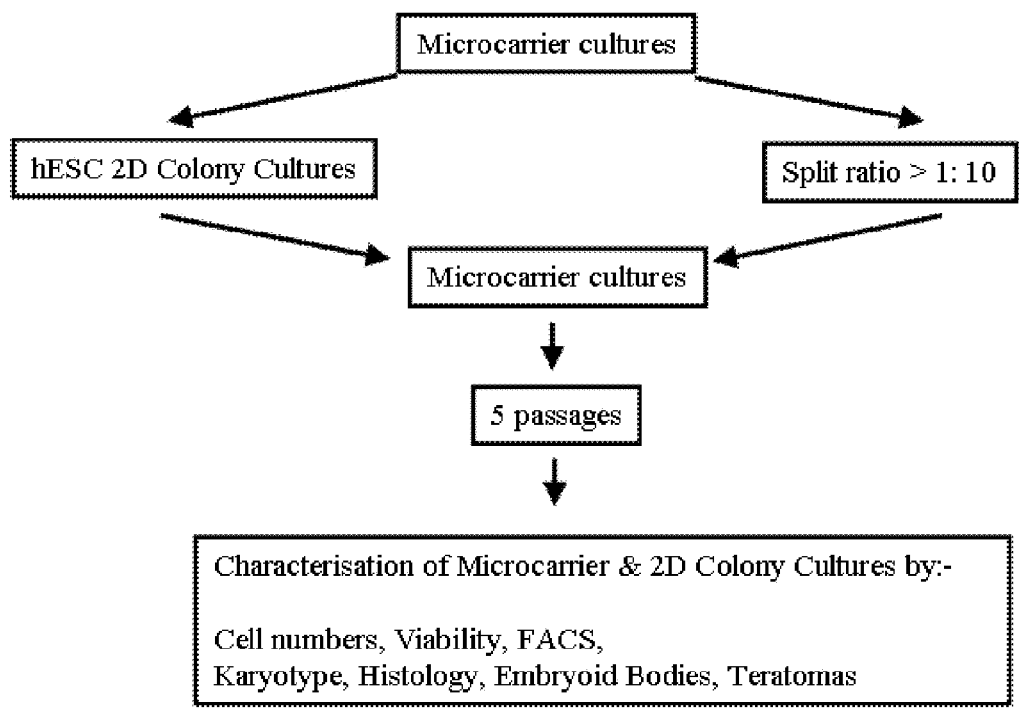
FIG. 3. Seeding of hESC cultures (HES-2 & HES-3), passaging and quality control. Workflow of transferring microcarriers cultures back to 2D colony cultures as well as continually passaging microcarrier cultures followed by characterization of the cultures by cell numbers, viability, flow cytometry of pluripotent markers, histology, karyotype, embryoid body and teratoma formation.

FIG. 3 shows that microcarrier cultures can be transferred back to 2D colony cultures or continually passaged on microcarriers at much higher split ratios of greater than 1 to 10 (in extreme cases up to 1 to 26 ratio) compared to the typical split ratio of 1:4 to 1:5 when passaging from 2D colony cultures to colony cultures. Microcarrier cultures have been passaged for at least 12 passages (currently the cells have been passaged for 13 passages so far). Characterisation of these cultures in comparison to control 2D colony cultures based on cell numbers, viability, flow cytometry of pluripotent markers, histology and karyotype will be shown in the following figures. The cultured cells are capable of differentiation into embryoid bodies and formation of teratomas.

Figure 4:
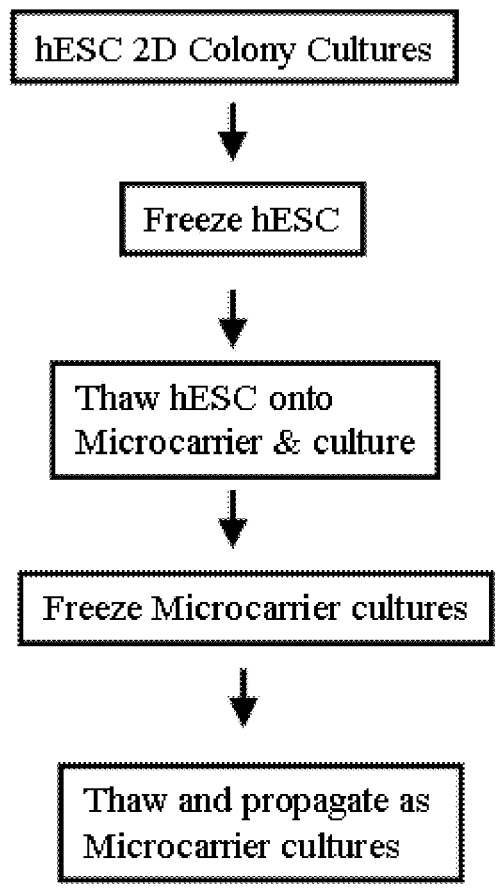
FIG. 4 shows that the microcarriers described here can support freezing of hESC cultures. Workflow of freezing 2D colony hESC cultures and thawing hESC directly onto microcarriers for culturing. Microcarrier cultures are also frozen, thawed and propagated again.

FIG. 4 shows a work flow of the freezing of hESC. Conventional 2D colony cultures are frozen and these cells are subsequently thawed and seeded directly onto microcarriers. Resulting cultures retained a high viability and expressed pluripotent markers. hESC grown on microcarriers are also frozen together with the microcarriers. Upon subsequent thawing they are able to continue to propagate as microcarrier cultures.

Figure 5:
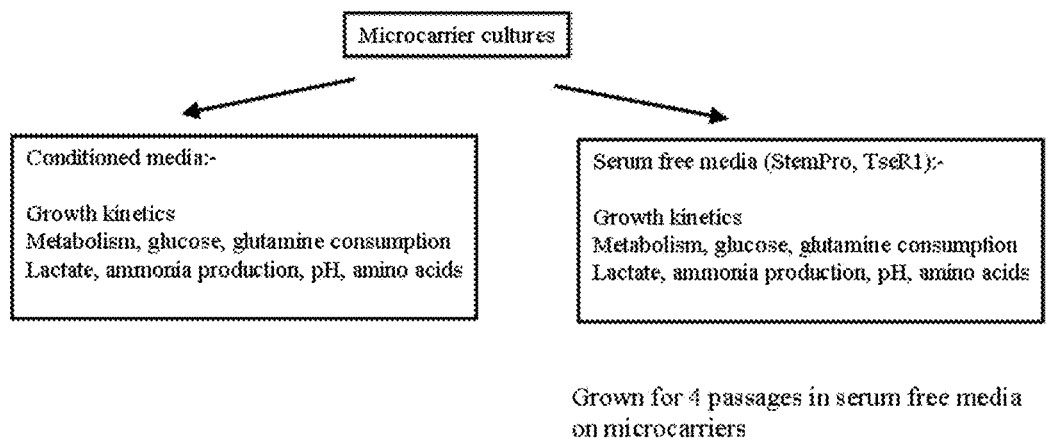
FIG. 5. Growth kinetics and metabolism in Knock Out conditioned media and defined media. Measurements of growth kinetics, metabolism of glucose, glutamine, lactate, ammonia, amino acids and pH of microcarriers cultured in conditioned media as well as 2 commercial serum free media, StemPro and mTeSR-1.

Measurements of the growth kinetics and metabolism of hESC such as glucose and glutamine consumption, lactate and ammonia production, pH and amino acid consumption/production are performed in microcarrier cultures supplemented with feeder conditioned media, as shown in FIG. 5.

These parameters are compared with the control 2D colony cultures. Similarly, growth kinetics and metabolism of hESC are measured in 2 commercially available serum free media, StemPro and mTeSR-1. These media are more amenable for reformulation to achieve better growth by controlling the concentrations of major energy sources such as glucose and glutamine thereby reducing dramatic pH drops at the end of the cultures. To date, hESC on microcarriers have been grown for >5 passages in these 2 serum free media, while retaining their pluripotent markers.

Besides the conventional matrigel coatings on microcarriers, other coatings are also tested such as hyaluronic acid, heparan sulphate, dextran sulphate, heparin sulphate and chondroitin sulphate, to which hESC are able to attach and grow. Microcarrier cultures are also agitated at 100 and 150 rpm and passaged to determine if they could retain their pluripotent markers.

Microcarriers of different charges DE52, DE53 and Q53 are all able to grow hESC. Furthermore, Carboseed, microporous and macroporous carbon microcarriers are able to support the growth of hESC.

Spherical, hydrophilic microcarriers (Tosoh) of different diameters (10 and 65 microns) are coated with different charges. Co-cultures of immortal feeders with hESC are also demonstrated to allow pluripotent expansion of hESC. Microcarrier cultures are also scaled up from 5 ml static cultures to larger 50 ml spinner cultures and their growth kinetics are followed.

Example 2

Human Embryonic Stem and Human iPS Cell Lines

Human embryonic stem cell lines, HES-2 (46X, X), and HES-3 (46X, X) are obtained from ES Cell International. The cells are frozen and stored in liquid nitrogen as a suspension of 200×200 μm cell clumps obtained from 2D colony culture or as cell-microcarrier aggregates obtained from microcarrier cultures. Human iPS cells (iMR90) were obtained from J. Thomson (University of Wisconsin)

Example 3

Microcarriers: Cellulose Cylindrical Microcarriers

DE-52, DE-53 and QA-52 microgranular cylindrical shape anion exchange chromatography matrices (Whatman) are used as microcarriers for cell propagation.

DE-52 and DE-53 microcarriers are charged with tertiary amines (DEAE) at small ion exchange capacity of 1 and 2 milli-equivalents per gram dry material respectively.

QA-52 microcarriers are charged with quaternary amine (QAE) at small ion exchange capacity of 1 milli-equivalent per gram dry material. The microcarriers are equilibrated with $Ca^{2+}Mg^{2+}$ free Phosphate Buffered Saline (pH=7.2) and sterilized by autoclaving in batches of 5 grams per 100 ml.

Matrigel coated microcarriers are prepared by overnight incubation of 20 mg microcarrier in 4 ml of matrigel solution (diluted 1:30) at 4° C. Coating of microcarriers with negatively charged polymers is done by overnight incubation (4° C.) of microcarriers in polymer solutions.

20 mg of microcarriers to the following polymer solutions are tested. 1 ml of 0.5 mg/ml hyaluronic acid from bovine vitreous humor solution; 1.5 ml 2 mg/ml of hyaluronic sodium from *streptococcus* solution; 1 ml 0.25 mg/ml heparan sulphate from bovine kidney; 1 ml 0.25 mg/ml heparan sulphate fast moving fraction from porcine intestinal mucosa; 1.5 ml dextran sulphate sodium (MW=500,000); 410 mg/ml of hyaluronic acid sodium salt from *streptococcus* at dilution factors of 1:10, 1:20, 1:40 and 1:80; 200 mg/ml of Heparin sodium salt at dilution factors of 1:10, 1:20, 1:40 and 1:80 and 7.09 mg/ml of chondroitin sulphate a sodium from bovine trachea at dilution factors of 1:10, 1:20, 1:40 and 1:80. All coatings materials are purchased from Sigma.

Example 4

Microcarriers: Derivatized Hydrophilic Beaded Microcarriers

TSKgel Tresyl-5Pw and Toyopearl AF-Tresyl-650 (TOSOH Bioscience LLC, Montgomeryville, Pa., USA) having inert hydrophilic hydroxylated methacrylic matrix, tresyl active group and bead diameter of 10 and 65 μm respectively are used as the base for microcarrier preparation.

Coupling of proteins to the beads are done according to the manufacturer instructions. Protamine sulphate (Sigma, Catalogue number P3369), Poly-L-lysine hydrobromide (Sigma, Catalogue number P1399 or P5899) at concentrations ranging from 0 to 20 mg/ml beads are coupled to the beads in order to generate various degree of charging.

Matrigel is coupled to the beads at a concentration of 0.5 ml per ml of beads. After coupling the beads are blocked by Tris buffer. Sterilization of the beads is done by gamma radiation (8 minutes exposure at radiation doses between 7 to 10 kGreys/hr).

Example 5

Microcarriers: Carboseed Microcarriers

SM1010 (1 mm) microporous and SH1010 (1 mm) macroporous, bio-inert, turbostratic carbon microcarriers (Blue Membranes GmbH, Wiesbaden, Germany; also Cinvention AG, Nano-Composite Systems. Rheingaustr. 190-196, 65203 Wiesbaden, Germany) are used for hESC culture. Microcarriers are sterilized using 70% of Ethanol and UV light.

After sterilization, microcarriers are incubated with sterile water, which is changed daily to remove all shedding carbon particles. After 7 days, some microcarriers will sink due to degassing and some will float. The sunken microcarriers are coated with matrigel or fibronectin and seeded with hESC in 24-well plates.

All microcarriers are washed with growth medium prior to their use.

Example 6

Cell Culture: Conditioned Medium (CM)

For preparation of mouse embryonic fibroblast conditioned medium (MEF-CM), gelatin treated culture dishes are seeded with $1.4 \times 10^5$ cells $cm^{-2}$ of the mitomycin-C treated immortalized ΔE-MEF in F-DMEM media (90% DMEM high glucose supplemented with 10% FBS, 2 mM L-glutamine and 25 U/ml penicillin and 25 μmg/ml streptomycin, Invitrogen) as described previously (Choo et al, 2006). After 24 h, the media is changed to KNOCKOUT (KO) medium, which contained 85% KO-DMEM supplemented with 15% KO serum replacer, 1 mM L-glutamine, 1% nonessential amino acids and 0.1 mM 2-mercaptoethanol and 4-8 ng $ml^{-1}$ of basic fibroblast growth factor (Invitrogen). The CM is collected every 24 h after KO medium is added into the dish. The CM is filtered (0.22 μm) and supplemented with an additional 8 ng $ml^{-1}$ of recombinant human basic fibroblast growth factor (Invitrogen).

Example 7

Cell Culture: 2D Colony Culture

Cells are cultured at 37° C./5% $CO_2$ on Matrigel-coated culture dishes (incubated at 4° C. overnight with matrigel (Becton Dickinson), diluted in cold KO-DMEM, 1:30 dilution). Cells are routinely maintained in organ culture dishes (OCD) with 1 ml of media. Experiments comparing 2D colony cultures with microcarrier cultures are carried out in 6 well dishes with 5 mls of media.

The media used are either CM from MEF feeders (described above), StemPro hESC serum free media (Invitrogen) or mTeSR-1 serum free media (Cell Technologies). Medium is changed daily. The static colony cultures are passaged weekly either by enzymatic treatment with collagenase (Choo et al, 2004) or trypLE Express (Invitrogen) or by mechanical dissection using the StemPro EZPassage Stem Cell Passaging Tool (Invitrogen)

Example 8

Cell Culture: 3D Microcarrier Cultures

Cells suspension obtained either from dispersed 2D colony culture or directly from liquid nitrogen storage (200×200 μm tissue obtained from 2D colony culture or as cell-microcarriers aggregates) are seeded at concentrations of $0.1$-$0.3 \times 10^6$/ml on microcarrier suspension (4 mg/ml).

In some experiments, in order to ensure more homogeneous culture, the cell inoculum is screened through 100 and 500 μm mesh sieve before its addition to the microcarrier suspension. Cells are cultured at 37° C./5% $CO_2$ on non attachment 6 well dishes (Corning) in static condition or agitated at 100 or 150 rpm (IKA Orbital Shaker). The media used are either MEF-CM or defined media. Medium is changed daily.

The cultures are passaged weekly following either enzymatic treatment with collagenase or trypLE or following mechanical dissociating by repeated pipetting at a split ratio of 1:2 to 1:10. Replating of microcarrier cultures to 2D colony culture is done by placing confluent cell-microcarrier aggregates on matrigel coated 6 cm tissue culture petridish with 8 mls of media, and culturing the cells for 7 days.

All microcarrier and 2D colony cultures have matrigel coating on the surfaces unless otherwise stated and are carried out in 6 well plates with daily exchange of 5 mls of media.

Example 9

Growth Kinetics, Metabolism and Doubling Times

Cell growth is monitored by counting the cells adhering to the microcarriers using the nuclei count method. Single cell suspensions of hESC culture (following treatment with 0.25% trypsin-EDTA, Invitrogen, or TrypLE Express and passed through 40 micron mesh screen) are used for determining cell viability (trypan blue exclusion method) and for Flow cytometry analysis.

Graphs of cell number versus time are plotted in order to estimate the specific growth rate of cells during the exponential growth phase. From this, the doubling time ($t_d$) is calculated using the following equation, $t_d = \ln(2)/\mu$ where μ is the specific growth rate ($hr^{-1}$) Glucose, glutamine, lactic acid and ammonium concentration (Nova Bioprofile 100 Plus) amino acid concentration (Shimadzu Prominence HPLC) and pH is measured daily in supernatant samples for monitoring cell metabolism.

Example 10

Flow Cytometry

Expression levels of extracellular antigens SSEA-4, TRA-1-60 and intracellular transcription factor, Oct-4 in hESC populations are assessed by immunofluorescence using flow cytometry. Cells are harvested as single cell suspensions using trypsin or trypLE express, filtered through a 40 μm sieve (BD) fixed, permeabilised (Caltag Laboratories) and incubated with primary antibodies to SSEA-4 (1:1 dilution, Developmental Studies Hybridomas Bank, MC-813-70), TRA-1-60 (1:50 dilution, Chemicon, MAB4360/4381) and to Oct-4 (1:20 dilution, Santa Cruz).

Cells are then washed with 1% BSA/PBS, and incubated in the dark with a 1:500 dilution of goat α-mouse antibody FITC-conjugated (DAKO). After incubation, the cells are again washed and resuspended in 1% BSA/PBS for analysis on a FACScan (Becton Dickinson FACS Calibur). All incubations are performed at room temperature for 15 min.

Example 11

In Vitro Differentiation

To induce hESC differentiation in vitro, HES-2 and HES-3 cells are harvested as clumps and cultured as embryoid bodies (EB) for 8 days in EB-medium (80% KO-DMEM, 20% FCS, 25 U/ml penicillin, 25 μg/ml streptomycin, 2 mM L-glutamine, 0.1 mM NEAA, and 0.1 mM 2-mercaptoethanol) on non-adherent suspension culture dishes (Corning).

Subsequently, the EB are dissociated with trypsin and plated on gelatinized culture dishes in EB-medium for an additional 14 days.

Example 12

RNA Isolation and Reverse Transcription PCR (RT-PCR)

Total RNA is isolated from hESC using NucleoSpin RNA II Kit from Macherey Nagel and quantified by ultraviolet spectrophotometry (Nanodrop) Standard reverse transcription reactions are performed with 1 μg total RNA using oligo dT primers and ImProm II reverse transcriptase (Promega).

The PCR is carried out using primers specific to alpha-feto protein (AFP), amylase, neurofilament heavy chain (NFH), keratin-15, heart and neural crest derivatives 1 (HAND1) and Msh homeo box homolog 1 (MSX1), which represents differentiation markers from the 3 germ layers. The cycling parameters used for amplification are 30 cycles of 95° C. for 30 sec, 60° C. for 30 sec and 72° C. for 30 sec. This is followed by a final extension at 72° C. for 10 min.

The amplified products are visualized on 1% agarose gels and stained with ethidium bromide.

Example 13

SCID Mouse Models

Four to five million cells from either 2D cultures, replated or suspension 3D microcarrier aggregates are harvested by mechanical dissociation, resuspended in PBS and injected with a sterile 22G needle into the rear leg muscle of 4 week old female SCID mice.

Animals that develop tumours about 9-10 weeks after injection are sacrificed and the tumours are dissected and fixed in 10% formalin. Tumours are embedded in paraffin, sectioned and examined histologically after hematoxylin and eosin staining.

Example 14

Karyotyping

Actively growing cultures of hESC are arrested in the metaphase stage following incubation with colcemid solution diluted in 1 ml KO-medium for 15-16 h at 37° C./5% $CO_2$. Cytogenetics analysis is outsourced to the Cytogenetics Laboratories at the KK Women's and Children's Hospital, Singapore.

Example 15

Spinner Cultures hESC is seeded to a siliconised (Sigmacote, SL2 Sigma-Aldrich) 100 ml Bellco spinner flask at a density of $3 \times 10^5$ cells/ml to 5 mg/ml of microcarriers, in an initial volume of 25 ml without agitation inside a controlled incubator with 37° C. and 5% $CO_2$.

The reactor volume is increased to 50 ml with fresh conditioned medium and agitated at 30 rpm, 12 h after inoculation. 80% of the spent medium is removed daily and replaced with fresh conditioned medium. Daily samples are taken for cell counts and metabolite analysis.

Example 16

Seeding of hESC Cultures, Passaging and Quality Control 2D colony cultures seeded on microcarriers expressed pluripotent markers and showed high viability (data not shown), which are subsequently passaged onto microcarriers. hESC (HES-3 cell line) microcarrier cultures which have been passed through 100 or 500 micron sieves and reseeded on microcarriers retain high expression of the pluripotent markers Oct-4, SSEA-4 and TRA-1-60 after 7 days of culture.

Figure 6A:
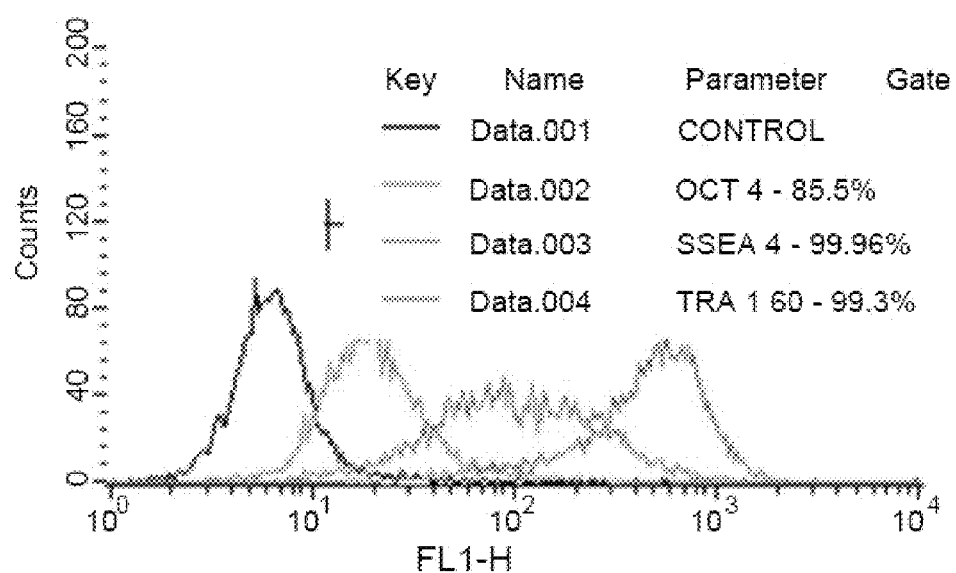
FIG. 6A shows maintenance of pluripotent markers after mechanical dissociation: passaging cells through with 100 and 500 micron mesh and seeding microcarriers. FACS of pluripotent markers Oct-4, SSEA-4 and TRA-1-60 after hESC has been passed through a 100 micron mesh.
Figure 6B:
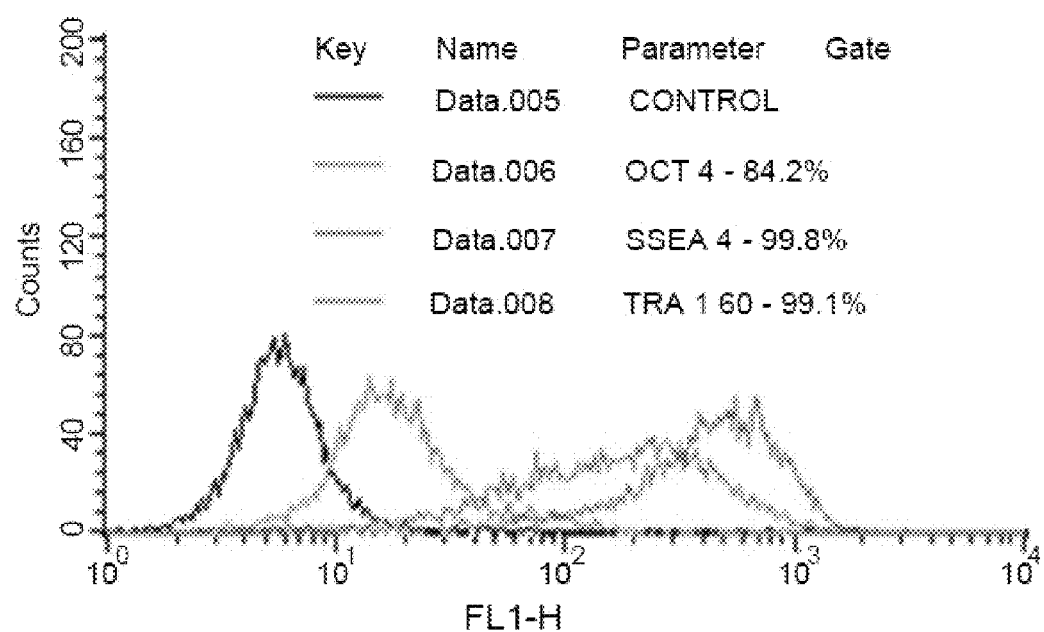
FIG. 6B shows maintenance of pluripotent markers after mechanical breakage of cells on microcarriers by pipetting followed by 1:10 dilution to seed new microcarriers. FACS of pluripotent markers Oct-4, SSEA-4 and TRA-1-60 after hESC have been subject to pipetting followed by 1 in 10 dilution onto microcarriers.

FIG. 6A shows the expression of markers for the 100 micron sieve treatment. Similarly, hESC on microcarriers which have been mechanically dissociated by pipetting followed by seeding on new microcarriers at 1:10 dilution, also show high expression of pluripotent markers Oct-4, SSEA-4 and TRA-1-60 after 7 days of culture (FIG. 6B).

Figure 6C:
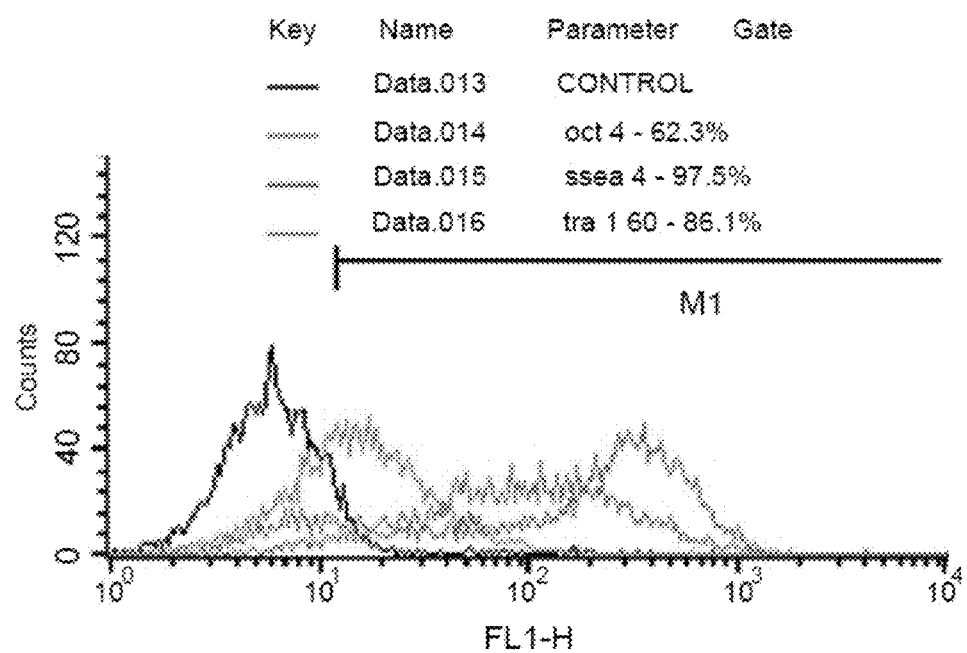
FIG. 6C shows a control of 2D colony cultures.
Figure 6D:
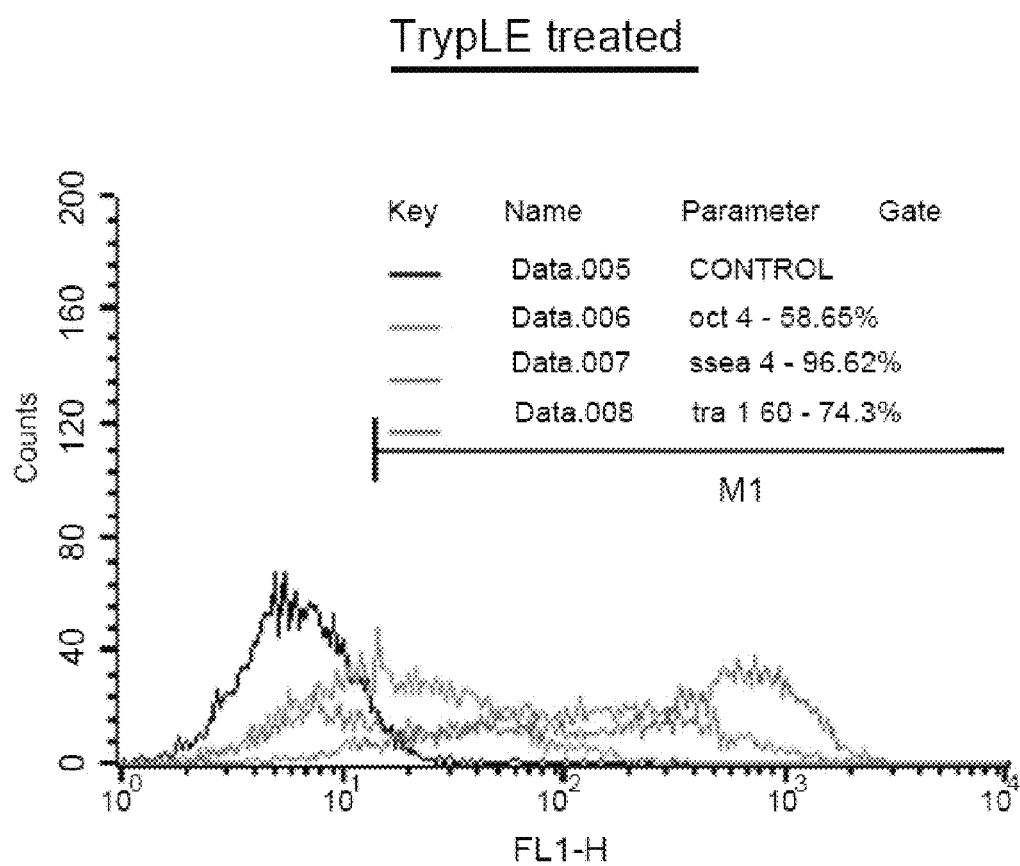
FIG. 6D shows maintenance of pluripotent markers after enzymatic dissociation: TrypLE treated hESC are seeded on microcarriers. Cell counts taken on day 7=4.3 E6 cells/well.

Enzymatic dissociation of hESC from microcarriers by trypLE show similar levels of Oct-4 expression as the control 2D colony cultures (about 60%) and high levels of SSEA-4 and TRA-1-60 expression after 7 days of culture achieving about 4 million cells in 5 mls per well of a 6 well plate (FIG. 6C and FIG. 6D). Viability of the cells passaged by both methods are >90% (data not shown).

Figure 7A:
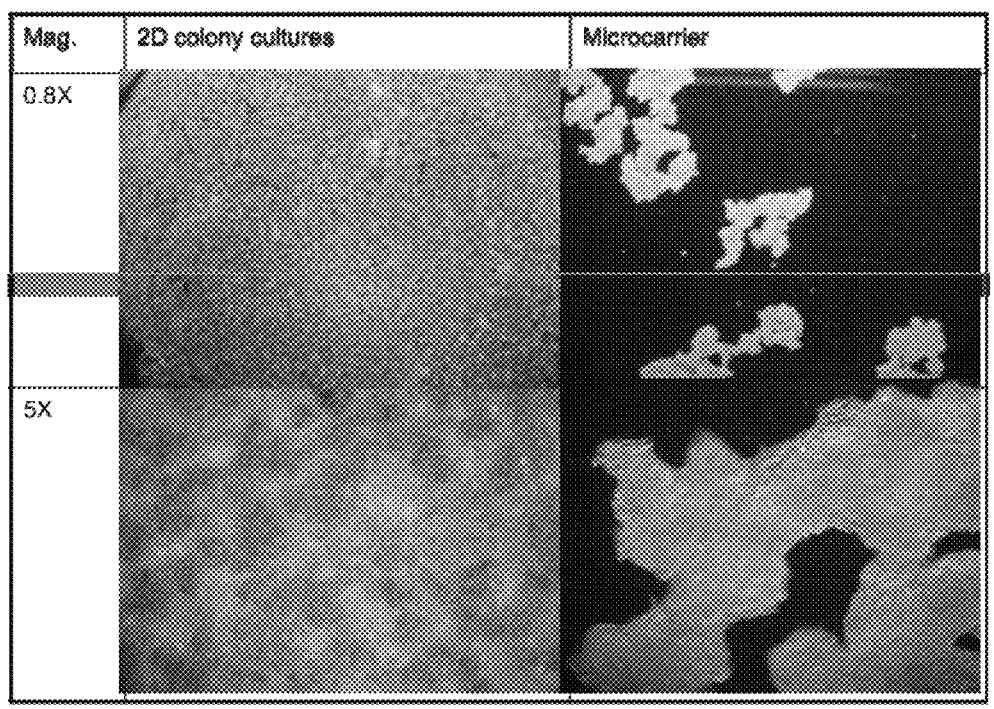
FIG. 7A. Photos of hESC in 2D colony cultures and on microcarriers at 0.8× and 5× magnifications.

Visual observation of microcarriers after 7 days, show that hESC form large clusters of aggregates. Note that there are no differentiated cystic regions in these aggregates in FIG. 7A shown at the 2 different magnifications. Typical control 2D colony cultures after 7 days are shown on the left, showing complete coverage of the plate (FIG. 7A).

Figure 7B:
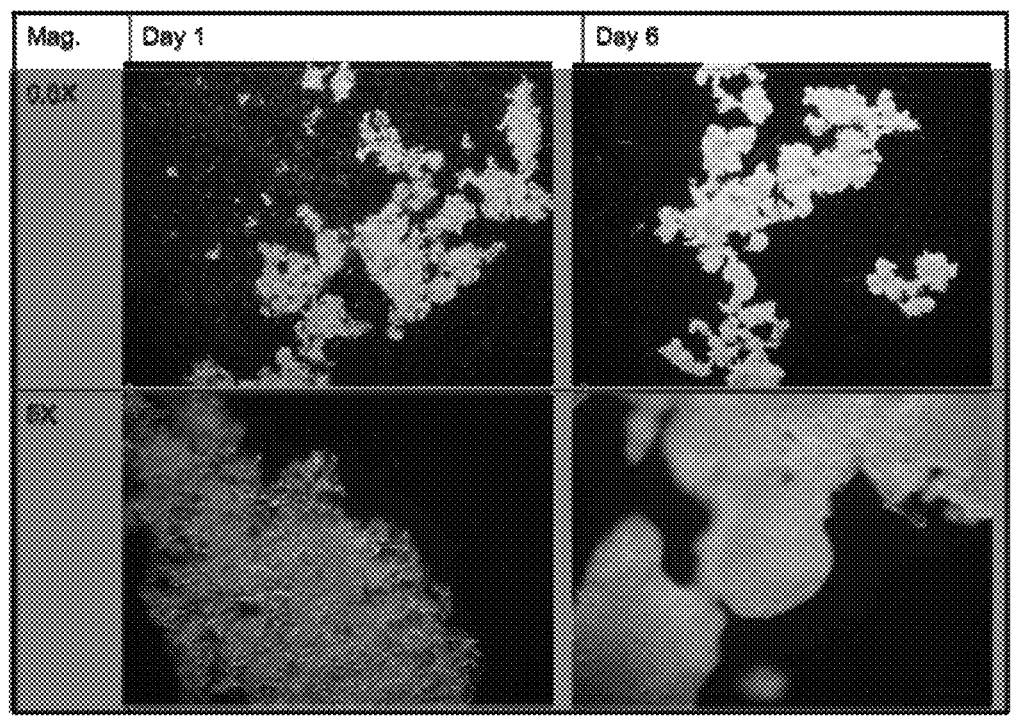
FIG. 7B hESC at days 1 and 6 on microcarriers at 0.8× and 5× magnifications.

FIG. 7B shows the efficient attachment of hESC on day 1 and spreading to colonise the cellulose microcarriers after 6 days at two magnifications.

Figure 8A:
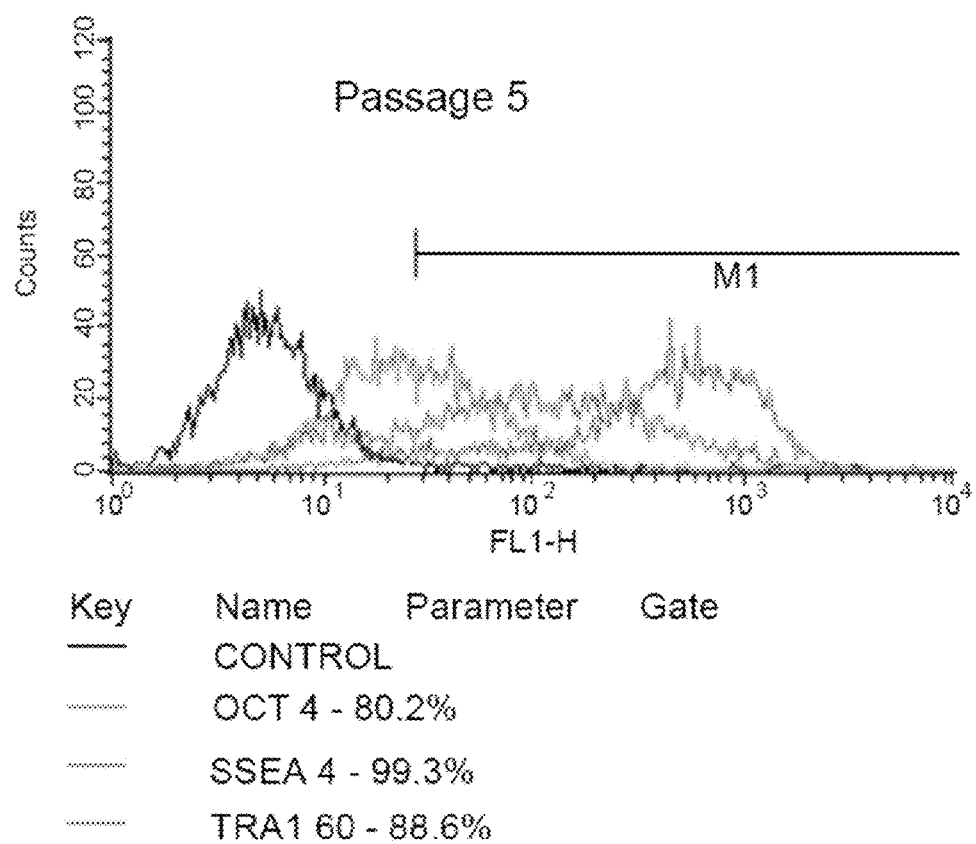
FIG. 8A. FACS of pluripotent markers Oct-4, SSEA-4 and TRA-1-60 after passage 5.
Figure 8B:
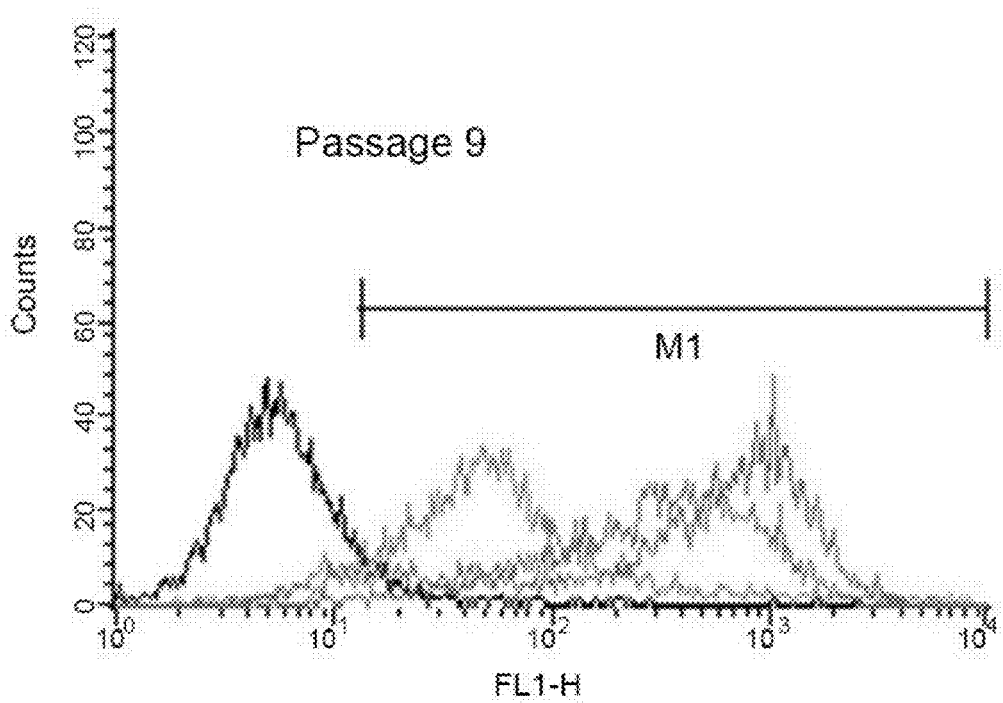
FIG. 8B. FACS of pluripotent markers Oct-4, SSEA-4 and TRA-1-60 after passage 9.

FIG. 8A and FIG. 8B show that pluripotent markers Oct-4, SSEA-4 and TRA-1-60 are expressed at greater than 80% to 90% at passage 5 and 9 respectively for hESC grown on microcarriers, showing that culture on this new platform is stable.

Figure 8C:
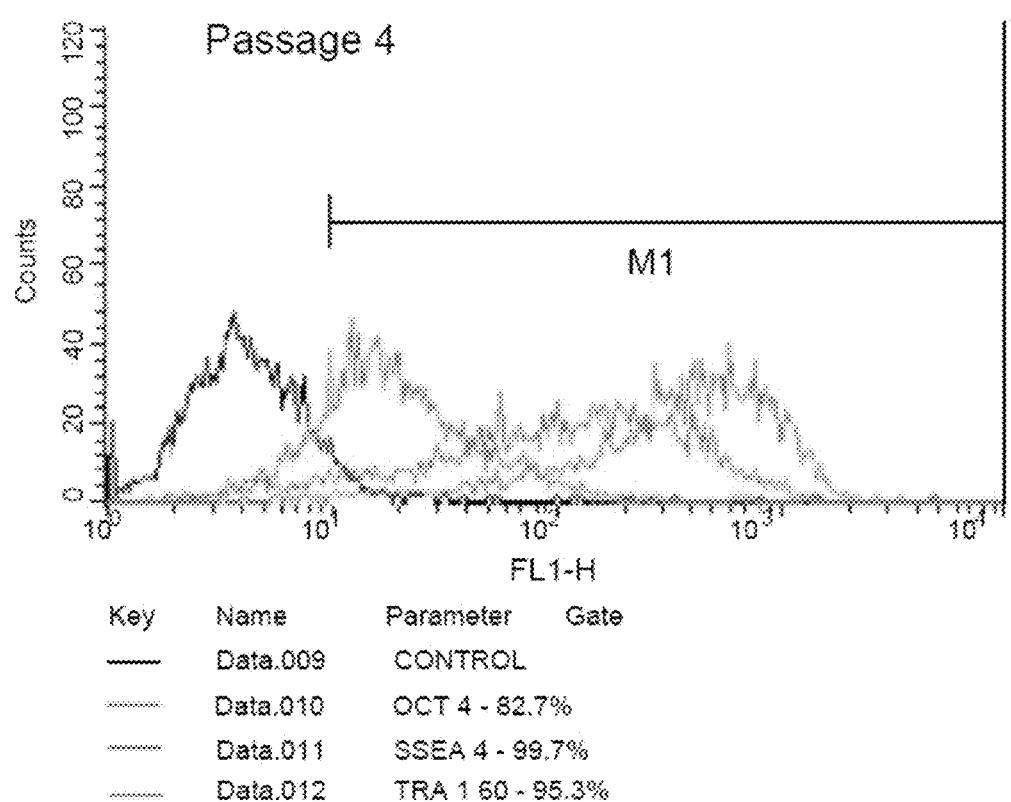
FIG. 8C and FIG. 8D show stable FACS of hESC at passages 4 and 6 on matrigel coated static microcarriers. Nuclei count range from 7 to 8 million/well.
Figures 8D, 8E:
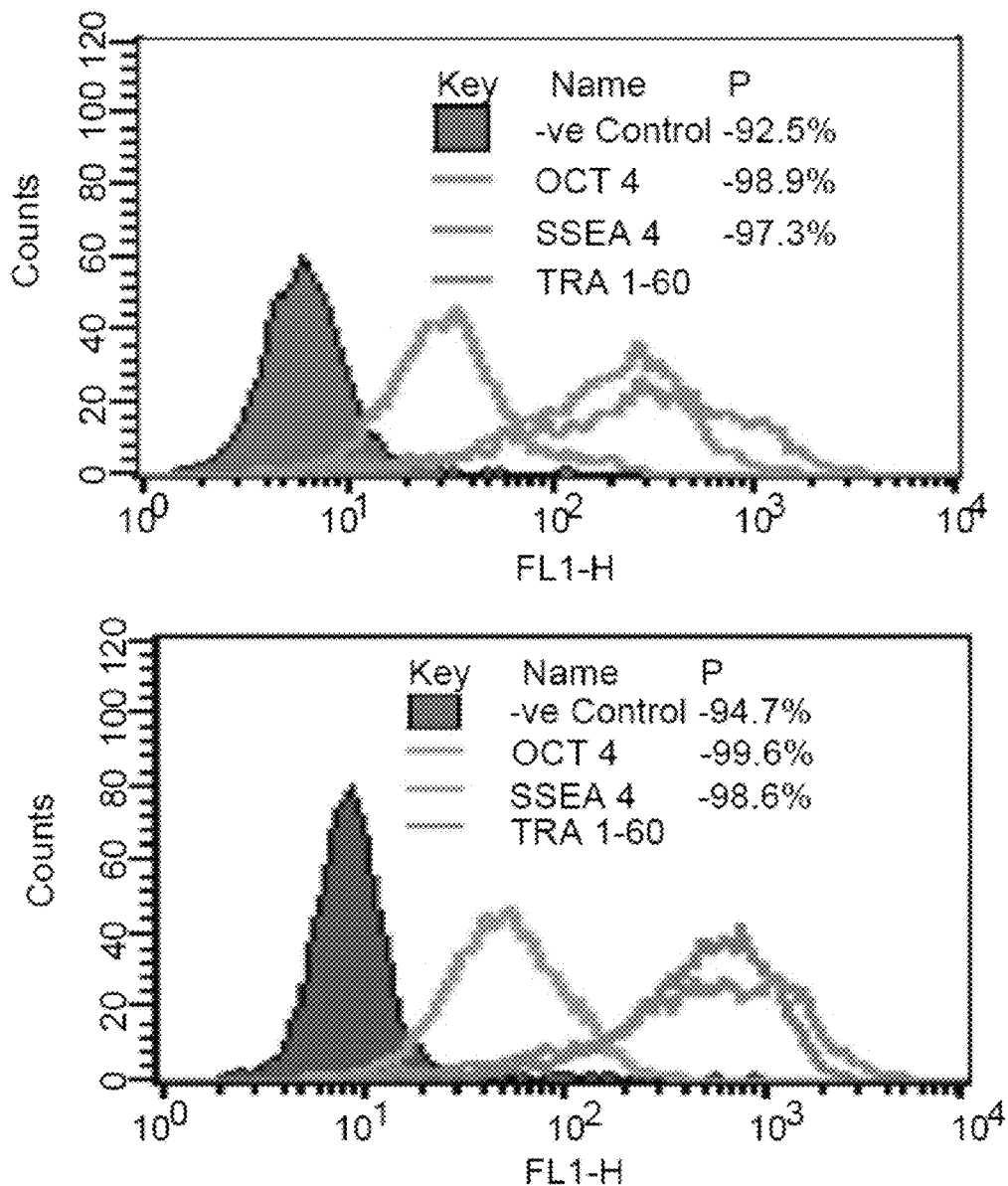
FIG. 8E. FACS of pluripotent markers Oct-4, SSEA-4 and TRA-1-60 in control 2D colony culture. Nuclei count is typically only 2 to 4 million/well.

FIG. 8C, FIG. 8D and FIG. 8E show another set of repeated experiments of hESC passaged on microcarriers indicating that they stably express pluripotent markers Oct-4, SSEA-4 and TRA-1-60 (>80-90% for all markers) at passage 4 and 6 compared to the 2D colony control cultures. Typically, total cell numbers per 6 well plate achieved in microcarriers cultures are 7 to 8 million per well compared to only 2 to 4 million per well in 2D colony control cultures.

Figure 9:
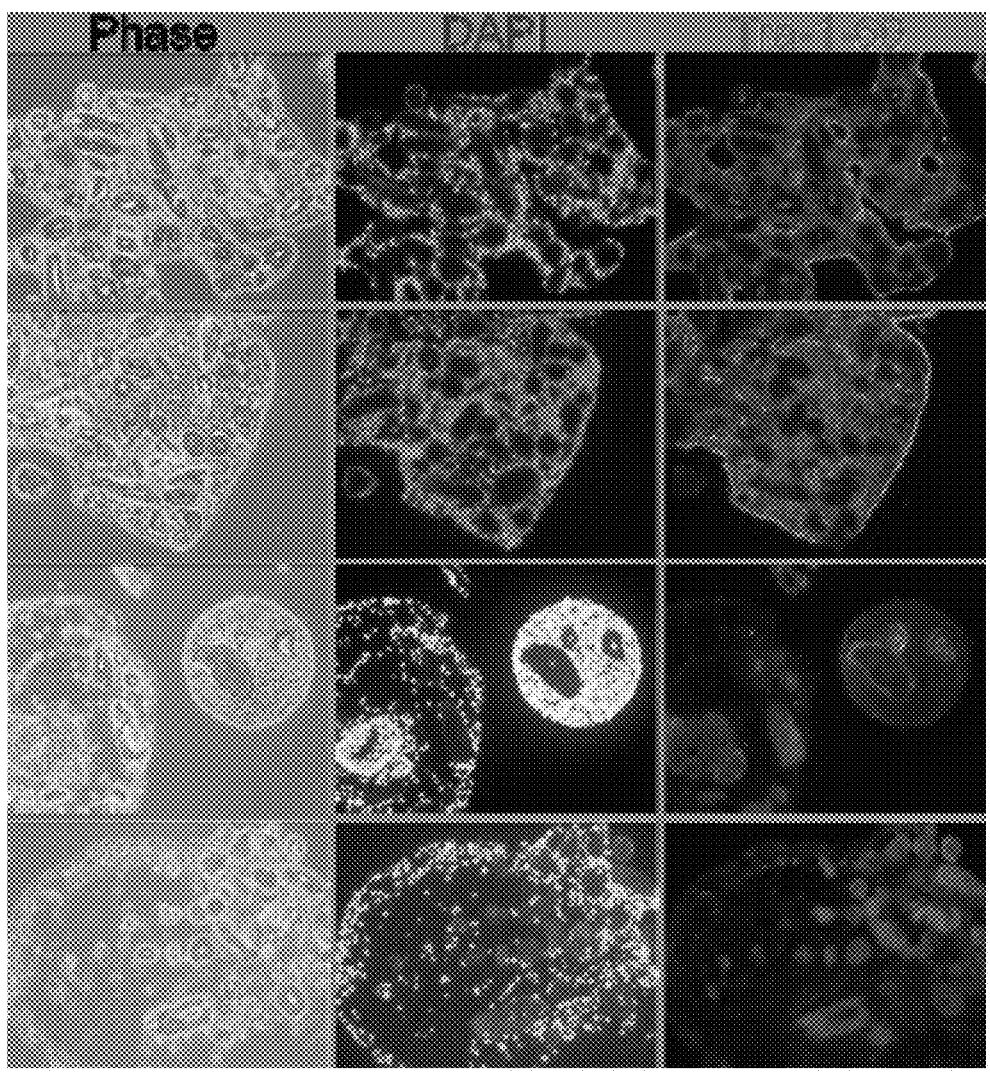
FIG. 9. Seeding of hESC cultures (HES-3), passaging and quality control. Histological analysis of microcarrier cultures in conditioned media and KO media by phase contrast, staining with DAPI and TRA-1-60. Histological Analysis of hESC Cellulose Microcarrier Cultures; HES-3 at passage 3. Row 1: Mechanical dissociation, Matrigel coated microcarriers in CM, static. Row 2: trypLE enzyme harvest, Matrigel coated microcarriers in CM, static. Row 3: Native microcarriers in CM Suspension at 100 rpm. Row 4: Native microcarriers in CM static.

Histological analysis of microcarrier cultures in FIG. 9 shows that the hESC are growing around the cellulose beads (dark objects in phase contrast). DAPI (blue) stains the nuclei of the cells, while the pluripotent surface marker, TRA-1-60 (red) is expressed by the hESC on the microcarriers. The first 2 rows shows hESC grown on matrigel coated microcarriers and MEF-CM where cells are well distributed around the microcarriers and strongly express TRA-1-60, and the last 2 rows show hESC grown on native microcarriers without matrigel coating in MEF-CM media where TRA-1-60 is less strongly expressed.

Figure 10A:
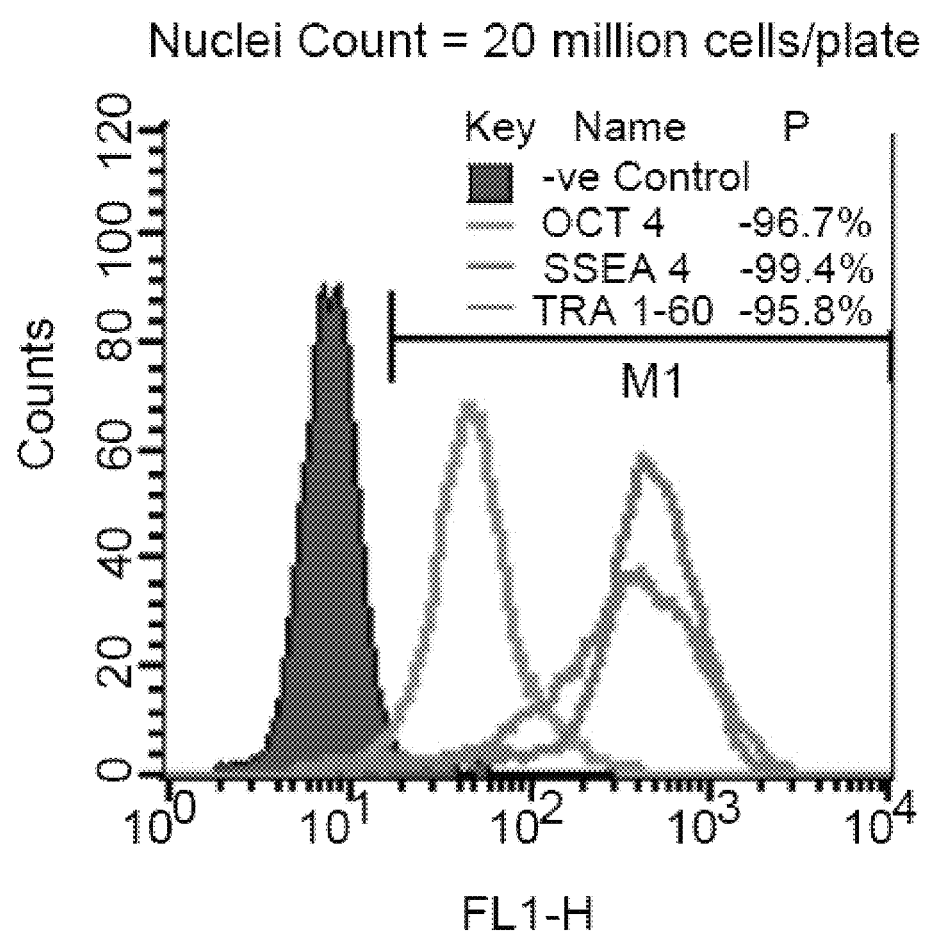
FIG. 10A. FACS of pluripotent markers Oct-4, SSEA-4 and TRA-1-60 after replating microcarrier cultures onto a 6 cm petridish.

FIG. 10A shows that hESC can be replated from microcarriers to 2D colony cultures and retain high expression levels of the pluripotent markers Oct-4, SSEA-4 and TRA-1-60, (>95%). Cells from the microcarriers spread out and colonise the surface and achieved 20 million cells on a matrigel coated 6 cm tissue culture petridish (FIG. 10B).

Example 17

Freezing of hESC Cultures

Figure 11A:
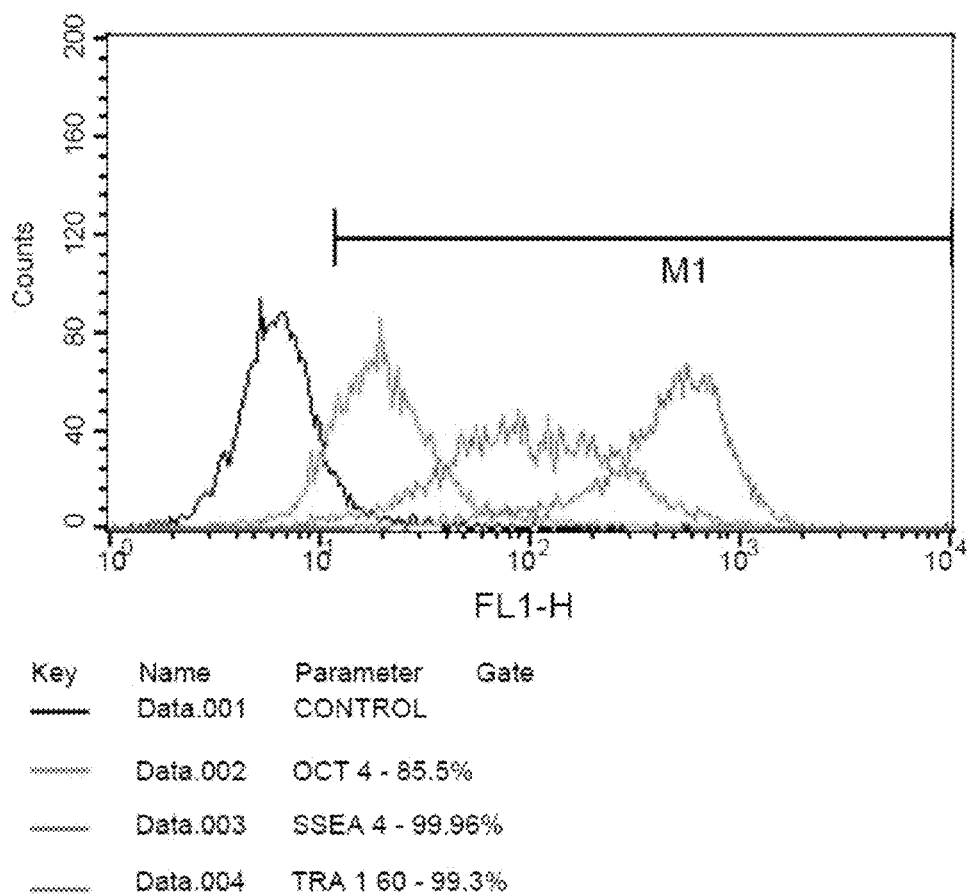
FIG. 11A. FACS of pluripotent markers Oct-4, SSEA-4 and TRA-1-60 after frozen hESC colonies were thawed directly onto microcarriers. Nuclei count on day 7=4.2×10E6 cells/well in a 6 well plate.

FIG. 11A shows that frozen hESC colonies can be thawed directly onto microcarriers which quickly capture the cells. After 7 days, the cells express high levels of Oct-4, SSEA-4 and TRA-1-60 and reach about 4.2 million cells in 5 mls per well of a 6 well plate.

Figure 11B:
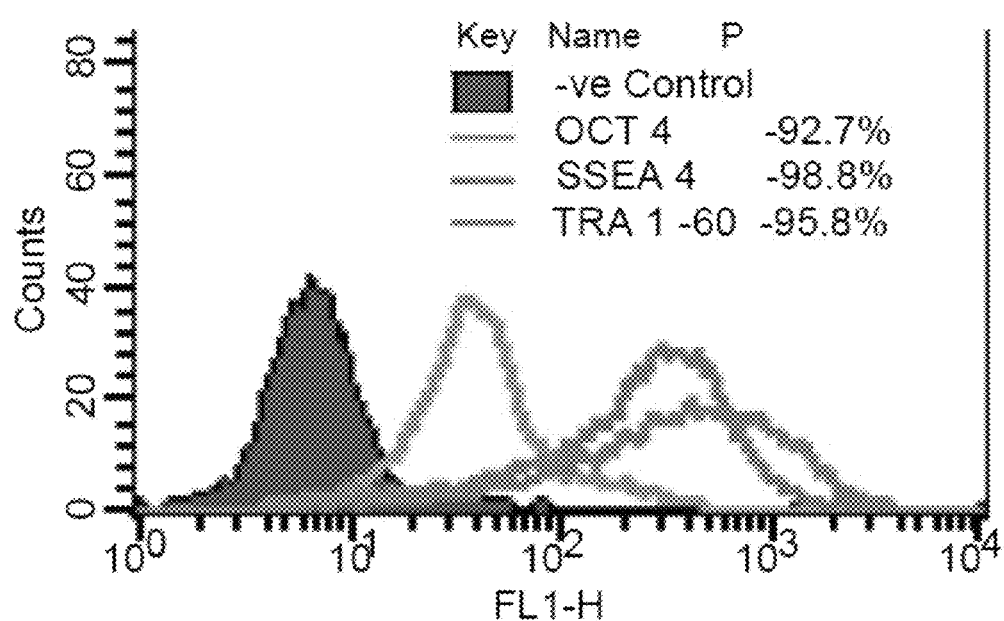
FIG. 11B. FACS of pluripotent markers Oct-4, SSEA-4 and TRA-1-60 of hESC on microcarriers after being frozen, thawed and cultured with their respective cell counts. Nuclei Count on day 14=7.14×$10^6$ cells/well. Note: cells were cultured over a longer period of time due to cell death post thawing. Cells regained normal growth rate over time.

Alternatively, hESC can be frozen on the microcarriers and also thawed. In this case, because of partial cell death post thawing hESC are cultured for a longer period of time (14 days) before they regain normal growth. hESC also express high levels of Oct-4, SSEA-4 and TRA-1-60 and reach about 7 million cells in 5 mls per well of a 6 well plate, as shown in FIG. 11B.

Example 18

Growth Kinetics and Metabolism in Knock Out Conditioned Media and Defined Media hESC are seeded at 0.67 million cells/well in a 6 well plate which had 20 mg/ml of microcarriers in 5 mls of media. Control 2D colony cultures are also seeded at the same cell numbers.

Figure 12:
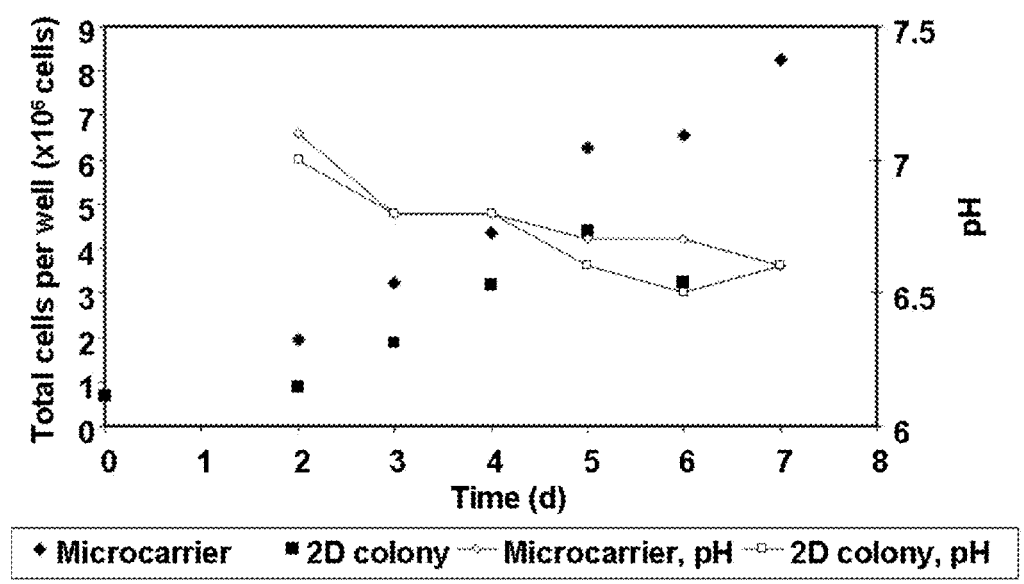
FIG. 12. Growth kinetics and metabolism in Knock Out conditioned media. Comparison of hESC growth kinetics on microcarriers vs. 2D colony cultures. Growth kinetics of hESC on microcarriers vs. 2D colony cultures and their associated pH profiles. Seeding density of 0.67×10E6 cells/well (20 mg/ml of microcarriers in 5 mls of media).
Figure 13A:
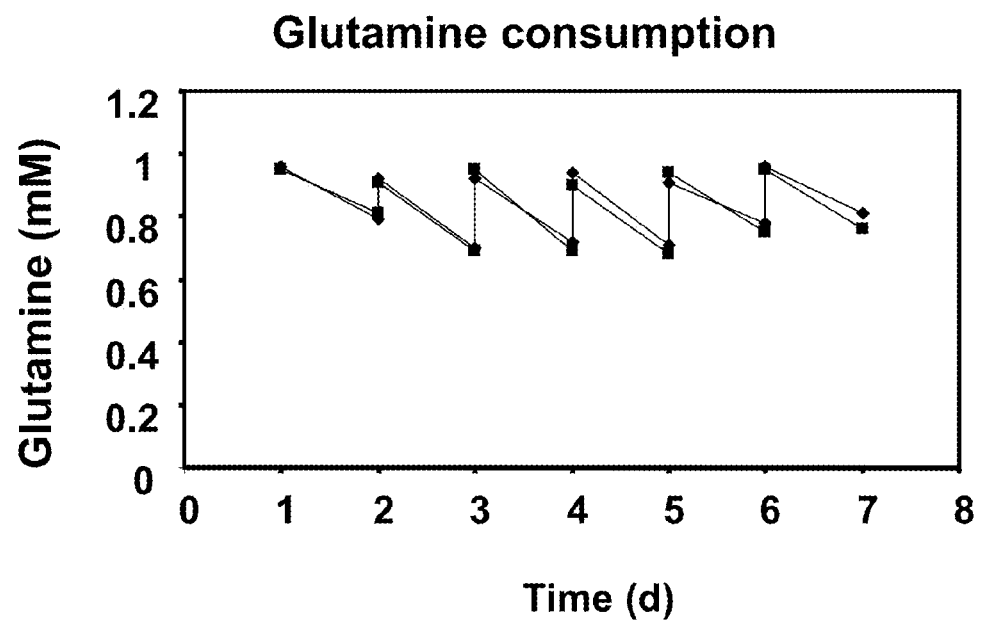
FIG. 13. Growth kinetics and metabolism in Knock Out conditioned media. Comparison of metabolism of hESC on microcarriers vs. 2D colony cultures. Daily glucose and glutamine consumption profiles and lactate and ammonia production profiles of hESC on microcarriers vs. 2D colony cultures. Glutamine consumption over time is shown in FIG. 13A; glucose consumption over time is shown in FIG. 13B; lactate production over time is shown in FIG. 13C; and ammonium production is shown in FIG. 13D.
Figure 13B:
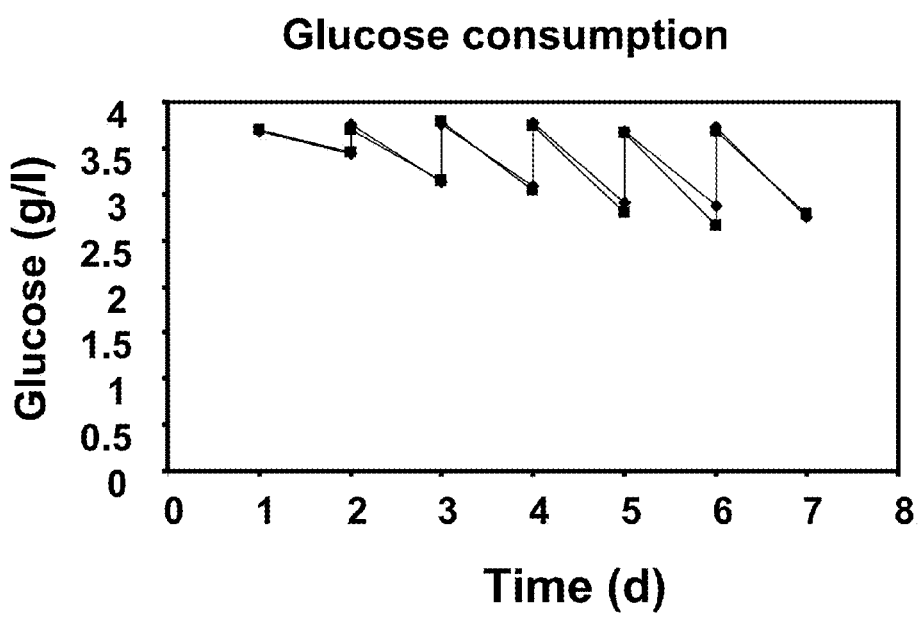
Figure 13C:
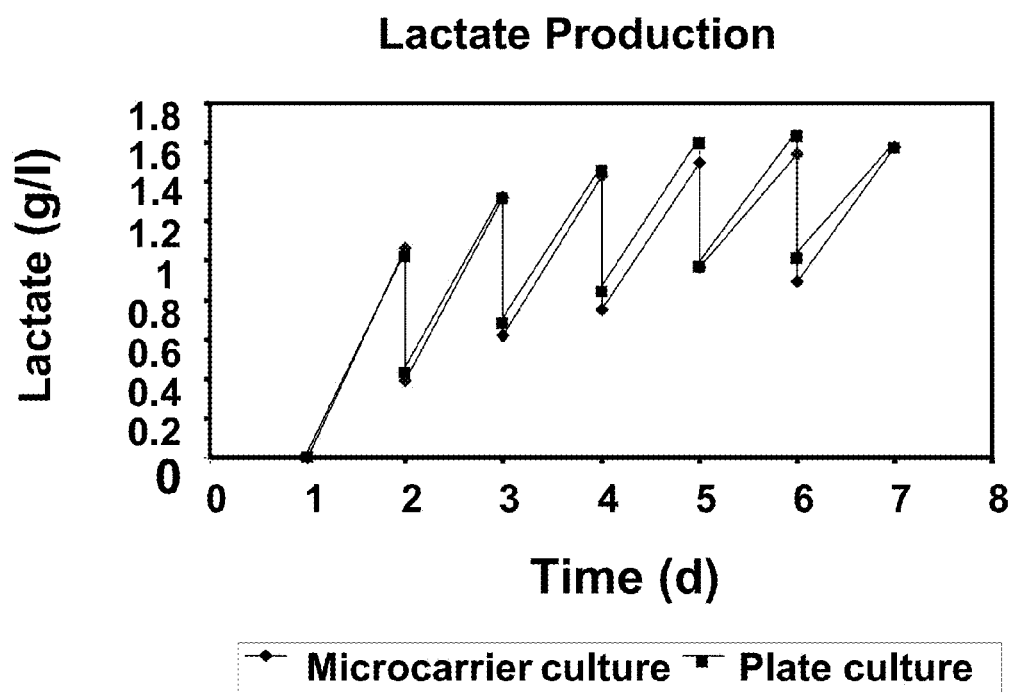
Figure 13D:
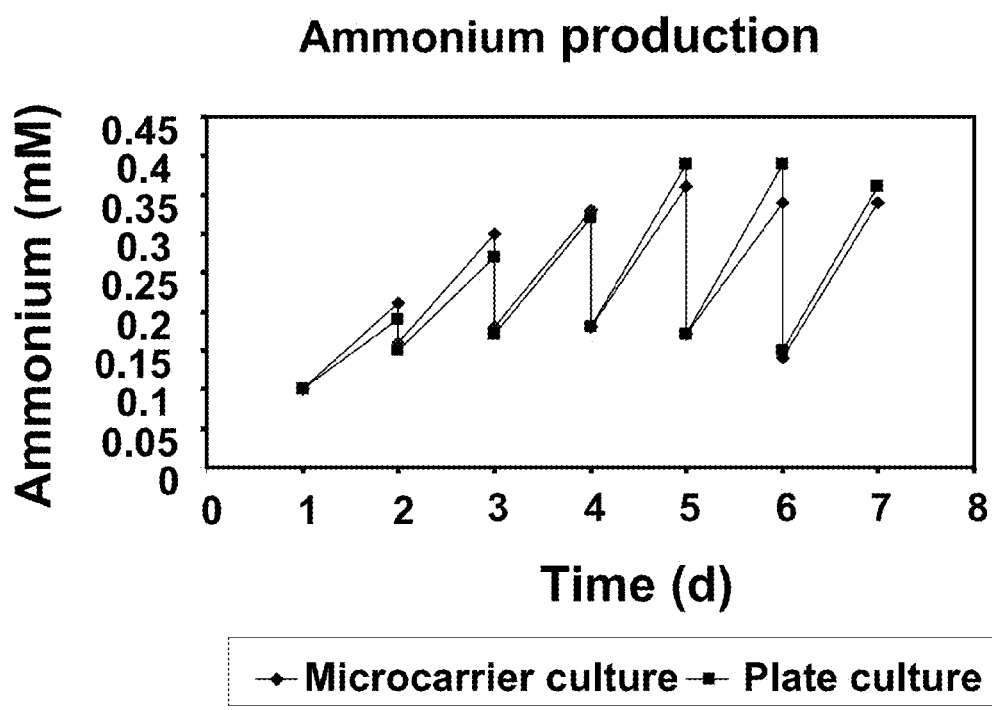
Figure 14A:
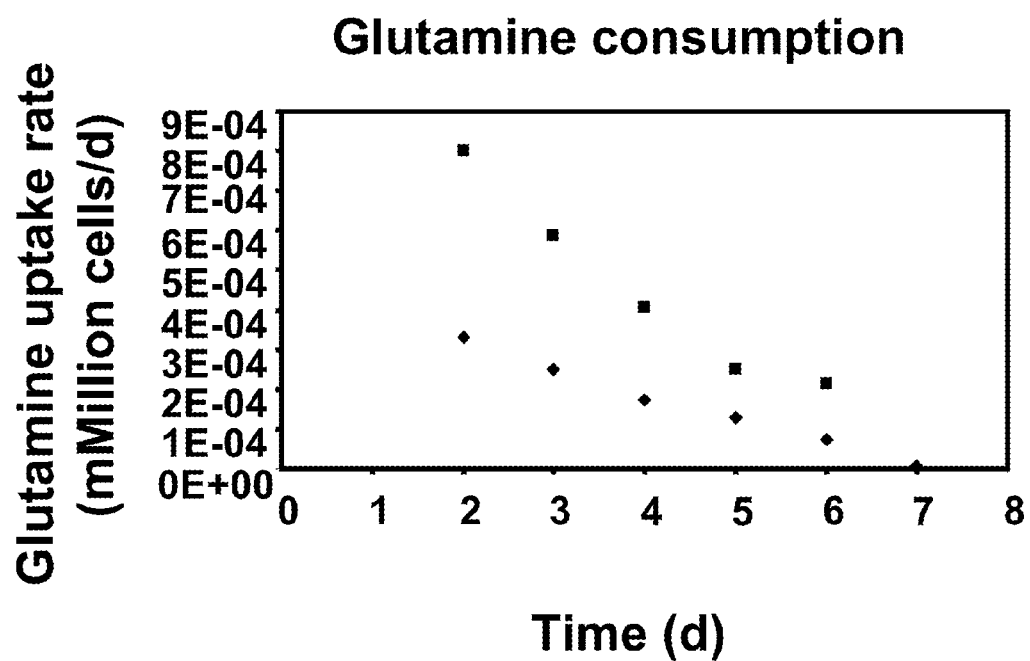
FIG. 14A shows glutamine consumption over time.
Figure 14B:
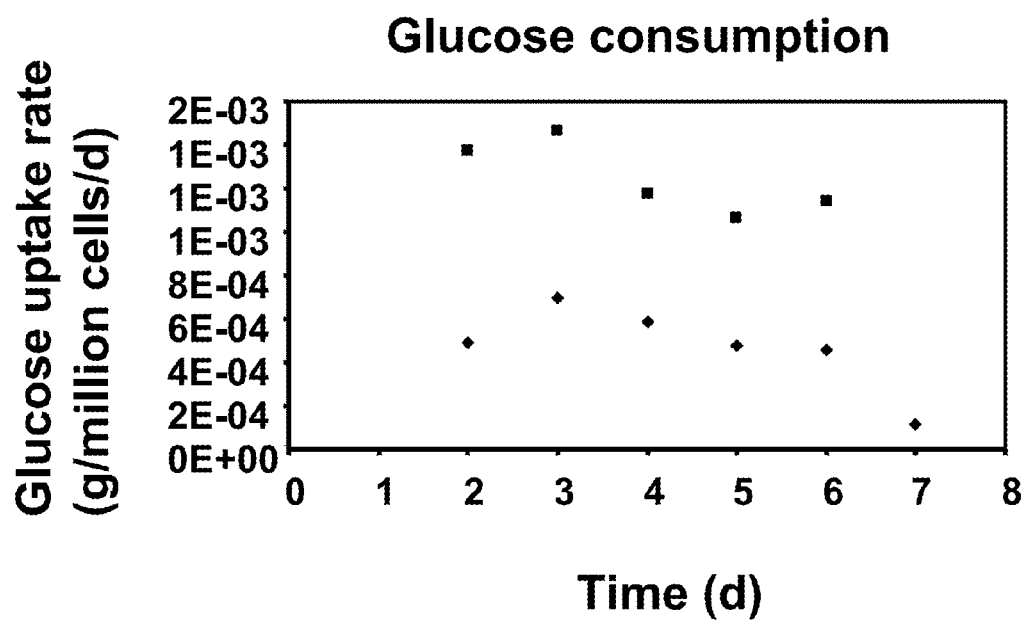
FIG. 14B shows glucose consumption over time.
Figure 14C:
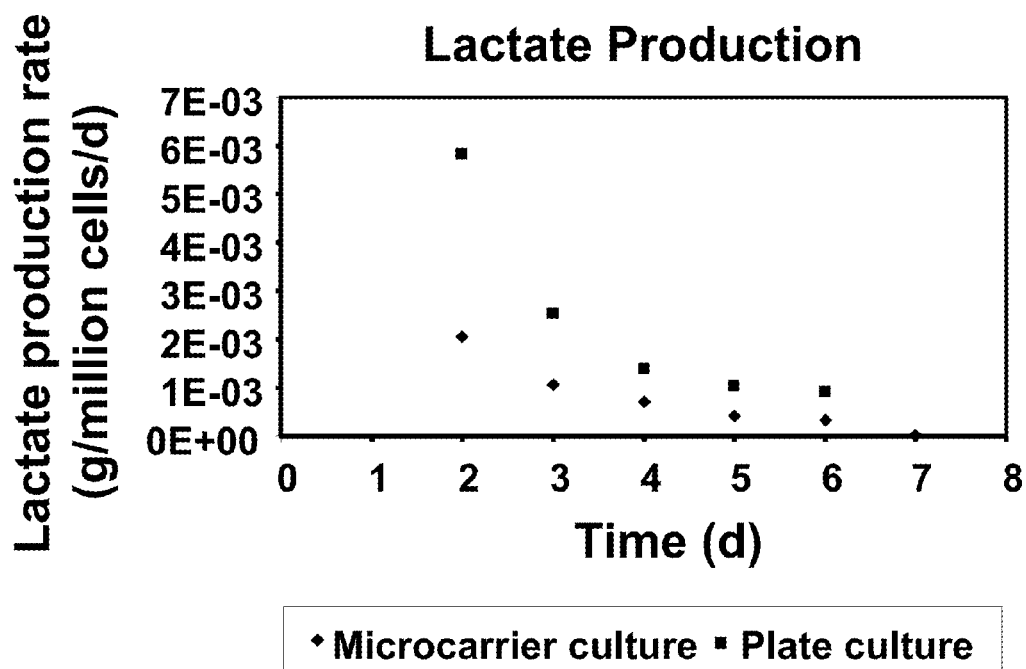
FIG. 14C shows lactate production over time.
Figure 14D:
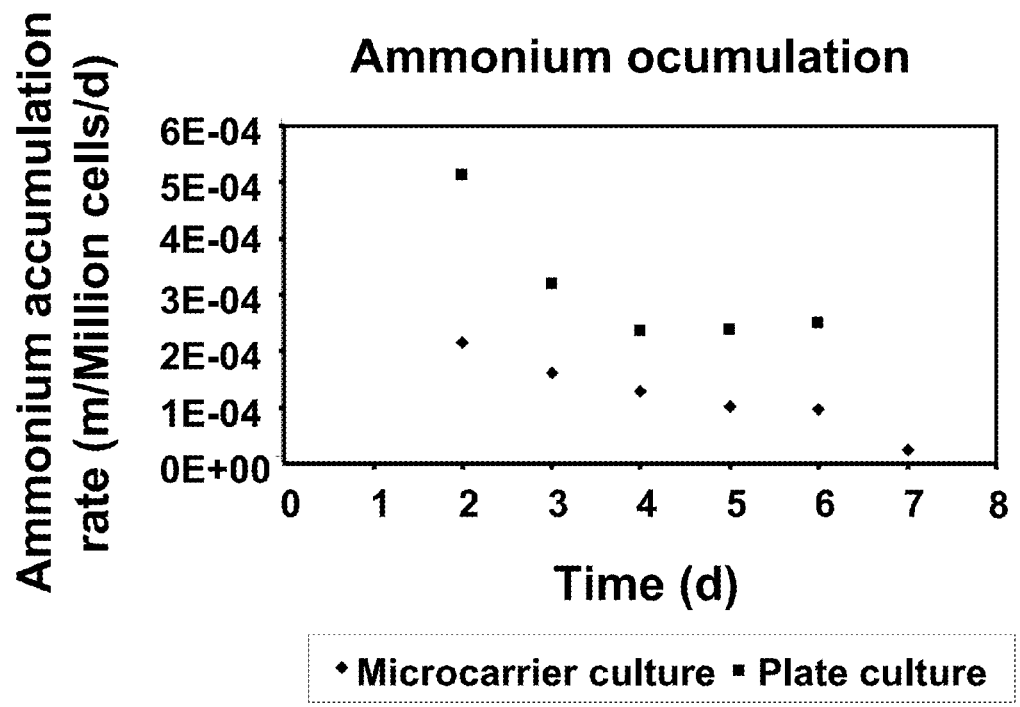
FIG. 14D shows ammonium accumulation over time.

Microcarrier cultures grew at an exponential rate and reached more than 8 million cells per well of a 6 well plate compared to the 2D colony control which peaked at about 4 million cells per well on day 5 due to surface limitation and dropped to 3 million cells per well at day 6 as shown in FIG. 12. The pH profiles show that both cultures drop to about 6.5 by day 6 or 7, however this drop is more drastic for the 2D colony control culture.

FIG. 13 shows that the glutamine and glucose consumption profiles are virtually identical for microcarrier vs. 2D colony cultures, as are the lactate and ammonia production profiles for both cultures.

However, specific consumption rates of glutamine and glucose are much lower in microcarrier cultures (approximately half) compared to 2D colony cultures indicating more efficient metabolism in microcarrier cultures. Similarly there are much lower specific production rates of waste products such as lactate and ammonia in microcarrier cultures compared to 2D colony cultures as shown in FIG. 14.

Figure 15:
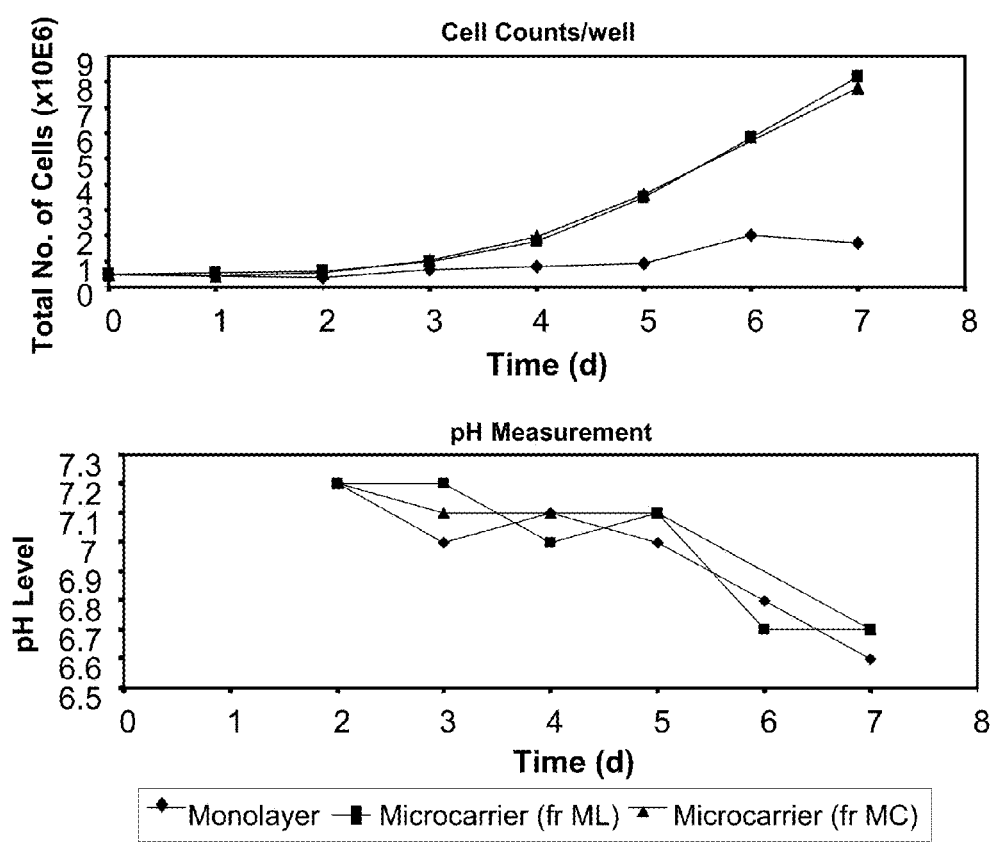
FIG. 15. Growth kinetics and metabolism in Knock Out conditioned media. Comparing inoculation from 2D colony cultures and microcarriers cultures. Growth kinetics of hESC on microcarriers (seeded from 2D colonies or from microcarriers) vs. 2D colony cultures controls and their associated pH profiles. Cell counts/well: Seeding density of 5×10E5 cells/well. Higher cell numbers for microcarriers. Split ratio 1:18. Doubling times: microcarriers=33 hours. 2D colony cultures=58 hours. pH measurement: for all 3 conditions, steeper drop in pH after $5^{th}$ day.

FIG. 15 is a repeat experiment confirming that microcarrier cultures grow at an exponential rate and achieve over 8 million cells per well compared to 2D control cultures which in this case only reached 2 million cells per well. The growth rate is equivalent whether microcarriers are seeded from 2D colony cultures or from another microcarrier culture. Doubling times are 33 hours which is similar to a normal control culture. In this case, the 2D colony culture achieved a longer doubling time of 58 hours. pH profiles show that the trends for the 3 conditions, are very similar with a sharp drop after day 5 to pH 6.6, especially for the 2D colony culture.

Figure 16:
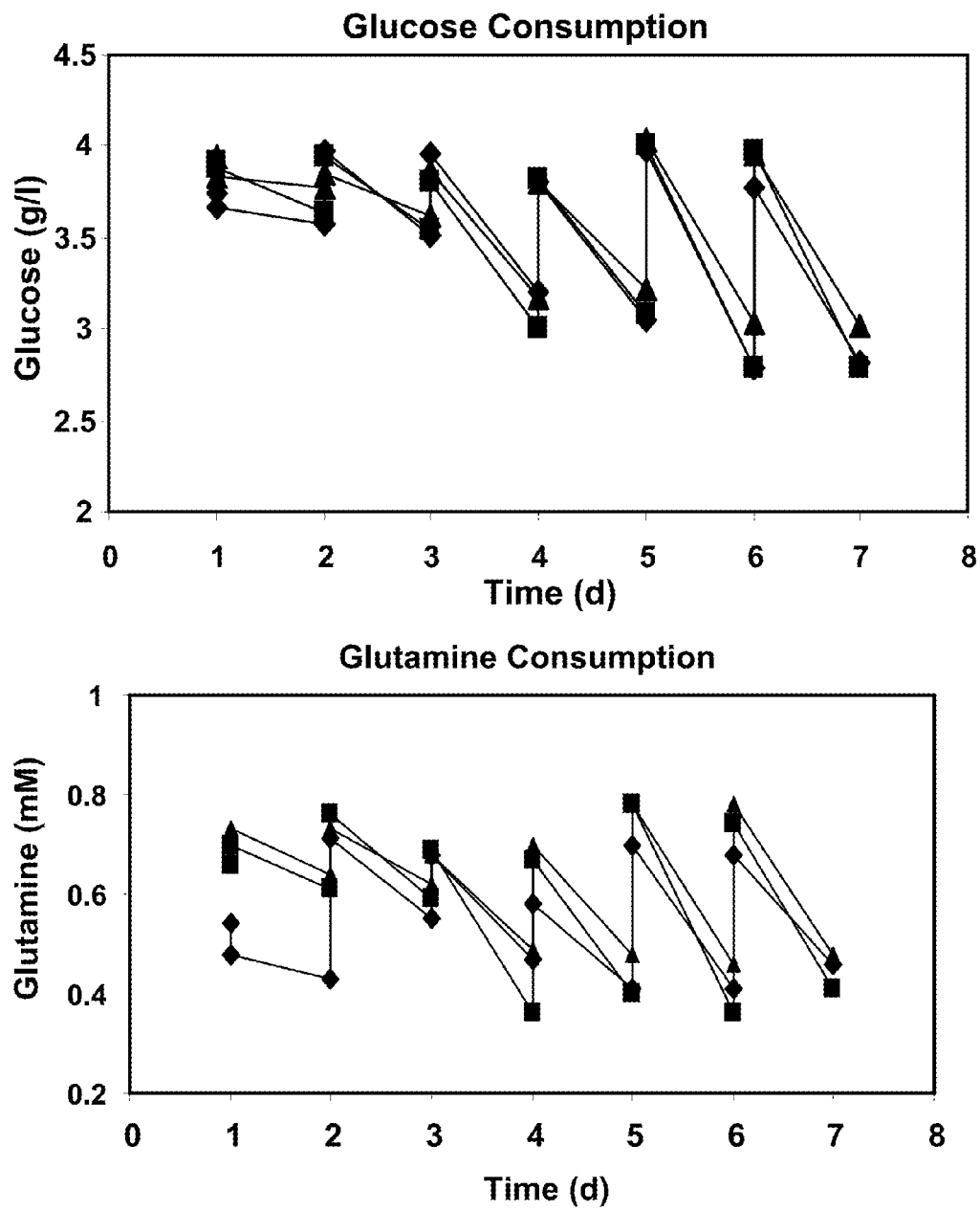
FIG. 16. Growth kinetics and metabolism in Knock Out conditioned media. Comparison of metabolism of hESC on microcarriers vs. 2D colony cultures. Comparison of metabolism of hESC on microcarriers vs. 2D colony cultures. Daily glucose and glutamine consumption profiles and lactate and ammonia production profiles of hESC on microcarriers (seeded from 2D colonies or from microcarriers) vs. 2D colony cultures.
Figure 16:
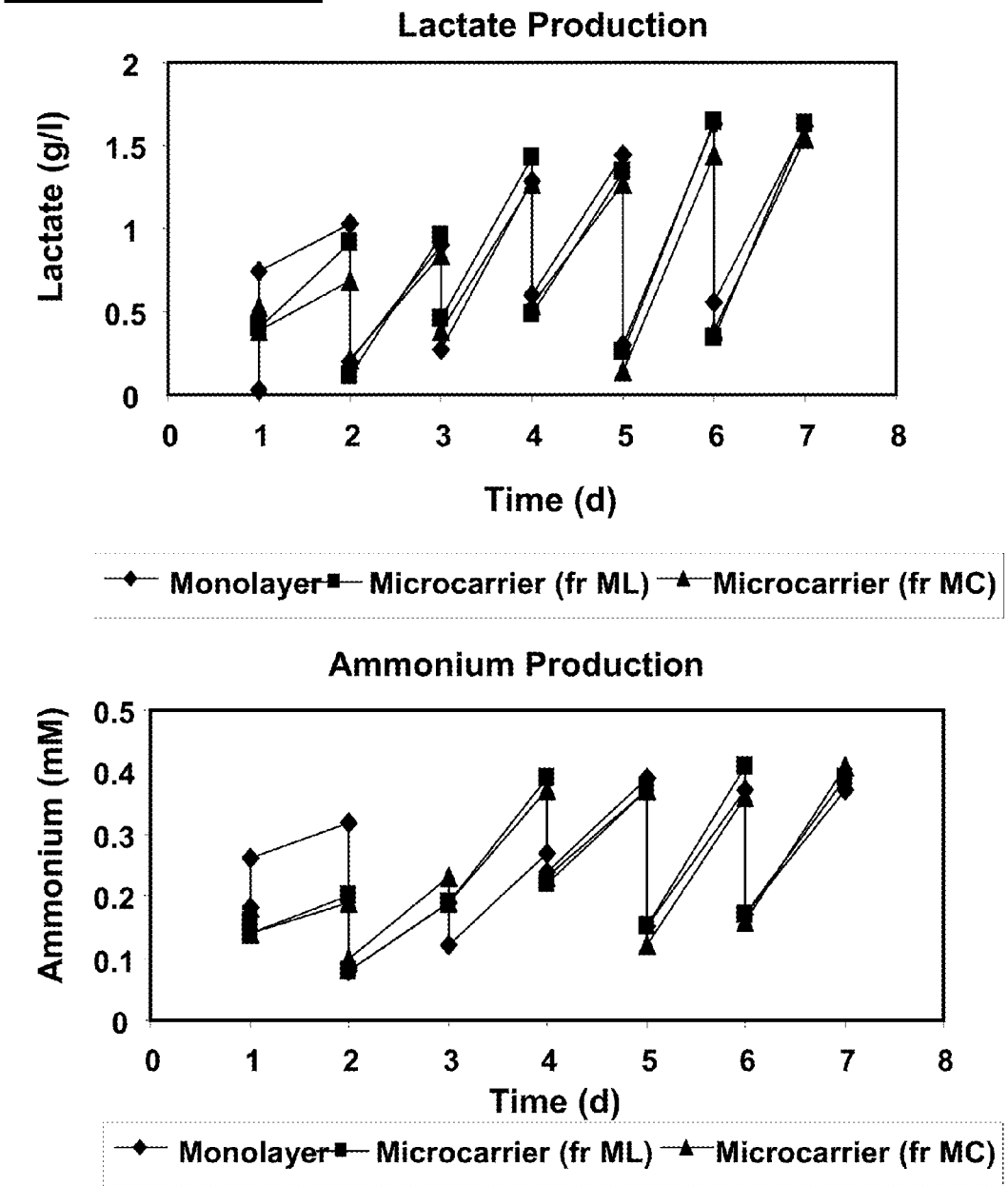

Except for the first 2 days, glutamine and glucose consumption profiles are very similar for microcarrier vs. 2D colony cultures, as are the lactate and ammonia production profiles for both cultures shown in FIG. 16.

Similar to the previous experiments, specific consumption rates of glutamine and glucose are much lower in microcarrier cultures compared to 2D colony cultures indicating more efficient metabolism in microcarrier cultures.

Figure 17:
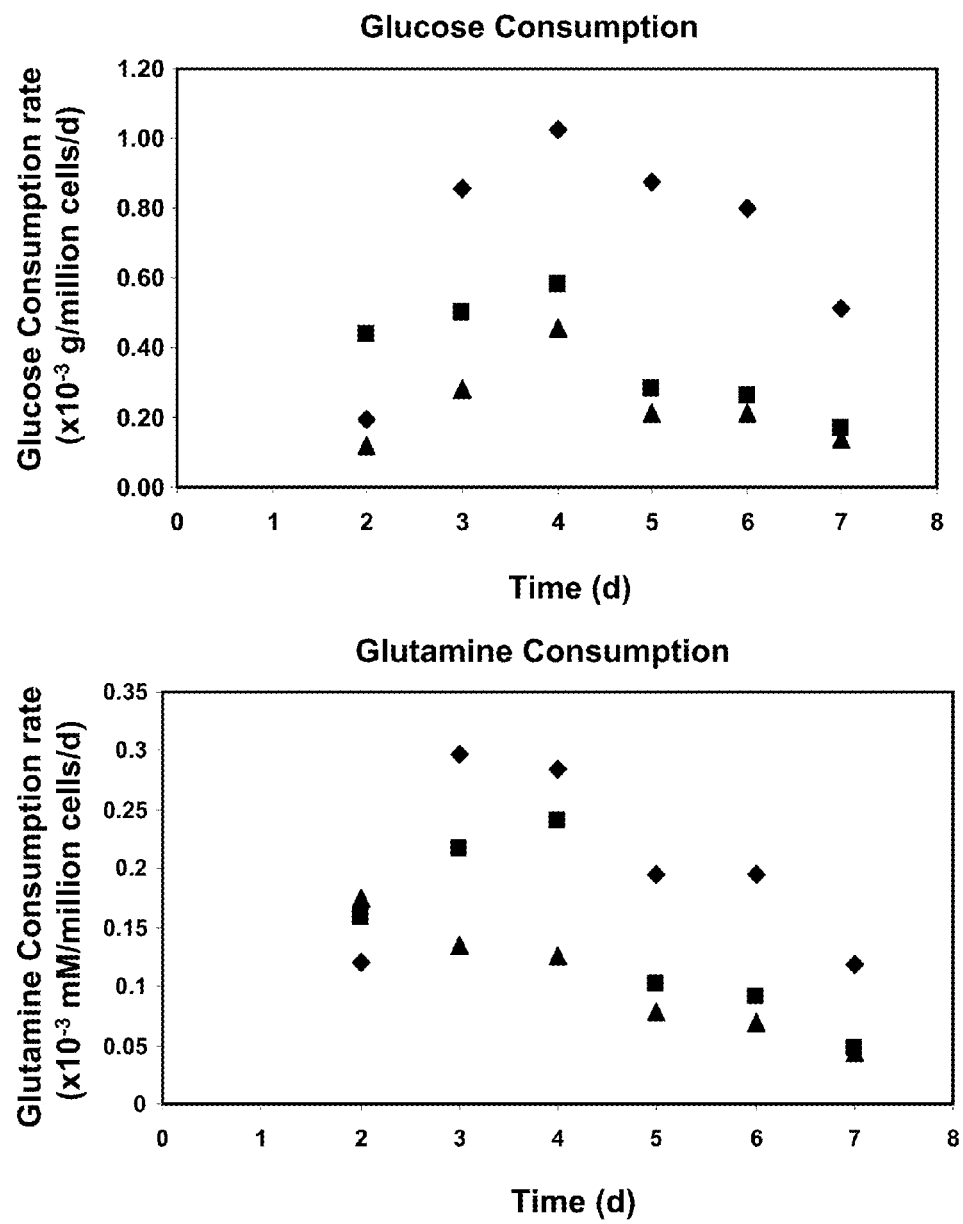
FIG. 17. Growth kinetics and metabolism in Knock Out conditioned media. Comparison of metabolism of hESC on microcarriers vs. 2D colony cultures. Specific consumption rates of glutamine and glucose profiles and lactate and ammonia production rates of hESC on microcarriers (seeded from 2D colonies or from microcarriers) vs. 2D colony cultures.
Figure 17:
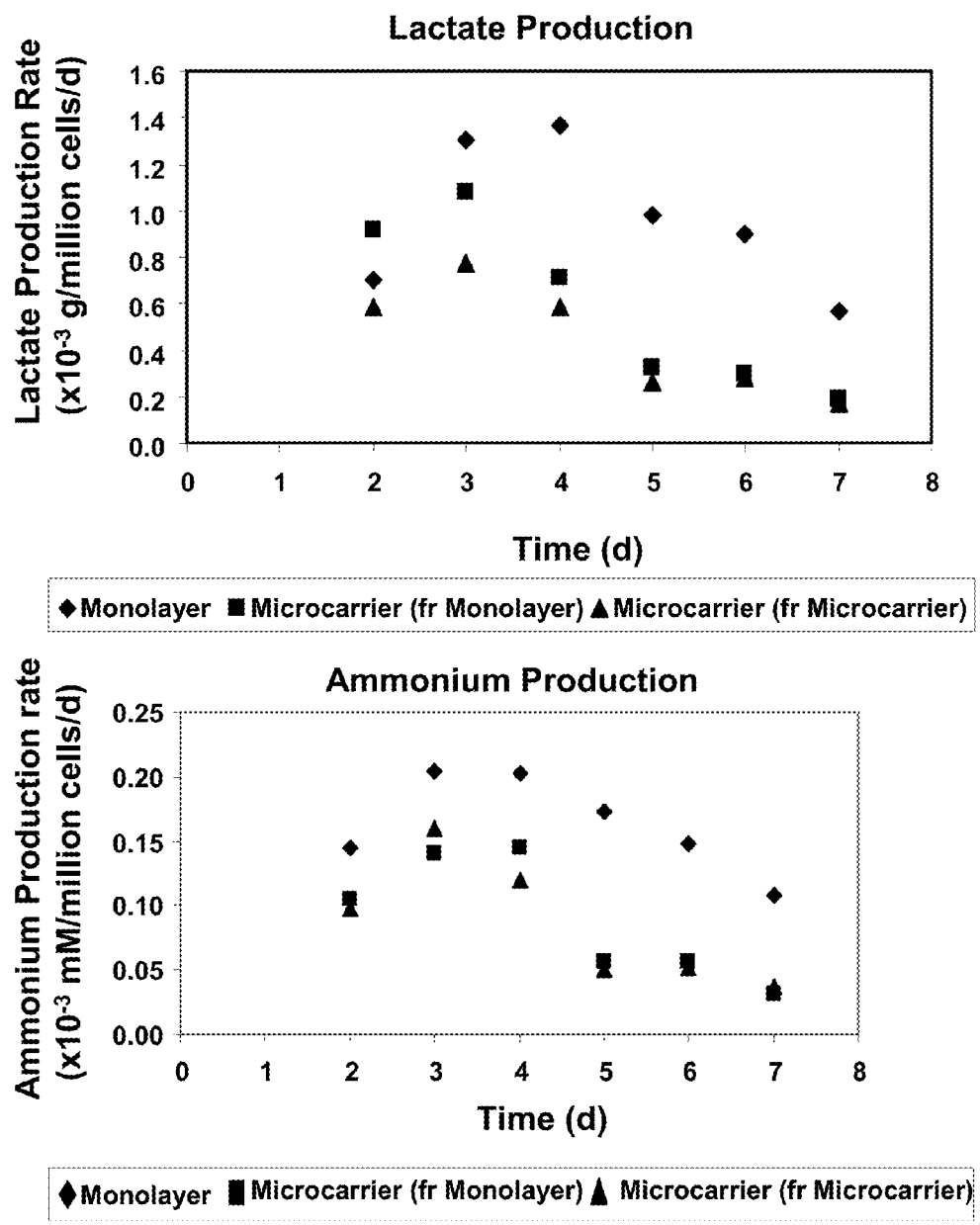

FIG. 17 shows that except for the first 3 days, glucose and glutamine consumption appears to be a little higher for the microcarrier culture inoculated from 2D colony cultures than the microcarrier culture inoculated from microcarrier cultures. There are also lower specific production rates of waste products such as lactate and ammonia in microcarrier cultures compared to 2D colony cultures, especially after day 5. Analysis of amino acid profiles show that glutamine, arginine, serine, cystine, valine, methionine, lysine, isoleucine, leucine, and phenylalanine are consumed, whereas proline, glutamic acid and alanine are produced by hESC (data not shown).

Figure 18:
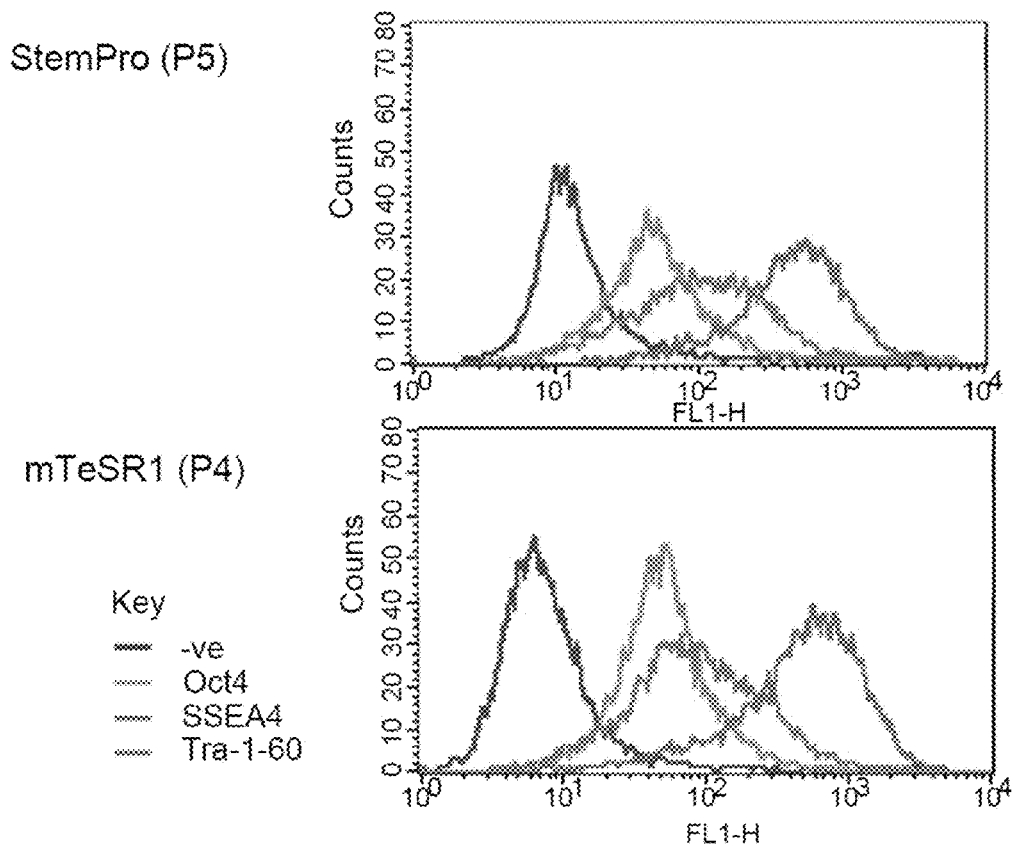
FIG. 18. Growth kinetics and metabolism in serum free defined media. FACS of pluripotent markers Oct-4, SSEA-4 and TRA-1-60 of hESC on microcarriers in StemPro serum free media (passage 5) and mTeSR-1 (passage 4).

FIG. 18 illustrates that hESC grown on microcarriers, continue to express pluripotent markers Oct-4, SSEA-4 and TRA-1-60 at passage 5 for StemPro and passage 4 for mTeSR-1, which are both commercial serum free defined media. Growth kinetics,

| Dilution ratio | Chondroitin Sulphate | Heparin Sulphate | Hyaluronic Acid |
|---|---|---|---| metabolism of glucose, glutamine lactate, ammonia, and amino acids are measured for these 2 media.

Example 19

Coating of Carriers (Hyaluronic Acid, Heparan Sulphate, Dextran Sulphate, Etc.)

Five defined coatings are tested as alternatives compared to matrigel, the standard coating for growing hESC. These are 2 sources of heparan sulphate from bovine kidney and the fast moving fraction from porcine, 2 sources of hyaluronic acid from bovine vitreous humor and *streptococcus*, as well as dextran sulphate.

Two other negative controls, namely microcarriers coated with MEF-CM and KO media are also compared.

|  | (7.09 mg/ml) | (0.25 mg/ml) | (0.5 mg/ml) |
|---|---|---|---|
| 1:10 | — | 9.6 × 10⁵ cells/well | 1.17 × 10⁶ cells/well |
| 1:20 | 8.3 × 10⁵ cells/well | 1.03 × 10⁶ cells/well | 7.7 × 10⁵ cells/well |
| 1:40 | 6.5 × 10⁵ cells/well | 1.18 × 10⁶ cells/well | 8.3 × 10⁵ cells/well |
| 1:80 | 5.5 × 10⁵ cells/well | 1.12 × 10⁶ cells/well | 5.4 × 10⁵ cells/well |

Figure 19:
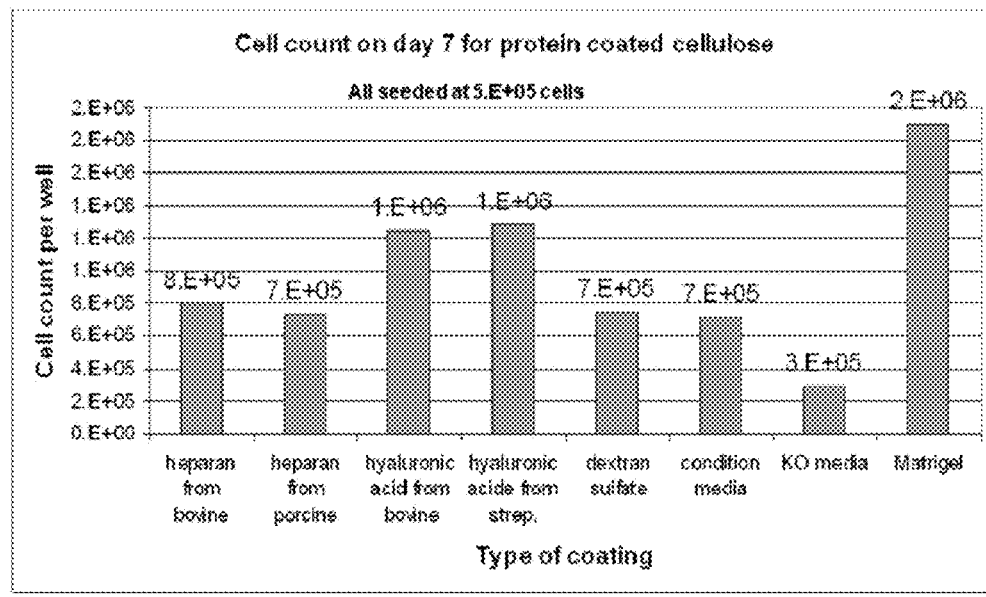
FIG. 19. Coating of carriers. Hyaluronic acid, heparan sulphate, dextran sulphate. Cell counts on day 7 of cellulose microcarriers coated with heparin sulphate, hyaluronic acid, dextran sulphate, conditioned media, KO media and matrigel.

Initial results shown in FIG. 19 indicate that hyaluronic acid is the most promising alternative to matrigel, although matrigel still enables higher cell numbers to be achieved after 7 days of growth. hESC continue to express the 3 pluripotent markers on these defined coatings (data not shown).

Table E1 shows that 3 types of coatings (chondroitin sulphate, heparin sulphate and hyaluronic acid) on cellulose microcarriers are able to support the growth of hESC, achieving between 0.5 to 1.2×10⁶ cells per well which are better than the controls which are only coated with Knock Out (KO) serum replacer or MEF-CM, these achieved about 0.4×10⁶ cells per well. This is comparable with matrigel coated microcarriers which reached 2×10⁶ cells per well as shown in FIG. 19.

Table E1. Coating of carriers Hyaluronic acid, heparin sulphate, chondroitin sulphate Controls: KO=4.3 E5 cells/well; CM=4.4 E5 cells/well. Three types of coatings, chondroitin sulphate, heparin sulphate and hyaluronic acid on cellulose microcarriers that are able to support the growth of hESC, achieving between 0.5 to 1.2 million cells per well. Controls which are only coated with Knock Out (KO) serum replacer or conditioned media (CM) achieved less than 0.5 million cells per well.

The microcarrier is coated with other extracellular matrices like collagen, fibronectin, vitronectin and laminin, and the above experiment is repeated.

Example 20

Figure 20:
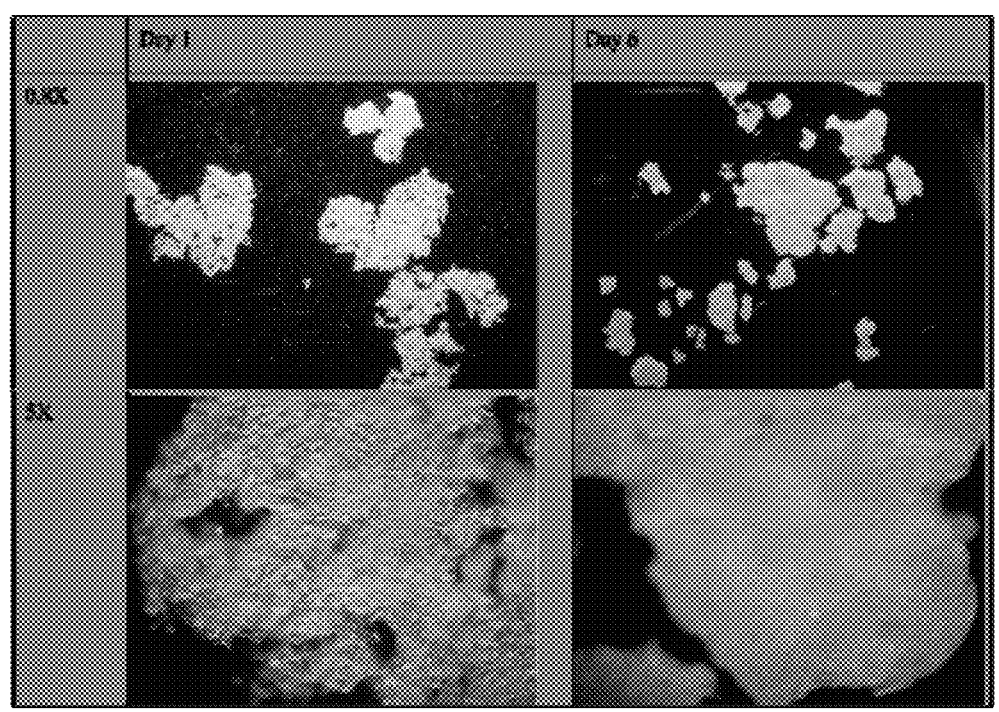
FIG. 20. Agitation of hESC on matrigel coated microcarriers at 100 rpm. Photos of hESC at day 1 and 6 on microcarriers agitated at 100 rpm at 0.8× and 5× magnifications.

Agitation at 100 and 150 rpm hESC are also cultured on microcarriers and agitated at 100 and 150 rpm in 6 well plates. Microcarriers aggregate together at day 1 and form clumps of different sizes at day 6 at 100 rpm with no visible cystic regions showing that hESC remain pluripotent (FIG. 20).

Figure 21A:
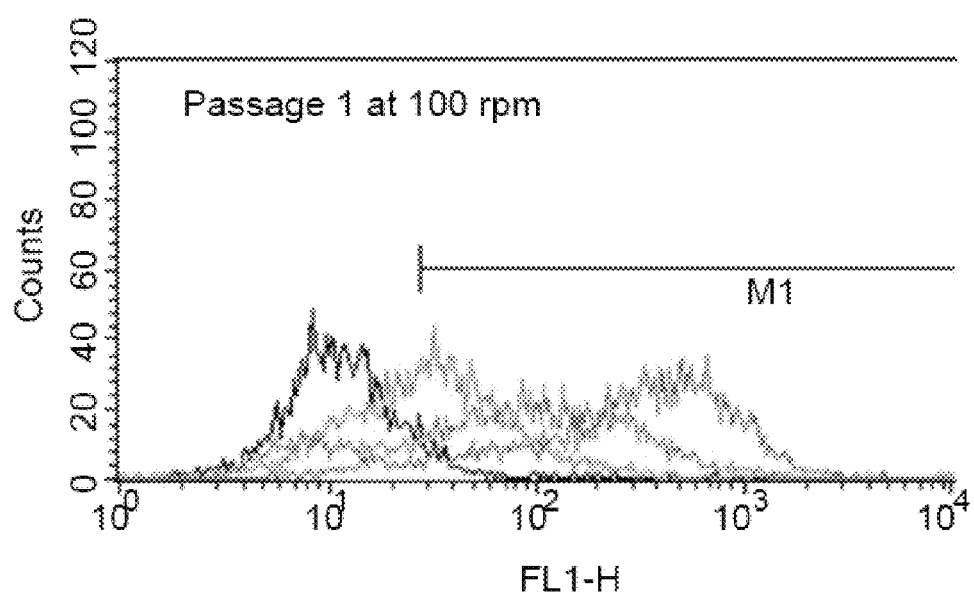
FIG. 21A. FACS of pluripotent markers Oct-4, SSEA-4 and TRA-1-60 of hESC on microcarriers agitated at 100 rpm.
Figure 21B:
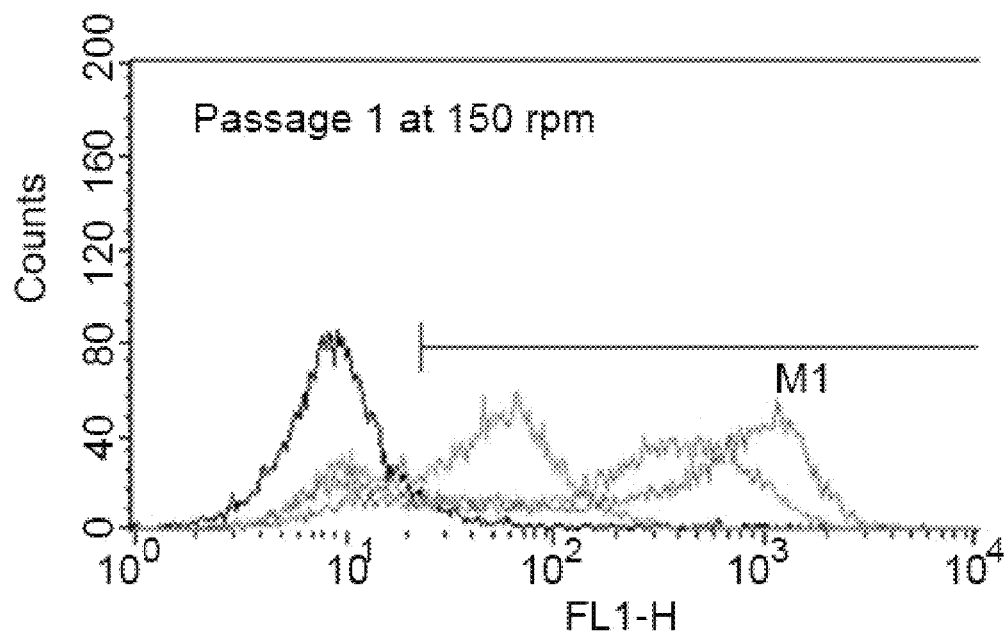
FIG. 21B. FACS of pluripotent markers Oct-4, SSEA-4 and TRA-1-60 of hESC on microcarriers agitated at 150 rpm.

Oct-4 expression is partially downregulated at 100 and 150 rpm to 56% and 68% in FIG. 21A and FIG. 21B respectively, but SSEA-4 and TRA-1-60 continue to be highly expressed at passage 1 in both conditions.

Figure 22:
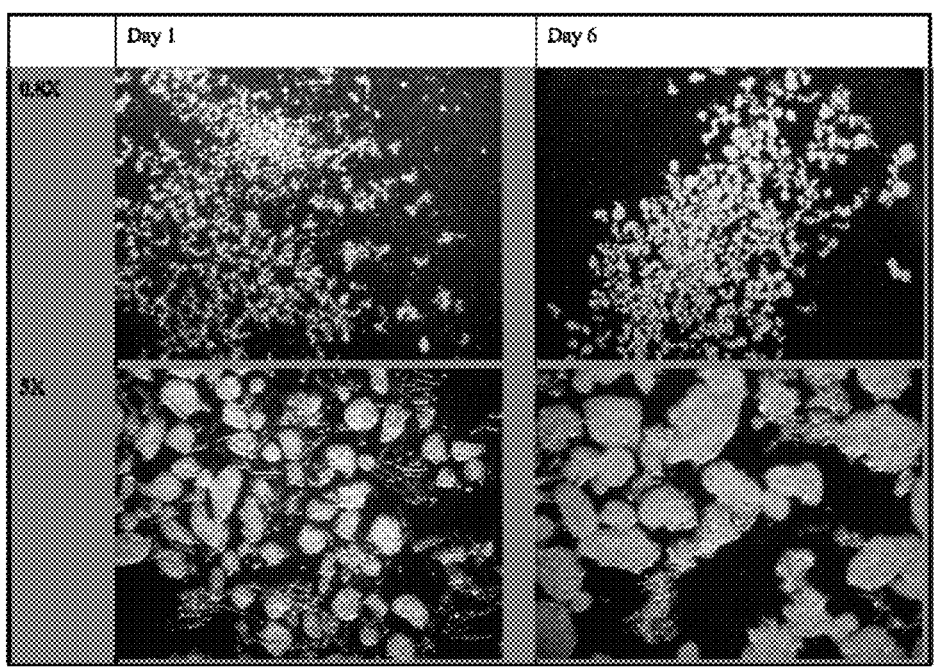
FIG. 22. Agitation of hESC on matrigel coated microcarriers at 150 rpm. Photos of hESC at day 1 and 6 on microcarriers agitated at 150 rpm at 0.8× and 5× magnifications.
Figure 23A:
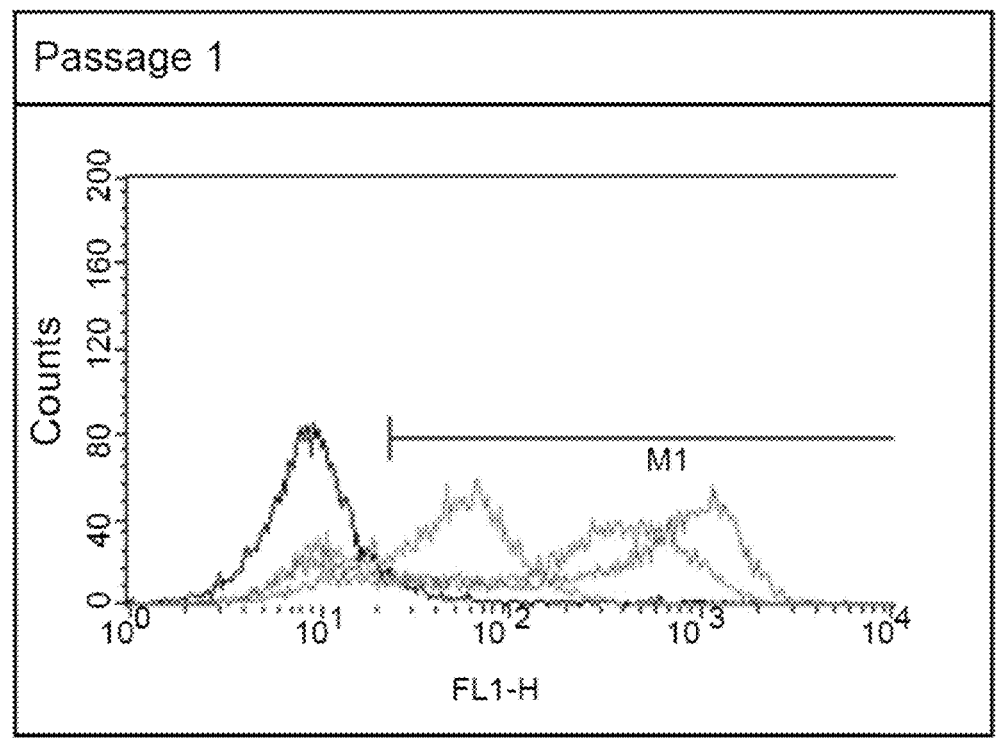
FIG. 23A shows the FACS results for passage 1.
Figure 23B:
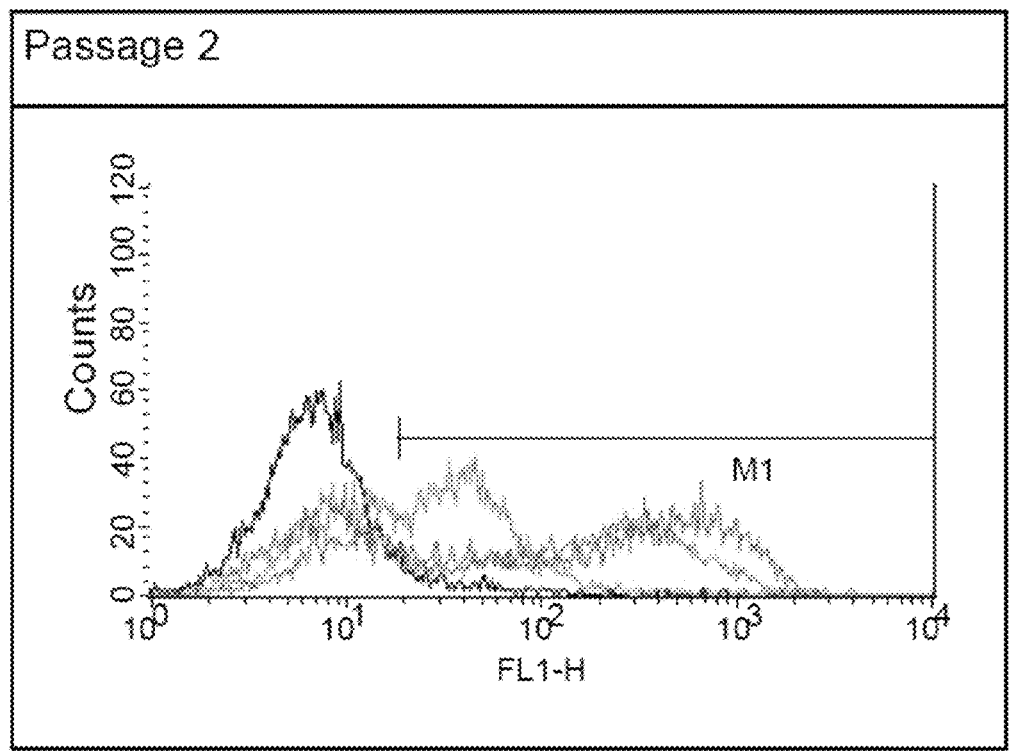
FIG. 23B shows the FACS results for passage 2.

Microcarriers aggregate together in tighter clumps at day 1 at 150 rpm and continue to grow as smaller clumps at day 6 (compared to 100 rpm microcarrier cultures) with no visible cystic regions showing that hESC remain pluripotent in FIG. 22. Oct-4 expression is partially downregulated at 57.5%, and the percentage population of cells expressing surface markers SSEA-4 and TRA-1-60 are lower at 75% and 70% respectively in 150 rpm cultures at passage 2 compared to passage 1 as shown in FIG. 23. Nevertheless, hESC is able to be grown at this agitation speed.

Figure 24:
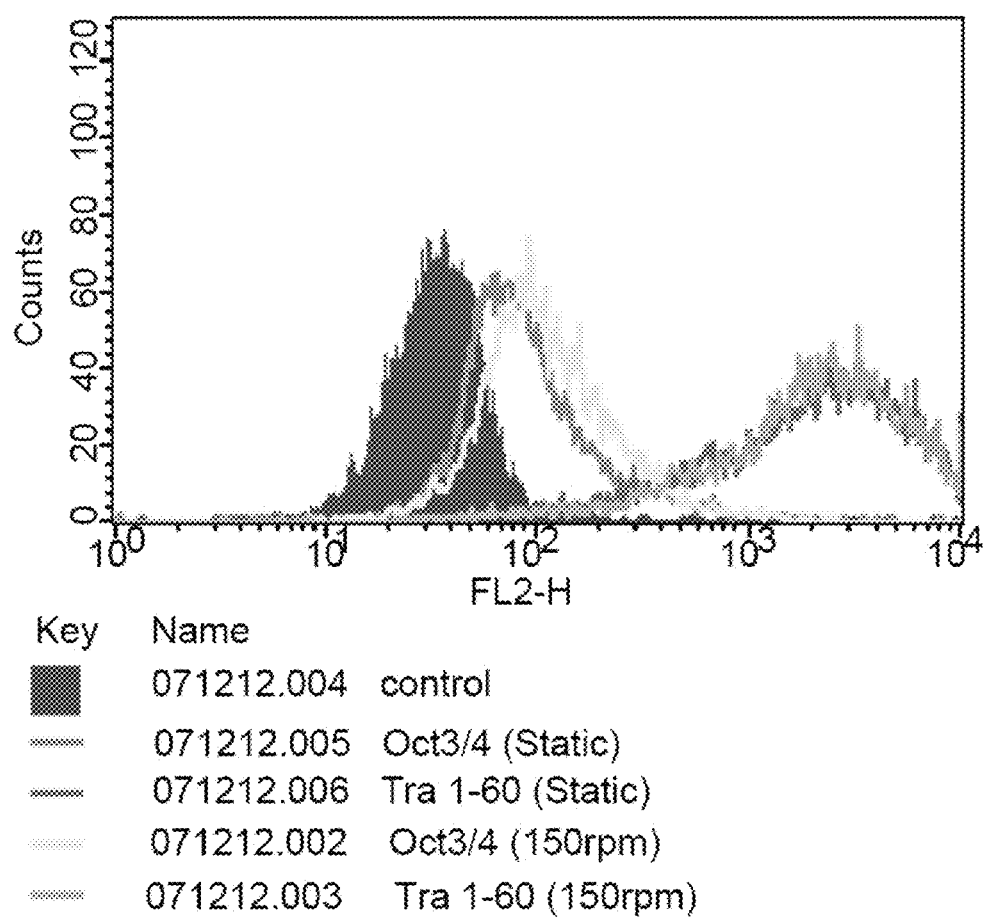
FIG. 24. HES-2 on microcarriers in static and 150 rpm cultures at passage 2. FACS of pluripotent markers Oct-4, and TRA-1-60 of hESC (HES-2 cell line) from 2D colony and microcarrier cultures agitated at 150 rpm at passage 2.
Figure 25:
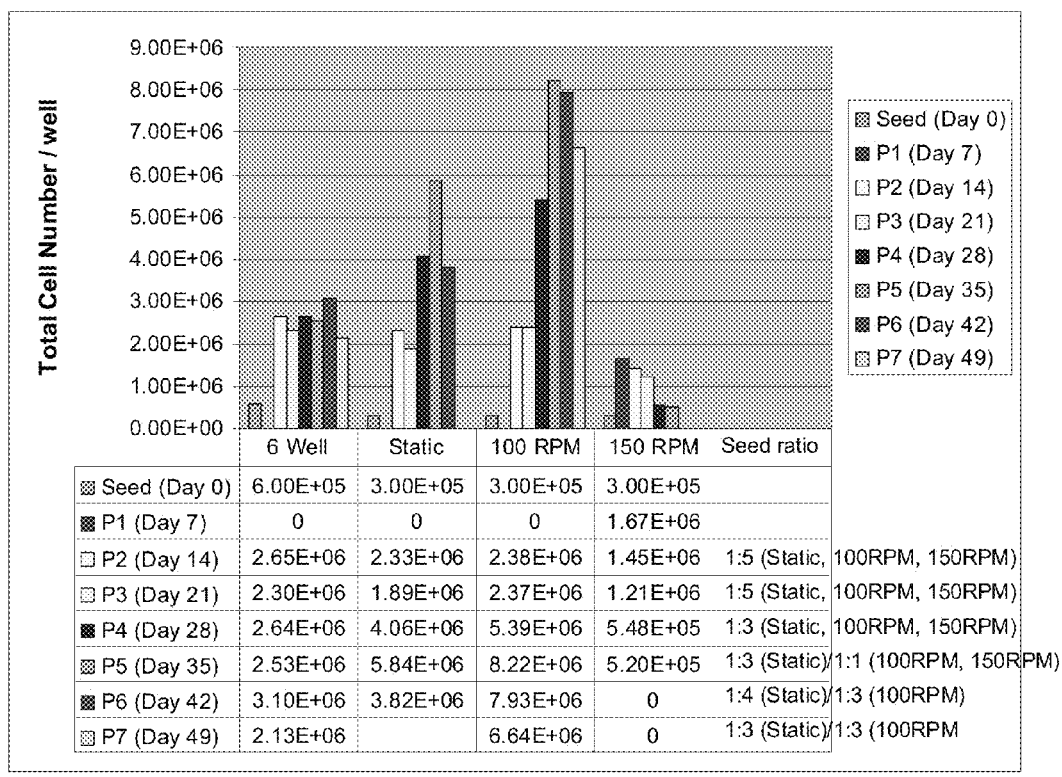
FIG. 25. HES-2 in 2D colony cultures vs. microcarriers cultures in static, 100 rpm and 150 rpm. Cell counts of hESC cultured in 2D colony, microcarriers in static conditions, agitated at 100 and 150 rpm over 7 consecutive passages.

FIG. 24 shows that Oct-4 and TRA-1-60 expression of a second cell line (HES-2) are similar for microcarrier cultures grown in static and at 150 rpm at passage 2. FIG. 25 shows total cell numbers during the continuous passaging of the HES-2 cell line for 7 passages in control 2D colony cultures, microcarriers in static, 100 rpm and 150 rpm conditions. hESC grown in control 2D colony cultures routinely achieved between 2 to 3 million cells per well.

Figure 26A:
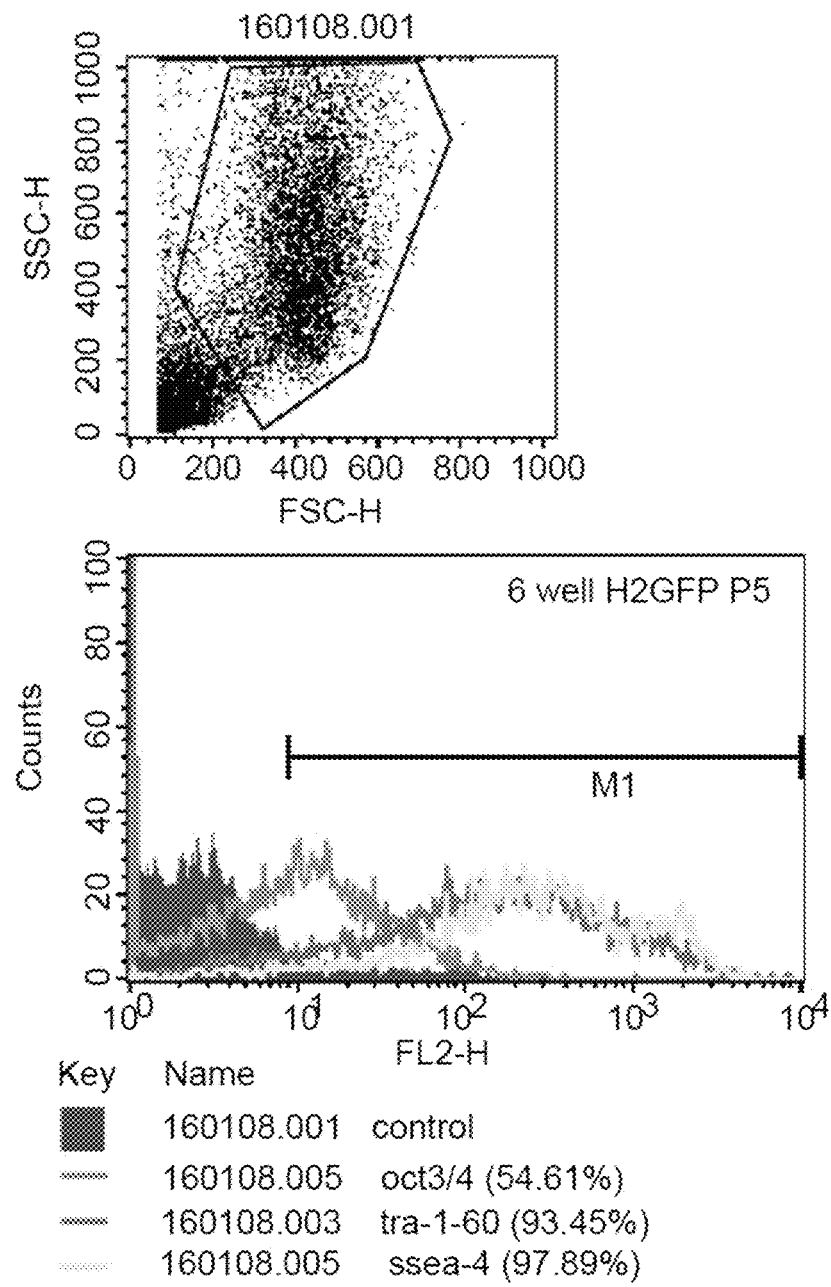
FIG. 26A. FACS of pluripotent markers Oct-4, SSEA-4 and TRA-1-60 of hESC cultured in 2D colony.
Figure 26B:
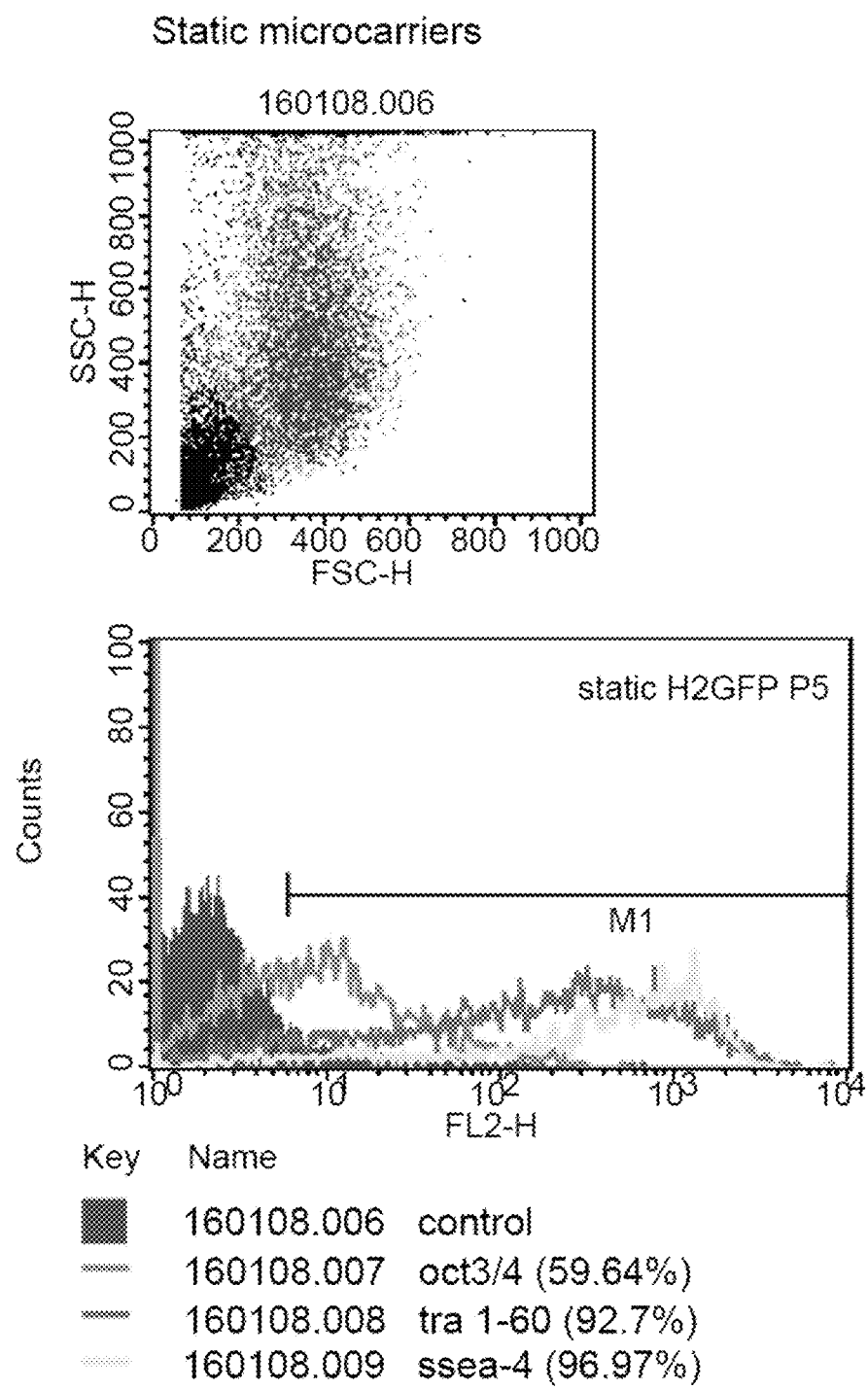
FIG. 26B. FACS of pluripotent markers Oct-4, SSEA-4 and TRA-1-60 of hESC cultured in microcarriers in static conditions.
Figure 26C:
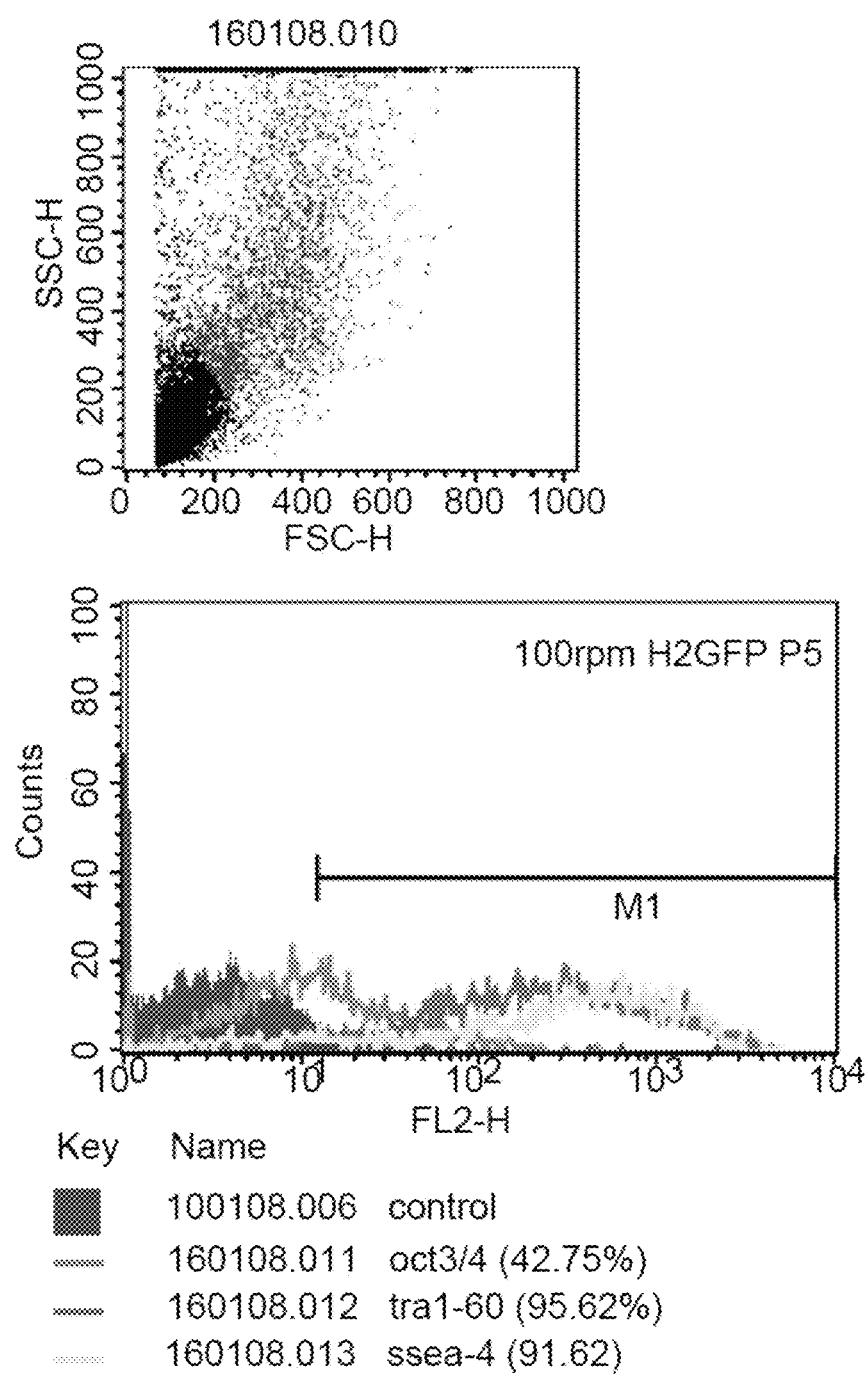
FIG. 26C. FACS of pluripotent markers Oct-4, SSEA-4 and TRA-1-60 of hESC cultured and agitated at 100 rpm at passage 5.

Whereas hESC grown on static microcarriers could achieve up to 6 million cells per well, while hESC agitated at 100 rpm could achieve up to 8 million cells per well. At 150 rpm, growth is not optimal and cells could not be passaged beyond week 5. FIG. 26A, FIG. 26B and FIG. 26C show that the expression levels of pluripotent markers Oct-4 (42 to 50%), SSEA-4, and TRA-1-60 (both greater than 90%) in the static microcarrier and microcarrier agitated at 100 rpm conditions, are stable and remained at very similar to levels to the 2D colony control cultures for the HES-2 line at passage 5.

Example 21

Charges of Carriers—DE52, DE53, Q53

DE53 is the charge on microcarriers that is routinely used in all experiments unless otherwise stated. Cellulose microcarriers of low (DE52), high (DE53) tertiary amine charges and high (QA52) quaternary amine charges are tested for their ability to support the culture of hESC and essentially they show equivalent cell numbers can be achieved at all charges, as shown in Table E2.

Table E2 below shows that cellulose microcarriers of low, medium and high charges tested for their ability to support the culture of hESC essentially show equivalent cell numbers can be achieved at all charges. Surprisingly, at passage 2, the higher charged microcarrier, QA52, achieved a phenomenally high cell number of over 13 million cells. DE53 is the charge on microcarriers that is routinely used in all experiments unless otherwise stated.

| Type of Carrier | Passage 0 | Passage 1 | Passage 2 |
| --- | --- | --- | --- |
| DE52 | $2.64 \times 10^6$ cells/well | $2.91 \times 10^6$ cells/well | $7.08 \times 10^6$ cells/well Seeding = $5.6 \times 10^5$ cells/well |
| DE53 | $3.64 \times 10^6$ cells/well | $3.45 \times 10^6$ cells/well | $7.32 \times 10^6$ cells/well Seeding = $7.7 \times 10^5$ cells/well |
| QA52 | $4.51 \times 10^6$ cells/well | $3.18 \times 10^6$ cells/well | $13.4 \times 10^6$ cells/well Seeding = $7.6 \times 10^5$ cells/well |

Table E2. Counts on day 7. Note: Seeding density of 8E5 cells/well for P0 and P1 on cellulose microcarriers. Three charges of cellulose microcarriers were passaged continuously for 3 passages, showing that hESC achieve cell numbers of between 2.6 to 13.4 million cells per well.

Figure 27A:
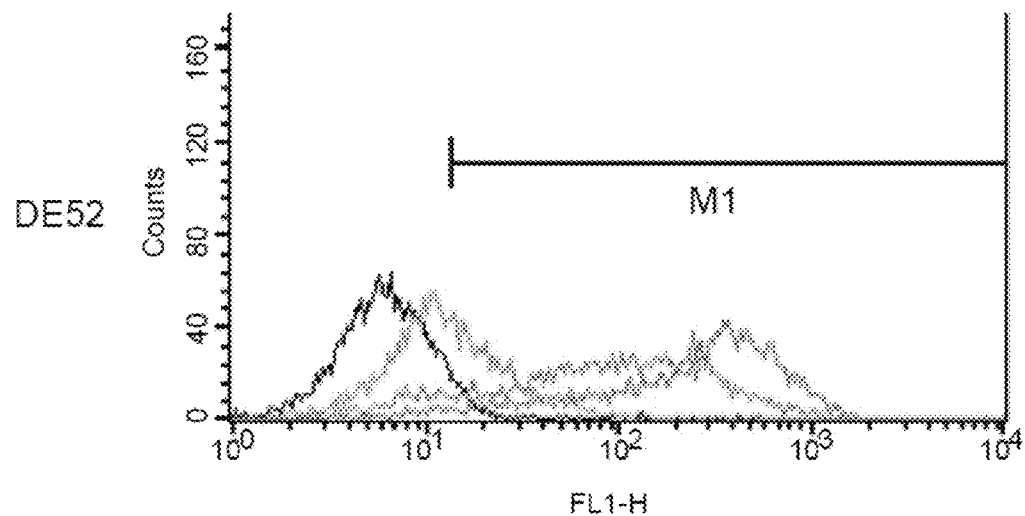
FIG. 27A. FACS of pluripotent markers Oct-4, SSEA-4 and TRA-1-60 of hESC cultured in cellulose microcarriers DE52.
Figure 27B:
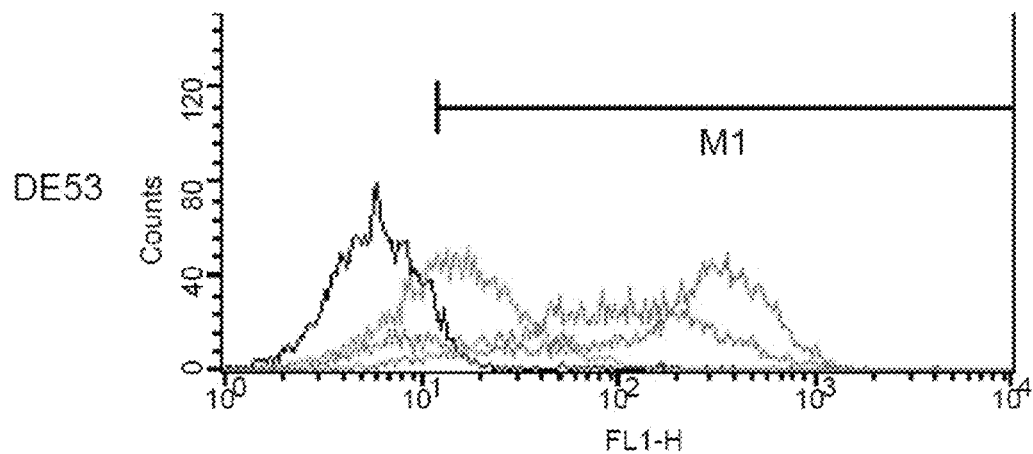
FIG. 27B. FACS of pluripotent markers Oct-4, SSEA-4 and TRA-1-60 of hESC cultured in cellulose microcarriers DE53.
Figure 27C:
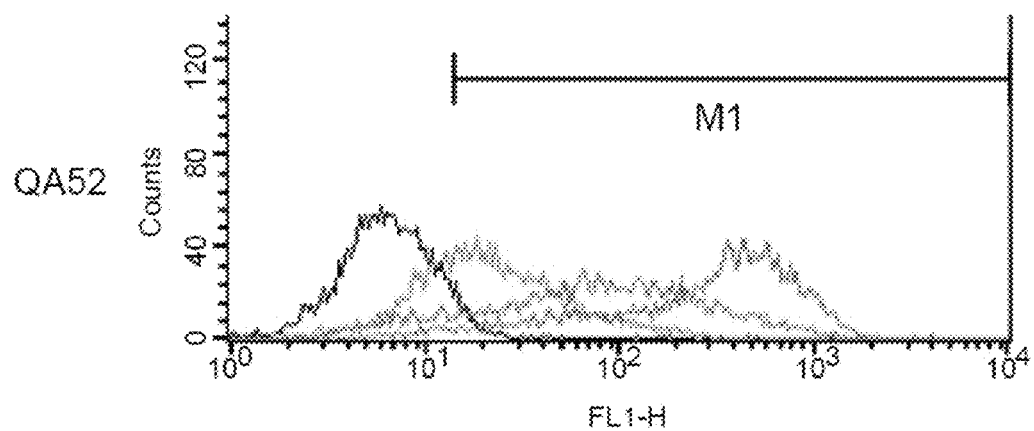
FIG. 27C. FACS of pluripotent markers Oct-4, SSEA-4 and TRA-1-60 of hESC cultured in cellulose microcarriers QA52 at passage 3.
Figure 28:
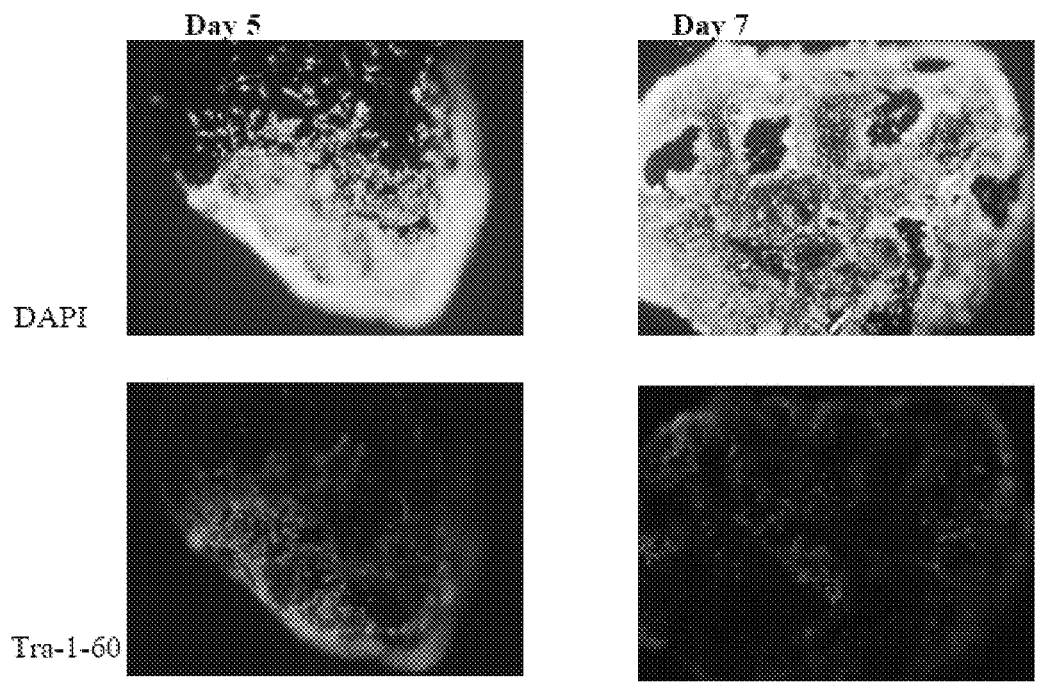
FIG. 28. Sizes and shapes of carriers—spherical carbon beads. hESC on carbon carboseed microcarriers. Histological analysis of microcarrier cultures on carbon microcarriers stained with DAPI and TRA-1-60 on day 5. Histological analysis of microcarrier cultures on carbon microcarriers stained with DAPI and TRA-1-60 on day 7.

At passage 2, the higher charged microcarrier, QA52, achieved a high cell number of over 13 million cells per well. Expression of Oct-4, SSEA-4 and TRA-1-60 continued to be stable and are equivalent for hESC grown on cellulose microcarriers of low, medium and high charges at passage 3 as shown in FIG. 27A, FIG. 27B and FIG. 27C.

Example 22

Sizes and Shapes Carriers—Spherical Carbon and Tosoh Beads (Different Diameters)

Microporous (SM1010) carbon microcarriers are able to attach and grow hESC on the surface on days 5 and 7 as shown by the DAPI nuclei stain and TRA-1-60 pluripotent marker, shown in FIG. 28A and FIG. 28B.

Figure 29:
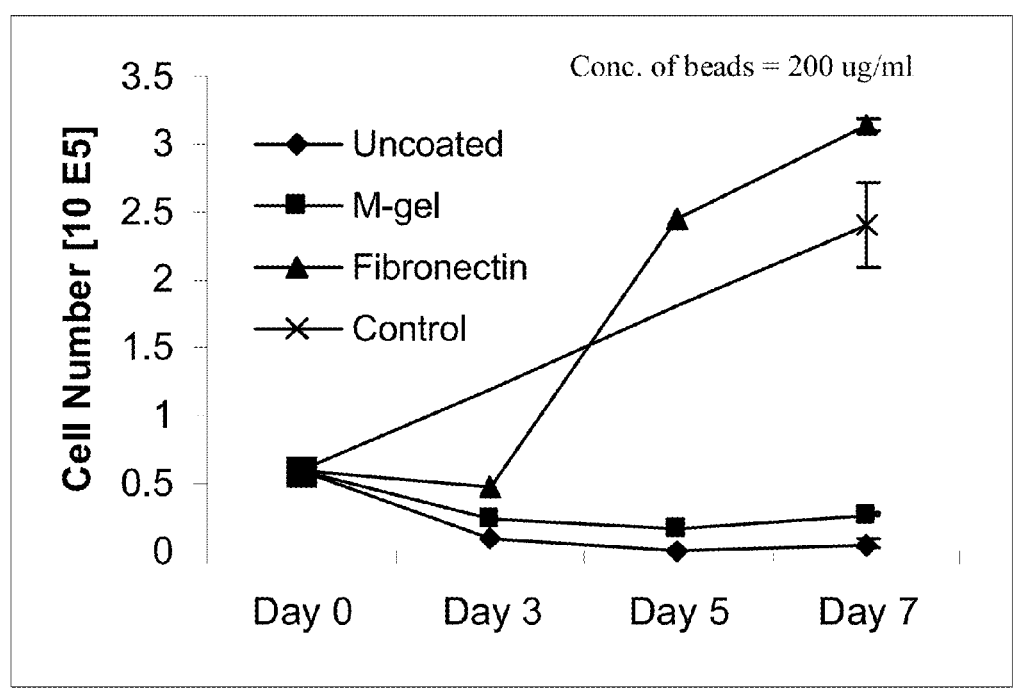
FIG. 29. Sizes and shapes of carriers—spherical carbon beads. HES3 growth on microporous carbon (SH1010) microcarriers with different coatings compared to control in a 24 well plate. Growth kinetics of hESC on uncoated, SH1010 microporous carbon microcarriers, coated with fibronectin or matrigel and compared to 2D colony controls.

FIG. 29 shows that microporous carbon microcarriers coated with fibronectin achieved higher cell numbers of 0.3 million cells per well compared to control 2D colony cultures which achieved 0.25 million cells per well.

Figure 30:
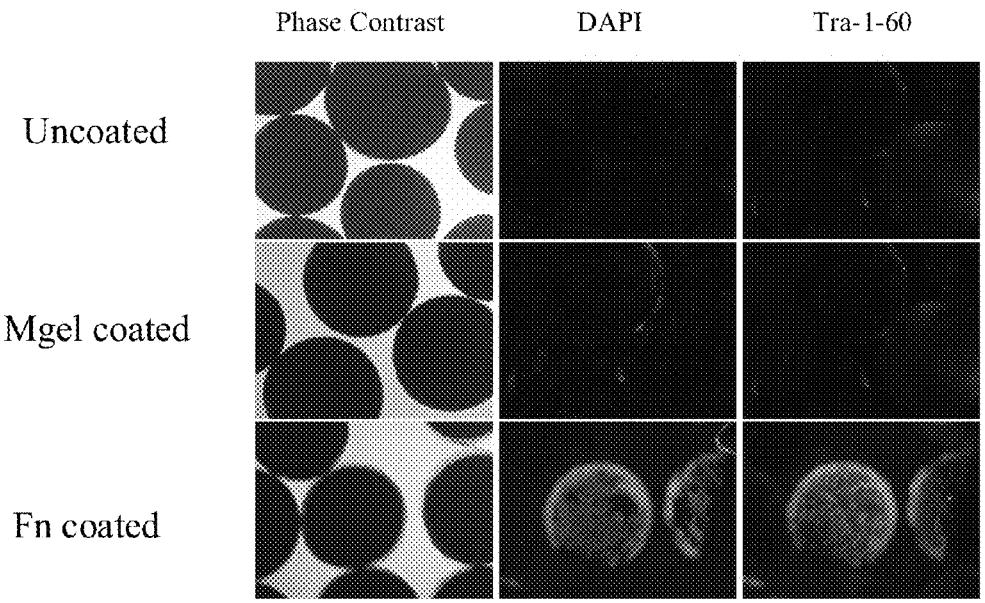
FIG. 30. Sizes and shapes of carriers—spherical carbon beads. Stained beads: day 3. Histological analysis of hESC cultures on microporous carbon microcarriers by phase contrast, stained with DAPI and TRA-1-60 on uncoated, matrigel or fibronectin coated microcarriers on day 3.
Figure 31:
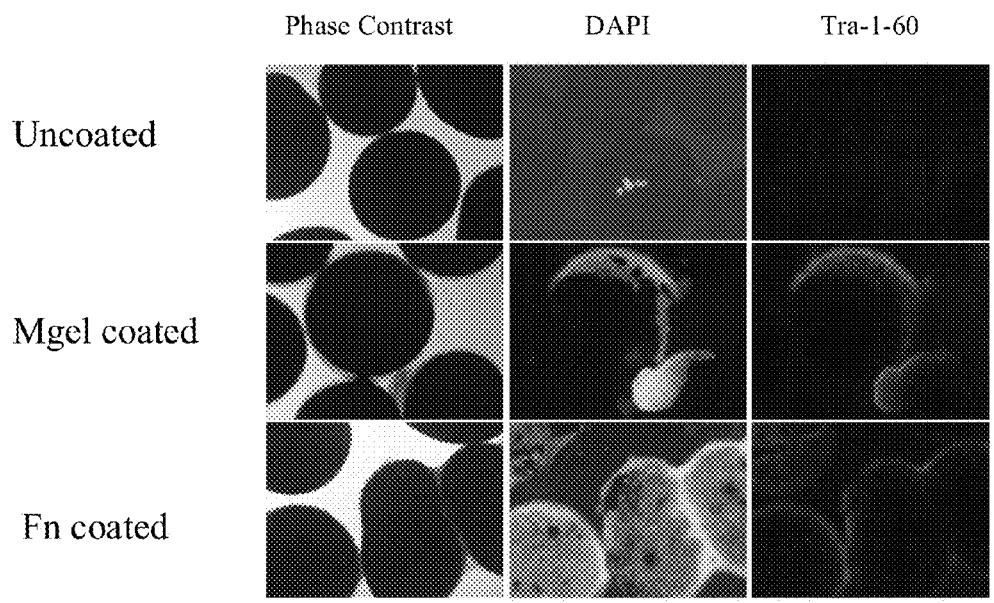
FIG. 31. Sizes and shapes of carriers—spherical carbon beads. Stained beads: day 5. Histological analysis of hESC cultures on microporous carbon microcarriers by phase contrast, stained with DAPI and TRA-1-60 on uncoated, matrigel or fibronectin coated microcarriers on day 5.
Figure 32:
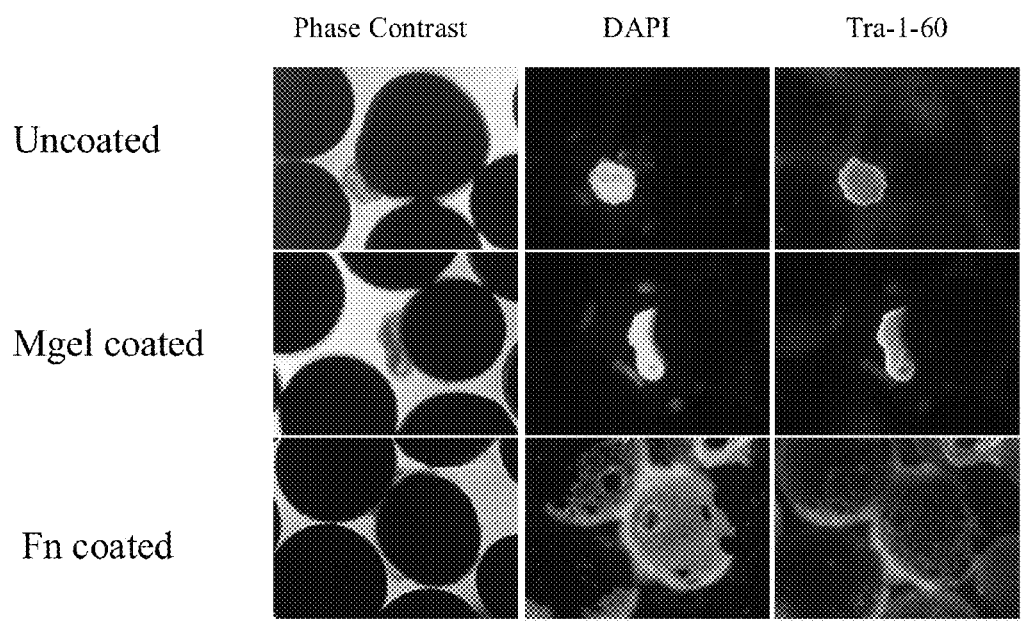
FIG. 32. Sizes and shapes of carriers—spherical carbon beads. Stained beads: day 7. Histological analysis of hESC cultures on microporous carbon microcarriers by phase contrast, stained with DAPI and TRA-1-60 on uncoated, matrigel or fibronectin coated microcarriers on day 7.
Figure 33A:
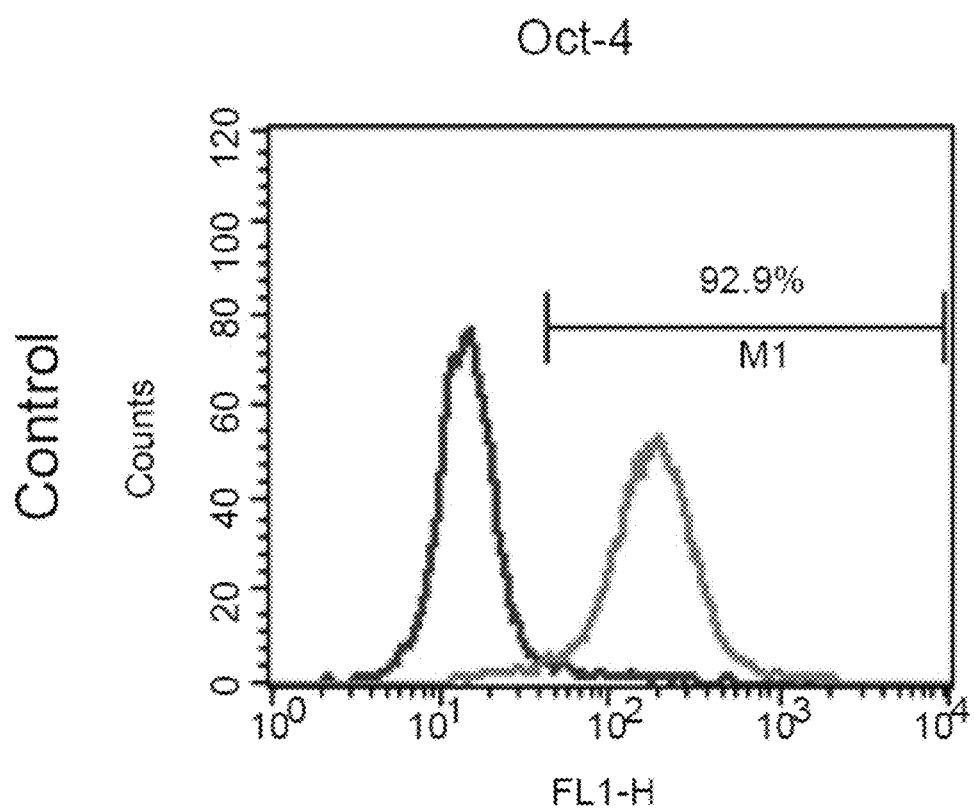
FIG. 33. Sizes and shapes of carriers—spherical carbon beads. FACS analysis and comparison of Oct-4, Tra-1-60 and SSEA-4 expression levels between Fn coated carbon beads (D-F) and control (A-C) at day 7 are shown in FIG. 33A (Oct-4 expression level comparison), FIG. 33B (Tra-1-60 expression level comparison), FIG. 33C (SSCA-4 expression level comparison). FACS of pluripotent markers Oct-4, SSEA-4 and TRA-1-60 of hESC cultured in 2D colony controls and on fibronectin coated macroporous carbon microcarriers are shown in FIG. 33D (FACS of Oct-4), FIG. 33E (FACS of SSEA-4), and FIG. 33F (FACS of Tra-1-60).
Figure 33B:
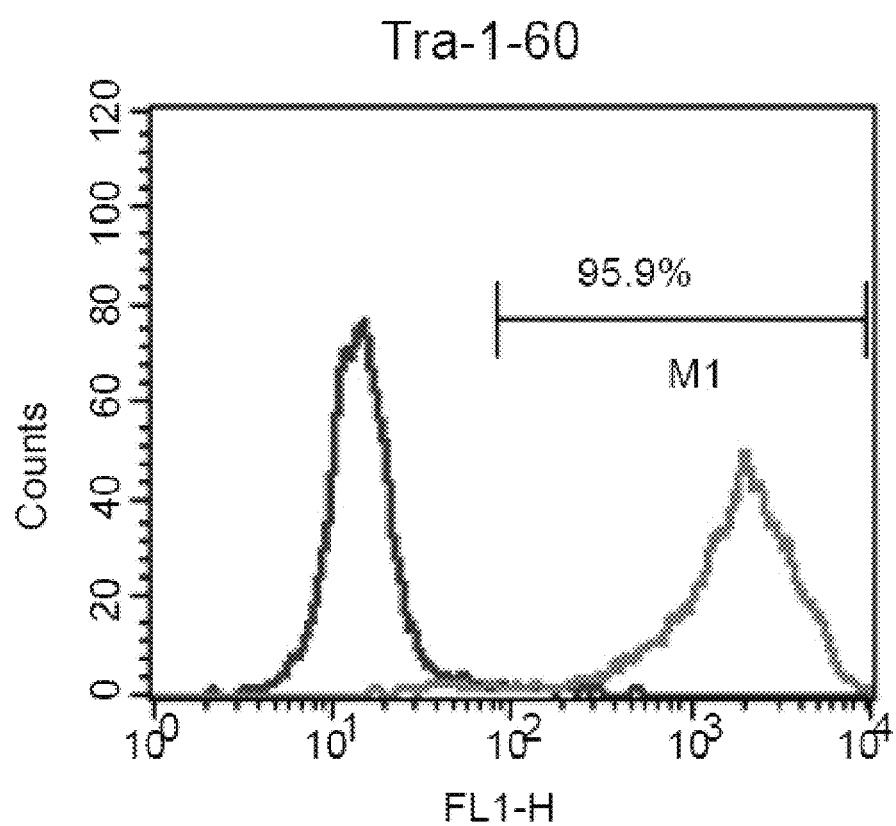
Figure 33C:
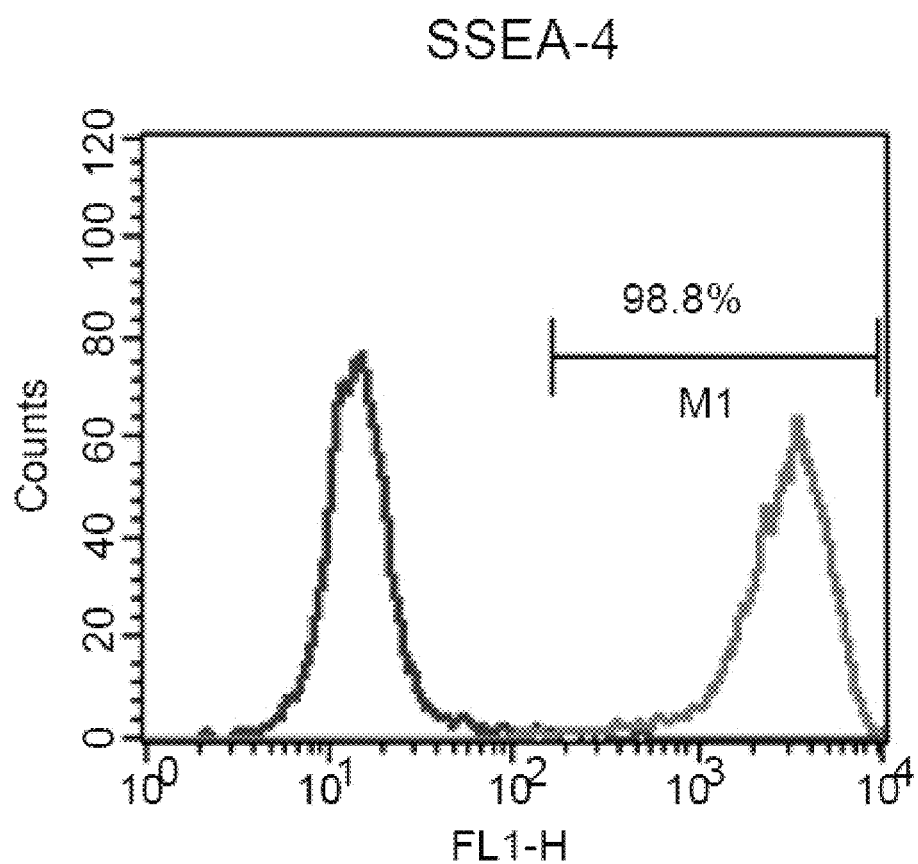
Figure 33D:
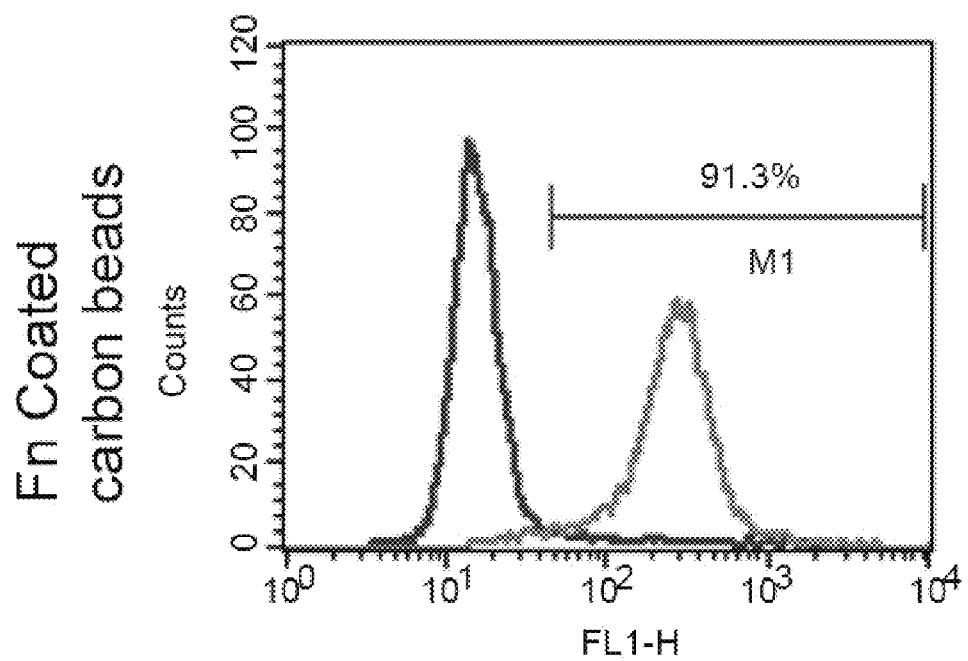
Figure 33E:
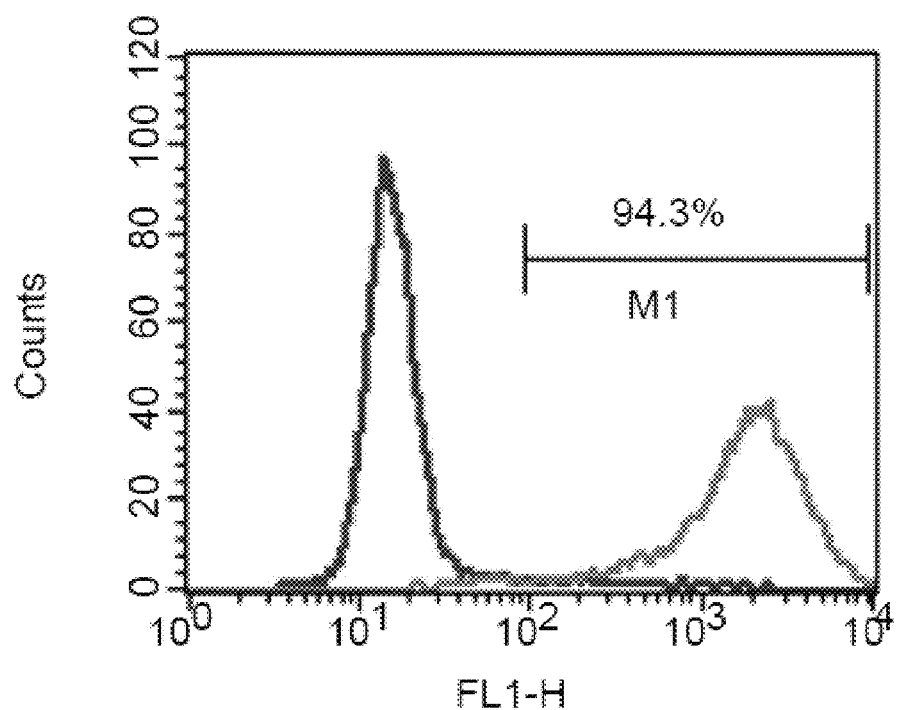
Figure 33F:
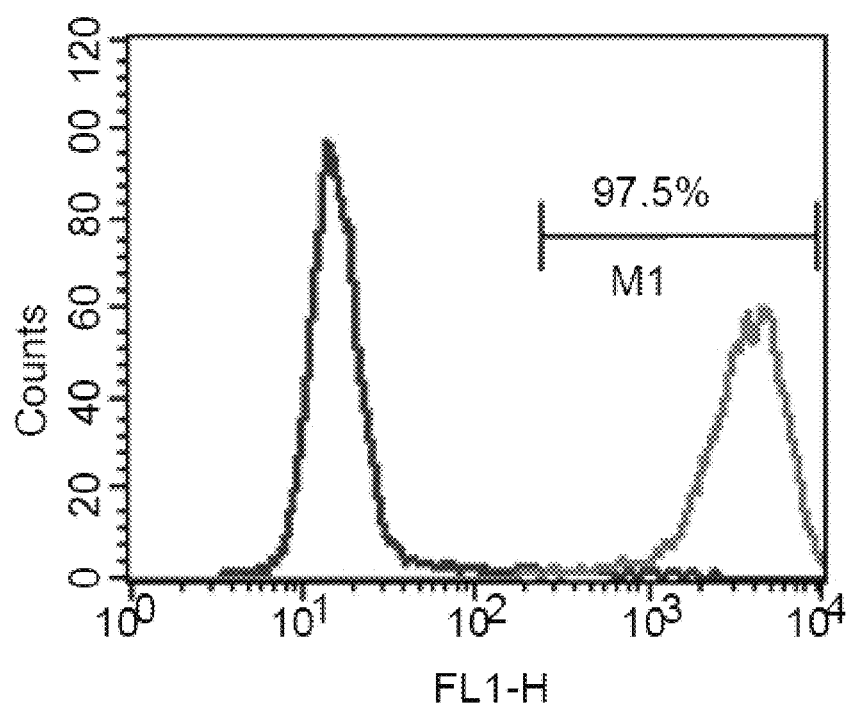

Carbon microcarriers viewed in phase contrast and stained with DAPI or TRA-1-60 on days 3, 5 and 7 are shown in FIG. 30, FIG. 31 and FIG. 32, indicating that hESC spread more evenly on fibronectin coated microporous microcarriers and aggregate the microcarriers together in the later days.

FACS profiles of 3 pluripotent markers Oct-4, TRA-1-60 and SSEA-4 (all greater than 90% expression) of hESC harvested from fibronectin coated carbon microcarriers at day 7 are shown in FIG. 33.

Figure 34A:
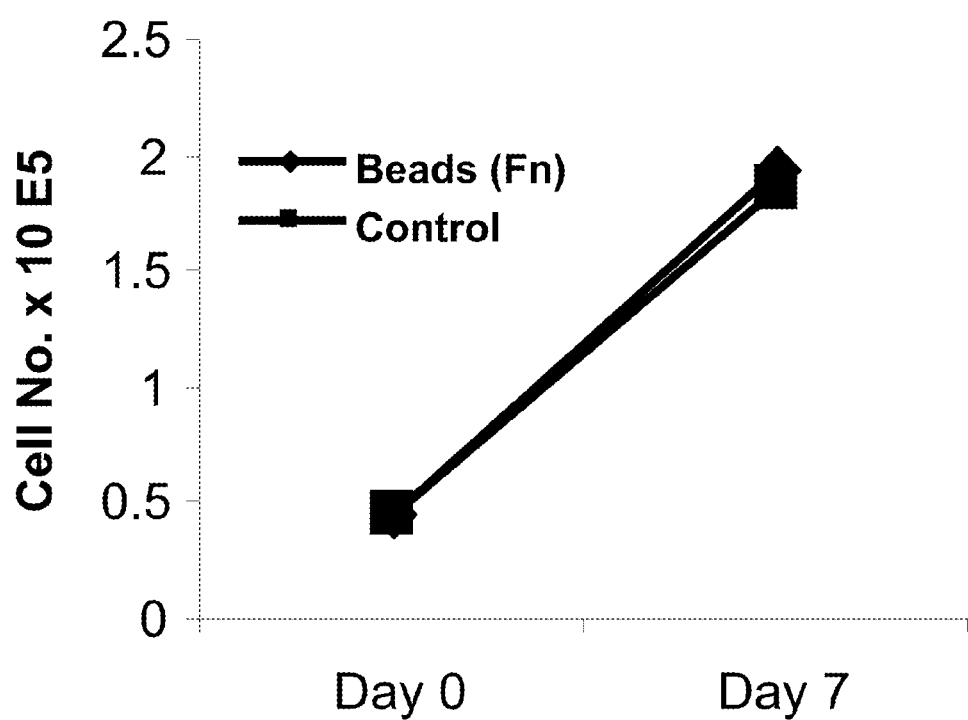
FIG. 34A. Growth of hESC in 2D colony controls and on fibronectin coated microporous carbon microcarriers. Viabilities >95%.
Figure 34B:
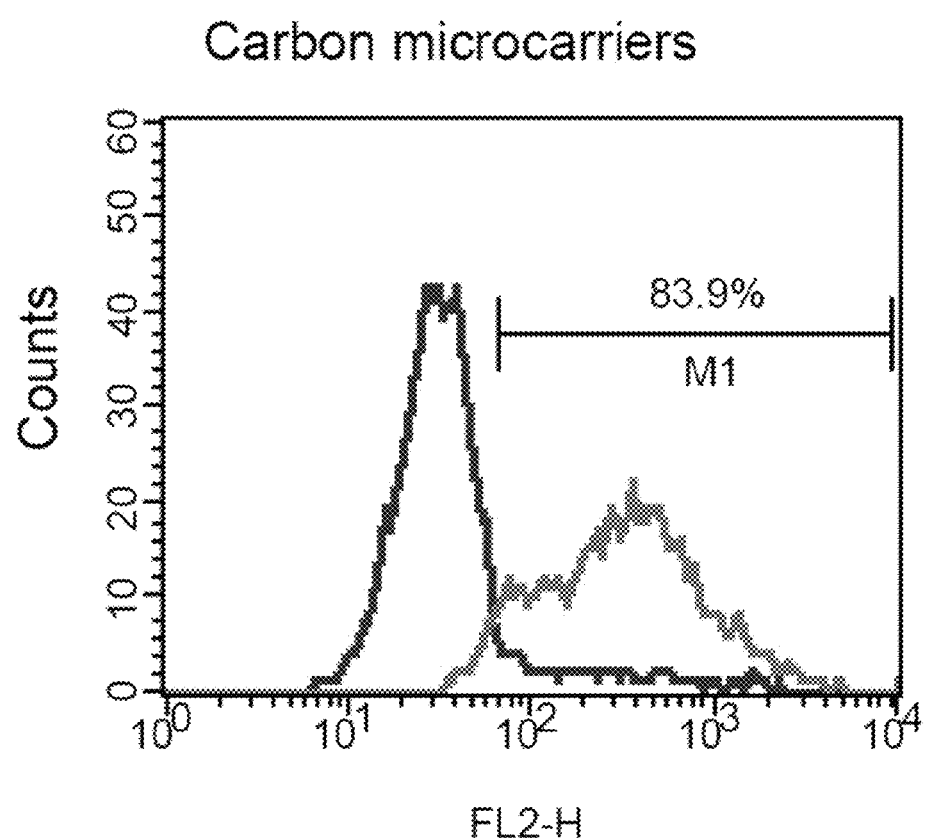
FIGS. 34B and 34C. FACS of pluripotent marker Oct-4 in both conditions (B: Carbon microcarriers and C: Control).
Figure 34C:
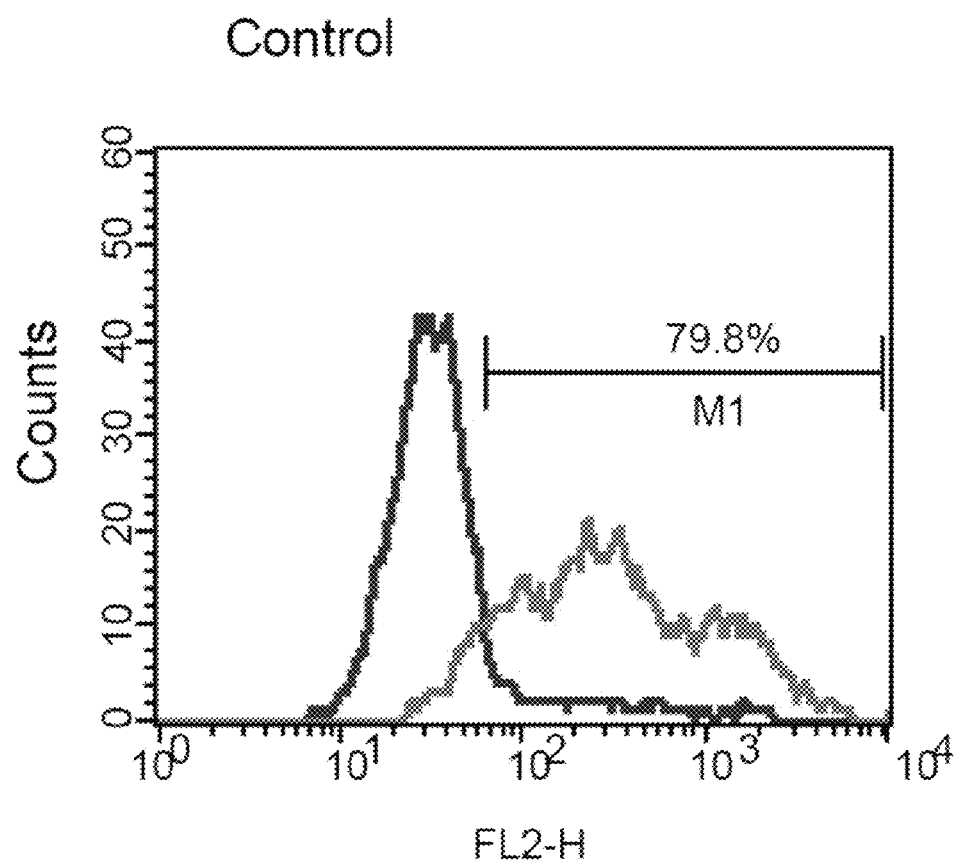

A second hESC line HES-2 is also grown on fibronectin coated, microporous carbon microcarriers and achieved similar cell numbers as 2D colony controls (FIG. 34A) and retained high viabilities, greater than 95%. Cells from both conditions continue to express similar levels of Oct-4 of around 80% (FIG. 34B).

Figure 35:
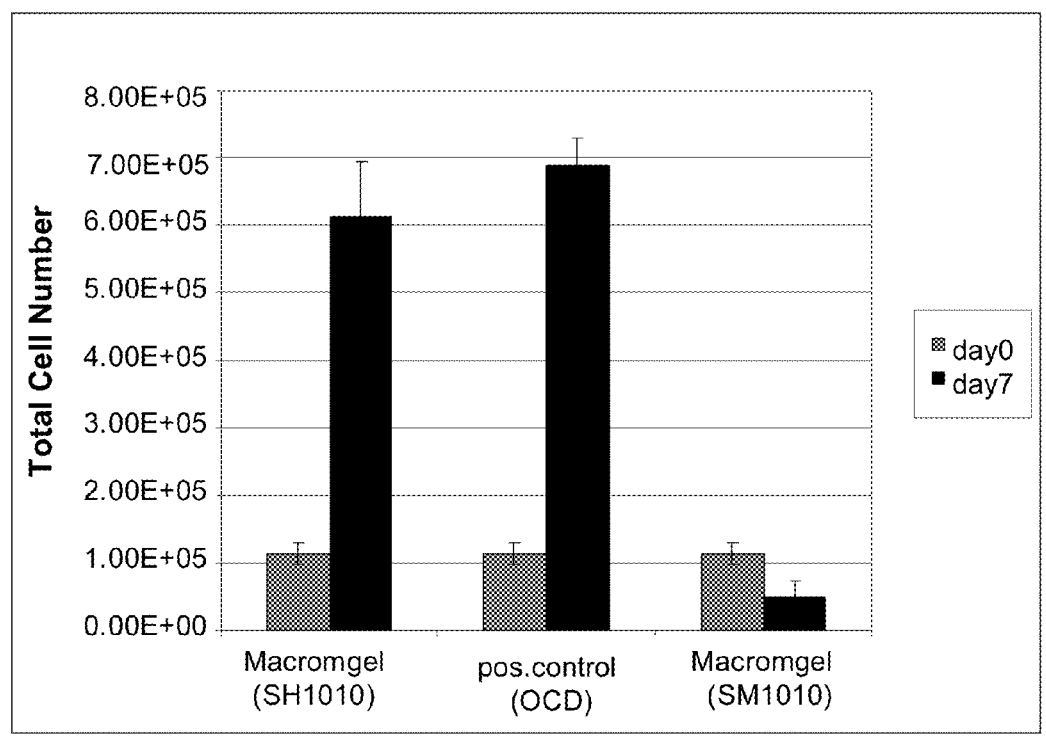
FIG. 35. Sizes and shapes of carriers—spherical carbon beads. Comparison of SH1010 and SM1010 microcarriers vs. the 2D colony control (OCD). Growth of hESC in 2D colony controls and on fibronectin coated macroporous (SH1010) and microporous (SM1010) carbon microcarriers FIG. 36. Sizes and shapes of carriers—spherical carbon beads. FACS of pluripotent markers Oct-4 and TRA-1-60 of hESC cultured on fibronectin coated macroporous carbon microcarriers.

Matrigel coated macroporous carbon microcarriers (SH1010) are able to achieve cell numbers similar to 2D colony controls, whereas matrigel coated microporous (SM1010) microcarriers did not perform as well (FIG. 35).

Figure 36:
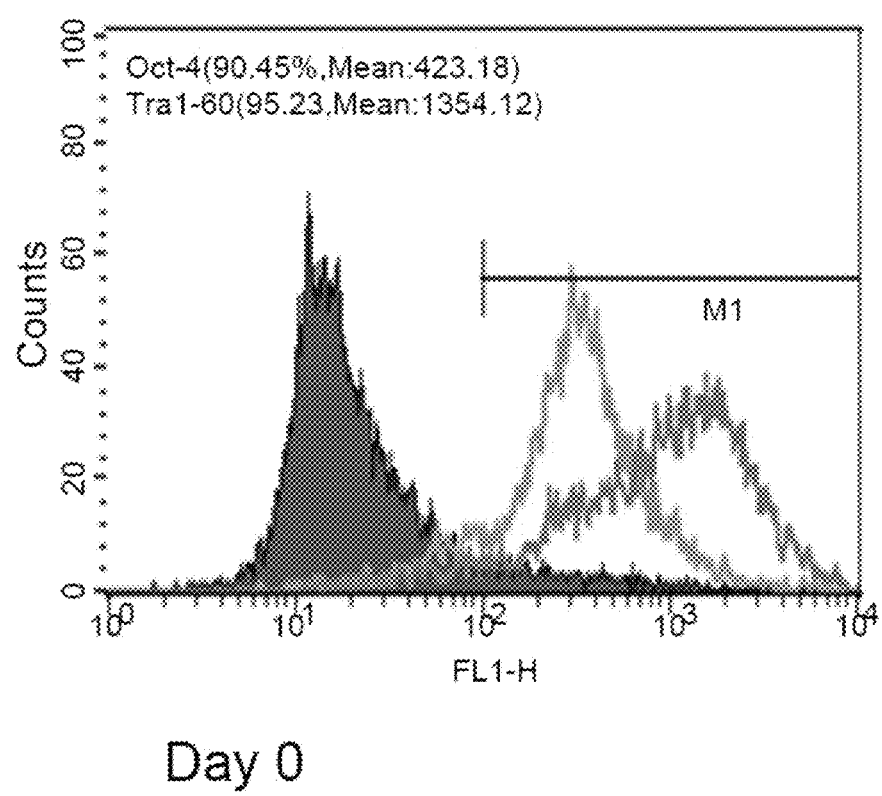
Figure 36:
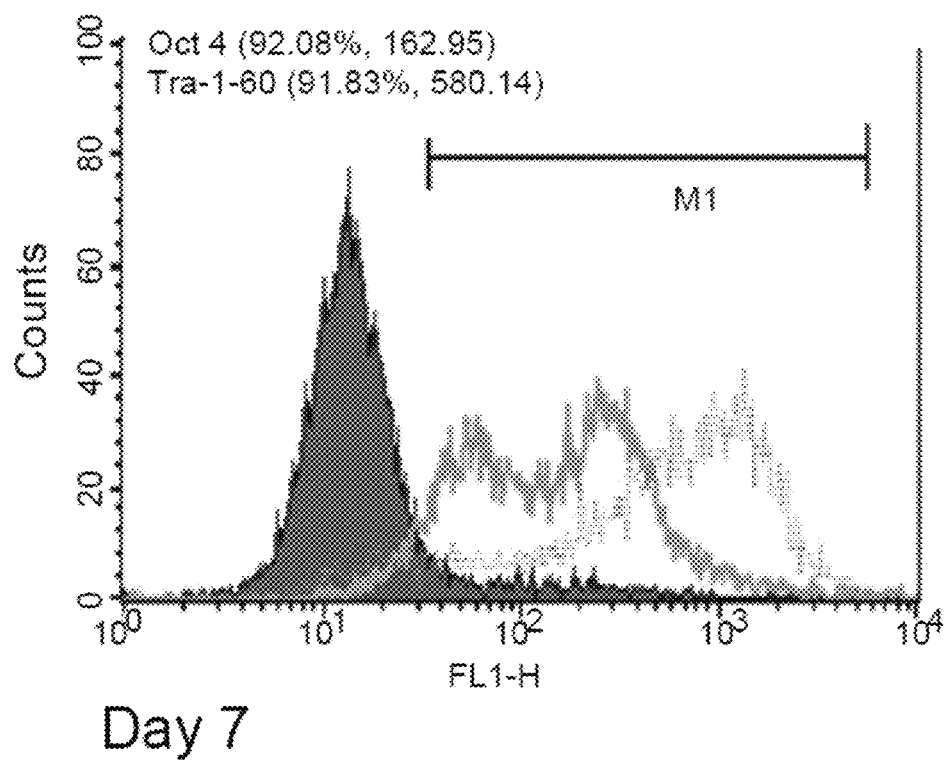

FIG. 36 shows that hESC cultured on the SH1010 microcarriers after 7 days are still pluripotent, as >90% of the population expressed the pluripotent markers Oct-4 and TRA-1-60.

FIG. 37 shows that hESC covered most of the surface area of the SH1010 microcarriers, whereas for microcarriers with specification SM1010 there are fewer cells attached.

Figure 38:
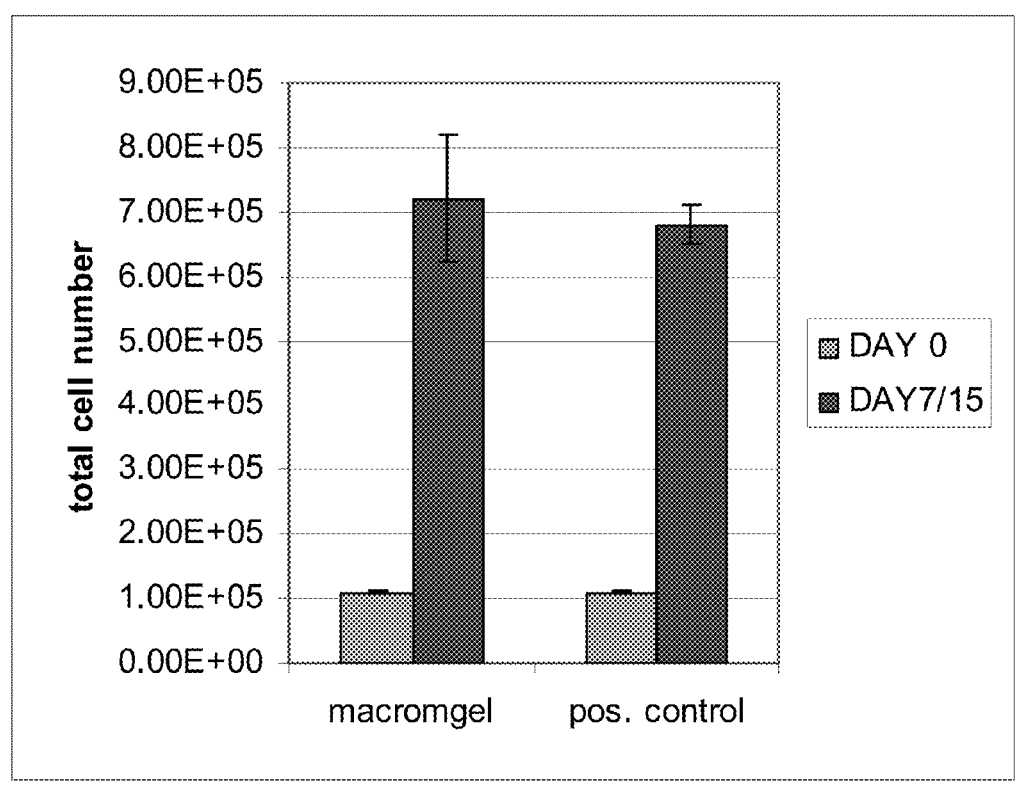
FIG. 38. Sizes and shapes of carriers—spherical carbon beads. 15 day old microcarrier cultures. Growth of hESC on matrigel coated macroporous carbon microcarriers over 15 days compared to 2D colony controls over 7 days.

FIG. 38 shows that hESC cultured on SH1010 microcarriers for 15 days achieved similar cell numbers as the 2D colony control cultures grown for 7 days.

Figure 39:
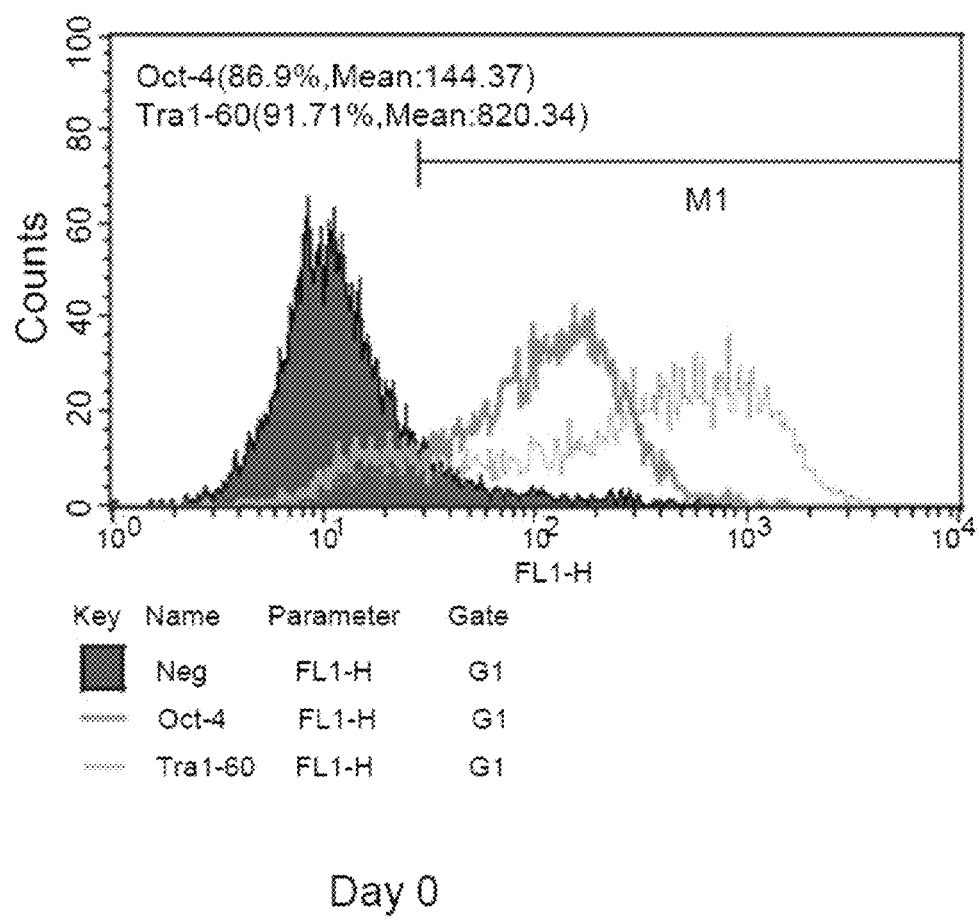
FIG. 39. Sizes and shapes of carriers—spherical carbon beads. FACS of pluripotent markers Oct-4 and TRA-1-60 of hESC cultured on macroporous carbon microcarriers over 15 days.
Figure 39:
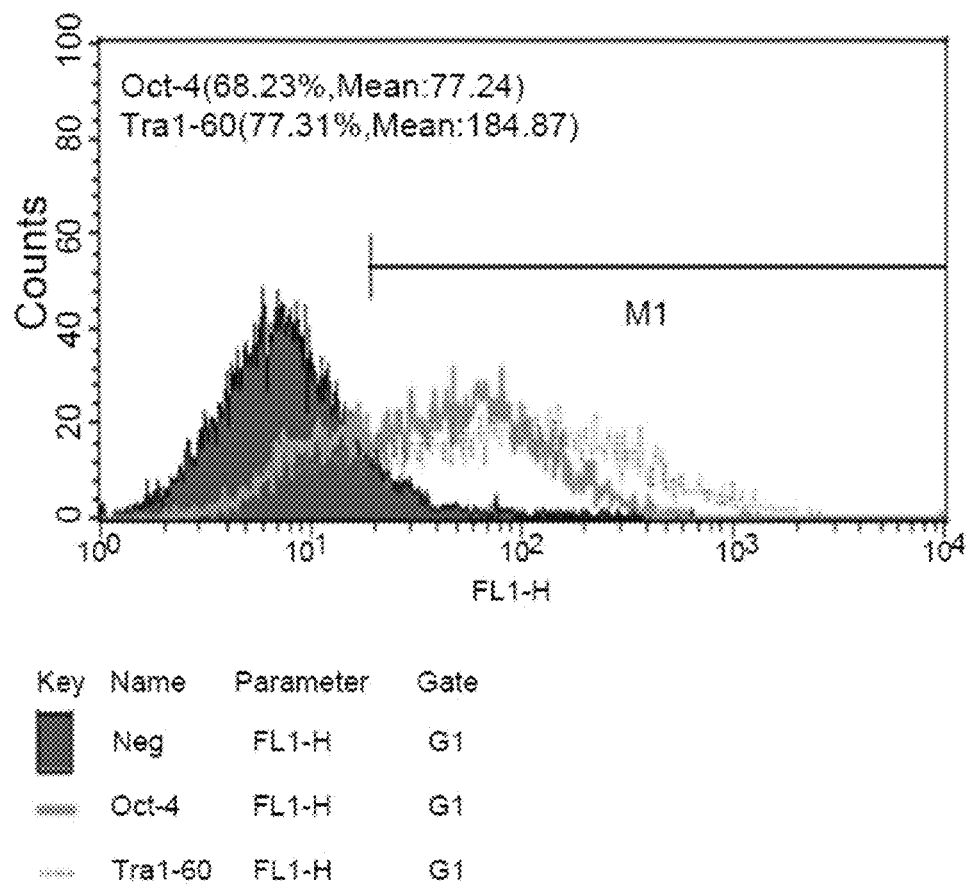

FIG. 39 shows that Oct-4 and TRA-1-60 pluripotent markers continue to be expressed 15 days after inoculation.

Figure 40:
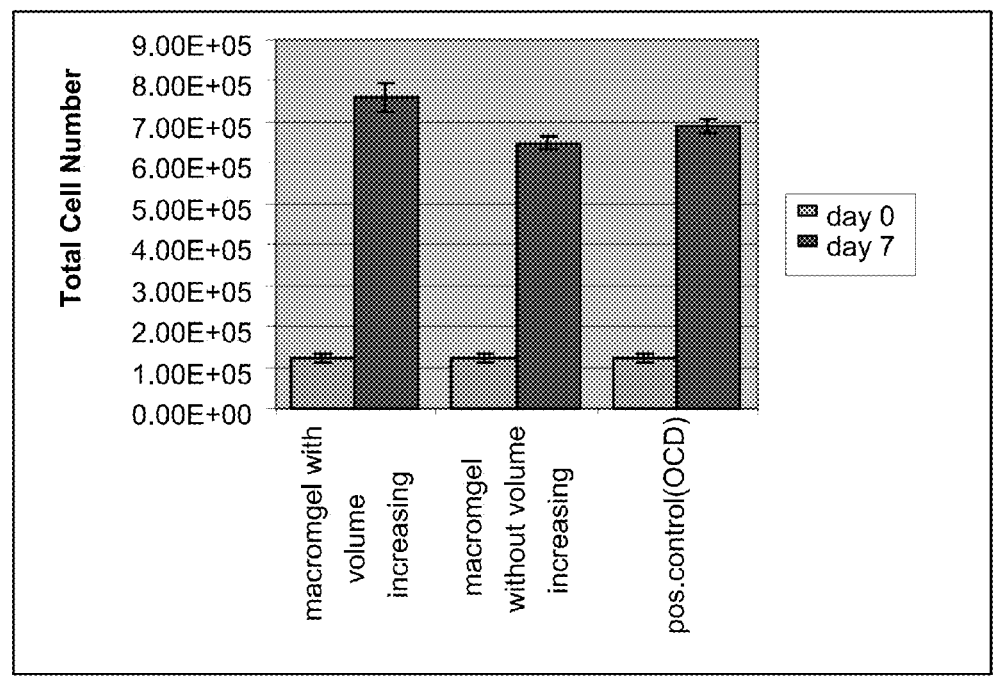
FIG. 40. Sizes and shapes of carriers—spherical carbon beads. Increased feeding of conditioned media Growth of hESC on carbon microcarriers with 2× volume vs. 1× volume feeding vs. 2D colony controls.

FIG. 40 shows that increasing the feeding with twice the volume of MEF-CM of microcarrier cultures marginally increased the cell numbers compared to microcarriers with 1× volume feeding.

Figure 41:
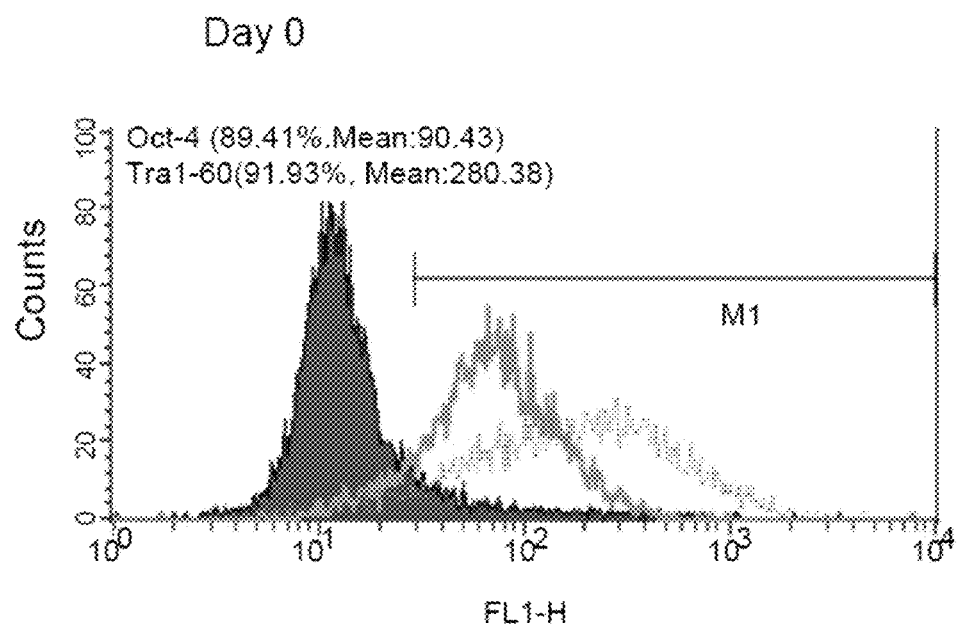
FIG. 41. Sizes and shapes of carriers—spherical carbon beads. FACS of pluripotent markers Oct-4 and TRA-1-60 of hESC cultured on macroporous carbon microcarriers with 2× volume feeding.
Figure 41:
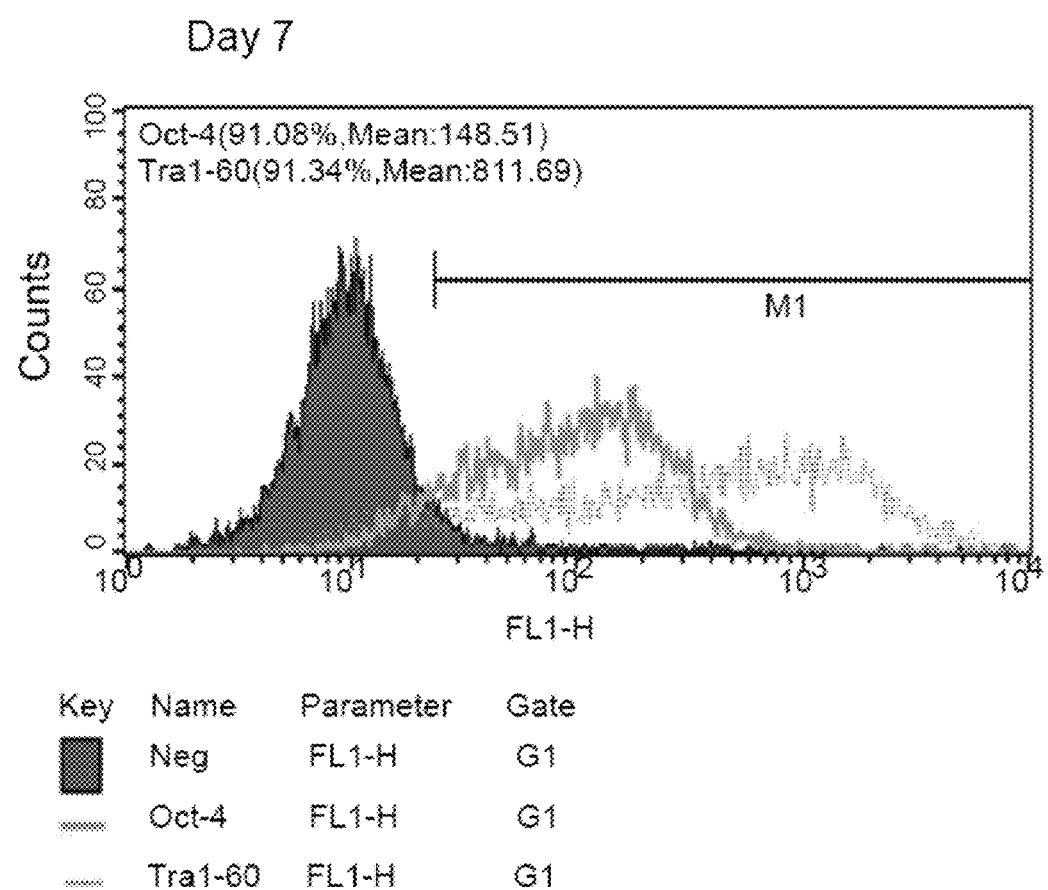

FIG. 41 shows that the expression of pluripotent markers Oct-4 and TRA-1-60 by hESC cultured on the beads with twice the volume of MEF-CM feeding is more than 90 percent.

FIG. 42 shows that hESC are well distributed on the macroporous microcarriers as indicated by the DAPI, phalloidin and TRA-1-60 stains.

Figure 43A:
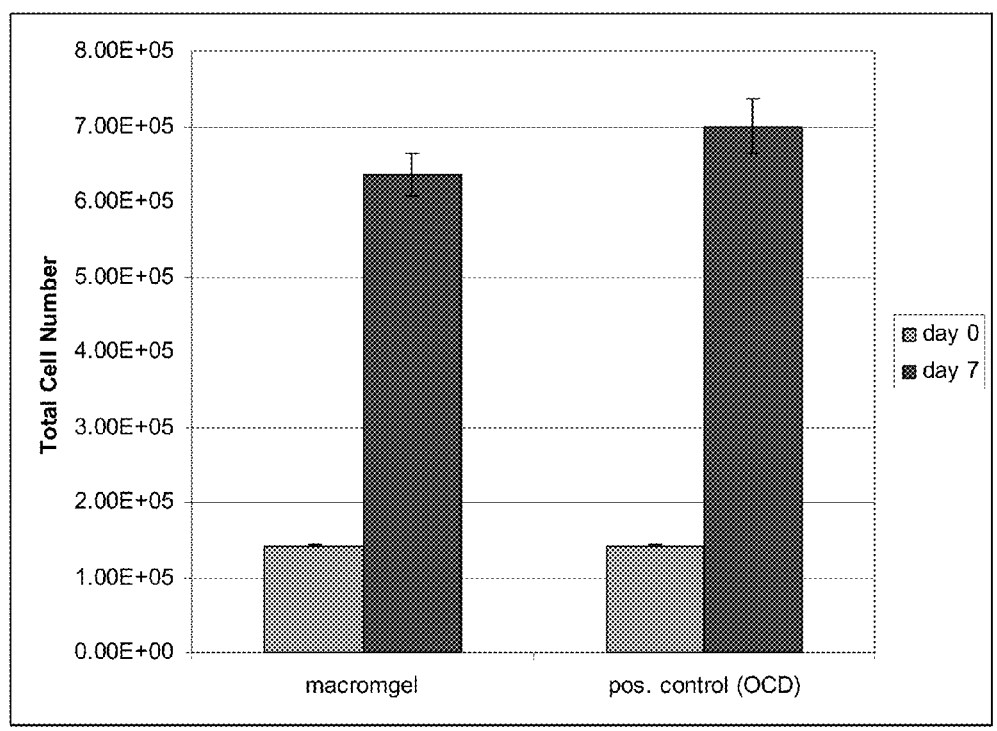
(FIG. 43A). Duplicate experiments with another cell line (HES-2) grown on macroporous microcarriers vs. 2D colony controls.
Figure 43B:
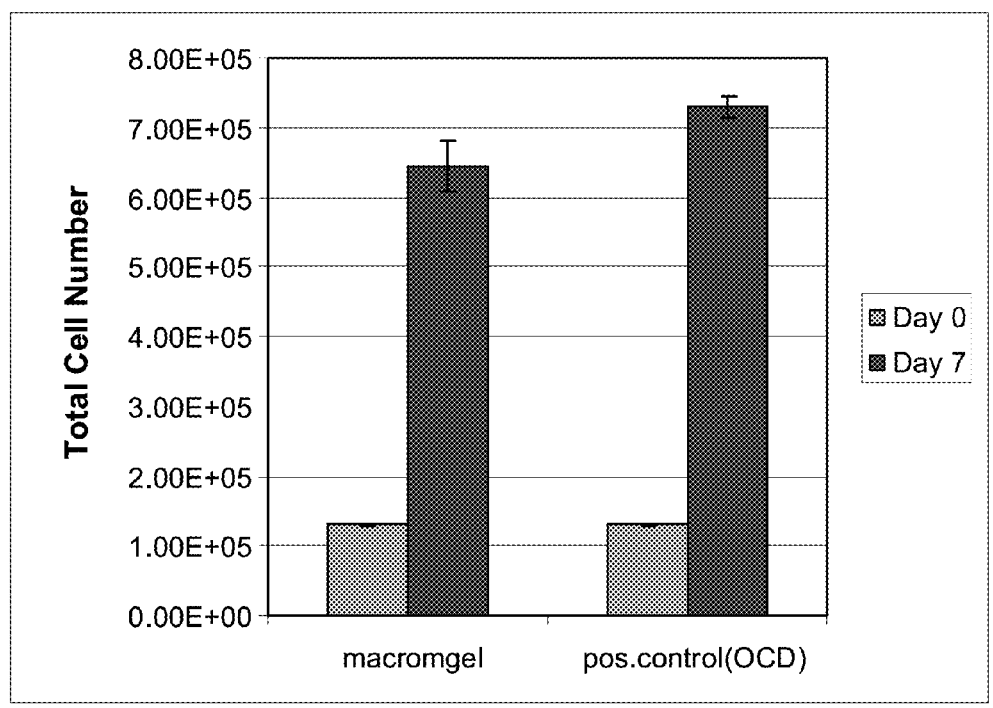
(FIG. 43B).

FIG. 43A and FIG. 43B show replicate experiments with a second cell line HES-2 which is also successfully cultured on SH1010 macroporous microcarriers and achieved similar cell numbers as the 2D colony control of about 0.65 to 0.7 million cells per well.

Figure 44:
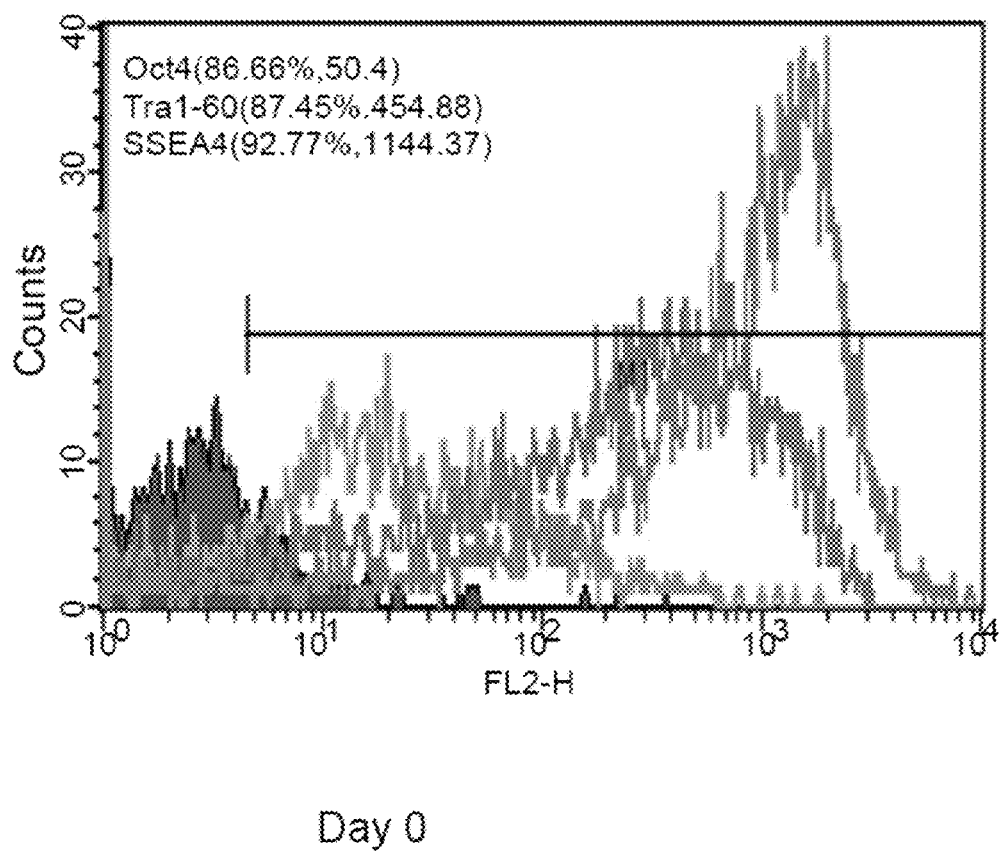
FIG. 44. Sizes and shapes of carriers—spherical carbon beads. FACS of pluripotent markers Oct-4 and TRA-1-60 of HES-2 cell line cultured on macroporous carbon microcarriers after 7 days.
Figure 44:
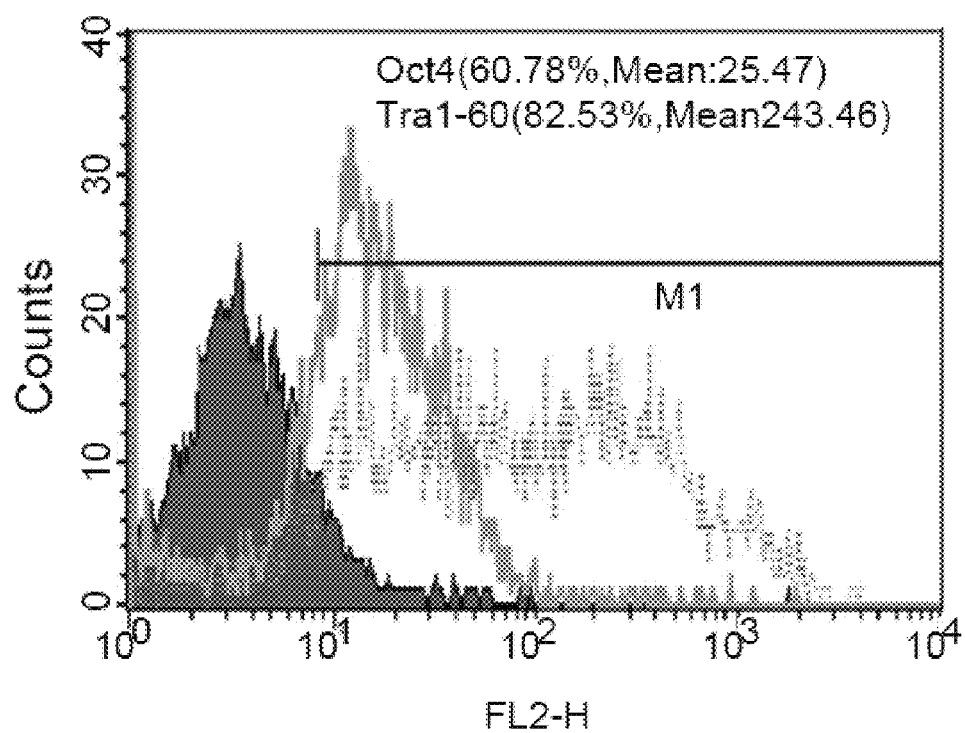

FIG. 44 shows that HES-2 expression of the pluripotent markers Oct-4 and TRA-1-60 is still high after 7 days of culture on SH1010 microcarriers.

Figure 45:
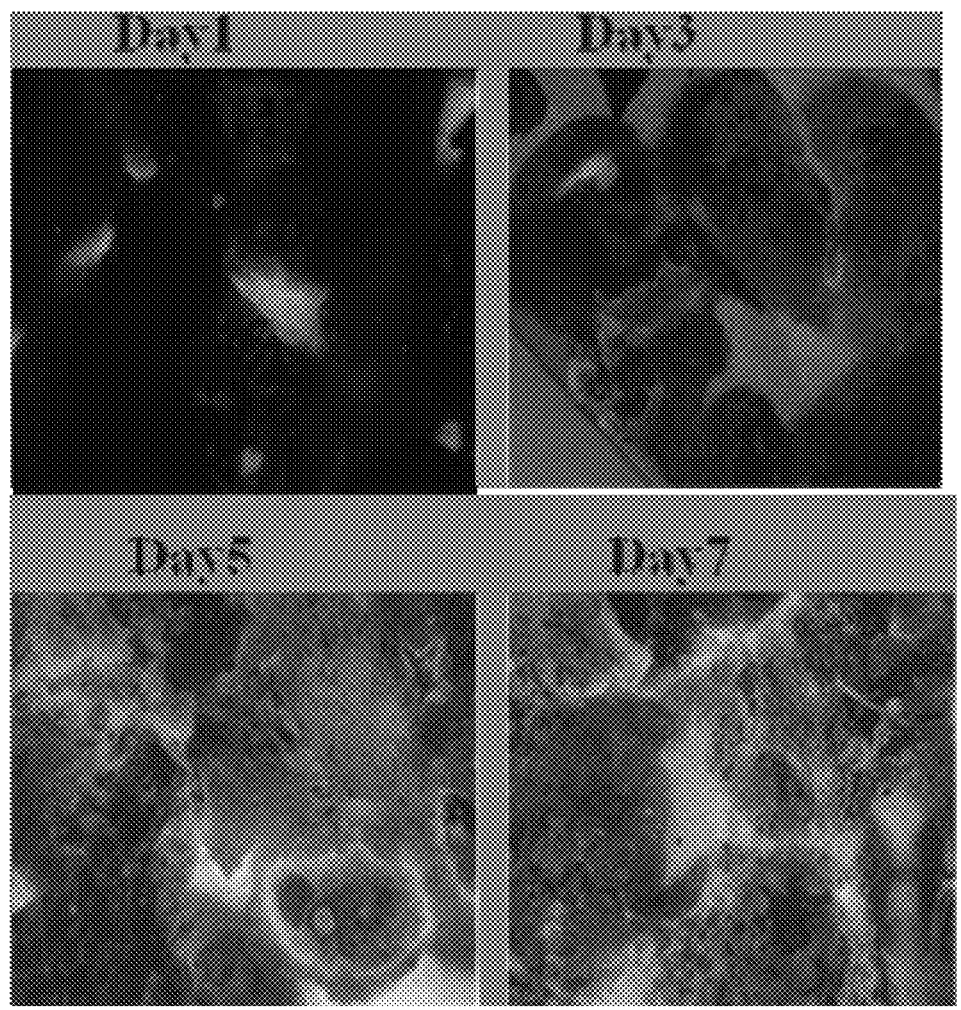
FIG. 45. Sizes and shapes of carriers—spherical carbon beads. Images were taken every two days under the fluorescence microscope with 4× Magnification. The pictures show that the GFP cell cultured on the microcarriers grew from day 1 to day 7. Photos of fluorescent HES-2 GFP cell line growing on macroporous carbon microcarriers over 7 days.

FIG. 45 shows that the HES2-GFP cells spread evenly on the microcarriers from day 1 to day 7. Macroporous microcarriers seeded with hESC in high (every 30 mins) and low mixing (every 2 hrs) enable hESC growth to reach between 0.6 to 0.8 million cells per well which is lower than the 1.2 million cells per well achieved by 2D colony controls after 7 days as shown FIG. 46A.

Figure 46A:
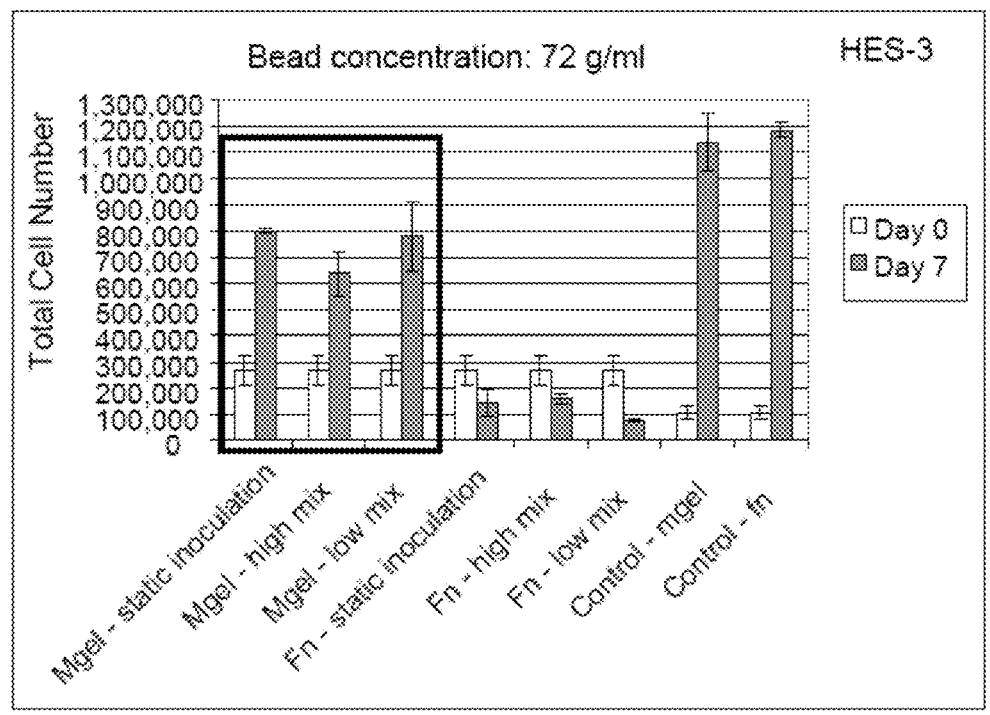
FIG. 46A. Growth of hESC on carbon microcarriers after inoculation on static, high mixing (every 30 mins) and low mixing (every 2 hrs) coated with matrigel or fibronectin vs. 2D colony controls coated with matrigel or fibronectin. High mix—every 30 mins. Low mix—every 2 hrs. Mixing during inoculation does not reduce cell growth on 1 mm beads. FACS of pluripotent markers Oct-4, SSEA-4 and TRA-1-60 under these conditions.
Figure 46B:
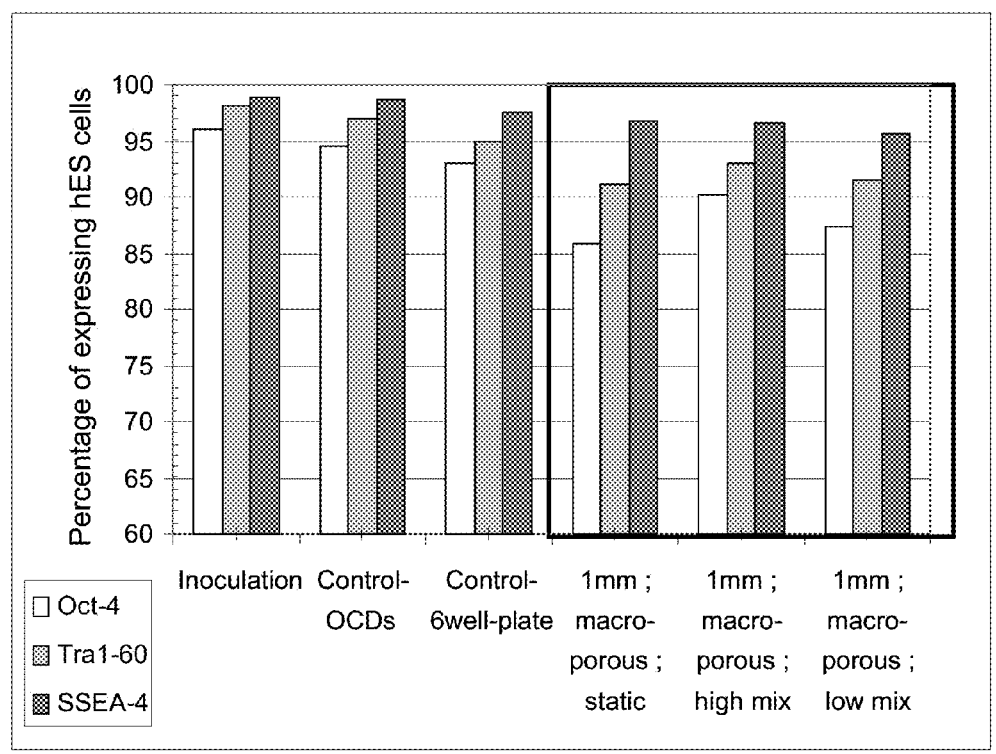
FIG. 46B. Expression of pluripotent markers Oct-4, Tra-1-60 and SSEA-4 are stable.

However, extending the cultures to 12 days on microcarriers enabled the cell numbers to reach 1.2 million cells per well. Pluripotent markers Oct-4, TRA-1-60 and SSEA-4 also appear stable above 85% for microcarriers vs. controls as shown in FIG. 46B.

The above experiment is conducted on hESC grown on hydrophilic Tosoh microcarriers and the relevant data is measured.

Example 23

Co-Culture and Feeders on Microcarriers

Figure 47A:
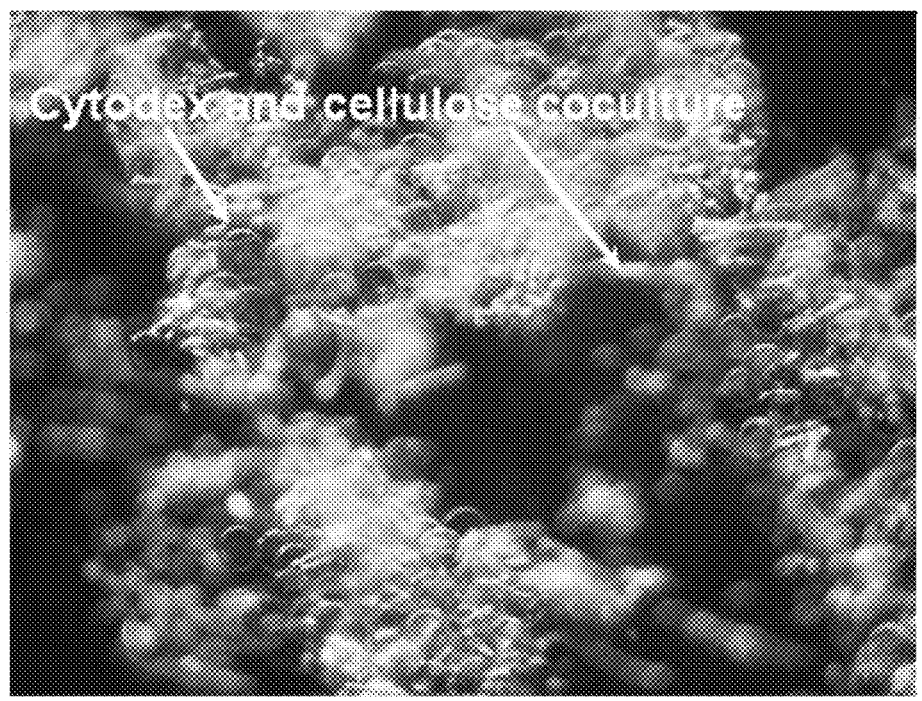
FIG. 47A. Photo of co-cultures of feeders on Cytodex with hESC on cellulose microcarriers.
Figure 47B:
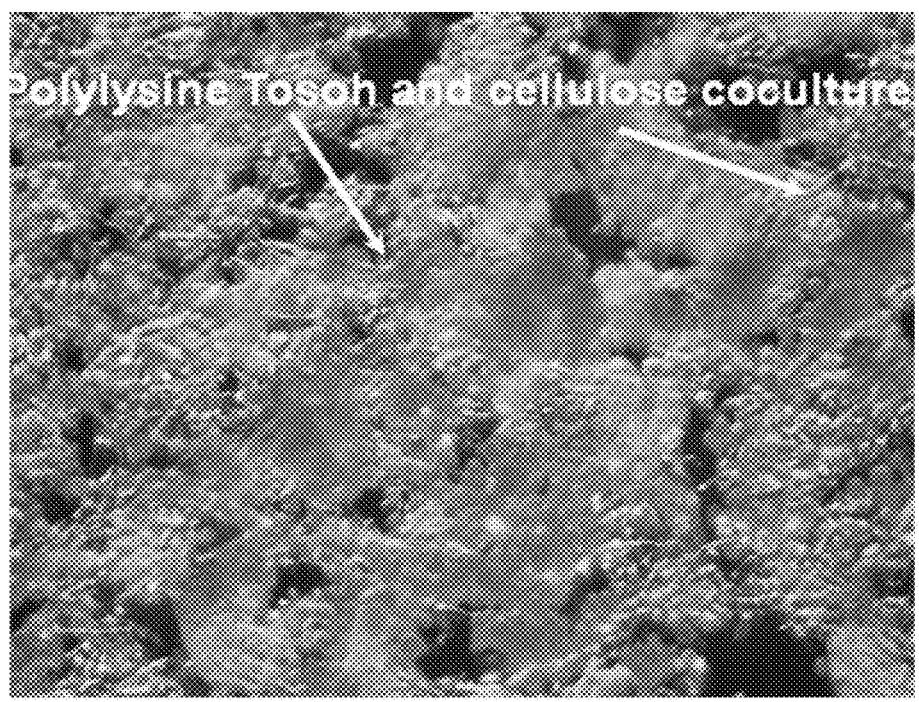
FIG. 47B. Photo of feeders on polylysine coated Tosoh with hESC on cellulose microcarriers.

FIG. 47A shows spherical Cytodex microcarriers with feeders amongst cellulose microcarriers seeded with hESC, whilst FIG. 47B shows polylysine coated Tosoh microcarriers with feeders amongst cellulose microcarriers seeded with hESC in static cultures.

Figure 48A:
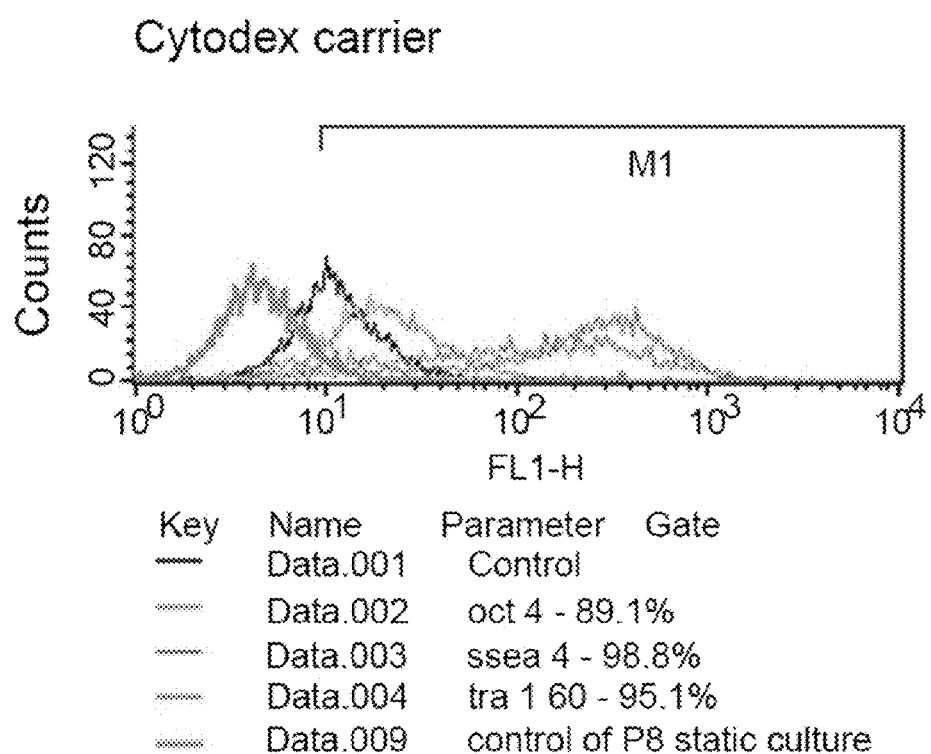
FIG. 48A. FACS of pluripotent markers Oct-4, SSEA-4 and TRA-1-60 of co-cultures of feeders on Cytodex with hESC on cellulose microcarriers.
Figure 48B:
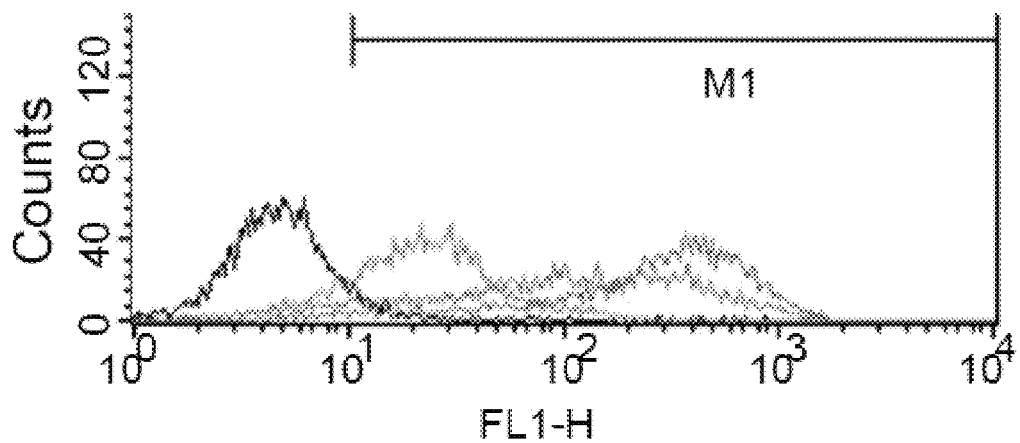
FIG. 48B. FACS of pluripotent markers Oct-4, SSEA-4 and TRA-1-60 of co-cultures of feeders on polylysine coated Tosoh with hESC on cellulose microcarriers.

FIG. 48A and FIG. 48B indicate that there is high expression of the 3 pluripotent markers Oct-4, SSEA-4 and TRA-1-60 by hESC cultured on both the Cytodex and polylysine coated Tosoh microcarriers co-cultures respectively. Table E3 shows that cell numbers achieved on the 3 co-culture methods of feeders on Cytodex, polylysine coated Tosoh, and DE53 microcarriers, together with hESC on DE53 microcarriers range from 2.6 to 5.5 million cells per well after 7 days. These numbers are higher than 2D colony cultures which typically achieve 2 million cells per well.

Table E3 below shows cell numbers achieved on the 3 co-culture methods range from 2.6 to 5.5 million cells after 7 days.

| Experiments | hESC seeding density at $1.2 \times 10^6$ cells/well 1 | hESC seeding density at $0.8 \times 10^6$ cells/well 2 |
|---|---|---|
| Feeders on Cytodex 3 | $5.5 \times 10^6$ cells/well | $3.7 \times 10^6$ cells/well |
| Feeders on Tosoh polylysine with matrigel | $2.6 \times 10^6$ cells/well | $4.2 \times 10^6$ cells/well |
| Feeders on matrigel coated DE53 | — | $3.7 \times 10^6$ cells/well |

Table E3. Co-culture of feeders on 3 different microcarriers with hESC on cellulose DE 53 microcarriers, with cell counts after 7 days. Control 2D colony cultures=2×106 cells/well. Co-culture of feeders on 3 different microcarriers with hESC on cellulose DE 53 microcarriers. Cell counts ranged from 2.6 to 5.5 million cells per well after 7 days.

Example 24

Spinner Cultures

Figure 49:
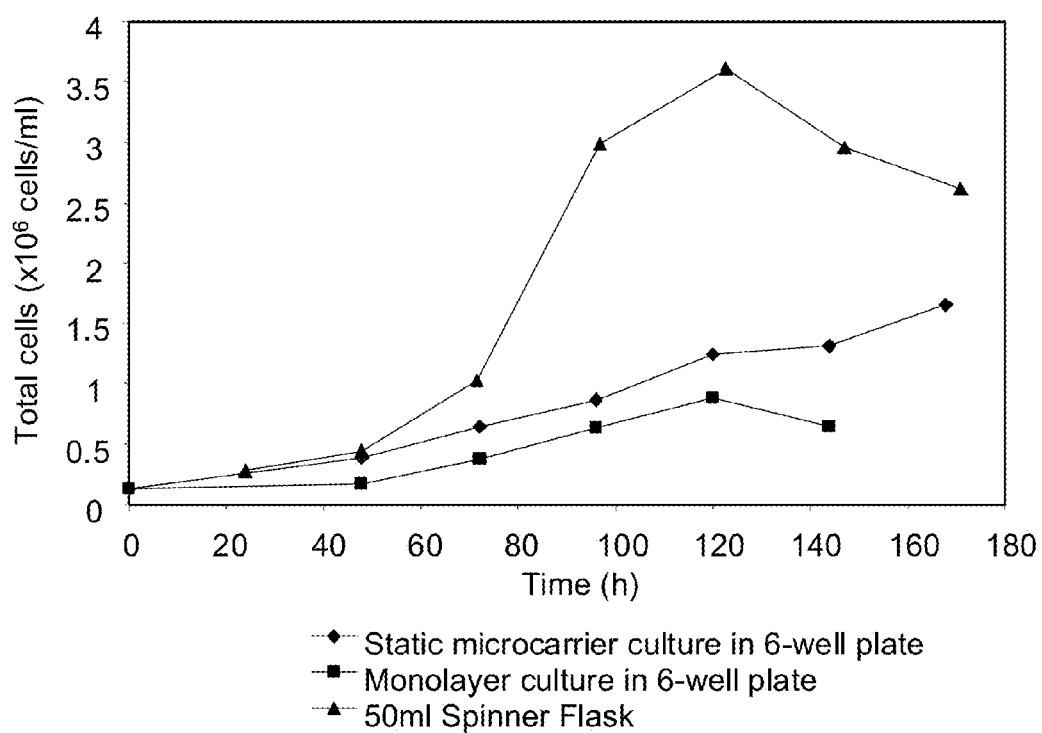
FIG. 49. Spinner cultures. Exponential growth profile of hESC in 50 ml spinner cultures on microcarriers compared to static microcarrier and 2D colony cultures.

FIG. 49 shows that hESC grow at an exponential rate on cellulose microcarriers reaching 3.6 million cells/ml, 5 days after seeding with 0.3 million cells/ml in the 50 ml spinner culture which is significantly higher than the static microcarrier culture which reached 1.7 million cells/ml, and the 2D colony control which only reached 0.9 million cells/ml.

Example 25

Karyotype

Figure 50:
FIG. 50. Characterisation data, normal karyotypes at passage 6. Normal karyotype of HES-2 and HES-3 cell lines after 6 consecutive passages (equivalent to 24 cell doublings) on cellulose microcarriers.

FIG. 50 shows that both hESC lines HES-2 and HES-3 have a normal karyotype after 6 continuous passage on microcarrier cultures, which is equivalent to approximately 24 population doublings.

Example 26

Seeding of feeders on Tosoh, Cytodex 1 and DE53 Microcarriers for Co-Culture with hESC on DE53 Microcarriers Inactivated feeders (MEFs) were first seeded onto Tosoh, Cytodex 1 or DE53 microcarriers. hESC on matrigel coated microcarriers were introduced to the culture 24 h later in the growth medium consisting of Knockout DMEM supplemented with Knockout Serum Replacement, glutamine, 2-mercaptoethanol, non-essential amino acid stock and basic FGF (Invitrogen).

Cells for seeding the microcarrier cultures were taken from confluent matrigel coated tissue culture plates and harvested using STEMPRO® EZPassage™ Tool (Invitrogen). Microcarrier cultures were seeded at cell concentrations of between 1 to $3 \times 10^5$ cells/ml.

Example 27

Preparation of Cytodex 1, 3 and Hillex Microcarriers

Cytodex 1 and 3 (GE Healthcare) and Hillex (Hyclone) were prepared according to manufacturer protocols, which consisted of hydration, rinsing and sterilization of the microcarriers by autoclaving. Coating with matrigel was performed in the same way as for DE53 cellulose microcarriers. Five mg of microcarriers were coated with 1 ml of KO medium containing 33 µl of matrigel stock solution. Both uncoated and matrigel coated microcarrier cultures were seeded at cell concentration of between 1 to $3 \times 10^5$ cells/ml.

Example 28

Coating of Extracellular Matrices (Hyaluronic Acid, Heparin, Chondroitin Sulphate, Fibronectin, Collagen 1, 4, Laminin) on DE53 and Cytodex 3 Microcarriers The coating of extracellular matrices (Hyaluronic acid, Heparin, Chondroitin sulphate) on cellulose microcarriers followed these conditions:—
Heparin: 0.44 mg Heparin/mg DE53 (equivalent to 1:10 dilution)
Chondroitin: 0.91 mg Chondroitin/mg DE53 (equivalent to 1:10 dilution)
Hyaluronic acid: 0.016 mg Hyaluronic acid/mg DE53 (equivalent to 1:10 dilution)
For hyaluronic acid and heparin coated microcarriers in combination with other extracellular matrices the follow conditions were used:
Fibronectin: 20 µg/mg DE53
Laminin: 2 µg/mg DE53
Collagen I: 20 µg/mg DE53
Collagen IV: 20 µg/mg DE53
For the Cytodex 3 experiment, the following coating concentrations were used:—
Laminin: 2 to 4 µg/mg Cytodex 3
Fibronectin: 20 µg/mg Cytodex 3

Example 29

Continuous Passaging of hESC on DE53 Cellulose Microcarriers to Passage 23

Figure 51:
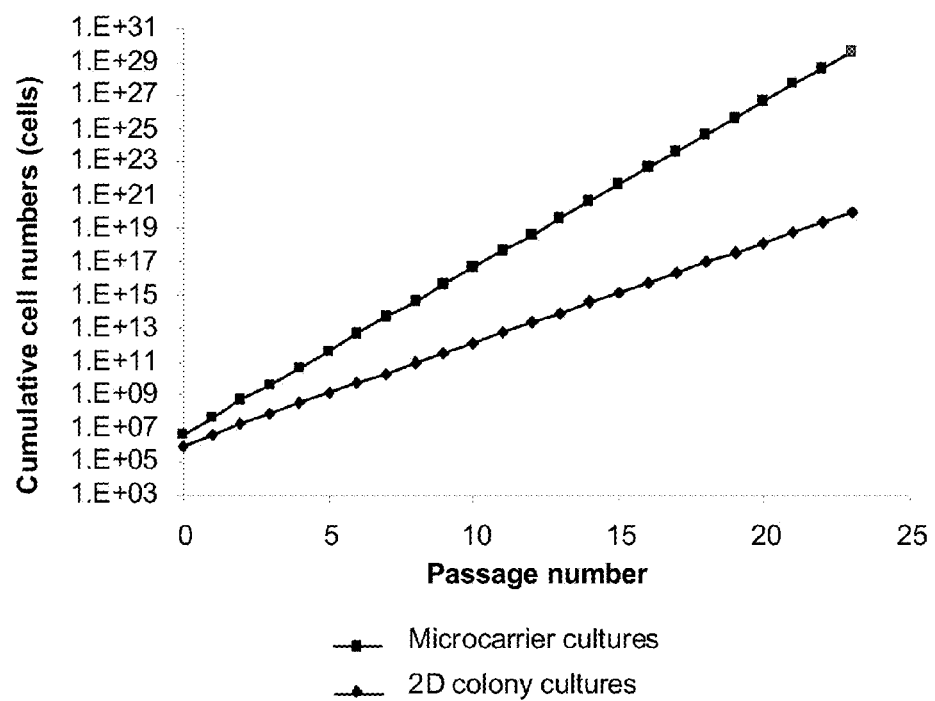
FIG. 51. Comparison of hESC growth on cellulose microcarrier vs. 2D colony cultures.
Figure 52:
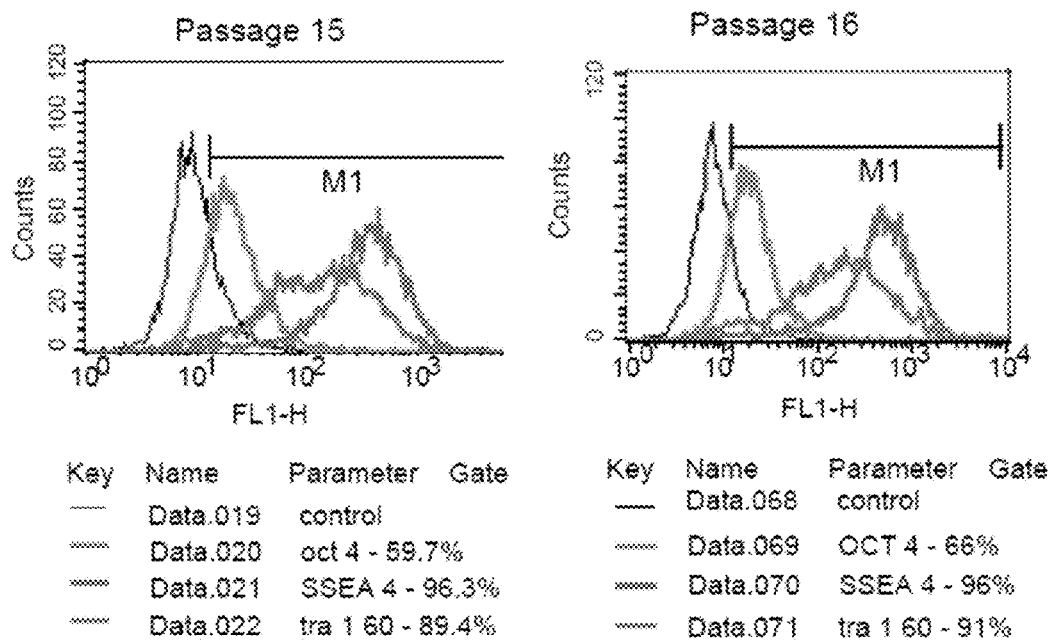
FIG. 52. Oct4, SSEA4 and TRA-1-60 expression at passage 15 and 16 of hESC culture on Matrigel coated DE53 carriers.

FIG. 51 shows that hESC grown on cellulose microcarriers that have been passaged for 23 passages retain their higher growth rate than the growth rate of hESC grown on 2D colony cultures. Typically the split ratio during passaging in microcarrier cultures is 1:10 and for 2D colony cultures is 1:4. Thus by the $23^{rd}$ passage there is a 10 log difference in total cell numbers that can be achieved in microcarrier cultures. FIG. 52 shows that the expression of pluripotent markers, Oct4, SSEA4 and TRA-1-60 continues to be stable at passages 15 and 16 with high cell densities of 9.4 and 7.1 million cells/well respectively. FIG. 53 further shows robust expression of Oct4, SSEA4 and TRA-1-60 at passages 21 to 23 and when microcarriers are replated onto 2D colony cultures, the expression of these markers continues to be high and stable.

Example 30

Characterisation of hESC Cultured on Cellulose Microcarriers (Karyotyping, RT-PCR of Embryoid Bodies and Teratoma Formation)

Figure 54A:
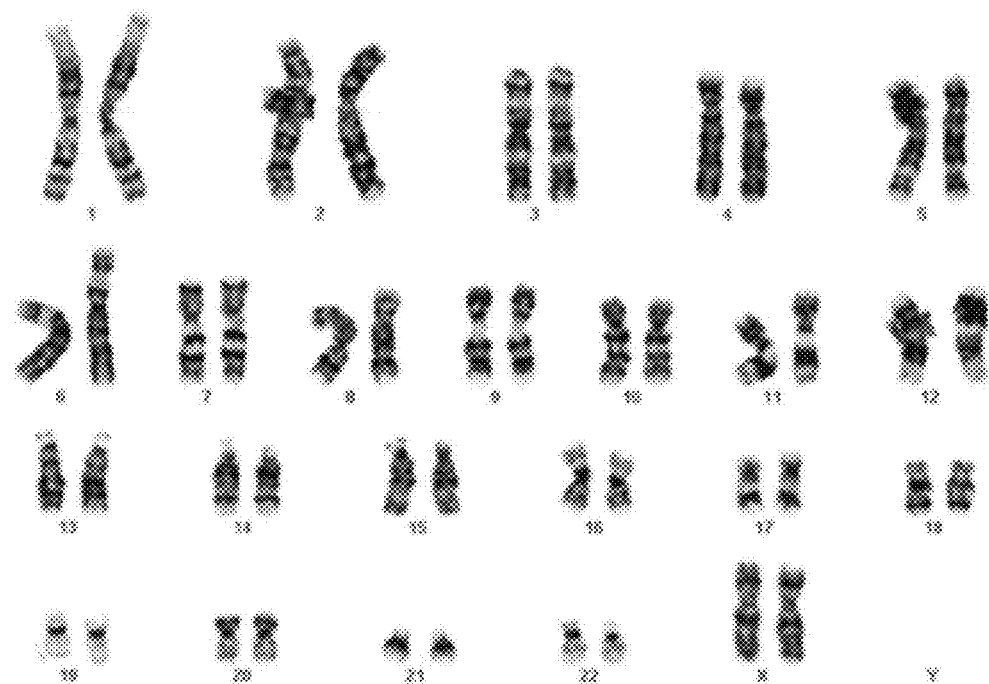
FIG. 54. Microcarrier cultures of HES-3 retain a normal 46XX karyotype as late as passages 22 and 25. Passage 22 karyotype is shown in FIG. 54A; passage 25 karyotype is shown in FIG. 54B.
Figure 54B:
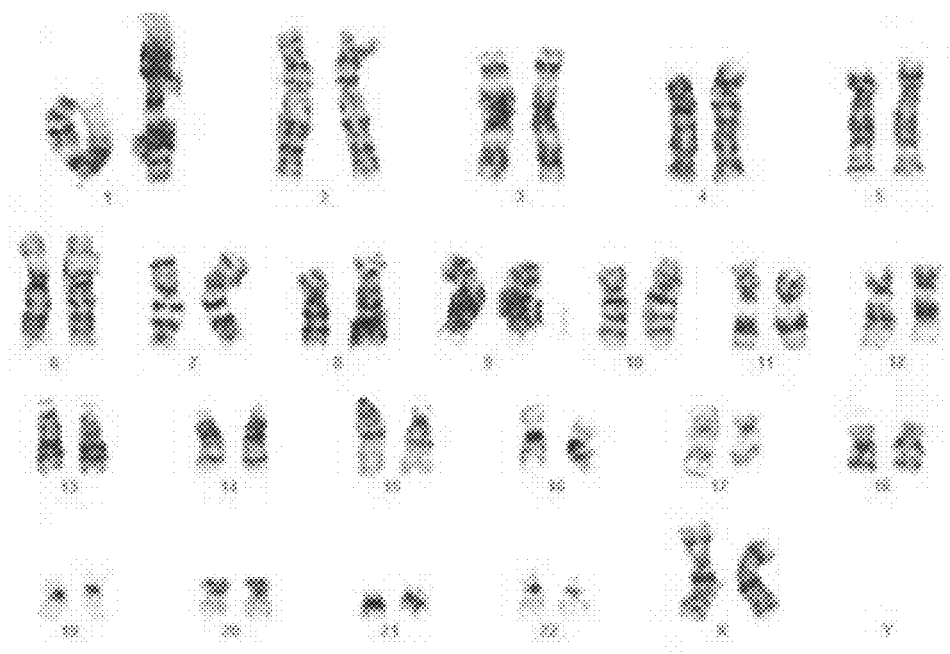
Figure 55:
FIG. 55. Microcarrier cultures of HES-2 retain a normal 46XX karyotype as late as passage 14.
Figure 56:
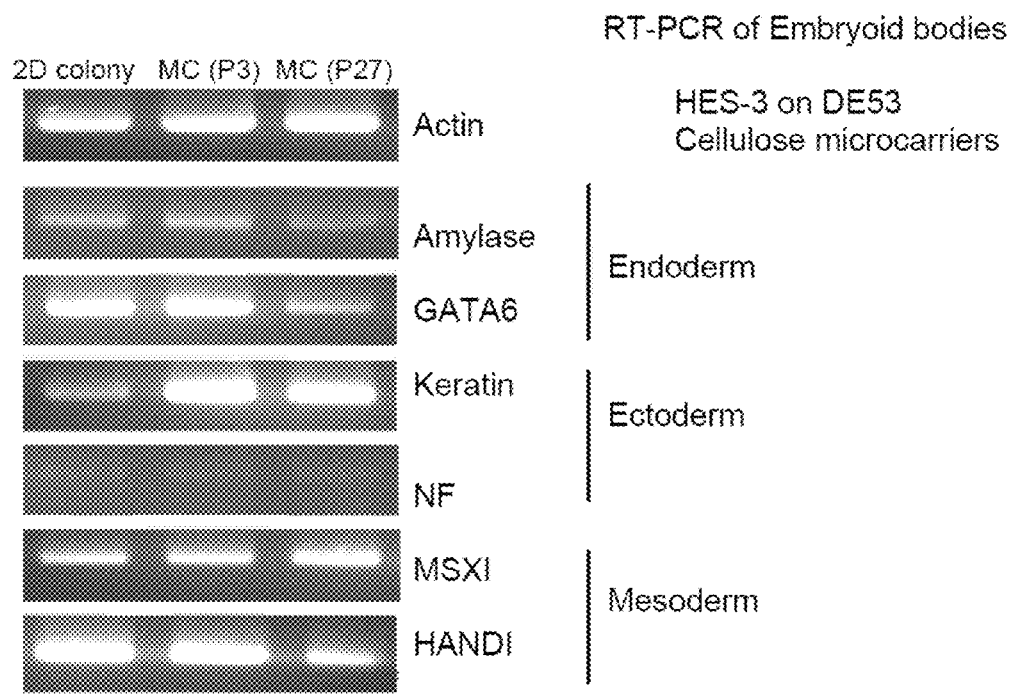
FIG. 56. hESC from microcarrier cultures at passage 3 and 27 differentiated into embryoid bodies and were able to form cells of the 3 germ layers represented by genes of the endoderm (amylase and GATA6), ectoderm (keratin and neurofilament, NF) and mesoderm (MSX1 and HAND1).
Figure 57:
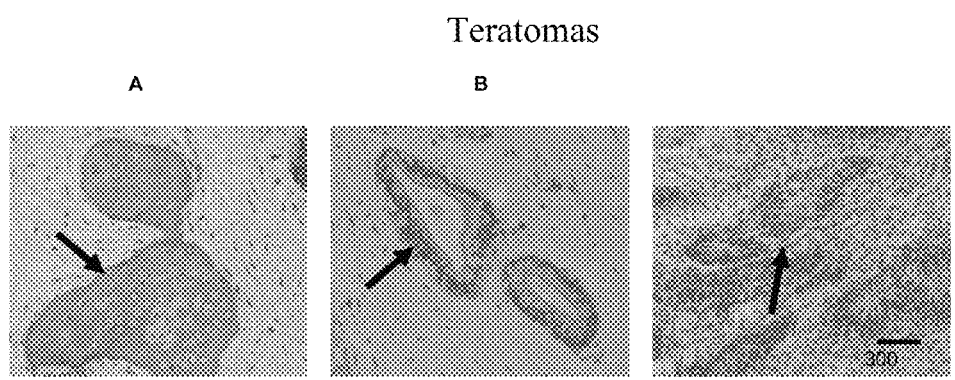
FIG. 57. (A-C) Teratomas were formed with cells of the 3 germ layers from FIG. 56.

FIG. 54 shows that microcarrier cultures of HES-3 continue to retain a normal 46XX karyotype as late as passages 22 and 25. FIG. 55 shows that microcarrier cultures of HES-2 also retain a normal 46XX karyotype as late as passage 14. When hESC from microcarrier cultures at passage 3 and 27 were differentiated into embryoid bodies, they were able to form cells of the 3 germ layers represented by genes of the endoderm (amylase and GATA6), ectoderm (keratin and neurofilament, NF) and mesoderm (MSX1 and HAND1), see FIG. 56. Teratomas were also formed with cells of the 3 germ layers as shown in FIG. 57.

Example 31

Figure 58:
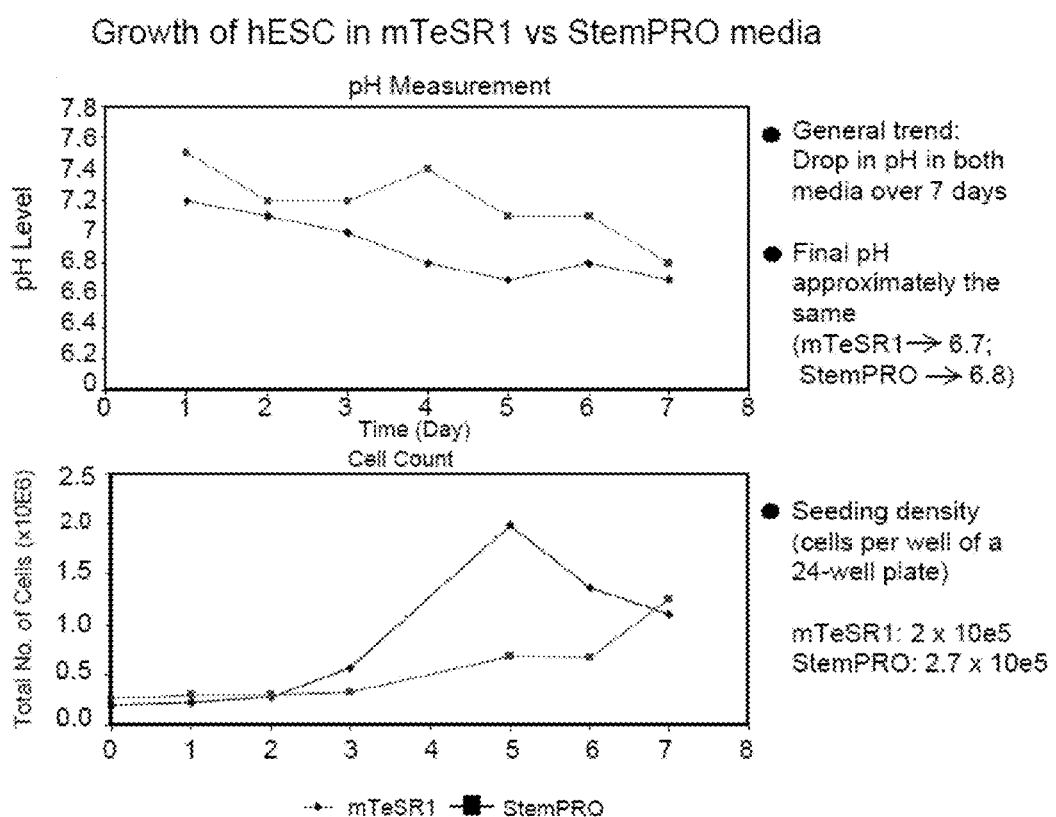
FIG. 58. Growth of hESC on microcarriers in mTeSR1 vs StemPRO media.
Figure 59:
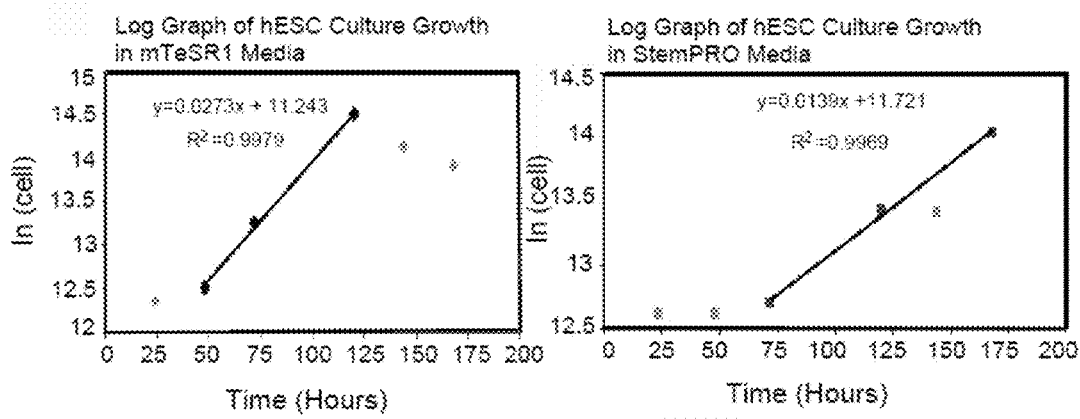
FIG. 59. Comparison of doubling time of hESC on microcarriers in mTeSR1 vs StemPRO media.
Figure 60:
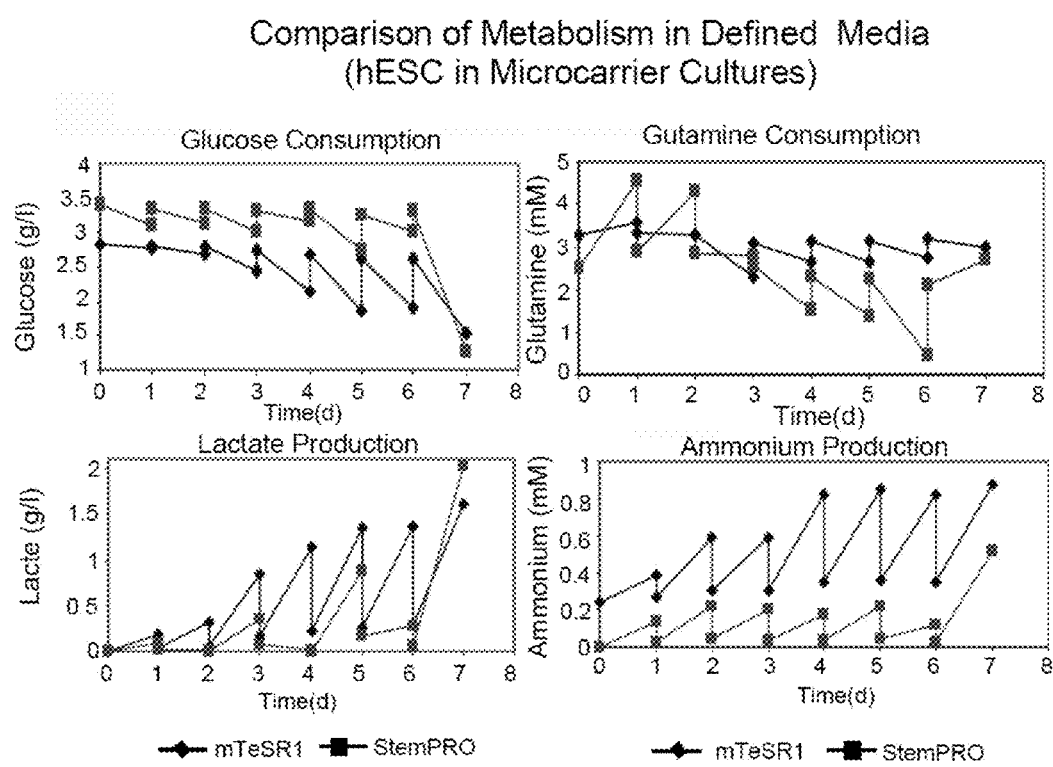
FIG. 60. Comparison of metabolism in defined media (mTeSR1 vs StemPRO) for hESC microcarrier cultures.
Figure 61:
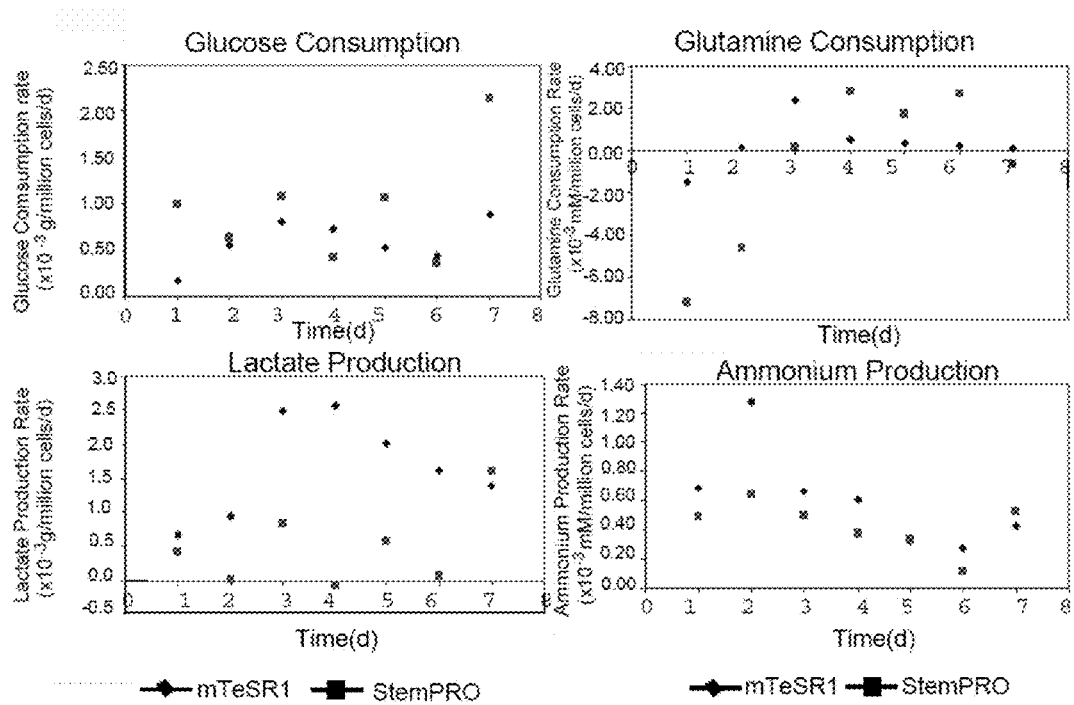
FIG. 61. Comparison of metabolism in defined media (mTeSR1 vs StemPRO) for hESC microcarrier cultures.
Figure 62:
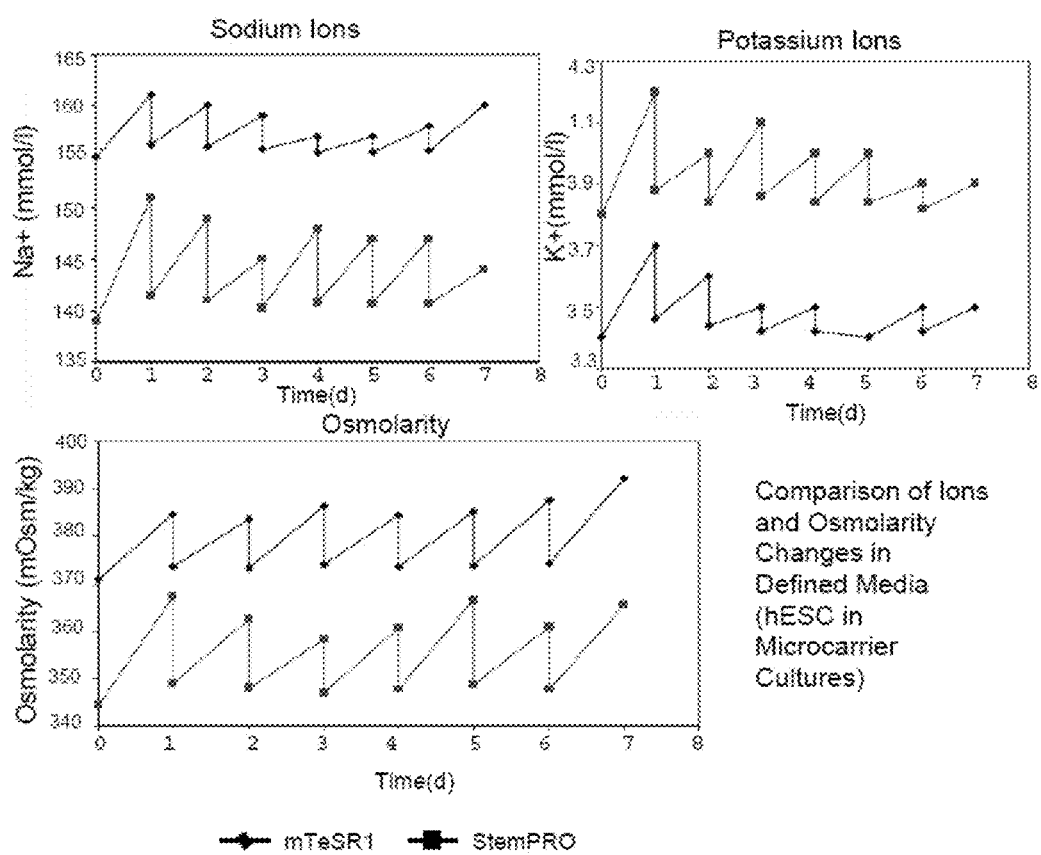
FIG. 62. Comparison of ions and osmolarity in defined media (mTeSR1 vs StemPRO) for hESC microcarrier cultures.

Serum Free Media Cellulose Microcarrier Cultures of hESC with Amino Acid Metabolism Data FIG. 58 shows microcarrier cultures of hESC in 2 serum free media, mTeSR1 and StemPRO with cell numbers reaching 2 and 1.5 million respectively, after being seeded at $2-2.7 \times 10^5$ cells. pH drops to about 6.7 indicating active cell growth over the 7 days. FIG. 59 compares the growth rate and doubling time of mTeSR1 (BD Biosciences) and StemPRO (Invitrogen) microcarrier cultures. mTeSR1 was observed to have a faster doubling time of 25 hours vs. StemPRO of 49 hours. FIG. 60 compares the metabolism of glucose and glutamine consumption as well as lactate and ammonium production for the 2 serum free media. The specific glucose and glutamine consumption rates and ammonium production rates appear to be similar for the 2 media, except for the initial stage when there was glutamine production from Glutamax in StemPRO media. However lactate production rates are higher for mTeSR1 compared to StemPRO microcarrier cultures (FIG. 61). There is also an increase in sodium and potassium ions which contributes to the increase in osmolarity of the spent media, with mTeSR1 having the higher osmolarity (FIG. 62).

Figure 63A:
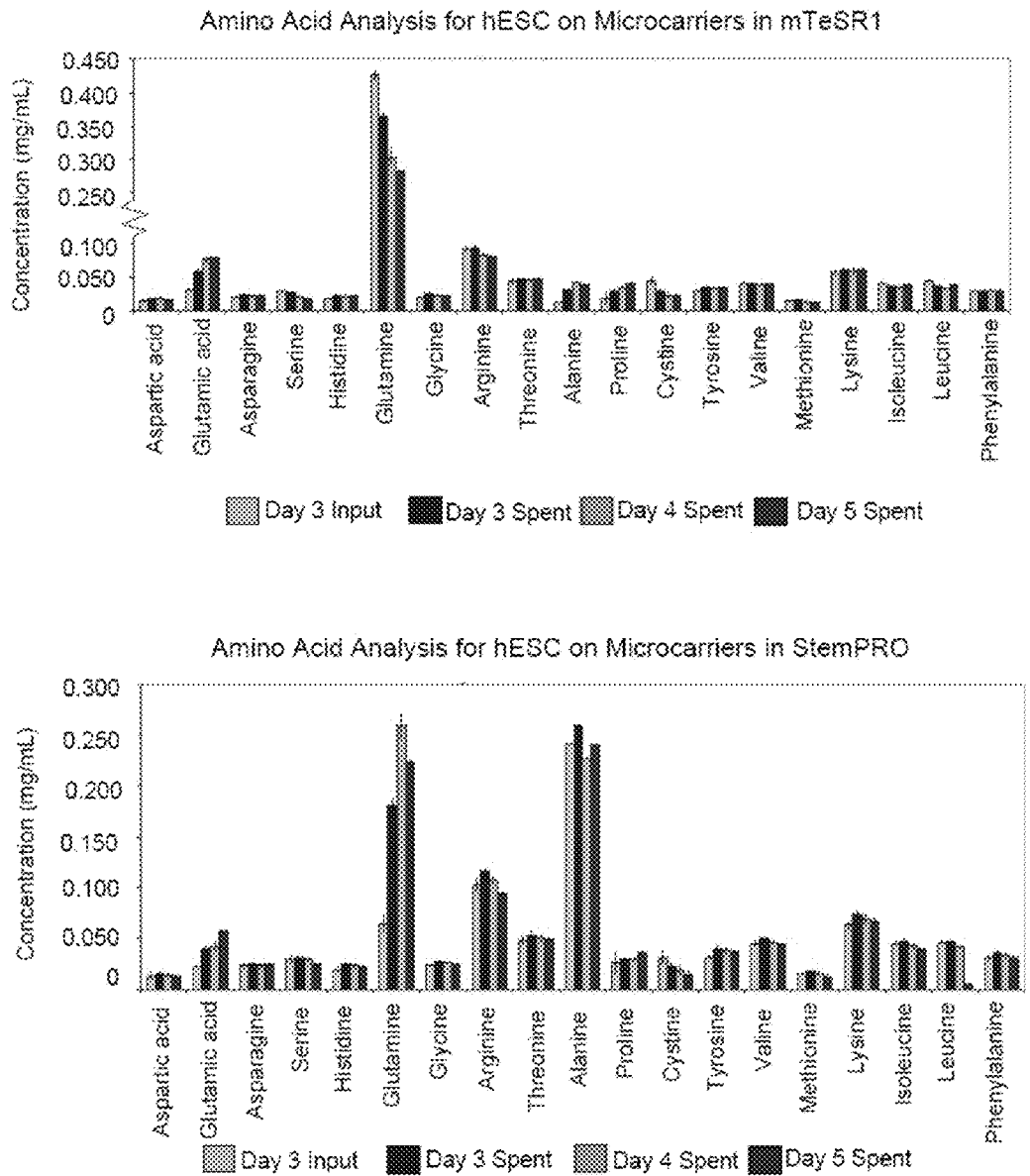
FIG. 63. Amino acid analysis in defined media (mTeSR1 vs StemPRO) for hESC microcarrier cultures.
Figure 64A:
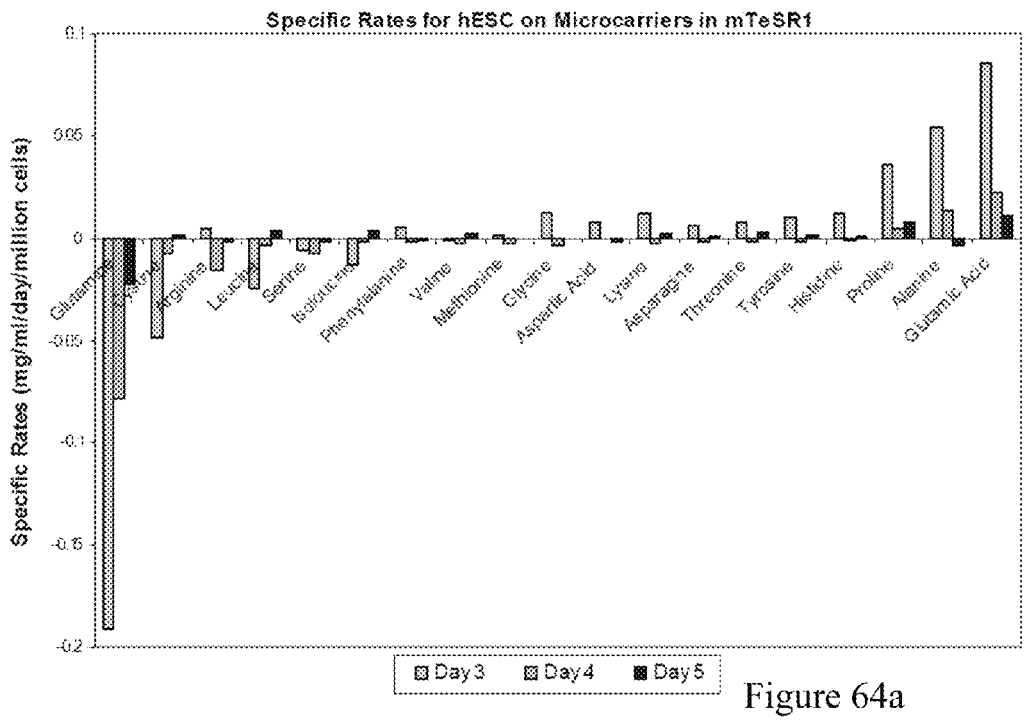
FIG. 64. (a) Consumption rates of amino acids for hESC microcarrier cultures in mTeSR1. (b) Consumption rates of amino acids for hESC microcarrier cultures in StemPRO.
Figure 64B:
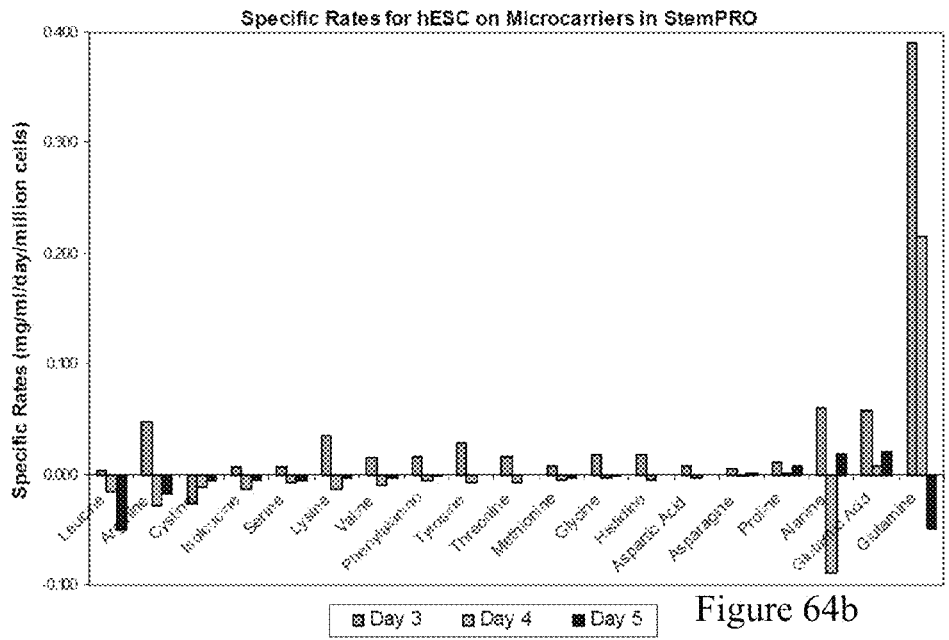

Table 1 summarises the amino acids that are consumed and those that are produced in both mTeSR1 and StemPRO media. The amino acids which were consumed were arginine, cystine, glutamine, isoleucine, leucine, methionine and serine. Those that were produced were alanine, glutamic acid and proline, whilst the rest did not change significantly. Table 2 provides more detailed information on the individual levels of these amino acids that are consumed and produced by hESC in mTeSR1 and StemPRO serum free media, respectively. The data confirms that arginine, cystine, glutamine, isoleucine, leucine, methionine and serine are most significantly consumed and that alanine, glutamic acid and proline are the most significantly produced amino acids. FIG. 63 shows the concentration changes of the 20 amino acids over 3 days in mTeSR1 and StemPRO serum free media from which the specific consumption rates of the individual amino acids can be calculated which are shown in FIGS. 64a and 64b. As can be seen surprisingly, the vast majority of the amino acids are hardly consumed in the 2 media.

Figure 65:
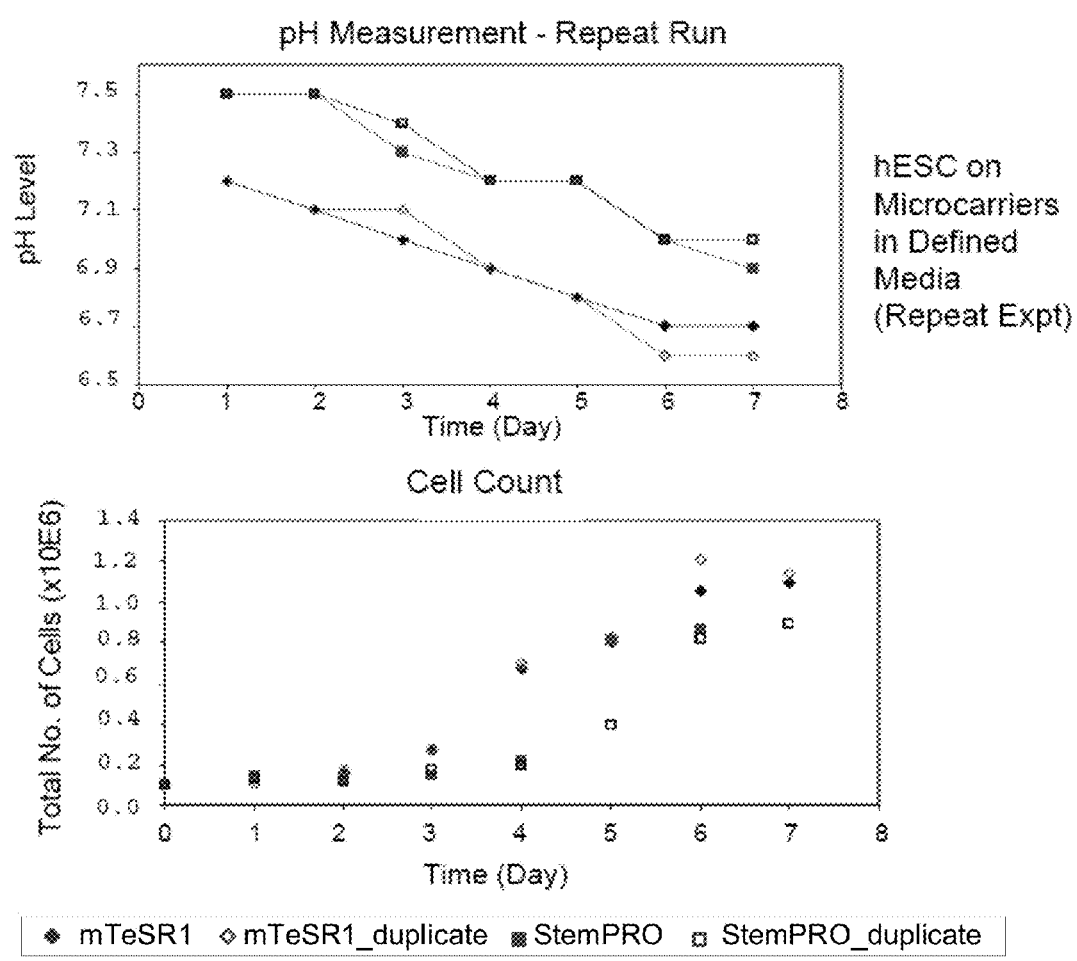
FIG. 65. pH and total no. of cells for hESC microcarrier culture in mTeSR1 and StemPRO.
Figure 66:
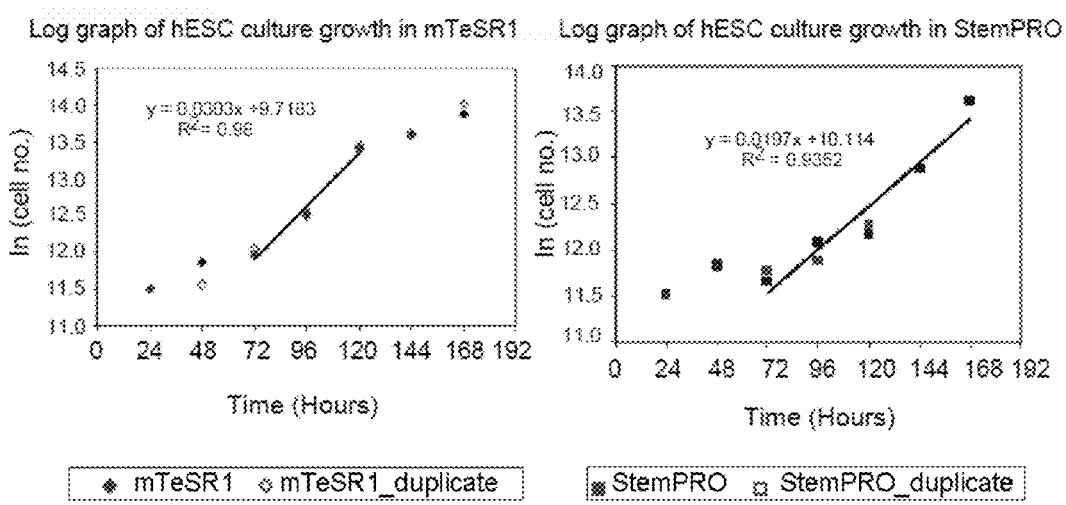
FIG. 66. Growth kinetics for hESC microcarrier culture in mTeSR1 and StemPRO.

FIG. 65 shows a repeat experiment of microcarrier cultures in StemPRO and mTeSR1 serum free media with both media reaching a similar cell number of 1 million cells at the end of 7 days. The pH drop in mTeSR1 appears to reach a lower point than StemPRO media. FIG. 66 confirms that mTeSR 1 has a faster doubling time of 23 hours compared to StemPRO media (35 hours) in the microcarrier cultures.

Example 32

Spinner Flask, Cellulose Microcarrier Culture of 2 hESC Cell Lines

Figure 67:
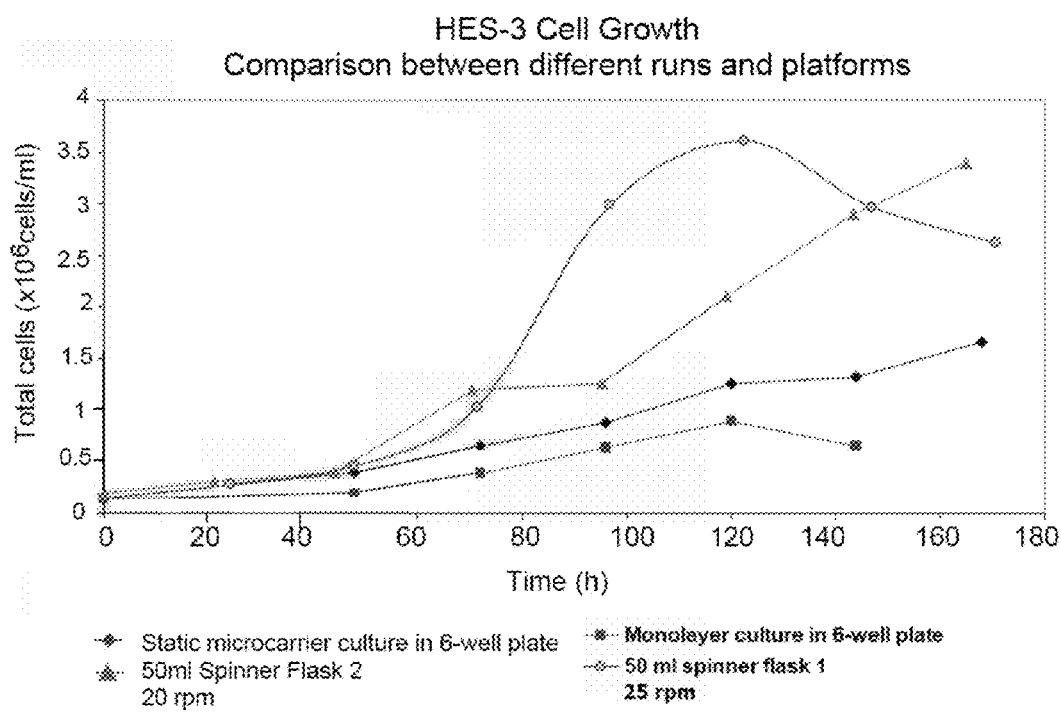
FIG. 67. HES-3 cell growth. Comparison of static microcarrier culture, 50 ml spinner flask at 20 rpm agitation, monolayer culture and 50 ml spinner flask at 25 rpm agitation.
Figure 68:
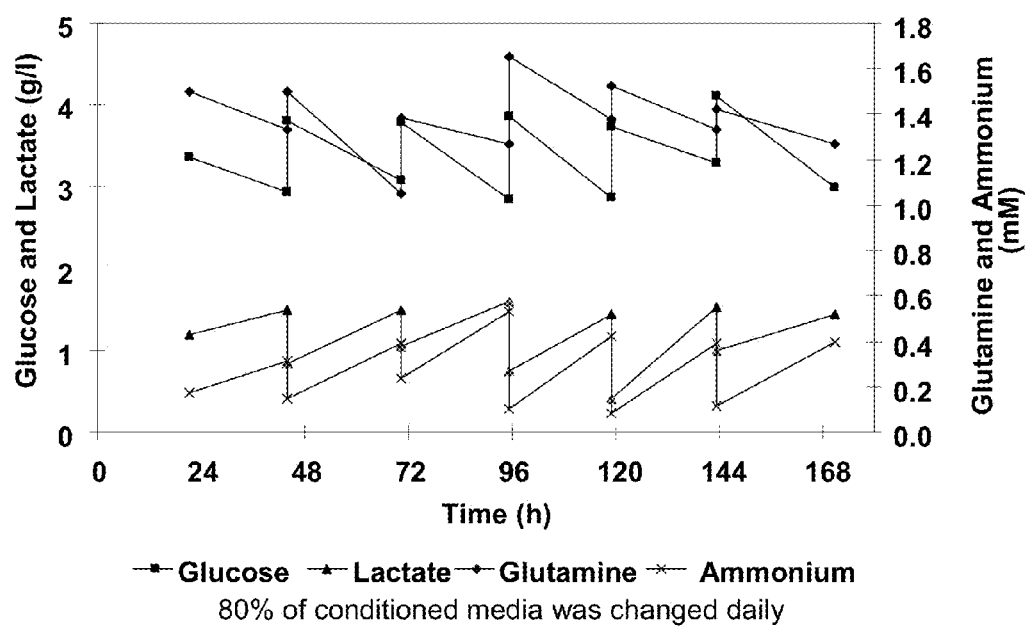
FIG. 68. Metabolite analysis of conditioned media from microcarrier spinner flask culture.
Figure 69:
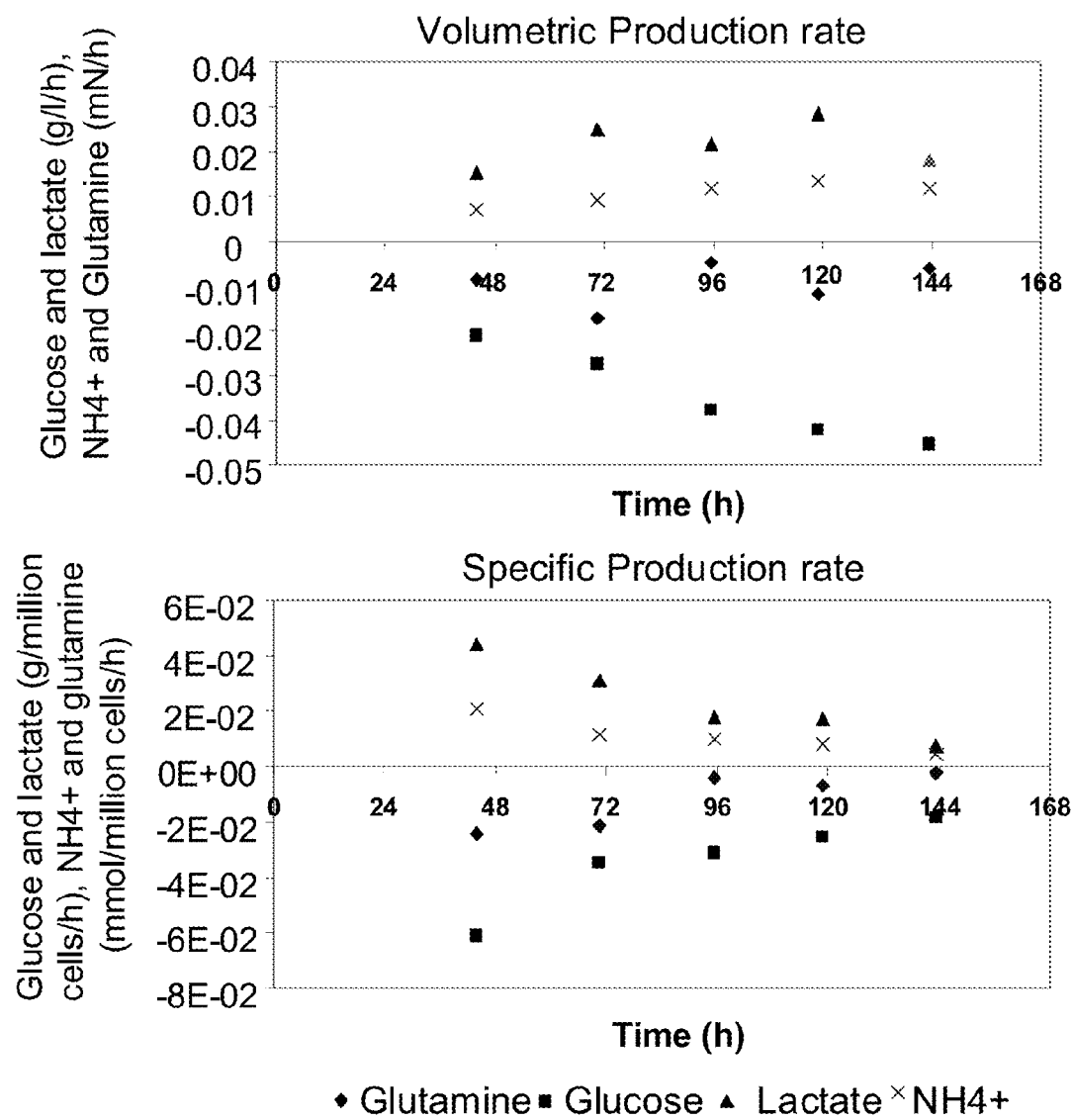
FIG. 69. Specific metabolite production rates in conditioned media microcarrier spinner flask culture.
Figure 70:
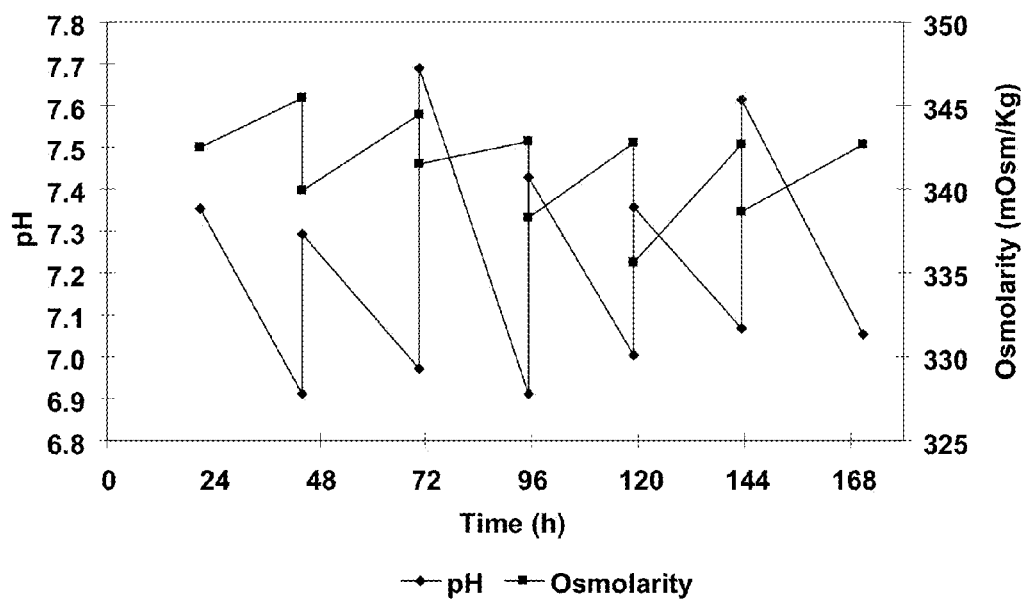
FIG. 70. pH and osmolarity conditions from microcarrier spinner flask culture.
Figure 71:
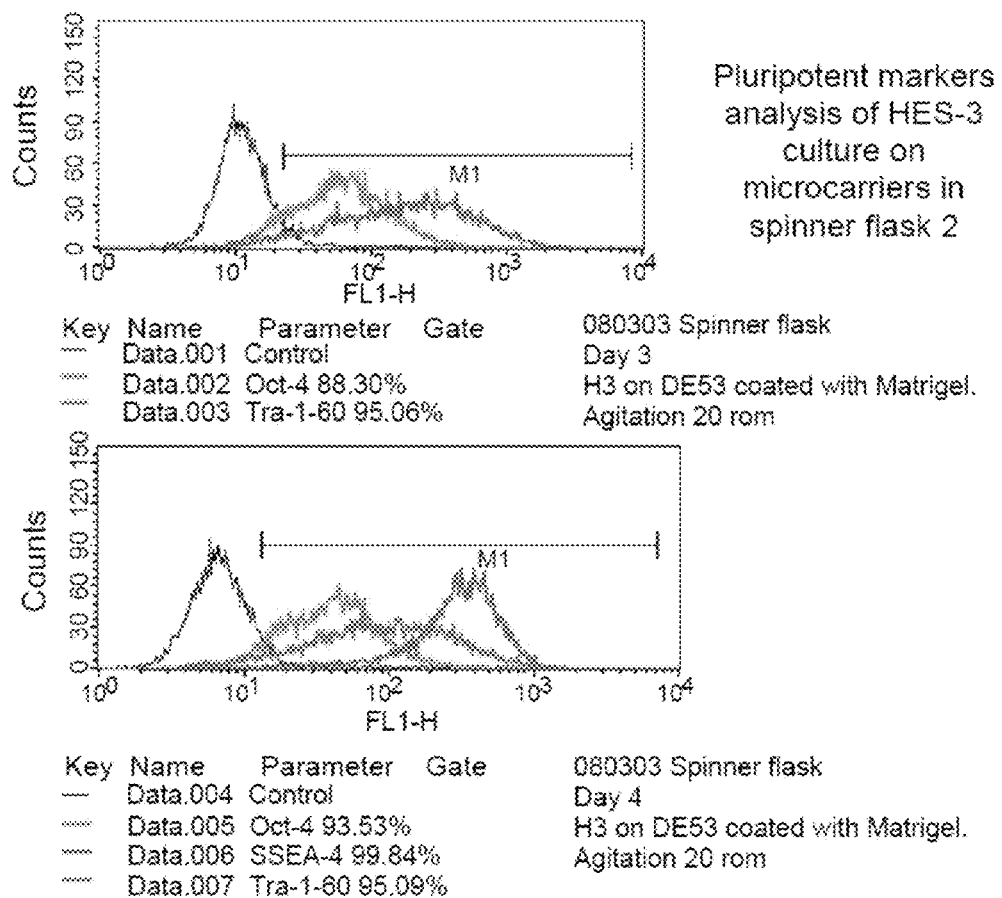
FIG. 71. Expression of Oct4, SSEA4 and TRA-1-60 in microcarrier spinner flask culture. Pluripotent markers Oct4, SSEA4 and TRA-1-60 remain high on days 3 and 4.

FIG. 67 shows a second spinner flask culture of the HES-3 cell line, which once again is able to achieve a cell density of about 3.5 million cells/ml by 7 days, comparable to the first spinner flask experiment. These cell densities are again significantly higher than the static microcarrier cultures and 2D colony cultures. FIG. 68 shows the consumption of glucose and glutamine and the production of lactate and ammonium for the second spinner flask culture. These concentrations are translated into volumetric and specific consumption rates of glucose and glutamine and the production rates of lactate and ammonium, shown in FIG. 69. FIG. 70 further shows the sharp pH drops each day before and after feeding with conditioned media and likewise the increases in osmolarity of the media each day. FIG. 71 shows that the pluripotent markers Oct4, SSEA4 and TRA-1-60 remain high on days 3 and 4 while the morphology of the hESC remain as tight aggregates on the microcarriers on days 4 and 5 as shown in FIG. 72.

Figure 73:
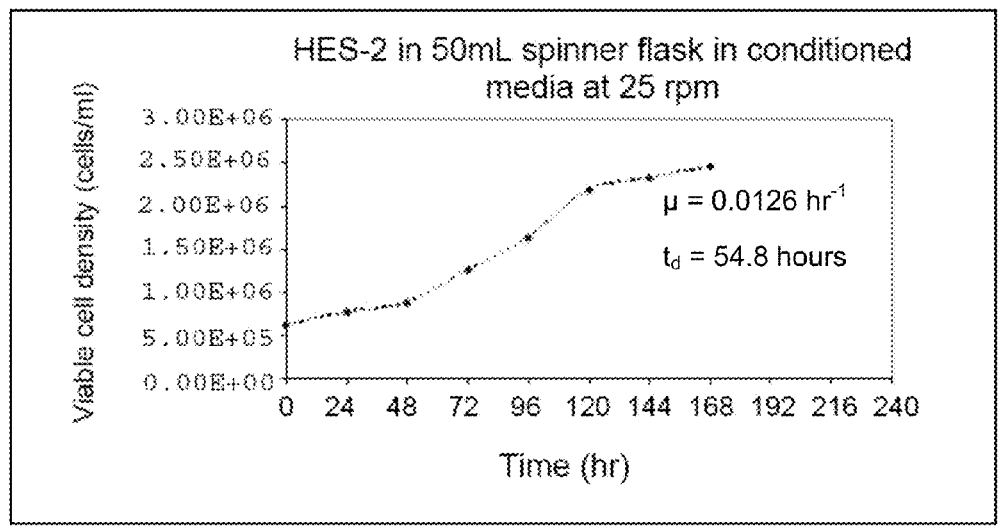
FIG. 73. HES-2 Growth in microcarrier spinner flask culture.
Figure 74:
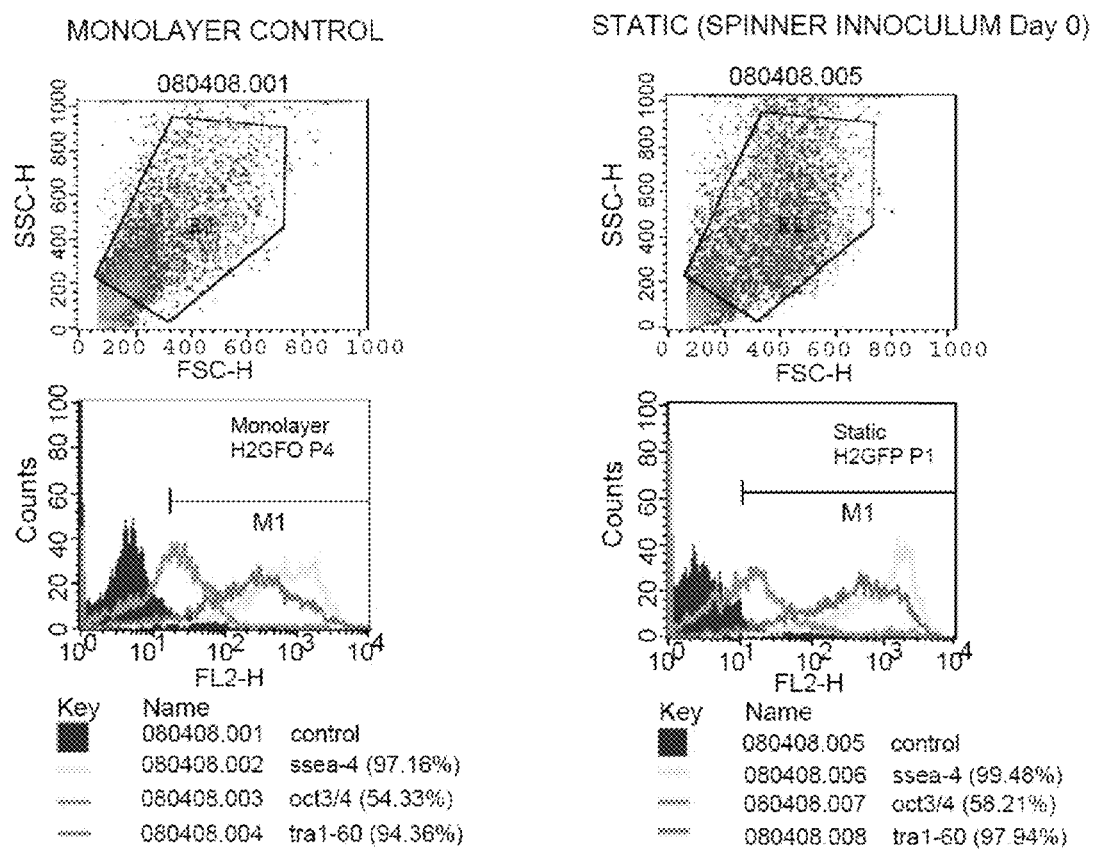
FIG. 74. Expression of pluripotent markers Oct4, SSEA4 and TRA-1-60 in microcarrier spinner flask culture were equivalent to the 2D colony control at the start of the spinner culture.
Figure 75:
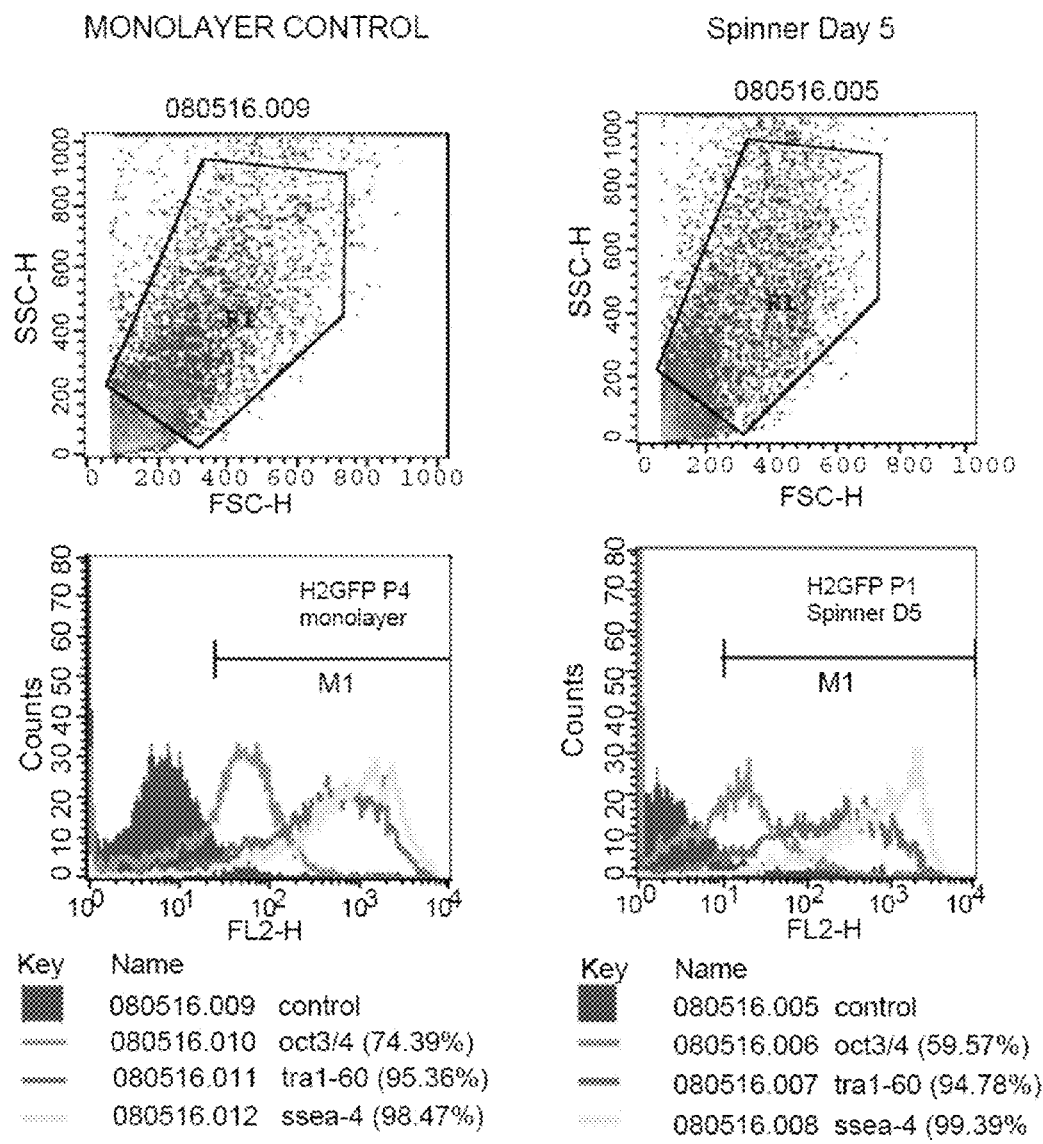
FIG. 75. Expression of pluripotent markers Oct4, SSEA4 and TRA-1-60 in microcarrier spinner flask culture continue to be high and equivalent to the control static cultures on days 5 and 7 when peak cell densities were achieved.

FIG. 73 shows another cell line HES-2 grown on microcarriers in spinner flask culture stirred at 25 rpm, which was able to achieve 2.5 million cells/ml, with a doubling time of approximately 55 hours. FACS analysis of the cells show that the expression of pluripotent markers Oct4, SSEA4 and TRA-1-60 were equivalent to the 2D colony control at the start of the spinner culture (FIG. 74). Expression of these markers continue to be high and equivalent to the control static cultures on days 5 and 7 when peak cell densities were achieved, as shown in FIG. 75. hESC form large aggregates of cells around the microcarriers on days 5 and 7 as shown in FIG. 76.

It has been demonstrated that spinner flask cultures with microcarriers is a scaleable method of expanding hESC in a bioreactor. If a density of 3.5 million cells/ml is achieved in a 100 ml spinner flask this would be equivalent to producing hESC in 175 organ culture dishes (OCD) each with 2 million cells/ml as shown in FIG. 77.

Example 33

Figure 78:
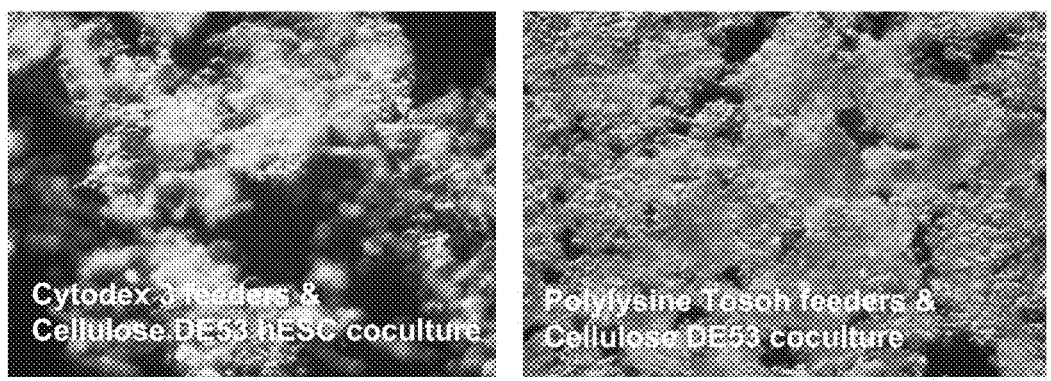
FIG. 78. hESC grown on cellulose microcarriers together with mouse feeders on Cytodex, and polylysine coated Tosoh beads coated with feeders and co cultured with hESC on cellulose DE53 microcarriers.
Figure 79:
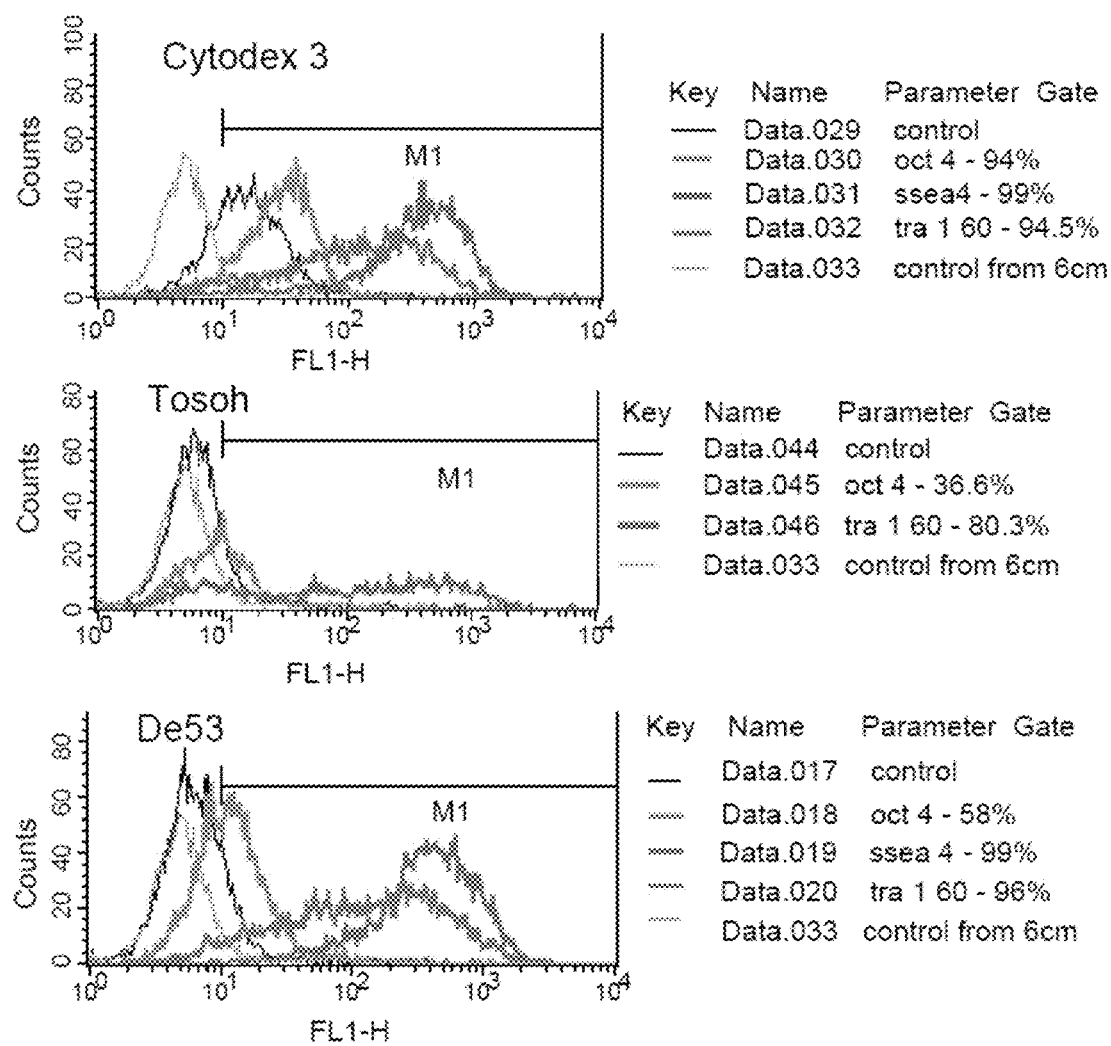
FIG. 79. Oct4, SSEA4 and TRA-1-60 at passage 1 for the 3 co-cultures on hESC with feeder cells on Cytodex 3, Tosoh and DE53 microcarriers respectively.
Figure 80:
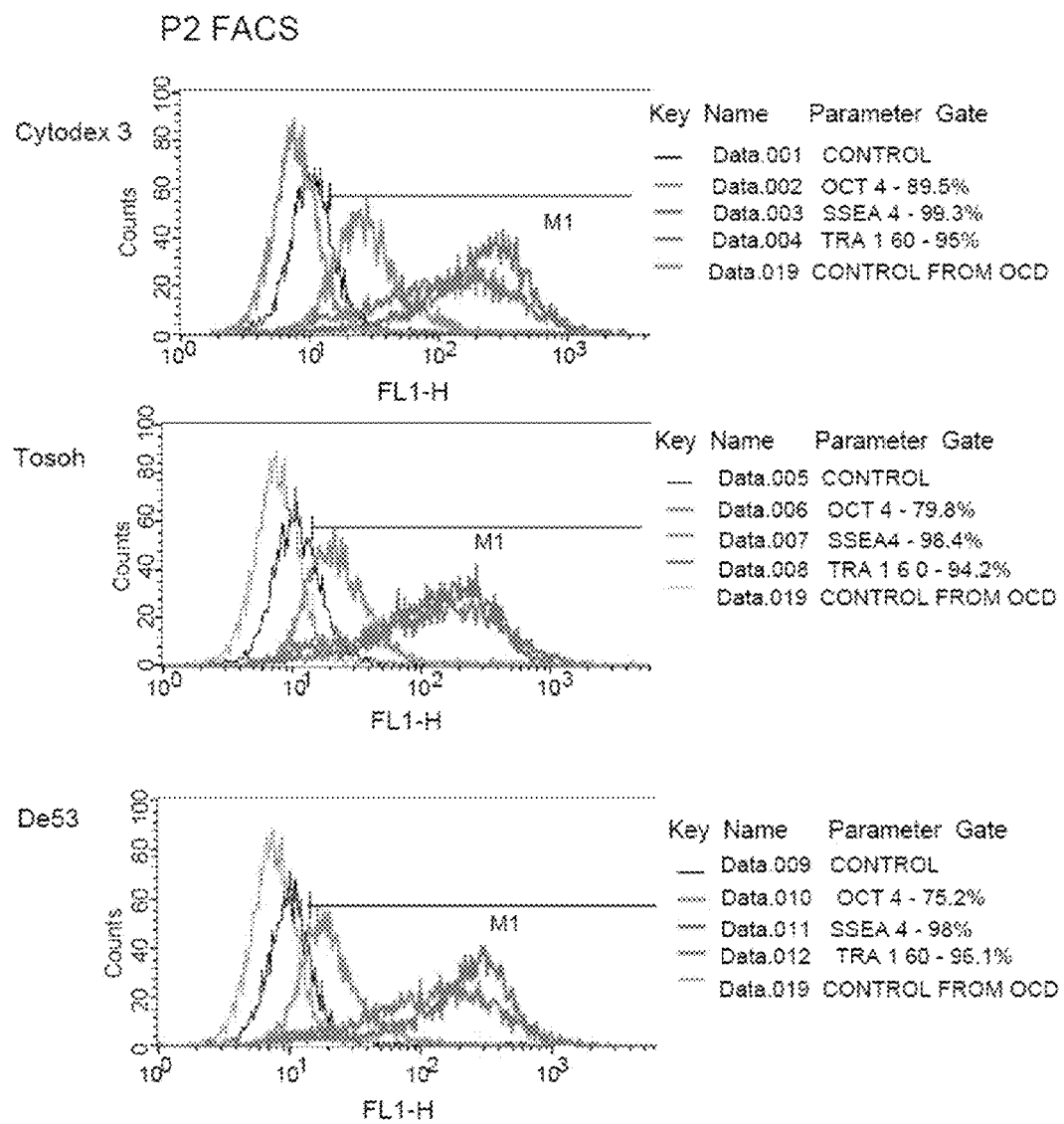
FIG. 80. Robust expression of Oct4, SSEA4 and TRA-1-60 at passage 2 in the 3 different co-cultures with Cytodex 3, Tosoh and DE53 microcarriers which are equivalent or better than the control with matrigel coated microcarriers (see FIG. 79).
Figure 81:
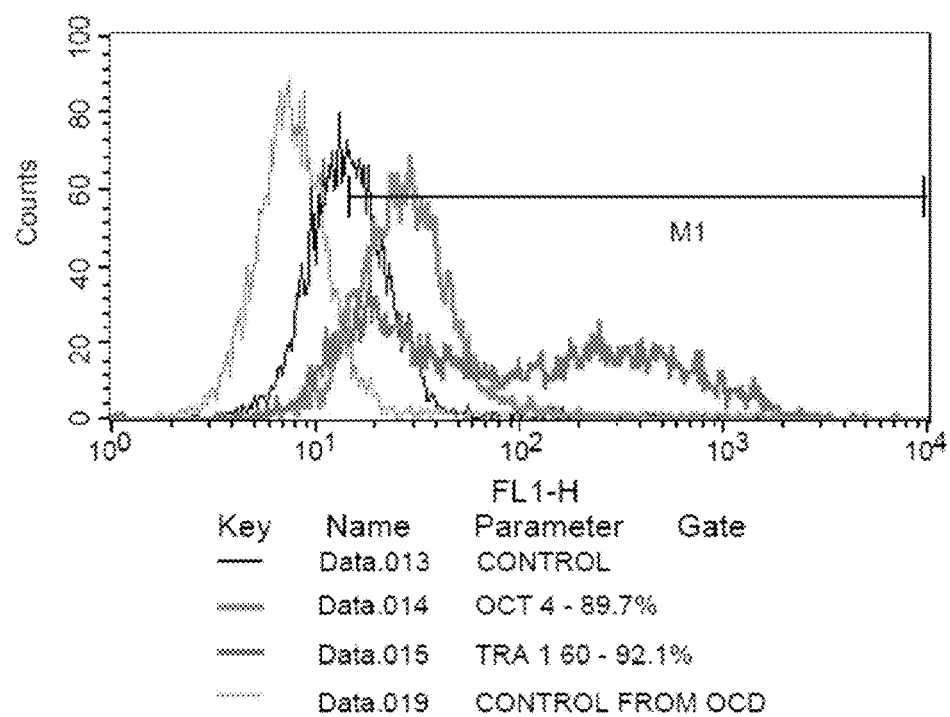
FIG. 81. Oct4, and TRA-1-60 expression from hESC on Matrigel coated DE53 microcarriers.

Cocultures of Feeders on Spherical or DE53 Microcarriers with hESC Grown on DE53 Cellulose Microcarriers We also determined if hESC on cellulose DE53, could be supported with co cultures of feeders on spherical Cytodex 3 and Tosoh microcarriers. Feeder cells were attached to uncoated microcarriers and hESC were attached to Matrigel coated microcarriers. FIG. 78 shows pictures of hESC grown on cellulose microcarriers together with mouse feeders on Cytodex, and polylysine coated Tosoh beads coated with feeders and co cultured with hESC on cellulose DE53 microcarriers. Table 3 indicates the cell densities of hESC in co cultures with feeders on the 2 spherical microcarriers as well as co culture on cellulose DE53 microcarriers at P0 and P1 passages. Cell numbers were equivalent to the control of hESC on DE53 microcarriers coated with matrigel. FIG. 79 shows the FACS at P1 for the 3 co-cultures on hESC with feeders on Cytodex 3, Tosoh and DE53 microcarriers respectively. High expression levels of the 3 pluripotent markers were observed for the Cytodex 3 co cultured with DE53 and co cultures of DE53. Table 4 shows that cell numbers of hESC in the 3 co cultures were about 2 times higher compared to the control on matrigel coated microcarriers. FIG. 80 shows robust expression of the 3 pluripotent markers at passage 2 in the 3 different co cultures with Cytodex 3, Tosoh and DE53 microcarriers which are equivalent or better than the control with matrigel coated microcarriers (FIG. 81).

Example 34 hESC Culture on Small and Large Spherical Tosoh Microcarriers

Next we tested if alternative large and small spherical Tosoh microcarriers could support hESC growth over the long term.

Figure 82:
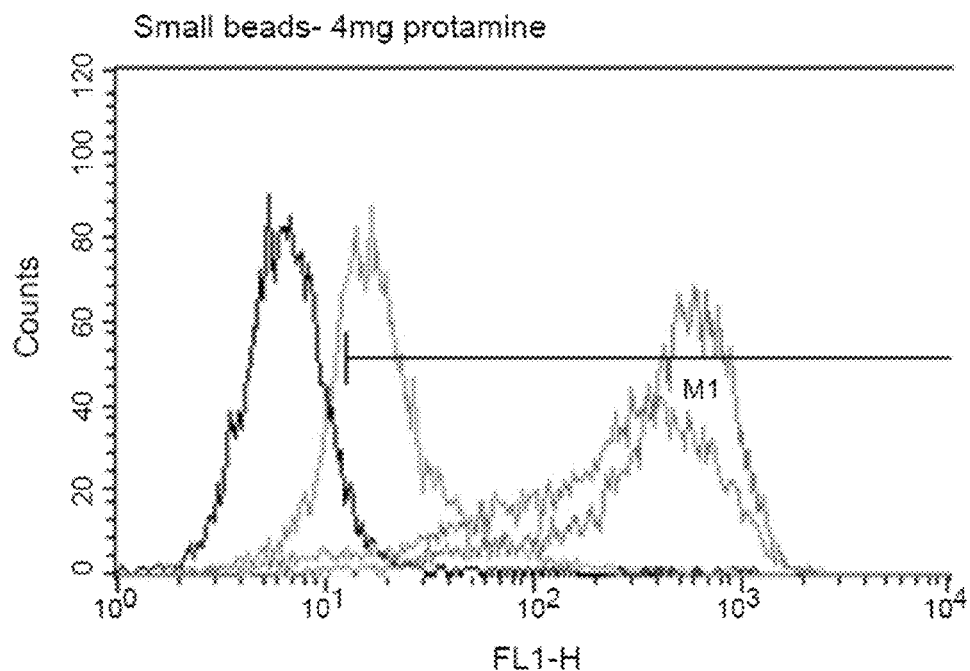
FIG. 82. Expression of pluripotent markers Oct4, SSEA4 and TRA-1-60 at passage P1 on Tosoh microcarriers (10 μm and 65 μm) with 4 mg protamine (10 μm), 0.2 mg protamine+Matrigel (10 μm), 4 mg protamine+Matrigel (10 μm), 4 mg protamine+Matrigel (65 μm).
Figure 82:
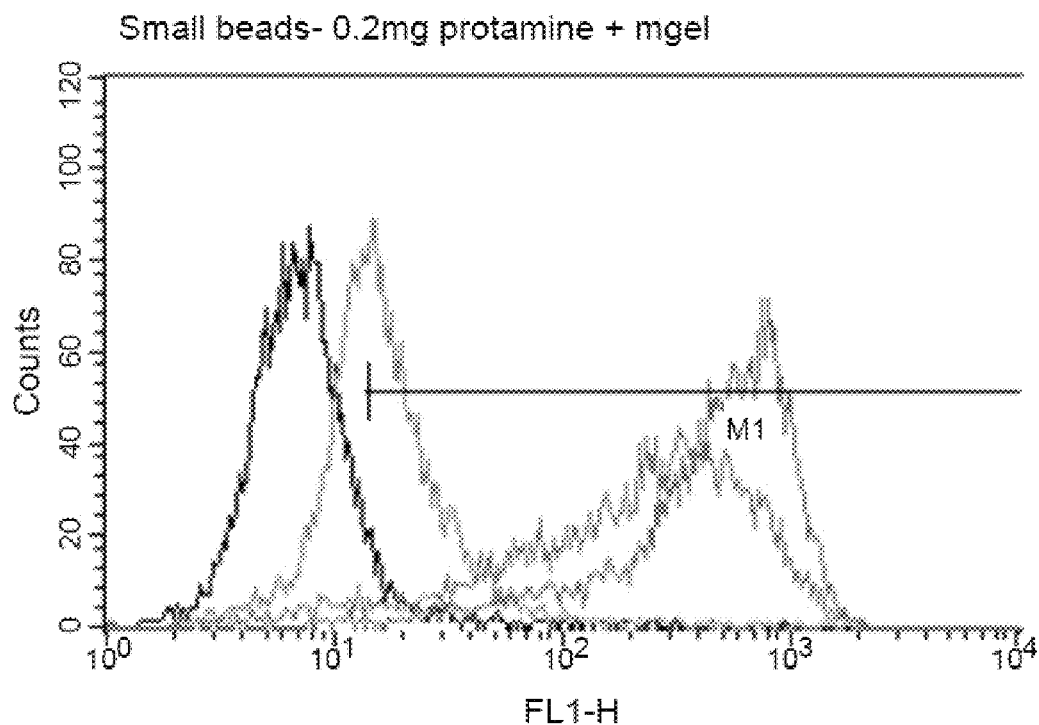
Figure 82:
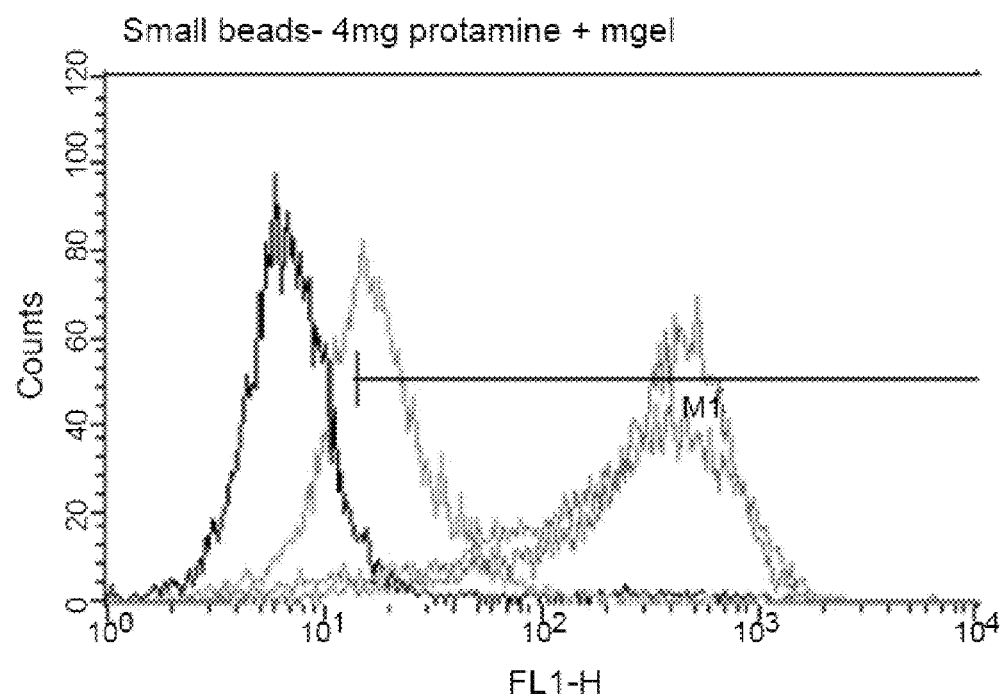
Figure 82:
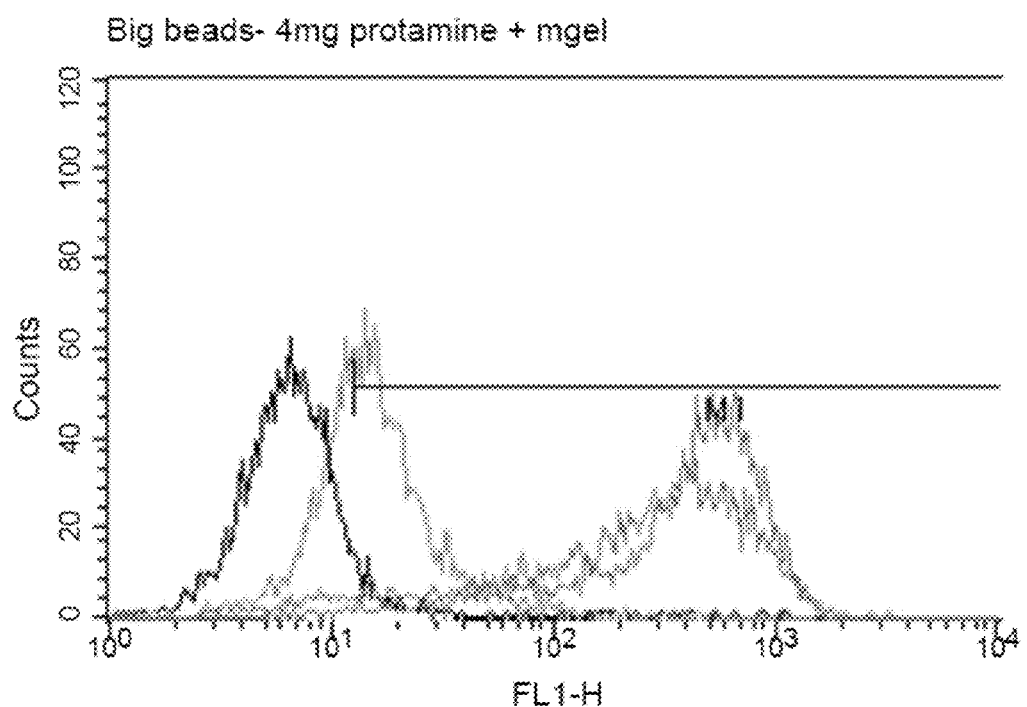
Figure 83A:
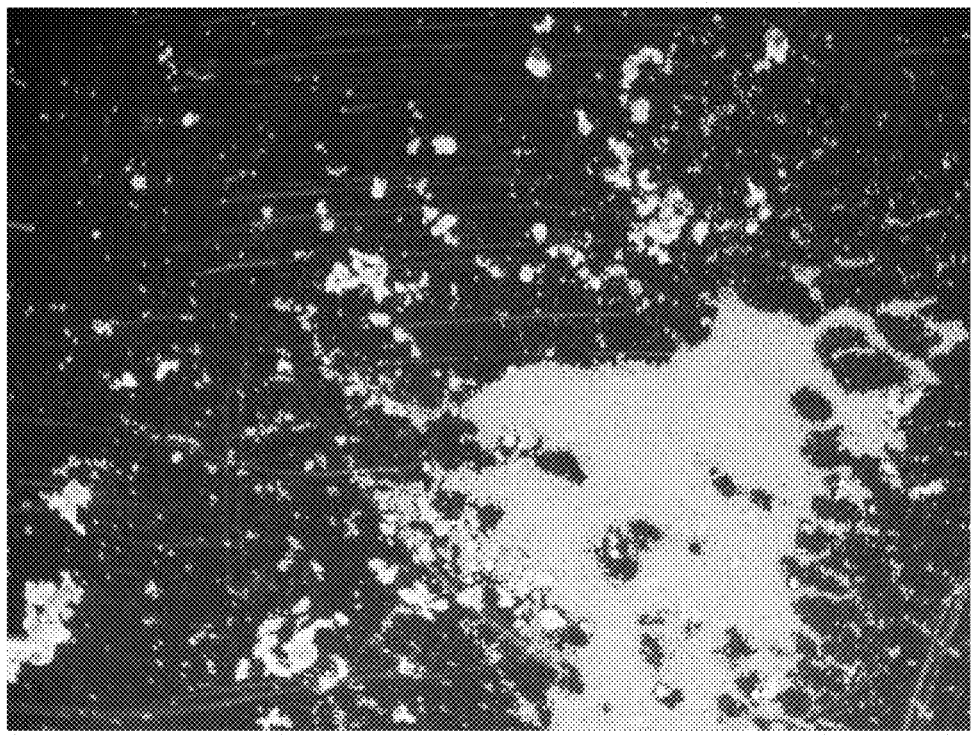
(FIG. 83A) Poly-L-Lysine only, (FIG. 83B) Matrigel coated Poly-L-Lysine (using concentrated matrigel stock), (FIG. 83C) Matrigel coated Poly-L-Lysine (using routine microcarrier coating method, 30× dilution matrigel solution).
Figure 83B:
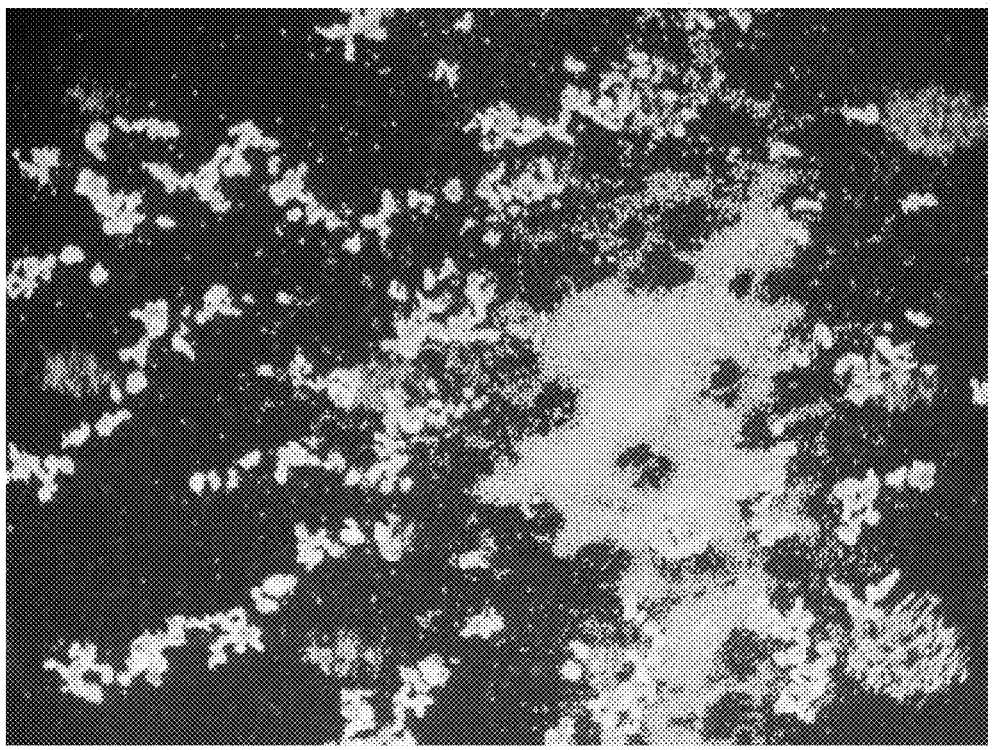
FIG. 83. Polylysine Tosoh beads without and with matrigel coatings at stock and 30× diluted concentrations.
Figure 83C:
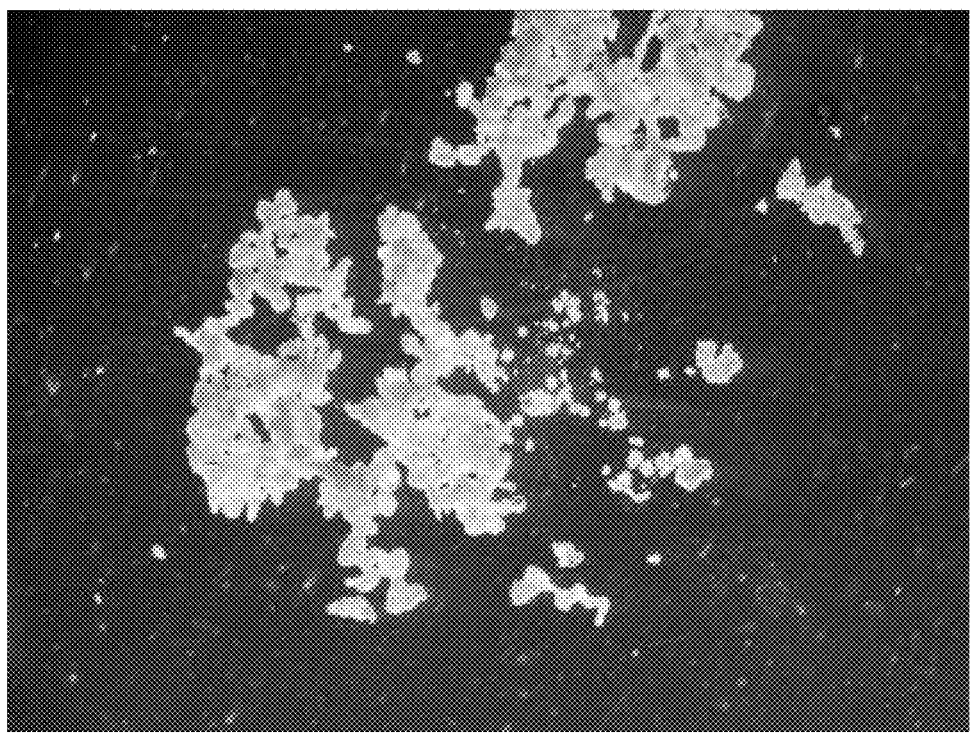
Figure 84A:
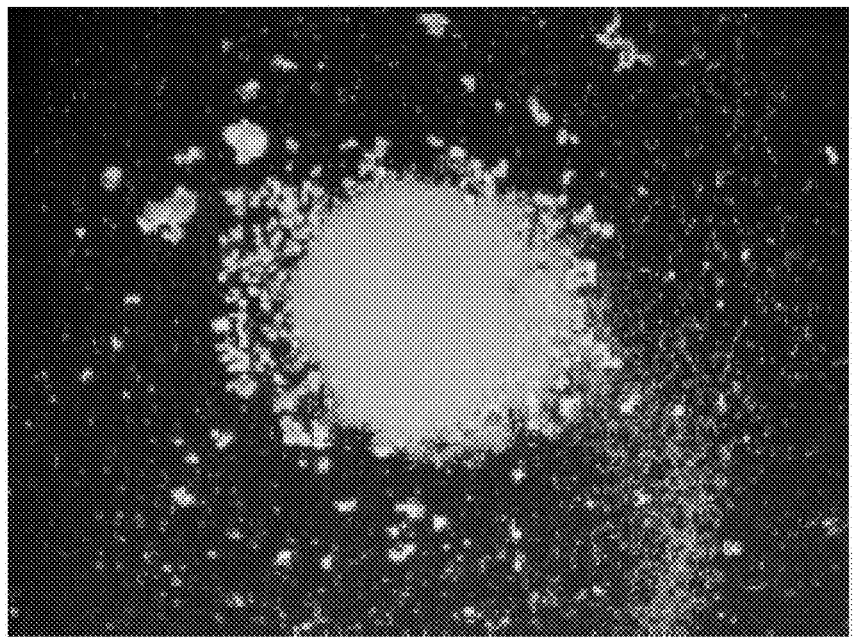
(FIG. 84A) Protamine only, (FIG. 84B) Matrigel coated Protamine beads (using concentrated matrigel stock), (FIG. 84C) Matrigel coated Protamine beads (using routine microcarrier coating method, 30× dilution matrigel solution).
Figure 84B:
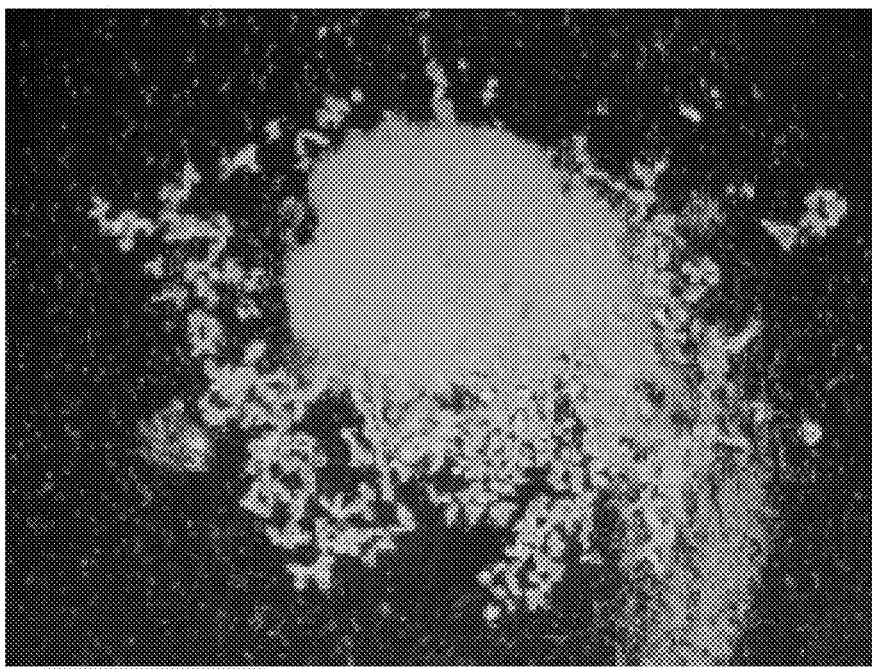
FIG. 84. Protamine Tosoh beads without and with matrigel coatings at stock and 30× diluted concentrations.
Figure 84C:
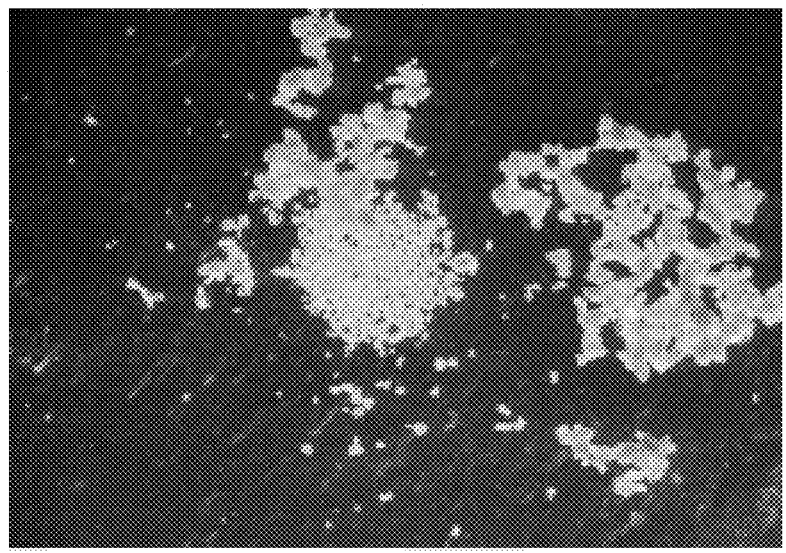

Table 5 shows both small (10 micron) large (65 micron) Tosoh microcarriers with and without matrigel coatings supported hESC growth at P0 and P1. FIG. 82 shows that the expression of pluripotent markers Oct4, SSEA4 and TRA-1-60 were high at passage P1 in these 4 conditions. FIG. 83 shows polylysine Tosoh beads without and with matrigel coatings at stock and 30× diluted concentrations. hESC formed the largest cell aggregates at 30× diluted matrigel concentration. FIG. 84 shows protamine Tosoh beads without and with matrigel coatings at stock and 30× diluted concentrations. Again 30× diluted matrigel coated beads formed larger hESC aggregates.

Example 35 hESC Culture on Large Tosoh Microcarriers with Matrigel

Figure 85:
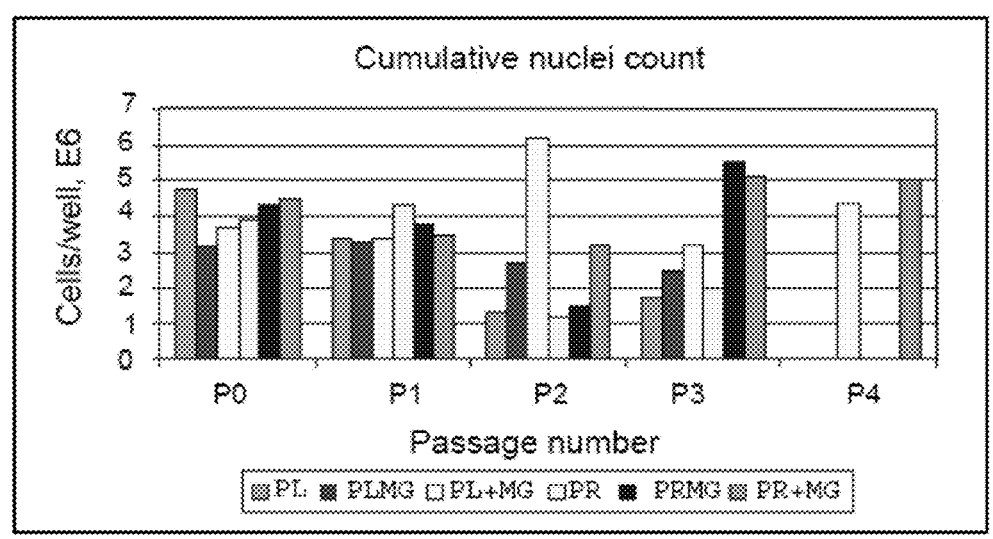
FIG. 85. Cell numbers of both polylysine and protamine coated Tosoh beads (65 micron) with and without matrigel for 4 passages.
Figure 86:
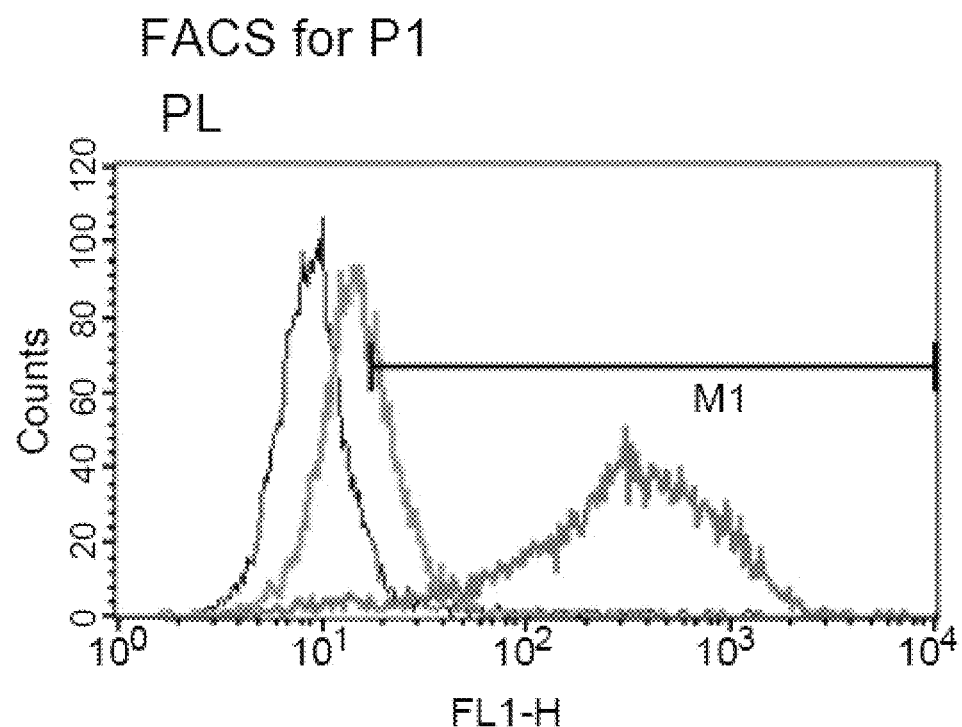
FIG. 86. Expression of pluripotent markers Oct4 and TRA-1-60 for hESC on polylysine Tosoh microcarriers without and with matrigel at passage 1.
Figure 86:
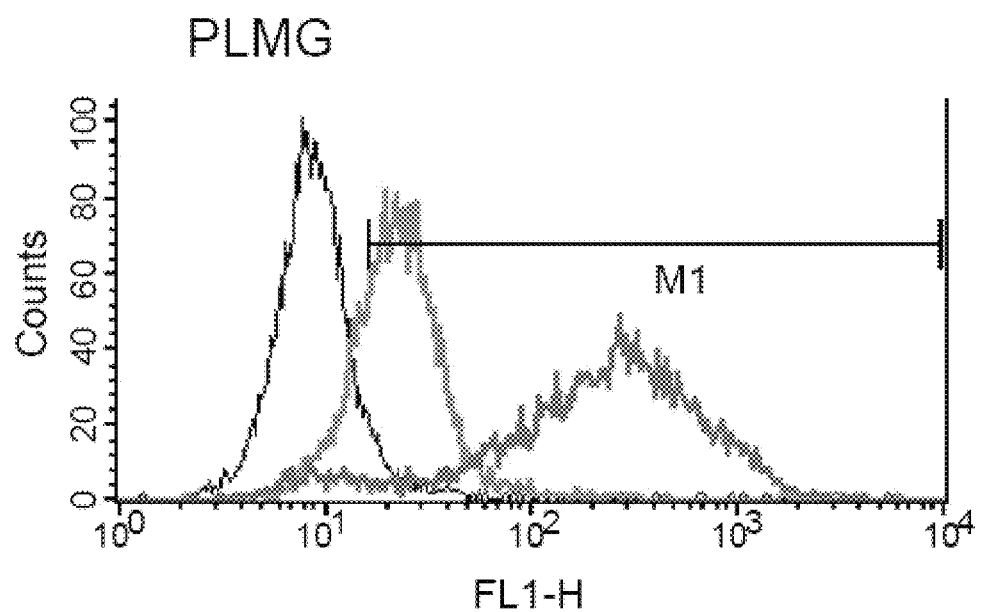
Figure 86:
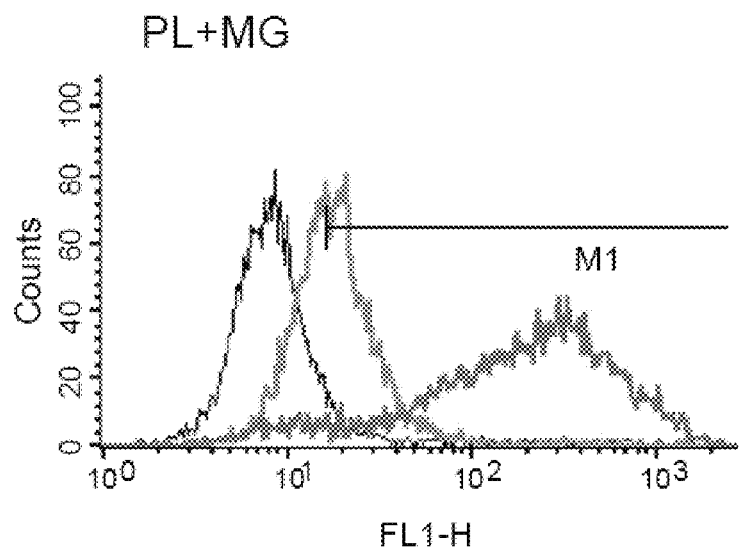
Figure 87:
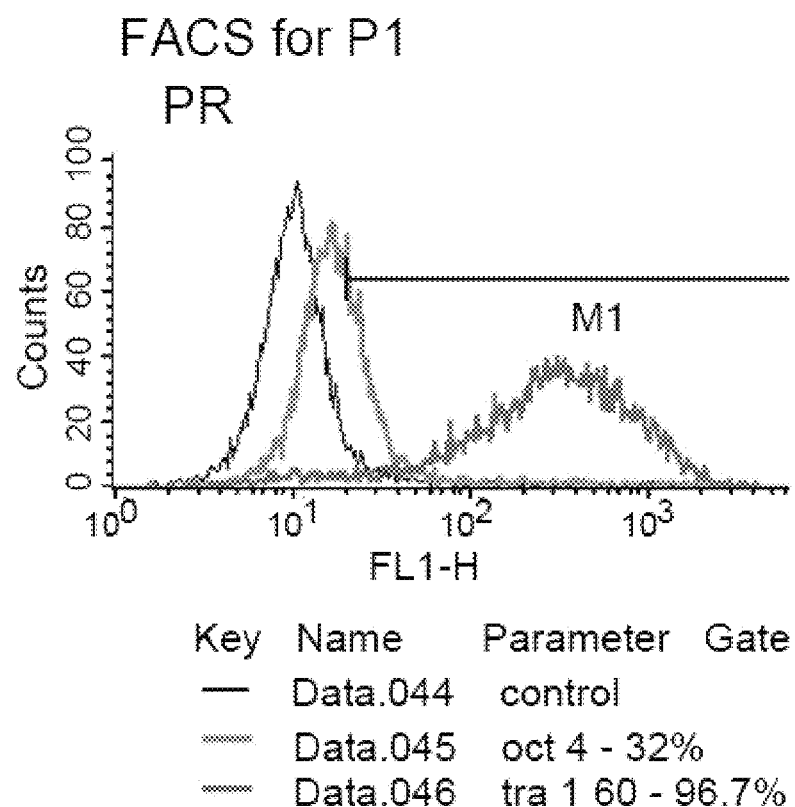
FIG. 87. Expression of pluripotent markers Oct4 and TRA-1-60 for hESC on protamine Tosoh microcarriers without and with matrigel at passage 1.
Figure 87:
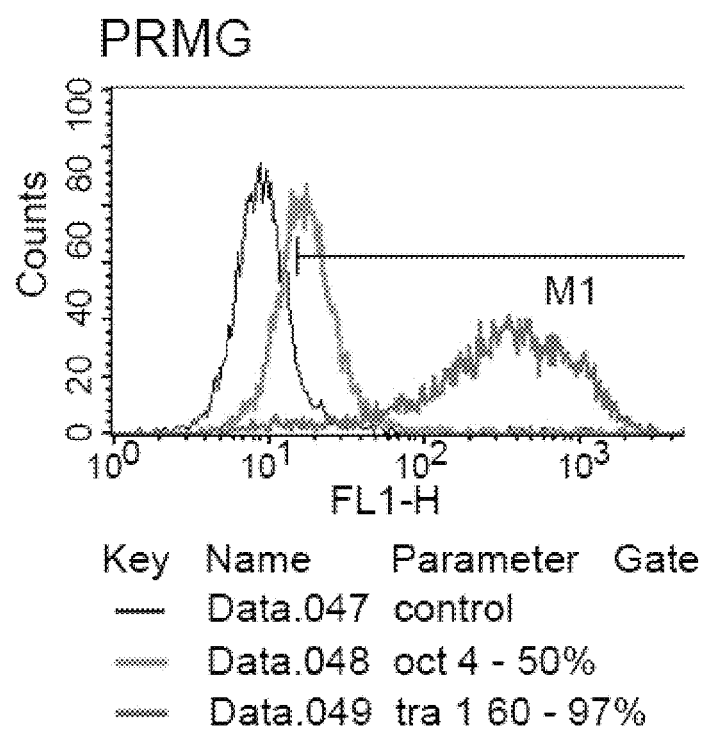
Figure 87:
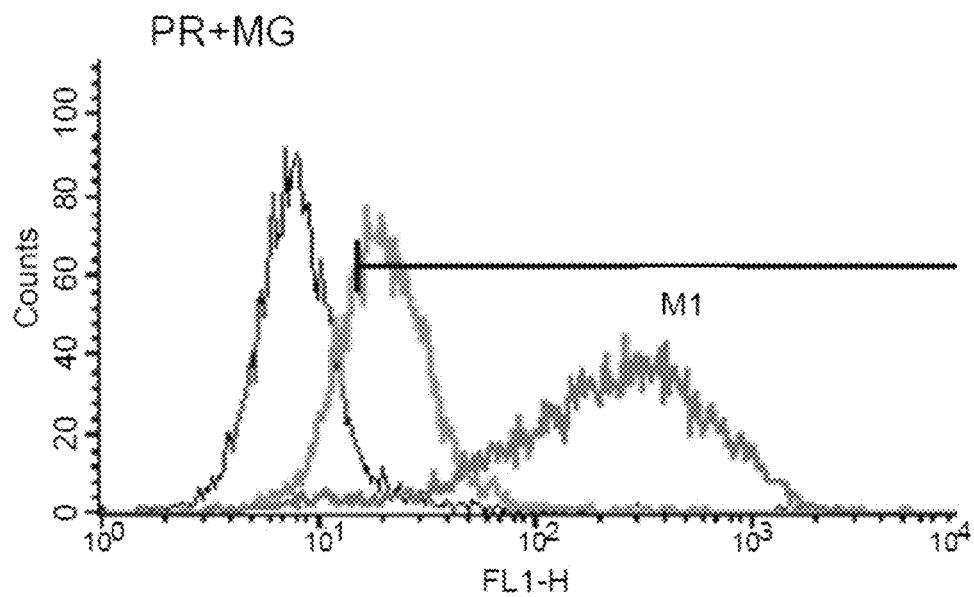
Figure 88:
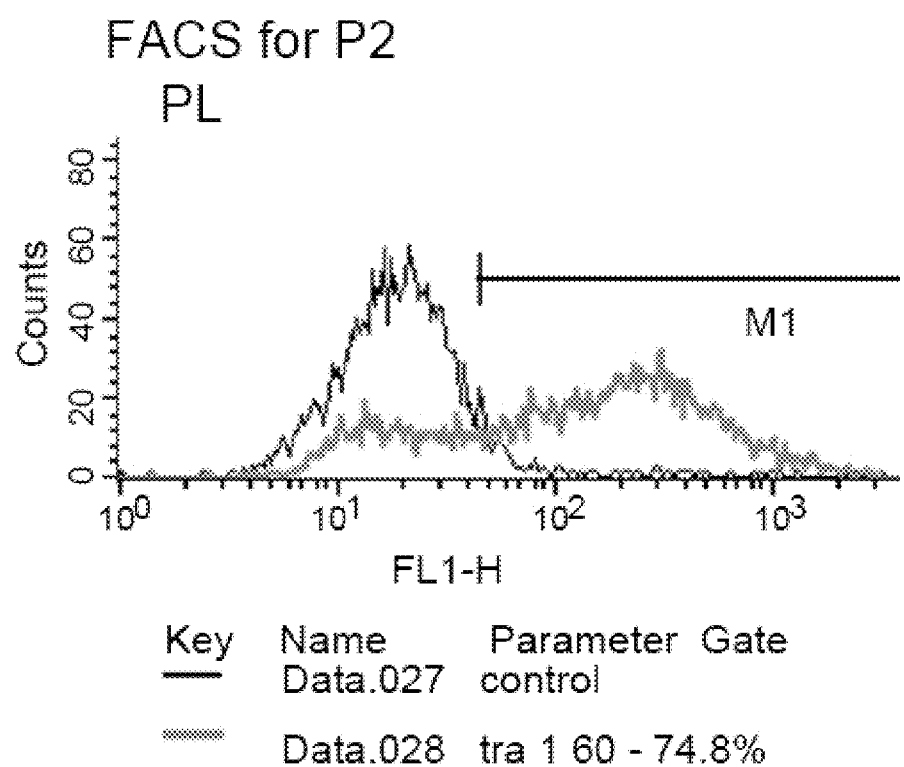
FIG. 88. Expression of pluripotent marker TRA-1-60 for hESC on matrigel coated polylysine Tosoh microcarriers at passage 2.
Figure 88:
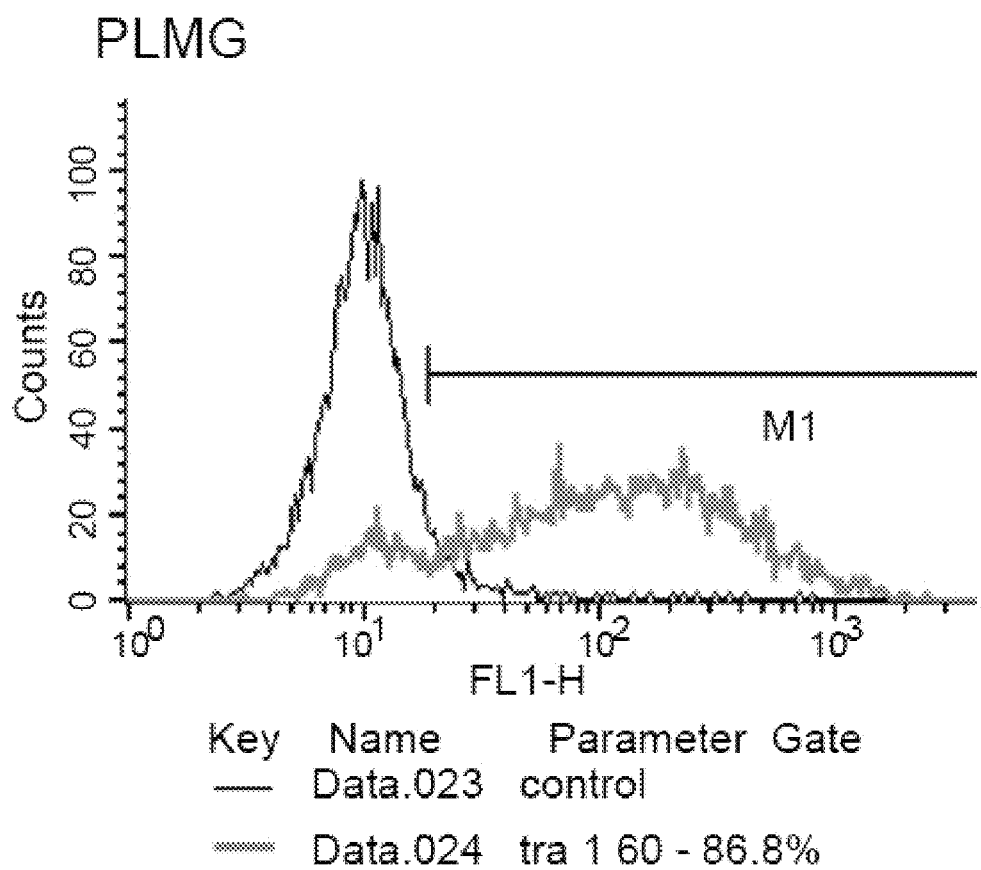
Figure 89:
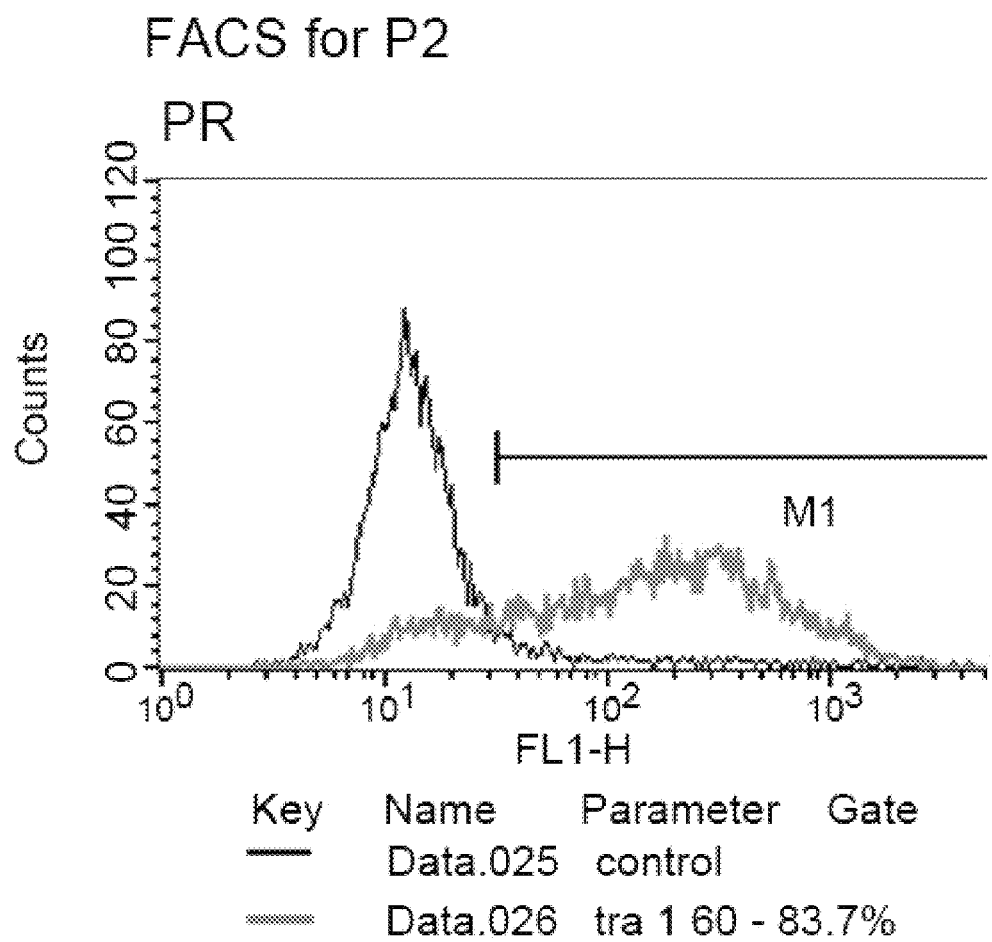
FIG. 89. Expression of pluripotent marker TRA-1-60 of hESC on matrigel coated protamine Tosoh microcarriers at passage 2.
Figure 89:
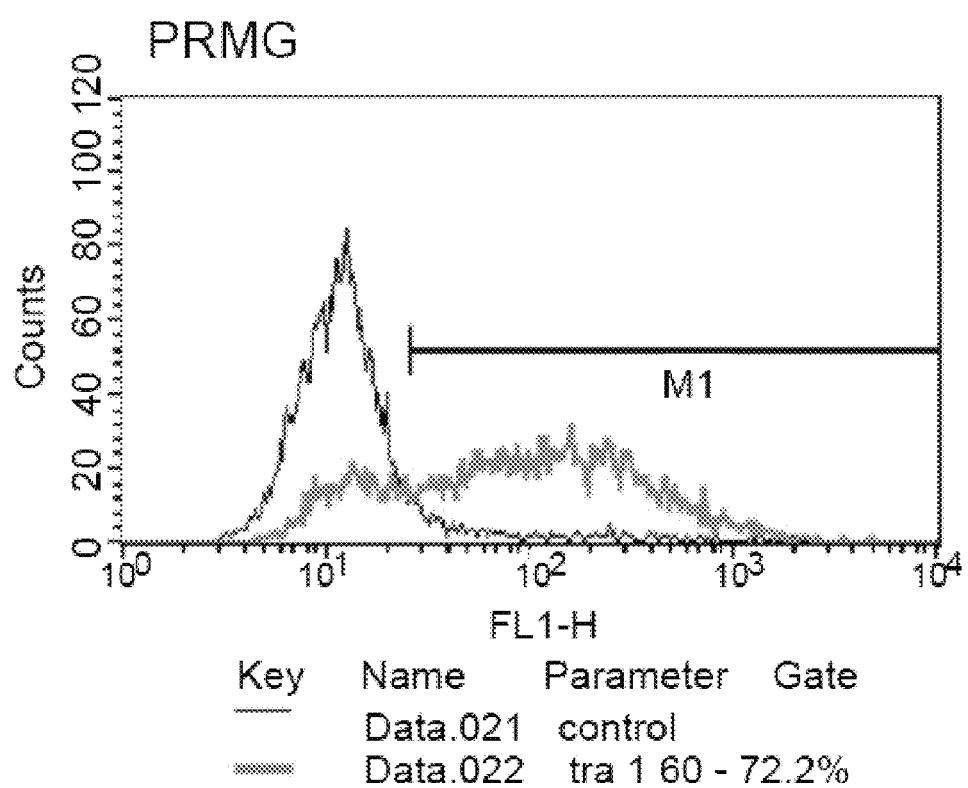
Figure 91:
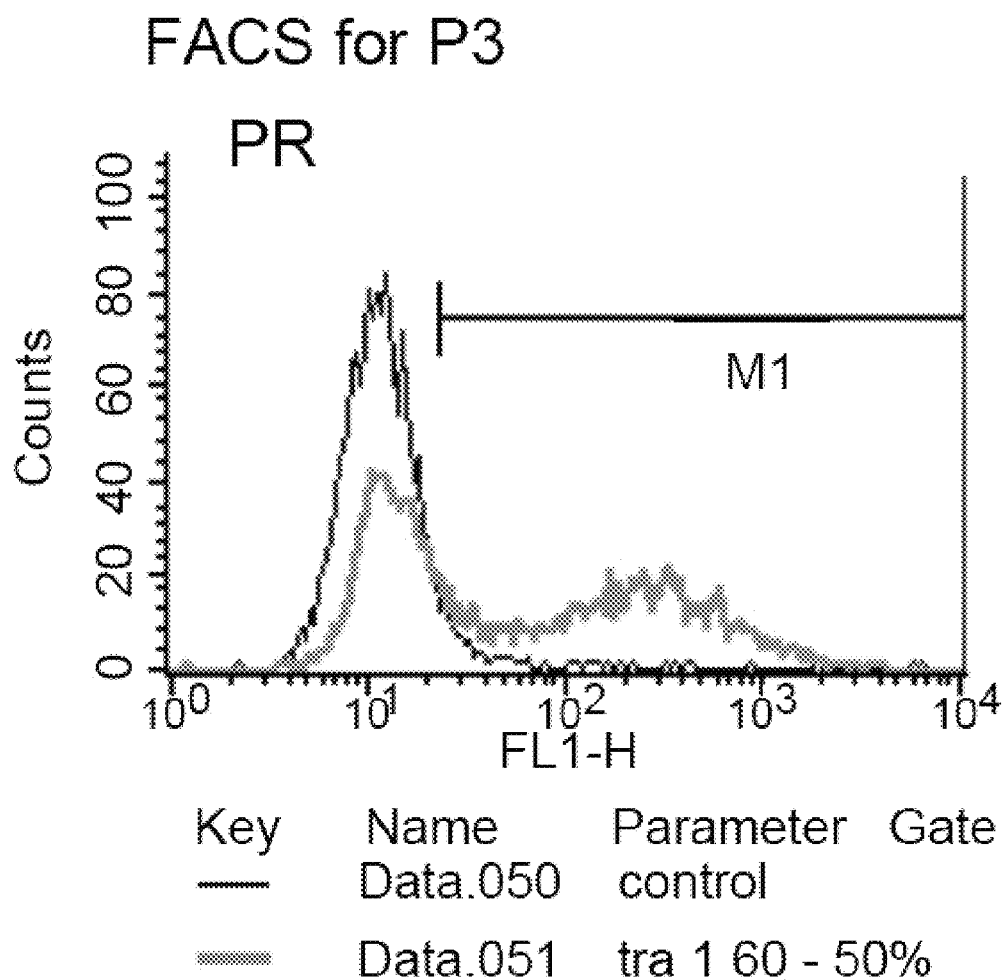
FIG. 91. Expression of pluripotent marker TRA-1-60 of hESC on matrigel coated protamine Tosoh microcarriers at passage 3.
Figure 91:
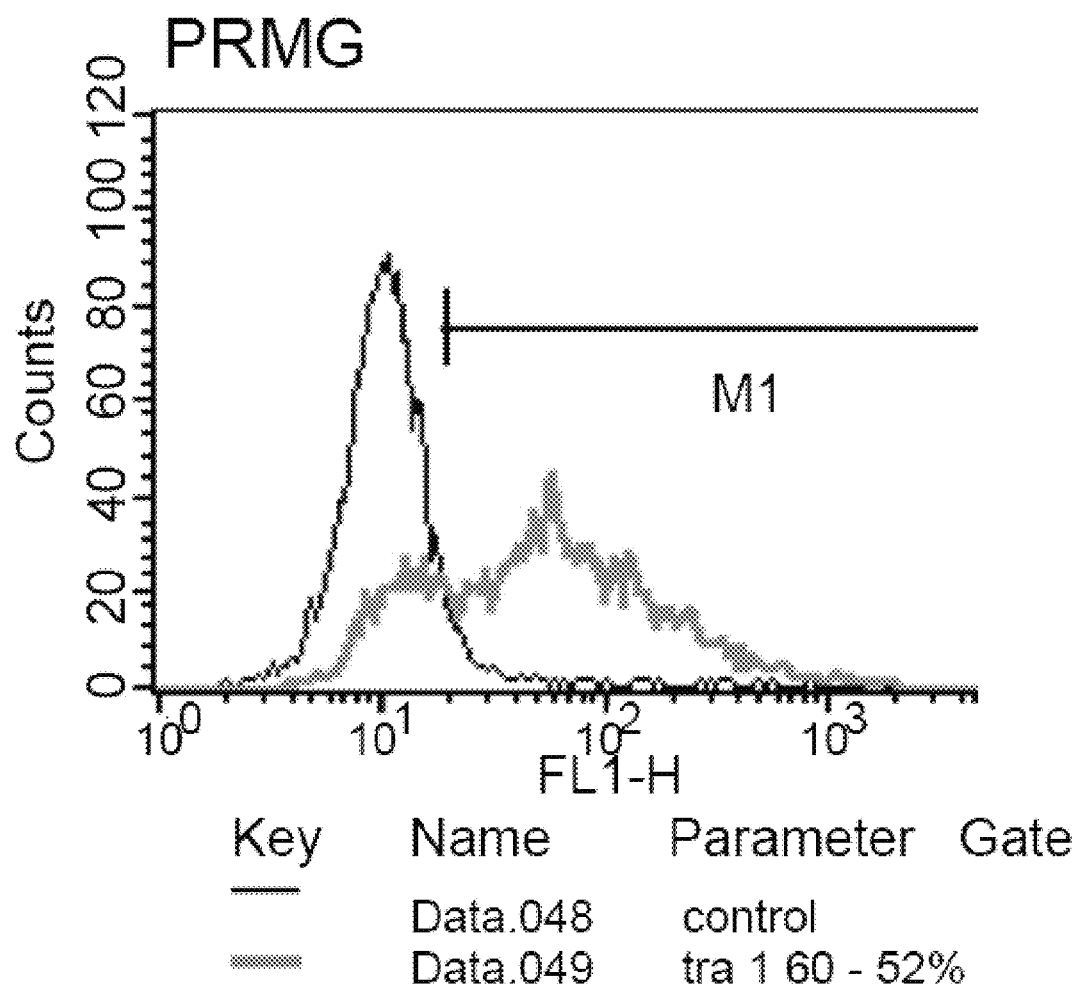
Figure 91:
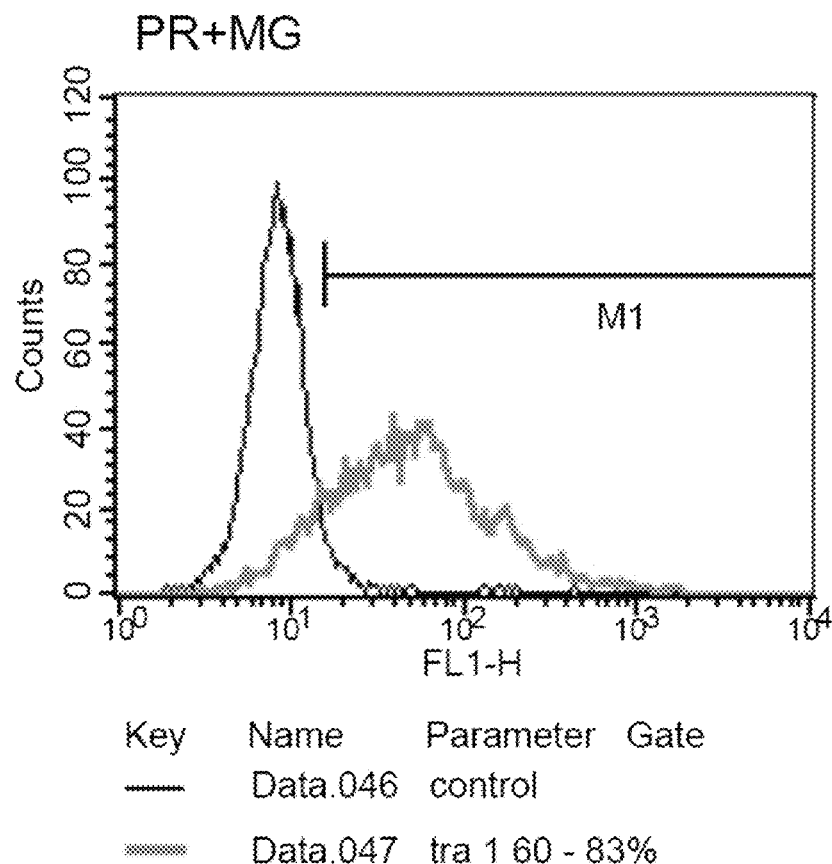
Figure 92:
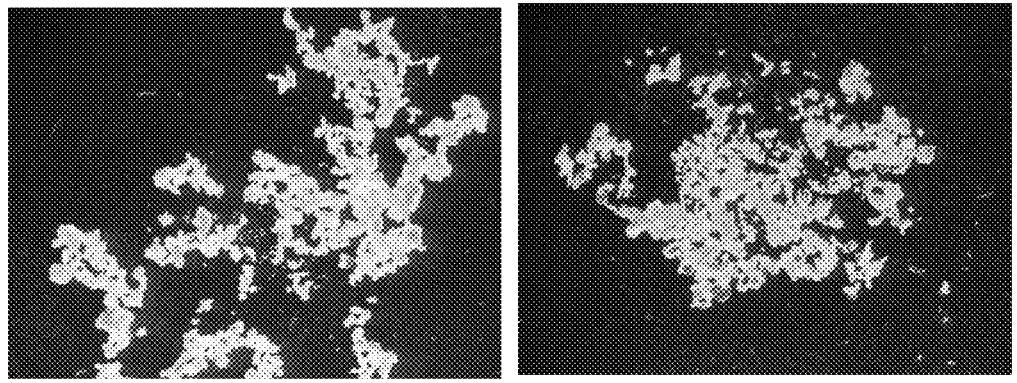
FIG. 92. At passage 4 hESC continue to form undifferentiated aggregates on large polylysine and protamine Tosoh beads coated with matrigel.
Figure 93:
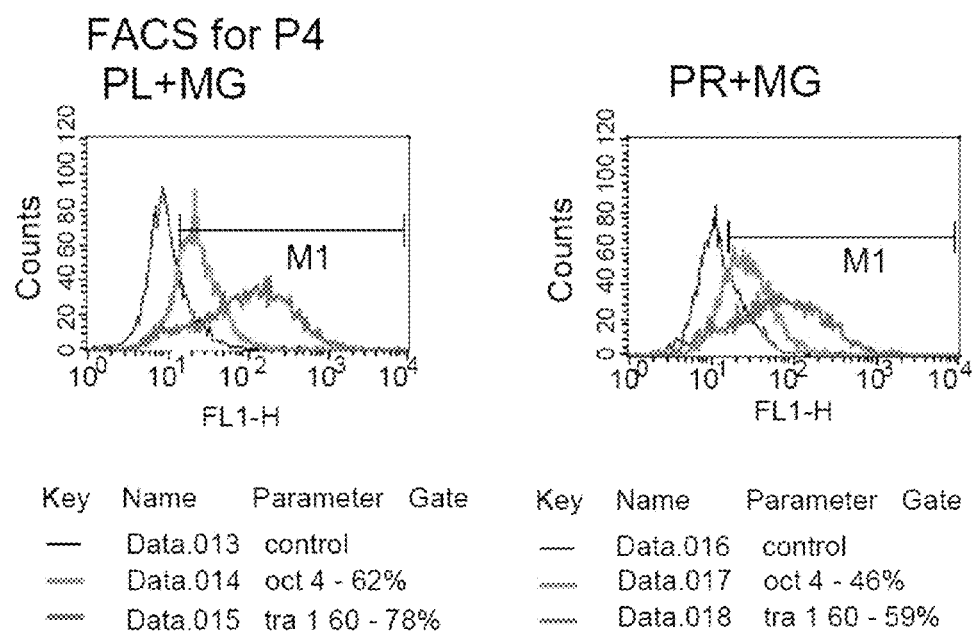
FIG. 93. Continued expression of pluripotent markers Oct4 and TRA-1-60 of hESC on matrigel coated polylysine and protamine microcarriers at passage 4.
Figure 94:
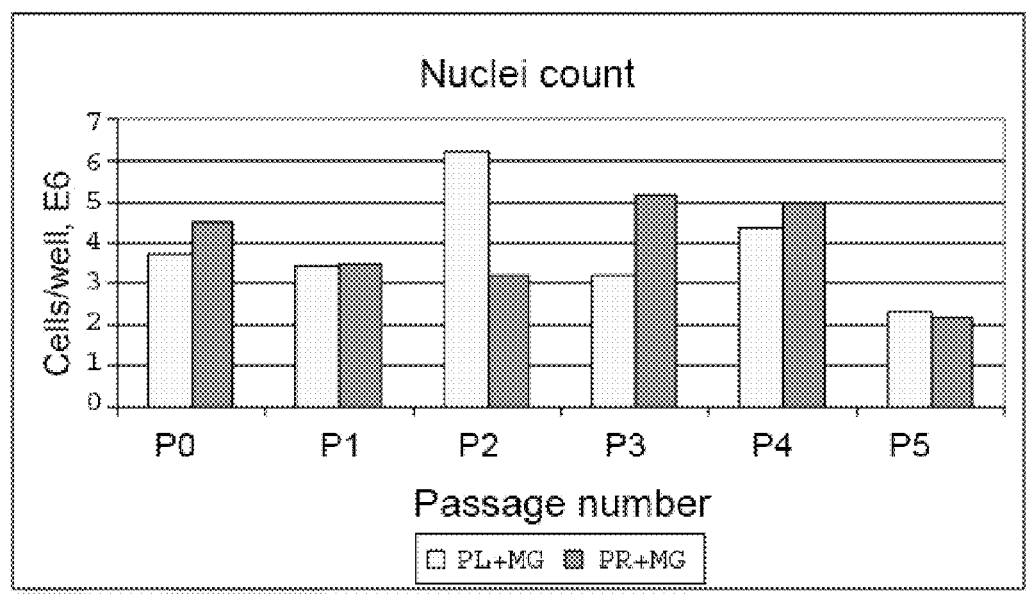
FIG. 94. Stable cell counts of hESC grown for 5 passages on polylysine and protamine Tosoh beads with matrigel coating.
Figure 95:
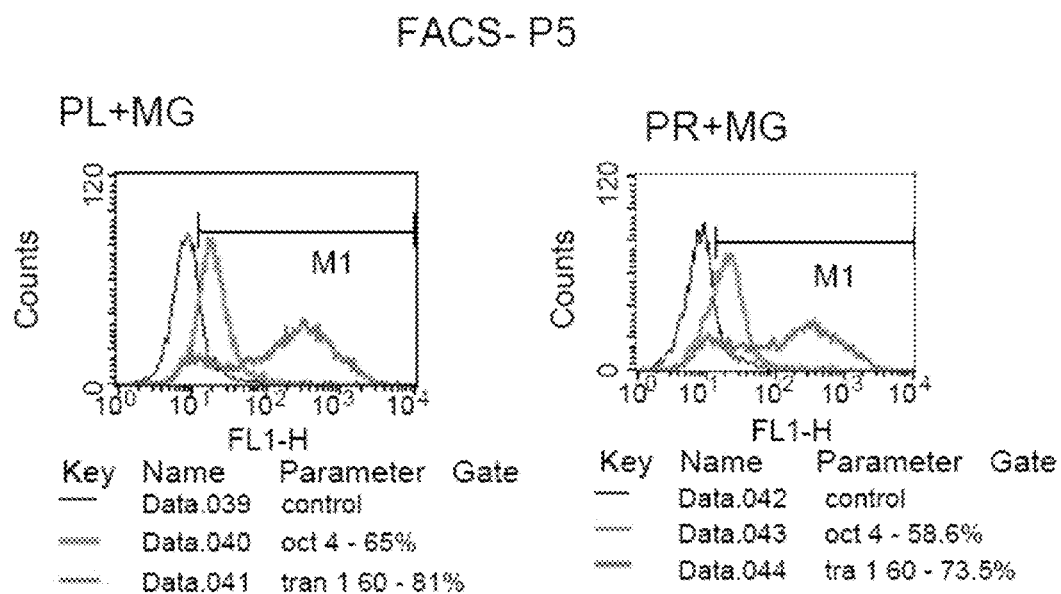
FIG. 95. Continued expression of pluripotent markers Oct4 and TRA-1-60 of hESC on polylysine and protamine Tosoh beads with matrigel coating at passage 5.
Figure 96:
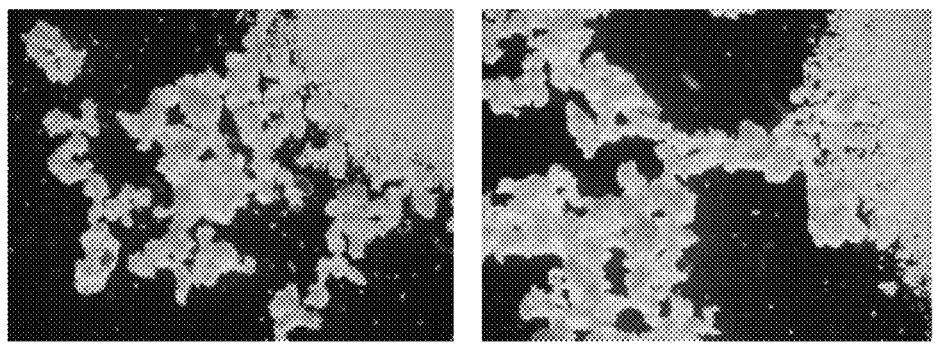
FIG. 96. hESC aggregates on polylysine and protamine Tosoh microcarriers at passage 5.

Table 6 and FIG. 85 show the cell numbers of both polylysine and protamine coated Tosoh beads (65 micron) with and without matrigel for 4 passages. By passage 4, only the beads with matrigel coating survived, but those with matrigel coupled to the beads and without matrigel did not grow after passage 3. "Coupling" was done when Matrigel was added to the polylysine and protamine coated beads immediately and then stored for use over several weeks. For "coating", Matrigel was freshly added to the beads only during the week of culture. FIG. 36 shows the expression of pluripotent markers Oct4 and TRA-1-60 of hESC on polylysine Tosoh microcarriers without and with matrigel at P1. Oct4 expression was lowest for the microcarriers without matrigel. FIG. 87 shows the expression of pluripotent markers Oct4 and TRA-1-60 of hESC on protamine Tosoh microcarriers without and with matrigel at P1. Again Oct4 expression was lowest for the microcarriers without matrigel. FIG. 38 shows the expression of pluripotent marker TRA-1-60 of hESC is better on matrigel coated polylysine Tosoh microcarriers at P2. Similarly, FIG. 89 shows the expression of pluripotent marker TRA-1-60 of hESC is better on matrigel coated protamine Tosoh microcarriers at P2. FIG. 90 continues to show that expression of pluripotent marker TRA-1-60 of hESC is better on matrigel coated polylysine Tosoh microcarriers at P3. FIG. 91 shows the expression of pluripotent marker TRA-1-60 of hESC is highest on matrigel coated protamine Tosoh microcarriers at P3. At passage 4, hESC still continue to form undifferentiated aggregates on large polylysine and protamine Tosoh beads coated with matrigel (FIG. 92). FIG. 93 shows the continued expression of pluripotent markers Oct4 and TRA-1-60 of hESC on matrigel coated polylysine and protamine microcarriers at passage 4. FIG. 94 shows the relatively stable cell counts of hESC grown for 5 passages on polylysine and protamine Tosoh beads with matrigel coating. FIG. 95 shows the continued expression of pluripotent markers Oct4 and TRA-1-60 of hESC at passage 5, while FIG. 96 shows the hESC aggregates on polylysine and protamine Tosoh microcarriers at P5.

Figure 97:
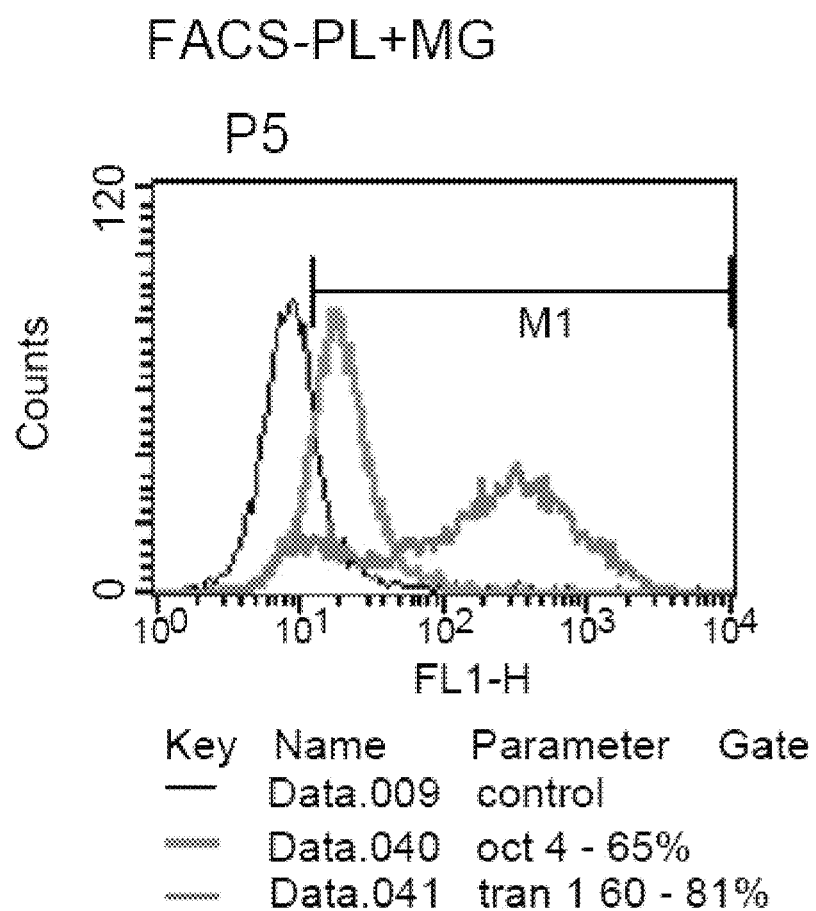
FIG. 97. With optimization of microcarrier concentrations to 48,000 beads per million cells, expression of pluripotent markers Oct4 and TRA-1-60 recovered to higher levels between passages 6 and 7 for Matrigel coated polylysine Tosoh microcarriers. Note: main focus of experiment at this stage was to optimise the number of beads to cells. Optimised at 48,000 beads to around seeding of $10^6$ cells per well.
Figure 97:
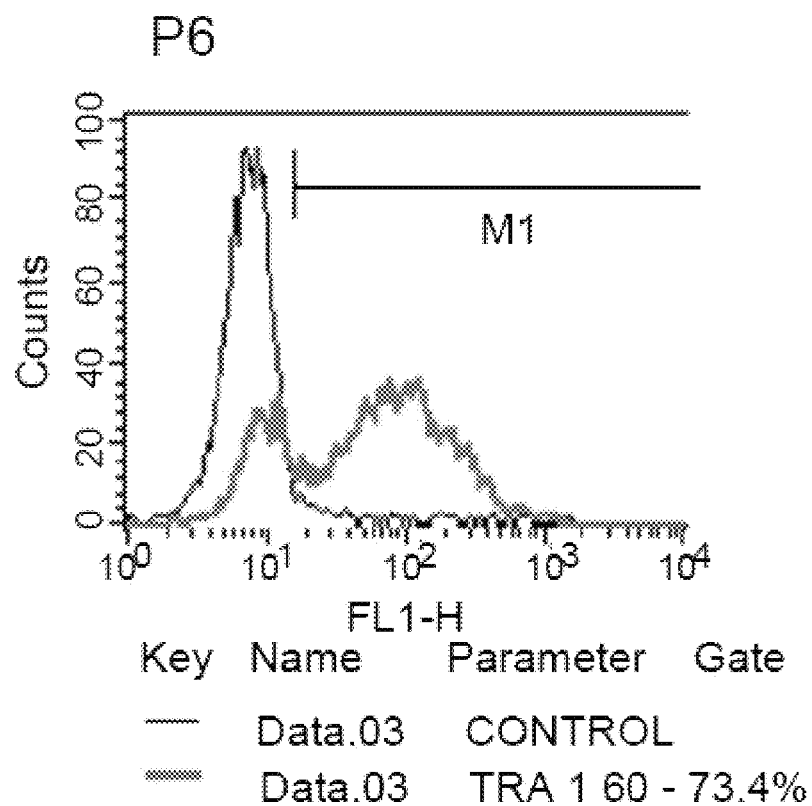
Figure 97:
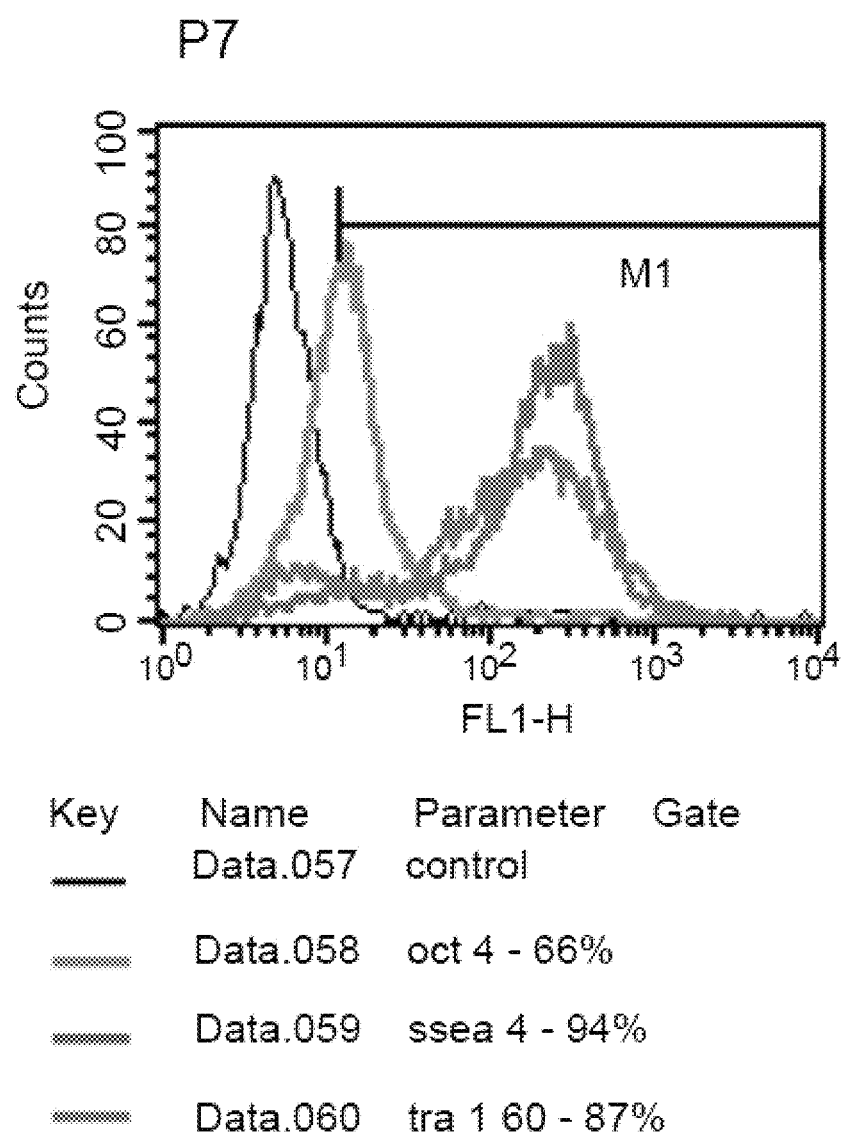
Figure 98:
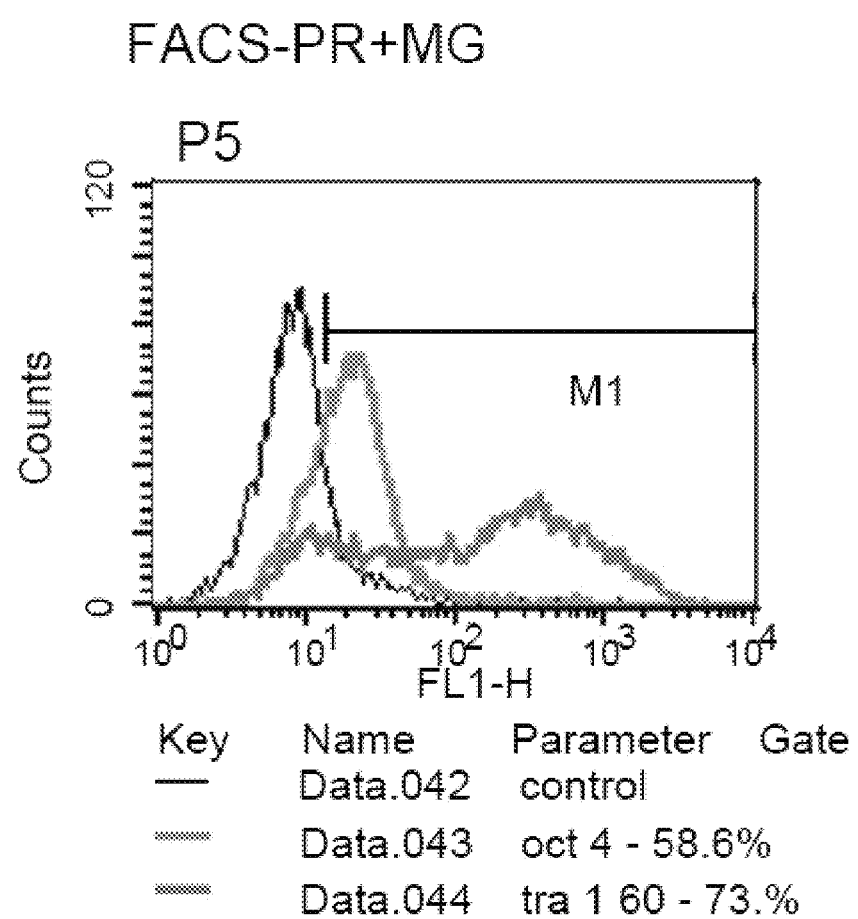
FIG. 98. With optimization of microcarrier concentrations to 48,000 beads per million cells, expression of pluripotent markers Oct4 and TRA-1-60 recovered to higher levels between passages 6 and 7 for Matrigel coated protamine Tosoh microcarriers. Note: main focus of experiment at this stage was to optimise number of beads to cells. Optimised at 48,000 beads to around seeding of $10^6$ cells per well.
Figure 98:
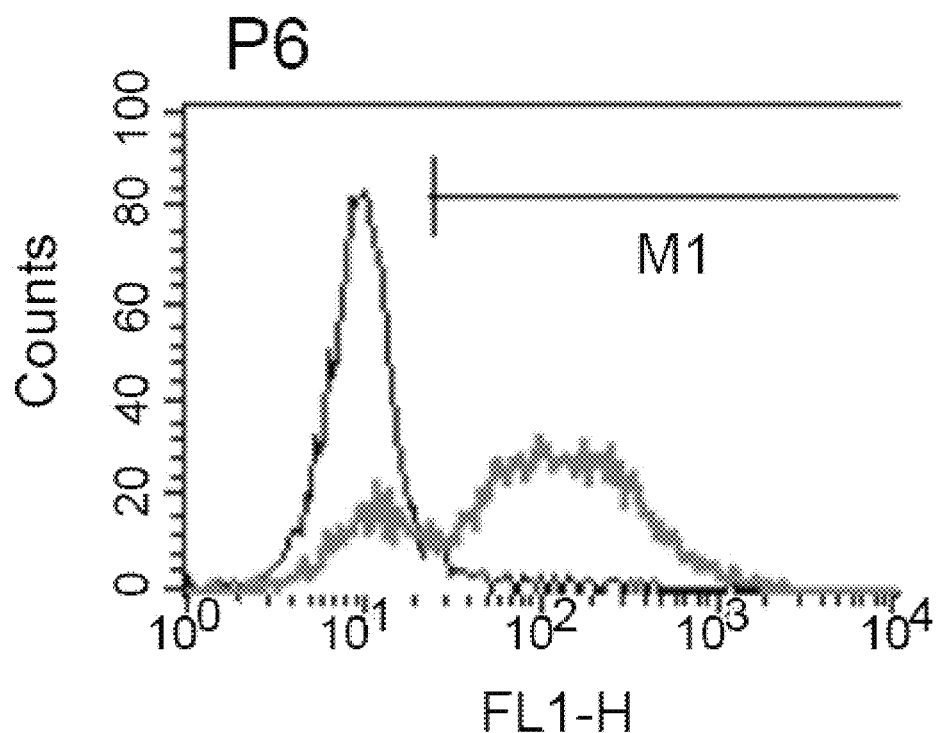
Figure 98:
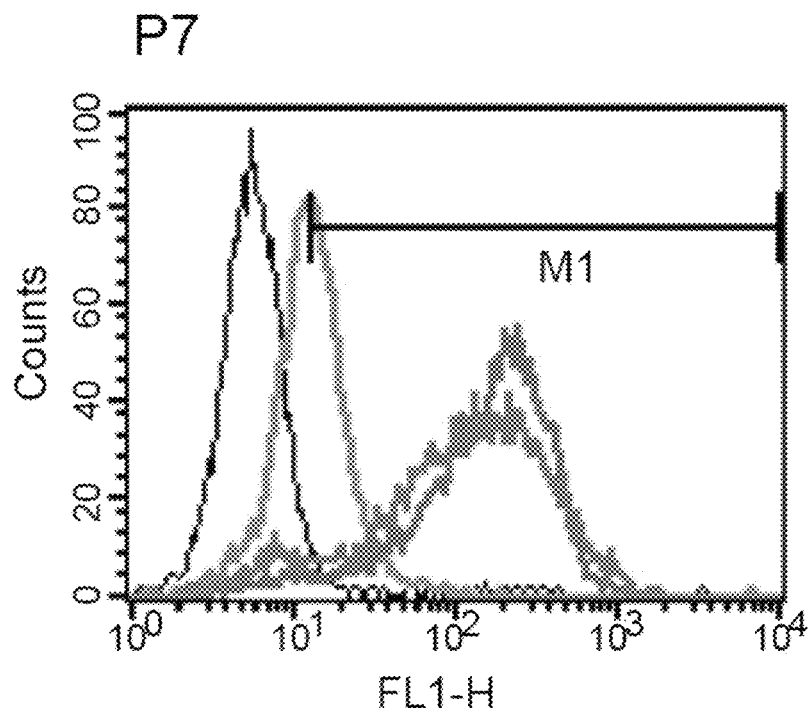

Between passage 6 and passage 7, with further optimization of microcarrier concentrations to 48,000 beads per million cells, the expression of pluripotent markers Oct4 and TRA-1-60 recovered to higher levels for both the matrigel coated polylysine and protamine Tosoh microcarriers, as shown in FIGS. 97 and 98.

Example 36 hESC Culture on Cytodex 3 with and without Matrigel and with Laminin and Fibronectin Coatings As Cytodex 3 is commonly used for cell culture, we also compared its performance compared to DE53 and Tosoh microcarriers. Furthermore, it was alleged by Terstegge et al (US patent application 2007/0264713 A 1) that Cytodex 3 alone without any coatings could be used for culture of hESC in static and agitated conditions.

Figure 99:
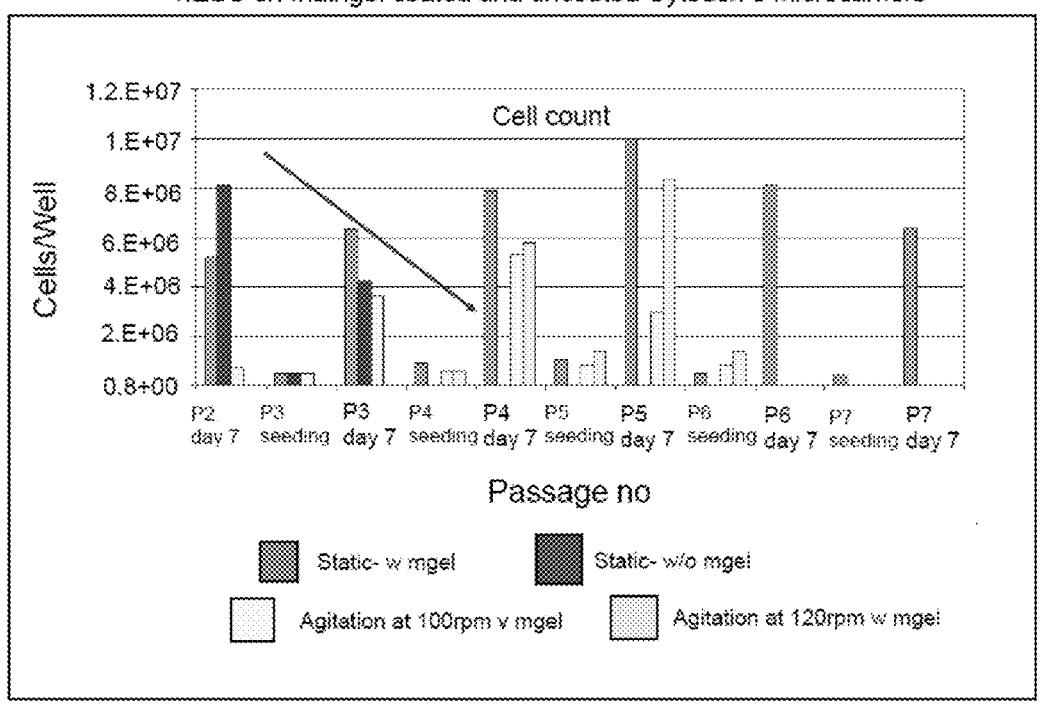
FIG. 99. By passage 5 Cytodex 3 microcarriers coated with matrigel enabled hESC growth in both agitated (both 100 and 120 rpm) and non-agitated conditions.
Figure 100:
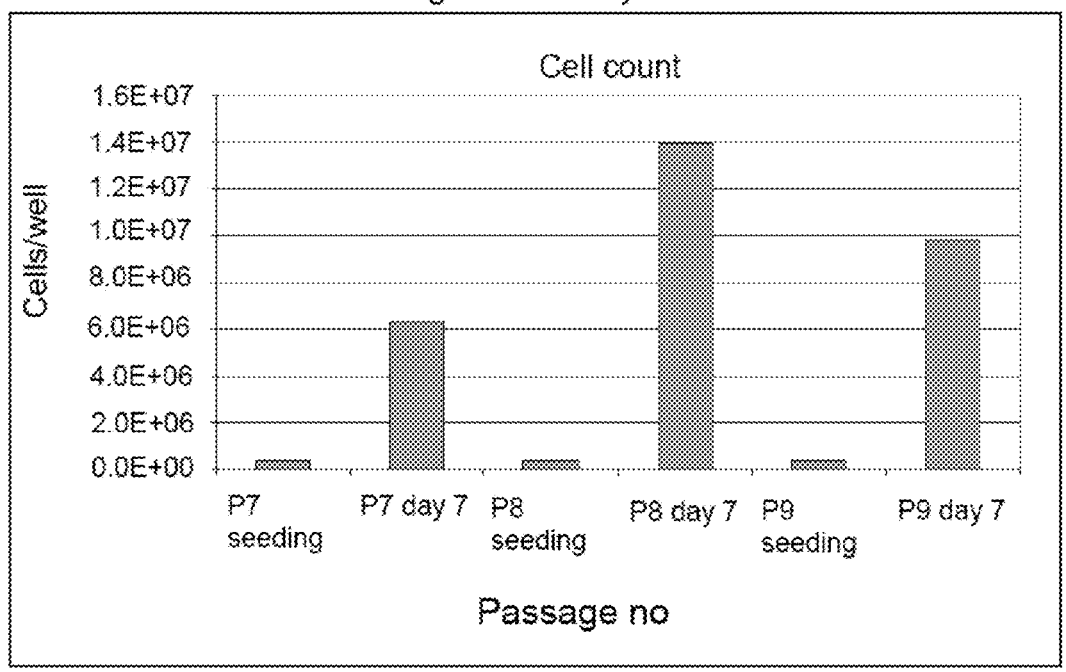
FIG. 100. By passage 7 hESC on the non-agitated matrigel coated Cytodex 3 microcarriers continued to survive and grow to passage 9.

Table 7 shows that the cell numbers of hESC grown were relatively stable on Cytodex 3 microcarriers coated with matrigel and without matrigel cultured in non-agitated and agitated conditions for 3 passages. However, by passage 5 only the microcarriers coated with matrigel enabled hESC growth in both agitated (both 100 and 120 rpm) and non-agitated conditions as shown in FIG. 99. There is a sharp fall off in cell numbers in uncoated Cytodex 3 microcarriers. Then by passage 7, only hESC on the non-agitated matrigel coated Cytodex 3 microcarriers continued to survive and grow to passage 9 as shown in FIG. 100.

Figure 101:
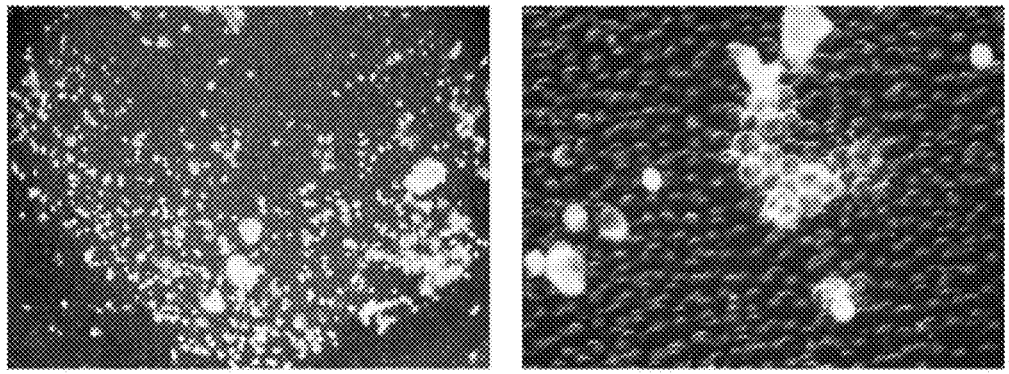
FIG. 101. hESC is sparsely coated on Cytodex 3 microcarriers without matrigel.
Figure 102:
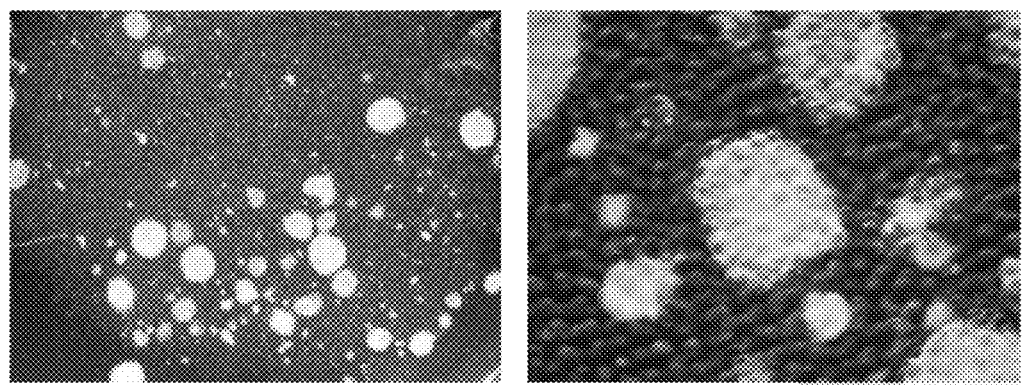
FIG. 102. Large clusters of hESC on Cytodex 3 microcarriers without matrigel agitated at 100 rpm.
Figure 103:
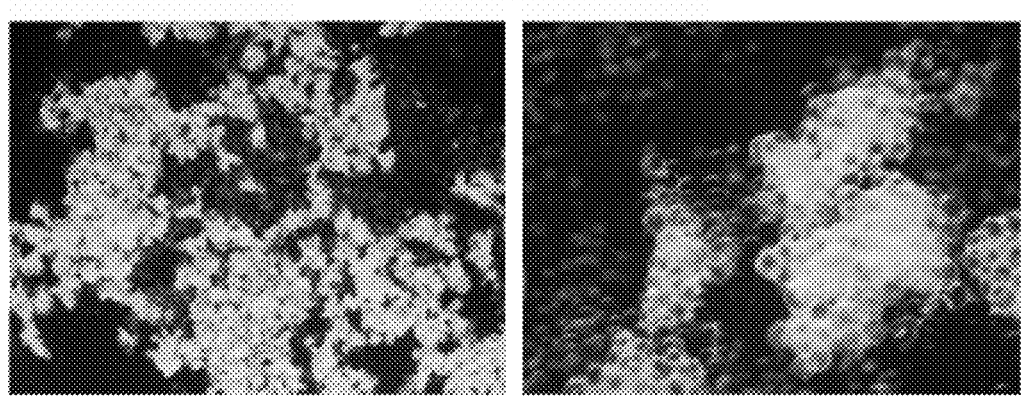
FIG. 103. Confluent growth of hESC on matrigel coated Cytodex 3 microcarriers in non-agitated conditions.
Figure 104:
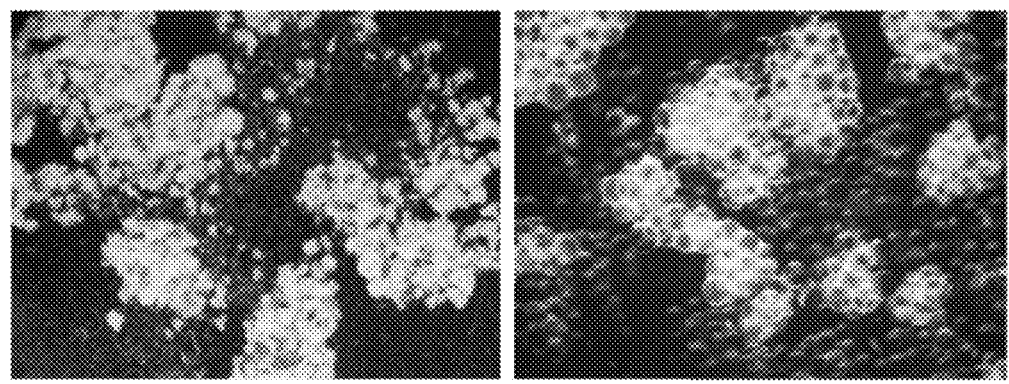
FIG. 104. Confluent growth of hESC on matrigel coated Cytodex 3 microcarriers in agitated conditions (100 rpm).
Figure 105:
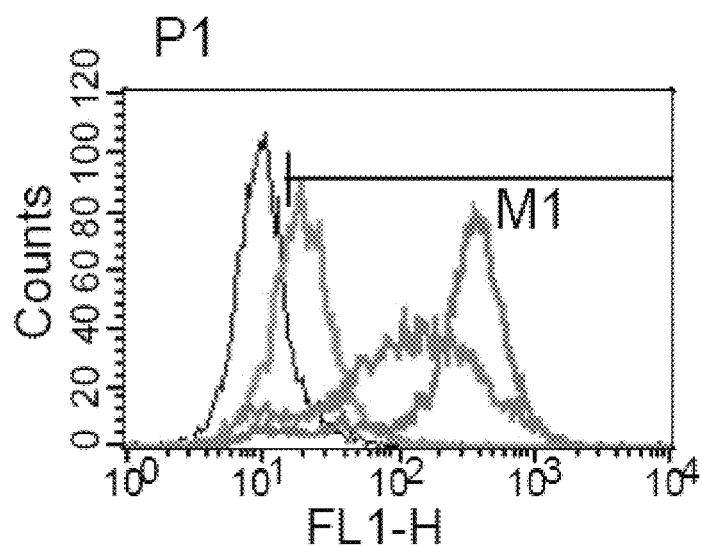
FIG. 105. Expression of the pluripotent markers Oct4 and TRA-1-60 is down regulated by passage 3 on Cytodex 3 without matrigel.
Figure 105:
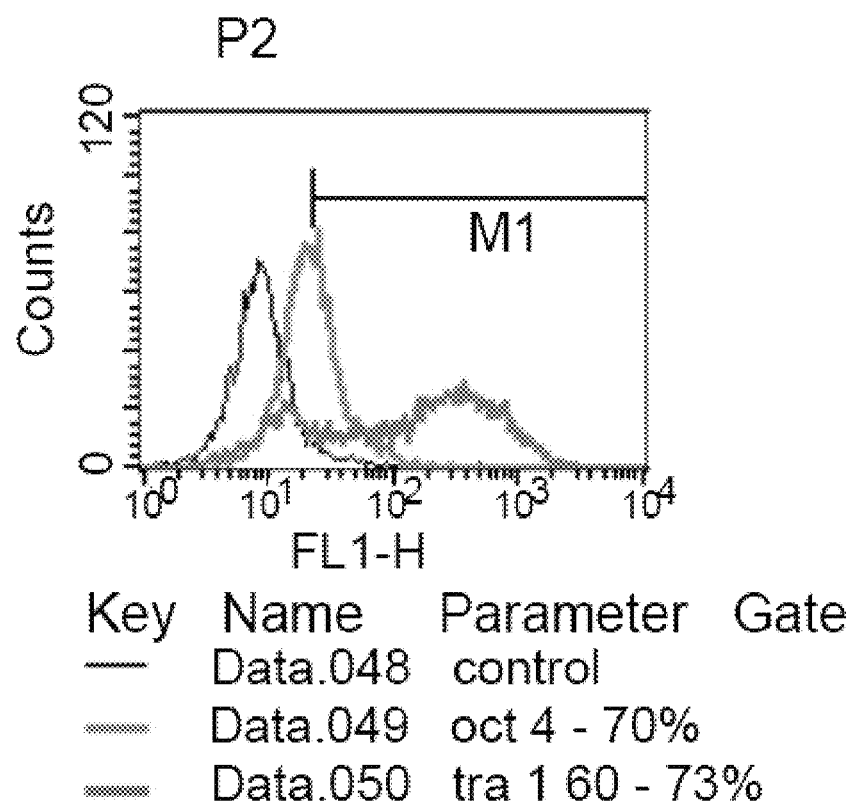
Figure 105:
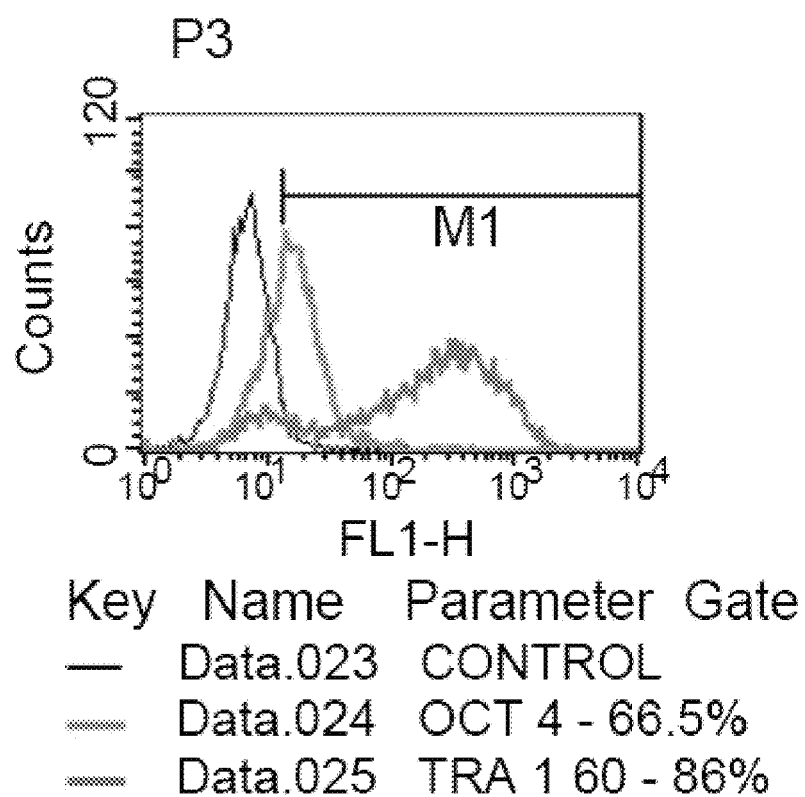
Figure 106:
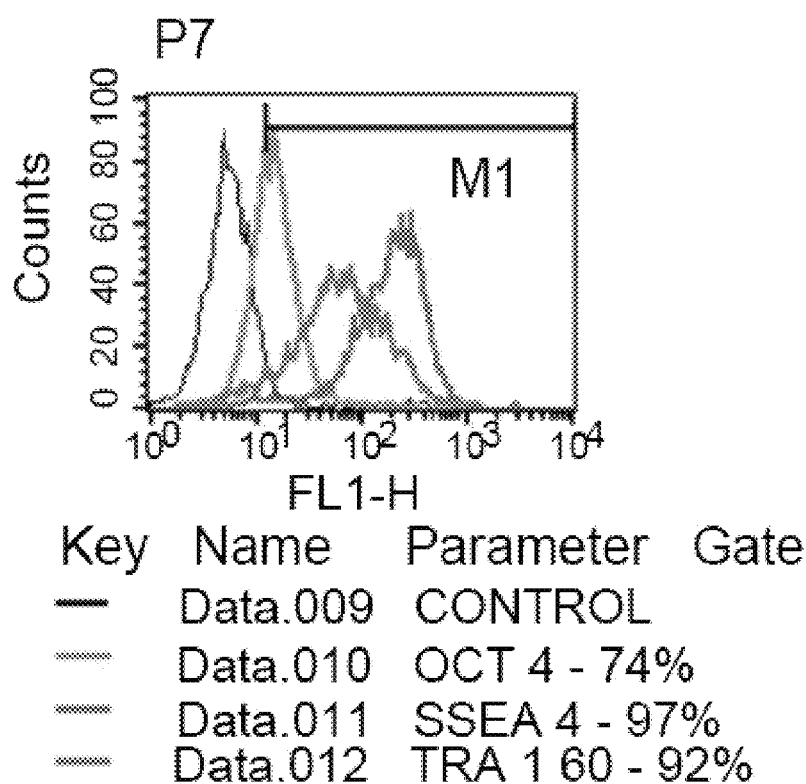
FIG. 106. Oct4, SSEA4 and TRA-1-60 are robustly expressed even at passage 9 for matrigel coated Cytodex 3 microcarriers.
Figure 106:
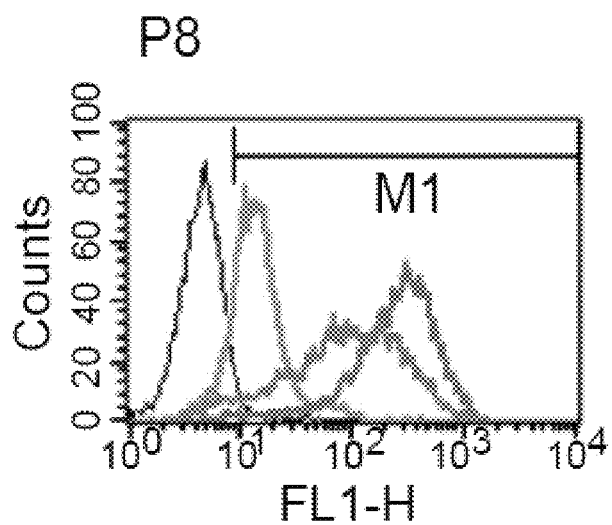
Figure 106:
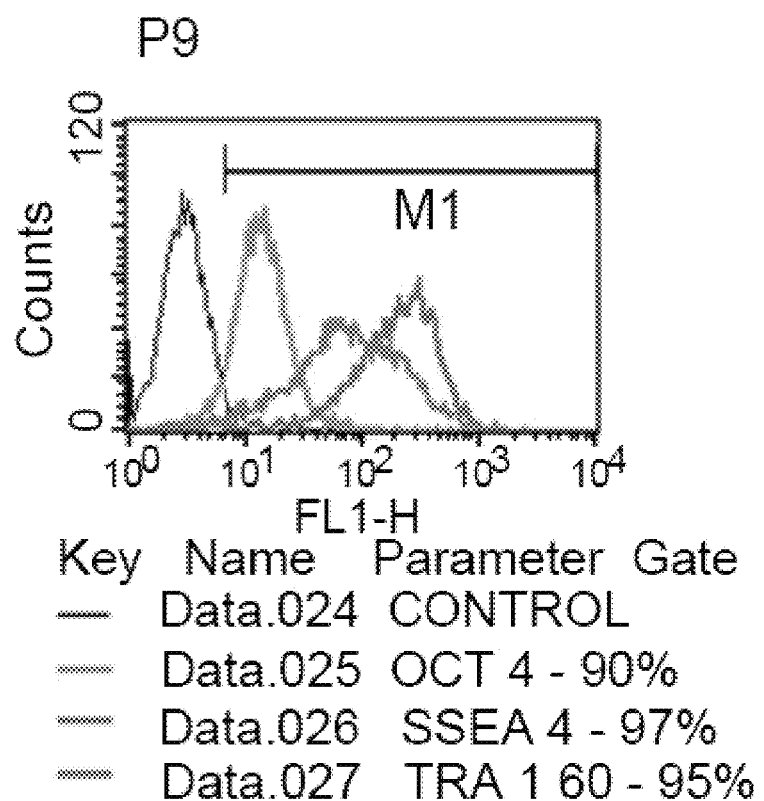
Figure 107:
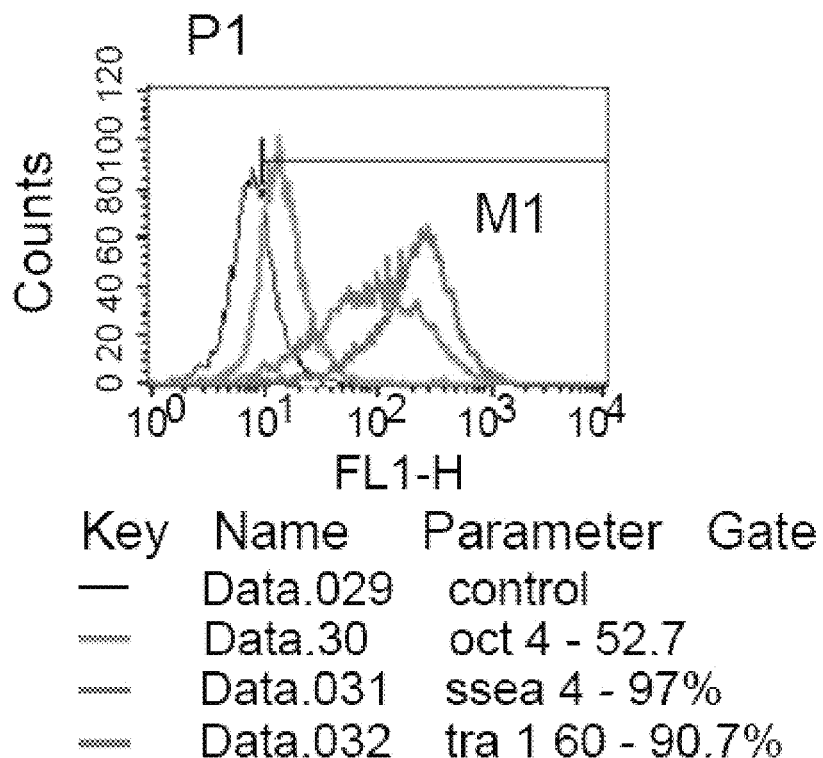
FIG. 107. hESC grown on Cytodex 3 without matrigel in agitated conditions down regulates pluripotent markers by passage 3.
Figure 107:
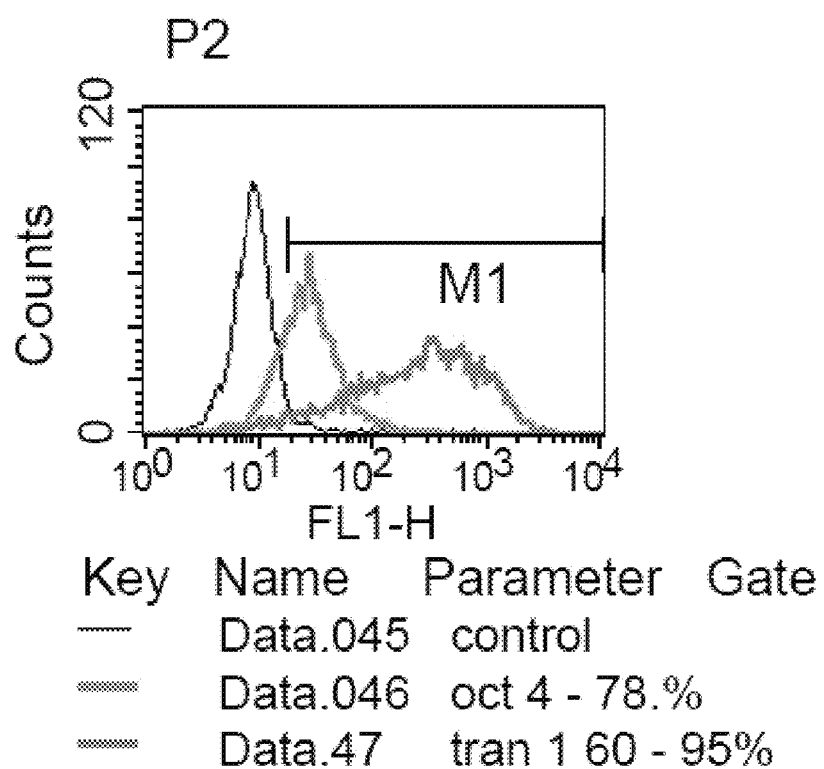
Figure 107:
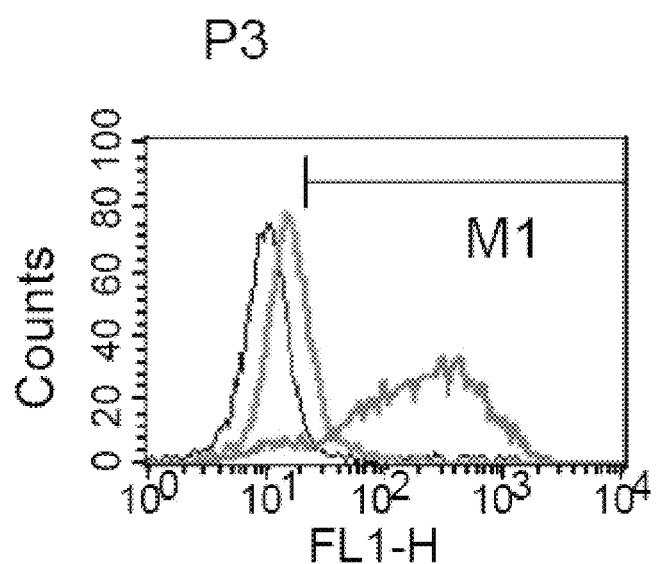
Figure 108:
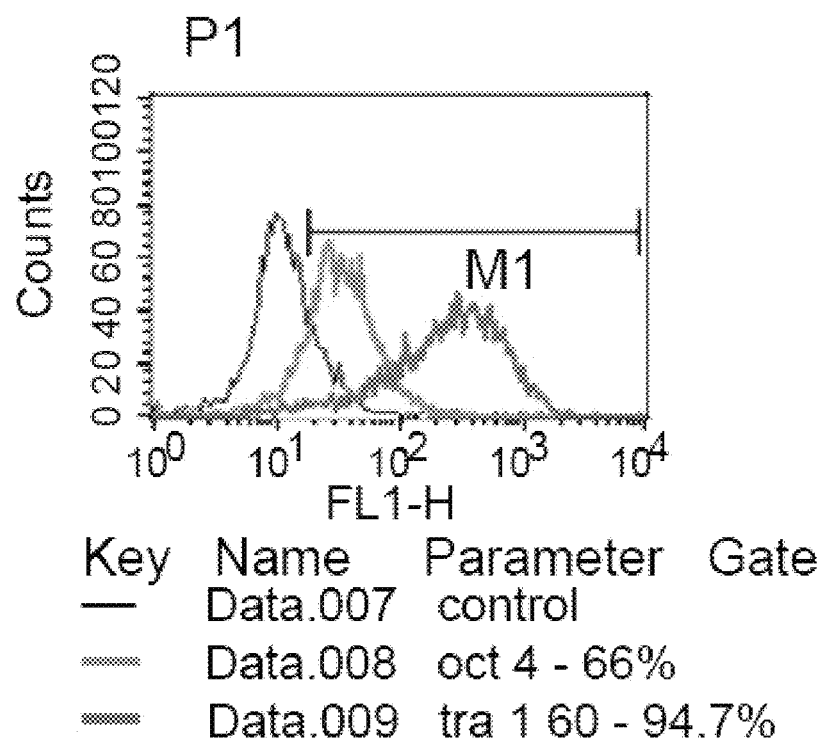
FIG. 108. hESC grown on Cytodex 3 with matrigel coating in agitated conditions down regulates pluripotent markers Oct4 and TRA-1-60 by passage P3.
Figure 108:
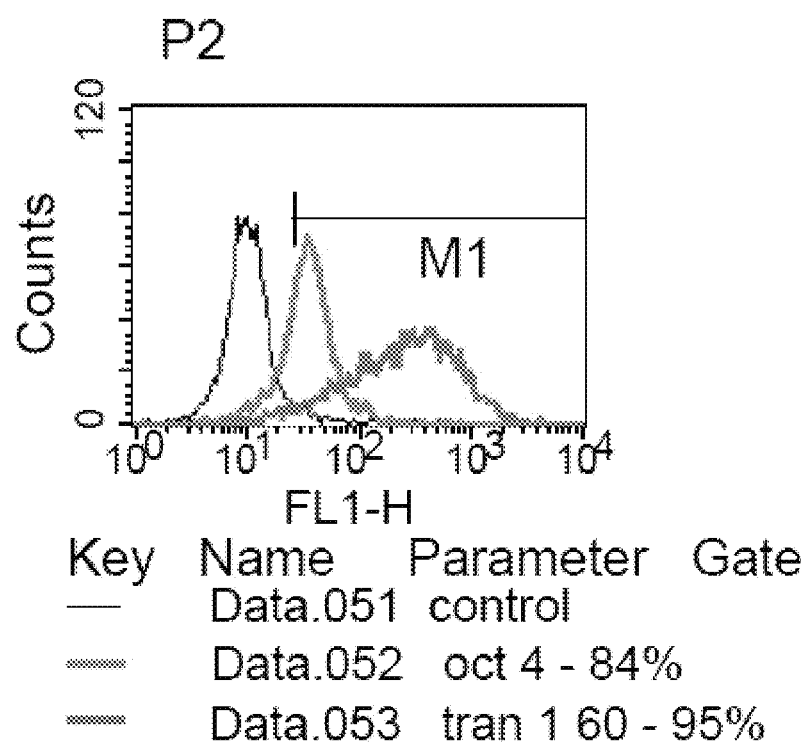
Figure 108:
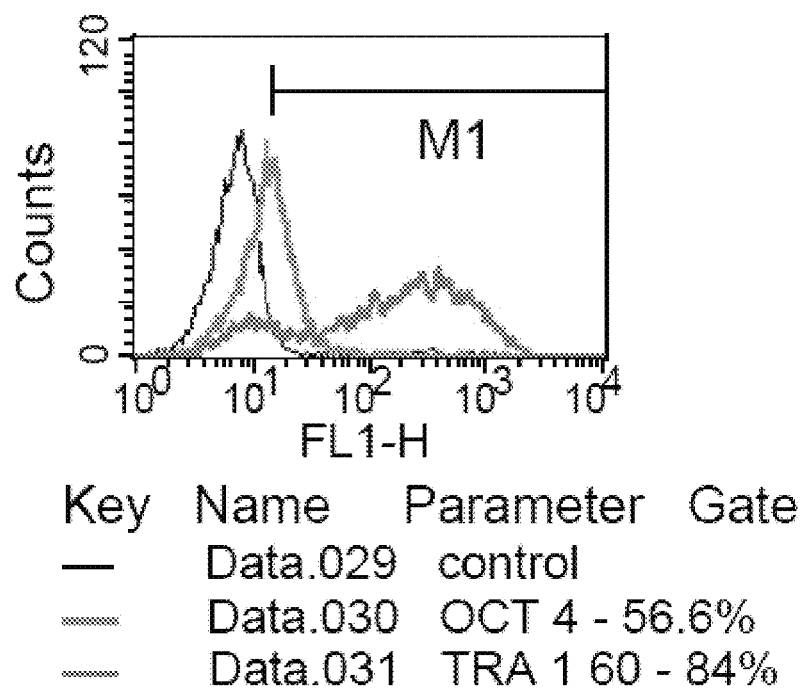

FIG. 101 shows hESC is sparsely coated on Cytodex 3 microcarriers without matrigel: FIG. 102 shows large clusters of hESC on Cytodex 3 microcarriers without matrigel agitated at 100 rpm. Whereas FIGS. 103 and 104 show more confluent growth of hESC on matrigel coated Cytodex 3 microcarriers in non-agitated and agitated conditions respectively. FACS analysis of the pluripotent markers Oct4 and TRA-1-60 are down regulated by P3 on Cytodex 3 without matrigel (FIG. 105). However, FACS of all 3 markers of Oct4, SSEA4 and TRA-1-60 are still robustly expressed even at P9 for matrigel coated Cytodex 3 microcarriers (FIG. 106). FIG. 107 shows that hESC grown on Cytodex 3 without matrigel in agitated conditions down regulate pluripotent markers by P3; this down regulation is also seen with matrigel coated Cytodex 3 in agitated conditions by P3 (FIG. 108).

Figure 109:
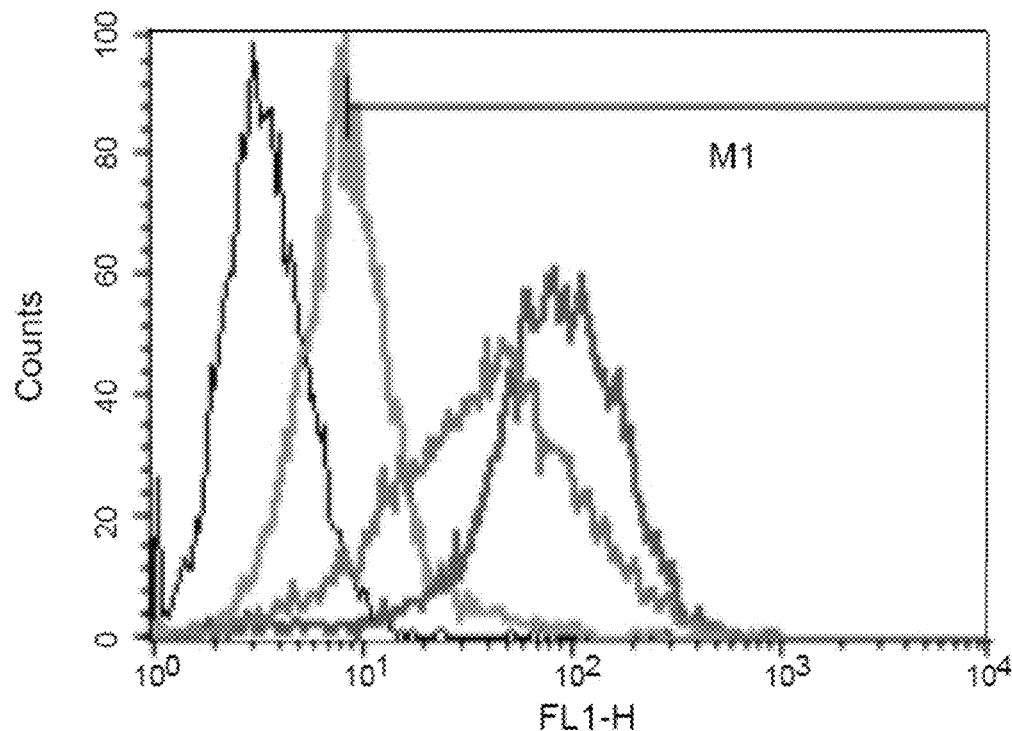
FIG. 109. By passage 13, matrigel coated Cytodex 3 microcarriers in static conditions still supports hESC strongly expressing Oct4, SSEA4 and TRA-1-60, whereas the cells on fibronectin and laminin coated Cytodex 3 have shown decrease in the expression of pluripotent markers at passage 6.
Figure 109:
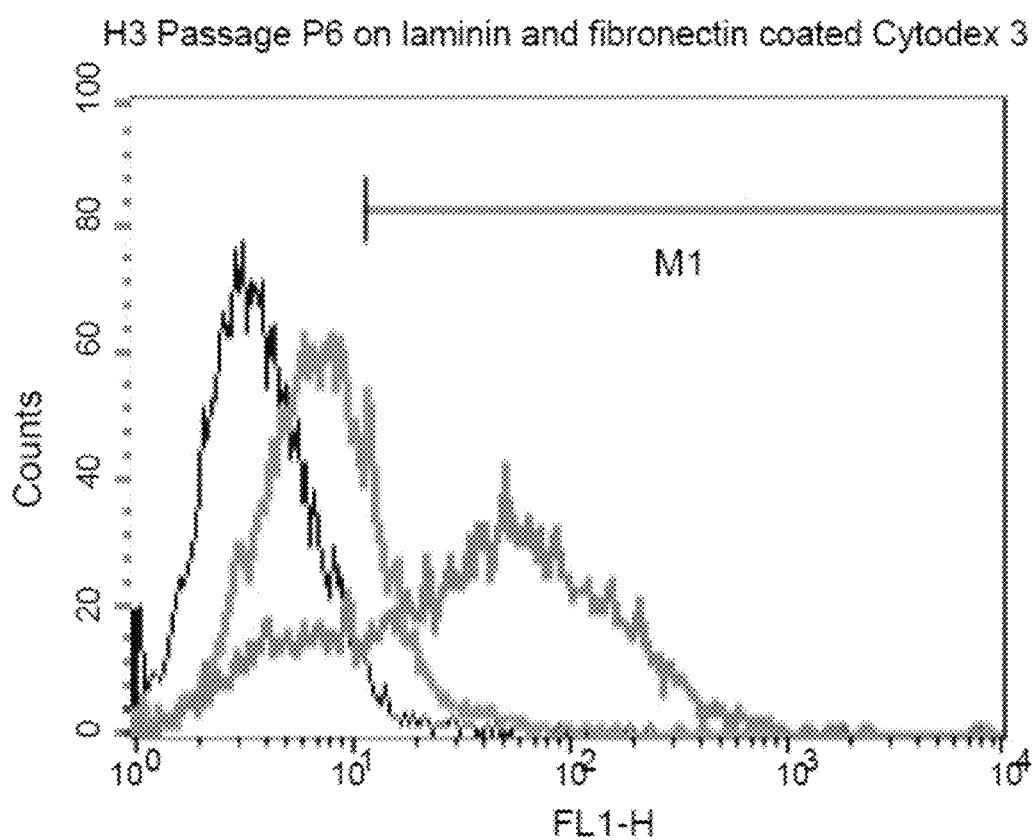
Figure 110:
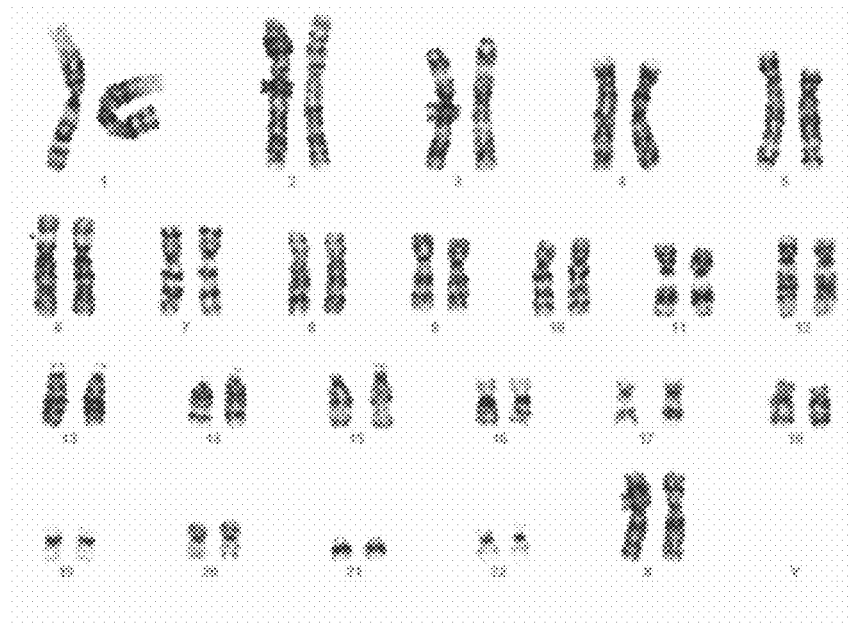
FIG. 110. Karyotyping of the hESC showed a normal 46XX karyotype after 11 passages on Cytodex 3 coated with matrigel.

By passage 13, matrigel coated Cytodex 3 microcarriers in static conditions could still support hESC which strongly expressed the 3 pluripotent markers as shown in FIG. 109. In contrast, hESC grown on laminin and fibronectin coated on Cytodex 3 at passage 6 show partial down regulation of Oct4 and TRA-1-60 markers. This experiment was performed to simulate matrigel which has collagen, laminin and fibronectin. Furthermore, karyotyping of the hESC showed a normal 46XX karyotype after 11 passages on Cytodex 3 coated with matrigel in FIG. 110.

Example 37 hESC Culture on Cytodex 1 and Hillex Microcarriers with and without Matrigel

We also evaluated charged microcarriers Cytodex 1 and Hillex microcarriers alone without any coatings for their ability to support hESC. Again, an earlier patent by Crook et al claimed that these microcarriers alone without matrigel coating could support hESC culture for 3 to 5 passages in static cultures (WO 2008/004990 A2). A subsequent publication by the same group, (Phillips et al, 2008) revealed that they could only achieve 3 fold expansion at every passage and that hESC could not be expanded on Hillex microcarriers by passage 6 even though pluripotent markers were retained.

Figure 111:
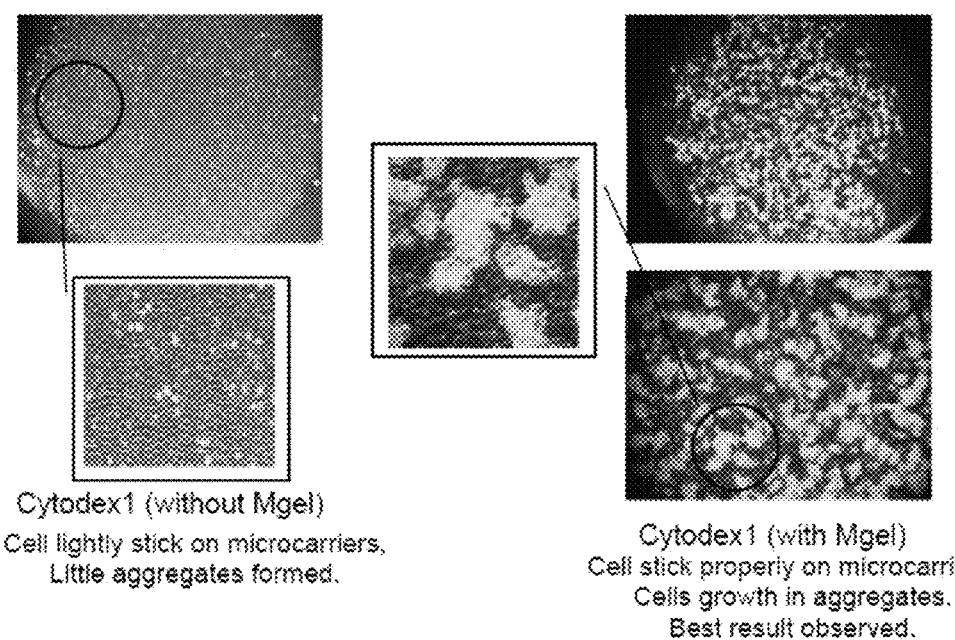
FIG. 111. hESC growing on Cytodex 1 with and without matrigel coating.
Figure 112:
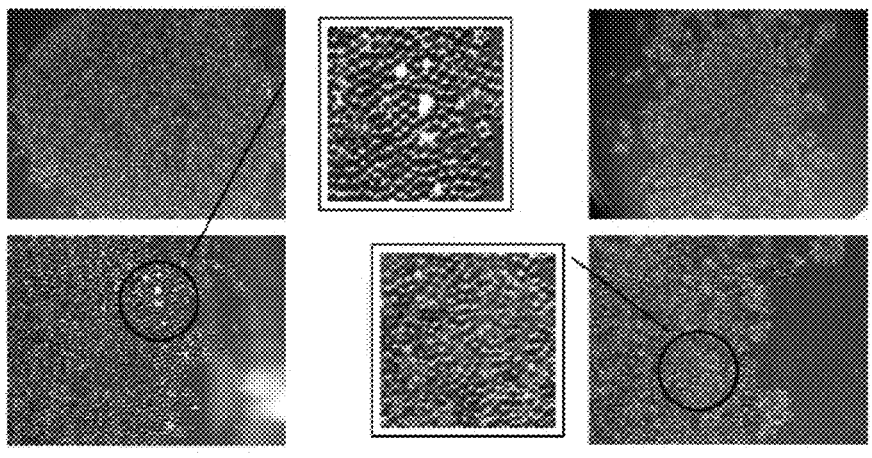
FIG. 112. hESC growing on Hillex microcarriers with and without matrigel coating.
Figure 113:
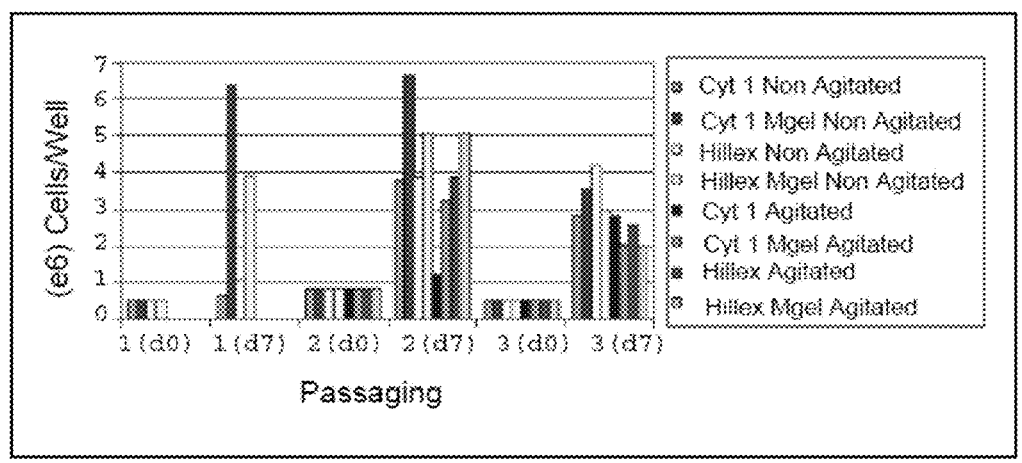
FIG. 113. Cell counts of hESC on Hillex and Cytodex 1 microcarriers with and without matrigel, with and without agitation after 3 passages.
Figure 114:
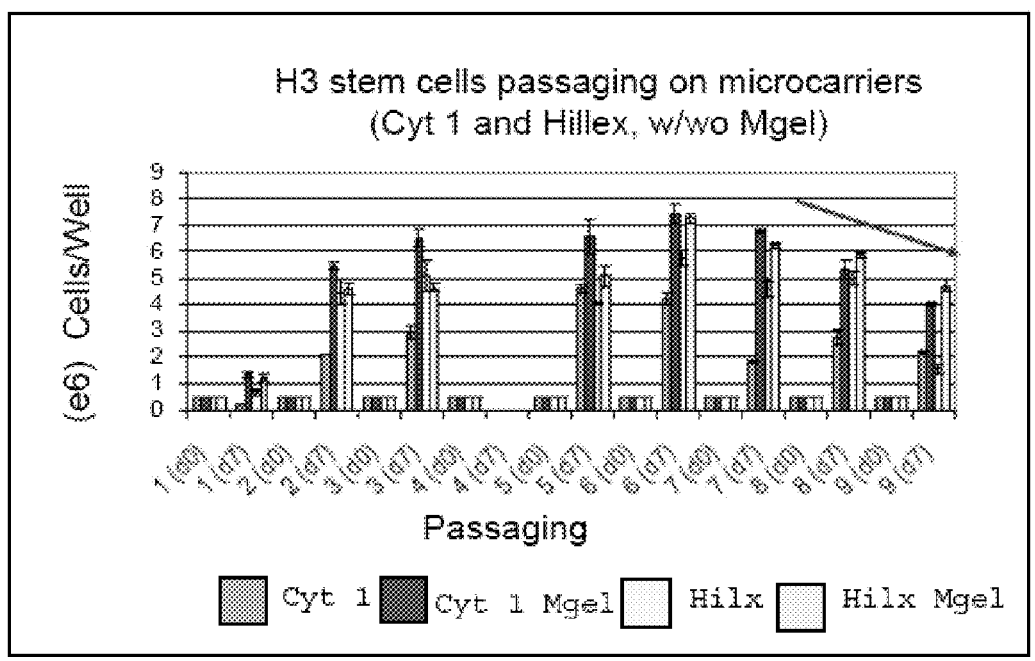
FIG. 114. Static (non-agitated) cultures of Hillex and Cytodex 1 microcarriers with and without matrigel can be passaged up to passage 9.
Figure 115:
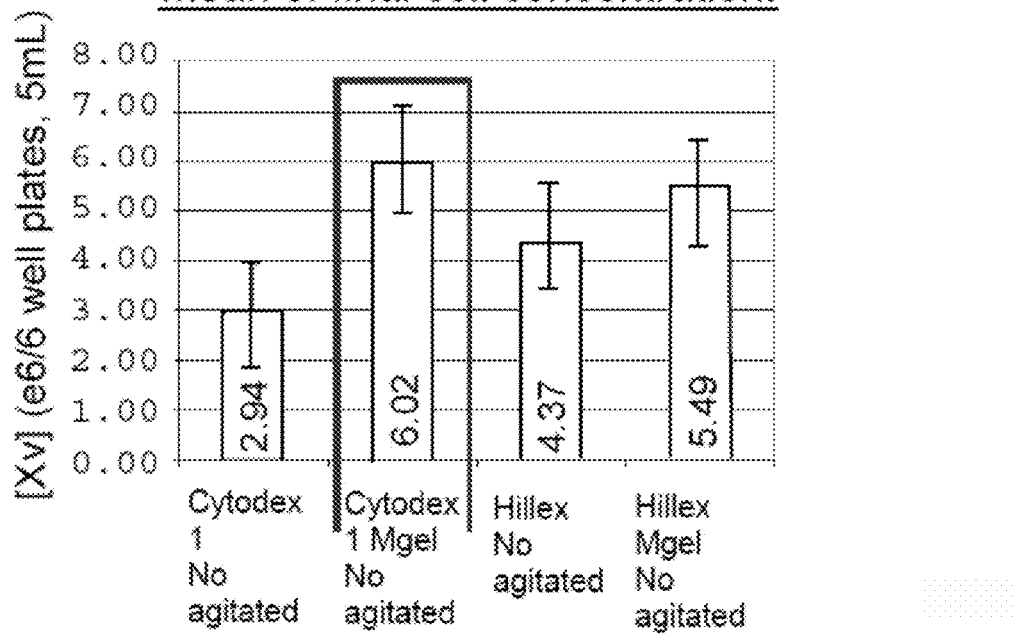
FIG. 115. Mean cell concentration and mean fold expansion of hESC grown on Cytodex 1 and Hillex microcarriers with and without matrigel.
Figure 115:
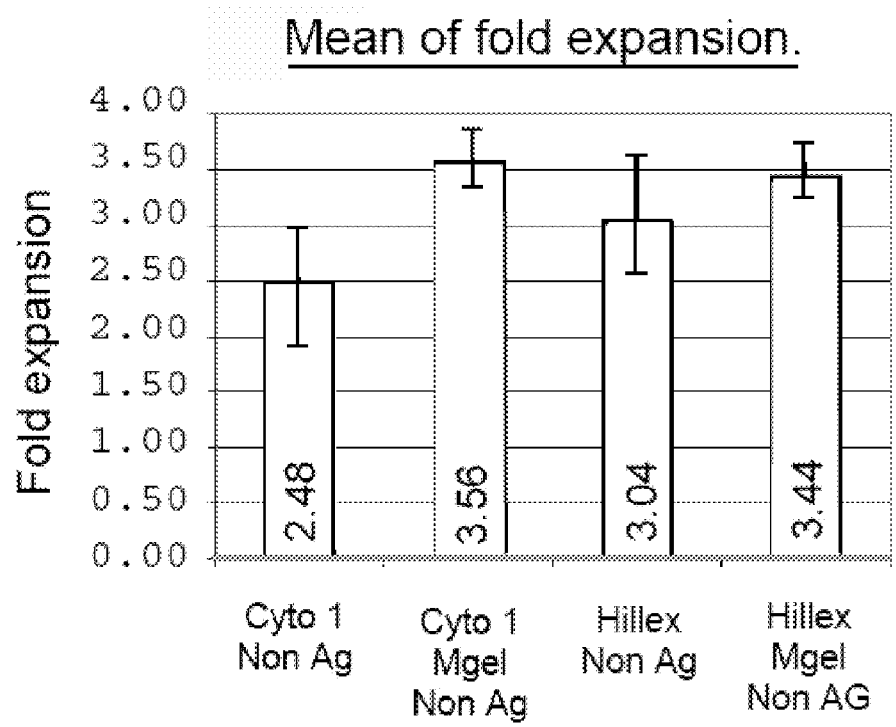

FIG. 111 shows hESC growing on Cytodex 1 with and without matrigel coating, hESC on matrigel coated Cytodex grow as larger aggregates compared to uncoated microcarriers. FIG. 112 shows hESC growing on Hillex microcarriers with and without matrigel coating. Hillex microcarriers adsorb phenol red from the media and tend to aggregate together. hESC stick less well on these microcarriers with or without matrigel. FIG. 113 shows the cell counts of hESC on these 2 types of microcarriers with and without agitation after 3 passages. After 3 passages, the cell numbers tend to drop in the Cytodex 1 and Hillex microcarrier cultures with agitation and were discontinued as they could not be passaged. However, static (or non-agitated) cultures of these microcarriers with and without matrigel could be passaged up to passage 9 as shown in FIG. 114, but the final cell numbers tended to drop after passage 7. FIG. 115 summarises the mean cell concentration and mean fold expansion of hESC grown on Cytodex 1 and Hillex microcarriers with and without matrigel. On average, higher cell concentrations with matrigel were achieved on Cytodex 1 which was comparable to cellulose microcarriers.

Figure 116:
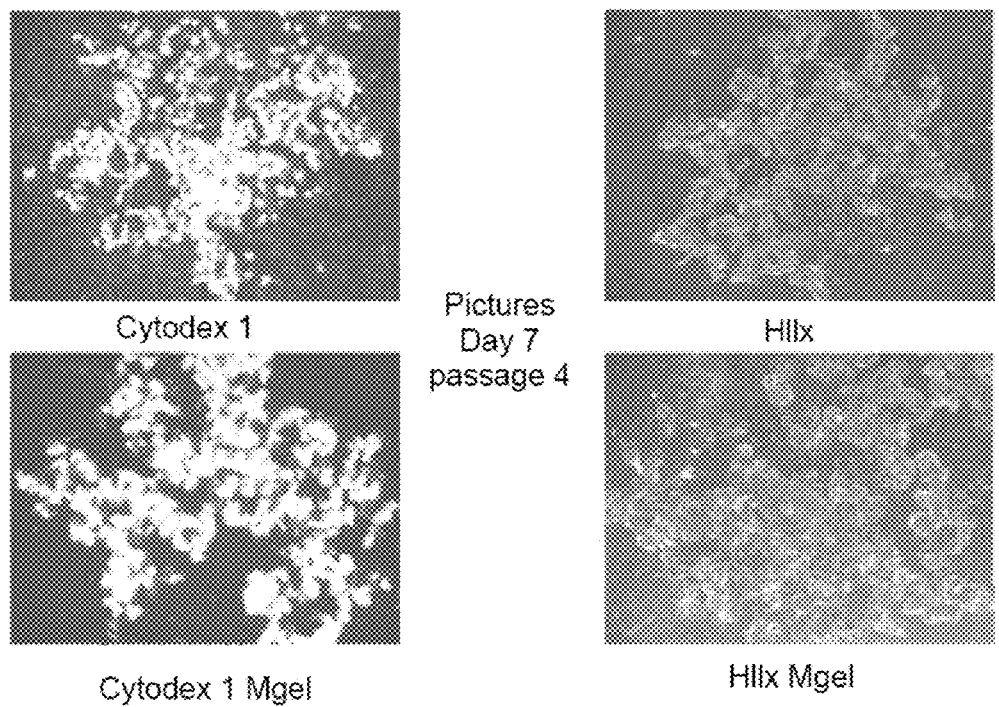
FIG. 116. Matrigel coated Cytodex 1 and Hillex microcarriers are more confluent than uncoated microcarriers. Hillex microcarriers continue to stain red with phenol red from the media.
Figure 117:
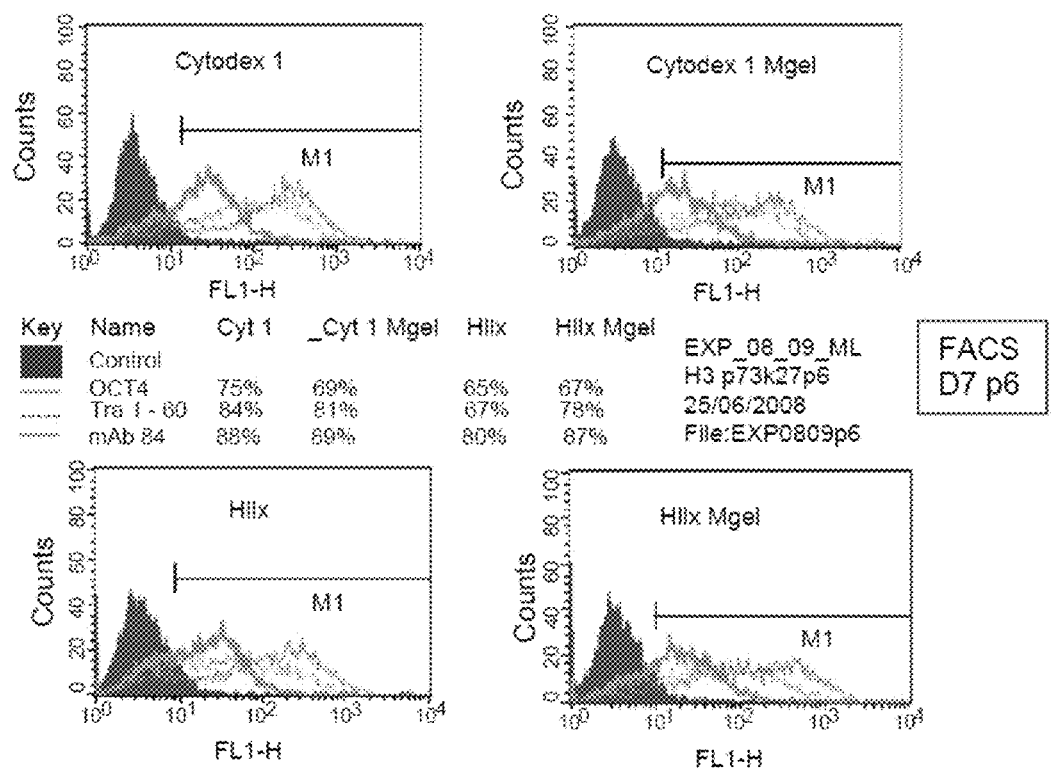
FIG. 117. Representative plot of hESC pluripotent markers (Oct4, TRA-1-60 and mAb 84) for Cytodex 1 and Hillex with and without Matrigel at passage 6.
Figure 118:
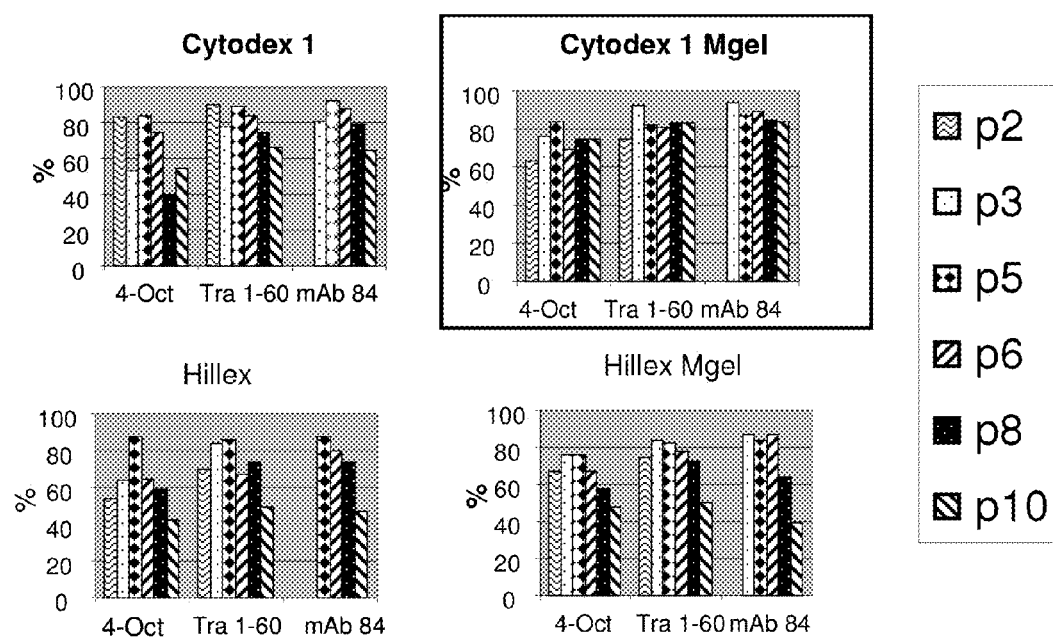
FIG. 118. FACS analysis of the 3 pluripotent markers Oct4, TRA-1-60 and mAb 84 at different passages (2 to 10 passages) for Cytodex 1 and Hillex with and without Matrigel. Approximately after 6 passages the expression of surface markers started to decrease gradually. The Matrigel coating provides more stability to the culture when Cytodex 1 is used, and Hillex produces similar results with and without matrigel coating. Cytodex 1 with Matrigel is a more stable platform than Hillex; Cytodex 1 with Matrigel coating is able to maintain the expression surface markers.

FIG. 116 shows matrigel coated Cytodex 1 and Hillex microcarriers are indeed more confluent than uncoated microcarriers, though Hillex microcarriers continue to stain red with phenol red from the media. FIG. 117 shows a representative plot of the 3 pluripotent markers Oct4, TRA-1-60 and mAb 84 of the 4 conditions at passage 6, with matrigel coated microcarriers performing better than the uncoated microcarriers. FIG. 118 summarises the FACS analysis of the 3 pluripotent markers Oct4, TRA-1-60 and mAb 84 at different passages for the 4 conditions indicating that these markers tend to fall after passage 6 except for Cytodex 1 coated with matrigel which was the most stable condition after 10 passages. Hillex with matrigel on the other hand showed a drop in these markers perhaps due to the adsorption of phenol red to the microcarriers. By passage 13, only hESC cultured on Cytodex 1 with matrigel still expressed the 3 pluripotent markers, whilst the other 3 microcarrier conditions had differentiated as shown by the reduced expression levels of the 3 markers (FIG. 69). Karyotypes for the 4 microcarrier conditions were normal at passage 7 (FIG. 120).

Example 38

Different Extracellular Matrix Coatings on DE53 Cellulose Microcarriers for hESC Culture We further examined if alternative extracellular matrices (ECMs) could be used as substitutes for matrigel for the support of hESC on microcarriers.

Table 8 shows the cell numbers of hESC grown on cellulose microcarriers after 7 days with different coatings of chondroitin sulphate (CS), heparin (HS) and hyaluronic acid (HA) diluted from 1:10 to 1:80 from their initial stock concentrations, compared to controls grown with coatings of KO media and conditioned media (CM) at passage P0. At passage P1, the cell numbers of hESC are greater than 1 million/well for all 3 coatings and are similar to the control with coating of KO media as shown in Table 9. FIG. 121 shows the expression of pluripotent markers Oct4, SSEA4 and TRA-1-60 at P1 with coatings of chondroitin sulphate, heparin and hyaluronic acid compared to the coating with KO media in FIG. 122. It appears that qualitatively, the coating with hyaluronic acid at 1:10 dilution is the preferred one for support of hESC, of the 3 coatings tested as the 3 pluripotent markers are the least down regulated with HA coating.

Other combinations of these ECMs including fibronectin were also tested and the cell numbers achieved at passages P0 and P1 are shown in Table 10. HA with fibronectin appeared to enable the best cell growth at P1. FIGS. 123 and 124 show pictures of the cellulose microcarriers coated with the different combinations of ECMs (fibronectin, HA and heparin salt (HS)) which continue to form tight aggregates of cells without any obvious cystic regions around the aggregates. However, when FACS for the pluripotent marker TRA-1-60 was performed, there was significant down regulation of this marker, by P1 with these ECM combinations, as shown in FIGS. 125 and 126.

Additional ECMs such as collagen I, IV and laminin were also tested for the support of hESC and Table 11 shows the cell numbers achieved with the different ECM combinations from P1 to P3. These cell numbers are also shown in FIG. 127 which shows a general downtrend in the cell numbers with each passage on the various ECMs.

FIG. 128 shows the morphology of the hESC on different combinations of ECMs with HA coated on cellulose microcarriers. Similarly, FIG. 129 shows the morphology of the hESC on different combinations of ECMs with HS coated on cellulose microcarriers. In general the combinations with HA have a denser aggregation of hESC on the microcarriers than the HS combinations. HA alone also appears to support more dense aggregates than HS alone in FIG. 130. And FIG. 131 shows that HA in combination with collagen I, IV, laminin and fibronectin appear to form denser cell aggregates than the ECM combinations with HS. Finally, a complete matrix of HA, HS and the other 4 ECMs are also shown to support hESC in FIG. 131.

FIGS. 132 to 135 show that the pluripotent markers Oct4, SSEA4 and TRA-1-60 after 3 passages continued to be expressed on the various combinations of ECMs, as described in Table 11, on cellulose microcarriers. However, there is some down-regulation of the levels of these markers compared to matrigel coated microcarriers.

Example 39

Hyaluronic Acid on DE53 Cellulose Microcarriers for hESC Culture

As HA looked the most promising as an alternative ECM to matrigel for the support of hESC, cells were passaged on HA coated cellulose microcarriers for multiple passages. As shown in FIG. 136, there continued to be robust growth and expression of the pluripotent markers Oct4, and TRA-1-60 (FIG. 137) for 3 passages (passage 4 to 6) which were comparable to the control 2D colony cultures. FIG. 138 shows continued high expression of the pluripotent marker, TRA-1-60 at passages 8 and 9 on HA coated microcarriers. Finally, FIG. 139 shows the morphology of dense hESC aggregates, grown on HA coated cellulose microcarriers at passage 6 at 2 different magnifications.

Example 40

Growth and Propagation of Human iPS cells on Microcarriers

Example 40.1

Human iPS (IMR90) cells were cultured in suspension culture on Matrigel coated DE53 microcarriers at 20 mg/well (4 mg/ml) in MEF condition KO-medium with 100 ng/ml bFGF (5 ml/well). The cellulose microcarriers were seeded from iPS (IMR90) cells passaged 8 times on feeder cells in 2D culture followed by adaptation on Matrigel for 5 passages in 2D culture (iPS IMR90PMGP5).

FIG. 162 shows confluent growth of human iPS cells on cellulose microcarriers. FIGS. 163 and 164 show that the iPS cells were successfully cultured from 3 through 10 weekly passages whilst retaining strong expression of OCT4, MAB84 and TRA-1-60 at passage 10. Cell growth was robust with cell densities of 3 to 8 million cells/ml achieved after every passage.

Example 40.2

Microcarriers Cultures of Human iPS Cells in Serum Free Media in mTeSR1

Two human iPS cell lines were continuously passaged over 2 or 3 weeks on Matrigel coated cellulose microcarriers in serum free media, mTeSR1. FIG. 186 shows increasing cell numbers and stable expression of pluripotent markers, Oct-4 and mAb 84.

Continuous passaging of human iPS cells (Reprocell, Japan) on Matrigel coated cellulose microcarriers was achieved.

Example 41

Cardiomyocyte Differentiation on Microcarriers

The ability to differentiate hESC into cardiomyocytes was investigated using microcarriers having different extracellular matrix (ECM) coatings. Cell expansion and differentiation was investigated using different ECM coatings. Differentiation was also investigated using different media supplements. Seeding of hESC from microcarriers to microcarriers followed by differentiation was also investigated.

Example 41.1

Differentiation

DE53 cellulose microcarriers were coated in one of Matrigel, Laminin, Vitronectin, Fibronectin (FIG. 165), or used uncoated. Tosoh 65 microcarriers were protamine derivatised and optionally coated in Laminin (FIG. 165). The microcarriers were coated overnight with the respective ECM in cold room under agitation. On the next day each well (5 ml) was seeded with $2.5 \times 10^6$ cells/well from 2D colony cultures which were collagenased and scraped. Plates were then kept under agitation for 1 hour after seeding.

Aggregates formed in the cultures were fed with conditioned media (CM) and bFGF for 2 days, with medium refreshed daily. On day 3, cultures were switched to bSFS differentiation medium with MAP kinase inhibitor, SB203580 (5 µM). Cultures were washed with bSFS for 1 hour and bSFS medium with inhibitor refreshed on 3 times a week (Monday, Wednesday, Friday) for the duration of the differentiation experiment. The cells used were HES-3 p33kK46.

FIGS. 166 and 167 show that beating areas were obtained with all coated microcarriers tested. Aggregates of EBs on microcarriers were larger than EBs made without microcarriers. FIG. 167 shows the increase in the number of beating EBs on microcarriers over 19 days. Laminin and Fibronectin coatings were particularly good at generating beating areas, whilst there were no beating EBs in the absence of microcarriers

Example 41.2

Expansion and Differentiation

To determine whether differentiated hESC expand on microcarriers, the following microcarrier coatings were tested:
1. Uncoated cellulose DE53
2. Laminin coated (20 μg) on 15 mg cellulose DE53 overnight
3. Matrigel coated on cellulose DE53 overnight A seeding ratio of $1.6 \times 10^6$ cells/well from 2D cultures (collagenased and scraped) was used. Cultures were fed with CM until aggregates were formed (3 days) washed with bSFS for 1 hour and later switched to differentiation medium+SB203580 (5 μM). Sampling of 2 wells for beatings and cell counts was performed on days 0, 4, 7 and 12. Cells used were H3 p33kK50. Day 14 aggregates are shown in FIG. 168. FIG. 169 shows expansion of cells on the different ECM coatings on microcarriers by 2 to 5 fold, averaged from cell counts taken at days 7 and 13 after initiation of differentiation.

The effect of Laminin and Fibronectin coatings (1 or 3 μg/g cellulose) on the percentage of beating embryoid bodies was also tested. FIG. 184 shows laminin coating to provide an improved number of beating aggregates compared with fibronectin coated or uncoated microcarriers.

Example 41.3

Differentiation with Different Media Supplements

A range of media and supplements was screened for their effect on differentiation.

DE53 cellulose microcarriers (3 mg/ml in 6 well plates) were conditioned for 2 hours in CM in static conditions. They were then seeded with $3 \times 10^6$ cells/well of hESC harvested from 2D cultures (collagenase and scraper in 4 directions). After seeding cultures were agitated (100 rpm) for 15 minutes before switching to static conditions.

Cultures in CM were formed as aggregates for 2 days, washed with bSFS and then switched to differentiation medium+SB203580 (5 μM) and different media supplements (0.1% HySoy, 1% BSA, 1× lipid mixture or combinations of these—see FIG. 170). Cells used were H3 p33kK47.

FIG. 171 shows the effect of media supplements on enhancing cardiomyocyte formation on uncoated microcarriers. All media supplements tested enhanced cardiomyocyte formation compared to bSFS alone without supplements, in uncoated microcarrier cultures.

FIG. 185 shows a significant improvement in the number of beating embryoid bodies or cardiomyocytes for hESC cultured on laminin coated DE53 cellulose microcarriers in the presence of chemically defined lipid, vitamin or Soy Hydrolysate media supplements.

Example 41.4

Differentiation with hESC Seeded from Microcarriers to Microcarriers using Different Media Supplements DE53 cellulose microcarriers (3 mg/ml) were conditioned for 4 hours in CM and seeded with $1.6 \times 10^6$ cells/well in 6 well plates. Cultures were agitated (100 rpm) for 1 hour before switching to static conditions.

Cultures in CM formed aggregates for 4 days, and then were switched either to bSFS differentiation medium+SB203580 (5 μM) and various additives (see FIG. 172) or DMEM/F12 medium with lipid supplement+SB203580 (5 μM). Cells used were H3 p33kK30p2.

FIG. 172 shows that the Lipid mixture, BSA and Hy-Soy additives all independently improved the total number of beating aggregates compared to bSFS alone without supplements, in uncoated microcarrier cultures.

Example 41.5

Differentiation of hESC on Negatively Charged Microcarriers

Microgranular carboxymethyl cellulose CM52 negatively charged microcarriers (20 mg/well, 4 mg/ml) were seeded with HES-3 cells, suspension cultured and passaged. Differentiation was shown by large cystic regions (data not shown) within passage 1 with or without Matrigel coating. Cell densities were higher on Matrigel coated microcarriers than uncoated microcarriers. This indicates that whilst negatively charged microcarriers may not support pluripotent growth of hESC, they can support differentiation of hESC.

Example 41.6

Efficient Cell Harvesting from Aggregates for Further Analysis hESC may be harvested from microcarrier cultures by direct enzymatic treatments (e.g. Trypsin or Tryple).

|      |         | % Viability | % Recovery |
|------|---------|-------------|------------|
| DE53 | Trypsin | 64          | 10.2       |
|      | Tryple  | 57          | 9.8        |

A two step protocol involving pretreatment with collagenase and enzymatic treatment (trypsin) was found to improve the harvest of hESC from microcarriers.

|      |   | % Viability | % Recovery |
|------|---|-------------|------------|
| DE53 | A | 87          | 64.1       |
|      | B | 90          | 88.3       |

To harvest cardiomyocytes from microcarriers, a two step protocol involving pretreatment with collagenase and enzymatic treatment with trypsin or Tryple was found to improve harvesting efficiency.

|      |          | % Viability | % Recovery |
|------|----------|-------------|------------|
| DE53 | Acutase  | 64          | 20.2       |
|      | Solution | 76          | 22.1       |
|      | Trypsin  | 90          | 46.7       |
|      | Tryple   | 87          | 37.0       |
|      | Dispase  | 71          | 5.4        |

Example 41.7

Human iPS cells, IMR90 Embryoid Body Formation and Cardiomyocyte Differentiation Human iPS cells on Matrigel coated cellulose DE53 microcarriers at passage 13 were differentiated by transferring the microcarriers to EB media (KO basal medium+20% serum+ non-essential amino acids) for 14 days in suspension followed by being re-plated on gelatin coated 6 cm tissue culture dish for 7 days. Several beating aggregates were observed. Two of the beating aggregates were transferred to a new 6 cm dish coated with gelatin for further observation. After 23 days all beating clumps were still actively beating.

Example 41.7

Additional Differentiation Experiments

HES-2 hESC cultured on laminin coated microcarriers (2 micrograms/mg of microcarriers) were used to successfully generate beating aggregates (3 replicates) in day 18 samples.

iPS ES4SKIN cells cultured on laminin coated microcarriers (1 microgram/mg of microcarriers) were used successfully to generate beating aggregates in day 8 samples.

Human iPS foreskin cells formed 25% of beating embryoid bodies at day 12 in serum free media on laminin coated cellulose microcarriers.

Example 41.8

Differentiation to Endoderm Lineage hESC were differentiated towards the endoderm lineage (e.g. pancreatic islets cells, hepatocytes, lung) by agitating (40 rpm) hESC Matrigel coated microcarrier suspension cultures in spinner flasks, and also by agitation (120 rpm) in 6 well plates. Down regulation of pluripotent markers Oct4, Mab84 and Tra-1-60 was observed with upregulation of the endoderm genes GATA6 and alpha fetoprotein. Considered together with the results shown in FIG. 73 (Example 32), these results indicate that lower rates of agitation can be used to culture cells and maintain the pluripotent/multipotent status of the cells and that higher rates of agitation can be used to induce differentiation.

Example 42

Culture of Human Embryonic Stem Cell Derived Mesenchymal Stem Cells on Microcarriers The differentiation of human embryonic stem cells to reproducibly provide clinically compliant mesenchymal stem cells (MSCs) is described in Lian et al (Derivation of Clinically Compliant MSCs from CD105+, CD24− differentiated human ESCs. Stem Cells 2007; 25:425-436). They describe a protocol that can be used to reproducibly generate highly similar and clinically compliant MSC populations from hESCs by trypsinizing and propagating hESCs without feeder support in medium supplemented with FGF2 and PDGF AB followed by sorting for CD105+ and CD24− cells. The MSCs obtained were remarkably similar to bone marrow MSCs (BM-MSCs) and satisfied the morphologic, phenotypic and functional criteria commonly used to identify MSCs, i.e. adherent monolayer with a fibroblastic phenotype, a surface antigen profile that is CD29+, CD44+, CD49a+, CD49e+, CD105+, CD166+, CD34− and CD45−, and a differentiation potential that includes adipogenesis, chondrogenesis and osteogenesis. Lian et al describe the use of Hues9 and H1 hESCs to generate their MSCs.

We used the protocol of Lian et al to generate hESC derived MSCs and cultured and passaged these MSCs on uncoated microcarriers to confirm that microcarriers can be used to support the continued culture, growth and passage of cells obtained from the differentiation of hESC, and in particular of hESC derived adult stem cells.

Example 42.1

Variation of Microcarrier Concentration in Spinner Flasks

Cytodex 3 microcarriers were seeded with hESC derived MSCs at different microcarrier concentrations (1.5, 3 and 5 carriers/ml) and cultured in spinner cultures agitated at 40 rpm in 50% media changed every 3 days. FIGS. 174 and 175 show the growth of the hESC derived MSC on microcarriers. The best growth was obtained using the lowest microcarrier concentration tested.

Example 42.2

Variation of Cell Seeding Concentration in Spinner Flasks

Cytodex 3 microcarriers were seeded with a range of concentrations of hESC derived MSC cells (from 5 to 14 cells/ microcarrier) at 3 mg/ml microcarrier in spinner cultures agitated at 40 rpm in 50% media changed every 3 days. FIGS. 176 and 177 show higher final cell densities obtained with higher starting cell concentrations.

Example 42.3

Comparison of Monolayer and Microcarrier Culture

The growth of hESC derived MSCs on Cytodex 3 microcarriers was compared with the growth of hESC derived MSCs in monolayer culture with daily media exchange. FIGS. 178 and 179 show that hESC derived MSCs grown on microcarriers achieved a faster doubling time and a higher cell density.

Example 42.4

Passaging of hESC Derived MSCs on Microcarriers hESC derived MSCs were passaged on Cytodex 3 microcarriers by two methods:
 (i) addition of 50% new microcarriers; or
 (ii) detachment of cells with tryplE enzyme followed by addition of new microcarriers.

All cultures were fed daily. FIGS. 180 and 181 show that in both cases the cells achieved similar doubling times and cell densities over 3 passages. FIGS. 182 and 183 show the positive expression at day 10 of the 5 MSC markers CD73, CD90, CD105, CD29 and CD44 and negative expression of CD34 and CD45 by hESC derived MSC on Cytodex 3 microcarriers when passaged by the two methods described.

Example 43

Fed Batch Culture in StemPRO Media

FIG. 187 shows the results of controlled low glucose feeding (2 g/l daily) on cell density of hESC in microcarrier suspension culture using StemPRO media, as compared to cultures fed daily with StemPRO only. Low glucose feeding resulted in higher cell densities.

Reduced lactate production and improved pH control was also observed in DMEM/F12 media.

Example 44

A Scalable Bioprocess for hESC Derived Cardiomyocyte Production

A heart infarct could involve an irreversible loss of around 2 billion cardiomyocytes. The production of human cardiomyocytes in large numbers is an important goal as it has significant implications for clinical trials in big animals, drug discovery and also development of future cell therapies. Because of the characteristics of pluripotency, human embryonic stem cells (hESC) can provide a source for cardiomyocytes. Although some studies of undifferentiated hESC growth in scalable microcarriers platform have been conducted (Oh S. K. et al. (2009). Stem Cell Research. 2(3): 219-230.), only a few cardiomyocyte differentiation protocols derived from hESC have been described by the scientific community and the scalability of these proposed bioprocesses is still not clear.

The aim of this investigation was to develop a scalable bioprocess for cardiomyocyte production on a microcarrier suspension culture platform. We investigated how 1) the seeding conditions and 2) different types of microcarriers affected cardiomyocyte differentiation efficiency. Laminin coated microcarriers provided better cell attachment and higher differentiation efficiency than uncoated microcarriers. Seeding directly into bSFS (differentiation medium) generated more cardiomyocytes compared to conditioning for 2 days in feeder conditioned medium. In addition, several kinds of microcarriers were tested for differentiation efficiency (DE53, Cytodex 1, Cytodex 3, Tosoh 10 micron and FACT). Different aggregate size distributions were observed for each carrier type which determined the cell expansion fold and differentiation efficiency. The best result of 0.7 cardiomyocytes/hESC initially seeded was achieved in Tosoh 10 microcarrier cultures. Finally, the beating aggregates were characterized by immunohistological analysis and qRT-PCR. Results show positive staining for cardio-specific markers (Tropinin I, α-Sarchomeric actinin, MLC, ANP and desmin) and also up regulation of cardio-specific genes (NKX2.5, MLC, MHC, ANP).

The promising results obtained show that it is possible to define a fully scalable cardiomyocyte production platform in 3-dimensional microcarrier suspension cultures.

Materials and Methods.
  Cell Culture.
  Human Embryonic stem cell line, HES-3(46X, X) was obtained from ES Cell International (ESI). The cells were co-cultured with mitomycin-C-inactivated Human Feeders (HFF-1) in gelatin-coated 6 cm culture dishes. Media (KO-media) used in culture composed of 85% KO-DMEM, 15% KO Serum Replacer, 1 mM L-glutamine, 1% non-essential amino acids, 0.1 mM 2-mercaptoethanol, 25 U/mL penicillin, 25 µg/mL streptomycin and 4-8 ng/ml of bFGF (Invitrogen). Routine culture consisted of daily refreshing of media. Passaging of cells was done weekly following Choo et al. 2004 (Choo, A. B. et al. (2004). Biotechnol. Bioeng. 88(3): 321-331.).

Microcarriers.
  TSKgel Tresyl-5PW (TOSOH), Cytodex 1 (GE Healthcare), Cytodex 3 (GE Healthcare), DE53(Whatman) and FACT (HyClone).
  Differentiation.
  Media used in differentiation cultures composed of 97% DMEM, 2 mM L-glutamine, 0.182 mM Sodium Pyruvate, 1% non-essential amino acids, 0.1 mM 2-mercaptoethanol, 5.6 mg/L Transferrin (Invitrogen), and 20 ug/L Sodium Selenite. p38 MAPK inhibitor SB203580 (Sigma), was added at 5 µM, as previously reported by Xu X Q et al. 2008 (Xu, X. Q. et al. (2008). Differentiation. 76(9): 958-970.). Media was refreshed every 2-3 days.
  Quantification of Cardiomyocytes.
  Beatings. Aggregates were scored for contractility under a phase contrast microscope. Multiple beating areas within the same aggregate or EB were not scored separately. Scores were calculated as percentage over all aggregates. FACS. Cells were harvested as single cell suspension using TrypLE Express (Invitrogen), fixed and permeabilized (Caltag Laboratories), and incubated with MF20 (1:200, Develop. studies Hybridoman Bank) and α-Sarchomeric Actinin (1:100, Sigma). Cells were then subsequently washed with 1% BSA/PBS and incubated in the dark with Anti-mouse antibody FITC-conjugated (1:500, DAKO). The cells were then washed and resuspended in 1% BSA/PBS- for analysis on a FACScan (Becton Dickinson FACS calibur).
Results.
  Effect of Seeding Conditions on Differentiation Efficiency.
  The seeding conditions, which have been pointed out as a key parameter in our preliminary studies, are important to achieve proper cell attachment and aggregate formation. Direct seeding in differentiation medium or feeder conditioned medium (CM) for 2 days (supplemented with bFGF) were tested on laminin coated, uncoated and embryoid bodies culture. The aggregate formation of each were compared. Although conditioned aggregates in CM colonized the microcarriers better and the cells attached more homogenously along the carriers surface, they differentiated less efficiently as can be observed from the beating aggregates score (FIG. 205a) and also in terms of percentage of population stained positive for MF20 in flow cytometry analysis (FIG. 205b). Cell aggregates were spread too thinly on the rod shaped carriers, reducing the mass aggregation necessary for efficient differentiation. In contrast, cells seeded directly in bSFS medium formed bigger aggregates with more critical cell mass, promoting more efficient differentiation. On the other hand, laminin coated microcarriers improved cell attachment and aggregation, reducing cell death and consequently lower cell debris accumulation was observed. The differences in the results between different conditions in FIGS. 205a and 205b can be explained by the size of the beating area in the aggregates in the laminin coated carriers in bSFS medium, and is further supported by MF20 FACS staining.
  Effect of Microcarrier Shape & Size on Differentiation Efficiency and Yield of Cardiomyocytes/hESC Seeded.
  FIGS. 193-195 and FIG. 206 show results of cardiomyocyte differentiation cultures conducted with different kinds of microcarriers: DE53, FACT, Cytodex 1, Cytodex 3, Tosoh 10 compared to embryoid bodies. FIG. 195 shows size distribution of the aggregates formed at day 2 after differentiation. FIG. 193 shows maximum % of beating aggregates scored from day 10 to 16 after differentiation and % of positively stained cells for MF20 and α-Sarchomeric actinin at day 16. FIGS. 194 and 206 show cell expansion fold and ratio of cardiomyocytes produced at the end of the culture over hESC seeded.

Microcarrier shape, size and concentration are also key parameters to control to improve cell attachment and aggregate sizes. Rod shape carriers (DE53), spherical carriers with diameter approximately 100-200 μm (Cytodex 1 and 3, FACT) and spherical carriers with 10 μm diameter (Tosoh 10) were compared to embryoid bodies. Each carrier type showed a different aggregate size distribution (FIG. 195). Although embryoid body sizes between 400 and 800 μm enhanced cardiomyocyte differentiation accordingly to a previous work published by Niebruegge S. et al. 2009 (Niebruegge S et al. (2009). Biotechnol. Bioeng. 102(2): 493-507), in our microcarrier experiments, this was not observed in the % of beatings aggregates scored, nor in the FACS analysis (FIG. 193). This difference can be explained because aggregates composed of both carriers and cells are larger than embryoid bodies and thus the optimum aggregate size range for cardiomyocytes differentiation may be larger. However, the cell expansion fold clearly depends on the aggregate size distribution (FIG. 194). The smallest aggregates (below 200 μm) tend to disaggregate causing a higher cell death. Aggregate sizes from 200 to 600 μm enhance the cell growth as reflected in the higher expansion fold achieved at the end of the cultures. These aggregate sizes do not limit nutrient transfer into the aggregates and also provides a higher surface to volume ratio and thus offers more surface for culture expansion. In microcarrier cultures, the ratio between the hESC seeded and the cardiomyocytes obtained are generally higher than the culture with embryoid bodies (FIG. 206). The best cardiomyocyte outcome was observed when Tosoh 10 microcarriers were used, reaching up to 0.7 cardiomyocyte for each hESC seeded.

Cardiomyocytes Characterization.

The gene expression profile of beating aggregates in comparison to undifferentiated hESC shows a consistent overexpression of both late cardiomyocyte genes like MHC, MLC and ANF (Hesx1), and also early cardio genes like NKX2.5 at day 16 (FIG. 207a). Pluripotent genes such as Nanog or OCT4 are definitely downregulated after 16 days of differentiation cultures. Immunohistology of beating aggregates were performed using cardio-specific markers (FIG. 207b). In general, for all the markers analyzed, most prominent staining was observed around the cystic structures and at the peripheries of the aggregates than in the central areas. This can be explained by the observation that cells located on the aggregate surface could be more exposed to differentiation factors released in the medium and also to the inhibitor used to drive the differentiation.

In conclusion, cardiomyocyte differentiation of hESC have been developed successfully on several kinds of microcarriers suspension cultures. The results presented are promising to define a fully scalable cardiomyocyte production platform in 3-dimensional suspension cultures. This platform could provide the scientific community with large numbers of cardiomyocytes for heart therapy studies and drug discovery.

Since the cardiomyocyte population in the differentiated cultures is around 20-30% in the best cases, downstream purification steps may also be required for future cardiomyocyte applications.

Example 45

Identifying Microcarriers and Extracellular Matrices for the Culture of Undifferentiated Human Embryonic Stem Cells in Suspension Advances in stem cell technology bring us closer to the realization of cell-based therapy and regenerative medicine. Traditionally, human embryonic stem cells (hESC) have been cultured as standard monolayer cultures on feeder cells or extracellular matrix (ECM). However, the scale-up of hESC in monolayer cultures is not practical.

Recently, culturing human embryonic stem cells (hESC) in suspension has been developed using microcarriers. This is a significant achievement to address the process development issues of hESC expansion. In this study, we evaluated the physical properties (size, shape, surface charges and porosity) of microcarriers on hESC growth and pluripotency.

Furthermore, as ECM is still considered to be critical for survival and growth of hESC on microcarriers, all previous work used Matrigel-coated microcarriers for long term cultivation of undifferentiated hESC. Poor cell attachment and loss of pluripotency were usually shown for hESC grown on uncoated-microcarrier. In order to have a robust and reliable platform for large scale hESC production with minimal animal-derived components, we need a substitute cell attachment substrate to replace Matrigel. Thus, we screened major molecular components of ECM i.e. proteoglycans, non-proteoglycan polysaccharides and glycoproteins.

Materials and Methods

Human Embryonic Stem Cell and the Culture Medium.

Human embryonic stem cells (hES-3) from ES Cell International were grown in Conditioned Medium obtained from mitomycin C-treated Mouse Embryonic Fibroblast (MEF-CM).

Microcarriers and Extracellular Matrices Preparation.

As per manufacturers' instructions. Cellulose-based anion exchangers (DE53, DE52 and QA52) and cation exchanger (CM52) were obtained from Whatman. Toyopearl AF-Tresyl-650 with mean particle size 65 μm (Tosoh 65) and TSKgel Tresyl-5PW with mean particle mean size 10 μm (Tosoh 10) were obtained from Tosoh Bioscience and coupled with protamine sulfate (PR) or poly-L-Lysine (PL) to positively charge the bead surfaces.

Differentiation Study.

Spontaneous differentiation of hESCs on microcarriers was generated in vitro through the induction of embryoid bodies (EBs). EBs were generated by exchanging the MEF-CM to the EB medium (80% Knockout-DMEM/F12, 20% fetus bovine serum, 1 mM Glutamine, 1% (v/v) non-essential amino acids, 25 U/ml penicillin, 25 μg/ml streptomycin, 0.1 mM 2-mercaptoethanol).

Results are shown in FIGS. 208-210. Cells on smaller microcarriers (Tosoh 65, Tosoh 10) formed cell-microcarrier aggregates with the microcarriers embedded inside. Similar cell growth on both microporous and smooth microcarriers was observed. Poor cell growth on negative charged microcarriers was observed. No significant differences in cell growth and pluripotency were observed for hESC grown on rod-shaped microcarriers of different charge strength. hESC on microporous microcarrier showed differentiation after two passages while maintaining similar cell growth and without Matrigel coating. Microcarriers were able to support long term cultivation of hESC in an undifferentiated state but only when coated with Matrigel. Normal karyotype was observed in hESC cultured on DE53 Matrigel-coated microcarriers for 25 passages. Hyaluronic Acid (HA) was identified as a potential attachment substrate for culturing undifferentiated hESC on microcarrier. After 2 passages, only cells on DE53 coated with HA were able to maintain cell growth. Laminin was also identified as a potential attachment substrate. Laminin-coated microcarriers were able to sustain long term cultivation of hESC and differentiation showing expression of genes from three lineages.

We found that hESCs were able to attach on coated-microcarriers and grow despite the differences in microcarrier properties. We identified hyaluronic acid from *Streptococcus zooepidemicus*, non-proteoglycan polysaccharide, as possible xeno-free substrate for the cultivation of hESC on microcarriers. hESC culture grown on a defined matrix laminin resulted in similar cell yield while retaining its differentiation capability as hESC grown on a Matrigel-coated surface.

3D suspension cultures of hESC will become important to enable volumetric increase of hESC production in controlled bioreactors for future cell therapies. The results contained in FIGS. 211-215 demonstrate:
1. Long term culture of hESC on rod and spherical shaped microcarriers coated with Matrigel and hyaluronic acid in conditioned and serum free media.
2. Spinner cultures of hESC with microcarriers.
3. Differentiation of hESC to cardiomyocytes in microcarrier cultures.
4. Long term culture of human iPS on rod shaped microcarriers.

Example 46

Expansion and Directed Differentiation of Human Induced Pluripotent Stem Cells on Microcarriers to the Neural Lineage It has been shown that human induced pluripotent stem cells (hiPSC) can be derived from patients with neurodegenerative disease such as amyotrophic lateral sclerosis (Dimos J T et. Al. (2008) Science 321(5893), 1218-21), familial dysautonomia ((Lee G et. Al. (2009) Nature 461(7262), 402-6)) and spinal muscular atrophy ((Ebert A D et. Al. (2009) Nature 457(7227), 277-80)). These patient-specific cells are suitable for the modeling of neurodegenerative diseases, the screening of possible drugs and possible cell replacement therapy. Hence, there will soon be a need for large scale expansion of these cells.

In this way, these differentiated hiPSC can be used as patient-specific disease models to understand the pathology of the disease, to test potential drugs and in the future, to be used in cell replacement therapy. For large scale drug screening or cell replacement therapy, a large number of these cells would be required. Traditionally, tissue culture plates are used to grow hiPSC but their limited growth area makes them impractical for producing large quantities of cells.

Materials and Methods hiPSC grown in 2D culture: hiPSC (iPS IMR90) were obtained from James Thomson (Yu J. et. Al. (2007) Science. 318(5858), 1917-20) and were grown in mTeSR™ culture media on hESC-qualified Matrigel™-coated tissue culture plates.

hiPSC grown in MC culture: 2D cultured cells in mTeSR™ 1 media were enzymatically passaged onto hESC-qualified Matrigel™-coated microcarriers (MC), a cellulose based anion exchanger (DE53) obtained from Whatman. At the next passage, these cells were mechanically passaged to fresh batch of coated MC in mTeSR™ 1 media. hiPSC static MC culture was mechanically passaged and used to seed spinner (100 ml) MC culture.

In-vitro spontaneous differentiation study: mTeSR™ 1 media of the MC culture was changed to the EB media (90% Knockout-DMEM/F12, 10% fetus bovine serum, 1 mM Glutamine (L-glut), 1% (v/v) non-essential amino acids (NEAA), 1× penicillin/streptomycin (PS), 0.1 mM 2-mercaptoethanol (2ME)). After 7 days, cell aggregates were re-plated onto gelatin-coated tissue culture plates with EB media and culture was continued for 14 days.

In-vitro directed differentiation study: mTeSR™ 1 media of the MC culture was changed to the KO media (90% Knockout-DMEM/F12, 10% KnockOut™ Serum Replacement, 1 mM L-glut, 1% (v/v) NEAA, 1×PS, 0.1 (2ME)). After 4 days, media was exchanged for N2B27 media (95% DMEM/F12, 0.5% L-glut, 1% N2, 2% B27, 0.5% PS, 1% NEAA, 0.09% 2ME) spiked with Noggin. After 10 days, N2B27 media was spiked with EGF and FGF2. After 7 days, cell aggregates were re-plated onto laminin-coated tissue culture plates.

Results

We have developed a microcarrier based serum free medium (mTeSR1™) platform for hiPSC using hESC-qualified Matrigel™ coated cellulose microcarriers. This static microcarrier platform achieved comparable cell concentrations as conventional 2D culture (static microcarriers: $1.47 \times 10^6$ cells/ml; conventional 2D: $1.79 \times 10^6$ cells/ml).

Static hiPSC-microcarrier culture could be continuously cultured for at least 22 passages showing high expression of OCT-4 (71.6%) and Tra-1-60 (92.3%) while maintaining stable karyotype (FIGS. 216, 217). These cells could also differentiate spontaneously in-vitro and in-vivo to the three germ layers (FIG. 218).

hiPSC-microcarrier complexes were successfully cultured in spinner (100 ml) culture, in which the hiPSC exhibited 20 fold expansion (FIGS. 219, 220 and 221).

These hiPSC were directly differentiated on the microcarriers to neural precursors expressing Pax6 and Nestin, neurons expressing Map2 and β-tubulin III and GFAP expressing astrocytes. Further scale-up of hiPSC on microcarrier in spinner flask system was also possible achieving a cell yield of $6.16 \times 10^6$ cells/ml while maintaining high expression of OCT-4, Tra 1-60 and mAb 84 and ability to be directly differentiated to neural lineages (FIGS. 222 and 223). This study shows that hiPSC on microcarriers in suspension can be expanded and directly differentiated to neural lineages and it is a possible avenue to achieve large quantities of patient-specific neuronal cells.

Example 47

Development of Microcarrier Based Cellular Expansion Technique for the Clinical Application of Human Fetal MSC Materials and Methods Human fetal MSC and the culture conditions: Human fetal MSC were obtained from Experimental Fetal Medicine Group, Department of Obstetrics and Gynecology, Yong Loo Lin School of Medicine, National University of Singapore and National University Hospital System and was grown in Dulbecco's Modified Eagle Medium with GlutaMAX™ supplemented with 10% fetal bovine serum and 0.5% penicillin and stretomycin. Expansion of the hfMSc was performed in spinner (100 ml) flask at 40 rpm.

Microcarriers preparation: Commercially available microcarriers Cytodex 1 and Cytodex 3 were purchased from GE Healthcare, Cultispher GL from Sigma-aldrich and P102-L from Hyclone. Each microcarrier was prepared as per manufacturers' instructions.

Osteogenic differentiation studies: Osteogenic differentiation of hfMSC was carried out by harvesting the cells from Cytodex 3 or tissue culture flasks using type 1 collagenase and trypsin respectively, plated onto culture dishes and fed with osteogenic induction medium (D10 medium supplemented with 10 mM β-glycerophosphate, 10-8M dexamethasone and 0.2 mM ascrobic acid). Comparisons were done on hfMSC expanded using tissue culture flasks and Cytodex 3 by measuring the calcium content deposition and ALP activity using calcium assay kit (BioAssay Systems, USA) and SensoLyte™ pNPP Alkaline Phosphatase Assay Kit (AnaSpec, USA).

Results

Growth kinetics of hfMSC on various microcarriers: Spherical microcarriers (Cytodex 1, Cytodex 3 and P102-L) were able to support fast and high cellular proliferation as compared to the porous microcarrier (Cultispher GL). Cytodex 1 and Cytodex 3 produced a higher cell viability as compare to P102-L in the first five days of the culture. See FIGS. 224, 225 and 226.

hfMSC morphology on various type of microcarriers: Cells grown on Cultispher GL (microporous microcarrier) and P102-L (spherical, small polystyrene beads) tended to form aggregates, which can be undesirable for harvesting. hfMSC spread as monolayer on Cytodex 1 (spherical, positively charged surface) and Cytodex 3 (spherical, denatured type 1 collagen coated).

Flow cytometry analysis (CD 105)—fhMSC before osteogenic differentiation: Human fetal MSC that were expanded and harvested using type I collagenase had a noticeable drop in the immunophenotypic marker, CD 105, by 17%. See FIGS. 227 A and 227 B.

Osteogenic differentiation studies: Human fetal MSC cultured on Cytodex 3 in spinner flask has osteogenic differentiation capacity. Human fetal MSC harvested from microcarriers have less ALP activity and calcium deposition as compared to hfMSC expanded on tissue culture flask. See FIGS. 228 A and 228B—positive Alizarin Red staining of calcium deposition was confirmed in the hfMSC monolayer cultures.

We investigated establishment of a microcarrier based cellular expansion technique for the clinical application of human fetal mesenchymal stem cell (hfMSC). Several commercially available microcarriers including the Cytodex 1, Cytodex 3, Cultispher GL and P102-L were compared for culturing hfMSC in spinner flasks. Results revealed that Cytodex 1 and 3 are suitable for hfMSC expansion as they support fast and high cellular proliferation without aggregations.

Further investigation demonstrated that Cytodex 3 microcarrier expansion with harvesting technique by type I collagenase yields a maximum alkaline phosphatase activity and calcium deposit in its third week of osteogenic differentiation at 210 ng/ml and 19 mg/dl, respectively, as compared to traditional petri dish culture of 280 ng/ml of alkaline phosphatase activity and 35 mg/dl of calcium deposit in its third and fourth week of osteogenic differentiation respectively.

In conclusion, microcarrier based cellular expansion technique is able to support fast and high cellular expansion of hfMSC.

REFERENCES

Baker, Monya (2007-12-06). Adult cells reprogrammed to pluripotency, without tumors. Nature Reports Stem Cells.
P W Burridge et al. 2006. Defined Medium with polyvinyl alcohol (PVA), Activin A and bFGF. Stem Cells. 2007 April; 25(4):929-38. Epub 2006 Dec. 21.
Choo, A. B., Padmanabhan, J., Chin, A., Fong, W. J., Oh, S. K. W. (2005). Immortalized feeders for the scale-up of human embryonic stem cells in feeder and feeder-free conditions. J. Biotechnol. 122:130-141.
Choo, A. B., Padmanabhan, J., Chin, A. C., Oh, S. K. W. (2004). Expansion of pluripotent human embryonic stem cells on human feeders. Biotechnol. Bioeng. 88:321-331.
Chung Y, Klimanskaya I, Becker S, et al. Embryonic and extraembryonic stem cell lines derived from single mouse blastomeres. Nature. 2006; 439:216-219.
Chung Y, Klimanskaya I, Becker S, et al. Human embryonic stem cell lines generated without embryo destruction. Cell Stem Cell. 2008; 2:113-117
Dang et al., Stem Cells 2004, 22(3):2 75-82.
Dang S M, Gerecht-Nir S, Chen J, Itskovitz-Eldor J, Zandstra P W. (2004). Controlled, scalable embryonic stem cell differentiation culture. Stem Cells. 22(3):275-82.
Dang S M, Zandstra P W. (2005). Scalable production of embryonic stem cell-derived cells. Methods Mol. Biol. 290:353-64.
Evans, M. J., and Kaufman, M. H. (1981). Establishment in culture of pluripotential cells from mouse embryos. Nature 292, 154-156.
Fok E Y, Zandstra P W. Shear-controlled single-step mouse embryonic stem cell expansion and embryoid body-based differentiation. Stem Cells. 2005 October; 23(9):1333-42. Epub 2005 Aug. 4.
Gallimore, P. H., and Richardson, C. R. (1973). An improved banding technique exemplified in the karyotype analysis of two strains of rat. Chromosoma 41, 259-263.
Gerecht Nir et al., Biotechnol Bioeng. 2004, 86(5): 493-502.
Hay et al. (2008). Highly efficient differentiation of hESCs to functional hepatic endoderm requires ActivinA and Wnt3a signalling. PNAS Vol. 105. No. 34 12310-12306.
Hewitt, Z., Priddle, H., Thomson, A. J., et al. (2007). Ablation of undifferentiated human embryonic stem cells by exploiting innate immunity against the beta-galactosyltransferase epitope. Stem Cells 25, 10-18.257-265.
J Itskovitz-Eldor, M Schuldiner, D Karsenti, A Eden, O Yanuka, M Amit, H Soreq, N Benvenisty. Differentiation of human embryonic stem cells into embryoid bodies compromising the three embryonic germ layers. Mol. Med. 2000 February; 6 (2):88-95.
Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., et al. (2002). Pluripotency of mesenchymal stem cells derived from adult marrow. Nature 418, 41-49.
Chris H. Jo et al. Fetal mesenchymal stem cells derived from human umbilical cord sustain primitive characteristics during extensive expansion. Cell Tissue Res (2008) 334:423-433.
Kaji et al. Virus-free induction of pluripotency and subsequent excision of reprogramming factors. Nature. Online publication 1 Mar. 2009.
Kanatsu-Shinohara, M., Inoue, K., Lee, J., Yoshimoto, M., Ogonuki, N., Mild, H., Baba, S., Kato, T., Kazuki, Y., Toyokuni, S., et al. (2004). Generation of pluripotent stem cells from neonatal mouse testis. Cell 119, 1001-1012.
Kim et al. Ex vivo characteristics of human amniotic membrane-derived stem cells. Cloning Stem Cells 2007 Winter; 9(4):581-94.
King, J. A. and Miller, W. M. (2007). Bioreactor development for stem cell expansion and controlled differentiation. Current Opinion in Chemical Biology. 11:394-398.
Klimanskaya I, Chung Y, Becker S, Lu S J, Lanza R. Human embryonic stem cell lines derived from single blastomeres. Nature 2006; 444:512.
Klimanskaya I, Chung Y, Becker S, et al. Human embryonic stem cell lines derived from single blastomeres. Nature. 2006; 444:481-485.

Kotler, M., Reuveny, S., Mizrahi, A. and Shahar, A. (1985). Ion exchange capacity of DEAE microcarriers determined the growth pattern of cells in culture. Develop. Biol. Stand. 60, 255-261.

Kroon et al. (2008) Pancreatic endoderm derived from human embryonic stem cells generates glucose-responsive insulin-secreting cells in vivo. Nat Biotechnol April; 26(4): 443-52.

M A Laflamme et al. 2007. Culture sequentially supplemented with Activin A for 24 h, and BMP 4 for 4 days. Nat. Biotechnol. 2007 September; 25(9):1015-24. Epub 2007 Aug. 26.

Lei et al Xeno-free derivation and culture of human embryonic stem cells: current status, problems and challenges. Cell Research (2007) 17:682-688.

Lazar, A., Silberstein, L., Reuveny, S, and Mizrahi, A. (1987). Microcarriers as a culturing system of insect cells and viruses. Develop. Biol. Stand. 66, 315-323.

Lian et al. Derivation of Clinically Compliant MSCs from CD105+, CD24-differentiated human ESCs. Stem Cells 2007; 25:425-436.

Lin et al. Multilineage potential of homozygous stem cells derived from metaphase II oocytes. Stem Cells. 2003; 21(2):152-61

Maherali N, et. al. Directly reprogrammed fibroblasts show global epigenetic remodeling and widespread tissue contribution. Cell Stem Cell 2007; 1:55-70

Martin, G. R. (1981). Isolation of a pluripotent cell line from early mouse embryos cultured in medium conditioned by teratocarcinoma stem cells. Proc. Natl. Acad. Sci. USA 78, 7634-7638.

Matsui, Y., Zsebo, K., and Hogan, B. L. (1992). Derivation of pluripotential embryonic stem cells from murine primordial germ cells in culture. Cell 70, 841-847.

McWhir, J., Wojtacha, D., and Thomson, A. J. (2006). Routine culture and differentiation of human embryonic stem cells. In Human Embryonic Stem Cells Protocols: Methods in Molecular Biology, vol. 331. K. Turksen, ed. (Humana Press, Clifton, N.J.) pp. 77-90.

Niebrugge et al (2009). Generation of Human Embryonic Stem Cell-Derived Mesoderm and Cardiac Cells Using Size-Specified Aggregates in an Oxygen-Controlled Bioreactor. Biotechnology and Bioengineering. Vol. 102, no. 2, Feb. 1, 2009.

Winston Costa Pereira et al. Reproducible methodology for the isolation of mesenchymal stem cells from human umbilical cord and its potential for cardiomyocyte generation J Tissue Eng Regen Med 2008; 2: 394-399.

Oh S K W and Choo A B H (2006). Human embryonic stem cell technology: Large scale amplification and differentiation. Cytotechnology 50(1-3): 181-190.

Oh S. K. et al. (2009). *Stem Cell Research*. 2(3): 219-230.

R Passier et al. 2005. Serum free media in cocultures (FBS inhibits cardiomyocytes differentiation). Curr Opin Biotechnol. 2005 October; 16(5):498-502. Review. Stem Cells. 2005 June-July; 23(6):772-80.

Phillips et al. J. Biotechnol 2008, Attachment and growth of human embryonic stem cells on microcarriers. Journal of Biotechnology 138 (2008) 24-32.

Phillips et al., 2008. Efficient expansion of clinical-grade human fibroblasts on microcarriers: Cells suitable for ex vivo expansion of clinical-grade hESCs. Journal of Biotechnology 134 (2008) 79-87.

Ralph Graichen, Xiuqin Xu, Stefan R Braam, Thavamalar Balakrishnan, Siti Norfiza, Shirty Sieh, Set Yen Soo, Su Chin Tham, Christine Mummery, Alan Colman, Robert Zweigerdt, Bruce P Davidson. Enhanced cardiomyogenesis of human embryonic stem cells by a small molecular inhibitor of p38 MAPK. Differentiation 2007 (November 15).

Reuveny, S., Bino, T., Rosenberg, H. and Mizrahi A. (1980). A new cellulose-based microcarrier culturing system. Develop. Biol. Stand. 46, 137-145.

Reuveny, S., Mizrahi, A., Shahar, A. and Kotler, M. (1984). Role of substrate in determining the growth topology of transformed and non-transformed cells in culture. Cell Biol. Internat. Rep. 8, 539-549.

Reuveny, S., Silberstein, L. and Mizrahi, A. (1982). DE-52 and DE-53 cellulose microcarriers. I. Growth of primary and established anchorage-dependent-cells. In Vitro 18, 92-98.

Reuveny, S., Silberstein, L., Shahar, A., Freeman, A. and Mizrahi, A. (1982). Cell and virus propagation on cylindrical cellulose based microcarriers. Develop. Biol. Stand. 50, 115-123.

Shahar, A., Amir, A., Reuveny, S, and Mizrahi, A. (1989). Dissociated cerebral cultures on microcarriers. In: "A dissection and tissue culture, Manual of the nervous system" (Eds. Shahar, A. and Haber, B.). Alan R. Liss N.Y. pp. 164-166.

Shahar, A., Amir, A., Reuveny, S., Silberstein, L. and Mizrahi, A (1984). Neuronal cultures on microcarriers: Dissociated spiral cord cells. Develop. Biol. Stand. 55, 22-30.

Shahar, A., Mizrahi, A., Reuveny, S., Zimman, A. and Shainberg, A. (1985). Differentiation of myoblasts with nerve cells on microcarrier in culture. Develop. Biol. Stand. 60, 263-268.

Shahar, A., Reuveny, S., Amir, A., Kotler, M. and Mizrahi, A. (1983). Synoptogenesis and myelination in dissociated cerebral microcarrier cell culture. J. Neuroscience Res. 9, 339-348.

Shahar, A., Reuveny, S., David, Y., Hamdorf, G., Terborg, M. and Cervos-Navarro, J. (1990). Selective adherence of neurons and glia cells in dissociated cerebral and spinal cord microcarrier cultures. J. Biotechnology 16:221-232.

Shahar, A., Reuveny, S., Mizrahi, A. and Shainberg, A. (1984). Differentiation of dissociated embryonic central nervous system cells and of myoblast cultured on microcarriers. Att. Del Accademia di Medicina di Torino, 167, 33-38.

Shahar, A., Reuveny, S., Zhang, M., Espinosa de los Monteros, A., de Vellis, J. and Shainberg, A. (1992) Differentiation of myoblasts and CNS cells growth either separately or as co-cultures on microcarriers. Cytotechnology 9: 107-115.

Shainberg, A., Isac, A., Reuveny, S., Mizrahi, A. and Shahar, A. (1983). Myogenesis in microcarrier culture. Cell. Biol. Inter. Rep. 7, 72-74.

Takahashi K, Tanabe K, Ohnuki M, Narita M, Ichisaka T, Tomoda K, Yamanaka S. (2007). Induction of pluripotent stem cells from adult human fibroblasts by defined factors. Cell. 131(5):861-72.

Takahashi, K. & Yamanaka, S. Induction of pluripotent stem cells from mouse embryonic and adult fibroblast cultures by defined factors. Cell 2006; 126:663-676

Thomson J A, Yu J, et al. Induced Pluripotent Stem Cell Lines Derived from Human Somatic Cells. Science DOI: 10.1126/science.1151526

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Troyer & Weiss. Concise Review: Wharton's Jelly-Derived Cells Are a primitive Stromal Cell Population. Stem Cells 2008:26:591-599.

Wartenberg et al. Lab Invest. 1998 October; 78(10): 1301-14.

Wernig M, et. al. In vitro reprogramming of fibroblasts into a pluripotent ES-cell-like state. Nature 2007; 448:318-24

X Q Xu et al. 2008. SB203580 (p38 MAP kinase inhibitor) PGI2 (prostaglandin member accumulated in END2-CM). Differentiation. 2008 November; 76(9):958-70. Epub 2008 Jun. 13.

Yamanaka S, et al. Induction of Pluripotent Stem Cells from Adult Human Fibroblasts by Defined Factors. doi:10.1016/j.cell.2007.11.019

Yamanaka S, et. al. Generation of germline-competent induced pluripotent stem cells. Nature 2007; 448:313-7

Shinya Yamanaka. Strategies and New Developments in the Generation of Patient-Specific Pluripotent Stem Cells. Cell Stem Cell 1, Jul. 2007 ᵃ2007 Elsevier Inc.

L Yang et al. 2008. Defined medium supplemented with BMP4 (1 day), BMP4, Activin A and bFGF (days 1-4), Activin A and bFGF (days 4-8), and DKK1 and VEGF. Nature. 2008 May 22; 453(7194):524-8. Epub 2008 Apr. 23.

Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. Induced pluripotent stem cell lines derived from human somatic cells. Science. 318(5858):1917-20. Epub 2007 Nov. 20.

Zandstra et al., Tissue Eng. 2003, 9: 767-778.

Zhang X, Stojkovic P, Przyborski S, et al. Derivation of human embryonic stem cells from developing and arrested embryos. Stem Cells 2006; 24:2669-2676.

WO 2008/004990

US 2007/0264713

WO2007/030870

WO2007/070964

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

The invention claimed is:

1. A method for achieving stable, long-term culture, expansion, and differentiation of stem cells in vitro, the method comprising:
    (i) attaching stem cells to a plurality of first microcarriers to form microcarrier-stem cell complexes, wherein the surface of the first microcarriers is coated in an extracellular matrix component;
    (ii) culturing the microcarrier-stem cell complexes in suspension culture;
    (iii) passaging the cultured cells from (ii); and
    (iv) repeating steps (i)-(iii) through 7 passages,
    wherein stem cells are expanding between each passage, wherein stem cells in the culture after step (iv) are pluripotent or multipotent, whereby stable, long-term culture and expansion of stem cells are achieved in suspension in vitro, wherein the achievement of stable, long-term culture is characterized by 50% or more of the stem cells in the culture after step (iv) have the ability to differentiate, if pluripotent, into endoderm, ectoderm, and mesoderm, if multipotent, into cells of a limited number of types within a particular lineage, and retain at least one stem cell characteristic selected from the group consisting of expression of a pluripotency marker, cell viability, and normal karyotype, and wherein the achievement of expansion is characterized by the number of cultured, expanded cells at the end of step (ii) being at least 0.2 order of magnitude greater than the number of cells attached to the microcarriers in step (i);
    (v) transferring pluripotent or multipotent stem cells obtained from (iv) to a plurality of second microcarriers to form microcarrier-stem cell complexes, wherein the surface of the second microcarriers is coated in a matrix or is uncoated; and
    (vi) culturing the microcarrier-stem cell complexes from (v) in suspension culture under conditions that induce the differentiation of the stem cells.

2. The method of claim 1 wherein the stem cells are embryonic stem cells, or induced pluripotent stem cells.

3. The method of claim 1 wherein the stem cells are human or primate.

4. The method of claim 1 wherein the microcarriers are rod-shaped.

5. The method of claim 1 wherein the extracellular matrix component of (i) and the matrix of (v) are the same.

6. The method of claim 1 wherein the extracellular matrix component of (i) and the matrix of (v) are different.

7. The method of claim 1 wherein the method further comprises:
    (vii) transferring differentiated stem cells obtained from step (vi) to a plurality of third microcarriers to form microcarrier-stem cell complexes, where the surface of the third microcarriers is coated in a second matrix or is uncoated; and
    (viii) culturing the microcarrier-stem cell complexes from (vii) in suspension culture under conditions that induce the further differentiation of the differentiated stem cells.

8. The methods of claim 1 wherein in step (iv), steps (i)-(iii) are repeated through one of: at least 8 passages, at least 9 passages, at least 10 passages, at least 11 passages, at least 12 passages, at least 13 passages, at least 14 passages, at least 15 passages, at least 16 passages, at least 17 passages, at least 18 passages, at least 19 passages, at least 20 passages, at least 21 passages, at least 22 passages, at least 23 passages, at least 24 passages, at least 25 passages, at least 30 passages, at least 40 passages, at least 50 passages, at least 60 passages, at least 70 passages, at least 80 passages, at least 90 passages, or at least 100 passages.

9. The method of claim 1 wherein the matrix comprises one or more of hyaluronic acid, laminin, fibronectin, vitronectin, collagen, elastin, heparan sulfate, dextran, dextran sulphate, and chondroitin sulphate.

10. The method of claim 1 wherein the matrix comprises a mixture of laminin, collagen I, heparan sulfate proteoglycans, and entactin 1.

11. The method of claim 1 wherein the microcarrier comprises or consists of one or more of cellulose, dextran, hydroxylated methacrylate, collagen, gelatin, polystyrene, plastic, glass, ceramic, and silicone.

12. The method of claim 1 wherein the stem cells are pluripotent, and the conditions in step (vi) induce the differentiation of the stem cells into endoderm, ectoderm, or mesoderm.

13. The method of claim 1 wherein the stem cells are pluripotent, and the conditions in step (vi) induce the differentiation of the stem cells into an embyroid body.

14. The method of claim 1 wherein the conditions in step (vi) induce the differentiation of the stem cells into one of cardiomyocytes, cardiac mesoderm, adipocytes, osteocytes, hepatocytes, hepatic endoderm, pancreatic islet cells, pancreatic endoderm, insulin producing cells, neural tissue, neuroectoderm, epidermal tissue, surface ectoderm, bone, cartilage, muscle, ligament, tendon, and other connective tissue.

15. The method of claim 1 wherein the method comprises culturing the stem cells in serum-free media.

\* \* \* \* \*